US009233961B2

(12) United States Patent
Chatterjee et al.

(10) Patent No.: US 9,233,961 B2
(45) Date of Patent: Jan. 12, 2016

(54) COMPOUNDS AND COMPOSITIONS FOR THE TREATMENT OF PARASITIC DISEASES

(71) Applicants: Arnab Kumar Chatterjee, San Diego, CA (US); Fang Liang, Encinitas, CA (US); Casey Jacob Nelson Mathison, San Diego, CA (US); Pranab Kumar Mishra, West Bengal (IN); Valentina Molteni, San Diego, CA (US); Advait Suresh Nagle, San Diego, CA (US); Frantisek Supek, San Diego, CA (US); Liying Jocelyn Tan, Singapore (SG); Agnes Vidal, Spring Valley, CA (US); Michael Herman Gelb, Seattle, WA (US); Frederick Simmons Buckner, Seattle, WA (US); Hari Babu Tatipaka, Pradesh (IN); Neil Richard Norcross, Dundee (GB); John Robert Gillespie, Seattle, WA (US)

(72) Inventors: Arnab Kumar Chatterjee, San Diego, CA (US); Fang Liang, Encinitas, CA (US); Casey Jacob Nelson Mathison, San Diego, CA (US); Pranab Kumar Mishra, West Bengal (IN); Valentina Molteni, San Diego, CA (US); Advait Suresh Nagle, San Diego, CA (US); Frantisek Supek, San Diego, CA (US); Liying Jocelyn Tan, Singapore (SG); Agnes Vidal, Spring Valley, CA (US); Michael Herman Gelb, Seattle, WA (US); Frederick Simmons Buckner, Seattle, WA (US); Hari Babu Tatipaka, Pradesh (IN); Neil Richard Norcross, Dundee (GB); John Robert Gillespie, Seattle, WA (US)

(73) Assignees: Novartis AG, Basel (CH); University of Washington through its Center for Commercialization, Seattle, WA (US)

(*) Notice: Subject to any disclaimer, the term of this patent is extended or adjusted under 35 U.S.C. 154(b) by 0 days.

(21) Appl. No.: 14/209,536

(22) Filed: Mar. 13, 2014

(65) Prior Publication Data
US 2014/0275013 A1 Sep. 18, 2014

Related U.S. Application Data

(60) Provisional application No. 61/790,936, filed on Mar. 15, 2013.

(51) Int. Cl.
| C07D 471/02 | (2006.01) |
| A61K 31/50 | (2006.01) |
| A61K 31/415 | (2006.01) |
| C07D 473/00 | (2006.01) |
| C07D 471/04 | (2006.01) |
| C07D 487/04 | (2006.01) |
| C07D 498/04 | (2006.01) |

(52) U.S. Cl.
CPC ............ *C07D 473/00* (2013.01); *C07D 471/04* (2013.01); *C07D 487/04* (2013.01); *C07D 498/04* (2013.01)

(58) Field of Classification Search
CPC .............................. C07D 471/04; A61K 31/40
USPC ............ 544/373; 546/118, 112; 514/393, 249
See application file for complete search history.

(56) References Cited

U.S. PATENT DOCUMENTS

| 4,038,396 | A | 7/1977 | Shen et al. |
| 4,582,837 | A | 4/1986 | Hauel et al. |
| 5,077,408 | A | 12/1991 | Guillaumet et al. |
| 5,434,150 | A | 7/1995 | Austel et al. |
| 2005/0101647 | A1 | 5/2005 | Oda et al. |
| 2005/0214901 | A1 | 9/2005 | Ealick et al. |
| 2005/0282853 | A1 | 12/2005 | Boykin et al. |
| 2007/0148185 | A1 | 6/2007 | Rathore et al. |
| 2009/0163545 | A1 | 6/2009 | Goldfarb |
| 2010/0168084 | A1 | 7/2010 | Huber et al. |
| 2011/0053915 | A1 | 3/2011 | Ivaschenko et al. |
| 2011/0182812 | A1 | 7/2011 | Szardenings et al. |
| 2014/0274926 | A1 | 9/2014 | Chatterjee et al. |
| 2014/0275119 | A1 | 9/2014 | Liang et al. |

FOREIGN PATENT DOCUMENTS

| CA | 2011222 A1 | 9/1990 |
| DE | 4129603 A1 | 3/1993 |

(Continued)

OTHER PUBLICATIONS

Al-Salabi, et al., "Purine Nucleobase Transport in Amastigotes of Leishmania mexicana: Involvement in Allopurinol Uptake", Antimicrobial Agents and Chemotherapy, Sep. 2005, vol. 49, No. 9, pp. 3682-3689, American Society for Microbiology, US.

(Continued)

*Primary Examiner* — Andrew D Kosar
*Assistant Examiner* — Raymond Covington
(74) *Attorney, Agent, or Firm* — Chihang Amy Smith; Genomics Institute of the Novartis Research Foundation

(57) ABSTRACT

The present invention provides compounds of formula I:

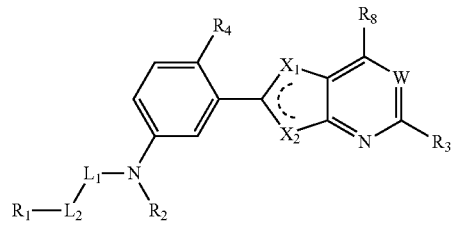

or a pharmaceutically acceptable salt, tautomer, or stereoisomer, thereof, wherein the variables are as defined herein. The present invention further provides pharmaceutical compositions comprising such compounds and methods of using such compounds for treating, preventing, inhibiting, ameliorating, or eradicating the pathology and/or symptomology of a disease caused by a parasite, such as Leishmaniasis, Human African Trypanosomiasis and Chagas disease.

20 Claims, No Drawings

(56) References Cited

FOREIGN PATENT DOCUMENTS

| | | | |
|---|---|---|---|
| DE | 4304650 A1 | 8/1994 | |
| EP | 700906 A1 | 3/1996 | |
| EP | 1460067 A1 | 9/2004 | |
| WO | 9806703 A1 | 2/1998 | |
| WO | 9810779 A1 | 3/1998 | |
| WO | 0170743 A1 | 9/2001 | |
| WO | 0196336 A2 | 12/2001 | |
| WO | 0236580 A2 | 5/2002 | |
| WO | 0238153 A1 | 5/2002 | |
| WO | 0244126 A2 | 6/2002 | |
| WO | 02075318 A2 | 9/2002 | |
| WO | 03011219 A2 | 2/2003 | |
| WO | 03042185 A1 | 5/2003 | |
| WO | 03045929 A1 | 6/2003 | |
| WO | 2004024897 A2 | 3/2004 | |
| WO | 2005013950 A2 | 2/2005 | |
| WO | 2005014598 A1 | 2/2005 | |
| WO | 2005023761 A2 | 3/2005 | |
| WO | 2005030206 A1 | 4/2005 | |
| WO | 2006066913 A2 | 6/2006 | |
| WO | 2006066914 A2 | 6/2006 | |
| WO | 2006101456 A1 | 9/2006 | |
| WO | 2007014707 A1 | 2/2007 | |
| WO | 2007017143 A1 | 2/2007 | |
| WO | 2007019417 A1 | 2/2007 | |
| WO | 2007028135 A2 | 3/2007 | |
| WO | 2008007900 A1 | 1/2008 | |
| WO | 2008021388 A1 | 2/2008 | |
| WO | 2008048991 A2 | 4/2008 | |
| WO | 2008100376 A2 | 8/2008 | |
| WO | 2008118122 A2 | 10/2008 | |
| WO | 2008128968 A1 | 10/2008 | |
| WO | 2009005551 A2 | 1/2009 | |
| WO | 2009005675 A1 | 1/2009 | |
| WO | 2009006389 A2 | 1/2009 | |
| WO | 2009051454 A2 | 4/2009 | |
| WO | 2009077956 A2 | 6/2009 | |
| WO | 2009112445 A1 | 9/2009 | |
| WO | 2009151546 A2 | 12/2009 | |
| WO | 2010027746 A2 | 3/2010 | |
| WO | WO 2010117935 * | 10/2010 | 546/112 |
| WO | 2011027249 A2 | 3/2011 | |
| WO | 2011153377 A2 | 8/2011 | |
| WO | 2012088411 A1 | 6/2012 | |
| WO | 2012130633 A1 | 10/2012 | |
| WO | 2013024282 A2 | 2/2013 | |
| WO | 2013078254 A1 | 5/2013 | |
| WO | WO 2013/078254 * | 5/2013 | 546/118 |
| WO | 2013147711 A1 | 10/2013 | |
| WO | 2013009827 A1 | 1/2014 | |
| WO | 2014003124 A1 | 1/2014 | |
| WO | 2014012511 A1 | 1/2014 | |
| WO | 2014028968 A1 | 2/2014 | |
| WO | 2014151630 A2 | 9/2014 | |
| WO | 2014151729 A1 | 9/2014 | |
| WO | 2014151784 A1 | 9/2014 | |

OTHER PUBLICATIONS

Hwang, et al., "Optimization of Chloronitrobenzamides (CNBs) as Therapeutic Leads for Human African Trypanosomiasis (HAT)", Journal of Medicinal Chemistry, Mar. 13, 2013, vol. 56, pp. 2850-2860.

Lan, et al., "Molecular modeling studies on imidazol [4,5-b]pyridine derivatives as Aurora A kinase inhibitors using 3D-QSAR and docking approaches", European Journal of Medicinal Chemistry, 2011, vol. 46, pp. 77-94.

Middleton, et al., "Synthesis of Imidazo[4,5-b]- and [4,5-c]pyridines", J. Heterocyclic Chem., 1980, vol. 17, pp. 1757-1760.

Savarino, et al., "Aminophenyl-X-azolopyridines as Precursors of Heterocyclic Azo Dyes", J. Heterocyclic Chem., 1989, vol. 26, pp. 289-292.

Verlinde, et al., "Selective Inhibition of Trypanosomal Glyceraldehyde-3-phosphate Dehydrogenase by Protein Structure-Based Design: Toward New Drugs for the Treatment of Sleeping Sickness", J. Med. Chem., 1994, vol. 37, pp. 3605-3613; American Chemical Society.

Ferrins, et al., "3-(Oxazolo[4,5-pyridin-2-yl)anlidies as a novel class of potent inhibitors for the kinetoplastid Trypanosoma brucei, the causative agent for human African trypanosomiasis", European Journal of Medicinal Chemistry, 2013, vol. 66, pp. 450-465, Elsevier Massson SAS.

Wu, et al., "Discovery and Mechanism Study of SIRT1 Activators that Promote the Deacetylation of Fluorophore-Labeled Substrate", Journal of Medicinal Chemistry, 2013, vol. 56, No. 3, pp. 761-780, American Chemical Society.

Bemis, et al., "Discovery of oxazolo[4,5-b]pyridines and related heterocyclic analogs as noval SIRT1 activators", Bioorganic & Medicinal Chemistry Letters, 2009, vol. 19, pp. 2350-2353, Elsevier Ltd.

Cheng, et al., "High-throughput identification of antibacterials against methiciliin-resistant Staphylococcus aureas (MRSA) and the transglycosylase", Bioorganic & Medicinal Chemistry, 2010, vol. 18, pp. 8512-8529, Elsevier Ltd.

Park, et al., "3D-QSAR of SIRT1 Activators Targeting Against Diet-Induced Metabolic Syndrome", Bull. Korean Chem. Soc., 2009, vol. 30, No. 9, pp. 2117-2120.

Vu, et al., "Discovery of Imidazo[1,2-b]thiazole Derivatives as Novel SIRT1 Activators", Journal of Medicinal Chemistry, 2009, vol. 52, pp. 1275-1283, American Chemical Society.

Chakraborty, et al., "Studies on ornithine decarboxylase of Leishmania donovani: structure modeling and inhibitor docking", Medicinal Chemistry Research, 2013, vol. 22, pp. 466-478.

Tatipaka, et al., "Substituted 2-Phenyl-Imidazopyridines: A New Class of Drug Leads for Human African Trypanosomiasis", Journal of Medicinal Chemistry, Dec. 19, 2013, vol. 57, No. 3, pp. 828-835, American Chemical Society.

Novinson, et al., "Novel Heterocyclic Nitrofurfural Hydrazones. In Vivo Antitryanosomal Activity", Journal of Medicinal Chemistry, 1976, vol. 19, No. 4, pp. 512-516.

Database Registry Chemical Abstracts Service, Columbus, Ohio, US, Aug. 14, 2007, Database accession No. 944581-06-0.

Caballero, et al., "Triazolopyrimidine compounds containing first-row transition metals and their activity against the neglected infectous Chagas disease and leishmaniasis", European Journal of Medicinal Chemistry, 2014, vol. 85, pp. 526-534, Elsevier Masson SAS.

Caballero, et al., "Lanthanide complexes containing 5-methyl-1,2,4-triazolo[1,5-a] pyrimidine-7(4H)-one and their therapeutic potential to fight leishmaniasis and Chagas disease", Journal of Inorganic Biochemistry, 2014, vol. 138, pp. 39-46, Elsevier Inc.

De Rycker, et al., "Comparison of a High-Throughput High-Content Intracellular Leishmania donovani Assay with an Axenic Amastrigote Assay", Antimicrobial Agents and Chemotherapy, 2013, vol. 57, No. 7, pp. 2913-2922.

* cited by examiner

COMPOUNDS AND COMPOSITIONS FOR THE TREATMENT OF PARASITIC DISEASES

CROSS-REFERENCE TO RELATED APPLICATION

This application claims the benefit of priority to U.S. Provisional Patent Application No. 61/790,936 filed 15 Mar. 2013. The full disclosure of said application is incorporated herein by reference in its entirety and for all purposes.

BACKGROUND OF THE INVENTION

1. Field of the Invention

The invention provides a class of compounds, pharmaceutical compositions comprising such compounds and methods of using such compounds to treat or prevent Leishmaniasis, Human African trypanosomiasis, and/or Chagas disease.

2. Background

Leishmaniasis is a disease caused by protozoan parasites that belong to the genus *Leishmania* and is transmitted by the bite of certain species of sand fly.

Leishmaniasis is mostly a disease of the developing world, and is rarely known in the developed world outside a small number of cases, mostly in instances where troops are stationed away from their home countries. Leishmaniasis can be transmitted in many tropical and subtropical countries, and is found in parts of about 88 countries. Approximately 350 million people live in these areas. The settings in which leishmaniasis is found range from rainforests in Central and South America to deserts in West Asia and the Middle East. It affects as many as 12 million people worldwide, with 1.5-2 million new cases each year. The visceral form of leishmaniasis has an estimated incidence of 500,000 new cases and 60,000 deaths each year. More than 90 percent of the world's cases of visceral leishmaniasis are in India, Bangladesh, Nepal, Sudan, and Brazil. Kabul is estimated as the largest center of cutaneous leishmaniasis in the world, with approximately 67,500 cases as of 2004.

There are four main forms of Leishmaniasis. Cutaneous leishmaniasis is the most common form of leishmaniasis. Visceral leishmaniasis, also called kala-azar, is the most serious form in which the parasites migrate to the vital organs. Visceral leishmaniasis is caused by the parasite *Leishmania donovani*, and is potentially fatal if untreated.

Currently, no vaccines are in routine use.

The two main therapies for visceral leishmaniasis are the antimony derivatives sodium stibogluconate (Pentostam®) and meglumine antimoniate (Glucantim®). Sodium stibogluconate has been used for about 70 years and resistance to this drug is a growing problem. In addition, the treatment is relatively long and painful, and can cause undesirable side effects. Amphotericin (AmBisome) is now the treatment of choice. Miltefosine (Impavido), and paromomycin are the other treatment alternatives. These drugs are known to produce a definitive cure in >90% of patients. Amphotericin (AmBisome) is expansive and has to be given intravenously; it is not affordable to most patients affected. Paromomycin, although affordable, requires intramuscular injections for 3 weeks; compliance is a major issue. Miltefosine is an oral drug and has shown to be more effective and better tolerated than other drugs. However, there are problems associated with the use of miltefosine that arise from its teratogenicity and pharmacokinetics. Miltefosine was shown to be much slower eliminated from the body and was still detectable five months after the end of treatment. The presence of subtherapeutic miltefosine concentrations in the blood beyond five months after treatment might contribute to the selection of resistant parasites and, moreover, the measures for preventing the teratogenic risks of miltefosine must be reconsidered. This led to some reluctance to taking Miltefosine by affected populations.

The Drugs for Neglected Diseases Initiative is actively facilitating the search for novel therapeutics. Our invention meets that needs.

Human African trypanosomiasis (HAT), also known as African sleeping sickness, is a vector-borne parasitic disease caused by the protozoa *Trypanosoma brucei*. There are two subspecies that infect humans, *T.b. gambiense* and *T.b. rhodesiense*, with the former accounting for over 95% of reported cases and the latter accounting for the remaining reported cases. The parasites are transmitted to humans by tsetse fly (*Glossina* genus) bites which have acquired their infection from human beings or from animals harboring the human pathogenic parasites.

The disease has been recorded as occurring in 36 countries, all in subtropical and equatorial Africa. It is endemic in southeast Uganda and western Kenya. In 1995, the WHO estimated that 300,000 people were afflicted with the disease. In its 2001 report, the WHO set the figure of people at risk of infection at 60 million, of which only 4 to 5 million had access to any kind of medical monitoring. In 2006, the WHO estimated that about 70,000 people could have the disease, and many cases are believed to go unreported. About 48,000 people died of sleeping sickness in 2008. Public health efforts in prevention and the eradication of the tsetse fly population have proven to be successful in controlling the spread of the disease; under 10,000 new cases were reported in 2009 according to WHO figures, which represents a huge decrease from the estimated 300,000 new cases in 1998.

African trypanosomiasis symptoms occur in two stages. In the first stage, known as the haemolymphatic phase, the trypanosomes multiply in subcutaneous tissues, blood and lymph. The haemolymphatic phase is characterized by bouts of fever, headaches, joint pains and itching. In the second stage, the neurological phase, the parasites cross the blood-brain barrier to infect the central nervous system. It is in this stage when more obvious signs and symptoms of the disease appear: changes of behaviour, confusion, sensory disturbances and poor coordination. Disturbance of the sleep cycle, which gives the disease its name, is an important feature of the second stage of the disease. Without treatment, the disease is invariably fatal, with progressive mental deterioration leading to coma, systemic organ failure, and death.

Four drugs are registered for the treatment of sleeping sickness. The protocol depends on the stage of the disease. The current standard treatment for first-stage disease is intravenous or intramuscular pentamidine (for *T.b. gambiense*), or intravenous suramin (for *T.b. rhodesiense*). The current standard treatment for second-stage disease is: Intravenous melarsoprol, or interavenous melarsoprol in combination with oral nifurtimox, intravenous eflornithine only or eflornithine in combination with nifurtimox. All of the drugs have undesirable or sometime serious side effects. For example, 3-10% of patients those injected with Melarsoprol (Arsobal), an organoarsenical, developed reactive encephalopathy (convulsions, progressive coma, or psychotic reactions), and 10-70% of such cases result in death.

Chagas disease, also called American trypanosomiasis, is a tropical parasitic disease caused by the flagellate protozoan *Trypanosoma cruzi*. *T. cruzi* is commonly transmitted to humans and other mammals by the blood-sucking "kissing bugs" of the subfamily Triatominae (family *Reduviidae*).

Chagas disease is contracted primarily in the Americas. It is endemic in twenty one Central and Latin American countries; particularly in poor, rural areas of Mexico, Central America, and South America. Large-scale population movements from rural to urban areas of Latin America and to other regions of the world have increased the geographic distribution of Chagas disease, and cases have been noted in many countries, particularly in Europe. Although there are triatomine bugs in the U.S., only very rarely vectorborne cases of Chagas disease have been documented.

Each year, an estimated 10 to 15 million people across the world are infected with Chagas disease, most of who do not know they are infected. Every year, 14,000 people die as a consequence of the disease. In Central and South America, Chagas kills more people than any other parasite-borne disease, including malaria. By applying published seroprevalence figures to immigrant populations, CDC estimates that more than 300,000 persons with *Trypanosoma cruzi* infection live in the United States. Most people with Chagas disease in the United States acquired their infections in endemic countries.

Chagas disease has an acute and a chronic phase. If untreated, infection is lifelong. Acute Chagas disease occurs immediately after infection, may last up to a few weeks or months, and parasites may be found in the circulating blood. Infection may be mild or asymptomatic. There may be fever or swelling around the site of inoculation (where the parasite entered into the skin or mucous membrane). Rarely, acute infection may result in severe inflammation of the heart muscle or the brain and lining around the brain. The initial acute phase is responsive to antiparasitic treatments, with 60-90% cure rates. Following the acute phase, most infected people enter into a prolonged asymptomatic form of disease (called "chronic indeterminate") during which few or no parasites are found in the blood. During this time, most people are unaware of their infection. Many people may remain asymptomatic for life and never develop Chagas-related symptoms. However, an estimated 20-30% of infected people will develop debilitating and sometimes life-threatening medical problems over the course of their lives.

The symptoms of Chagas disease vary over the course of an infection. In the early, acute stage, symptoms are mild and usually produce no more than local swelling at the site of infection. The initial acute phase is responsive to antiparasitic treatments, with 60-90% cure rates. After 4-8 weeks, individuals with active infections enter the chronic phase of Chagas disease that is asymptomatic for 60-80% of chronically infected individuals through their lifetime.

There is no vaccine against Chagas disease. Treatment for Chagas disease focuses on killing the parasite and managing signs and symptoms.

During the acute phase of Chagas disease, the drugs currently available for treatment are benznidazole and nifurtimox. Once Chagas disease reaches the chronic phase, medications aren't effective for curing the disease. Instead, treatment depends on the specific signs and symptoms. However, problems with these current therapies include their diverse side effects, the length of treatment, and the requirement for medical supervision during treatment. Resistance to the two frontline drugs has already occurred. The antifungal agent Amphotericin b has been proposed as a second-line drug, but this drug is costly and relatively toxic.

In view of the foregoing, it is desirable to develop novel compounds as antiparasitic agents.

SUMMARY OF THE INVENTION

The invention therefore provides a compound of the formula (I):

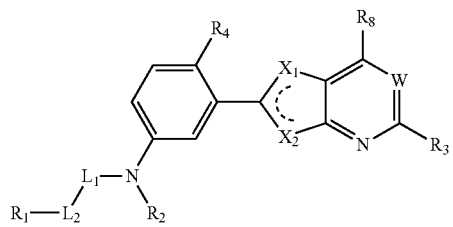

or a pharmaceutical acceptable salt, tautomer or stereoisomer thereof, wherein $X_1$ is N or O, or $NR_5$;
$X_2$ is N or $NR_7$, provided that one of $X_1$ and $X_2$ is N;
W is $CR_6$ or N;
$L_1$ is a bond, —C(O)— or —S(O)$_2$—;
$L_2$ is selected from a bond, —$CR_{9a}R_{9b}$—, —$NR_{10}$—, and —O—, wherein $R_{9a}$ is hydrogen, halo or $C_{1-4}$alkyl, $R_{9b}$ is selected from hydrogen, halo, hydroxyl, $C_{1-4}$alkyl, and $C_{1-4}$alkoxy; and $R_{10}$ is hydrogen or $C_{1-4}$alkyl;
$R_1$ is selected from hydrogen, $C_{1-6}$alkyl, $C_{1-4}$alkoxy, $C_{6-10}$aryl, $C_{5-10}$heteroaryl, $C_{3-7}$cycloalkyl, $C_{5-6}$heterocycloalkyl, and $C_{9-10}$heterocyclyl, wherein
   the $C_{1-6}$alkyl or $C_{1-4}$alkoxy is unsubstituted or substituted with 1 to 2 substituents independently selected from halo, hydroxy, $C_{1-4}$alkoxy, $C_{5-6}$aryloxy, hydroxycarbonyl, $C_{1-4}$alkoxycarbonyl, amino, $C_{1-4}$alkyamino, $C_{1-4}$alkoxycarbonylamino, $C_{5-6}$aryl, and $C_{5-6}$heterocycloalkyl; and
   the $C_{6-10}$aryl and $C_{5-10}$heteroaryl, $C_{3-7}$cycloalkyl, $C_{5-6}$heterocycloalkyl or $C_{9-10}$heterocyclyl is unsubstituted or substituted with 1 to 3 substituents independently selected from halo, cyano, hydroxyl, oxo, $C_{1-4}$alkyl, benzyl, halo$C_{1-4}$alkyl, $C_{1-4}$alkoxy$C_{1-4}$alkyl, $C_{1-4}$alkylamino$C_{1-4}$alkyl, $C_{1-4}$alkoxy, halo$C_{1-4}$alkoxy, amino, $C_{1-4}$alkylamino, $C_{1-4}$alkoxycarbonyl, $C_{1-4}$alkylthio, $C_{1-4}$alkylsulfonyl, $C_{5-6}$heteroaryl, halo$C_{5-6}$heteroaryl, $C_{3-6}$cycloalkyl, and $C_{5-6}$heterocycloalkyl; or —N($R_2$)-$L_1$-$L_2$-$R_1$ together forms a nitro group;
$R_2$ is hydrogen, $C_{1-4}$alkyl or —C(O)$C_{5-6}$heteroaryl;
$R_3$ is hydrogen, halo or $C_{1-4}$alkyl;
$R_4$ is selected from hydrogen, halo, $C_{1-4}$alkyl, halo$C_{1-4}$alkyl, $C_{1-4}$alkylsulfonyl, $C_{5-6}$heteroaryl, and $C_{5-6}$heterocycloalkyl;
$R_5$ is selected from hydrogen, $C_{1-4}$alkyl, —C(O)O$C_{1-4}$alkyl, wherein the $C_{1-4}$alkyl portion of $C_{1-4}$alkyl or —C(O)O$C_{1-4}$alkyl is unsubstituted or substituted by amino, $C_{1-4}$alkylamino, or $C_{5-6}$heterocycloalkyl;
$R_6$ is selected from halo, cyano, $C_{1-4}$alkyl, $C_{1-4}$alkenyl, $C_{1-4}$alkoxy, $C_{1-4}$alkylsulfonyl, $C_{3-6}$cycloalkylsulfonyl, $C_{1-4}$alkylphosphinyl oxide, $C_{1-4}$alkylcarbonylamino, phenyl, $C_{5-6}$heteroaryl, $C_{5-6}$heteraryl, $C_{4-6}$heterocycloalkyl, and $C_{6-10}$heterocyclyl, wherein
   the $C_{1-6}$alkyl, $C_{1-4}$alkenyl or $C_{1-4}$alkoxy of $R_6$ is unsubstituted or substituted by 1 to 2 substituents independently selected from halo, amino, $C_{1-4}$alkylamino, and hydroxyl-substituted $C_{1-4}$alkylamino;
   the pheny or $C_{5-6}$heteroaryl of $R_6$ is unsubstituted or substituted by 1 to 2 substituents independently selected from halo, cyano, $C_{1-4}$alkyl, halo$C_{1-4}$alkyl, $C_{1-4}$alkylamino$C_{1-4}$alkyl, amino$C_{1-4}$alkyl, $C_{4-6}$heterocycloalky$C_{1-4}$alkyl, $C_{1-4}$alkylsilanyl$C_{1-4}$alkoxy$C_{1-4}$alkyl, $C_{1-4}$alkoxy, halo$C_{1-4}$alkoxy, $C_{1-4}$alkoxy$C_{1-4}$alkoxy, amino$C_{1-4}$alkoxy, phenyl$C_{1-4}$ alkoxy, $C_{5-6}$heteroaryl$C_{1-4}$alkoxy, $C_{3-6}$cycloalky$C_{1-4}$alkoxy, $C_{3-6}$heterocycloalky$C_{1-4}$alkoxy, $C_{1-4}$alkylcarbonyl, aminocarbonyl, $C_{1-4}$alkylaminocarbonyl, $C_{1-4}$alkoxycarbonyl, amino, $C_{1-4}$alkylamino, $C_{4-6}$heterocycloalkyl$C_{1-4}$alkylamino, $C_{4-6}$heterocycloalkyl$C_{1-4}$alkylamino, —NHC(O)R$_{14}$ S(O)$_2$R$_{15}$, phenyl, $C_{5-6}$heteraryl, $C_{5-6}$heterocycloalkyl, and $C_{9-10}$heterocyclyl;

the $C_{3-6}$heterocycloalkyl or $C_{6-10}$heterocyclyl of R$_6$ is unsubstituted or substituted by 1 to 2 substituents independently selected from $C_{1-4}$alkyl, oxo, and $C_{1-4}$alkoxycarbonyl, wherein R$_{14}$ is selected from $C_{1-4}$alkyl, amino$C_{1-4}$alkyl, amino, $C_{1-4}$alkylamino, cyclopropylamino, $C_{1-4}$alkoxy, $C_{1-4}$alkylsulfonyl, and $C_{1-4}$alkylaminosulfonyl R$_{15}$ is selected from $C_{1-4}$alkyl, amino, $C_{3-6}$cycloalkyl, and $C_{5-6}$heterocycloalkyl; and the phenyl, $C_{5-6}$heteraryl, $C_{5-6}$heterocycloalkyl or $C_{9-10}$heterocyclyl substituent of the phenyl or $C_{5-6}$heteroaryl of R$_6$ is unsubstituted or substituted by 1 to 3 substituents independently selected from $C_{1-4}$alkyl and oxo;

R$_7$ is selected from hydrogen, $C_{1-4}$alkyl and —C(O)C$_{5-6}$heteroaryl; and R$_8$ is hydrogen or halo.

In a second aspect, the present invention provides a pharmaceutical composition which contains a compound of the invention selected from Formula I, a N-oxide derivative, individual isomers and mixture of isomers thereof; or a pharmaceutically acceptable salt thereof, in admixture with one or more suitable excipients.

In a third aspect, the present invention provides a method of treating a disease in an animal in which a compound of the invention can prevent, inhibit or ameliorate the pathology and/or symptomology of a disease caused by a parasite of the *Leishmania* genus, for example, *Leishmania donovani, Leishmania infantum, Leishmania braziliensis, Leishmania panamensis, Leishmania guayanensis, Leishmania amazonensis, Leishmania mexicana, Leishmania tropica, Leishmania major, Trypanosoma cruzi*, and *Trypanosoma brucei* and a parasite of the *Trypanosoma* genus, for example, *Trypanosoma cruzi* and *Trypanosoma brucei*, which method comprises administering to the animal a therapeutically effective amount of a compound selected from Formula I, an N-oxide derivative, individual isomers and mixture of isomers thereof, or a pharmaceutically acceptable salt thereof.

In a fourth aspect, the present invention provides a compound of Formula I, an N-oxide derivative, individual isomers and mixture of isomers thereof, or a pharmaceutically acceptable salt thereof, for treating, preventing, inhibiting, ameliorating, or eradicating the pathology and/or symptomology of a disease caused by a parasite of the *Leishmania* genus, for example, *Leishmania donovani, Leishmania infantum, Leishmania braziliensis, Leishmania panamensis, Leishmania guayanensis, Leishmania amazonensis, Leishmania mexicana, Leishmania tropica, Leishmania major, Trypanosoma cruzi*, and *Trypanosoma brucei* and a parasite of the *Trypanosoma* genus, such as, for example, *Trypanosoma cruzi* and *Trypanosoma brucei*. Particularly, the parasite is a *Leishmania*, and the disease is Leishmanaisis.

In a fifth aspect, the present invention provides the use of a compound selected from Formula I, an N-oxide derivative, individual isomers and mixture of isomers thereof, or a pharmaceutically acceptable salt thereof, in the manufacture of a medicament for treating a disease caused by a parasite in an animal. The disease may be Leishmaniasis, Human African Trypanosomiasis and/or Chagas disease.

Unless specified otherwise, the term "compounds of the present invention" refers to compounds of Formula (I) and subformulae thereof, salts of the compound, hydrates or solvates of the compounds, salts, as well as all stereoisomers (including diastereoisomers and enantiomers), tautomers and isotopically labeled compounds (including deuterium substitutions). Compounds of the present invention further comprise polymorphs of compounds of formula I (or subformulae thereof) and salts thereof.

DETAILED DESCRIPTION OF THE INVENTION

Definitions

For purposes of interpreting this specification, the following definitions will apply and whenever appropriate, terms used in the singular will also include the plural and vice versa.

"Acyl" as used herein refers to the radical —C(=O)R$_a$, where R$_a$ is hydrogen or a non-hydrogen substituent on the carbonyl carbon, forming different carbonyl-containing groups including, but are not limited to, acids, acid halides, aldehydes, amides, esters, and ketones.

"Alkoxy" as used herein refers the radical —O-alkyl, wherein the alkyl is as defined herein. C$_X$alkoxy and C$_{X-Y}$alkoxy as used herein describe alkoxy groups where X and Y indicate the number of carbon atoms in the alkyl chain. Representative examples of C$_{1-10}$alkoxy include, but are not limited to, methoxy, ethoxy, propoxy, 2-propoxy, butoxy, tert-butoxy, pentyloxy, hexyloxy, heptyloxy, octyloxy and decyloxy. The alkyl portion of the alkoxy may be optionally substituted, and the substituents include those described for the alkyl group below.

"Alkyl" as used herein refers to a fully saturated branched or unbranched hydrocarbon chain having up to 10 carbon atoms. C$_X$alkyl and C$_{X-Y}$alkyl as used herein describe alkyl groups where X and Y indicate the number of carbon atoms in the alkyl chain. For example, C$_{1-10}$ alkyl refers to an alkyl radical as defined above containing one to ten carbon atoms. C$_{1-10}$ alkyl includes, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. Alkyl represented along with another radical like arylalkyl, heteroarylalkyl, alkoxyalkyl, alkoxyalkyl, alkylamino, where the alkyl portion shall have the same meaning as described for alkyl and is bonded to the other radical. For example, (C$_{6-10}$)aryl(C$_{1-3}$)alkyl includes, benzyl, phenylethyl, 1-phenylethyl, 3-phenylpropyl, 2-thienylmethyl, 2-pyridinylmethyl and the like.

Unless stated otherwise specifically in the specification, an alkyl group may be unsubstituted or substituted by one or more substituents to the extent that such substitution makes sense chemically. Typical substituents include, but are not limited to halo, hydroxyl, alkoxy, cyano, amino, acyl, aryl, arylalkyl, and cycloalkyl, or an heteroforms of one of these groups, and each of which can be substituted by the substituents that are appropriate for the particular group.

"Alkenyl" as used herein refers to a straight or branched, hydrocarbon chain having up to 10 carbon atoms and at least one carbon-carbon double bond. C$_X$alkenyl and C$_{X-Y}$alkenyl as used herein describe alkenyl groups where X and Y indicate the number of carbon atoms in the alkenyl chain. Examples of C$_{2-7}$alkenyl include vinyl, allyl, isopropenyl, pentenyl, hexenyl, heptenyl, 1-propenyl, 2-butenyl, 2-methyl-2-butenyl, and the like. The alkenyl may be optionally substituted, and the substituents include those described for the alkyl group descried herein.

"Alkynyl" as used herein refers to a straight or branched, hydrocarbon chain having up to 10 carbon atoms and at least one carbon-carbon triple bond. $C_X$alkenyl and $C_{X-Y}$alkenyl as used herein describe alkynyl groups, where X and Y indicate the number of carbon atoms in the alkynyl chain. For example, $C_{2-7}$alkenyl include, but are not limited to, ethynyl, propargyl, 3-methyl-1-pentynyl, 2-heptynyl and the like. An alkynyl may be optionally substituted, and the substituents include those described for the alkyl group described herein.

"Alkylene" as used herein refers to a divalent alkyl group defined herein. Examples of $C_{1-10}$alkylene includes, but are not limited to, methylene, ethylene, n-propylene, iso-propylene, n-butylene, sec-butylene, iso-butylene, tert-butylene, n-pentylene, isopentylene, neopentylene, n-hexylene, 3-methylhexylene, 2,2-dimethylpentylene, 2,3-dimethylpentylene, n-heptylene, n-octylene, n-nonylene and n-decylene. An alkylene group may be optionally substituted, and the substituents include those described for the alkyl group described herein.

"Alkenylene" as used herein refers to a divalent alkenyl group defined herein. Examples of $C_{1-3}$alkenylene include, but are not limited to, ethene-1,2-diyl, propene-1,3-diyl, and methylene-1,1-diyl. An alkenylene may be optionally substituted, and the substituents include those described for the alkyl group described herein.

"Alkynylene" as used herein refers to a divalent alkynyl group defined herein. Examples of alkynylene include ethyne-1,2-diylene, propyne-1,3-diylene, and the like. An alkynylene may be optionally substituted, and the substituents include those described for the alkyl group described herein.

"Amino" as used herein refers to the radical —NH$_2$. When an amino is described as "substituted" or "optionally substituted", the term includes NR'R" wherein each R' and R" is independently H, or is an alkyl, alkenyl, alkynyl, acyl, aryl, aryl, cycloalkyl, arylalkyl cycloalkylalkyl group or a heteroform of one of these groups, and each of the alkyl, alkenyl, alkynyl, acyl, aryl, arylalkyl or groups or heteroforms of one of these groups, each of which is optionally substituted with the substituents described herein as suitable for the corresponding group.

The term "amino" also includes forms wherein R' and R" are linked together to form a 3-8 membered ring which may be saturated, unsaturated or aromatic and which contains 1-3 heteroatoms independently selected from N, O and S as ring members, and which is optionally substituted with the substituents described as suitable for alkyl groups or, if NR'R" is an aromatic group, it is optionally substituted with the substituents described as typical for heteroaryl groups.

Unless indicated otherwise, the compounds of the invention containing amino moieties may include protected derivatives thereof. Suitable protecting groups for amino moieties include acetyl, tert-butoxycarbonyl, benzyloxycarbonyl, and the like.

"Alkylamino" as used herein refers to the radical —NR$_a$R$_b$, where at least one of, or both, R$_a$ and R$_b$ are an alkyl group as described herein. An $C_{1-4}$alkylamino group includes —NHC$_{1-4}$alkyl and —N(C$_{1-4}$alkyl)$_2$; e.g., —NHCH$_3$, —N(CH$_3$)$_2$, —NH(CH$_2$CH$_3$), —N(CH$_2$CH$_3$)$_2$, and the like.

"Aromatic" as used herein refers to a moiety wherein the constituent atoms make up an unsaturated ring system, where all atoms in the ring system are sp$^2$ hybridized and the total number of pi electrons is equal to 4n+2. An aromatic ring may be such that the ring atoms are only carbon atoms or may include carbon and non-carbon atoms (see Heteroaryl).

"Aryl" as used herein refers to a 6-14 membered monocyclic or polycyclic aromatic ring assembly where all the ring atoms are carbon atoms. Typically, the aryl is a 6 membered monocyclic, a 10-12 membered bicyclic or a 14-membered fused tricyclic aromatic ring system. $C_X$aryl and $C_{X-Y}$aryl as used herein describe an aryl group where X and Y indicate the number of carbon atoms in the ring system. $C_{6-14}$aryls include, but are not limited to, phenyl, biphenyl, naphthyl, azulenyl, and anthracenyl.

An aryl may be unsubstituted or substituted by 1-5 (such as one, or two, or three) substituents independently selected from the group consisting of hydroxy, thiol, cyano, nitro, $C_{1-4}$alkyl, $C_{1-4}$alkenyl, $C_{1-4}$alkynyl, $C_{1-4}$alkoxy, thio$C_{1-4}$alkyl, $C_{1-4}$alkenyloxy, $C_{1-4}$alkynyloxy, halogen, $C_{1-4}$alkylcarbonyl, carboxy, $C_{1-4}$alkoxycarbonyl, amino, $C_{1-4}$alkylamino, di-$C_{1-4}$alkylamino, $C_{1-4}$alkylaminocarbonyl, di-$C_{1-4}$alkylaminocarbonyl, $C_{1-4}$alkylcarbonylamino, $C_{1-4}$alkylcarbonyl($C_{1-4}$alkyl)amino, sulfonyl, sulfamoyl, alkylsulfamoyl, $C_{1-4}$alkylaminosulfonyl, aryl, heteroaryl, cycloalkyl and heterocycloalkyl, wherein each of the afore-mentioned substitutents may be further substituted by one or more substituents independently selected from halogen, alkyl, hydroxyl or $C_{1-4}$alkoxy groups.

When an "aryl" is represented along with another radical like "arylalkyl", "aryloxyalkyl", "aryloxycarbonyl", "aryloxy-carbonylalkyl", the aryl portion shall have the same meaning as described in the above-mentioned definition of "aryl".

"Aryloxy" as used herein, refers to the radical —O-aryl, wherein aryl is as defined herein.

"Bicyclic" or "bicyclyl" as used here in refers to a ring assembly of two rings where the two rings are fused together, linked by a single bond or linked by two bridging atoms. The rings may be a carbocyclyl, a heterocyclyl, or a mixture thereof.

"Bridging ring" as used herein refers to a polycyclic ring system where two ring atoms that are common to two rings are not directly bound to each other. One or more rings of the ring system may also comprise heteroatoms as ring atoms. Non-exclusive examples of bridging rings include norbornanyl, 7-oxabicyclo[2.2.1]heptanyl, adamantanyl, and the like.

"Carbamoyl" as used herein refers to the radical —C(O)NR$_a$— where R$_a$ is H, or is an alkyl, alkenyl, alkynyl, acyl, aryl, or arylalkyl group or a heteroform of one of these groups, and each of the alkyl, alkenyl, alkynyl, acyl, aryl, arylalkyl or heteroforms of one of these groups is optionally substituted with the substituents described herein as suitable for the corresponding group.

"Carbamate" as used herein refers to the radical —OC(O)NR$_a$R$_b$ where R$_a$ and R$_b$ are each independently H, or is an alkyl, alkenyl, alkynyl, acyl, aryl, or arylalkyl group or a heteroform of one of these groups, and each of the alkyl, alkenyl, alkynyl, acyl, aryl, arylalkyl or heteroforms of one of these groups is optionally substituted with the substituents described herein as suitable for the corresponding group.

"Cycloalkyl", as used herein, means a radical comprising a non-aromatic, saturated or partially unsaturated, monocyclic, bicyclic, tricyclic, fused, bridged or spiro polycyclic hydrocarbon ring system of 3-20 carbon atoms. $C_X$cycloalkyl and $C_{X-Y}$cycloalkyl are typically used where X and Y indicate the number of carbon atoms in the ring assembly. For example, $C_{3-6}$cycloalkyl includes cyclopropyl, cyclobutyl, cyclopentyl, cyclohexyl, cyclohexenyl, 2,5-cyclohexadienyl.

Exemplary monocyclic cycloalkyl include, but are not limited to, cyclopropyl, cyclobutyl, cyclopentyl, cyclopentenyl, cyclohexyl and cyclohexenyl and the like. Exemplary bicyclic cycloalkyls include bornyl, norbornanyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl. Exemplary tricyclic cycloalkyl groups include, for example, adamantyl.

A cycloalkyl may be unsubstituted or substituted by one, or two, or three, or more substituents independently selected from the group consisting of hydroxyl, thiol, cyano, nitro, oxo, alkylimino, $C_{1-4}$alkyl, $C_{1-4}$alkenyl, $C_{1-4}$alkynyl, $C_{1-4}$alkoxy, $C_{1-4}$thioalkyl, $C_{1-4}$alkenyloxy, $C_{1-4}$alkynyloxy, halogen, $C_{1-4}$alkylcarbonyl, carboxy, $C_{1-4}$alkoxycarbonyl, amino, $C_{1-4}$alkylamino, di-$C_{1-4}$alkylamino, $C_{1-4}$alkylaminocarbonyl, di-$C_{1-4}$alkylaminocarbonyl, $C_{1-4}$alkylcarbonylamino, $C_{1-4}$alkylcarbonyl($C_{1-4}$alkyl)amino, sulfonyl, sulfamoyl, alkylsulfamoyl, $C_{1-4}$alkylaminosulfonyl where each of the afore-mentioned hydrocarbon groups (e.g., alkyl, alkenyl, alkynyl, alkoxy residues) may be further substituted by one or more residues independently selected at each occurrence from halogen, hydroxyl or $C_{1-4}$alkoxy groups.

"Cycloalkylene", as used herein, refers to a divalent radical comprising a cycloalkyl ring assembly as defined herein.

"Cycloalkoxy", as used herein, refers to —O-cycloalkyl, wherein the cycloalkyl is defined herein. Representative examples of $C_{3-12}$cycloalklyoxy include, but are not limited to, monocyclic groups such as cyclopropoxy, cyclobutoxy, cyclopentyloxy, cyclopentenyloxy, cyclohexyloxy and cyclohexenyloxy and the like. Exemplary bicyclic hydrocarbon groups include bornyloxy, indyloxy, hexahydroindyloxy, tetrahydronaphthyloxy, decahydronaphthyloxy, bicyclo[2.1.1]hexyloxy, bicyclo[2.2.1]heptyloxy, bicyclo[2.2.1]heptenyloxy, 6,6-dimethylbicyclo[3.1.1]heptyloxy, 2,6,6-trimethylbicyclo[3.1.1]heptyloxy, bicyclo[2.2.2]octyloxy and the like. Exemplary tricyclic hydrocarbon groups include, for example, adamantyloxy.

"Cyano", as used herein, refers to the radical —CN.

"$EC_{50}$", refers to the molar concentration of an inhibitor or modulator that produces 50% efficacy.

"Fused ring", as used herein, refers to a multi-ring assembly wherein the rings comprising the ring assembly are so linked that the ring atoms that are common to two rings are directly bound to each other. The fused ring assemblies may be saturated, partially saturated, aromatics, carbocyclics, heterocyclics, and the like. Non-exclusive examples of common fused rings include decalin, naphthalene, anthracene, phenanthrene, indole, benzofuran, purine, quinoline, and the like.

"Halo" or "halogen" as used herein refers to fluoro, chloro, bromo, and iodo.

"Haloalkyl", or halo-substituted-alkyl" as used herein, refers to an alkyl as defined herein, which is substituted by one or more halo atoms defined herein. The haloalkyl can be mono-haloalkyl, dihaloalkyl or polyhaloalkyl including perhaloalkyl. A monohaloalkyl can have one iodo, bromo, chloro or fluoro within the alkyl group. Dihaloalky and polyhaloalkyl groups can have two or more of the same halo atoms or a combination of different halo groups within the alkyl. $C_X$haloalkyl and $C_{X-Y}$haloalkyl are typically used where X and Y indicate the number of carbon atoms in the alkyl chain. Non-limiting examples of $C_{1-4}$haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A $C_{1-4}$ perhaloalkyl group refers to a $C_{1-4}$alkyl group having all hydrogen atoms replaced with halo atoms.

"Heteroaryl", as used herein, refers to a 5-14 membered ring assembly (e.g., a 5-7 membered monocycle, an 8-10 membered bicycle, or a 13-14 membered tricyclic ring system) having 1 to 8 heteroatoms selected from N, O and S as ring atoms and the remaining ring atoms are carbon atoms. The nitrogen atoms of such heteroaryl rings can be optionally quaternerized and the sulfur atoms of such heteroaryl rings can be optionally oxidized. $C_X$heteroaryl and $C_{X-Y}$heteroaryl as used herein describe heteroaryls where X and Y indicate the number of ring atoms in the heteroaryl ring. Typical $C_{5-7}$heteroaryl groups include thienyl, furanyl, imidazolyl, pyrazolyl, pyrrolyl, pyrrolinyl, thiazolyl, 1,3,4-thiadiazolyl, isothiazolyl, oxazolyl, oxadiazole isoxazolyl, triazolyl, tetrazolyl, pyridyl, pyridazinyl, pyrazinyl, pyrazinyl, pyrimidinyl, and the like. Bicyclic or tricyclic $C_{8-14}$heteroaryls include, but are not limited to, those derived from benzo[b]furan, benzo[b]thiophene, benzimidazole, imidazo[4,5-c]pyridine, quinazoline, thieno[2,3-c]pyridine, thieno[3,2-b]pyridine, thieno[2,3-b]pyridine, quinazolinyl, pteridinyl, indolizine, imidazo[1,2a]pyridine, quinoline, quinolinyl, isoquinoline, phthalazine, quinoxaline, naphthyridine, naphthyridinyl, quinolizine, indolyl, indole, isoindole, indazole, indoline, benzoxazole, benzopyrazole, benzothiazole, imidazo[1,5-a]pyridine, pyrazolo[1,5-a]pyridine, imidazo[1,2-a]pyrimidine, imidazo[1,2-c]pyrimidine, imidazo[1,5-a]pyrimidine, imidazo[1,5-c]pyrimidine, pyrrolo[2,3-b]pyridine, pyrrolo[2,3-c]pyridine, pyrrolo[3,2-c]pyridine, pyrrolo[3,2-b]pyridine, pyrrolo[2,3-d]pyrimidine, pyrrolo[3,2-d]pyrimidine, pyrrolo[2,3-b]pyrazine, pyrazolo[1,5-a]pyridine, pyrrolo[1,2-b]pyridazine, pyrrolo[1,2-c]pyrimidine, pyrrolo[1,2-a]pyrimidine, pyrrolo[1,2-a]pyrazine, triazo[1,5-a]pyridine, pteridine, purine, purinyl, carbazole, acridine, phenazine, phenothiazene, phenoxazine, 1,2-dihydropyrrolo[3,2,1-hi]indole, indolizine, pyrido[1,2-a]indole and 2(1H)-pyridinone.

A heteroaryl may be unsubstituted or substituted with one or more substituents independently selected from hydroxyl, thiol, cyano, nitro, $C_{1-4}$alkyl, $C_{1-4}$alkenyl, $C_{1-4}$alkynyl, $C_{1-4}$alkoxy, thio$C_{1-4}$alkyl, $C_{1-4}$alkenyloxy, $C_{1-4}$alkynyloxy, halogen, $C_{1-4}$alkylcarbonyl, carboxy, $C_{1-4}$alkoxycarbonyl, amino, $C_{1-4}$alkylamino, di-$C_{1-4}$alkylamino, $C_{1-4}$alkylaminocarbonyl, di-$C_{1-4}$alkylaminocarbonyl, $C_{1-4}$alkylcarbonylamino, $C_{1-4}$alkylcarbonyl($C_{1-4}$alkyl)amino, sulfonyl, sulfamoyl, alkylsulfamoyl, $C_{1-4}$alkylaminosulfonyl where each of the afore-mentioned hydrocarbon groups (e.g., alkyl, alkenyl, alkynyl, alkoxy residues) may be further substituted by one or more residues independently selected at each occurrence from halogen, hydroxyl or $C_{1-4}$alkoxy groups.

When a heteroaryl is represented along with another radical like "heteroaryloxy", "heteroaryloxyalkyl", "heteroaryloxycarbonyl", the heteroaryl portion shall have the same meaning as described in the above-mentioned definition of "heteroaryl".

"Heteroaryloxy", as used herein, refers to an —O-heteroaryl group, wherein the heteroaryl is as defined in this application.

"Heteroatom", as used herein, refers to an atom that is not a carbon atom. Particular examples of heteroatoms include, but are not limited to nitrogen, oxygen, and sulfur.

"Heterocycloalkyl", as used herein, refers to a 4-20 membered, non-aromatic, saturated or partially unsaturated, monocyclic or polycyclic ring system, comprising 1-8 heteroatoms as ring atoms and that the remaining ring atoms are carbon atoms. The heteroatoms are selected from N, O, and S, preferably O and N. The nitrogen atoms of the heterocycloalkyl can be optionally quaternerized and the sulfur atoms of the heterocycloalkyl can be optionally oxidized. The heterocycloalkyl can include fused or bridged rings as well as spirocyclic rings. $C_x$heterocycloalkyl and $C_{x-y}$heterocycloalkyl are typically used where X and Y indicate the number of ring atoms in the ring. Typically, the heterocycloalkyl is 4-8-membered monocyclic ring containing 1 to 3 heteroatoms, a 7 to 12-membered bicyclic ring system containing 1-5 heteroatoms, or a 10-15-membered tricyclic ring system containing 1 to 7 heteroatoms. Examples of $C_{4-6}$heterocycloalkyl include azetidinyl, tetrahydrofuran (THF), dihydrofuran, 1,4-dioxane, morpholine, 1,4-dithiane, piperazine, piperidine, 1,3-dioxolane, imidazolidine, imidazoline, pyrazolidinyl, pyrroline, pyrrolidine, tetrahydropyran, dihydropyran, oxathiolane, dithiolane, 1,3-dioxane, 1,3-dithiane, oxathiane, thiomorpholine, and the like A heterocycloalkyl may be unsubstituted or substituted with 1-5 substituents (such as one, or two, or three) each independently selected from hydroxyl, thiol, cyano, nitro, oxo, alkylimino, $C_{1-4}$alkyl, $C_{1-4}$alkenyl, $C_{1-4}$alkynyl, $C_{1-4}$alkoxy, $C_{1-4}$thioalkyl, $C_{1-4}$alkenyloxy, $C_{1-4}$alkynyloxy, halogen, $C_{1-4}$alkylcarbonyl, carboxy, $C_{1-4}$alkoxycarbonyl, amino, $C_{1-4}$alkylamino, di-$C_{1-4}$alkylamino, $C_{1-4}$alkylaminocarbonyl, di-$C_{1-4}$alkylaminocarbonyl, $C_{1-4}$alkylcarbonylamino, $C_{1-4}$alkylcarbonyl($C_{1-4}$alkyl)amino, sulfonyl, sulfamoyl, alkylsulfamoyl, $C_{1-4}$alkylaminosulfonyl where each of the afore-mentioned hydrocarbon groups (e.g., alkyl, alkenyl, alkynyl, alkoxy residues) may be further substituted by one or more residues independently selected at each occurrence from halogen, hydroxyl or $C_{1-4}$alkoxy groups. When a heterocycloalkyl forms part of other groups like "heterocycloalkyl-alkyl", "heterocycloalkoxy", "heterocycloalkyl-aryl", the heteroaryl portion shall have the same meaning as described in the above-mentioned definition of "heteroaryl"

"Heterocycloalkylene", as used herein, refers to a cycloalkylene, as defined in this application, provided that one or more of the ring member carbon atoms is replaced by a heteroatom.

"Heterocycloalkyl fused to a phenyl" as used herein, refers to a bicyclic fused ring system that one of the ring is heterocycloalkyl as defined above and the other ring is a phenyl. A heterocycloalkyl fused to a phenyl includes but are not limited to benzo[b][1,4]oxazinyl, oxo-benzo[b][1,4]oxazinyl, tetrahydroquinoxalinyl, tetrahydroquinolinyl, indolinyl, benzo[d]imidazolyl, and the like.

"Heterocyclyl", "heterocycle" or "heterocyclo", as used herein, refers to a 3-20 membered, monocyclic or polycyclic ring system containing at least one heteroatom moiety selected from the group consisting of N, O, SO, $SO_2$, (C=O), and S, and preferably N, O, S, optionally containing one to four additional heteroatoms in each ring. $C_x$heterocyclyl and $C_{x-y}$heterocyclyl are typically used where X and Y indicate the number of ring atoms in the ring system. Unless otherwise specified, a heterocyclyl may be saturated, partially unsaturated, aromatic or partially aromatic.

Hydroxy, as used herein, refers to the radical —OH.

"Hydroxyalkyl" or "hydroxyl-substituted alkyl" as used herein, refers to an alkyl as defined herein, having one or more of the available hydrogen of the alkyl replaced by a hydroxyl group. For example, a hydroxy$C_{1-4}$alkyl includes, but are not limited to, —$CH_2CH_2OH$, —$CH(OH)CH_2CH_2OH$, —$CH(OH)CH_2CH(OH)CH_3$.

"Nitro", as used herein, refers to the radical —$NO_2$.

"Oxo", as used herein, refers to the divalent radical =O

"Protected derivatives" means derivatives of inhibitors in which a reactive site or sites are blocked with protecting groups. Protected derivatives are useful in the preparation of inhibitors or in themselves may be active as inhibitors. Examples of protected group includes, but are not limited to, acetyl, tetrahydropyran, methoxymethyl ether, β-methoxyethoxymethyl ether, ρ-methoxybenzyl, methylthiomethyl ether, pivaloyl, silyl ether, carbobenzyloxy, benzyl, tert-butoxycarbonyl, ρ-methoxyphenyl, 9-fluorenylmethyloxycarbonyl, acetals, ketals, acylals, dithianes, methylesters, benzyl esters, tert-butyl esters, and silyl esters. A comprehensive list of suitable protecting groups can be found in T. W. Greene, *Protecting Groups in Organic Synthesis*, 3rd edition, John Wiley & Sons, Inc. 1999.

"Unsubstituted or substituted" or "optionally substituted" as used herein indicate the substituent bound on the available valance of a named group or radical. "Unsubstituted" as used herein indicates that the named group or radical will have no further non-hydrogen substituents. "Substituted" or "optionally substituted" as used herein indicates that at least one of the available hydrogen atoms of named group or radical has been (or may be) replaced by a non-hydrogen substituent.

"Substituted terminally" as used herein referred to a substituent replacing a hydrogen at a terminal position of the parent molecule. For example $C_{1-4}$alkyl substituted terminally by an amino means —$C_{1-4}$alkylene-amino, which includes —$(CH_2)$—$NH_2$, —$(CH_2)_2$—$NH_2$, —$(CH_2)_3$—$NH_2$, —$(CH_2)CH_2(CH_2$—$NH_2)$, —$(CH_2)_4$—$NH_2$, —$C(CH_2)(CH_2CH_2$—$NH_2)$—$C(CH_3)_2(CH_2$—$NH_2)$, and the like.

Unless otherwise specified, examples of substituents may include, but are not limited to, halo, nitro, cyano, thio, oxy, hydroxy, carbonyloxy, $C_{1-6}$alkoxy, $C_{6-10}$aryloxy, hetero $C_{5-10}$aryloxy, carbonyl, oxycarbonyl, aminocarbonyl, amino, $C_{1-6}$alkylamino, sulfonamido, imino, sulfonyl, sulfinyl, $C_{1-6}$alkyl, $C_{1-6}$haloalkyl, hydroxy$C_{1-6}$alkyl, carbonyl$C_{1-6}$alkyl, thiocarbonyl$C_{1-10}$alkyl, sulfonyl$C_{1-6}$alkyl, sulfinyl $C_{1-6}$alkyl, $C_{1-10}$azaalkyl, imino$C_{1-6}$alkyl, $C_{3-12}$cycloalkyl $C_{1-6}$alkyl, $C_{4-15}$heterocycloalkyl$C_{1-6}$alkyl, $C_{6-10}$aryl$C_{1-6}$alkyl, $C_{5-10}$heteroaryl$C_{1-6}$alkyl, $C_{10-12}$bicycloaryl$C_{1-6}$alkyl, $C_{9-12}$heterobicycloaryl$C_{1-6}$alkyl, $C_{3-12}$cycloalkyl, $C_{4-12}$heterocycloalkyl, $C_{9-12}$bicycloalkyl, $C_{3-12}$heterobicycloalkyl, $C_{4-12}$aryl, hetero$C_{1-10}$aryl, $C_{9-12}$bicycloaryl and $C_{4-12}$heterobicycloaryl.

"Sulfamoyl" as used herein refers to the radical —$S(O)_2$ $NR_aR_b$ where $R_a$ and $R_b$ are independently H, or is an alkyl, alkenyl, alkynyl, acyl, aryl, aryl, cycloalkyl, arylalkyl cycloalkylalkyl group or a heteroform of one of these groups, and each of the alkyl, alkenyl, alkynyl, acyl, aryl, arylalkyl groups or heteroforms of one of these groups, is optionally substituted with the substituents described herein as suitable for the corresponding group.

"Sulfanyl" as used herein, means the radical —S—.

"Sulfinyl", as used herein, means the radical —S(O)—. It is noted that the term "sulfinyl" when referring to a monovalent substituent can alternatively refer to a substituted sulfinyl group, —S(=O)R, where R is hydrogen or a non-hydrogen substituent on the sulfur atom forming different sulfinyl groups including sulfinic acids, sulfinamides, sulfinyl esters, and sulfoxides.

"Sulfonyl", as used herein, means the radical —$S(O)_2$—. It is noted that the term "sulfonyl" when referring to a monovalent substituent can alternatively refer to a substituted sulfonyl group, —$S(=O)_2R$, where R is hydrogen or a non-hydrogen substituent on the sulfur atom forming different sulfonyl groups including sulfonic acids, sulfonamides, sulfonate esters, and sulfones.

"Thiocarbonyl", as used herein, refers to the radical —C(=S)—. It is noted that the term thiocarbonyl when referring to a monovalent substituent can alternatively refer to a substituted thiocarbonyl group, —C(=S)R, where R is hydrogen or a non-hydrogen substituent on the carbon atom forming different thiocarbonyl groups including thioacids, thioamides, thioesters, and thioketones.

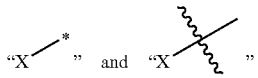

are symbols denoting the point of attachment of X, to other part of the molecule.

Any definition herein may be used in combination with any other definition to describe a composite structural group. By convention, the trailing element of any such definition is that which attaches to the parent moiety. For example, the composite group alkoxyalkyl would represent an alkoxy group attached to the parent molecule through an alkyl group.

It is noted in regard to all of the definitions provided herein that the definitions should be interpreted as being open ended in the sense that further substituents beyond those specified may be included. Hence, a $C_1$ alkyl indicates that there is one carbon atom but does not indicate what are the substituents on the carbon atom. Hence, a $C_1$ alkyl comprises methyl (i.e., —$CH_3$) as well as —$CR_aR_bR_c$ where $R_a$, $R_b$, and $R_c$ may each independently be hydrogen or any other substituent where the atom attached to the carbon is not a hydrogen atom. Hence, —$CF_3$, —$CH_2OH$ and —$CH_2CN$, for example, are all $C_1$alkyls.

Description of the Preferred Embodiments

The invention provides a novel class of compounds, pharmaceutical compositions comprising such compounds and methods of using such compounds to treat or prevent diseases or disorders associated with a parasite. In particular, the compounds can be used to treat leishmaniasis, Human Trypanosomiasis and/or Chagas disease. The compounds of the invention are effective in inhibiting, ameliorating, or eradicating the pathology and/or symptomology of the parasite.

The invention therefore provides a compound of the formula (I):

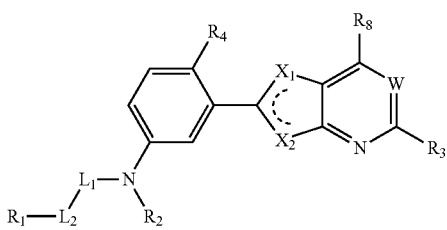

or a pharmaceutical acceptable salt, tautomer or stereoisomer thereof, wherein $X_1$ is N or O, or $NR_5$;
$X_2$ is N or $NR_7$, provided that one of $X_1$ and $X_2$ is N;
W is $CR_6$ or N;
$L_1$ is a bond, —C(O)— or —S(O)$_2$—;
$L_2$ is selected from a bond, —$CR_{9a}R_{9b}$—, —$NR_{10}$—, and —O—, wherein $R_{9a}$ is hydrogen, halo or $C_{1-4}$alkyl, $R_{9b}$ is selected from hydrogen, halo, hydroxyl, $C_{1-4}$alkyl, and $C_{1-4}$alkoxy; and $R_{10}$ is hydrogen or $C_{1-4}$alkyl;

$R_1$ is selected from hydrogen, $C_{1-6}$alkyl, $C_{1-4}$alkoxy, $C_{6-10}$aryl, $C_{5-10}$heteroaryl, $C_{3-7}$cycloalkyl, $C_{5-6}$heterocycloalkyl, and $C_{9-10}$heterocyclyl, wherein the $C_{1-6}$alkyl or $C_{1-4}$alkoxy is unsubstituted or substituted with 1 to 2 substituents independently selected from halo, hydroxy, $C_{1-4}$alkoxy, $C_{5-6}$aryloxy, hydroxycarbonyl, $C_{1-4}$alkoxycarbonyl, amino, $C_{1-4}$alkyamino, $C_{1-4}$alkoxycarbonylamino, $C_{5-6}$aryl, and $C_{5-6}$heterocycloalkyl; and the $C_{6-10}$aryl and $C_{5-10}$heteroaryl, $C_{3-7}$cycloalkyl, $C_{5-6}$heterocycloalkyl or $C_{9-10}$heterocyclyl is unsubstituted or substituted with 1 to 3 substituents independently selected from halo, cyano, hydroxyl, oxo, $C_{1-4}$alkyl, benzyl, halo$C_{1-4}$alkyl, $C_{1-4}$alkoxy$C_{1-4}$alkyl, $C_{1-4}$alkylamino$C_{1-4}$alkyl, $C_{1-4}$alkoxy, halo $C_{1-4}$alkoxy, amino, $C_{1-4}$alkylamino, $C_{1-4}$alkoxycarbonyl, $C_{1-4}$alkylthio, $C_{1-4}$alkylsulfonyl, $C_{5-6}$heteroaryl, halo$C_{5-6}$heteroaryl, $C_{3-6}$cycloalkyl, and $C_{5-6}$heterocycloalkyl; or —N($R_2$)-$L_1$-$L_2$-$R_1$ together forms a nitro group;

$R_2$ is hydrogen, $C_{1-4}$alkyl or —C(O)$C_{5-6}$heteroaryl;
$R_3$ is hydrogen, halo or $C_{1-4}$alkyl;
$R_4$ is selected from hydrogen, halo, $C_{1-4}$alkyl, halo$C_{1-4}$alkyl, $C_{1-4}$alkylsulfonyl, $C_{5-6}$heteroaryl, and $C_{5-6}$heterocycloalkyl;
$R_5$ is selected from hydrogen, $C_{1-4}$alkyl, —C(O)OC$_{1-4}$alkyl, wherein the $C_{1-4}$alkyl portion of $C_{1-4}$alkyl or —C(O)OC$_{1-4}$alkyl is unsubstituted or substituted by amino, $C_{1-4}$alkylamino, or $C_{5-6}$heterocycloalkyl;
$R_6$ is selected from halo, cyano, $C_{1-4}$alkyl, $C_{1-4}$alkenyl, $C_{1-4}$alkoxy, $C_{1-4}$alkylsulfonyl, $C_{3-6}$cycloalkylsulfonyl, $C_{1-4}$alkylphosphinyl oxide, $C_{1-4}$alkylcarbonylamino, phenyl, $C_{5-6}$heteroaryl, $C_{5-6}$heteraryl, $C_{4-6}$heterocycloalkyl, and $C_{6-10}$heterocyclyl, wherein the $C_{1-6}$alkyl, $C_{1-4}$alkenyl or $C_{1-4}$alkoxy of $R_6$ is unsubstituted or substituted by 1 to 2 substituents independently selected from halo, amino, $C_{1-4}$alkylamino, and hydroxyl-substituted $C_{1-4}$alkylamino;

the pheny or $C_{5-6}$heteroaryl of $R_6$ is unsubstituted or substituted by 1 to 2 substituents independently selected from halo, cyano, $C_{1-4}$alkyl, halo$C_{1-4}$alkyl, $C_{1-4}$alkylamino$C_{1-4}$alkyl, amino$C_{1-4}$alkyl, $C_{4-6}$heterocycloalkyC$_{1-4}$alkyl, $C_{1-4}$alkylsilanylC$_{1-4}$alkoxyC$_{1-4}$alkyl, $C_{1-4}$alkoxy, halo$C_{1-4}$alkoxy, $C_{1-4}$alkoxyC$_{1-4}$alkoxy, amino$C_{1-4}$alkoxy, phenyl $C_{1-4}$alkoxy, $C_{5-6}$heteroarylC$_{1-4}$alkoxy, $C_{3-6}$cycloalkyC$_{1-4}$alkoxy, $C_{3-6}$heterocycloalkyC$_{1-4}$alkoxy, $C_{1-4}$alkylcarbonyl, aminocarbonyl, $C_{1-4}$alkylaminocarbonyl, $C_{1-4}$alkoxycarbonyl, amino, $C_{1-4}$alkylamino, $C_{4-6}$heterocycloalkyC$_{1-4}$alkylamino, $C_{4-6}$heterocycloalkyC$_{1-4}$alkylamino, —NHC(O)R$_{14}$ S(O)$_2$R$_{15}$, phenyl, $C_{5-6}$heteraryl, $C_{5-6}$heterocycloalkyl, and $C_{9-10}$heterocyclyl;

the $C_{3-6}$heterocycloalkyl or $C_{6-10}$heterocyclyl of $R_6$ is unsubstituted or substituted by 1 to 2 substituents independently selected from $C_{1-4}$alkyl, oxo, and $C_{1-4}$alkoxycarbonyl, wherein $R_{14}$ is selected from $C_{1-4}$alkyl, amino$C_{1-4}$alkyl, amino, $C_{1-4}$alkylamino, cyclopropylamino, $C_{1-4}$alkoxy, $C_{1-4}$alkylsulfonyl, and $C_{1-4}$alkylaminosulfonyl;

$R_{15}$ is selected from $C_{1-4}$alkyl, amino, $C_{3-6}$cycloalkyl, and $C_{5-6}$heterocycloalkyl; and the phenyl, $C_{5-6}$heteraryl, $C_{5-6}$heterocycloalkyl or $C_{9-10}$heterocyclyl substituent of the phenyl or $C_{5-6}$heteroaryl of $R_6$ is unsubstituted or substituted by 1 to 3 substituents independently selected from $C_{1-4}$alkyl and oxo;

$R_7$ is selected from hydrogen, $C_{1-4}$alkyl and —C(O) $C_{5-6}$heteroaryl; and $R_8$ is hydrogen or halo.

In another embodiment of the above embodiment of the compounds of the invention, in one variation, $X_1$ is N. In another variation, $X_2$ is N. In still another variation, $X_2$ is $NR_7$.

In another embodiment of the above embodiment of the compounds of the invention, W is N.

In another embodiment of the above embodiments and variations of the compound of the invention, the compound is of Formula ia:

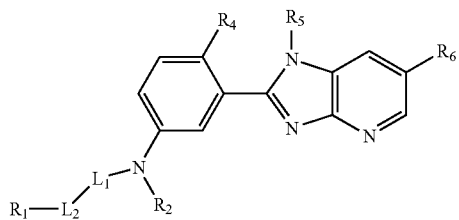

ia or a pharmaceutically acceptable salt, tautomer, or stereoisomer thereof; wherein the variables are as described in the first embodiments above.

In another embodiment of the above embodiments and variations of the compounds of the invention, the compound is of Formula ib:

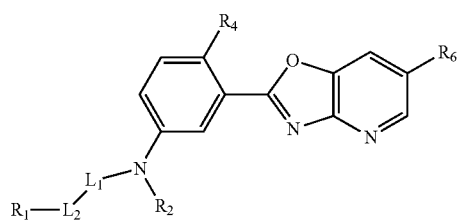

Ib or a pharmaceutically acceptable salt, tautomer, or stereoisomer thereof; wherein the variables are as described in the first embodiments above.

In another embodiment of the above embodiments and variations of the compounds of the invention, L is —C(O)— or —S(O)$_2$—. In one variation, $L_1$ is —C(O)—. In one variation, $L_1$ is —S(O)$_2$—.

In another embodiment of the above embodiments and variations of the compounds of the invention, $L_1$ is —C(O)— or —S(O)$_2$—. In one variation, $L_1$ is —C(O)—. In another variation, $L_1$ is —S(O)$_2$—.

In another embodiment of the above embodiments and variations of the compounds of the invention, $L_2$ is selected from a bond, —CR$_{9a}$R$_{9b}$—, —NR$_{10}$—, and —O—, wherein R$_{9a}$ is selected from hydrogen, fluoro, hydroxyl, methyl, isopropyl and methoxy, R$_{9b}$ is selected from hydrogen, fluoro and methyl, and R$_{10}$ is selected from hydrogen, methyl, ethyl, and isopropyl. In one variation, $L_2$ is a bond, —CH$_2$—, —NH—, or O. In another variation, $L_2$ is a bond. In still another variation, $L_2$ is —CH$_2$—.

In another embodiment of the above embodiments and variations of the compounds of the invention, in one variation, $R_1$ is selected from hydrogen, $C_{1-6}$alkyl, $C_{1-6}$alkoxy, $C_{6-10}$aryl, $C_{5-10}$heteroaryl, $C_{3-7}$cycloalkyl, $C_{5-6}$heterocycloalkyl, and $C_{9-10}$heterocyclyl, wherein the $C_{1-6}$alkyl or $C_{1-6}$alkoxy is unsubstituted or substituted with 1 to 2 substituents independently selected from —OH, fluoro, —CF$_3$, OCH$_3$, phenoxy. —C(O)OH, —NH$_2$, —N(CH$_3$)$_2$, —N(CH$_2$CH$_3$)$_2$, —N(CH(CH$_3$)$_2$)$_2$, —NHC(O)OC(CH$_3$)$_3$, phenyl, and morpholinyl;

the $C_{6-10}$aryl, $C_{5-10}$heteroaryl, $C_{3-7}$cycloalkyl, $C_{5-6}$heterocycloalkyl, or $C_{9-10}$heterocyclyl is unsubstituted or substituted by 1 to 3 substituents independently selected from fluoro, chloro, cyano, oxo, hydroxy, methyl, ethyl, isopropy, t-butyl, trifluoromethyl, methoxymethyl, dimethylaminomethyl, benzyl, methoxy, ethoxy, trifluoromethoxy, t-butoxycarbony dimethylamino, methylthio, methylsulfonyl, fluorophenyl, triazolyl, pyrimidinyl, cyclopropyl, piperidinyl, and morpholinyl.

In another variation, $R_1$ is $C_{1-6}$alkyl or $C_{1-4}$alkoxy, each of which is unsubstituted or substituted with 1 to 2 substituents independently selected from halo, hydroxy, $C_{1-4}$alkoxy, $C_{5-6}$aryloxy, hydroxycarbonyl, $C_{1-4}$alkoxycarbonyl, amino, $C_{1-4}$alkyamino, $C_{1-4}$alkoxycarbonylamino, $C_{5-6}$aryl, and $C_{5-6}$heterocycloalkyl.

In another variation, $R_1$ is selected from methyl, ethyl, propyl, isopropyl, isobutyl, t-butyl, hexyl, and methoxy, each of which is unsubstituted or substituted with 1 to 2 substituents independently selected from —OH, fluoro, —CF$_3$, OCH$_3$, phenoxy. —C(O)OH, —NH$_2$, —N(CH$_3$)$_2$, —N(CH$_2$CH$_3$)$_2$, —N(CH(CH$_3$)$_2$)$_2$, —NHC(O)OC(CH$_3$)$_3$, phenyl, and morpholinyl.

In still another variation, $R_1$ is selected from methyl, ethyl, propyl, isopropyl, isobutyl, methoxy, —(CH$_2$)$_{1-2}$OH, —(CH$_2$)$_2$C(O)OH, —(CH$_2$)$_{1-2}$NH$_2$, —C(CH$_3$)$_2$NH$_2$, —(CH$_2$)$_{2-3}$—N(CH$_3$)$_2$, —(CH$_2$)$_6$N(CH$_3$)$_2$, —(CH$_2$)$_6$N(CH$_2$CH$_3$)$_2$, —(CH$_2$)$_2$N(CH(CH$_3$)$_2$)$_2$, —C(CH$_3$)$_2$NHC(O)OC(CH$_3$)$_3$, —CH$_2$NHC(O)OC(CH$_3$)$_3$, —CH$_2$-phenoxy, —CH$_2$C($^2$H)$_3$, —(CH$_2$)$_2$F, —CH$_2$CF$_3$, —CH$_2$-phenyl, and —(CH$_2$)$_2$OCH$_3$.

In still another variation, $R_1$ is selected from $C_{6-10}$aryl, $C_{5-10}$heteroaryl, $C_{3-7}$cycloalkyl, $C_{5-6}$heterocycloalkyl, and $C_{9-10}$heterocyclyl, each of which is unsubstituted or substituted by 1 to 3 substituents independently selected from fluoro, chloro, cyano, oxo, hydroxy, methyl, ethyl, isopropy, t-butyl, trifluoromethyl, methoxymethyl, dimethylaminomethyl, benzyl, methoxy, ethoxy, trifluoromethoxy, t-butoxycarbony dimethylamino, methylthio, methylsulfonyl, fluorophenyl, triazolyl, pyrimidinyl, cyclopropyl, piperidinyl, and morpholinyl.

In still another variation, $R_1$ is selected from phenyl, pyrrolyl, pyrazolyl, imidazolyl, triazolyl, furanyl, oxazolyl, isoxazolyl, oxadiazolyl, thiophenyl, thiazolyl, isothiazolyl, pyridinyl, pyridazinyl, pyrazinyl, pyrimidinyl, pyrazolo[1,5-a]pyridinyl, cyclopropyl, cyclobutyl, cyclopentyl, cyclohexyl, bicyclo[2.2.1]heptan-2-yl, azetidinyl, oxetanyl, pyrrolidinyl, imidazolidinyl, tetrahydrofuranyl, piperidinyl, piperazinyl, tetrahydropyranyl, morpholinyl, azabicyclo[3.1.0]hexanyl, tetrahydroisoquinolinyl, dihydrobenzofuranyl, chromanyl, tetrahydroisoquinolinyl, tetrahydro-naphthyridinyl, and dihydrobenzofuranyl, each of which is unsubstituted or substituted by 1-3 substituents independently selected from fluoro, chloro, cyano, oxo, hydroxy, methyl, ethyl, isopropy, t-butyl, trifluoromethyl, methoxymethyl dimethylaminomethyl, benzyl, methoxy, ethoxy, trifluoromethoxy, t-butoxycarbony, dimethylamino, methylthio, methylsulfonyl, fluorophenyl, triazolyl, pyrimidinyl, cyclopropyl, piperidinyl, and morpholinyl.

In still another variation, $R_1$ is selected from —CH$_2$-4-fluorophenyl, —OCH$_2$CH$_3$, —O(CH$_2$)$_2$OCH$_3$, —OCH(CH$_3$)$_2$, —O-cyclopentyl, —N(CH$_3$)(OCH$_3$), —N(CH(CH$_3$)$_2$)$_2$, cyclopentoxy, 3-chlorophenyl, 2-chlorophenyl, 2,4dimethoxyphenyl, 4-trifluoromethyphenyl, pyrrol-2-yl, furan-2-yl, 5-fluorofuran-2-yl, 5-chlorofuran-2-yl, 5-cyano-furan-2-yl, 5-methylfuranyl, 5-dimethylaminomethyl-furan-2-yl, 4-methylthiophen-2-yl, isothiazol-5-yl, thiazol-4-yl, 5-t-butyloxadiazol-2-yl, pyrazinyl, cyclopentyl, pyrrolidinyl, 3,3-difluoropyrrolidinyl, and 2-oxoindolin-6-yl.

In yet another variation, $R_1$ is selected from isopropoxy, furan-2-yl, pyrazin-2-yl, cyclopentyl, pyrrolidinyl, and 3,3-difluoro-pyrrolidinyl. In yet another variation, $R_1$ is selected from isopropoxy.

In yet another variation, $R_1$ is selected from pyrrolidinyl, unsubstituted or substituted with 1-2 substituents independently selected halo, cyano, $C_{1-4}$alkyl, $C_{1-4}$alkoxy, amino, $C_{1-4}$alkylamino, and $C_{1-4}$alkoxycarbonyl. In another variation, $R_1$ is unsubstituted pyrrolidinyl.

In still another variation, $R_1$ is selected from furan-2-yl, unsubstituted or substituted with 1-2 substituents independently selected halo, cyano, $C_{1-4}$alkyl, $C_{1-4}$alkoxy, amino, $C_{1-4}$alkylamino, and $C_{1-4}$alkoxycarbonyl. In still another variation, $R_1$ is selected from furan-2-yl.

In another embodiment of the above embodiments and variations of the compounds of the invention, in one variation, $R_2$ is hydrogen, methyl, or —C(O)-furan-2-yl. In a particular variation, $R_2$ is hydrogen.

In another embodiment of the above embodiments and variations of the compounds of the invention, in one variation, $R_3$ is hydrogen, halo or methyl. In a preferred variation, $R_3$ is hydrogen.

In another embodiment of the above embodiments and variations of the compounds of the invention, in one variation, $R_4$ is selected from hydrogen, fluoro, chloro, methyl, trifluoromethyl, methylsulfonyl, pyridin3-yl, and morpholinyl. In still another variation, $R_4$ is methyl or trifluoromethyl. In another variation, $R_4$ is halo. In a particular variation, $R_4$ is hydrogen.

In another embodiment of the above embodiments and variations of the compounds of the invention, in one variation, $R_5$ is selected from hydrogen, —CH$_2$O(CH$_3$), —(CH$_2$)$_2$-morpholinyl, —(CH$_2$)$_2$N(CH$_3$)$_2$, —C(O)OCH(CH$_3$)$_2$, and —C(O)O(CH$_3$). In another variation, $R_5$ is —C(O)OCH(CH$_3$)$_2$. In one particular variation, $R_5$ is hydrogen.

In another embodiment of the above embodiments and variations of the compounds of the invention, in one variation, $R_7$ is selected from hydrogen, methyl, ethyl, isopropyl, methoxymethyl, and —C(O)-furan-2-yl. In another variation, $R_7$ is hydrogen or $C_{1-4}$alkyl. In a particular variation, $R_7$ is hydrogen.

In another embodiment of the above embodiments and variations of the compounds of the invention, in one variation, $R_8$ is hydrogen or halo. In a particular variation, $R_8$ is hydrogen.

In another embodiment of the above embodiments and variations of the compounds of the invention, in one variation, $R_6$ is selected from halo, cyano, $C_{1-4}$alkyl, $C_{1-4}$alkenyl, $C_{1-4}$alkoxy, $C_{1-4}$alkylsulfonyl, $C_{3-6}$cycloalkylsulfonyl, $C_{1-4}$alkylphosphinyl oxide, $C_{1-4}$alkylcarbonylamino, phenyl, $C_{5-6}$heteroaryl, $C_{5-6}$heteraryl, $C_{4-6}$heterocycloalkyl, $C_{6-10}$heterocyclyl, wherein
  the $C_{1-6}$alkyl, $C_{1-4}$alkenyl or $C_{1-4}$alkoxy of $R_6$ is unsubstituted or substituted by 1 to 2 substituents independently selected from halo, —NH$_2$, —NH(CH$_3$), —N(CH$_3$)$_2$, —NH(CH$_2$CH$_3$), N(CH$_2$CH$_3$)$_2$, —NHCH$_2$CH(OH) (CH$_3$), —NHCH(CH$_3$)CH$_2$(OH);
  the phenyl or $C_{5-6}$heteroaryl of $R_6$ is unsubstituted or substituted by 1 to 2 substituents independently selected from fluoro, chloro, cyano, methyl, trifluoromethyl, —(CH$_2$)—N(CH$_3$)$_2$, —(CH$_2$)$_2$—N(CH$_3$)$_2$, —CH(CH$_3$)$_2$CH$_2$NH$_2$, —CH$_2$O(CH$_2$)$_2$Si(CH$_3$)$_3$, —(CH$_2$)$_{1-2}$-morpholinyl, methoxy, ethoxy, trifluoromethoxy, —O(CH$_2$)$_2$OCH$_3$, —O(CH$_2$)$_2$N(CH$_3$)$_2$, —OCH$_2$-phenyl, —OCH$_2$-5-methylisoxazol-3-yl, —O(CH$_2$)$_2$-1H-imidazol-1-yl, —O(CH$_2$)$_2$-1H-pyrazol-1-yl, —OCH$_2$-cyclopropyl, —OCH$_2$-oxiran-2-yl, —O(CH$_2$)$_2$-pyrrolidin-1-yl, —OCH$_2$-tetrahydro-2H-pyran-4-yl, —O(CH$_2$)$_2$-piperidin-1-yl, —O(CH$_2$)$_2$-4-methylpiperazin-1-yl, —O(CH$_2$)$_{2-3}$-morpholinyl, —OCH$_2$CH(OH)CH$_2$-morpholinyl, —C(O)CH$_3$, —C(O)NH$_2$, —C(O)NHCH$_3$, —C(O)OCH$_3$, —NH$_2$, —NHCH$_3$, —N(CH$_3$)$_2$, —NH(CH$_2$)$_2$-morpholinyl, —NHC(O)CH$_3$, —NHC(O)CH(CH$_3$)$_2$, —NHC(O)CH$_2$CH(CH$_3$)$_2$, —NHC(O)CH$_2$NH$_2$, —NHC(O)(CH$_2$)$_2$NH$_2$, —NHC(O)NH$_2$, —NHC(O)NHCH$_3$, —NHC(O)NH-cyclopropyl, —NHC(O)OCH$_3$, —NHC(O)OCH(CH$_3$)$_2$, —NHC(O)OC(CH$_3$)$_3$, —N(CH$_3$)C(O)OC(CH$_3$)$_3$, —NHS(O)$_2$CH$_3$, —NHS(O)$_2$CH(CH$_3$)$_2$, —NHS(O)$_2$NH(CH$_3$), —S(O)$_2$CH$_3$, —S(O)$_2$NH$_2$, —S(O)$_2$-pyrrolidinyl, phenyl, pyrazolyl, pyrrolidinyl, piperidinyl, piperazinyl, $C_{1-4}$alkylpiperazinyl, pyrrolidinyl, piperidinyl, morpholinyl, $C_{1-4}$alkyldihydro-2H-benzo[b][1,4]oxazinyl, and dioxoimidazolidinyl; and
the $C_{3-6}$heterocycloalkyl or $C_{6-9}$heterocyclyl of $R_6$ is unsubstituted or substituted by 1 to 2 substituents independently selected from methyl and —C(O)OC(CH$_3$)$_3$.

In one variation, $R_6$ is selected from phenyl, $C_{5-6}$heteroaryl, the $C_{3-6}$heterocycloalkyl and $C_{6-10}$heterocyclyl, wherein
  the phenyl or $C_{5-6}$heteroaryl is selected from phenyl, pyrazolyl, furanyl, thiophenyl, pyridinyl, pyrimidinyl, imidazolyl,
  the $C_{3-6}$heterocycloalkyl or $C_{6-10}$heterocyclyl is selected from piperidinyl, piperazinyl and morpholinyl; dihyropyridinyl, tetrahydropyridinyl, indolinyl, 2-oxo-indolinyl, dihydro-2H-benzo[b][1,4]oxazin-yl and benzo[d][1,3]dioxolanyl.

In another variation, $R_6$ is selected from phenyl, $C_{5-6}$heteroaryl, the $C_{3-6}$heterocycloalkyl and $C_{6-10}$heterocyclyl, wherein
  the phenyl or $C_{5-6}$heteroaryl is selected from pyrazol-4-yl, pyrazol-3-yl, furan-3-yl, thiophen-1-yl, thiophen-2-yl, thiophen-3-yl, pyridin-3-yl, pyridin-4-yl, pyrimidin-5-yl, and imidazol-4-yl; each of which is unsubstituted or substituted by 1 to 2 substituents independently selected from fluoro, chloro, cyano, methyl, trifluoromethyl, —(CH$_2$)—N(CH$_3$)$_2$, —(CH$_2$)$_2$—N(CH$_3$)$_2$, —CH(CH$_3$)$_2$CH$_2$NH$_2$, —CH$_2$O(CH$_2$)$_2$Si(CH$_3$)$_3$, (CH$_2$)$_{1-2}$-morpholinyl, methoxy, ethoxy, trifluoromethoxy, —O(CH$_2$)$_2$OCH$_3$, —O(CH$_2$)$_2$N(CH$_3$)$_2$, —OCH$_2$-phenyl, —OCH$_2$-5-methylisoxazol-3-yl, —O(CH$_2$)$_2$-1H-imidazol-1-yl, —O(CH$_2$)$_{2-1}$H-pyrazol-1-yl, —OCH$_2$-cyclopropyl, —OCH$_2$-oxiran-2-yl, —O(CH$_2$)$_2$-pyrrolidin-1-yl, —OCH$_2$-tetrahydro-2H-pyran-4-yl, —O(CH$_2$)$_2$-piperidin-1-yl, —O(CH$_2$)$_2$-4-methylpiperazin-1-yl, —O(CH$_2$)$_{2-3}$-morpholinyl, —OCH$_2$CH(OH)CH$_2$-morpholinyl, —C(O)CH3, —C(O)NH2, —C(O)NHCH3, —C(O)OCH3, —NH$_2$, —NHCH$_3$, —N(CH$_3$)$_2$, —NH(CH$_2$)$_2$-morpholinyl, —NHC(O)CH$_3$, —NHC(O)CH(CH$_3$)$_2$, —NHC(O)CH$_2$CH(CH$_3$)$_2$, —NHC(O)CH$_2$NH$_2$, —NHC(O)(CH$_2$)$_2$NH$_2$, —NHC(O)NH$_2$, —NHC(O)NHCH$_3$, —NHC(O)NH-cyclopropyl, —NHC(O)OCH$_3$, —NHC(O)OCH(CH$_3$)$_2$, —NHC(O)OC(CH$_3$)$_3$, —N(CH$_3$)C(O)OC(CH$_3$)$_3$, —NHS(O)$_2$CH$_3$, —NHS(O)$_2$CH(CH$_3$)$_2$, —NHS(O)$_2$NH(CH$_3$), —S(O)$_2$CH$_3$, —S(O)$_2$NH$_2$, —S(O)$_2$-pyrrolidin-1-yl, phenyl, pyrazolyl, pyrrolidinyl, piperidinyl, piperazinyl, C$_{1-4}$alkylpiperazinyl, pyrrolidin-1-yl, piperidin-4-yl, morpholinyl, C$_{1-4}$alkyldihydro-2H-benzo[b][1,4]oxazinyl, and dioxoimidazolidinyl; and the C$_{3-6}$heterocycloalkyl or C$_{6-10}$heterocyclyl are selected from piperidin-1-yl, piperazin-1-yl, morpholinyl, dihyropyridinyl, 1,2,3,6-tetrahydropyridin-4-yl, indolin-5-yl, 2-oxo-indolin-5-yl, 3,4-dihydro-2H-benzo[b][1,4]oxazin-7-yl, and benzo[d][1,3]dioxolan-5-yl, each of which is unsubstituted or substituted by 1 to 2 substituents independently selected from methyl and —C(O)OC(CH$_3$)$_3$.

In another variation, R$_6$ is selected from chloro, bromo, cyano, methyl, ethyl, ethenyl, trifluoromethyl, —(CH$_2$)$_2$-morpholinyl, ethoxy, amino, —N(H)C(O)CH$_3$, —N(H)C(O)OCH$_3$, —NHC(O)OC(CH$_3$)$_3$, phenyl, pyridinyl, pyrimidinyl, 1-t-butylcarbonyl-5,6-dihyropyridin-4-yl, 4-methyl-3,4-dihydro-2H-benzo[b][1,4]oxazin-7-yl, 1-methyl-indolin-5-yl, and 2-oxo-indolin-5-yl, wherein the phenyl is unsubstituted or substituted with 1 to 2 substituents independently selected from fluoro-, chloro, cyano, —CF$_3$, —NH$_2$, —(CH$_2$)$_2$—N(CH$_3$)$_2$, —C(CH$_3$)$_2$CH$_2$NH$_2$, 4-methyl-piperazinyl, —(CH$_2$)$_{1-2}$-morpholinyl, —OCH$_3$, —OCF$_3$, 4-O(CH$_2$)$_2$OCH$_3$, 4-O(CH$_2$)N(CH$_3$)$_2$, —O(CH$_2$)-cyclopropyl, —OCH$_2$-oxiranyl, —O(CH$_2$)-pyrrolidinyl, —O(CH$_2$)-tetrahyropyanyl, —O(CH$_2$)-(5-methylisooxazolyl), —O(CH$_2$)-methylpiperizinyl, —O(CH$_2$)$_{2-3}$-morpholinyl, —OCH$_2$-imidazolyl, —O(CH$_2$)$_2$-pyrazolyl, —C(O)OCH$_3$, —NHCH$_3$, —N(CH$_3$)$_2$, —NHC(O)CH$_3$, —NHC(O)CH$_3$, —NHC(O)CH(CH$_3$)$_2$—, —N(H)C(O)CH$_2$CH(CH$_3$)$_2$, —N(H)C(O)OCH$_3$, —NHC(O)OCH(CH$_3$)$_2$, —NHC(O)OC(CH$_3$)$_3$, —N(CH$_3$)C(O)OC(CH$_3$)$_3$, —N(H)C(O)CH$_2$NH$_2$—, —NHC(O)NH-cyclopropyl, —S(O)$_2$CH$_3$, —N(H)S(O)$_3$CH(CH$_3$)$_2$, —S(O)$_2$-Pyrrolidin-1-yl, -pyrrolidinyl, -piperidinyl, -4-CH(CH$_3$)$_2$-piperazinyl, -2,4-dioxoimidazolidinyl, and 2-oxo-indolinyl; and the pyridinyl or pyrimidinyl is unsubstituted or substituted with 1 to 2 substituents independently selected from fluoro, methyl, —(CH$_2$)$_2$-morpholinyl, methoxy, —C(O)NHCH$_3$, amino, —N(CH$_3$)$_2$, —NHC(O)CH$_3$, pyrazol-4-yl, thiophen-3-y, thiophen-2-y, —CH$_2$O(CH$_2$)$_2$Si(CH$_3$)$_3$-1-imidazol4-yl, and -methylpyrazol-3-y.

In another variation, R$_6$ is selected from bromo, cyano, —(CH$_2$)$_2$-morpholinyl, amino, —N(H)C(O)OCH$_3$, phenyl, 2-fluoro-pyridin-4-yl, 2-C(O)NHCH$_3$pyridin5-yl, -2-(morpholinylethyl)pyridin-5-yl, thiophen3-yl, and —CH$_2$O(CH$_2$)$_2$Si(CH$_3$)$_3$-1-imidazol4-yl, wherein the phenyl is unsubstituted or substituted at the para-position by a substituent independently selected from —(CH$_2$)$_2$N(CH$_2$)$_2$, —O(CH$_2$)$_2$OCH$_3$, —O(CH$_2$)$_2$-pyrazolyl, —O(CH$_2$)-5-methylisooxazolyl, —O(CH$_2$)$_{2-3}$-morpholinyl, —NHCH$_3$, —N(H)C(O)CH(CH$_3$)$_2$, —N(H)C(O)CH$_2$CH(CH$_3$)$_2$, —NHC(O)C(CH$_3$)$_3$, —N(H)C(O)CH$_2$NH$_2$, —N(H)C(O)OCH$_3$, and —N(CH$_3$)C(O)OC(CH$_3$)$_3$, or at the ortho-position by a substituent selected from amino and —NHC(O)OCH(CH$_3$)$_2$.

In another variation, R$_6$ is phenyl, unsubstituted or substituted with 1 to 2 substituents independently selected from fluoro-, chloro, cyano, —CF$_3$, —NH$_2$, —(CH$_2$)$_2$—N(CH$_3$)$_2$, —C(CH$_3$)$_2$CH$_2$NH$_2$, 4-methyl-piperazinyl, —(CH$_2$)$_{1-2}$-morpholinyl, —OCH$_3$, —OCF$_3$, 4-O(CH$_2$)$_2$OCH$_3$, 4-O(CH$_2$)N(CH$_3$)$_2$, —O(CH$_2$)-cyclopropyl, —OCH$_2$-oxiranyl, —O(CH$_2$)-pyrrolidinyl, —O(CH$_2$)-tetrahyropyanyl, —O(CH$_2$)-(5-methylisooxazolyl), —O(CH$_2$)-methylpiperiz-inyl, —O(CH$_2$)$_{2-3}$-morpholinyl, —OCH$_2$-imidazolyl, —O(CH$_2$)$_2$-pyrazolyl, —C(O)OCH$_3$, —NHCH$_3$, —N(CH$_3$)$_2$, —NHC(O)CH$_3$, —NHC(O)CH$_3$, —NHC(O)CH(CH$_3$)$_2$, —N(H)C(O)CH$_2$CH(CH$_3$)$_2$, —N(H)C(O)OCH$_3$, —NHC(O)OCH(CH$_3$)$_2$, —NHC(O)OC(CH$_3$)$_3$, —N(CH$_3$)C(O)OC(CH$_3$)$_3$, —N(H)C(O)CH$_2$NH$_2$—, —NHC(O)NH-cyclopropyl, —S(O)$_2$CH$_3$, —N(H)S(O)$_3$CH(CH$_3$)$_2$, —S(O)$_2$-pyrrolidin-1-yl, pyrrolidinyl, piperidinyl, 4-CH(CH$_3$)$_2$-piperazinyl, 2,4-dioxoimidazolidinyl, and 2-oxo-indolinyl.

In another variation, R$_6$ is phenyl, unsubstituted or substituted at the para-position by a substituent independently selected from —(CH$_2$)$_2$N(CH$_3$)$_2$, —O(CH$_2$)$_2$OCH$_3$, —O(CH$_2$)$_2$-pyrazolyl, —O(CH$_2$)-5-methylisooxazolyl, —O(CH$_2$)$_{2-3}$-morpholinyl, —NHCH$_3$, —N(H)C(O)CH(CH$_3$)$_2$, —N(H)C(O)CH$_2$CH(CH$_3$)$_2$, —NHC(O)C(CH$_3$)$_3$, —N(H)C(O)CH$_2$NH$_2$, —N(H)C(O)OCH$_3$, and —N(CH$_3$)C(O)OC(CH$_3$)$_3$.

In still another variation, R$_6$ is selected from cyano, chloro, bromo, methyl, ethyl, propyl, isopropyl, isobutyl, ethenyl, trifluoromethyl, —CH$_2$NH$_2$, —CH$_2$NHCH$_2$CH(OH)(CH$_3$), —CH$_2$NHCH(CH$_3$)CH$_2$(OH), —(CH$_2$)$_{1-3}$NH(CH$_3$), —(CH$_2$)$_{1-3}$N(CH$_3$)$_2$, —(CH$_2$)$_{1-3}$NH(CH$_2$CH$_3$), —(CH$_2$)$_{1-3}$N(CH$_2$CH$_3$)$_2$, —NHC(O)CH$_3$, —S(O)$_2$CH$_3$, —S(O)$_2$-cyclopropyl, and —P(O)(CH$_3$)$_3$.

In still another variation, R$_6$ is selected from chloro, bromo, cyano, methyl, ethyl, ethenyl, trifluoromethyl, —(CH$_2$)$_2$-morpholinyl, ethoxy, amino, —N(H)C(O)CH$_3$, —N(H)C(O)OCH$_3$, and —NHC(O)OC(CH$_3$)$_3$.

In one particular embodiment of the compounds of the invention, the compounds are of Formula 1c:

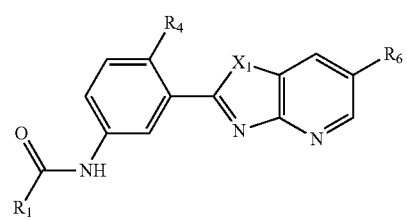

1c wherein

X$_1$ is O or NR$_5$;

R$_1$ is selected from —CH$_2$-4-fluorophenyl, —OCH$_2$CH$_3$, —O(CH$_2$)$_2$OCH$_3$, —OCH(CH$_3$)$_2$, —O-cyclopentyl, —N(CH$_3$)(OCH$_3$), —N(CH(CH$_3$)$_2$)$_2$, cyclopentoxy, 3-chlorophenyl, 2-chlorophenyl, 2,4dimethoxyphenyl, 4-trifluoromethyphenyl, pyrrol-2-yl, furan-2-yl, 5-fluorofuran-2-yl, 5-chlorofuran-2-yl, 5-cyanofuran-2-yl, 5-methylfuranyl, 5-dimethylaminomethyl-furan-2-yl, 4-methylthiophen-2-yl, isothiazol-5-yl, thiazol-4-yl, 5-t-butyloxadiazol-2-yl, pyrazinyl, cyclopentyl, pyrrolidinyl, 3,3-difluoropyrrolidinyl, and 2-oxoindolin-6-yl;

R$_4$ is selected from hydrogen, halo, C$_{1-4}$alkyl, and halo C$_{1-4}$alkyl;

R$_5$ is selected from hydrogen, —CH$_2$O(CH$_3$), —(CH$_2$)$_2$-morpholinyl, —(CH$_2$)$_2$N(CH$_3$)$_2$, —C(O)OCH(CH$_3$)$_2$, and —C(O)O(CH$_3$);

R$_6$ is selected from chloro, bromo, cyano, methyl, ethyl, ethenyl, trifluoromethyl, —(CH$_2$)$_2$-morpholinyl, ethoxy, amino, —N(H)C(O)CH$_3$, —N(H)C(O)OCH$_3$, —NHC(O)OC(CH$_3$)$_3$, phenyl, pyridinyl, pyrimidinyl, 1-t-butylcarbonyl-5,6-dihyropyridin-4-yl, 4-methyl-3,4-dihydro-2H-benzo[b][1,4]oxazin-7-yl, 1-methyl-indolin-5-yl, and 2-oxo-indolin-5-yl, wherein the phenyl is unsubstituted or substituted by 1 to 2 substituents independently selected from fluoro-, chloro, cyano, —CF$_3$, —NH$_2$, —(CH$_2$)$_2$—N(CH$_3$)$_2$, —C(CH$_3$)$_2$CH$_2$NH$_2$, 4-methyl-piperazinyl, —(CH$_2$)$_{1-2}$-morpholinyl, —OCH$_3$, —OCF$_3$, 4-O (CH$_2$)$_2$OCH$_3$, 4-O(CH$_2$)N(CH$_3$)$_2$, —O(CH$_2$)-cyclopropyl, —OCH$_2$-oxiranyl, —O(CH$_2$)-pyrrolidinyl, —O(CH$_2$)-tetrahyropyanyl, —O(CH$_2$)-(5-methylisooxazolyl, —O(CH$_2$)-methylpiperizinyl, —O(CH$_2$)$_{2-3}$-morpholinyl, —OCH$_2$-imidazolyl, —O(CH$_2$)$_2$-pyrazolyl, —C(O)OCH$_3$, —NHCH$_3$, —N(CH$_3$)$_2$, —NHC(O)CH$_3$, —NHC(O)CH$_3$, —NHC(O)CH(CH$_3$)$_2$—, —N(H)C(O)CH$_2$CH (CH$_3$)$_2$, —N(H)C(O)OCH$_3$, —NHC(O)OCH(CH$_3$)$_2$, —NHC(O)OC(CH$_3$)$_3$, —N(CH$_3$)C(O)OC(CH$_3$)$_3$, —N(H)C(O)CH$_2$NH$_2$—, —NHC(O)NH-cyclopropyl, —S(O)$_2$CH$_3$, —N(H)S(O)$_3$CH(CH$_3$)$_2$, —S(O)$_2$-pyrrolidin-1-yl, pyrrolidinyl, piperidinyl, 4-CH (CH$_3$)$_2$-piperazinyl, -2,4-dioxoimidazolidinyl, and 2-oxo-indolinyl; and the pyridinyl or pyrimidinyl is unsubstituted or substituted with 1 to 2 substituents independently selected from fluoro, methyl, —(CH$_2$)$_2$-morpholinyl, methoxy, —C(O)NHCH$_3$, amino, —N(CH$_3$)$_2$, —NHC(O) CH$_3$, pyrazol-4-yl, thiophen-3-y, thiophen-2-y, —CH$_2$O(CH$_2$)$_2$Si(CH$_3$)$_3$-1-imidazol4-yl, and -methylpyrazol-3-y.

In one embodiment of the above particular embodiment and variations of the compounds of the invention, in one variation, $X_1$ is O. In another variation, $X_1$ is NR$_5$.

In one embodiment of the above particular embodiment and variations of the compounds of the invention, in one variation, $R_1$ is selected from isopropoxy, furan-2-yl, pyrazin-2-yl, cyclopentyl, pyrrolidinyl, and 3,3-difluoro pyrrolidinyl. In another variation, $R_1$ is isopropoxy. In still another variation, $R_1$ is pyrrolidinyl, unsubstituted or substituted by a substituent selected from halo, cyano, C$_{1-4}$alkyl, C$_{1-4}$alkoxy, amino, C$_{1-4}$alkylamino, and C$_{1-4}$alkoxycarbonyl. In a particular embodiment, wherein $R_1$ is unsubstituted pyrrolidinyl.

In one embodiment of the above particular embodiment and variations of the compounds of the invention, in one variation, $R_4$ is halo or C$_{1-4}$alkyl. In another variation, $R_4$ is halo.

In one embodiment of the above particular embodiment and variations of the compounds of the invention, $R_5$ is hydrogen.

In one embodiment of the above particular embodiment and variations of the compounds of the invention, in one variation, $R_6$ is selected from bromo, cyano, —(CH$_2$)$_2$-morpholinyl, amino, —N(H)C(O)OCH$_3$, phenyl, 2-fluoro-pyridin-4-yl, 2-C(O)NHCH$_3$pyridin5-yl, -2-(morpholinylethyl) pyridin-5-yl, thiophen3-yl, and —CH$_2$O(CH$_2$)$_2$Si(CH$_3$)$_3$-1-imidazol4-yl, wherein the phenyl is unsubstituted or substituted at the para-position by a substituent independently selected from —(CH$_2$)$_2$N(CH$_3$)$_2$, —O(CH$_2$)$_2$OCH$_3$, —O(CH$_2$)$_2$-pyrazolyl, —O(CH$_2$)-5-methylisooxazolyl, —O (CH$_2$)$_{2-3}$-morpholinyl, —NHCH$_3$, —N(H)C(O)CH (CH$_3$)$_2$, —N(H)C(O)CH$_2$CH(CH$_3$)$_2$, —NHC(O)C (CH$_3$)$_3$, —N(H)C(O)CH$_2$NH$_2$, —N(H)C(O)OCH$_3$, and —N(CH$_3$)C(O)OC(CH$_3$)$_3$, or at the ortho-position by a substituent selected from amino and —NHC(O)OCH (CH$_3$)$_2$.

In another variation, $R_6$ is phenyl, unsubstituted or substituted at the para-position by a substituent independently selected from —(CH$_2$)$_2$N(CH$_3$)$_2$, —O(CH$_2$)$_2$OCH$_3$, —O(CH$_2$)$_2$-pyrazolyl, —O(CH$_2$)-5-methylisooxazolyl, —O(CH$_2$)$_{2-3}$-morpholinyl, —NHCH$_3$, —N(H)C(O)CH (CH$_3$)$_2$, —N(H)C(O)CH$_2$CH(CH$_3$)$_2$, —NHC(O)C(CH$_3$)$_3$, —N(H)C(O)CH$_2$NH$_2$, —N(H)C(O)OCH$_3$, and —N(CH$_3$)C (O)OC(CH$_3$)$_3$.

In another variation, $R_6$ is selected from chloro, bromo, cyano, methyl, ethyl, ethenyl, trifluoromethyl, —(CH$_2$)$_2$-morpholinyl, ethoxy, amino, —N(H)C(O)CH$_3$, —N(H)C(O) OCH$_3$, and —NHC(O)OC(CH$_3$)$_3$.

Particular examples of compounds or a pharmaceutically acceptable salt, tautomer or stereoisomer thereof, according to the present invention include, but are not limited to: N-(4-chloro-3-{6-methyl-1H-imidazo[4,5-b]pyridin-2-yl}phenyl)-furan-2-carboxamide; N-(4-chloro-3-{6-chloro-1H-imidazo[4,5-b]pyridin-2-yl}phenyl)-furan-2-carboxamide; N-(4-chloro-3-{7-methyl-1H-imidazo[4,5-b]pyridin-2-yl}phenyl)-furan-2-carboxamide; N-[4-chloro-3-(7H-purin-8-yl)phenyl]furan-2-carboxamide; N-(4-chloro-3-{5,6-dimethyl-1H-imidazo[4,5-b]pyridin-2-yl}phenyl)furan-2-carboxamide; N-[4-chloro-3-(6-{4-[2-(morpholin-4-yl)ethyl]phenyl}-1H-imidazo[4,5-b]pyridin-2-yl)phenyl]furan-2-carboxamide; N-{4-chloro-3-[6-(6-acetamidopyridin-3-yl)-1H-imidazo[4,5-b]pyridin-2-yl]phenyl}furan-2-carboxamide; N-{4-chloro-3-[6-(2-acetamidophenyl)-1H-imidazo[4,5-b]pyridin-2-yl]phenyl}furan-2-carboxamide; N-{4-chloro-3-[6-(2-methoxypyrimidin-5-yl)-1H-imidazo[4,5-b]pyridin-2-yl]phenyl}furan-2-carboxamide; N-{4-chloro-3-[6-(pyridin-4-yl)-1H-imidazo[4,5-b]pyridin-2-yl]phenyl}furan-2-carboxamide; N-[4-chloro-3-(6-{6-[2-(morpholin-4-yl)ethoxy]pyridin-3-yl}-1H-imidazo[4,5-b]pyridin-2-yl) phenyl]furan-2-carboxamide; N-{3-[6-(4-aminophenyl)-1H-imidazo[4,5-b]pyridin-2-yl]-4-chlorophenyl}furan-2-carboxamide; N-(4-chloro-3-{6-[4-(3-methylbutanamido) phenyl]-1H-imidazo[4,5-b]pyridin-2-yl}phenyl)furan-2-carboxamide; N-[4-chloro-3-(6-{1-[2-(morpholin-4-yl) ethyl]-1H-pyrazol-4-yl}-1H-imidazo[4,5-b]pyridin-2-yl) phenyl]furan-2-carboxamide; N-[4-chloro-3-(6-{4-[(dimethylamino)methyl]phenyl}-1H-imidazo[4,5-b] pyridin-2-yl)phenyl]furan-2-carboxamide; N-(4-chloro-3-{6-[4-(morpholin-4-ylmethyl)phenyl]-1H-imidazo[4,5-b] pyridin-2-yl}phenyl)furan-2-carboxamide; N-{3-[6-(2-aminopyrimidin-5-yl)-1H-imidazo[4,5-b]pyridin-2-yl]-4-chlorophenyl}furan-2-carboxamide; N-{4-chloro-3-[6-(4-acetamidophenyl)-1H-imidazo[4,5-b]pyridin-2-yl] phenyl}furan-2-carboxamide; N-{3-[6-(4-carbamoylphenyl)-1H-imidazo[4,5-b]pyridin-2-yl]-4-chlorophenyl}furan-2-carboxamide; N-{4-chloro-3-[6-(4-cyanophenyl)-1H-imidazo[4,5-b]pyridin-2-yl] phenyl}furan-2-carboxamide; N-[4-chloro-3-(6-{4-[2-(piperidin-1-yl)ethoxy]phenyl}-1H-imidazo[4,5-b]pyridin-2-yl)phenyl]furan-2-carboxamide; N-(4-chloro-3-{6-[4-(4-methylpiperazin-1-yl)phenyl]-1H-imidazo[4,5-b]pyridin-2-yl}phenyl)furan-2-carboxamide; N-{3-[6-(2-aminophenyl)-1H-imidazo[4,5-b]pyridin-2-yl]-4-chlorophenyl}furan-2-carboxamide; N-{3-[6-(6-aminopyridin-3-yl)-1H-imidazo [4,5-b]pyridin-2-yl]-4-chlorophenyl}furan-2-carboxamide; N-(4-chloro-3-{6-[4-(trifluoromethoxy)phenyl]-1H-imidazo[4,5-b]pyridin-2-yl}phenyl)furan-2-carboxamide; N-(4-chloro-3-{6-[4-(oxan-4-ylmethoxy)phenyl]-1H-imidazo[4,5-b]pyridin-2-yl}phenyl)furan-2-carboxamide; N-{3-[6-(2H-1,3-benzodioxol-5-yl)-1H-imidazo[4,5-b]pyridin-2-yl]-4-chlorophenyl}furan-2-carboxamide; N-(4-chloro-3-{6-[4-(methylamino)phenyl]-1H-imidazo[4,5-b] pyridin-2-yl}phenyl)-furan-2-carboxamide; N-{4-chloro-3-[6-(6-methoxypyridin-3-yl)-1H-imidazo[4,5-b]pyridin-2-yl] phenyl}furan-2-carboxamide; N-(4-chloro-3-{6-ethyl-1H-imidazo[4,5-b]pyridin-2-yl}phenyl)furan-2-carboxamide;

propan-2-yl N-(4-{2-[2-chloro-5-(furan-2-amido)phenyl]-1H-imidazo[4,5-b]pyridin-6-yl}phenyl)carbamate; N-(3-{6-[4-(carbamoylamino)phenyl]-1H-imidazo[4,5-b]pyridin-2-yl}-4-chlorophenyl)furan-2-carboxamide; N-(4-chloro-3-{6-[4-(morpholin-4-yl)phenyl]-1H-imidazo[4,5-b]pyridin-2-yl}phenyl)furan-2-carboxamide; tert-butyl N-(4-{2-[2-chloro-5-(furan-2-amido)phenyl]-1H-imidazo[4,5-b]pyridin-6-yl}-2-methoxyphenyl)carbamate; methyl 4-{2-[2-chloro-5-(furan-2-amido)phenyl]-1H-imidazo[4,5-b]pyridin-6-yl}benzoate; N-(4-chloro-3-{6-[4-(cyclopropylmethoxy)phenyl]-1H-imidazo[4,5-b]pyridin-2-yl}phenyl)furan-2-carboxamide; propan-2-yl N-(2-{2-[2-chloro-5-(furan-2-amido)phenyl]-1H-imidazo[4,5-b]pyridin-6-yl}phenyl)carbamate; N-{4-chloro-3-[6-({[(2S)-1-hydroxypropan-2-yl]amino}methyl)-1H-imidazo[4,5-b]pyridin-2-yl]phenyl}furan-2-carboxamide; N-{4-chloro-3-[6-(2,6-dimethylpyridin-4-yl)-1H-imidazo[4,5-b]pyridin-2-yl]phenyl}furan-2-carboxamide; N-[4-chloro-3-(6-{4-[2-(1H-pyrazol-1-yl)ethoxy]phenyl}-1H-imidazo[4,5-b]pyridin-2-yl)phenyl]furan-2-carboxamide; N-(3-{6-[4-(trifluoromethoxy)phenyl]-1H-imidazo[4,5-b]pyridin-2-yl}phenyl)furan-2-carboxamide; N-(4-chloro-3-{6-[4-(2,5-dioxoimidazolidin-4-yl)phenyl]-1H-imidazo[4,5-b]pyridin-2-yl}phenyl)furan-2-carboxamide; N-{4-chloro-3-[6-(2-oxo-2,3-dihydro-1H-indol-5-yl)-1H-imidazo[4,5-b]pyridin-2-yl]phenyl}furan-2-carboxamide; N-[4-chloro-3-(6-{4-[(5-methyl-1,2-oxazol-3-yl)methoxy]phenyl}-1H-imidazo[4,5-b]pyridin-2-yl)phenyl]furan-2-carboxamide; N-[4-chloro-3-(6-{4-[(cyclopropylcarbamoyl)amino]phenyl}-1H-imidazo[4,5-b]pyridin-2-yl)phenyl]furan-2-carboxamide; N-{4-chloro-3-[6-(4-methanesulfonylphenyl)-1H-imidazo[4,5-b]pyridin-2-yl]phenyl}furan-2-carboxamide; N-(3-{6-[4-(benzyloxy)phenyl]-1H-imidazo[4,5-b]pyridin-2-yl}-4-chlorophenyl)furan-2-carboxamide; N-{4-chloro-3-[6-(3-chloro-4-methoxyphenyl)-1H-imidazo[4,5-b]pyridin-2-yl]phenyl}furan-2-carboxamide; N-(4-chloro-3-{6-[4-methoxy-3-(pyrrolidine-1-sulfonyl)phenyl]-1H-imidazo[4,5-b]pyridin-2-yl}phenyl)furan-2-carboxamide; N-{4-chloro-3-[6-(pyridin-3-yl)-1H-imidazo[4,5-b]pyridin-2-yl]phenyl}furan-2-carboxamide; N-{4-chloro-3-[6-(2-fluoropyridin-4-yl)-1H-imidazo[4,5-b]pyridin-2-yl]phenyl}furan-2-carboxamide; N-(4-chloro-3-{6-[2-fluoro-6-(2-methoxyethoxy)pyridin-3-yl]-1H-imidazo[4,5-b]pyridin-2-yl}phenyl)furan-2-carboxamide; N-(4-chloro-3-{6-[4-(2-methylpropanamido)phenyl]-1H-imidazo[4,5-b]pyridin-2-yl}phenyl)furan-2-carboxamide; 5-{2-[2-chloro-5-(furan-2-amido)phenyl]-1H-imidazo[4,5-b]pyridin-6-yl}-N-methylpyridine-2-carboxamide; N-[4-chloro-3-(6-{4-[2-(pyrrolidin-1-yl)ethoxy]phenyl}-1H-imidazo[4,5-b]pyridin-2-yl)phenyl]furan-2-carboxamide; N-(4-chloro-3-{6-[4-(1H-pyrazol-1-yl)phenyl]-1H-imidazo[4,5-b]pyridin-2-yl}phenyl)furan-2-carboxamide; N-[4-chloro-3-(6-{4-[(methylcarbamoyl)amino]phenyl}-1H-imidazo[4,5-b]pyridin-2-yl)phenyl]furan-2-carboxamide; methyl N-(4-{2-[2-chloro-5-(furan-2-amido)phenyl]-1H-imidazo[4,5-b]pyridin-6-yl}phenyl)carbamate; N-{4-chloro-3-[6-(1-methyl-2,3-dihydro-1H-indol-5-yl)-1H-imidazo[4,5-b]pyridin-2-yl]phenyl}furan-2-carboxamide; N-(4-chloro-3-{6-[4-(2-methoxyethoxy)phenyl]-1H-imidazo[4,5-b]pyridin-2-yl}phenyl)furan-2-carboxamide; N-{4-chloro-3-[6-(2,6-dimethoxypyridin-3-yl)-1H-imidazo[4,5-b]pyridin-2-yl]phenyl}furan-2-carboxamide; N-[4-chloro-3-(6-{4-[4-(propan-2-yl)piperazin-1-yl]phenyl}-1H-imidazo[4,5-b]pyridin-2-yl)phenyl]furan-2-carboxamide; tert-butyl 4-{2-[2-chloro-5-(furan-2-amido)phenyl]-1H-imidazo[4,5-b]pyridin-6-yl}-1,2,3,6-tetrahydropyridine-1-carboxylate; N-(4-chloro-3-{6-[4-(methylcarbamoyl)phenyl]-1H-imidazo[4,5-b]pyridin-2-yl}phenyl)furan-2-carboxamide; N-(4-chloro-3-{6-[6-(dimethylamino)pyridin-3-yl]-1H-imidazo[4,5-b]pyridin-2-yl}phenyl)furan-2-carboxamide; N-{4-chloro-3-[6-(4-sulfamoylphenyl)-1H-imidazo[4,5-b]pyridin-2-yl]phenyl}furan-2-carboxamide; N-(4-chloro-3-{6-[4-(dimethylamino)phenyl]-1H-imidazo[4,5-b]pyridin-2-yl}phenyl)furan-2-carboxamide; N-(4-chloro-3-{6-[4-(pyrrolidin-1-yl)phenyl]-1H-imidazo[4,5-b]pyridin-2-yl}phenyl)furan-2-carboxamide; N-[4-chloro-3-(6-{4-[2-(dimethylamino)ethoxy]phenyl}-1H-imidazo[4,5-b]pyridin-2-yl)phenyl]furan-2-carboxamide; N-{4-chloro-3-[6-(1,2,3,6-tetrahydropyridin-4-yl)-1H-imidazo[4,5-b]pyridin-2-yl]phenyl}furan-2-carboxamide; N-[4-chloro-3-(6-{4-[2-(1H-imidazol-1-yl)ethoxy]phenyl}-1H-imidazo[4,5-b]pyridin-2-yl)phenyl]furan-2-carboxamide; N-{4-chloro-3-[6-(4-methyl-3,4-dihydro-2H-1,4-benzoxazin-7-yl)-1H-imidazo[4,5-b]pyridin-2-yl]phenyl}furan-2-carboxamide; N-{4-chloro-3-[6-(4-methyl-1H-pyrazol-3-yl)-1H-imidazo[4,5-b]pyridin-2-yl]phenyl}furan-2-carboxamide; N-(4-chloro-3-{6-ethenyl-1H-imidazo[4,5-b]pyridin-2-yl}phenyl)furan-2-carboxamide; N-(4-chloro-3-{6-propyl-1H-imidazo[4,5-b]pyridin-2-yl}phenyl)furan-2-carboxamide; N-{4-chloro-3-[6-(2-methylpropyl)-1H-imidazo[4,5-b]pyridin-2-yl]phenyl}furan-2-carboxamide; N-{4-chloro-3-[6-(propan-2-yl)-1H-imidazo[4,5-b]pyridin-2-yl]phenyl}furan-2-carboxamide; N-(4-chloro-3-{6-methyl-1H-imidazo[4,5-b]pyridin-2-yl}phenyl)-2-(2,3-difluorophenyl)acetamide; N-(4-chloro-3-{6-methyl-1H-imidazo[4,5-b]pyridin-2-yl}phenyl)-5-methyl-1,2-oxazole-3-carboxamide; N-(4-chloro-3-{6-methyl-1H-imidazo[4,5-b]pyridin-2-yl}phenyl)-4-methyl-1,3-thiazole-2-carboxamide; N-(4-chloro-3-{6-methyl-1H-imidazo[4,5-b]pyridin-2-yl}phenyl)-2-(4-chlorophenyl)-2-methylpropanamide; N-(4-chloro-3-{6-methyl-1H-imidazo[4,5-b]pyridin-2-yl}phenyl)-2-[4-(dimethylamino)phenyl]acetamide; N-(4-chloro-3-{6-methyl-1H-imidazo[4,5-b]pyridin-2-yl}phenyl)pyridine-2-carboxamide; N-(4-chloro-3-{6-methyl-1H-imidazo[4,5-b]pyridin-2-yl}phenyl)-5-(morpholin-4-yl)pyridine-2-carboxamide; N-(4-chloro-3-{6-methyl-1H-imidazo[4,5-b]pyridin-2-yl}phenyl)-2-(3-chlorophenyl)acetamide; 5-chloro-N-(4-chloro-3-{6-methyl-1H-imidazo[4,5-b]pyridin-2-yl}phenyl)furan-2-carboxamide; N-(4-chloro-3-{6-methyl-1H-imidazo[4,5-b]pyridin-2-yl}phenyl)-2-(2,6-difluorophenyl)acetamide; N-(4-chloro-3-{6-methyl-1H-imidazo[4,5-b]pyridin-2-yl}phenyl)-2-(3-methyl-1,2-oxazol-5-yl)acetamide; 3-chloro-N-(4-chloro-3-{6-methyl-1H-imidazo[4,5-b]pyridin-2-yl}phenyl)benzamide; N-(4-chloro-3-{6-methyl-1H-imidazo[4,5-b]pyridin-2-yl}phenyl)-5-fluorofuran-2-carboxamide; N-(4-chloro-3-{6-methyl-1H-imidazo[4,5-b]pyridin-2-yl}phenyl)-1,2-thiazole-5-carboxamide; N-(4-chloro-3-{6-methyl-1H-imidazo[4,5-b]pyridin-2-yl}phenyl)pyridazine-4-carboxamide; N-(4-chloro-3-{6-methyl-1H-imidazo[4,5-b]pyridin-2-yl}phenyl)-2-ethoxypyridine-4-carboxamide; N-(4-chloro-3-{6-methyl-1H-imidazo[4,5-b]pyridin-2-yl}phenyl)-5-[(dimethylamino)methyl]furan-2-carboxamide; N-(4-chloro-3-{6-methyl-1H-imidazo[4,5-b]pyridin-2-yl}phenyl)-1H-imidazole-2-carboxamide; N-(4-chloro-3-{6-methyl-1H-imidazo[4,5-b]pyridin-2-yl}phenyl)-2-[4-(trifluoromethyl)phenyl]acetamide; N-(4-chloro-3-{6-methyl-1H-imidazo[4,5-b]pyridin-2-yl}phenyl)-2-(pyridin-3-yl)acetamide; 2,5-dichloro-N-(4-chloro-3-{6-methyl-1H-imidazo[4,5-b]pyridin-2-yl}phenyl)benzamide; N-(4-chloro-3-{6-methyl-1H-imidazo[4,5-b]pyridin-2-yl}phenyl)-3-(piperidin-1-yl)benzamide; N-(4-chloro-3-{6-methyl-1H-imidazo[4,5-b]pyridin-2-yl}phenyl)-1H- pyrrole-2-carboxamide; N-(4-chloro-3-{6-methyl-1H-imidazo[4,5-b]pyridin-2-yl}phenyl)-5-cyanopyridine-3-carboxamide; N-(4-chloro-3-{6-methyl-1H-imidazo[4,5-b]pyridin-2-yl}phenyl)-5-methylpyridine-3-carboxamide; N-(4-chloro-3-{6-methyl-1H-imidazo[4,5-b]pyridin-2-yl}phenyl)oxetane-2-carboxamide; N-(4-chloro-3-{6-methyl-1H-imidazo[4,5-b]pyridin-2-yl}phenyl)-1,3-oxazole-2-carboxamide; N-(4-chloro-3-{6-methyl-1H-imidazo[4,5-b]pyridin-2-yl}phenyl)-3,5-dimethyl-1,2-oxazole-4-carboxamide; N-(4-chloro-3-{6-methyl-1H-imidazo[4,5-b]pyridin-2-yl}phenyl)-5-methyl-1,3,4-oxadiazole-2-carboxamide; N-(4-chloro-3-{6-methyl-1H-imidazo[4,5-b]pyridin-2-yl}phenyl)-2-methyl-1,3-thiazole-4-carboxamide; N-(4-chloro-3-{6-methyl-1H-imidazo[4,5-b]pyridin-2-yl}phenyl)-2-methoxybenzamide; N-(4-chloro-3-{6-methyl-1H-imidazo[4,5-b]pyridin-2-yl}phenyl)-4-(morpholin-4-yl)benzamide; 2-chloro-N-(4-chloro-3-{6-methyl-1H-imidazo[4,5-b]pyridin-2-yl}phenyl)-4-methanesulfonylbenzamide; tert-butyl N-{1-[(4-chloro-3-{6-methyl-1H-imidazo[4,5-b]pyridin-2-yl}phenyl)carbamoyl]-1-methylethyl}carbamate; tert-butyl N-{[(4-chloro-3-{6-methyl-1H-imidazo[4,5-b]pyridin-2-yl}phenyl)carbamoyl]methyl}carbamate; N-(4-chloro-3-{6-methyl-1H-imidazo[4,5-b]pyridin-2-yl}phenyl)-1,3-oxazole-4-carboxamide; N-(4-chloro-3-{6-methyl-1H-imidazo[4,5-b]pyridin-2-yl}phenyl)-2-(2,4-difluorophenyl)acetamide; N-(4-chloro-3-{6-methyl-1H-imidazo[4,5-b]pyridin-2-yl}phenyl)-5-(trifluoromethyl)pyridine-2-carboxamide; 2-amino-N-(4-chloro-3-{6-methyl-1H-imidazo[4,5-b]pyridin-2-yl}phenyl)acetamide; N-(4-chloro-3-{6-methyl-1H-imidazo[4,5-b]pyridin-2-yl}phenyl)-3,3-difluorocyclobutane-1-carboxamide; N-(4-chloro-3-{6-methyl-1H-imidazo[4,5-b]pyridin-2-yl}phenyl)cyclobutanecarboxamide; N-(4-chloro-3-{6-methyl-1H-imidazo[4,5-b]pyridin-2-yl}phenyl)-2-(4-fluorophenyl)propanamide; N-(4-chloro-3-{6-methyl-1H-imidazo[4,5-b]pyridin-2-yl}phenyl)-2-phenoxyacetamide; N-(4-chloro-3-{6-methyl-1H-imidazo[4,5-b]pyridin-2-yl}phenyl)-2-[4-(trifluoromethoxy)phenyl]acetamide; N-(4-chloro-3-{6-methyl-1H-imidazo[4,5-b]pyridin-2-yl}phenyl)-2-(1H-1,2,4-triazol-1-yl)acetamide; N-(4-chloro-3-{6-methyl-1H-imidazo[4,5-b]pyridin-2-yl}phenyl)-2,3-dihydro-1-benzofuran-2-carboxamide; N-(4-chloro-3-{6-methyl-1H-imidazo[4,5-b]pyridin-2-yl}phenyl)-5-methyl-1H-pyrrole-2-carboxamide; N-(4-chloro-3-{6-methyl-1H-imidazo[4,5-b]pyridin-2-yl}phenyl)-2-(4-fluorophenyl)acetamide; N-(4-chloro-3-{6-methyl-1H-imidazo[4,5-b]pyridin-2-yl}phenyl)-5-methylfuran-2-carboxamide; 6-chloro-N-(4-chloro-3-{6-methyl-1H-imidazo[4,5-b]pyridin-2-yl}phenyl)pyrazine-2-carboxamide; N-(4-chloro-3-{6-methyl-1H-imidazo[4,5-b]pyridin-2-yl}phenyl)-1H-imidazole-5-carboxamide; N-(4-chloro-3-{6-methyl-1H-imidazo[4,5-b]pyridin-2-yl}phenyl)-2-methoxypyridine-4-carboxamide; N-(4-chloro-3-{6-methyl-1H-imidazo[4,5-b]pyridin-2-yl}phenyl)-3-methylfuran-2-carboxamide; N-(4-chloro-3-{6-methyl-1H-imidazo[4,5-b]pyridin-2-yl}phenyl)oxane-2-carboxamide; N-(4-chloro-3-{6-methyl-1H-imidazo[4,5-b]pyridin-2-yl}phenyl)-4-(morpholin-4-yl)butanamide; tert-butyl 3-[(4-chloro-3-{6-methyl-1H-imidazo[4,5-b]pyridin-2-yl}phenyl)carbamoyl]-3-methylazetidine-1-carboxylate; N-(4-chloro-3-{6-methyl-1H-imidazo[4,5-b]pyridin-2-yl}phenyl)-3-methoxybenzamide; 5-chloro-N-(4-chloro-3-{6-methyl-1H-imidazo[4,5-b]pyridin-2-yl}phenyl)pyrazine-2-carboxamide; N-(4-chloro-3-{6-methyl-1H-imidazo[4,5-b]pyridin-2-yl}phenyl)-6-methanesulfonylpyridine-3-carboxamide; N-(4-chloro-3-{6-methyl-1H-imidazo[4,5-b]pyridin-2-yl}phenyl)-2-(methylsulfanyl)pyrimidine-4-carboxamide; N-(4-chloro-3-{6-methyl-1H-imidazo[4,5-b]pyridin-2-yl}phenyl)oxolane-2-carboxamide; N-(4-chloro-3-{6-methyl-1H-imidazo[4,5-b]pyridin-2-yl}phenyl)-2,4-dimethyl-1,3-oxazole-5-carboxamide; N-(4-chloro-3-{6-methyl-1H-imidazo[4,5-b]pyridin-2-yl}phenyl)-3-methanesulfonylbenzamide; N-(4-chloro-3-{6-methyl-1H-imidazo[4,5-b]pyridin-2-yl}phenyl)-2-(4-chlorophenyl)-3-methylbutanamide; N-(4-chloro-3-{6-methyl-1H-imidazo[4,5-b]pyridin-2-yl}phenyl)-2-(3,4-difluorophenyl)acetamide; N-(4-chloro-3-{6-methyl-1H-imidazo[4,5-b]pyridin-2-yl}phenyl)-3-hydroxypropanamide; N-(4-chloro-3-{6-methyl-1H-imidazo[4,5-b]pyridin-2-yl}phenyl)-2-(4-chlorophenyl)acetamide; N-(4-chloro-3-{6-methyl-1H-imidazo[4,5-b]pyridin-2-yl}phenyl)-2-(pyrimidin-2-yl)acetamide; 2-(2,1-benzoxazol-3-yl)-N-(4-chloro-3-{6-methyl-1H-imidazo[4,5-b]pyridin-2-yl}phenyl)acetamide; N-(4-chloro-3-{6-methyl-1H-imidazo[4,5-b]pyridin-2-yl}phenyl)-2,4-dimethoxybenzamide; N-(4-chloro-3-{6-methyl-1H-imidazo[4,5-b]pyridin-2-yl}phenyl)-2-(pyridin-4-yl)acetamide; 2-chloro-N-(4-chloro-3-{6-methyl-1H-imidazo[4,5-b]pyridin-2-yl}phenyl)benzamide; N-(4-chloro-3-{6-methyl-1H-imidazo[4,5-b]pyridin-2-yl}phenyl)-2-(dimethylamino)benzamide; N-(4-chloro-3-{6-methyl-1H-imidazo[4,5-b]pyridin-2-yl}phenyl)-1-methyl-1H-pyrrole-2-carboxamide; 5-chloro-N-(4-chloro-3-{6-methyl-1H-imidazo[4,5-b]pyridin-2-yl}phenyl)thiophene-2-carboxamide; N-(4-chloro-3-{6-methyl-1H-imidazo[4,5-b]pyridin-2-yl}phenyl)-4-(trifluoromethyl)benzamide; N-(4-chloro-3-{6-methyl-1H-imidazo[4,5-b]pyridin-2-yl}phenyl)-2-methanesulfinylpyrimidine-4-carboxamide; N-(4-chloro-3-{6-methyl-1H-imidazo[4,5-b]pyridin-2-yl}phenyl)-1,2-oxazole-5-carboxamide; N-(4-chloro-3-{6-methyl-1H-imidazo[4,5-b]pyridin-2-yl}phenyl)-2-(4-methoxyphenyl)acetamide; N-(4-chloro-3-{6-methyl-1H-imidazo[4,5-b]pyridin-2-yl}phenyl)-1H-pyrazole-3-carboxamide; N-(4-chloro-3-{6-methyl-1H-imidazo[4,5-b]pyridin-2-yl}phenyl)-3-cyclopropyl-1H-pyrazole-5-carboxamide; N-(4-chloro-3-{6-methyl-1H-imidazo[4,5-b]pyridin-2-yl}phenyl)-4-(dimethylamino)butanamide; N-(4-chloro-3-{6-methyl-1H-imidazo[4,5-b]pyridin-2-yl}phenyl)-3-methyl-2-phenylbutanamide; N-(4-chloro-3-{6-methyl-1H-imidazo[4,5-b]pyridin-2-yl}phenyl)-5-methyl-1,2,4-oxadiazole-3-carboxamide; N-(4-chloro-3-{6-methyl-1H-imidazo[4,5-b]pyridin-2-yl}phenyl)-2-methyl-6-(trifluoromethyl)pyridine-3-carboxamide; N-(4-chloro-3-{6-methyl-1H-imidazo[4,5-b]pyridin-2-yl}phenyl)-3-methyloxetane-3-carboxamide; N-(4-chloro-3-{6-methyl-1H-imidazo[4,5-b]pyridin-2-yl}phenyl)-2,2-difluoro-2-phenylacetamide; N-(4-chloro-3-{6-methyl-1H-imidazo[4,5-b]pyridin-2-yl}phenyl)-2-(4-methoxyphenyl)propanamide; N-(4-chloro-3-{6-methyl-1H-imidazo[4,5-b]pyridin-2-yl}phenyl)-5-(pyrazin-2-yl)pyridine-2-carboxamide; N-(4-chloro-3-{6-methyl-1H-imidazo[4,5-b]pyridin-2-yl}phenyl)-2-(4-methylphenyl)acetamide; N-(4-chloro-3-{6-methyl-1H-imidazo[4,5-b]pyridin-2-yl}phenyl)-2-(2-oxo-1,2-dihydropyrimidin-1-yl)acetamide; N-(4-chloro-3-{6-methyl-1H-imidazo[4,5-b]pyridin-2-yl}phenyl)-2-(1H-1,2,3,4-tetrazol-5-yl)acetamide; N-(4-chloro-3-{6-methyl-1H-imidazo[4,5-b]pyridin-2-yl}phenyl)-2-(1H-1,2,3,4-tetrazol-1-yl)acetamide; N-(4-chloro-3-{6-methyl-1H-imidazo[4,5-b]pyridin-2-yl}phenyl)piperidine-2-carboxamide; N-(4-chloro-3-{6-methyl-1H-imidazo[4,5-b]pyridin-2-yl}phenyl)-4-methylpyridine-2-carboxamide; N-(4-chloro-3-{6-methyl-1H-imidazo[4,5-b]pyridin-2-yl}phenyl)-4-methoxypyridine-2-carboxamide; N-(4-chloro-3-{6-methyl- 1H-imidazo[4,5-b]pyridin-2-yl}phenyl)-3-hydroxypyrazine-2-carboxamide; N-(4-chloro-3-{6-methyl-1H-imidazo[4,5-b]pyridin-2-yl}phenyl)-5-methanesulfonylthiophene-2-carboxamide; N-(4-chloro-3-{6-methyl-1H-imidazo[4,5-b]pyridin-2-yl}phenyl)-2-methyl-5-(trifluoromethyl)-1,3-oxazole-4-carboxamide; N-(4-chloro-3-{6-methyl-1H-imidazo[4,5-b]pyridin-2-yl}phenyl)-1,3-oxazole-5-carboxamide; N-(4-chloro-3-{6-methyl-1H-imidazo[4,5-b]pyridin-2-yl}phenyl)-5-methylpyrazine-2-carboxamide; N-(4-chloro-3-{6-methyl-1H-imidazo[4,5-b]pyridin-2-yl}phenyl)-2,5-dimethyl-1,3-oxazole-4-carboxamide; N-(4-chloro-3-{6-methyl-1H-imidazo[4,5-b]pyridin-2-yl}phenyl)-2,3-dihydro-1-benzofuran-7-carboxamide; (2R)-N-(4-chloro-3-{6-methyl-1H-imidazo[4,5-b]pyridin-2-yl}phenyl)-2-methoxy-2-phenylacetamide; N-(4-chloro-3-{6-methyl-1H-imidazo[4,5-b]pyridin-2-yl}phenyl)-2-hydroxy-2-[4-(trifluoromethyl)phenyl]acetamide; N-(4-chloro-3-{6-methyl-1H-imidazo[4,5-b]pyridin-2-yl}phenyl)-2-hydroxyacetamide; N-(4-chloro-3-{6-methyl-1H-imidazo[4,5-b]pyridin-2-yl}phenyl)-3-(dimethylamino)benzamide; N-(4-chloro-3-{6-methyl-1H-imidazo[4,5-b]pyridin-2-yl}phenyl)-5-fluorothiophene-2-carboxamide; N-(4-chloro-3-{6-methyl-1H-imidazo[4,5-b]pyridin-2-yl}phenyl)pyridazine-3-carboxamide; N-(4-chloro-3-{6-methyl-1H-imidazo[4,5-b]pyridin-2-yl}phenyl)pyrimidine-5-carboxamide; N-(4-chloro-3-{6-methyl-1H-imidazo[4,5-b]pyridin-2-yl}phenyl)-2-methylpyridine-4-carboxamide; N-(4-chloro-3-{6-methyl-1H-imidazo[4,5-b]pyridin-2-yl}phenyl)-2,3-dimethylpyridine-4-carboxamide; 5-tert-butyl-N-(4-chloro-3-{6-methyl-1H-imidazo[4,5-b]pyridin-2-yl}phenyl)furan-2-carboxamide; N-(4-chloro-3-{6-methyl-1H-imidazo[4,5-b]pyridin-2-yl}phenyl)-2,4-dimethyl-1,3-thiazole-5-carboxamide; N-(4-chloro-3-{6-methyl-1H-imidazo[4,5-b]pyridin-2-yl}phenyl)-1,3-thiazole-2-carboxamide; N-(4-chloro-3-{6-methyl-1H-imidazo[4,5-b]pyridin-2-yl}phenyl)-4-methanesulfonylbenzamide; 2-amino-N-(4-chloro-3-{6-methyl-1H-imidazo[4,5-b]pyridin-2-yl}phenyl)-2-methylpropanamide; N-(4-chloro-3-{6-methyl-1H-imidazo[4,5-b]pyridin-2-yl}phenyl)-3-(morpholin-4-yl)benzamide; 3,5-dichloro-N-(4-chloro-3-{6-methyl-1H-imidazo[4,5-b]pyridin-2-yl}phenyl)benzamide; N-(4-chloro-3-{6-methyl-1H-imidazo[4,5-b]pyridin-2-yl}phenyl)-2-(1H-imidazol-1-yl)acetamide; N-(4-chloro-3-{6-methyl-1H-imidazo[4,5-b]pyridin-2-yl}phenyl)-3,4-dihydro-2H-1-benzopyran-2-carboxamide; N-(4-chloro-3-{6-methyl-1H-imidazo[4,5-b]pyridin-2-yl}phenyl)cyclopentanecarboxamide; N-(4-chloro-3-{6-methyl-1H-imidazo[4,5-b]pyridin-2-yl}phenyl)-3-methylazetidine-3-carboxamide; 3-[(4-chloro-3-{6-methyl-1H-imidazo[4,5-b]pyridin-2-yl}phenyl)carbamoyl]propanoic acid; N-(4-chloro-3-{6-methyl-1H-imidazo[4,5-b]pyridin-2-yl}phenyl)-2-phenylacetamide; N-(4-chloro-3-{6-methyl-1H-imidazo[4,5-b]pyridin-2-yl}phenyl)-3-methyl-1H-1,2,4-triazole-5-carboxamide; N-(4-chloro-3-{6-methyl-1H-imidazo[4,5-b]pyridin-2-yl}phenyl)cyclopentanecarboxamide; N-(4-chloro-3-{6-methyl-1H-imidazo[4,5-b]pyridin-2-yl}phenyl)-1,3-thiazole-4-carboxamide; N-(4-chloro-3-{6-methyl-1H-imidazo[4,5-b]pyridin-2-yl}phenyl)pyrazine-2-carboxamide; N-(4-chloro-3-{6-methyl-1H-imidazo[4,5-b]pyridin-2-yl}phenyl)-1-methyl-1H-imidazole-5-carboxamide; N-(4-chloro-3-{6-methyl-1H-imidazo[4,5-b]pyridin-2-yl}phenyl)pyridine-3-carboxamide; N-(4-chloro-3-{6-methyl-1H-imidazo[4,5-b]pyridin-2-yl}phenyl)-4-methylthiophene-2-carboxamide; N-(4-chloro-3-{6-methyl-1H-imidazo[4,5-b]pyridin-2-yl}phenyl)-4-(trifluoromethoxy)benzamide; N-(4-chloro-3-{6-methyl-1H-imidazo[4,5-b]pyridin-2-yl}phenyl)-4-methoxybenzamide; N-(4-chloro-3-{6-methyl-1H-imidazo[4,5-b]pyridin-2-yl}phenyl)pyridine-4-carboxamide; N-(4-chloro-3-{6-methyl-1H-imidazo[4,5-b]pyridin-2-yl}phenyl)-1-methyl-1H-pyrazole-5-carboxamide; 2-fluoroethyl N-(4-chloro-3-{6-methyl-1H-imidazo[4,5-b]pyridin-2-yl}phenyl)carbamate; ethyl N-(4-chloro-3-{6-methyl-1H-imidazo[4,5-b]pyridin-2-yl}phenyl)carbamate; propan-2-yl N-(4-chloro-3-{6-methyl-1H-imidazo[4,5-b]pyridin-2-yl}phenyl)carbamate; ethyl N-(4-chloro-3-{6-methyl-1H-imidazo[4,5-b]pyridin-2-yl}phenyl)carbamate; cyclopentyl N-(4-chloro-3-{6-methyl-1H-imidazo[4,5-b]pyridin-2-yl}phenyl)carbamate; ethyl N-(4-chloro-3-{6-methyl-1H-imidazo[4,5-b]pyridin-2-yl}phenyl)carbamate; 2-methylpropyl N-(4-chloro-3-{6-methyl-1H-imidazo[4,5-b]pyridin-2-yl}phenyl)carbamate; 2-methoxyethyl N-(4-chloro-3-{6-methyl-1H-imidazo[4,5-b]pyridin-2-yl}phenyl)carbamate; cyclohexyl N-(4-chloro-3-{6-methyl-1H-imidazo[4,5-b]pyridin-2-yl}phenyl)carbamate; benzyl N-(4-chloro-3-{6-methyl-1H-imidazo[4,5-b]pyridin-2-yl}phenyl)carbamate; methyl N-(4-chloro-3-{6-methyl-1H-imidazo[4,5-b]pyridin-2-yl}phenyl)carbamate; 2,2,2-trifluoroethyl N-(4-chloro-3-{6-methyl-1H-imidazo[4,5-b]pyridin-2-yl}phenyl)carbamate; 1-(4-chloro-3-{6-methyl-1H-imidazo[4,5-b]pyridin-2-yl}phenyl)-3-[2-(dimethylamino)ethyl]urea; 1-(4-chloro-3-{6-methyl-1H-imidazo[4,5-b]pyridin-2-yl}phenyl)-3-[6-(diethylamino)hexyl]urea; 1-(4-chloro-3-{6-methyl-1H-imidazo[4,5-b]pyridin-2-yl}phenyl)-3-[6-(dimethylamino)hexyl]urea; (2R)-N-(4-chloro-3-{6-methyl-1H-imidazo[4,5-b]pyridin-2-yl}phenyl)-4,4-difluoro-2-(3-fluorophenyl)pyrrolidine-1-carboxamide; N-(4-chloro-3-{6-methyl-1H-imidazo[4,5-b]pyridin-2-yl}phenyl)-3-azabicyclo[3.1.0]hexane-3-carboxamide; 1-(4-chloro-3-{6-methyl-1H-imidazo[4,5-b]pyridin-2-yl}phenyl)-3-cyclopentyl-3-methylurea; 1-(4-chloro-3-{6-methyl-1H-imidazo[4,5-b]pyridin-2-yl}phenyl)-3-methyl-3-(oxolan-3-yl)urea; N-(4-chloro-3-{6-methyl-1H-imidazo[4,5-b]pyridin-2-yl}phenyl)-3-(dimethylamino)pyrrolidine-1-carboxamide; (3R)-N-(4-chloro-3-{6-methyl-1H-imidazo[4,5-b]pyridin-2-yl}phenyl)-3-fluoropyrrolidine-1-carboxamide; (3S)-N-(4-chloro-3-{6-methyl-1H-imidazo[4,5-b]pyridin-2-yl}phenyl)-3-fluoropyrrolidine-1-carboxamide; 3-{2-[bis(propan-2-yl)amino]ethyl}-1-(4-chloro-3-{6-methyl-1H-imidazo[4,5-b]pyridin-2-yl}phenyl)urea; N-(4-chloro-3-{6-methyl-1H-imidazo[4,5-b]pyridin-2-yl}phenyl)morpholine-4-carboxamide; 1-(4-chloro-3-{6-methyl-1H-imidazo[4,5-b]pyridin-2-yl}phenyl)-3-methylurea; N-(4-chloro-3-{6-methyl-1H-imidazo[4,5-b]pyridin-2-yl}phenyl)piperidine-1-carboxamide; 1-(4-chloro-3-{6-methyl-1H-imidazo[4,5-b]pyridin-2-yl}phenyl)-3-methoxy-3-methylurea; 3-(4-chloro-3-{6-methyl-1H-imidazo[4,5-b]pyridin-2-yl}phenyl)-1-methyl-1-phenylurea; 1-(4-chloro-3-{6-methyl-1H-imidazo[4,5-b]pyridin-2-yl}phenyl)-3-ethyl-3-methylurea; 1-(4-chloro-3-{6-methyl-1H-imidazo[4,5-b]pyridin-2-yl}phenyl)-3,3-dimethylurea; N-(4-chloro-3-{6-methyl-1H-imidazo[4,5-b]pyridin-2-yl}phenyl)-4-methylpiperazine-1-carboxamide; N-(4-chloro-3-{6-methyl-1H-imidazo[4,5-b]pyridin-2-yl}phenyl)pyrrolidine-1-carboxamide; N-(4-chloro-3-{6-methyl-1H-imidazo[4,5-b]pyridin-2-yl}phenyl)-2-oxoimidazolidine-1-carboxamide; 1-(4-chloro-3-{6-methyl-1H-imidazo[4,5-b]pyridin-2-yl}phenyl)-3-cyclobutylurea; 3-(4-chloro-3-{6-methyl-1H-imidazo[4,5-b]pyridin-2-yl}phenyl)-1-[4-(trifluoromethyl)phenyl]urea; 1-(4-chloro-3-{6-methyl-1H-imidazo[4,5-b]pyridin-2-yl}phenyl)-3-(propan-2-yl)urea; N-(4-chloro-3-{6-methyl-1H-imidazo[4,5-b]pyridin-2-yl}phenyl)-1- phenylmethanesulfonamide; N-(4-chloro-3-{6-methyl-1H-imidazo[4,5-b]pyridin-2-yl}phenyl)thiophene-2-sulfonamide; N-(4-chloro-3-{6-methyl-1H-imidazo[4,5-b]pyridin-2-yl}phenyl)-1-[4-(trifluoromethyl)phenyl]methanesulfonamide; N-(4-chloro-3-{6-methyl-1H-imidazo[4,5-b]pyridin-2-yl}phenyl)-3,5-dimethyl-1,2-oxazole-4-sulfonamide; N-(4-chloro-3-{6-methyl-1H-imidazo[4,5-b]pyridin-2-yl}phenyl)piperidine-1-sulfonamide; N-(4-chloro-3-{6-methyl-1H-imidazo[4,5-b]pyridin-2-yl}phenyl)-2-methylpropane-1-sulfonamide; 4-chloro-N-(4-chlorophenyl)-3-{6-methyl-1H-imidazo[4,5-b]pyridin-2-yl}aniline; 4-(4-chloro-3-{6-methyl-1H-imidazo[4,5-b]pyridin-2-yl}phenyl)morpholine; N-(4-chloro-3-{6-methyl-1H-imidazo[4,5-b]pyridin-2-yl}phenyl)-6-(1H-1,2,4-triazol-1-yl)pyridin-3-amine; 2-N-(4-chloro-3-{6-methyl-1H-imidazo[4,5-b]pyridin-2-yl}phenyl)-5-N,5-N-dimethylpyridine-2,5-diamine; N-(4-chloro-3-{6-methyl-1H-imidazo[4,5-b]pyridin-2-yl}phenyl)-5-(morpholin-4-yl)pyridin-2-amine; N-(4-chloro-3-{6-methyl-1H-imidazo[4,5-b]pyridin-2-yl}phenyl)-2-methanesulfonyl-1,2,3,4-tetrahydroisoquinolin-5-amine; N-(4-chloro-3-{6-methyl-1H-imidazo[4,5-b]pyridin-2-yl}phenyl)-5-methylpyridin-2-amine; 6-[(4-chloro-3-{6-methyl-1H-imidazo[4,5-b]pyridin-2-yl}phenyl)amino]pyridine-3-carbonitrile; N-(4-chloro-3-{6-methyl-1H-imidazo[4,5-b]pyridin-2-yl}phenyl)-2-(morpholin-4-yl)pyridin-3-amine; 6-benzyl-N-(4-chloro-3-{6-methyl-1H-imidazo[4,5-b]pyridin-2-yl}phenyl)-5,6,7,8-tetrahydro-2,6-naphthyridin-1-amine; 4-chloro-N-(furan-2-ylmethyl)-3-{6-methyl-1H-imidazo[4,5-b]pyridin-2-yl}aniline; N-(4-Fluoro-3-(6-methyl-3H-imidazo[4,5-b]pyridin-2-yl)phenyl)furan-2-carboxamide; 3-amino-N-(4-fluoro-3-{6-methyl-1H-imidazo[4,5-b]pyridin-2-yl}phenyl)propanamide; 4-[2-(dimethylamino)ethoxy]-N-(4-fluoro-3-{6-methyl-1H-imidazo[4,5-b]pyridin-2-yl}phenyl)benzamide; N-(4-fluoro-3-{6-methyl-1H-imidazo[4,5-b]pyridin-2-yl}phenyl)-1,2-oxazole-5-carboxamide; (2R,4R)-N-(4-fluoro-3-{6-methyl-1H-imidazo[4,5-b]pyridin-2-yl}phenyl)-4-hydroxypyrrolidine-2-carboxamide; N-(4-fluoro-3-{6-methyl-1H-imidazo[4,5-b]pyridin-2-yl}phenyl)acetamide; (2S)-N-(4-fluoro-3-{6-methyl-1H-imidazo[4,5-b]pyridin-2-yl}phenyl)pyrrolidine-2-carboxamide; N-(4-fluoro-3-{6-methyl-1H-imidazo[4,5-b]pyridin-2-yl}phenyl)pyrazolo[1,5-a]pyridine-2-carboxamide; 4-(dimethylamino)-N-(4-fluoro-3-{6-methyl-1H-imidazo[4,5-b]pyridin-2-yl}phenyl)butanamide; N-{4-chloro-3-[6-(trifluoromethyl)-1H-imidazo[4,5-b]pyridin-2-yl]phenyl}furan-2-carboxamide; N-{4-chloro-3-[6-(trifluoromethyl)-1H-imidazo[4,5-b]pyridin-2-yl]phenyl}-5-[(dimethylamino)methyl]furan-2-carboxamide; 2-chloro-N-{4-chloro-3-[6-(trifluoromethyl)-1H-imidazo[4,5-b]pyridin-2-yl]phenyl}benzamide; N-{4-chloro-3-[6-(trifluoromethyl)-1H-imidazo[4,5-b]pyridin-2-yl]phenyl}-5-methylfuran-2-carboxamide; N-{4-chloro-3-[6-(trifluoromethyl)-1H-imidazo[4,5-b]pyridin-2-yl]phenyl}-2-(3-chlorophenyl)acetamide; N-{4-chloro-3-[6-(trifluoromethyl)-1H-imidazo[4,5-b]pyridin-2-yl]phenyl}-5-cyanofuran-2-carboxamide; N-{4-chloro-3-[6-(trifluoromethyl)-1H-imidazo[4,5-b]pyridin-2-yl]phenyl}cyclopentanecarboxamide; N-{4-chloro-3-[6-(trifluoromethyl)-1H-imidazo[4,5-b]pyridin-2-yl]phenyl}-5-fluoropyridine-3-carboxamide; N-{4-chloro-3-[6-(trifluoromethyl)-1H-imidazo[4,5-b]pyridin-2-yl]phenyl}-5-fluorofuran-2-carboxamide; N-{4-chloro-3-[6-(trifluoromethyl)-1H-imidazo[4,5-b]pyridin-2-yl]phenyl}pyrazine-2-carboxamide; N-(4-chloro-3-{6-cyano-1H-imidazo[4,5-b]pyridin-2-yl}phenyl)furan-2-carboxamide; propan-2-yl N-(4-chloro-3-{6-cyano-1H-imidazo[4,5-b]pyridin-2-yl}phenyl)carbamate; propan-2-yl 2-(2-chloro-5-{[(propan-2-yloxy)carbonyl]amino}phenyl)-6-cyano-1H-imidazo[4,5-b]pyridine-1-carboxylate; ethyl N-(4-chloro-3-{6-cyano-1H-imidazo[4,5-b]pyridin-2-yl}phenyl)carbamate; methyl N-(4-chloro-3-{6-cyano-1H-imidazo[4,5-b]pyridin-2-yl}phenyl)carbamate; N-(4-chloro-3-{6-phenyl-1H-imidazo[4,5-b]pyridin-2-yl}phenyl)pyrrolidine-1-carboxamide; N-(4-chloro-3-{6-[4-(methylamino)phenyl]-1H-imidazo[4,5-b]pyridin-2-yl}phenyl)pyrrolidine-1-carboxamide; N-{4-chloro-3-[6-(4-fluorophenyl)-1H-imidazo[4,5-b]pyridin-2-yl]phenyl}pyrrolidine-1-carboxamide; N-(4-chloro-3-{6-[4-(piperazin-1-yl)phenyl]-1H-imidazo[4,5-b]pyridin-2-yl}phenyl)pyrrolidine-1-carboxamide; N-[4-fluoro-3-(6-{4-[2-(morpholin-4-yl)ethoxy]phenyl}-1H-imidazo[4,5-b]pyridin-2-yl)phenyl]pyrrolidine-1-carboxamide; methyl N-[4-(2-{2-chloro-5-[(pyrrolidin-1-yl)carbonylamino]phenyl}-1H-imidazo[4,5-b]pyridin-6-yl)phenyl]carbamate; N-{4-chloro-3-[6-(4-methanesulfonylphenyl)-1H-imidazo[4,5-b]pyridin-2-yl]phenyl}pyrrolidine-1-carboxamide; N-(4-fluoro-3-{6-[1-(piperidin-4-yl)-1H-pyrazol-4-yl]-1H-imidazo[4,5-b]pyridin-2-yl}phenyl)pyrrolidine-1-carboxamide; N-[4-chloro-3-(6-{4-[2-(morpholin-4-yl)ethoxy]phenyl}-1H-imidazo[4,5-b]pyridin-2-yl)phenyl]pyrrolidine-1-carboxamide; N-{4-chloro-3-[6-(thiophen-3-yl)-1H-imidazo[4,5-b]pyridin-2-yl]phenyl}pyrrolidine-1-carboxamide; N-[4-chloro-3-(6-{3-[2-(morpholin-4-yl)ethoxy]phenyl}-1H-imidazo[4,5-b]pyridin-2-yl)phenyl]pyrrolidine-1-carboxamide; N-[4-chloro-3-(6-{4-[3-(morpholin-4-yl)propoxy]phenyl}-1H-imidazo[4,5-b]pyridin-2-yl)phenyl]pyrrolidine-1-carboxamide; N-(4-chloro-3-{6-[4-(2-methoxyethoxy)phenyl]-1H-imidazo[4,5-b]pyridin-2-yl}phenyl)pyrrolidine-1-carboxamide; N-(3-{6-[4-(1-amino-2-methylpropan-2-yl)phenyl]-1H-imidazo[4,5-b]pyridin-2-yl}-4-chlorophenyl)pyrrolidine-1-carboxamide; N-[4-chloro-3-(6-{4-[2-hydroxy-3-(morpholin-4-yl)propoxy]phenyl}-1H-imidazo[4,5-b]pyridin-2-yl)phenyl]pyrrolidine-1-carboxamide; N-{4-chloro-3-[6-(1-{[2-(trimethylsilyl)ethoxy]methyl}-1H-imidazol-4-yl)-1H-imidazo[4,5-b]pyridin-2-yl]phenyl}pyrrolidine-1-carboxamide; N-{4-chloro-3-[6-(1H-imidazol-4-yl)-1H-imidazo[4,5-b]pyridin-2-yl]phenyl}pyrrolidine-1-carboxamide; tert-butyl N-[4-(2-{2-chloro-5-[(pyrrolidin-1-yl)carbonylamino]phenyl}-1H-imidazo[4,5-b]pyridin-6-yl)phenyl]-N-methylcarbamate; N-(4-fluoro-3-{6-phenyl-1H-imidazo[4,5-b]pyridin-2-yl}phenyl)pyrrolidine-1-carboxamide; N-(4-fluoro-3-{6-[4-(oxiran-2-ylmethoxy)phenyl]-1H-imidazo[4,5-b]pyridin-2-yl}phenyl)pyrrolidine-1-carboxamide; N-[4-fluoro-3-(6-{4-[2-(4-methylpiperazin-1-yl)ethoxy]phenyl}-1H-imidazo[4,5-b]pyridin-2-yl)phenyl]pyrrolidine-1-carboxamide; N-(4-fluoro-3-{6-[4-(2-methoxyethoxy)phenyl]-1H-imidazo[4,5-b]pyridin-2-yl}phenyl)pyrrolidine-1-carboxamide; N-{4-fluoro-3-[6-(2-methoxyphenyl)-3H-imidazo[4,5-b]pyridin-2-yl]phenyl}pyrrolidine-1-carboxamide; N-{3-[6-(3-chlorophenyl)-3H-imidazo[4,5-b]pyridin-2-yl]-4-fluorophenyl}pyrrolidine-1-carboxamide; N-{4-fluoro-3-[6-(3-methylphenyl)-3H-imidazo[4,5-b]pyridin-2-yl]phenyl}pyrrolidine-1-carboxamide; N-{3-[6-(3-aminophenyl)-3H-imidazo[4,5-b]pyridin-2-yl]-4-fluorophenyl}pyrrolidine-1-carboxamide; N-{4-fluoro-3-[6-(furan-3-yl)-3H-imidazo[4,5-b]pyridin-2-yl]phenyl}pyrrolidine-1-carboxamide; N-{4-fluoro-3-[6-(thiophen-3-yl)-3H-imidazo[4,5-b]pyridin-2-yl]phenyl}pyrrolidine-1-carboxamide; N-{4-fluoro-3-[6-(pyridin-3-yl)-3H-imidazo[4,5-b]pyridin-2-yl]phenyl}pyrrolidine-1-carboxamide; N-(3-{6-bromo-3H-imidazo[4,5-b]pyridin-2-yl}-4-fluorophenyl)-2,5-dihydro- 1H-pyrrole-1-carboxamide; N-{4-fluoro-3-[6-(4-fluoro-3-methylphenyl)-3H-imidazo[4,5-b]pyridin-2-yl]phenyl}pyrrolidine-1-carboxamide; N-{4-fluoro-3-[6-(thiophen-2-yl)-3H-imidazo[4,5-b]pyridin-2-yl]phenyl}pyrrolidine-1-carboxamide; N-{4-fluoro-3-[6-(3-methanesulfonamidophenyl)-3H-imidazo[4,5-b]pyridin-2-yl]phenyl}pyrrolidine-1-carboxamide; N-{3-[6-(6-chloropyridin-3-yl)-3H-imidazo[4,5-b]pyridin-2-yl]-4-fluorophenyl}pyrrolidine-1-carboxamide; N-{3-[6-(2-chloropyridin-4-yl)-3H-imidazo[4,5-b]pyridin-2-yl]-4-fluorophenyl}pyrrolidine-1-carboxamide; N-{4-fluoro-3-[6-(5-methylpyridin-3-yl)-3H-imidazo[4,5-b]pyridin-2-yl]phenyl}pyrrolidine-1-carboxamide; N-{4-fluoro-3-[6-(6-methoxypyridin-3-yl)-3H-imidazo[4,5-b]pyridin-2-yl]phenyl}pyrrolidine-1-carboxamide; N-(4-fluoro-3-{6-[2-(pyrrolidin-1-yl)pyridin-4-yl]-3H-imidazo[4,5-b]pyridin-2-yl}phenyl)pyrrolidine-1-carboxamide; N-{4-fluoro-3-[6-(pyrimidin-5-yl)-3H-imidazo[4,5-b]pyridin-2-yl]phenyl}pyrrolidine-1-carboxamide; N-{3-[6-(5-chloropyridin-3-yl)-3H-imidazo[4,5-b]pyridin-2-yl]-4-fluorophenyl}pyrrolidine-1-carboxamide; N-{4-fluoro-3-[6-(2-methoxypyrimidin-5-yl)-3H-imidazo[4,5-b]pyridin-2-yl]phenyl}pyrrolidine-1-carboxamide; tert-butyl N-[4-(2-{2-chloro-5-[(pyrrolidin-1-yl)carbonylamino]phenyl}-1H-imidazo[4,5-b]pyridin-6-yl)phenyl]-N-methylcarbamate; propan-2-yl N-(4-chloro-3-{6-phenyl-1H-imidazo[4,5-b]pyridin-2-yl}phenyl)carbamate; propan-2-yl N-{3-[6-(2-aminophenyl)-1H-imidazo[4,5-b]pyridin-2-yl]-4-chlorophenyl}carbamate; propan-2-yl N-{4-chloro-3-[6-(2-{[(propan-2-yloxy)carbonyl]amino}phenyl)-1H-imidazo[4,5-b]pyridin-2-yl]phenyl}carbamate; propan-2-yl 2-(2-chloro-5-{[(propan-2-yloxy)carbonyl]amino}phenyl)-6-(2-{[(propan-2-yloxy)carbonyl]amino}phenyl)-1H-imidazo[4,5-b]pyridine-1-carboxylate; propan-2-yl N-{4-[2-(2-chloro-5-{[(propan-2-yloxy)carbonyl]amino}phenyl)-1H-imidazo[4,5-b]pyridin-6-yl]phenyl}carbamate; propan-2-yl N-(3-{6-[4-(2-aminoacetamido)phenyl]-1H-imidazo[4,5-b]pyridin-2-yl}-4-chlorophenyl)carbamate; propan-2-yl N-(3-{6-[4-(3-aminopropanamido)phenyl]-1H-imidazo[4,5-b]pyridin-2-yl}-4-chlorophenyl)carbamate; propan-2-yl N-(3-{6-[2-(2-aminoacetamido)phenyl]-1H-imidazo[4,5-b]pyridin-2-yl}-4-chlorophenyl)carbamate; methyl N-{4-[2-(2-chloro-5-{[(propan-2-yloxy)carbonyl]amino}phenyl)-1H-imidazo[4,5-b]pyridin-6-yl]phenyl}carbamate; propan-2-yl N-(3-{6-[2-(3-aminopropanamido)phenyl]-1H-imidazo[4,5-b]pyridin-2-yl}-4-chlorophenyl)carbamate; methyl N-[4-(2-{2-chloro-5-[(3,3-difluoropyrrolidin-1-yl)carbonylamino]phenyl}-1H-imidazo[4,5-b]pyridin-6-yl)phenyl]carbamate; methyl N-[4-(2-{5-[(azetidin-1-yl)carbonylamino]-2-chlorophenyl}-1H-imidazo[4,5-b]pyridin-6-yl)phenyl]carbamate; N-(4-chloro-3-{6-[4-(methylamino)phenyl]-1H-imidazo[4,5-b]pyridin-2-yl}phenyl)-4-methylthiophene-2-carboxamide; N-(4-chloro-3-{6-[4-(methylamino)phenyl]-1H-imidazo[4,5-b]pyridin-2-yl}phenyl)cyclopentanecarboxamide; N-(4-chloro-3-{6-[4-(methylamino)phenyl]-1H-imidazo[4,5-b]pyridin-2-yl}phenyl)-5-[(dimethylamino)methyl]furan-2-carboxamide; N-(4-chloro-3-{6-[4-(methylamino)phenyl]-1H-imidazo[4,5-b]pyridin-2-yl}phenyl)pyrazine-2-carboxamide; N-(4-chloro-3-{6-[4-(methylamino)phenyl]-1H-imidazo[4,5-b]pyridin-2-yl}phenyl)-1,3-thiazole-4-carboxamide; 2-methoxyethyl N-(4-chloro-3-{6-[4-(methylamino)phenyl]-1H-imidazo[4,5-b]pyridin-2-yl}phenyl)carbamate; ethyl N-(4-chloro-3-{6-[4-(methylamino)phenyl]-1H-imidazo[4,5-b]pyridin-2-yl}phenyl)carbamate; N-{3-[6-(aminomethyl)-1H-imidazo[4,5-b]pyridin-2-yl]-4-chlorophenyl}furan-2-carboxamide; N-(3-(6-chloro-1H-imidazo[4,5-b]pyridin-2-yl)-4-fluorophenyl)pyrrolidine-1-carboxamide; 1-(3-{6-chloro-1H-imidazo[4,5-b]pyridin-2-yl}-4-fluorophenyl)-3,3-dimethylurea; 1-(3-{6-chloro-1H-imidazo[4,5-b]pyridin-2-yl}-4-fluorophenyl)-3,3-diethylurea; 3-(3-{6-chloro-1H-imidazo[4,5-b]pyridin-2-yl}-4-fluorophenyl)-1-[4-(trifluoromethyl)phenyl]urea; N-(3-{6-chloro-1H-imidazo[4,5-b]pyridin-2-yl}-4-fluorophenyl)furan-2-carboxamide; N-(3-{6-chloro-1H-imidazo[4,5-b]pyridin-2-yl}-4-fluorophenyl)-2,2-dimethylpropanamide; N-(3-{6-chloro-1H-imidazo[4,5-b]pyridin-2-yl}-4-fluorophenyl)-3-(piperidin-1-yl)propanamide; N-(3-{6-bromo-3H-imidazo[4,5-b]pyridin-2-yl}-4-fluorophenyl)-2-oxoimidazolidine-1-carboxamide; 1-(3-{6-bromo-3H-imidazo[4,5-b]pyridin-2-yl}-4-fluorophenyl)-3,3-diethylurea; 1-(3-{6-bromo-1H-imidazo[4,5-b]pyridin-2-yl}-4-fluorophenyl)-3,3-bis(propan-2-yl)urea; N-(3-{6-bromo-3H-imidazo[4,5-b]pyridin-2-yl}-4-fluorophenyl)-3,3-difluoropyrrolidine-1-carboxamide; N-(3-{6-bromo-3H-imidazo[4,5-b]pyridin-2-yl}-4-fluorophenyl)-2,5-dihydro-1H-pyrrole-1-carboxamide; N-(3-{6-bromo-1H-imidazo[4,5-b]pyridin-2-yl}-4-fluorophenyl)morpholine-4-carboxamide; N-(3-{6-bromo-3H-imidazo[4,5-b]pyridin-2-yl}-4-fluorophenyl)cyclopropanecarboxamide; N-(3-{6-bromo-3H-imidazo[4,5-b]pyridin-2-yl}-4-fluorophenyl)cyclopentanecarboxamide; N-(3-{6-bromo-1H-imidazo[4,5-b]pyridin-2-yl}-4-fluorophenyl)-1H-pyrazole-3-carboxamide; N-(3-{6-bromo-1H-imidazo[4,5-b]pyridin-2-yl}-4-chlorophenyl)-1,3-oxazole-4-carboxamide; ethyl N-(3-{6-bromo-1H-imidazo[4,5-b]pyridin-2-yl}-4-chlorophenyl)carbamate; 2-methoxyethyl N-(3-{6-bromo-1H-imidazo[4,5-b]pyridin-2-yl}-4-chlorophenyl)carbamate; N-(3-{6-bromo-1H-imidazo[4,5-b]pyridin-2-yl}-4-chlorophenyl)-5-[(dimethylamino)methyl]furan-2-carboxamide; N-(3-{6-bromo-1H-imidazo[4,5-b]pyridin-2-yl}-4-chlorophenyl)-5-fluorofuran-2-carboxamide; N-(3-{6-bromo-1H-imidazo[4,5-b]pyridin-2-yl}-4-chlorophenyl)cyclopentanecarboxamide; N-(3-{6-bromo-1H-imidazo[4,5-b]pyridin-2-yl}-4-chlorophenyl)pyrazine-2-carboxamide; N-{4-chloro-3-[6-(2-oxo-2,3-dihydro-1H-indol-5-yl)-1H-imidazo[4,5-b]pyridin-2-yl]phenyl}pyrazine-2-carboxamide; N-{4-chloro-3-[6-(2-oxo-2,3-dihydro-1H-indol-5-yl)-1H-imidazo[4,5-b]pyridin-2-yl]phenyl}cyclopentanecarboxamide; ethyl N-{4-chloro-3-[6-(2-oxo-2,3-dihydro-1H-indol-5-yl)-1H-imidazo[4,5-b]pyridin-2-yl]phenyl}carbamate; 2-methoxyethyl N-{4-chloro-3-[6-(2-oxo-2,3-dihydro-1H-indol-5-yl)-1H-imidazo[4,5-b]pyridin-2-yl]phenyl}carbamate; N-(4-fluoro-3-{6-phenyl-1H-imidazo[4,5-b]pyridin-2-yl}phenyl)-5-methylfuran-2-carboxamide; N-{4-fluoro-3-[6-(thiophen-3-yl)-1H-imidazo[4,5-b]pyridin-2-yl]phenyl}-5-methylfuran-2-carboxamide; N-(3-{5-chloro-3H-imidazo[4,5-b]pyridin-2-yl}-4-fluorophenyl)furan-2-carboxamide; N-(4-fluoro-3-{6-fluoro-3H-imidazo[4,5-b]pyridin-2-yl}phenyl)furan-2-carboxamide; N-(3-{6,7-dichloro-3H-imidazo[4,5-b]pyridin-2-yl}-4-fluorophenyl)furan-2-carboxamide; N-{3-[6-bromo-3-(methoxymethyl)-3H-imidazo[4,5-b]pyridin-2-yl]-4-chlorophenyl}pyrrolidine-1-carboxamide; N-{3-[6-bromo-1-(methoxymethyl)-1H-imidazo[4,5-b]pyridin-2-yl]-4-chlorophenyl}pyrrolidine-1-carboxamide; N-(3-{6-bromo-1-[2-(dimethylamino)ethyl]-1H-imidazo[4,5-b]pyridin-2-yl}-4-chlorophenyl)pyrrolidine-1-carboxamide; N-(3-{6-bromo-1-[2-(morpholin-4-yl)ethyl]-1H-imidazo[4,5-b]pyridin-2-yl}-4-chlorophenyl)pyrrolidine-1-carboxamide; 3-[4-fluoro-3-(6-{4-[2-(morpholin-4-yl)ethyl]phenyl}-[1,3]oxazolo[4,5-b]pyridin-2-yl)phenyl]-1-[4-(trifluoromethyl)phenyl]urea; 3-(3-{6-[4-(dimethylamino)phenyl]-[1,3]oxazolo[4,5-b]pyridin-2-yl}-4-fluorophenyl)-

1-[4-(trifluoromethyl)phenyl]urea; 3-{4-fluoro-3-[6-(6-{[2-(morpholin-4-yl)ethyl]amino}pyridin-3-yl)-[1,3]oxazolo[4,5-b]pyridin-2-yl]phenyl}-1-[4-(trifluoromethyl)phenyl]urea; 3-(4-fluoro-3-{6-[4-(morpholin-4-yl)phenyl]-[1,3]oxazolo[4,5-b]pyridin-2-yl}phenyl)-1-[4-(trifluoromethyl)phenyl]urea; 3-(4-fluoro-3-{6-[4-(methylamino)phenyl]-[1,3]oxazolo[4,5-b]pyridin-2-yl}phenyl)-1-[4-(trifluoromethyl)phenyl]urea; 3-{4-fluoro-3-[6-(3-methyl-1H-pyrazol-4-yl)-[1,3]oxazolo[4,5-b]pyridin-2-yl]phenyl}-1-[4-(trifluoromethyl)phenyl]urea; 3-(4-fluoro-3-{6-[4-(morpholin-4-ylmethyl)phenyl]-[1,3]oxazolo[4,5-b]pyridin-2-yl}phenyl)-1-[4-(trifluoromethyl)phenyl]urea; propan-2-yl N-(4-{2-[2-fluoro-5-({[4-(trifluoromethyl)phenyl]carbamoyl}amino)phenyl]-[1,3]oxazolo[4,5-b]pyridin-6-yl}phenyl)carbamate; 3-{4-fluoro-3-[6-(piperidin-1-yl)-[1,3]oxazolo[4,5-b]pyridin-2-yl]phenyl}-1-[4-(trifluoromethyl)phenyl]urea; 3-[4-fluoro-3-(6-{4-[2-(morpholin-4-yl)ethoxy]phenyl}-[1,3]oxazolo[4,5-b]pyridin-2-yl)phenyl]-1-[4-(trifluoromethyl)phenyl]urea; 3-(4-fluoro-3-{6-[4-(piperidin-1-yl)phenyl]-[1,3]oxazolo[4,5-b]pyridin-2-yl}phenyl)-1-[4-(trifluoromethyl)phenyl]urea; 3-{3-[6-(6-aminopyridin-3-yl)-[1,3]oxazolo[4,5-b]pyridin-2-yl]-4-fluorophenyl}-1-[4-(trifluoromethyl)phenyl]urea; N-(4-{2-[2-fluoro-5-({[4-(trifluoromethyl)phenyl]carbamoyl}amino)phenyl]-[1,3]oxazolo[4,5-b]pyridin-6-yl}phenyl)acetamide; methyl N-(4-{2-[2-fluoro-5-({[4-(trifluoromethyl)phenyl]carbamoyl}amino)phenyl]-[1,3]oxazolo[4,5-b]pyridin-6-yl}phenyl)carbamate; 3-(3-{6-[6-(dimethylamino)pyridin-3-yl]-[1,3]oxazolo[4,5-b]pyridin-2-yl}-4-fluorophenyl)-1-[4-(trifluoromethyl)phenyl]urea; N-(3-{6-bromo-[1,3]oxazolo[4,5-b]pyridin-2-yl}-4-fluorophenyl)-5-ethyl-1,3,4-oxadiazole-2-carboxamide; N-(3-{6-bromo-[1,3]oxazolo[4,5-b]pyridin-2-yl}-4-fluorophenyl)-3-ethyl-1,2,4-oxadiazole-5-carboxamide; N-(3-{6-bromo-[1,3]oxazolo[4,5-b]pyridin-2-yl}-4-fluorophenyl)-5-(propan-2-yl)-1,3,4-oxadiazole-2-carboxamide; N-(3-{6-bromo-[1,3]oxazolo[4,5-b]pyridin-2-yl}-4-fluorophenyl)-5-tert-butyl-1,3,4-oxadiazole-2-carboxamide; N-(3-{6-bromo-[1,3]oxazolo[4,5-b]pyridin-2-yl}-4-fluorophenyl)-1,3-oxazole-5-carboxamide; N-(3-{6-bromo-[1,3]oxazolo[4,5-b]pyridin-2-yl}-4-fluorophenyl)-4-methyl-1,3-oxazole-5-carboxamide; N-(3-{6-bromo-[1,3]oxazolo[4,5-b]pyridin-2-yl}-4-fluorophenyl)-1,3-oxazole-4-carboxamide; N-{4-fluoro-3-[6-(4-fluorophenyl)-[1,3]oxazolo[4,5-b]pyridin-2-yl]phenyl}furan-2-carboxamide; N-{4-fluoro-3-[6-(4-phenylphenyl)-[1,3]oxazolo[4,5-b]pyridin-2-yl]phenyl}furan-2-carboxamide; N-(3-{6-chloro-3H-imidazo[4,5-b]pyridin-2-yl}-4-fluorophenyl)furan-2-carboxamide; methyl N-(4-{2-[2-fluoro-5-(furan-2-amido)phenyl]-[1,3]oxazolo[4,5-b]pyridin-6-yl}phenyl)carbamate; N-(4-fluoro-3-{6-phenyl-[1,3]oxazolo[4,5-b]pyridin-2-yl}phenyl)pyrrolidine-1-carboxamide; N-(4-chloro-3-{6-phenyl-[1,3]oxazolo[4,5-b]pyridin-2-yl}phenyl)furan-2-carboxamide; methyl N-(4-{2-[2-chloro-5-(furan-2-amido)phenyl]-[1,3]oxazolo[4,5-b]pyridin-6-yl}phenyl)carbamate; N-(4-chloro-3-{6-methyl-[1,3]oxazolo[4,5-b]pyridin-2-yl}phenyl)furan-2-carboxamide; N-(4-chloro-3-{6-ethyl-[1,3]oxazolo[4,5-b]pyridin-2-yl}phenyl)furan-2-carboxamide; 4-fluoro-N,N-dimethyl-3-(6-{4-[2-(morpholin-4-yl)ethoxy]phenyl}-[1,3]oxazolo[4,5-b]pyridin-2-yl)aniline; and 4-fluoro-N-methyl-3-(6-{4-[2-(morpholin-4-yl)ethoxy]phenyl}-[1,3]oxazolo[4,5-b]pyridin-2-yl)aniline.

It is noted that the compounds of the present invention may be in the form of a pharmaceutically acceptable salt. It is further note that the compounds of the present invention may be a mixture of stereoisomers, or the compound may comprise a single stereoisomer.

Further compounds of the invention are detailed in the Examples, infra.

In another aspect, the present invention is directed to a pharmaceutical composition which includes as an active ingredient a compound according to any one of the above embodiments and variations in combination with a pharmaceutically acceptable carrier, diluent or excipient.

In another embodiment, the pharmaceutical composition is a solid formulation adapted for oral administration. In another embodiment, the composition is a liquid formulation adapted for oral administration. In yet another embodiment, the composition is a tablet. In still another embodiment, the composition is a liquid formulation adapted for parenteral administration.

In yet another embodiment, the pharmaceutical composition is adapted for administration by a route selected from the group consisting of orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, and intrathecally.

In another aspect, the present application is directed to a compound or a pharmaceutical composition according to any one of the above embodiments and variations for use in a therapeutic application.

In another aspect, the present application is directed to a compound or a pharmaceutical composition according to any one of the above embodiments and variations for use as a medicament.

In yet another aspect, the present invention is directed to a method for treating, preventing, inhibiting, ameliorating, or eradicating the pathology and/or symptomology of a disease caused by a parasite. The method involves administering to a subject a therapeutically effective amount of a compound or a pharmaceutical composition according to the above embodiments and variations.

In one embodiment of the method of the invention, the disease being treated is Leishmaniasis, Human African Trypanosomiasis, or Chagas disease.

In one embodiment of the method of the invention, the disease being treated is Leishmaniasis caused by the parasite *Leishmania donovani, Leishmania infantum, Leishmania braziliensis, Leishmania panamensis, Leishmania guayanensis, Leishmania amazonensis, Leishmania mexicana, Leishmania tropica*, or *Leishmania major*.

In a embodiment, the disease being treated is visceral Leishmaniasis caused by the parasite *Leishmania donovani*.

In another embodiment, the disease being treated is Human African Trypanosomiasis caused by *Trypanosoma brucei*, particularly, by the sub-species *Tb. gambiense* or *Tb. rhodesiense*.

In still another embodiment of the method of the invention, the disease being treated is Chagas disease, (also call American Trypanosomiasis) caused by *Trypanosoma cruzi*.

In the above method of the invention, the compounds or pharmaceutical compositions may be administered prior to, simultaneously with, or after a second agent. The second agent can be other drugs that are known for treating Leishmaniasis, Human African Trypanosomiasis, or Chagas diseases. In one particular variation for treating Leishmaniasis, the second agent is selected from meglumine antimoniate, stibogluconate, Amphotericin, Miltefosine and paromomycin. In another variation, for treating Human African Trypanosomiasis, the second agent is selected from pentamidine, suramin, melarsoprol, and eflornithine. In another particular variation of the method, for treating Chagas disease, the second agent is selected from benznidazole, nifurtimox or Amphotericin b.

In another aspect, the invention is directed to a compound, salt, steroisomer, or pharmaceutical composition thereof, according to any one of the above embodiments or variation, for treating, preventing, inhibiting, ameliorating, or eradicating the pathology and/or symptomology of a disease caused by the parasite *Leishmania donovani, Leishmania infantum, Leishmania braziliensis, Leishmania panamensis, Leishmania guayanensis, Leishmania amazonensis, Leishmania mexicana, Leishmania tropica, Leishmania major, Trypanosoma cruzi,* or *Trypanosoma brucei.* In one embodiment, the disease is visceral Leishmaniasis caused by *Leishmania donovani.* In another embodiment, the disease is Human African Trypanosomiasis caused by *Trypanosoma brucei.* In yet another embodiment, the disease is Chagas disease caused by *Trypanosoma cruzi.*

In still another aspect, the present invention is directed to the use of the compound, or a salt, a stereoisomer, or a pharmaceutical composition thereof, according to the any one of the above embodiments or variations in the manufacture of a medicament for treating, preventing, inhibiting, ameliorating, or eradicating the pathology and/or symptomology of a disease caused by *Leishmania donovani, Leishmania infantum, Leishmania braziliensis, Leishmania panamensis, Leishmania guayanensis, Leishmania amazonensis, Leishmania mexicana, Leishmania tropica, Leishmania major, Trypanosoma cruzi,* or *Trypanosoma brucei.* In one embodiment, the medicament is for treating visceral Leishmaniasis caused by *Leishmania donovani.* In another embodiment, the medicament is for treating Human African Trypanosomiasis caused by *Trypanosoma brucei.* In yet another embodiment, the medicament is for treating Chagas disease caused by *Trypanosoma cruzi.*

The medicament, in addition to the compound of the invention, may further include a second agent. The second agent may be other drugs that are known for treating Leishmaniasis, Human African Trypanosomiasis, or Chagas diseases. In one particular variation of the medicament, for treating Leishmaniasis, the second agent is selected from meglumine antimoniate, stibogluconate, Amphotericin, Miltefosine and paromomycin. In another particular variation of the medicament, for treating Human African Trypanosomiasis, the second agent is selected from pentamidine, suramin, melarsoprol, and eflornithine. In yet another particular variation of the medicament, for treating Chagas disease, the second agent is selected from benznidazole, nifurtimox or Amphotericin b.

In another aspect, the invention is related to a kit which comprises a compound of any one of the above embodiments and variations, and optionally a second therapeutic agent. In one particular variation, the kit comprises the compound in a multiple dose form.

Enumerated Embodiments

Various enumerated embodiments of the invention are described herein. It will be recognized that features specified in each embodiment may be combined with other specified features to provide further embodiments of the present invention.

In a first embodiment, the invention provides a compound of the formula (I), or a pharmaceutical acceptable salt, tautomer or stereoisomer thereof,

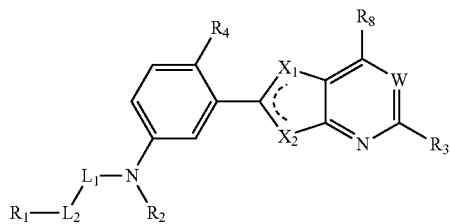

wherein
$X_1$ is N or O, or $NR_5$;
$X_2$ is N or $NR_7$, provided that one of $X_1$ and $X_2$ is N;
W is $CR_6$ or N;
$L_1$ is a bond, —C(O)— or —S(O)$_2$—,
$L_2$ is selected from a bond, —$CR_{9a}R_{9b}$—, —$NR_{10}$—, and —O—, wherein $R_{9a}$ is hydrogen, halo or $C_{1-4}$alkyl, $R_{9b}$ is selected from hydrogen, halo, hydroxyl, $C_{1-4}$alkyl, and $C_{1-4}$alkoxy; and $R_{10}$ is hydrogen or $C_{1-4}$alkyl;
$R_1$ is selected from hydrogen, $C_{1-6}$alkyl, $C_{1-4}$alkoxy, $C_{6-10}$aryl, $C_{5-10}$heteroaryl, $C_{3-7}$cycloalkyl, $C_{5-6}$heterocycloalkyl, and $C_{9-10}$heterocyclyl, wherein
the $C_{1-6}$alkyl or $C_{1-4}$alkoxy is unsubstituted or substituted with 1 to 2 substituents independently selected from halo, hydroxy, $C_{1-4}$alkoxy, $C_{5-6}$aryloxy, hydroxycarbonyl, $C_{1-4}$alkoxycarbonyl, amino, $C_{1-4}$alkyamino, $C_{1-4}$alkoxycarbonylamino, $C_{5-6}$aryl, and $C_{5-6}$heterocycloalkyl; and
the $C_{6-10}$aryl and $C_{5-10}$heteroaryl, $C_{3-7}$cycloalkyl, $C_{5-6}$heterocycloalkyl or $C_{9-10}$heterocyclyl is unsubstituted or substituted with 1 to 3 substituents independently selected from halo, cyano, hydroxyl, oxo, $C_{1-4}$alkyl, benzyl, halo$C_{1-4}$alkyl, $C_{1-4}$alkoxy$C_{1-4}$alkyl, $C_{1-4}$alkylamino$C_{1-4}$alkyl, $C_{1-4}$alkoxy, halo$C_{1-4}$alkoxy, amino, $C_{1-4}$alkylamino, $C_{1-4}$alkoxycarbonyl, $C_{1-4}$alkylthio, $C_{1-4}$alkylsulfonyl, $C_{5-6}$heteroaryl, halo$C_{5-6}$heteroaryl, $C_{3-6}$cycloalkyl, and $C_{5-6}$heterocycloalkyl; or —N($R_2$)-$L_1$-$L_2$-$R_1$ together forms a nitro group;
$R_2$ is hydrogen, $C_{1-4}$alkyl or —C(O)$C_{5-6}$heteroaryl;
$R_3$ is hydrogen, halo or $C_{1-4}$alkyl;
$R_4$ is selected from hydrogen, halo, $C_{1-4}$alkyl, halo$C_{1-4}$alkyl, $C_{1-4}$alkylsulfonyl, $C_{5-6}$heteroaryl, and $C_{5-6}$heterocycloalkyl;
$R_5$ is selected from hydrogen, $C_{1-4}$alkyl, —C(O)O$C_{1-4}$alkyl, wherein the $C_{1-4}$alkyl portion of $C_{1-4}$alkyl or —C(O)O$C_{1-4}$alkyl is unsubstituted or substituted by amino, $C_{1-4}$alkylamino, or $C_{5-6}$heterocycloalkyl;
$R_6$ is selected from halo, cyano, $C_{1-4}$alkyl, $C_{1-4}$alkenyl, $C_{1-4}$alkoxy, $C_{1-4}$alkylsulfonyl, $C_{3-6}$cycloalkylsulfonyl, $C_{1-4}$alkylphosphinyl oxide, $C_{1-4}$alkylcarbonylamino, phenyl, $C_{5-6}$heteroaryl, $C_{5-6}$heteraryl, $C_{4-6}$heterocycloalkyl, and $C_{6-10}$heterocyclyl, wherein
the $C_{1-6}$alkyl, $C_{1-4}$alkenyl or $C_{1-4}$alkoxy of $R_6$ is unsubstituted or substituted by 1 to 2 substituents independently selected from halo, amino, $C_{1-4}$alkylamino, and hydroxyl-substituted $C_{1-4}$alkylamino,
the pheny or $C_{5-6}$heteroaryl of $R_6$ is unsubstituted or substituted by 1 to 2 substituents independently selected from halo, cyano, $C_{1-4}$alkyl, halo$C_{1-4}$alkyl, $C_{1-4}$alkylamino$C_{1-4}$alkyl, amino$C_{1-4}$alkyl, $C_{4-6}$heterocycloalkyC$_{1-4}$alkyl, $C_{1-4}$alkylsilanylC$_{1-4}$alkoxyC$_{1-4}$alkyl, $C_{1-4}$alkoxy, halo$C_{1-4}$alkoxy, $C_{1-4}$alkoxyC$_{1-4}$alkoxy, amino$C_{1-4}$alkoxy, phenyl$C_{1-4}$alkoxy, $C_{5-6}$heteroarylC$_{1-4}$alkoxy, $C_{3-6}$cycloalkyC$_{1-4}$alkoxy, $C_{3-6}$heterocycloalkyC$_{1-4}$alkoxy, $C_{1-4}$alkylcarbonyl, aminocarbonyl, $C_{1-4}$alkylaminocarbonyl, $C_{1-4}$alkoxycarbonyl, amino, $C_{1-4}$alkylamino, $C_{4-6}$heterocycloalkyC$_{1-4}$alkylamino, $C_{4-6}$heterocycloalkyC$_{1-4}$alkylamino, —NHC(O)R$_{14}$ S(O)$_2$R$_{15}$, phenyl, $C_{5-6}$heteraryl, $C_{5-6}$heterocycloalkyl, and $C_{9-10}$heterocyclyl, the $C_{3-6}$heterocycloalkyl or $C_{6-10}$heterocyclyl of R$_6$ is unsubstituted or substituted by 1 to 2 substituents independently selected from $C_{1-4}$alkyl, oxo, and $C_{1-4}$alkoxycarbonyl wherein R$_{14}$ is selected from $C_{1-4}$alkyl, amino$C_{1-4}$alkyl, amino, $C_{1-4}$alkylamino, cyclopropylamino, $C_{1-4}$alkoxy, $C_{1-4}$alkylsulfonyl, and $C_{1-4}$alkylaminosulfonyl R$_{15}$ is selected from $C_{1-4}$alkyl, amino, $C_{3-6}$cycloalkyl, and $C_{5-6}$heterocycloalkyl, and the phenyl, $C_{5-6}$heteraryl, $C_{5-6}$heterocycloalkyl or $C_{9-10}$heterocyclyl substituent of the phenyl or $C_{5-6}$heteroaryl of R$_6$ is unsubstituted or substituted by 1 to 3 substituents independently selected from $C_{1-4}$alkyl and oxo;

R$_7$ is selected from hydrogen, $C_{1-4}$alkyl and —C(O)$C_{5-6}$heteroaryl; and R$_8$ is hydrogen or halo.

Embodiment 2. A compound of or a pharmaceutical acceptable salt, tautomer or stereoisomer thereof, according to Embodiment 1, wherein the compound is of Formula Ia:

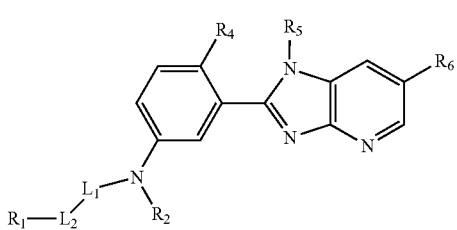

Ia

Embodiment 3. A compound of or a pharmaceutical acceptable salt, tautomer or stereoisomer thereof, according to Embodiment 1, wherein the compound is of Formula Ib:

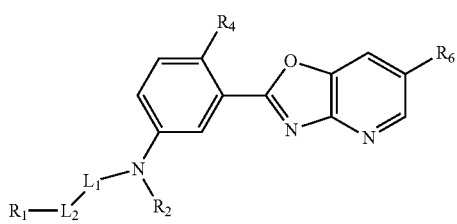

Ib

Embodiment 4. A compound of or a pharmaceutical acceptable salt, tautomer or stereoisomer thereof, according to Embodiments 1 to 3, wherein L$_1$ is —C(O)— or —S(O)$_2$—.

Embodiment 5. A compound of or a pharmaceutical acceptable salt, tautomer or stereoisomer thereof, according to Embodiments 1 to 3, L$_1$ is —C(O).

Embodiment 6. A compound of or a pharmaceutical acceptable salt, tautomer or stereoisomer thereof, according to Embodiments 1 to 5, wherein L$_2$ is selected from a bond, —CR$_{9a}$R$_{9b}$—, —NR$_{10}$—, and —O—, wherein R$_{9a}$ is selected from hydrogen, fluoro, hydroxyl, methyl, isopropyl and methoxy, R$_{9b}$ is selected from hydrogen, fluoro and methyl, and R$_{10}$ is selected from hydrogen, methyl, ethyl, and isopropyl.

Embodiment 7. A compound of or a pharmaceutical acceptable salt, tautomer or stereoisomer thereof, according to Embodiments 1 to 5, wherein L$_2$ is a bond, —CH$_2$—, —NH—, or O.

Embodiment 8. A compound of or a pharmaceutical acceptable salt, tautomer or stereoisomer thereof, according to Embodiments 1 to 5, wherein L$_2$ is a bond.

Embodiment 9. A compound of or a pharmaceutical acceptable salt, tautomer or stereoisomer thereof, according to Embodiments 1 to 8, wherein R$_1$ is selected from hydrogen, $C_{1-6}$alkyl, $C_{1-6}$alkoxy, $C_{6-10}$aryl, $C_{5-10}$heteroaryl, $C_{3-7}$cycloalkyl, $C_{5-6}$heterocycloalkyl, and $C_{9-10}$heterocyclyl, wherein the $C_{1-6}$alkyl or $C_{1-6}$alkoxy is unsubstituted or substituted with 1 to 2 substituents independently selected from —OH, fluoro, —CF$_3$, OCH$_3$, phenoxy. —C(O)OH, —NH$_2$, —N(CH$_3$)$_2$, —N(CH$_2$CH$_3$)$_2$, —N(CH(CH$_3$)$_2$)$_2$, —NHC(O)OC(CH$_3$)$_3$, phenyl, and morpholinyl;

the $C_{6-10}$aryl, $C_{5-10}$heteroaryl, $C_{3-7}$cycloalkyl, $C_{5-6}$heterocycloalkyl, or $C_{9-10}$heterocyclyl is unsubstituted or substituted by 1 to 3 substituents independently selected from fluoro, chloro, cyano, oxo, hydroxy, methyl, ethyl, isopropy, t-butyl, trifluoromethyl, methoxymethyl, dimethylaminomethyl, benzyl, methoxy, ethoxy, trifluoromethoxy, t-butoxycarbony dimethylamino, methylthio, methylsulfonyl, fluorophenyl, triazolyl, pyrimidinyl, cyclopropyl, piperidinyl, and morpholinyl.

Embodiment 10. A compound of or a pharmaceutical acceptable salt, tautomer or stereoisomer thereof, according to Embodiments 1 to 8, wherein R$_1$ is $C_{1-6}$alkyl or $C_{1-4}$alkoxy, each of which is unsubstituted or substituted with 1 to 2 substituents independently selected from halo, hydroxy, $C_{1-4}$alkoxy, $C_{5-6}$aryloxy, hydroxycarbonyl, $C_{1-4}$alkoxycarbonyl, amino, $C_{1-4}$alkyamino, $C_{1-4}$alkoxycarbonylamino, $C_{5-6}$aryl, and $C_{5-6}$heterocycloalkyl.

Embodiment 11. A compound of or a pharmaceutical acceptable salt, tautomer or stereoisomer thereof, according to Embodiments 1 to 8, wherein R$_1$ is selected from methyl, ethyl, propyl, isopropyl, isobutyl, t-butyl, hexyl, and methoxy, each of which is unsubstituted or substituted with 1 to 2 substituents independently selected from —OH, fluoro, —CF$_3$, OCH$_3$, phenoxy. —C(O)OH, —NH$_2$, —N(CH$_3$)$_2$, —N(CH$_2$CH$_3$)$_2$, —N(CH(CH$_3$)$_2$)$_2$, —NHC(O)OC(CH$_3$)$_3$, phenyl, and morpholinyl.

Embodiment 12. A compound of or a pharmaceutical acceptable salt, tautomer or stereoisomer thereof, according to Embodiments 1 to 8, wherein R$_1$ is selected from methyl, ethyl, propyl, isopropyl, isobutyl, methoxy, —(CH$_2$)$_{1-2}$OH, —(CH$_2$)$_2$C(O)OH, —(CH$_2$)$_{1-2}$NH$_2$, —C(CH$_3$)$_2$NH$_2$, —(CH$_2$)$_{2-3}$—N(CH$_3$)$_2$, —(CH$_2$)$_6$N(CH$_3$)$_2$, —(CH$_2$)$_6$N(CH$_2$CH$_3$)$_2$, —(CH$_2$)$_2$N(CH(CH$_3$)$_2$)$_2$, —C(CH$_3$)$_2$NHC(O)OC(CH$_3$)$_3$, —CH$_2$NHC(O)OC(CH$_3$)$_3$, —CH$_2$-phenoxy, —CH$_2$C($^2$H)$_3$, —(CH$_2$)$_2$F, —CH$_2$CF$_3$, —CH$_2$-phenyl, and —(CH$_2$)$_2$OCH$_3$.

Embodiment 13. A compound of or a pharmaceutical acceptable salt, tautomer or stereoisomer thereof, according to Embodiments 1 to 8, wherein R$_1$ is selected from $C_6$-$C_{5-10}$heteroaryl, $C_{3-7}$cycloalkyl, $C_{5-6}$heterocycloalkyl, and $C_{9-10}$heterocyclyl, each of which is unsubstituted or substituted by 1 to 3 substituents independently selected from fluoro, chloro, cyano, oxo, hydroxy, methyl, ethyl, isopropy, t-butyl, trifluoromethyl, methoxymethyl, dimethylaminomethyl, benzyl, methoxy, ethoxy, trifluoromethoxy, t-butoxycarbony dimethylamino, methylthio, methylsulfonyl, fluorophenyl, triazolyl, pyrimidinyl, cyclopropyl, piperidinyl, and morpholinyl.

Embodiment 14. A compound of or a pharmaceutical acceptable salt, tautomer or stereoisomer thereof, according to Embodiments $R_1$ is selected from phenyl, pyrrolyl, pyrazolyl, imidazolyl, triazolyl, furanyl, oxazolyl, isoxazolyl, oxadiazolyl, thiophenyl, thiazolyl, isothiazolyl, pyridinyl, pyridazinyl, pyrazinyl, pyrimidinyl, pyrazolo[1,5-a]pyridinyl, cyclopropyl, cyclobutyl, cyclopentyl, cyclohexyl, bicyclo[2.2.1]heptan-2-yl, azetidinyl, oxetanyl, pyrrolidinyl, imidazolidinyl, tetrahydrofuranyl, piperidinyl, piperazinyl, tetrahydropyranyl, morpholinyl, azabicyclo[3.1.0]hexanyl, tetrahydroisoquinolinyl, dihydrobenzofuranyl, chromanyl, tetrahydroisoquinolinyl, tetrahydro-naphthyridinyl, and dihydrobenzofuranyl, each of which is unsubstituted or substituted by 1-3 substituents independently selected from fluoro, chloro, cyano, oxo, hydroxy, methyl, ethyl, isopropy, t-butyl, trifluoromethyl, methoxymethyl dimethylaminomethyl, benzyl, methoxy, ethoxy, trifluoromethoxy, t-butoxycarbony, amino, dimethylamino, methylthio, methylsulfonyl, fluorophenyl, triazolyl, pyrimidinyl, cyclopropyl, piperidinyl, and morpholinyl.

Embodiment 15. A compound of or a pharmaceutical acceptable salt, tautomer or stereoisomer thereof, according to Embodiments $R_1$ is selected from —$CH_2$-4-fluorophenyl, —$OCH_2CH_3$, —$O(CH_2)_2OCH_3$, —$OCH(CH_3)_2$, —O-cyclopentyl, —$N(CH_3)(OCH_3)$, —$N(CH(CH_3)_2)_2$, cyclopentoxy, 3-chlorophenyl, 2-chlorophenyl, 2,4dimethoxyphenyl, 4-trifluoromethyphenyl, pyrrol-2-yl, furan-2-yl, 5-fluorofuran-2-yl, 5-chlorofuran-2-yl, 5-cyanofuran-2-yl, 5-methylfuranyl, 5-dimethylaminomethyl-furan-2-yl, 4-methylthiophen-2-yl, isothiazol-5-yl, thiazol-4-yl, 5-t-butyloxadiazol-2-yl, pyrazinyl, cyclopentyl, pyrrolidinyl, 3,3-difluoropyrrolidinyl, and 2-oxoindolin-6-yl.

Embodiment 16. A compound of or a pharmaceutical acceptable salt, tautomer or stereoisomer thereof, according to Embodiments 1 to 8, wherein $R_1$ is selected from isopropoxy, furan-2-yl, pyrazin-2-yl, cyclopentyl, pyrrolidinyl, and 3,3-difluoro-pyrrolidinyl.

Embodiment 17. A compound of or a pharmaceutical acceptable salt, tautomer or stereoisomer thereof, according to Embodiments 1 to 8, wherein $R_1$ is isopropoxy.

Embodiment 18. A compound of or a pharmaceutical acceptable salt, tautomer or stereoisomer thereof, according to Embodiments 1 to 8, wherein $R_1$ is pyrrolidiny, unsubstituted or substituted with 1-2 substituents independently selected from halo, cyano, $C_{1-4}$alkyl, $C_{1-4}$alkoxy, amino, $C_{1-4}$alkylamino, and $C_{1-4}$alkoxycarbonyl.

Embodiment 19. A compound of or a pharmaceutical acceptable salt, tautomer or stereoisomer thereof, according to Embodiments 1 to 8, wherein $R_1$ is unsubstituted pyrrolidinyl.

Embodiment 20. A compound of or a pharmaceutical acceptable salt, tautomer or stereoisomer thereof, according to Embodiments 1 to 8, wherein $R_1$ is furan-2-yl, unsubstituted or substituted with 1-2 substituents independently selected halo, cyano, $C_{1-4}$alkyl, $C_{1-4}$alkoxy, amino, $C_{1-4}$alkylamino, and $C_{1-4}$alkoxycarbonyl.

Embodiment 21. A compound of or a pharmaceutical acceptable salt, tautomer or stereoisomer thereof, according to Embodiments 1 to 8, wherein $R_1$ is furan-2-yl.

Embodiment 22. A compound of or a pharmaceutical acceptable salt, tautomer or stereoisomer thereof, according to Embodiments 1 to 21, wherein $R_2$ is hydrogen, methyl, or —C(O)-furan-2-yl.

Embodiment 23. A compound of or a pharmaceutical acceptable salt, tautomer or stereoisomer thereof, according to Embodiments 1 to 21, wherein $R_2$ is hydrogen.

Embodiment 24. A compound of or a pharmaceutical acceptable salt, tautomer or stereoisomer thereof, according to Embodiments 1 to 23, wherein $R_3$ is hydrogen, halo or methyl.

Embodiment 25. A compound of or a pharmaceutical acceptable salt, tautomer or stereoisomer thereof, according to Embodiments 1 to 23, wherein $R_3$ is hydrogen.

Embodiment 26. A compound of or a pharmaceutical acceptable salt, tautomer or stereoisomer thereof, according to Embodiments 1 to 25, wherein $R_4$ is selected from hydrogen, fluoro, chloro, methyl, trifluoromethyl, methylsulfonyl, pyridin3-yl, and morpholinyl.

Embodiment 27. A compound of or a pharmaceutical acceptable salt, tautomer or stereoisomer thereof, according to Embodiments 1 to 25, wherein $R_4$ is methyl or trifluoromethyl.

Embodiment 28. A compound of or a pharmaceutical acceptable salt, tautomer or stereoisomer thereof, according to Embodiments 1 to 25, wherein $R_4$ is halo.

Embodiment 29. A compound of or a pharmaceutical acceptable salt, tautomer or stereoisomer thereof, according to Embodiments 1 to 25, wherein $R_4$ is hydrogen.

Embodiment 30. A compound of or a pharmaceutical acceptable salt, tautomer or stereoisomer thereof, according to Embodiments 1-2 and 4 to 29, wherein $R_5$ is selected from hydrogen, —$CH_2O(CH_3)$, —$(CH_2)_2$-morpholinyl, —$(CH_2)_2N(CH_3)_2$, —$C(O)OCH(CH_3)_2$, and —$C(O)O(CH_3)$.

Embodiment 31. A compound of or a pharmaceutical acceptable salt, tautomer or stereoisomer thereof, according to Embodiments 1-2 and 4 to 29, wherein $R_5$ is —$C(O)OCH(CF_{13})_2$.

Embodiment 32. A compound of or a pharmaceutical acceptable salt, tautomer or stereoisomer thereof, according to Embodiments 1-2 and 4 to 29, wherein $R_5$ is hydrogen.

Embodiment 33. A compound of or a pharmaceutical acceptable salt, tautomer or stereoisomer thereof, according to Embodiments 1 and 4 to 29, wherein $R_7$ is selected from hydrogen, methyl, ethyl, isopropyl, methoxymethyl, and —C(O)-furan-2-yl.

Embodiment 34. A compound of or a pharmaceutical acceptable salt, tautomer or stereoisomer thereof, according to Embodiments 1 and 4 to 29, wherein $R_7$ is hydrogen or $C_{1-4}$alkyl.

Embodiment 35. A compound of or a pharmaceutical acceptable salt, tautomer or stereoisomer thereof, according to Embodiments 1 and 4 to 29, wherein $R_7$ is hydrogen.

Embodiment 36. A compound of or a pharmaceutical acceptable salt, tautomer or stereoisomer thereof, according to Embodiments 1 to 35, wherein $R_8$ is hydrogen or halo.

Embodiment 37. A compound of or a pharmaceutical acceptable salt, tautomer or stereoisomer thereof, according to Embodiments 1 to 35, wherein $R_8$ is hydrogen.

Embodiment 38. A compound of or a pharmaceutical acceptable salt, tautomer or stereoisomer thereof, according to Embodiments 1 to 37, wherein $R_6$ is selected from halo, cyano, $C_{1-4}$alkyl, $C_{1-4}$alkenyl, $C_{1-4}$alkoxy, $C_{1-4}$alkylsulfonyl, $C_{3-6}$cycloalkylsulfonyl, $C_{1-4}$alkylphosphinyl oxide, $C_{1-4}$alkylcarbonylamino, phenyl, $C_{5-6}$heteroaryl, $C_{5-6}$heteraryl, $C_{4-6}$heterocycloalkyl, $C_{6-10}$heterocyclyl, wherein
 the $C_{1-6}$alkyl, $C_{1-4}$alkenyl or $C_{1-4}$alkoxy of $R_6$ is unsubstituted or substituted by 1 to 2 substituents independently selected from halo, —$NH_2$, —$NH(CH_3)$, —$N(CH_3)_2$, —NH(CH$_2$CH$_3$), N(CH$_2$CH$_3$)$_2$, —NHCH$_2$CH(OH)(CH$_3$), —NHCH(CH$_3$)CH$_2$(OH);

the phenyl or C$_{5-6}$heteroaryl of R$_6$ is unsubstituted or substituted by 1 to 2 substituents independently selected from fluoro, chloro, cyano, methyl, trifluoromethyl, —(CH$_2$)—N(CH$_3$)$_2$, —(CH$_2$)$_2$—N(CH$_3$)$_2$, —CH(CH$_3$)$_2$CH$_2$NH$_2$, —CH$_2$O(CH$_2$)$_2$Si(CH$_3$)$_3$, —(CH$_2$)$_{1-2}$-morpholinyl, methoxy, ethoxy, trifluoromethoxy, —O(CH$_2$)$_2$OCH$_3$, —O(CH$_2$)$_2$N(CH$_3$)$_2$, —OCH$_2$-phenyl, —OCH$_2$-5-methylisoxazol-3-yl, —O(CH$_2$)$_2$-1H-imidazol-1-yl, —O(CH$_2$)$_2$-1H-pyrazol-1-yl, —OCH$_2$-cyclopropyl, —OCH$_2$-oxiran-2-yl, —O(CH$_2$)$_2$-pyrrolidin-1-yl, —OCH$_2$-tetrahydro-2H-pyran-4-yl, —O(CH$_2$)$_2$-piperidin-1-yl, —O(CH$_2$)$_2$-4-methylpiperazin-1-yl, —O(CH$_2$)$_{2-3}$-morpholinyl, —OCH$_2$CH(OH)CH$_2$-morpholinyl, —C(O)CH$_3$, —C(O)NH$_2$, —C(O)NHCH$_3$, —C(O)OCH$_3$, —NH$_2$, —NHCH$_3$, —N(CH$_3$)$_2$, —NH(CH$_2$)$_2$-morpholinyl, —NHC(O)CH$_3$, —NHC(O)CH(CH$_3$)$_2$, —NHC(O)CH$_2$CH(CH$_3$)$_2$, —NHC(O)CH$_2$NH$_2$, —NHC(O)(CH$_2$)$_2$NH$_2$, —NHC(O)NH$_2$, —NHC(O)NHCH$_3$, —NHC(O)NH-cyclopropyl, —NHC(O)OCH$_3$, —NHC(O)OCH(CH$_3$)$_2$, —NHC(O)OC(CH$_3$)$_3$, —N(CH$_3$)C(O)OC(CH$_3$)$_3$, —NHS(O)$_2$CH$_3$, —NHS(O)$_2$CH(CH$_3$)$_2$, —NHS(O)$_2$NH(CH$_3$), —S(O)$_2$CH$_3$, —S(O)$_2$NH$_2$, —S(O)$_2$-pyrrolidinyl, phenyl, pyrazolyl, pyrrolidinyl, piperidinyl, piperazinyl, C$_{1-4}$alkylpiperazinyl, pyrrolidinyl, piperidinyl, morpholinyl, C$_{1-4}$alkyldihydro-2H-benzo[b][1,4]oxazinyl, and dioxoimidazolidinyl; and the C$_{3-6}$heterocycloalkyl or C$_{6-9}$heterocyclyl of R$_6$ is unsubstituted or substituted by 1 to 2 substituents independently selected from methyl and —C(O)OC(CH$_3$)$_3$ Embodiment 39. A compound of or a pharmaceutical acceptable salt, tautomer or stereoisomer thereof, according to Embodiment 36, wherein R$_6$ is selected from phenyl, C$_{5-6}$heteroaryl, the C$_{3-6}$heterocycloalkyl and C$_{6-10}$heterocyclyl, wherein the phenyl or C$_{5-6}$heteroaryl is selected from phenyl, pyrazolyl, furanyl, thiophenyl, pyridinyl, pyrimidinyl, imidazolyl, the C$_{3-6}$heterocycloalkyl or C$_{6-10}$heterocyclyl is selected from piperidinyl, piperazinyl and morpholinyl; dihyropyridinyl, tetrahydropyridinyl, indolinyl, 2-oxo-indolinyl, dihydro-2H-benzo[b][1,4]oxazin-yl and benzo[d][1,3]dioxolanyl Embodiment 40. A compound of or a pharmaceutical acceptable salt, tautomer or stereoisomer thereof, according to Embodiments 1 to 37, wherein R$_6$ is selected from phenyl, C$_{5-6}$heteroaryl, the C$_{3-6}$heterocycloalkyl and C$_{6-10}$heterocyclyl, wherein the phenyl or C$_{5-6}$heteroaryl is selected from pyrazol-4-yl, pyrazol-3-yl, furan-3-yl, thiophen-1-yl, thiophen-2-yl, thiophen-3-yl, pyridin-3-yl, pyridin-4-yl, pyrimidin-5-yl, and imidazol-4-yl; each of which is unsubstituted or substituted by 1 to 2 substituents independently selected from fluoro, chloro, cyano, methyl, trifluoromethyl, —(CH$_2$)—N(CH$_3$)$_2$, —(CH$_2$)$_2$—N(CH$_3$)$_2$, —CH(CH$_3$)$_2$CH$_2$NH$_2$, —CH$_2$O(CH$_2$)$_2$Si(CH$_3$)$_3$, (CH$_2$)$_{1-2}$-morpholinyl, methoxy, ethoxy, trifluoromethoxy, —O(CH$_2$)$_2$OCH$_3$, —O(CH$_2$)$_2$N(CH$_3$)$_2$, —OCH$_2$-phenyl, —OCH$_2$-5-methylisoxazol-3-yl, —O(CH$_2$)$_2$-1H-imidazol-1-yl, —O(CH$_2$)$_2$-1H-pyrazol-1-yl, —OCH$_2$-cyclopropyl, —OCH$_2$-oxiran-2-yl, —O(CH$_2$)$_2$-pyrrolidin-1-yl, —OCH$_2$-tetrahydro-2H-pyran-4-yl, —O(CH$_2$)$_2$-piperidin-1-yl, —O(CH$_2$)$_2$-4-methylpiperazin-1-yl, —O(CH$_2$)$_{2-3}$-morpholinyl, —OCH$_2$CH(OH)CH$_2$-morpholinyl, —C(O)CH3, —C(O)NH2, —C(O)NHCH3, —C(O)OCH3, —NH$_2$, —NHCH$_3$, —N(CH$_3$)$_2$, —NH(CH$_2$)$_2$-morpholinyl, —NHC(O)CH$_3$, —NHC(O)CH(CH$_3$)$_2$, —NHC(O)CH$_2$CH(CH$_3$)$_2$, —NHC(O)CH$_2$NH$_2$, —NHC(O)(CH$_2$)$_2$NH$_2$, —NHC(O)NH$_2$, —NHC(O)NHCH$_3$, —NHC(O)NH-cyclopropyl, —NHC(O)OCH$_3$, —NHC(O)OCH(CH$_3$)$_2$, —NHC(O)OC(CH$_3$)$_3$, —N(CH$_3$)C(O)OC(CH$_3$)$_3$, —NHS(O)$_2$CH$_3$, —NHS(O)$_2$CH(CH$_3$)$_2$, —NHS(O)$_2$NH(CH$_3$), —S(O)$_2$CH$_3$, —S(O)$_2$NH$_2$, —S(O)$_2$-pyrrolidin-1-yl, phenyl, pyrazolyl, pyrrolidinyl, piperidinyl, piperazinyl, C$_{1-4}$alkylpiperazinyl, pyrrolidin-1-yl, piperidin-4-yl, morpholinyl, C$_{1-4}$alkyldihydro-2H-benzo[b][1,4]oxazinyl, and dioxoimidazolidinyl; and the C$_{3-6}$heterocycloalkyl or C$_{6-10}$heterocyclyl are selected from piperidin-1-yl, piperazin-1-yl, morpholinyl, dihyropyridinyl, 1,2,3,6-tetrahydropyridin-4-yl, indolin-5-yl, 2-oxo-indolin-5-yl, 3,4-dihydro-2H-benzo[b][1,4]oxazin-7-yl, and benzo[d][1,3]dioxolan-5-yl, each of which is unsubstituted or substituted by 1 to 2 substituents independently selected from methyl and —C(O)OC(CH$_3$)$_3$.

Embodiment 41. A compound of or a pharmaceutical acceptable salt, tautomer or stereoisomer thereof, according to Embodiments 1 to 37, wherein R$_6$ is selected from chloro, bromo, cyano, methyl, ethyl, ethenyl, trifluoromethyl, —(CH$_2$)$_2$-morpholinyl, ethoxy, amino, —N(H)C(O)CH$_3$, —N(H)C(O)OCH$_3$, —NHC(O)OC(CH$_3$)$_3$, phenyl, pyridinyl, pyrimidinyl, 1-t-butylcarbonyl-5,6-dihyropyridin-4-yl, 4-methyl-3,4-dihydro-2H-benzo[b][1,4]oxazin-7-yl, 1-methyl-indolin-5-yl, and 2-oxo-indolin-5-yl, wherein the phenyl is unsubstituted or substituted with 1 to 2 substituents independently selected from fluoro-, chloro, cyano, —CF$_3$, —NH$_2$, —(CH$_2$)$_2$—N(CH$_3$)$_2$, —C(CH$_3$)$_2$CH$_2$NH$_2$, 4-methyl-piperazinyl, —(CH$_2$)$_{1-2}$-morpholinyl, —OCH$_3$, —OCF$_3$, 4-O(CH$_2$)$_2$OCH$_3$, 4-O(CH$_2$)N(CH$_3$)$_2$, —O(CH$_2$)-cyclopropyl, —OCH$_2$-oxiranyl, —O(CH$_2$)-pyrrolidinyl, —O(CH$_2$)-tetrahyropyanyl, —O(CH$_2$)-(5-methylisooxazolyl, —O(CH$_2$)-methylpiperizinyl, —O(CH$_2$)$_{2-3}$-morpholinyl, —OCH$_2$-imidazolyl, —O(CH$_2$)$_2$-pyrazolyl, —C(O)OCH$_3$, —NHCH$_3$, —N(CH$_3$)$_2$, —NHC(O)CH$_3$, —NHC(O)CH$_3$, —NHC(O)CH(CH$_3$)$_2$—, —N(H)C(O)CH$_2$CH(CH$_3$)$_2$, —N(H)C(O)OCH$_3$, —NHC(O)OCH(CH$_3$)$_2$, —NHC(O)OC(CH$_3$)$_3$, —N(CH$_3$)C(O)OC(CH$_3$)$_3$, —N(H)C(O)CH$_2$NH$_2$—, —NHC(O)NH-cyclopropyl, —S(O)$_2$CH$_3$, —N(H)S(O)$_3$CH(CH$_3$)$_2$, —S(O)$_2$-pyrrolidin-1-yl, —pyrrolidinyl, -piperidinyl, -4-CH(CH$_3$)$_2$-piperazinyl, -2,4-dioxoimidazolidinyl, and 2-oxo-indolinyl; and the pyridinyl or pyrimidinyl is unsubstituted or substituted with 1 to 2 substituents independently selected from fluoro, methyl, —(CH$_2$)$_2$-morpholinyl, methoxy, —C(O)NHCH$_3$, amino, —N(CH$_3$)$_2$, —NHC(O)CH$_3$, pyrazol-4-yl, thiophen-3-y, thiophen-2-y, —CH$_2$O(CH$_2$)$_2$Si(CH$_3$)$_3$-1-imidazol4-yl, and -methylpyrazol-3-y.

Embodiment 42. A compound of or a pharmaceutical acceptable salt, tautomer or stereoisomer thereof, according to Embodiments 1 to 37, wherein R$_6$ is selected from bromo, cyano, —(CH$_2$)$_2$-morpholinyl, amino, —N(H)C(O)OCH$_3$, phenyl, 2-fluoro-pyridin-4-yl, 2-C(O)NHCH$_3$pyridin5-yl, -2-(morpholinylethyl)pyridin-5-yl, thiophen3-yl, and —CH$_2$O(CH$_2$)$_2$Si(CH$_3$)$_{3-1}$-imidazol4-yl, wherein the phenyl is unsubstituted or substituted at the para-position by a substituent independently selected from —(CH$_2$)$_2$N(CH$_3$)$_2$, —O(CH$_2$)$_2$OCH$_3$, —O(CH$_2$)$_2$-pyrazolyl, —O(CH$_2$)-5-methylisooxazolyl, —O(CH$_2$)$_{2-3}$-morpholinyl, —NHCH$_3$, —N(H)C(O)CH(CH$_3$)$_2$, —N(H)C(O)CH$_2$CH(CH$_3$)$_2$, —NHC(O)C(CH$_3$)$_3$, —N(H)C(O)CH$_2$NH$_2$, —N(H)C(O)OCH$_3$, and —N(CH₃)C(O)OC(CH₃)₃, or at the ortho-position by a substituent selected from amino and —NHC(O)OCH(CH₃)₂.

Embodiment 43. A compound of or a pharmaceutical acceptable salt, tautomer or stereoisomer thereof, according to Embodiments 1 to 37, wherein R₆ is phenyl, unsubstituted or substituted with 1 to 2 substituents independently selected from fluoro-, chloro, cyano, —CF₃, —NH₂, —(CH₂)₂—N(CH₃)₂, —C(CH₃)₂CH₂NH₂, 4-methyl-piperazinyl, —(CH₂)₁₋₂-morpholinyl, —OCH₃, —OCF₃, 4-O(CH₂)₂OCH₃, 4-O(CH₂)N(CH₃)₂, —O(CH₂)-cyclopropyl, —OCH₂-oxiranyl, —O(CH₂)-pyrrolidinyl, —O(CH₂)-tetrahyropyanyl, —O(CH₂)—(5-methylisooxazolyl, —O(CH₂)-methylpiperizinyl, —O(CH₂)₂₋₃-morpholinyl, —OCH₂-imidazolyl, —O(CH₂)₂-pyrazolyl, —C(O)OCH₃, —NHCH₃, —N(CH₃)₂, —NHC(O)CH₃, —NHC(O)CH₃, —NHC(O)CH(CH₃)₂—, —N(H)C(O)CH₂CH(CH₃)₂, —N(H)C(O)OCH₃, —NHC(O)OCH(CH₃)₂, —NHC(O)OC(CH₃)₃, —N(CH₃)C(O)OC(CH₃)₃, —N(H)C(O)CH₂NH₂—, —NHC(O)NH-cyclopropyl, —S(O)₂CH₃, —N(H)S(O)₃CH(CH₃)₂, —S(O)₂-pyrrolidin-1-yl, -pyrrolidinyl, -piperidinyl, -4-CH(CH₃)₂-piperazinyl, -2,4-dioxoimidazolidinyl, and 2-oxo-indolinyl.

Embodiment 44. A compound of or a pharmaceutical acceptable salt, tautomer or stereoisomer thereof, according to Embodiments 1 to 37, wherein R₆ is phenyl, unsubstituted or substituted at the para-position by a substituent independently selected from —(CH₂)₂N(CH₃)₂, —O(CH₂)₂OCH₃, —O(CH₂)₂-pyrazolyl, —O(CH₂)-5-methylisooxazolyl, —O(CH₂)₂₋₃-morpholinyl, —NHCH₃, —N(H)C(O)CH(CH₃)₂, —N(H)C(O)CH₂CH(CH₃)₂, —NHC(O)C(CH₃)₃, —N(H)C(O)CH₂NH₂, —N(H)C(O)OCH₃, and —N(CH₃)C(O)OC(CH₃)₃.

Embodiment 45. A compound of or a pharmaceutical acceptable salt, tautomer or stereoisomer thereof, according to Embodiments 1 to 37, wherein R₆ is selected from cyano, chloro, bromo, methyl, ethyl, propyl, isopropyl, isobutyl, ethenyl, trifluoromethyl, —CH₂NH₂, —CH₂NHCH₂CH(OH)(CH₃), —CH₂NHCH(CH₃)CH₂(OH), —(CH₂)₁₋₃NH(CH₃), —(CH₂)₁₋₃N(CH₃)₂, —(CH₂)₁₋₃NH(CH₂CH₃), —(CH₂)₁₋₃N(CH₂CH₃)₂, —NHC(O)CH₃, —S(O)₂CH₃, —S(O)₂-cyclopropyl, and —P(O)(CH₃)₃.

Embodiment 46. A compound of or a pharmaceutical acceptable salt, tautomer or stereoisomer thereof, according to Embodiments 1 to 37, wherein R₆ is selected from chloro, bromo, cyano, methyl, ethyl, ethenyl, trifluoromethyl, —(CH₂)₂-morpholinyl, ethoxy, amino, —N(H)C(O)CH₃, —N(H)C(O)OCH₃, and —NHC(O)OC(CH₃)₃.

Embodiment 47. A compound of or a pharmaceutical acceptable salt, tautomer or stereoisomer thereof, according to Embodiment 1, wherein the compound is of Formula 1c:

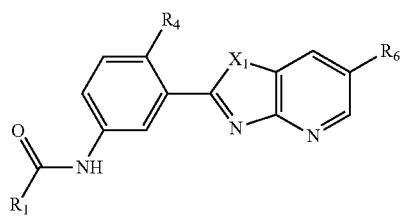

1c wherein
X₁ is O or NR₅;
R₁ is selected from —CH₂-4-fluorophenyl, —OCH₂CH₃, —O(CH₂)₂OCH₃, —OCH(CH₃)₂, —O-cyclopentyl, —N(CH₃)(OCH₃), —N(CH(CH₃)₂)₂, cyclopentoxy, 3-chlorophenyl, 2-chlorophenyl, 2,4dimethoxyphenyl, 4-trifluoromethyphenyl, pyrrol-2-yl, furan-2-yl, 5-fluorofuran-2-yl, 5-chlorofuran-2-yl, 5-cyanofuran-2-yl, 5-methylfuranyl, 5-dimethylaminomethyl-furan-2-yl, 4-methylthiophen-2-yl, isothiazol-5-yl, thiazol-4-yl, 5-t-butyloxadiazol-2-yl, pyrazinyl, cyclopentyl, pyrrolidinyl, 3,3-difluoropyrrolidinyl, and 2-oxoindolin-6-yl;
R₄ is selected from hydrogen, halo, C₁₋₄alkyl, and haloC₁₋₄alkyl;
R₅ is selected from hydrogen, —CH₂O(CH₃), —(CH₂)₂-morpholinyl, —(CH₂)₂N(CH₃)₂, —C(O)OCH(CH₃)₂, and —C(O)O(CH₃);
R₆ is selected from chloro, bromo, cyano, methyl, ethyl, ethenyl, trifluoromethyl, —(CH₂)₂-morpholinyl, ethoxy, amino, —N(H)C(O)CH₃, —N(H)C(O)OCH₃, —NHC(O)OC(CH₃)₃, phenyl, pyridinyl, pyrimidinyl, 1-t-butylcarbonyl-5,6-dihyropyridin-4-yl, 4-methyl-3,4-dihydro-2H-benzo[b][1,4]oxazin-7-yl, 1-methyl-indolin-5-yl, and 2-oxo-indolin-5-yl, wherein
the phenyl is unsubstituted or substituted by 1 to 2 substituents independently selected from fluoro-, chloro, cyano, —CF₃, —NH₂, —(CH₂)₂—N(CH₃)₂, —C(CH₃)₂CH₂NH₂, 4-methyl-piperazinyl, —(CH₂)₁₋₂-morpholinyl, —OCH₃, —OCF₃, 4-O(CH₂)₂OCH₃, 4-O(CH₂)N(CH₃)₂, —O(CH₂)-cyclopropyl, —OCH₂-oxiranyl, —O(CH₂)-pyrrolidinyl, —O(CH₂)-tetrahydropyanyl, —O(CH₂)-(5-methylisooxazolyl, —O(CH₂)-methylpiperizinyl, —O(CH₂)₂₋₃-morpholinyl, —OCH₂-imidazolyl, —O(CH₂)₂-pyrazolyl, —C(O)OCH₃, —NHCH₃, —N(CH₃)₂, —NHC(O)CH₃, —NHC(O)CH₃, —NHC(O)CH(CH₃)₂—, —N(H)C(O)CH₂CH(CH₃)₂, —N(H)C(O)OCH₃, —NHC(O)OCH(CH₃)₂, —NHC(O)OC(CH₃)₃, —N(CH₃)C(O)OC(CH₃)₃, —N(H)C(O)CH₂NH₂—, —NHC(O)NH-cyclopropyl, —S(O)₂CH₃, —N(H)S(O)₃CH(CH₃)₂, —S(O)₂-pyrrolidin-1-yl, -pyrrolidinyl, -piperidinyl, -4-CH(CH₃)₂-piperazinyl, -2,4-dioxoimidazolidinyl, and 2-oxo-indolinyl; and
the pyridinyl or pyrimidinyl is unsubstituted or substituted with 1 to 2 substituents independently selected from fluoro, methyl, —(CH₂)₂-morpholinyl, methoxy, —C(O)NHCH₃, amino, —N(CH₃)₂, —NHC(O)CH₃, pyrazol-4-yl, thiophen-3-y, thiophen-2-y, —CH₂O(CH₂)₂Si(CH₃)₃-1-imidazol4-yl, and -methylpyrazol-3-y.

Embodiment 48. A compound of or a pharmaceutical acceptable salt, tautomer or stereoisomer thereof, according to Embodiment 47, wherein X₁ is O.

Embodiment 49. A compound of or a pharmaceutical acceptable salt, tautomer or stereoisomer thereof, according to Embodiment 47, wherein X₁ is NR₅.

Embodiment 50. A compound of or a pharmaceutical acceptable salt, tautomer or stereoisomer thereof, according to Embodiments 47 to 49, wherein R₁ is selected from isopropoxy, furan-2-yl, pyrazin-2-yl, cyclopentyl, pyrrolidinyl, and 3,3-difluoro pyrrolidinyl.

Embodiment 51. A compound of or a pharmaceutical acceptable salt, tautomer or stereoisomer thereof, according to Embodiments 47 to 49, wherein R₁ is isopropoxy.

Embodiment 52. A compound of or a pharmaceutical acceptable salt, tautomer or stereoisomer thereof, according to Embodiments 47 to 49, wherein R₁ is pyrrolidinyl, unsubstituted or substituted by a substituent selected from halo, cyano, C₁₋₄alkyl, C₁₋₄alkoxy, amino, C₁₋₄alkylamino, and C₁₋₄alkoxycarbonyl.

Embodiment 53. A compound of or a pharmaceutical acceptable salt, tautomer or stereoisomer thereof, according to Embodiments 47 to 49, wherein $R_1$ is unsubstituted pyrrolidinyl.

Embodiment 54. A compound of or a pharmaceutical acceptable salt, tautomer or stereoisomer thereof, according to Embodiments 47 to 53, wherein $R_4$ is halo or $C_{1-4}$alkyl.

Embodiment 55. A compound of or a pharmaceutical acceptable salt, tautomer or stereoisomer thereof, according to Embodiments 47 to 53, wherein $R_4$ is halo.

Embodiment 56. A compound of or a pharmaceutical acceptable salt, tautomer or stereoisomer thereof, according to Embodiments 47 to 55, wherein $R_5$ is hydrogen.

Embodiment 57. A compound of or a pharmaceutical acceptable salt, tautomer or stereoisomer thereof, according to Embodiments 47 to 56, wherein $R_6$ is selected from bromo, cyano, —$(CH_2)_2$-morpholinyl, amino, —$N(H)C(O)OCH_3$, phenyl, 2-fluoro-pyridin-4-yl, 2-C(O)NHCH$_3$pyridin5-yl, -2-(morpholinylethyl)pyridin-5-yl, thiophen3-yl, and —$CH_2O(CH_2)_2Si(CH_3)_{3-1}$-imidazol4-yl, wherein
the phenyl is unsubstituted or substituted at the para-position by a substituent independently selected from —$(CH_2)_2N(CH_3)_2$, —$O(CH_2)_2OCH_3$, —$O(CH_2)_2$-pyrazolyl, —$O(CH_2)$-5-methylisooxazolyl, —$O(CH_2)_{2-3}$-morpholinyl, —$NHCH_3$, —$N(H)C(O)CH(CH_3)_2$, —$N(H)C(O)CH_2CH(CH_3)_2$, —$NHC(O)C(CH_3)_3$, —$N(H)C(O)CH_2NH_2$, —$N(H)C(O)OCH_3$, and —$N(CH_3)C(O)OC(CH_3)_3$, or at the ortho-position by a substituent selected from amino and —$NHC(O)OCH(CH_3)_2$.

Embodiment 58. A compound of or a pharmaceutical acceptable salt, tautomer or stereoisomer thereof, according to Embodiments 47 to 56, wherein $R_6$ is phenyl, unsubstituted or substituted at the para-position by a substituent independently selected from —$(CH_2)_2N(CH_3)_2$, —$O(CH_2)_2OCH_3$, —$O(CH_2)_2$-pyrazolyl, —$O(CH_2)$-5-methylisooxazolyl, —$O(CH_2)_{2-3}$-morpholinyl, —$NHCH_3$, —$N(H)C(O)CH(CH_3)_2$, —$N(H)C(O)CH_2CH(CH_3)_2$, —$NHC(O)C(CH_3)_3$, —$N(H)C(O)CH_2NH_2$, —$N(H)C(O)OCH_3$, and —$N(CH_3)C(O)OC(CH_3)_3$.

Embodiment 59. A compound of or a pharmaceutical acceptable salt, tautomer or stereoisomer thereof, according to Embodiments 47 to 56, wherein $R_6$ is selected from chloro, bromo, cyano, methyl, ethyl, ethenyl, trifluoromethyl, —$(CH_2)_2$-morpholinyl, ethoxy, amino, —$N(H)C(O)CH_3$, —$N(H)C(O)OCH_3$, and —$NHC(O)OC(CH_3)_3$.

Embodiment 60. A compound of or a pharmaceutical acceptable salt, tautomer or stereoisomer thereof, according to Embodiment 1, wherein the compound is selected from the group consisting of: N-(4-chloro-3-{6-methyl-1H-imidazo[4,5-b]pyridin-2-yl}phenyl)furan-2-carboxamide; N-(4-chloro-3-{6-chloro-1H-imidazo[4,5-b]pyridin-2-yl}phenyl)furan-2-carboxamide; N-(4-chloro-3-{7-methyl-1H-imidazo[4,5-b]pyridin-2-yl}phenyl)furan-2-carboxamide; N-[4-chloro-3-(7H-purin-8-yl)phenyl]furan-2-carboxamide; N-(4-chloro-3-{5,6-dimethyl-1H-imidazo[4,5-b]pyridin-2-yl}phenyl)furan-2-carboxamide; N-[4-chloro-3-(6-{4-[2-(morpholin-4-yl)ethyl]phenyl}-1H-imidazo[4,5-b]pyridin-2-yl)phenyl]furan-2-carboxamide; N-{4-chloro-3-[6-(6-acetamidopyridin-3-yl)-1H-imidazo[4,5-b]pyridin-2-yl]phenyl}furan-2-carboxamide; N-{4-chloro-3-[6-(2-acetamidophenyl)-1H-imidazo[4,5-b]pyridin-2-yl]phenyl}furan-2-carboxamide; N-{4-chloro-3-[6-(2-methoxypyrimidin-5-yl)-1H-imidazo[4,5-b]pyridin-2-yl]phenyl}furan-2-carboxamide; N-{4-chloro-3-[6-(pyridin-4-yl)-1H-imidazo[4,5-b]pyridin-2-yl]phenyl}furan-2-carboxamide; N-[4-chloro-3-(6-{6-[2-(morpholin-4-yl)ethoxy]pyridin-3-yl}-1H-imidazo[4,5-b]pyridin-2-yl)phenyl]furan-2-carboxamide; N-{3-[6-(4-aminophenyl)-1H-imidazo[4,5-b]pyridin-2-yl]-4-chlorophenyl}furan-2-carboxamide; N-(4-chloro-3-{6-[4-(3-methylbutanamido)phenyl]-1H-imidazo[4,5-b]pyridin-2-yl}phenyl)furan-2-carboxamide; N-[4-chloro-3-(6-{1-[2-(morpholin-4-yl)ethyl]-1H-pyrazol-4-yl}-1H-imidazo[4,5-b]pyridin-2-yl)phenyl]furan-2-carboxamide; N-[4-chloro-3-(6-{4-[(dimethylamino)methyl]phenyl}-1H-imidazo[4,5-b]pyridin-2-yl)phenyl]furan-2-carboxamide; N-(4-chloro-3-{6-[4-(morpholin-4-ylmethyl)phenyl]-1H-imidazo[4,5-b]pyridin-2-yl}phenyl)furan-2-carboxamide; N-{3-[6-(2-aminopyrimidin-5-yl)-1H-imidazo[4,5-b]pyridin-2-yl]-4-chlorophenyl}furan-2-carboxamide; N-{4-chloro-3-[6-(4-acetamidophenyl)-1H-imidazo[4,5-b]pyridin-2-yl]phenyl}furan-2-carboxamide; N-{3-[6-(4-carbamoylphenyl)-1H-imidazo[4,5-b]pyridin-2-yl]-4-chlorophenyl}furan-2-carboxamide; N-{4-chloro-3-[6-(4-cyanophenyl)-1H-imidazo[4,5-b]pyridin-2-yl]phenyl}furan-2-carboxamide; N-[4-chloro-3-(6-{4-[2-(piperidin-1-yl)ethoxy]phenyl}-1H-imidazo[4,5-b]pyridin-2-yl)phenyl]furan-2-carboxamide; N-(4-chloro-3-{6-[4-(4-methylpiperazin-1-yl)phenyl]-1H-imidazo[4,5-b]pyridin-2-yl}phenyl)furan-2-carboxamide; N-{3-[6-(2-aminophenyl)-1H-imidazo[4,5-b]pyridin-2-yl]-4-chlorophenyl}furan-2-carboxamide; N-{3-[6-(6-aminopyridin-3-yl)-1H-imidazo[4,5-b]pyridin-2-yl]-4-chlorophenyl}furan-2-carboxamide; N-(4-chloro-3-{6-[4-(trifluoromethoxy)phenyl]-1H-imidazo[4,5-b]pyridin-2-yl}phenyl)furan-2-carboxamide; N-(4-chloro-3-{6-[4-(oxan-4-ylmethoxy)phenyl]-1H-imidazo[4,5-b]pyridin-2-yl}phenyl)furan-2-carboxamide; N-{3-[6-(2H-1,3-benzodioxol-5-yl)-1H-imidazo[4,5-b]pyridin-2-yl]-4-chlorophenyl}furan-2-carboxamide; N-(4-chloro-3-{6-[4-(methylamino)phenyl]-1H-imidazo[4,5-b]pyridin-2-yl}phenyl)-furan-2-carboxamide; N-{4-chloro-3-[6-(6-methoxypyridin-3-yl)-1H-imidazo[4,5-b]pyridin-2-yl]phenyl}furan-2-carboxamide; N-(4-chloro-3-{6-ethyl-1H-imidazo[4,5-b]pyridin-2-yl}phenyl)furan-2-carboxamide; propan-2-yl N-(4-{2-[2-chloro-5-(furan-2-amido)phenyl]-1H-imidazo[4,5-b]pyridin-6-yl}phenyl)carbamate; N-(3-{6-[4-(carbamoylamino)phenyl]-1H-imidazo[4,5-b]pyridin-2-yl}-4-chlorophenyl)furan-2-carboxamide; N-(4-chloro-3-{6-[4-(morpholin-4-yl)phenyl]-1H-imidazo[4,5-b]pyridin-2-yl}phenyl)furan-2-carboxamide; tert-butyl N-(4-{2-[2-chloro-5-(furan-2-amido)phenyl]-1H-imidazo[4,5-b]pyridin-6-yl}-2-methoxyphenyl)carbamate; methyl 4-{2-[2-chloro-5-(furan-2-amido)phenyl]-1H-imidazo[4,5-b]pyridin-6-yl}benzoate; N-(4-chloro-3-{6-[4-(cyclopropylmethoxy)phenyl]-1H-imidazo[4,5-b]pyridin-2-yl}phenyl)furan-2-carboxamide; propan-2-yl N-(2-{2-[2-chloro-5-(furan-2-amido)phenyl]-1H-imidazo[4,5-b]pyridin-6-yl}phenyl)carbamate; N-{4-chloro-3-[6-({[(2S)-1-hydroxypropan-2-yl]amino}methyl)-1H-imidazo[4,5-b]pyridin-2-yl]phenyl}furan-2-carboxamide; N-{4-chloro-3-[6-(2,6-dimethylpyridin-4-yl)-1H-imidazo[4,5-b]pyridin-2-yl]phenyl}furan-2-carboxamide; N-[4-chloro-3-(6-{4-[2-(1H-pyrazol-1-yl)ethoxy]phenyl}-1H-imidazo[4,5-b]pyridin-2-yl)phenyl]furan-2-carboxamide; N-(3-{6-[4-(trifluoromethoxy)phenyl]-1H-imidazo[4,5-b]pyridin-2-yl}phenyl)furan-2-carboxamide; N-(4-chloro-3-{6-[4-(2,5-dioxoimidazolidin-4-yl)phenyl]-1H-imidazo[4,5-b]pyridin-2-yl}phenyl)furan-2-carboxamide; N-{4-chloro-3-[6-(2-oxo-2,3-dihydro-1H-indol-5-yl)-1H-imidazo[4,5-b]pyridin-2-yl]phenyl}furan-2-carboxamide; N-[4-chloro-3-(6-{4-[(5-methyl-1,2-oxazol-3-yl)methoxy]phenyl}-1H-imidazo[4,5-b]pyridin-2-yl)phenyl]furan-2-carboxamide; N-[4-chloro-3-(6-{4-[(cyclopropylcarbamoyl)amino]phenyl}-1H-imidazo

[4,5-b]pyridin-2-yl)phenyl]furan-2-carboxamide; N-{4-chloro-3-[6-(4-methanesulfonylphenyl)-1H-imidazo[4,5-b]pyridin-2-yl]phenyl}furan-2-carboxamide; N-(3-{6-[4-(benzyloxy)phenyl]-1H-imidazo[4,5-b]pyridin-2-yl}-4-chlorophenyl)furan-2-carboxamide; N-{4-chloro-3-[6-(3-chloro-4-methoxyphenyl)-1H-imidazo[4,5-b]pyridin-2-yl]phenyl}furan-2-carboxamide; N-(4-chloro-3-{6-[4-methoxy-3-(pyrrolidine-1-sulfonyl)phenyl]-1H-imidazo[4,5-b]pyridin-2-yl}phenyl)furan-2-carboxamide; N-{4-chloro-3-[6-(pyridin-3-yl)-1H-imidazo[4,5-b]pyridin-2-yl]phenyl}furan-2-carboxamide; N-{4-chloro-3-[6-(2-fluoropyridin-4-yl)-1H-imidazo[4,5-b]pyridin-2-yl]phenyl}furan-2-carboxamide; N-(4-chloro-3-{6-[2-fluoro-6-(2-methoxyethoxy)pyridin-3-yl]-1H-imidazo[4,5-b]pyridin-2-yl}phenyl)furan-2-carboxamide; N-(4-chloro-3-{6-[4-(2-methylpropanamido)phenyl]-1H-imidazo[4,5-b]pyridin-2-yl}phenyl)furan-2-carboxamide; 5-{2-[2-chloro-5-(furan-2-amido)phenyl]-1H-imidazo[4,5-b]pyridin-6-yl}-N-methylpyridine-2-carboxamide; N-[4-chloro-3-(6-{4-[2-(pyrrolidin-1-yl)ethoxy]phenyl}-1H-imidazo[4,5-b]pyridin-2-yl)phenyl]furan-2-carboxamide; N-(4-chloro-3-{6-[4-(1H-pyrazol-1-yl)phenyl]-1H-imidazo[4,5-b]pyridin-2-yl}phenyl)furan-2-carboxamide; N-[4-chloro-3-(6-{4-[(methylcarbamoyl)amino]phenyl}-1H-imidazo[4,5-b]pyridin-2-yl)phenyl]furan-2-carboxamide; methyl N-(4-{2-[2-chloro-5-(furan-2-amido)phenyl]-1H-imidazo[4,5-b]pyridin-6-yl}phenyl)carbamate; N-{4-chloro-3-[6-(1-methyl-2,3-dihydro-1H-indol-5-yl)-1H-imidazo[4,5-b]pyridin-2-yl]phenyl}furan-2-carboxamide; N-(4-chloro-3-{6-[4-(2-methoxyethoxy)phenyl]-1H-imidazo[4,5-b]pyridin-2-yl}phenyl)furan-2-carboxamide; N-{4-chloro-3-[6-(2,6-dimethoxypyridin-3-yl)-1H-imidazo[4,5-b]pyridin-2-yl]phenyl}furan-2-carboxamide; N-[4-chloro-3-(6-{4-[4-(propan-2-yl)piperazin-1-yl]phenyl}-1H-imidazo[4,5-b]pyridin-2-yl)phenyl]furan-2-carboxamide; tert-butyl 4-{2-[2-chloro-5-(furan-2-amido)phenyl]-1H-imidazo[4,5-b]pyridin-6-yl}-1,2,3,6-tetrahydropyridine-1-carboxylate; N-(4-chloro-3-{6-[4-(methylcarbamoyl)phenyl]-1H-imidazo[4,5-b]pyridin-2-yl}phenyl)furan-2-carboxamide; N-(4-chloro-3-{6-[6-(dimethylamino)pyridin-3-yl]-1H-imidazo[4,5-b]pyridin-2-yl}phenyl)furan-2-carboxamide; N-{4-chloro-3-[6-(4-sulfamoylphenyl)-1H-imidazo[4,5-b]pyridin-2-yl]phenyl}furan-2-carboxamide; N-(4-chloro-3-{6-[4-(dimethylamino)phenyl]-1H-imidazo[4,5-b]pyridin-2-yl}phenyl)furan-2-carboxamide; N-(4-chloro-3-{6-[4-(pyrrolidin-1-yl)phenyl]-1H-imidazo[4,5-b]pyridin-2-yl}phenyl)furan-2-carboxamide; N-(4-chloro-3-(6-{4-[2-(dimethylamino)ethoxy]phenyl}-1H-imidazo[4,5-b]pyridin-2-yl)phenyl]furan-2-carboxamide; N-{4-chloro-3-[6-(1,2,3,6-tetrahydropyridin-4-yl)-1H-imidazo[4,5-b]pyridin-2-yl]phenyl}furan-2-carboxamide; N-[4-chloro-3-(6-{4-[2-(1H-imidazol-1-yl)ethoxy]phenyl}-1H-imidazo[4,5-b]pyridin-2-yl)phenyl]furan-2-carboxamide; N-{4-chloro-3-[6-(4-methyl-3,4-dihydro-2H-1,4-benzoxazin-7-yl)-1H-imidazo[4,5-b]pyridin-2-yl]phenyl}furan-2-carboxamide; N-{4-chloro-3-[6-(4-methyl-1H-pyrazol-3-yl)-1H-imidazo[4,5-b]pyridin-2-yl]phenyl}furan-2-carboxamide; N-(4-chloro-3-{6-ethenyl-1H-imidazo[4,5-b]pyridin-2-yl}phenyl)furan-2-carboxamide; N-(4-chloro-3-{6-propyl-1H-imidazo[4,5-b]pyridin-2-yl}phenyl)furan-2-carboxamide; N-{4-chloro-3-[6-(2-methylpropyl)-1H-imidazo[4,5-b]pyridin-2-yl]phenyl}furan-2-carboxamide; N-{4-chloro-3-[6-(propan-2-yl)-1H-imidazo[4,5-b]pyridin-2-yl]phenyl}furan-2-carboxamide; N-(4-chloro-3-{6-methyl-1H-imidazo[4,5-b]pyridin-2-yl}phenyl)-2-(2,3-difluorophenyl)acetamide; N-(4-chloro-3-{6-methyl-1H-imidazo[4,5-b]pyridin-2-yl}phenyl)-5-methyl-1,2-oxazole-3-carboxamide; N-(4-chloro-3-{6-methyl-1H-imidazo[4,5-b]pyridin-2-yl}phenyl)-4-methyl-1,3-thiazole-2-carboxamide; N-(4-chloro-3-{6-methyl-1H-imidazo[4,5-b]pyridin-2-yl}phenyl)-2-(4-chlorophenyl)-2-methylpropanamide; N-(4-chloro-3-{6-methyl-1H-imidazo[4,5-b]pyridin-2-yl}phenyl)-2-[4-(dimethylamino)phenyl]acetamide; N-(4-chloro-3-{6-methyl-1H-imidazo[4,5-b]pyridin-2-yl}phenyl)pyridine-2-carboxamide; N-(4-chloro-3-{6-methyl-1H-imidazo[4,5-b]pyridin-2-yl}phenyl)-5-(morpholin-4-yl)pyridine-2-carboxamide; N-(4-chloro-3-{6-methyl-1H-imidazo[4,5-b]pyridin-2-yl}phenyl)-2-(3-chlorophenyl)acetamide; 5-chloro-N-(4-chloro-3-{6-methyl-1H-imidazo[4,5-b]pyridin-2-yl}phenyl)furan-2-carboxamide; N-(4-chloro-3-{6-methyl-1H-imidazo[4,5-b]pyridin-2-yl}phenyl)-2-(2,6-difluorophenyl)acetamide; N-(4-chloro-3-{6-methyl-1H-imidazo[4,5-b]pyridin-2-yl}phenyl)-2-(3-methyl-1,2-oxazol-5-yl)acetamide; 3-chloro-N-(4-chloro-3-{6-methyl-1H-imidazo[4,5-b]pyridin-2-yl}phenyl)benzamide; N-(4-chloro-3-{6-methyl-1H-imidazo[4,5-b]pyridin-2-yl}phenyl)-5-fluorofuran-2-carboxamide; N-(4-chloro-3-{6-methyl-1H-imidazo[4,5-b]pyridin-2-yl}phenyl)-1,2-thiazole-5-carboxamide; N-(4-chloro-3-{6-methyl-1H-imidazo[4,5-b]pyridin-2-yl}phenyl)pyridazine-4-carboxamide; N-(4-chloro-3-{6-methyl-1H-imidazo[4,5-b]pyridin-2-yl}phenyl)-2-ethoxypyridine-4-carboxamide; N-(4-chloro-3-{6-methyl-1H-imidazo[4,5-b]pyridin-2-yl}phenyl)-5-[(dimethylamino)methyl]furan-2-carboxamide; N-(4-chloro-3-{6-methyl-1H-imidazo[4,5-b]pyridin-2-yl}phenyl)-1H-imidazole-2-carboxamide; N-(4-chloro-3-{6-methyl-1H-imidazo[4,5-b]pyridin-2-yl}phenyl)-2-[4-(trifluoromethyl)phenyl]acetamide; N-(4-chloro-3-{6-methyl-1H-imidazo[4,5-b]pyridin-2-yl}phenyl)-2-(pyridin-3-yl)acetamide; 2,5-dichloro-N-(4-chloro-3-{6-methyl-1H-imidazo[4,5-b]pyridin-2-yl}phenyl)benzamide; N-(4-chloro-3-{6-methyl-1H-imidazo[4,5-b]pyridin-2-yl}phenyl)-3-(piperidin-1-yl)benzamide; N-(4-chloro-3-{6-methyl-1H-imidazo[4,5-b]pyridin-2-yl}phenyl)-1H-pyrrole-2-carboxamide; N-(4-chloro-3-{6-methyl-1H-imidazo[4,5-b]pyridin-2-yl}phenyl)-5-cyanopyridine-3-carboxamide; N-(4-chloro-3-{6-methyl-1H-imidazo[4,5-b]pyridin-2-yl}phenyl)-5-methylpyridine-3-carboxamide; N-(4-chloro-3-{6-methyl-1H-imidazo[4,5-b]pyridin-2-yl}phenyl)oxetane-2-carboxamide; N-(4-chloro-3-{6-methyl-1H-imidazo[4,5-b]pyridin-2-yl}phenyl)-1,3-oxazole-2-carboxamide; N-(4-chloro-3-{6-methyl-1H-imidazo[4,5-b]pyridin-2-yl}phenyl)-3,5-dimethyl-1,2-oxazole-4-carboxamide; N-(4-chloro-3-{6-methyl-1H-imidazo[4,5-b]pyridin-2-yl}phenyl)-5-methyl-1,3,4-oxadiazole-2-carboxamide; N-(4-chloro-3-{6-methyl-1H-imidazo[4,5-b]pyridin-2-yl}phenyl)-2-methyl-1,3-thiazole-4-carboxamide; N-(4-chloro-3-{6-methyl-1H-imidazo[4,5-b]pyridin-2-yl}phenyl)-2-methoxybenzamide; N-(4-chloro-3-{6-methyl-1H-imidazo[4,5-b]pyridin-2-yl}phenyl)-4-(morpholin-4-yl)benzamide; 2-chloro-N-(4-chloro-3-{6-methyl-1H-imidazo[4,5-b]pyridin-2-yl}phenyl)-4-methanesulfonylbenzamide; tert-butyl N-{1-[(4-chloro-3-{6-methyl-1H-imidazo[4,5-b]pyridin-2-yl}phenyl)carbamoyl]-1-methylethyl}carbamate; tert-butyl N-{[(4-chloro-3-{6-methyl-1H-imidazo[4,5-b]pyridin-2-yl}phenyl)carbamoyl]methyl}carbamate; N-(4-chloro-3-{6-methyl-1H-imidazo[4,5-b]pyridin-2-yl}phenyl)-1,3-oxazole-4-carboxamide; N-(4-chloro-3-{6-methyl-1H-imidazo[4,5-b]pyridin-2-yl}phenyl)-2-(2,4-difluorophenyl)acetamide; N-(4-chloro-3-{6-methyl-1H-imidazo[4,5-b]pyridin-2-yl}phenyl)-5-(trifluoromethyl)pyridine-2-carboxamide; 2-amino-N-(4-chloro-3-{6-methyl-1H- imidazo[4,5-b]pyridin-2-yl}phenyl)acetamide; N-(4-chloro-3-{6-methyl-1H-imidazo[4,5-b]pyridin-2-yl}phenyl)-3,3-difluorocyclobutane-1-carboxamide; N-(4-chloro-3-{6-methyl-1H-imidazo[4,5-b]pyridin-2-yl}phenyl)cyclobutanecarboxamide; N-(4-chloro-3-{6-methyl-1H-imidazo[4,5-b]pyridin-2-yl}phenyl)-2-(4-fluorophenyl)propanamide; N-(4-chloro-3-{6-methyl-1H-imidazo[4,5-b]pyridin-2-yl}phenyl)-2-phenoxyacetamide; N-(4-chloro-3-{6-methyl-1H-imidazo[4,5-b]pyridin-2-yl}phenyl)-2-[4-(trifluoromethoxy)phenyl]acetamide; N-(4-chloro-3-{6-methyl-1H-imidazo[4,5-b]pyridin-2-yl}phenyl)-2-(1H-1,2,4-triazol-1-yl)acetamide; N-(4-chloro-3-{6-methyl-1H-imidazo[4,5-b]pyridin-2-yl}phenyl)-2,3-dihydro-1-benzofuran-2-carboxamide; N-(4-chloro-3-{6-methyl-1H-imidazo[4,5-b]pyridin-2-yl}phenyl)-5-methyl-1H-pyrrole-2-carboxamide; N-(4-chloro-3-{6-methyl-1H-imidazo[4,5-b]pyridin-2-yl}phenyl)-2-(4-fluorophenyl)acetamide; N-(4-chloro-3-{6-methyl-1H-imidazo[4,5-b]pyridin-2-yl}phenyl)-5-methylfuran-2-carboxamide; 6-chloro-N-(4-chloro-3-{6-methyl-1H-imidazo[4,5-b]pyridin-2-yl}phenyl)pyrazine-2-carboxamide; N-(4-chloro-3-{6-methyl-1H-imidazo[4,5-b]pyridin-2-yl}phenyl)-1H-imidazole-5-carboxamide; N-(4-chloro-3-{6-methyl-1H-imidazo[4,5-b]pyridin-2-yl}phenyl)-2-methoxypyridine-4-carboxamide; N-(4-chloro-3-{6-methyl-1H-imidazo[4,5-b]pyridin-2-yl}phenyl)-3-methylfuran-2-carboxamide; N-(4-chloro-3-{6-methyl-1H-imidazo[4,5-b]pyridin-2-yl}phenyl)oxane-2-carboxamide; N-(4-chloro-3-{6-methyl-1H-imidazo[4,5-b]pyridin-2-yl}phenyl)-4-(morpholin-4-yl)butanamide; tert-butyl 3-[(4-chloro-3-{6-methyl-1H-imidazo[4,5-b]pyridin-2-yl}phenyl)carbamoyl]-3-methylazetidine-1-carboxylate; N-(4-chloro-3-{6-methyl-1H-imidazo[4,5-b]pyridin-2-yl}phenyl)-3-methoxybenzamide; 5-chloro-N-(4-chloro-3-{6-methyl-1H-imidazo[4,5-b]pyridin-2-yl}phenyl)pyrazine-2-carboxamide; N-(4-chloro-3-{6-methyl-1H-imidazo[4,5-b]pyridin-2-yl}phenyl)-6-methanesulfonylpyridine-3-carboxamide; N-(4-chloro-3-{6-methyl-1H-imidazo[4,5-b]pyridin-2-yl}phenyl)-2-(methylsulfanyl)pyrimidine-4-carboxamide; N-(4-chloro-3-{6-methyl-1H-imidazo[4,5-b]pyridin-2-yl}phenyl)oxolane-2-carboxamide; N-(4-chloro-3-{6-methyl-1H-imidazo[4,5-b]pyridin-2-yl}phenyl)-2,4-dimethyl-1,3-oxazole-5-carboxamide; N-(4-chloro-3-{6-methyl-1H-imidazo[4,5-b]pyridin-2-yl}phenyl)-3-methanesulfonylbenzamide; N-(4-chloro-3-{6-methyl-1H-imidazo[4,5-b]pyridin-2-yl}phenyl)-2-(4-chlorophenyl)-3-methylbutanamide; N-(4-chloro-3-{6-methyl-1H-imidazo[4,5-b]pyridin-2-yl}phenyl)-2-(3,4-difluorophenyl)acetamide; N-(4-chloro-3-{6-methyl-1H-imidazo[4,5-b]pyridin-2-yl}phenyl)-3-hydroxypropanamide; N-(4-chloro-3-{6-methyl-1H-imidazo[4,5-b]pyridin-2-yl}phenyl)-2-(4-chlorophenyl)acetamide; N-(4-chloro-3-{6-methyl-1H-imidazo[4,5-b]pyridin-2-yl}phenyl)-2-(pyrimidin-2-yl)acetamide; 2-(2,1-benzoxazol-3-yl)-N-(4-chloro-3-{6-methyl-1H-imidazo[4,5-b]pyridin-2-yl}phenyl)acetamide; N-(4-chloro-3-{6-methyl-1H-imidazo[4,5-b]pyridin-2-yl}phenyl)-2,4-dimethoxybenzamide; N-(4-chloro-3-{6-methyl-1H-imidazo[4,5-b]pyridin-2-yl}phenyl)-2-(pyridin-4-yl)acetamide; 2-chloro-N-(4-chloro-3-{6-methyl-1H-imidazo[4,5-b]pyridin-2-yl}phenyl)benzamide; N-(4-chloro-3-{6-methyl-1H-imidazo[4,5-b]pyridin-2-yl}phenyl)-2-(dimethylamino)benzamide; N-(4-chloro-3-{6-methyl-1H-imidazo[4,5-b]pyridin-2-yl}phenyl)-1-methyl-1H-pyrrole-2-carboxamide; 5-chloro-N-(4-chloro-3-{6-methyl-1H-imidazo[4,5-b]pyridin-2-yl}phenyl)thiophene-2-carboxamide; N-(4-chloro-3-{6-methyl-1H-imidazo[4,5-b]pyridin-2-yl}phenyl)-4-(trifluoromethyl)benzamide; N-(4-chloro-3-{6-methyl-1H-imidazo[4,5-b]pyridin-2-yl}phenyl)-2-methanesulfinylpyrimidine-4-carboxamide; N-(4-chloro-3-{6-methyl-1H-imidazo[4,5-b]pyridin-2-yl}phenyl)-1,2-oxazole-5-carboxamide; N-(4-chloro-3-{6-methyl-1H-imidazo[4,5-b]pyridin-2-yl}phenyl)-2-(4-methoxyphenyl)acetamide; N-(4-chloro-3-{6-methyl-1H-imidazo[4,5-b]pyridin-2-yl}phenyl)-1H-pyrazole-3-carboxamide; N-(4-chloro-3-{6-methyl-1H-imidazo[4,5-b]pyridin-2-yl}phenyl)-3-cyclopropyl-1H-pyrazole-5-carboxamide; N-(4-chloro-3-{6-methyl-1H-imidazo[4,5-b]pyridin-2-yl}phenyl)-4-(dimethylamino)butanamide; N-(4-chloro-3-{6-methyl-1H-imidazo[4,5-b]pyridin-2-yl}phenyl)-3-methyl-2-phenylbutanamide; N-(4-chloro-3-{6-methyl-1H-imidazo[4,5-b]pyridin-2-yl}phenyl)-5-methyl-1,2,4-oxadiazole-3-carboxamide; N-(4-chloro-3-{6-methyl-1H-imidazo[4,5-b]pyridin-2-yl}phenyl)-2-methyl-6-(trifluoromethyl)pyridine-3-carboxamide; N-(4-chloro-3-{6-methyl-1H-imidazo[4,5-b]pyridin-2-yl}phenyl)-3-methyloxetane-3-carboxamide; N-(4-chloro-3-{6-methyl-1H-imidazo[4,5-b]pyridin-2-yl}phenyl)-2,2-difluoro-2-phenylacetamide; N-(4-chloro-3-{6-methyl-1H-imidazo[4,5-b]pyridin-2-yl}phenyl)-2-(4-methoxyphenyl)propanamide; N-(4-chloro-3-{6-methyl-1H-imidazo[4,5-b]pyridin-2-yl}phenyl)-5-(pyrazin-2-yl)pyridine-2-carboxamide; N-(4-chloro-3-{6-methyl-1H-imidazo[4,5-b]pyridin-2-yl}phenyl)-2-(4-methylphenyl)acetamide; N-(4-chloro-3-{6-methyl-1H-imidazo[4,5-b]pyridin-2-yl}phenyl)-2-(2-oxo-1,2-dihydropyrimidin-1-yl)acetamide; N-(4-chloro-3-{6-methyl-1H-imidazo[4,5-b]pyridin-2-yl}phenyl)-2-(1H-1,2,3,4-tetrazol-5-yl)acetamide; N-(4-chloro-3-{6-methyl-1H-imidazo[4,5-b]pyridin-2-yl}phenyl)-2-(1H-1,2,3,4-tetrazol-1-yl)acetamide; N-(4-chloro-3-{6-methyl-1H-imidazo[4,5-b]pyridin-2-yl}phenyl)piperidine-2-carboxamide; N-(4-chloro-3-{6-methyl-1H-imidazo[4,5-b]pyridin-2-yl}phenyl)-4-methylpyridine-2-carboxamide; N-(4-chloro-3-{6-methyl-1H-imidazo[4,5-b]pyridin-2-yl}phenyl)-4-methoxypyridine-2-carboxamide; N-(4-chloro-3-{6-methyl-1H-imidazo[4,5-b]pyridin-2-yl}phenyl)-3-hydroxypyrazine-2-carboxamide; N-(4-chloro-3-{6-methyl-1H-imidazo[4,5-b]pyridin-2-yl}phenyl)-5-methanesulfonylthiophene-2-carboxamide; N-(4-chloro-3-{6-methyl-1H-imidazo[4,5-b]pyridin-2-yl}phenyl)-2-methyl-5-(trifluoromethyl)-1,3-oxazole-4-carboxamide; N-(4-chloro-3-{6-methyl-1H-imidazo[4,5-b]pyridin-2-yl}phenyl)-1,3-oxazole-5-carboxamide; N-(4-chloro-3-{6-methyl-1H-imidazo[4,5-b]pyridin-2-yl}phenyl)-5-methylpyrazine-2-carboxamide; N-(4-chloro-3-{6-methyl-1H-imidazo[4,5-b]pyridin-2-yl}phenyl)-2,5-dimethyl-1,3-oxazole-4-carboxamide; N-(4-chloro-3-{6-methyl-1H-imidazo[4,5-b]pyridin-2-yl}phenyl)-2,3-dihydro-1-benzofuran-7-carboxamide; (2R)-N-(4-chloro-3-{6-methyl-1H-imidazo[4,5-b]pyridin-2-yl}phenyl)-2-methoxy-2-phenylacetamide; N-(4-chloro-3-{6-methyl-1H-imidazo[4,5-b]pyridin-2-yl}phenyl)-2-hydroxy-2-[4-(trifluoromethyl)phenyl]acetamide; N-(4-chloro-3-{6-methyl-1H-imidazo[4,5-b]pyridin-2-yl}phenyl)-2-hydroxyacetamide; N-(4-chloro-3-{6-methyl-1H-imidazo[4,5-b]pyridin-2-yl}phenyl)-3-(dimethylamino)benzamide; N-(4-chloro-3-{6-methyl-1H-imidazo[4,5-b]pyridin-2-yl}phenyl)-5-fluorothiophene-2-carboxamide; N-(4-chloro-3-{6-methyl-1H-imidazo[4,5-b]pyridin-2-yl}phenyl)pyridazine-3-carboxamide; N-(4-chloro-3-{6-methyl-1H-imidazo[4,5-b]pyridin-2-yl}phenyl)pyrimidine-5-carboxamide; N-(4-chloro-3-{6-methyl-1H-imidazo[4,5-b]pyridin-2-yl}phenyl)-2-methylpyridine-4-carboxamide; N-(4-chloro-3-{6-methyl-1H-imidazo[4,5-b]pyridin-2-yl}phenyl)-2,3- dimethylpyridine-4-carboxamide; 5-tert-butyl-N-(4-chloro-3-{6-methyl-1H-imidazo[4,5-b]pyridin-2-yl}phenyl)furan-2-carboxamide; N-(4-chloro-3-{6-methyl-1H-imidazo[4,5-b]pyridin-2-yl}phenyl)-2,4-dimethyl-1,3-thiazole-5-carboxamide; N-(4-chloro-3-{6-methyl-1H-imidazo[4,5-b]pyridin-2-yl}phenyl)-1,3-thiazole-2-carboxamide; N-(4-chloro-3-{6-methyl-1H-imidazo[4,5-b]pyridin-2-yl}phenyl)-4-methanesulfonylbenzamide; 2-amino-N-(4-chloro-3-{6-methyl-1H-imidazo[4,5-b]pyridin-2-yl}phenyl)-2-methylpropanamide; N-(4-chloro-3-{6-methyl-1H-imidazo[4,5-b]pyridin-2-yl}phenyl)-3-(morpholin-4-yl)benzamide; 3,5-dichloro-N-(4-chloro-3-{6-methyl-1H-imidazo[4,5-b]pyridin-2-yl}phenyl)benzamide; N-(4-chloro-3-{6-methyl-1H-imidazo[4,5-b]pyridin-2-yl}phenyl)-2-(1H-imidazol-1-yl)acetamide; N-(4-chloro-3-{6-methyl-1H-imidazo[4,5-b]pyridin-2-yl}phenyl)-3,4-dihydro-2H-1-benzopyran-2-carboxamide; N-(4-chloro-3-{6-methyl-1H-imidazo[4,5-b]pyridin-2-yl}phenyl)cyclopentanecarboxamide; N-(4-chloro-3-{6-methyl-1H-imidazo[4,5-b]pyridin-2-yl}phenyl)-3-methylazetidine-3-carboxamide; 3-[(4-chloro-3-{6-methyl-1H-imidazo[4,5-b]pyridin-2-yl}phenyl)carbamoyl]propanoic acid; N-(4-chloro-3-{6-methyl-1H-imidazo[4,5-b]pyridin-2-yl}phenyl)-2-phenylacetamide; N-(4-chloro-3-{6-methyl-1H-imidazo[4,5-b]pyridin-2-yl}phenyl)-3-methyl-1H-1,2,4-triazole-5-carboxamide; N-(4-chloro-3-{6-methyl-1H-imidazo[4,5-b]pyridin-2-yl}phenyl)cyclopentanecarboxamide; N-(4-chloro-3-{6-methyl-1H-imidazo[4,5-b]pyridin-2-yl}phenyl)-1,3-thiazole-4-carboxamide; N-(4-chloro-3-{6-methyl-1H-imidazo[4,5-b]pyridin-2-yl}phenyl)pyrazine-2-carboxamide; N-(4-chloro-3-{6-methyl-1H-imidazo[4,5-b]pyridin-2-yl}phenyl)-1-methyl-1H-imidazole-5-carboxamide; N-(4-chloro-3-{6-methyl-1H-imidazo[4,5-b]pyridin-2-yl}phenyl)pyridine-3-carboxamide; N-(4-chloro-3-{6-methyl-1H-imidazo[4,5-b]pyridin-2-yl}phenyl)-4-methylthiophene-2-carboxamide; N-(4-chloro-3-{6-methyl-1H-imidazo[4,5-b]pyridin-2-yl}phenyl)-4-(trifluoromethoxy)benzamide; N-(4-chloro-3-{6-methyl-1H-imidazo[4,5-b]pyridin-2-yl}phenyl)-4-methoxybenzamide; N-(4-chloro-3-{6-methyl-1H-imidazo[4,5-b]pyridin-2-yl}phenyl)pyridine-4-carboxamide; N-(4-chloro-3-{6-methyl-1H-imidazo[4,5-b]pyridin-2-yl}phenyl)-1-methyl-1H-pyrazole-5-carboxamide; 2-fluoroethyl N-(4-chloro-3-{6-methyl-1H-imidazo[4,5-b]pyridin-2-yl}phenyl)carbamate; ethyl N-(4-chloro-3-{6-methyl-1H-imidazo[4,5-b]pyridin-2-yl}phenyl)carbamate; propan-2-yl N-(4-chloro-3-{6-methyl-1H-imidazo[4,5-b]pyridin-2-yl}phenyl)carbamate; ethyl N-(4-chloro-3-{6-methyl-1H-imidazo[4,5-b]pyridin-2-yl}phenyl)carbamate; cyclopentyl N-(4-chloro-3-{6-methyl-1H-imidazo[4,5-b]pyridin-2-yl}phenyl)carbamate; ethyl N-(4-chloro-3-{6-methyl-1H-imidazo[4,5-b]pyridin-2-yl}phenyl)carbamate; 2-methylpropyl N-(4-chloro-3-{6-methyl-1H-imidazo[4,5-b]pyridin-2-yl}phenyl)carbamate; 2-methoxyethyl N-(4-chloro-3-{6-methyl-1H-imidazo[4,5-b]pyridin-2-yl}phenyl)carbamate; cyclohexyl N-(4-chloro-3-{6-methyl-1H-imidazo[4,5-b]pyridin-2-yl}phenyl)carbamate; benzyl N-(4-chloro-3-{6-methyl-1H-imidazo[4,5-b]pyridin-2-yl}phenyl)carbamate; methyl N-(4-chloro-3-{6-methyl-1H-imidazo[4,5-b]pyridin-2-yl}phenyl)carbamate; 2,2,2-trifluoroethyl N-(4-chloro-3-{6-methyl-1H-imidazo[4,5-b]pyridin-2-yl}phenyl)carbamate; 1-(4-chloro-3-{6-methyl-1H-imidazo[4,5-b]pyridin-2-yl}phenyl)-3-[2-(dimethylamino)ethyl]urea; 1-(4-chloro-3-{6-methyl-1H-imidazo[4,5-b]pyridin-2-yl}phenyl)-3-[6-(diethylamino)hexyl]urea; 1-(4-chloro-3-{6-methyl-1H-imidazo[4,5-b]pyridin-2-yl}phenyl)-3-[6-(dimethylamino)hexyl]urea; (2R)-N-(4-chloro-3-{6-methyl-1H-imidazo[4,5-b]pyridin-2-yl}phenyl)-4,4-difluoro-2-(3-fluorophenyl)pyrrolidine-1-carboxamide; N-(4-chloro-3-{6-methyl-1H-imidazo[4,5-b]pyridin-2-yl}phenyl)-3-azabicyclo[3.1.0]hexane-3-carboxamide; 1-(4-chloro-3-{6-methyl-1H-imidazo[4,5-b]pyridin-2-yl}phenyl)-3-cyclopentyl-3-methylurea; 1-(4-chloro-3-{6-methyl-1H-imidazo[4,5-b]pyridin-2-yl}phenyl)-3-methyl-3-(oxolan-3-yl)urea; N-(4-chloro-3-{6-methyl-1H-imidazo[4,5-b]pyridin-2-yl}phenyl)-3-(dimethylamino)pyrrolidine-1-carboxamide; (3R)-N-(4-chloro-3-{6-methyl-1H-imidazo[4,5-b]pyridin-2-yl}phenyl)-3-fluoropyrrolidine-1-carboxamide; (3S)-N-(4-chloro-3-{6-methyl-1H-imidazo[4,5-b]pyridin-2-yl}phenyl)-3-fluoropyrrolidine-1-carboxamide; 3-{2-[bis(propan-2-yl)amino]ethyl}-1-(4-chloro-3-{6-methyl-1H-imidazo[4,5-b]pyridin-2-yl}phenyl)urea; N-(4-chloro-3-{6-methyl-1H-imidazo[4,5-b]pyridin-2-yl}phenyl)morpholine-4-carboxamide; 1-(4-chloro-3-{6-methyl-1H-imidazo[4,5-b]pyridin-2-yl}phenyl)-3-methylurea; N-(4-chloro-3-{6-methyl-1H-imidazo[4,5-b]pyridin-2-yl}phenyl)piperidine-1-carboxamide; 1-(4-chloro-3-{6-methyl-1H-imidazo[4,5-b]pyridin-2-yl}phenyl)-3-methoxy-3-methylurea; 3-(4-chloro-3-{6-methyl-1H-imidazo[4,5-b]pyridin-2-yl}phenyl)-1-methyl-1-phenylurea; 1-(4-chloro-3-{6-methyl-1H-imidazo[4,5-b]pyridin-2-yl}phenyl)-3-ethyl-3-methylurea; 1-(4-chloro-3-{6-methyl-1H-imidazo[4,5-b]pyridin-2-yl}phenyl)-3,3-dimethylurea; N-(4-chloro-3-{6-methyl-1H-imidazo[4,5-b]pyridin-2-yl}phenyl)-4-methylpiperazine-1-carboxamide; N-(4-chloro-3-{6-methyl-1H-imidazo[4,5-b]pyridin-2-yl}phenyl)pyrrolidine-1-carboxamide; N-(4-chloro-3-{6-methyl-1H-imidazo[4,5-b]pyridin-2-yl}phenyl)-2-oxoimidazolidine-1-carboxamide; 1-(4-chloro-3-{6-methyl-1H-imidazo[4,5-b]pyridin-2-yl}phenyl)-3-cyclobutylurea; 3-(4-chloro-3-{6-methyl-1H-imidazo[4,5-b]pyridin-2-yl}phenyl)-1-[4-(trifluoromethyl)phenyl]urea; 1-(4-chloro-3-{6-methyl-1H-imidazo[4,5-b]pyridin-2-yl}phenyl)-3-(propan-2-yl)urea; N-(4-chloro-3-{6-methyl-1H-imidazo[4,5-b]pyridin-2-yl}phenyl)-1-phenylmethanesulfonamide; N-(4-chloro-3-{6-methyl-1H-imidazo[4,5-b]pyridin-2-yl}phenyl)thiophene-2-sulfonamide; N-(4-chloro-3-{6-methyl-1H-imidazo[4,5-b]pyridin-2-yl}phenyl)-1-[4-(trifluoromethyl)phenyl]methanesulfonamide; N-(4-chloro-3-{6-methyl-1H-imidazo[4,5-b]pyridin-2-yl}phenyl)-3,5-dimethyl-1,2-oxazole-4-sulfonamide; N-(4-chloro-3-{6-methyl-1H-imidazo[4,5-b]pyridin-2-yl}phenyl)piperidine-1-sulfonamide; N-(4-chloro-3-{6-methyl-1H-imidazo[4,5-b]pyridin-2-yl}phenyl)-2-methylpropane-1-sulfonamide; 4-chloro-N-(4-chlorophenyl)-3-{6-methyl-1H-imidazo[4,5-b]pyridin-2-yl}aniline; 4-(4-chloro-3-{6-methyl-1H-imidazo[4,5-b]pyridin-2-yl}phenyl)morpholine; N-(4-chloro-3-{6-methyl-1H-imidazo[4,5-b]pyridin-2-yl}phenyl)-6-(1H-1,2,4-triazol-1-yl)pyridin-3-amine; 2-N-(4-chloro-3-{6-methyl-1H-imidazo[4,5-b]pyridin-2-yl}phenyl)-5-N,5-N-dimethylpyridine-2,5-diamine; N-(4-chloro-3-{6-methyl-1H-imidazo[4,5-b]pyridin-2-yl}phenyl)-5-(morpholin-4-yl)pyridin-2-amine; N-(4-chloro-3-{6-methyl-1H-imidazo[4,5-b]pyridin-2-yl}phenyl)-2-methanesulfonyl-1,2,3,4-tetrahydroisoquinolin-5-amine; N-(4-chloro-3-{6-methyl-1H-imidazo[4,5-b]pyridin-2-yl}phenyl)-5-methylpyridin-2-amine; 6-[(4-chloro-3-{6-methyl-1H-imidazo[4,5-b]pyridin-2-yl}phenyl)amino]pyridine-3-carbonitrile; N-(4-chloro-3-{6-methyl-1H-imidazo[4,5-b]pyridin-2-yl}phenyl)-2-(morpholin-4-yl)pyridin-3-amine; 6-benzyl-N-(4-chloro-3-{6-methyl-1H-imidazo[4,5-b]pyridin-2-yl}phenyl)-5,6,7,8-tetrahydro-2,6-naphthyridin-1-amine; 4-chloro-N-(furan-2-ylmethyl)-3-{6-methyl-1H-imidazo[4, 5-b]pyridin-2-yl}aniline; N-(4-Fluoro-3-(6-methyl-3H-imidazo[4,5-b]pyridin-2-yl)phenyl)furan-2-carboxamide; 3-amino-N-(4-fluoro-3-{6-methyl-1H-imidazo[4,5-b]pyridin-2-yl}phenyl)propanamide; 4-[2-(dimethylamino)ethoxy]-N-(4-fluoro-3-{6-methyl-1H-imidazo[4,5-b]pyridin-2-yl}phenyl)benzamide; N-(4-fluoro-3-{6-methyl-1H-imidazo[4,5-b]pyridin-2-yl}phenyl)-1,2-oxazole-5-carboxamide; (2R,4R)-N-(4-fluoro-3-{6-methyl-1H-imidazo[4,5-b]pyridin-2-yl}phenyl)-4-hydroxypyrrolidine-2-carboxamide; N-(4-fluoro-3-{6-methyl-1H-imidazo[4,5-b]pyridin-2-yl}phenyl)acetamide; (2S)-N-(4-fluoro-3-{6-methyl-1H-imidazo[4,5-b]pyridin-2-yl}phenyl)pyrrolidine-2-carboxamide; N-(4-fluoro-3-{6-methyl-1H-imidazo[4,5-b]pyridin-2-yl}phenyl)pyrazolo[1,5-a]pyridine-2-carboxamide; 4-(dimethylamino)-N-(4-fluoro-3-{6-methyl-1H-imidazo[4,5-b]pyridin-2-yl}phenyl)butanamide; N-{4-chloro-3-[6-(trifluoromethyl)-1H-imidazo[4,5-b]pyridin-2-yl]phenyl}furan-2-carboxamide; N-{4-chloro-3-[6-(trifluoromethyl)-1H-imidazo[4,5-b]pyridin-2-yl]phenyl}-5-[(dimethylamino)methyl]furan-2-carboxamide; 2-chloro-N-{4-chloro-3-[6-(trifluoromethyl)-1H-imidazo[4,5-b]pyridin-2-yl]phenyl}benzamide; N-{4-chloro-3-[6-(trifluoromethyl)-1H-imidazo[4,5-b]pyridin-2-yl]phenyl}-5-methylfuran-2-carboxamide; N-{4-chloro-3-[6-(trifluoromethyl)-1H-imidazo[4,5-b]pyridin-2-yl]phenyl}-2-(3-chlorophenyl)acetamide; N-{4-chloro-3-[6-(trifluoromethyl)-1H-imidazo[4,5-b]pyridin-2-yl]phenyl}-5-cyanofuran-2-carboxamide; N-{4-chloro-3-[6-(trifluoromethyl)-1H-imidazo[4,5-b]pyridin-2-yl]phenyl}cyclopentanecarboxamide; N-{4-chloro-3-[6-(trifluoromethyl)-1H-imidazo[4,5-b]pyridin-2-yl]phenyl}-5-fluoropyridine-3-carboxamide; N-{4-chloro-3-[6-(trifluoromethyl)-1H-imidazo[4,5-b]pyridin-2-yl]phenyl}-5-fluorofuran-2-carboxamide; N-{4-chloro-3-[6-(trifluoromethyl)-1H-imidazo[4,5-b]pyridin-2-yl]phenyl}pyrazine-2-carboxamide; N-(4-chloro-3-{6-cyano-1H-imidazo[4,5-b]pyridin-2-yl}phenyl)furan-2-carboxamide; propan-2-yl N-(4-chloro-3-{6-cyano-1H-imidazo[4,5-b]pyridin-2-yl}phenyl)carbamate; propan-2-yl 2-(2-chloro-5-{[(propan-2-yloxy)carbonyl]amino}phenyl)-6-cyano-1H-imidazo[4,5-b]pyridine-1-carboxylate; ethyl N-(4-chloro-3-{6-cyano-1H-imidazo[4,5-b]pyridin-2-yl}phenyl)carbamate; methyl N-(4-chloro-3-{6-cyano-1H-imidazo[4,5-b]pyridin-2-yl}phenyl)carbamate; N-(4-chloro-3-{6-phenyl-1H-imidazo[4,5-b]pyridin-2-yl}phenyl)pyrrolidine-1-carboxamide; N-(4-chloro-3-{6-[4-(methylamino)phenyl]-1H-imidazo[4,5-b]pyridin-2-yl}phenyl)pyrrolidine-1-carboxamide; N-{4-chloro-3-[6-(4-fluorophenyl)-1H-imidazo[4,5-b]pyridin-2-yl]phenyl}pyrrolidine-1-carboxamide; N-(4-chloro-3-{6-[4-(piperazin-1-yl)phenyl]-1H-imidazo[4,5-b]pyridin-2-yl}phenyl)pyrrolidine-1-carboxamide; N-[4-fluoro-3-(6-{4-[2-(morpholin-4-yl)ethoxy]phenyl}-1H-imidazo[4,5-b]pyridin-2-yl)phenyl]pyrrolidine-1-carboxamide; methyl N-[4-(2-{2-chloro-5-[(pyrrolidin-1-yl)carbonylamino]phenyl}-1H-imidazo[4,5-b]pyridin-6-yl)phenyl]carbamate; N-{4-chloro-3-[6-(4-methanesulfonylphenyl)-1H-imidazo[4,5-b]pyridin-2-yl]phenyl}pyrrolidine-1-carboxamide; N-(4-fluoro-3-{6-[1-(piperidin-4-yl)-1H-pyrazol-4-yl]-1H-imidazo[4,5-b]pyridin-2-yl}phenyl)pyrrolidine-1-carboxamide; N-[4-chloro-3-(6-{4-[2-(morpholin-4-yl)ethoxy]phenyl}-1H-imidazo[4,5-b]pyridin-2-yl)phenyl]pyrrolidine-1-carboxamide; N-{4-chloro-3-[6-(thiophen-3-yl)-1H-imidazo[4,5-b]pyridin-2-yl]phenyl}pyrrolidine-1-carboxamide; N-[4-chloro-3-(6-{3-[2-(morpholin-4-yl)ethoxy]phenyl}-1H-imidazo[4,5-b]pyridin-2-yl)phenyl]pyrrolidine-1-carboxamide; N-[4-chloro-3-(6-{4-[3-(morpholin-4-yl)propoxy]phenyl}-1H-imidazo[4,5-b]pyridin-2-yl)phenyl]pyrrolidine-1-carboxamide; N-(4-chloro-3-{6-[4-(2-methoxyethoxy)phenyl]-1H-imidazo[4,5-b]pyridin-2-yl}phenyl)pyrrolidine-1-carboxamide; N-(3-{6-[4-(1-amino-2-methylpropan-2-yl)phenyl]-1H-imidazo[4,5-b]pyridin-2-yl}-4-chlorophenyl)pyrrolidine-1-carboxamide; N-[4-chloro-3-(6-{4-[2-hydroxy-3-(morpholin-4-yl)propoxy]phenyl}-1H-imidazo[4,5-b]pyridin-2-yl)phenyl]pyrrolidine-1-carboxamide; N-{4-chloro-3-[6-(1-{[2-(trimethylsilyl)ethoxy]methyl}-1H-imidazol-4-yl)-1H-imidazo[4,5-b]pyridin-2-yl]phenyl}pyrrolidine-1-carboxamide; N-{4-chloro-3-[6-(1H-imidazol-4-yl)-1H-imidazo[4,5-b]pyridin-2-yl]phenyl}pyrrolidine-1-carboxamide; tert-butyl N-[4-(2-{2-chloro-5-[(pyrrolidin-1-yl)carbonylamino]phenyl}-1H-imidazo[4,5-b]pyridin-6-yl)phenyl]-N-methylcarbamate; N-(4-fluoro-3-{6-phenyl-1H-imidazo[4,5-b]pyridin-2-yl}phenyl)pyrrolidine-1-carboxamide; N-(4-fluoro-3-{6-[4-(oxiran-2-ylmethoxy)phenyl]-1H-imidazo[4,5-b]pyridin-2-yl}phenyl)pyrrolidine-1-carboxamide; N-(4-fluoro-3-(6-{4-[2-(4-methylpiperazin-1-yl)ethoxy]phenyl}-1H-imidazo[4,5-b]pyridin-2-yl)phenyl]pyrrolidine-1-carboxamide; N-(4-fluoro-3-{6-[4-(2-methoxyethoxy)phenyl]-1H-imidazo[4,5-b]pyridin-2-yl}phenyl)pyrrolidine-1-carboxamide; N-{4-fluoro-3-[6-(2-methoxyphenyl)-3H-imidazo[4,5-b]pyridin-2-yl]phenyl}pyrrolidine-1-carboxamide; N-{3-[6-(3-chlorophenyl)-3H-imidazo[4,5-b]pyridin-2-yl]-4-fluorophenyl}pyrrolidine-1-carboxamide; N-{4-fluoro-3-[6-(3-methylphenyl)-3H-imidazo[4,5-b]pyridin-2-yl]phenyl}pyrrolidine-1-carboxamide; N-{3-[6-(3-aminophenyl)-3H-imidazo[4,5-b]pyridin-2-yl]-4-fluorophenyl}pyrrolidine-1-carboxamide; N-{4-fluoro-3-[6-(furan-3-yl)-3H-imidazo[4,5-b]pyridin-2-yl]phenyl}pyrrolidine-1-carboxamide; N-{4-fluoro-3-[6-(thiophen-3-yl)-3H-imidazo[4,5-b]pyridin-2-yl]phenyl}pyrrolidine-1-carboxamide; N-{4-fluoro-3-[6-(pyridin-3-yl)-3H-imidazo[4,5-b]pyridin-2-yl]phenyl}pyrrolidine-1-carboxamide; N-(3-{6-bromo-3H-imidazo[4,5-b]pyridin-2-yl}-4-fluorophenyl)-2,5-dihydro-1H-pyrrole-1-carboxamide; N-{4-fluoro-3-[6-(4-fluoro-3-methylphenyl)-3H-imidazo[4,5-b]pyridin-2-yl]phenyl}pyrrolidine-1-carboxamide; N-{4-fluoro-3-[6-(thiophen-2-yl)-3H-imidazo[4,5-b]pyridin-2-yl]phenyl}pyrrolidine-1-carboxamide; N-{4-fluoro-3-[6-(3-methanesulfonamidophenyl)-3H-imidazo[4,5-b]pyridin-2-yl]phenyl}pyrrolidine-1-carboxamide; N-{3-[6-(6-chloropyridin-3-yl)-3H-imidazo[4,5-b]pyridin-2-yl]-4-fluorophenyl}pyrrolidine-1-carboxamide; N-{3-[6-(2-chloropyridin-4-yl)-3H-imidazo[4,5-b]pyridin-2-yl]-4-fluorophenyl}pyrrolidine-1-carboxamide; N-{4-fluoro-3-[6-(5-methylpyridin-3-yl)-3H-imidazo[4,5-b]pyridin-2-yl]phenyl}pyrrolidine-1-carboxamide; N-{4-fluoro-3-[6-(6-methoxypyridin-3-yl)-3H-imidazo[4,5-b]pyridin-2-yl]phenyl}pyrrolidine-1-carboxamide; N-(4-fluoro-3-{6-[2-(pyrrolidin-1-yl)pyridin-4-yl]-3H-imidazo[4,5-b]pyridin-2-yl}phenyl)pyrrolidine-1-carboxamide; N-{4-fluoro-3-[6-(pyrimidin-5-yl)-3H-imidazo[4,5-b]pyridin-2-yl]phenyl}pyrrolidine-1-carboxamide; N-{3-[6-(5-chloropyridin-3-yl)-3H-imidazo[4,5-b]pyridin-2-yl]-4-fluorophenyl}pyrrolidine-1-carboxamide; N-{4-fluoro-3-[6-(2-methoxypyrimidin-5-yl)-3H-imidazo[4,5-b]pyridin-2-yl]phenyl}pyrrolidine-1-carboxamide; tert-butyl N-[4-(2-{2-chloro-5-[(pyrrolidin-1-yl)carbonylamino]phenyl}-1H-imidazo[4,5-b]pyridin-6-yl)phenyl]-N-methylcarbamate; propan-2-yl N-(4-chloro-3-{6-phenyl-1H-imidazo[4,5-b]pyridin-2-yl}phenyl)carbamate; propan-2-yl N-{3-[6-(2-aminophenyl)-1H-imidazo[4,5-b]pyridin-2-yl]-4-chlorophenyl}carbamate; propan-2-yl N-{4-chloro-3-[6-(2-

{[(propan-2-yloxy)carbonyl]amino}phenyl)-1H-imidazo[4,5-b]pyridin-2-yl]phenyl}carbamate; propan-2-yl 2-(2-chloro-5-{[(propan-2-yloxy)carbonyl]amino}phenyl)-6-(2-{[(propan-2-yloxy)carbonyl]amino}phenyl)-1H-imidazo[4,5-b]pyridine-1-carboxylate; propan-2-yl N-{4-[2-(2-chloro-5-{[(propan-2-yloxy)carbonyl]amino}phenyl)-1H-imidazo[4,5-b]pyridin-6-yl]phenyl}carbamate; propan-2-yl N-(3-{6-[4-(2-aminoacetamido)phenyl]-1H-imidazo[4,5-b]pyridin-2-yl}-4-chlorophenyl)carbamate; propan-2-yl N-(3-{6-[4-(3-aminopropanamido)phenyl]-1H-imidazo[4,5-b]pyridin-2-yl}-4-chlorophenyl)carbamate; propan-2-yl N-(3-{6-[2-(2-aminoacetamido)phenyl]-1H-imidazo[4,5-b]pyridin-2-yl}-4-chlorophenyl)carbamate; methyl N-{4-[2-(2-chloro-5-{[(propan-2-yloxy)carbonyl]amino}phenyl)-1H-imidazo[4,5-b]pyridin-6-yl]phenyl}carbamate; propan-2-yl N-(3-{6-[2-(3-aminopropanamido)phenyl]-1H-imidazo[4,5-b]pyridin-2-yl}-4-chlorophenyl)carbamate; methyl N-[4-(2-{2-chloro-5-[(3,3-difluoropyrrolidin-1-yl)carbonylamino]phenyl}-1H-imidazo[4,5-b]pyridin-6-yl)phenyl]carbamate; methyl N-[4-(2-{5-[(azetidin-1-yl)carbonylamino]-2-chlorophenyl}-1H-imidazo[4,5-b]pyridin-6-yl)phenyl]carbamate; N-(4-chloro-3-{6-[4-(methylamino)phenyl]-1H-imidazo[4,5-b]pyridin-2-yl}phenyl)-4-methylthiophene-2-carboxamide; N-(4-chloro-3-{6-[4-(methylamino)phenyl]-1H-imidazo[4,5-b]pyridin-2-yl}phenyl) cyclopentanecarboxamide; N-(4-chloro-3-{6-[4-(methylamino)phenyl]-1H-imidazo[4,5-b]pyridin-2-yl}phenyl)-5-[(dimethylamino)methyl]furan-2-carboxamide; N-(4-chloro-3-{6-[4-(methylamino)phenyl]-1H-imidazo[4,5-b]pyridin-2-yl}phenyl)pyrazine-2-carboxamide; N-(4-chloro-3-{6-[4-(methylamino)phenyl]-1H-imidazo[4,5-b]pyridin-2-yl}phenyl)-1,3-thiazole-4-carboxamide; 2-methoxyethyl N-(4-chloro-3-{6-[4-(methylamino)phenyl]-1H-imidazo[4,5-b]pyridin-2-yl}phenyl)carbamate; ethyl N-(4-chloro-3-{6-[4-(methylamino)phenyl]-1H-imidazo[4,5-b]pyridin-2-yl}phenyl)carbamate; N-{3-[6-(aminomethyl)-1H-imidazo[4,5-b]pyridin-2-yl]-4-chlorophenyl}furan-2-carboxamide; N-(3-(6-chloro-1H-imidazo[4,5-b]pyridin-2-yl)-4-fluorophenyl)pyrrolidine-1-carboxamide; 1-(3-{6-chloro-1H-imidazo[4,5-b]pyridin-2-yl}-4-fluorophenyl)-3,3-dimethylurea; 1-(3-{6-chloro-1H-imidazo[4,5-b]pyridin-2-yl}-4-fluorophenyl)-3,3-diethylurea; 3-(3-{6-chloro-1H-imidazo[4,5-b]pyridin-2-yl}-4-fluorophenyl)-1-[4-(trifluoromethyl)phenyl]urea; N-(3-{6-chloro-1H-imidazo[4,5-b]pyridin-2-yl}-4-fluorophenyl)furan-2-carboxamide; N-(3-{6-chloro-1H-imidazo[4,5-b]pyridin-2-yl}-4-fluorophenyl)-2,2-dimethylpropanamide; N-(3-{6-chloro-1H-imidazo[4,5-b]pyridin-2-yl}-4-fluorophenyl)-3-(piperidin-1-yl)propanamide; N-(3-{6-bromo-3H-imidazo[4,5-b]pyridin-2-yl}-4-fluorophenyl)-2-oxoimidazolidine-1-carboxamide; 1-(3-{6-bromo-3H-imidazo[4,5-b]pyridin-2-yl}-4-fluorophenyl)-3,3-diethylurea; 1-(3-{6-bromo-1H-imidazo[4,5-b]pyridin-2-yl}-4-fluorophenyl)-3,3-bis(propan-2-yl)urea; N-(3-{6-bromo-3H-imidazo[4,5-b]pyridin-2-yl}-4-fluorophenyl)-3,3-difluoropyrrolidine-1-carboxamide; N-(3-{6-bromo-3H-imidazo[4,5-b]pyridin-2-yl}-4-fluorophenyl)-2,5-dihydro-1H-pyrrole-1-carboxamide; N-(3-{6-bromo-1H-imidazo[4,5-b]pyridin-2-yl}-4-fluorophenyl)morpholine-4-carboxamide; N-(3-{6-bromo-3H-imidazo[4,5-b]pyridin-2-yl}-4-fluorophenyl)cyclopropanecarboxamide; N-(3-{6-bromo-3H-imidazo[4,5-b]pyridin-2-yl}-4-fluorophenyl)cyclopentanecarboxamide; N-(3-{6-bromo-1H-imidazo[4,5-b]pyridin-2-yl}-4-fluorophenyl)-1H-pyrazole-3-carboxamide; N-(3-{6-bromo-1H-imidazo[4,5-b]pyridin-2-yl}-4-chlorophenyl)-1,3-oxazole-4-carboxamide; ethyl N-(3-{6-bromo-1H-imidazo[4,5-b]pyridin-2-yl}-4-chlorophenyl)carbamate; 2-methoxyethyl N-(3-{6-bromo-1H-imidazo[4,5-b]pyridin-2-yl}-4-chlorophenyl)carbamate; N-(3-{6-bromo-1H-imidazo[4,5-b]pyridin-2-yl}-4-chlorophenyl)-5-[(dimethylamino)methyl]furan-2-carboxamide; N-(3-{6-bromo-1H-imidazo[4,5-b]pyridin-2-yl}-4-chlorophenyl)-5-fluorofuran-2-carboxamide; N-(3-{6-bromo-1H-imidazo[4,5-b]pyridin-2-yl}-4-chlorophenyl)cyclopentanecarboxamide; N-(3-{6-bromo-1H-imidazo[4,5-b]pyridin-2-yl}-4-chlorophenyl)pyrazine-2-carboxamide; N-{4-chloro-3-[6-(2-oxo-2,3-dihydro-1H-indol-5-yl)-1H-imidazo[4,5-b]pyridin-2-yl]phenyl}pyrazine-2-carboxamide; N-{4-chloro-3-[6-(2-oxo-2,3-dihydro-1H-indol-5-yl)-1H-imidazo[4,5-b]pyridin-2-yl]phenyl}cyclopentanecarboxamide; ethyl N-{4-chloro-3-[6-(2-oxo-2,3-dihydro-1H-indol-5-yl)-1H-imidazo[4,5-b]pyridin-2-yl]phenyl}carbamate; 2-methoxyethyl N-{4-chloro-3-[6-(2-oxo-2,3-dihydro-1H-indol-5-yl)-1H-imidazo[4,5-b]pyridin-2-yl]phenyl}carbamate; N-(4-fluoro-3-{6-phenyl-1H-imidazo[4,5-b]pyridin-2-yl}phenyl)-5-methylfuran-2-carboxamide; N-{4-fluoro-3-[6-(thiophen-3-yl)-1H-imidazo[4,5-b]pyridin-2-yl]phenyl}-5-methylfuran-2-carboxamide; N-(3-{5-chloro-3H-imidazo[4,5-b]pyridin-2-yl}-4-fluorophenyl)furan-2-carboxamide; N-(4-fluoro-3-{6-fluoro-3H-imidazo[4,5-b]pyridin-2-yl}phenyl)furan-2-carboxamide; N-(3-{6,7-dichloro-3H-imidazo[4,5-b]pyridin-2-yl}-4-fluorophenyl)furan-2-carboxamide; N-{3-[6-bromo-3-(methoxymethyl)-3H-imidazo[4,5-b]pyridin-2-yl]-4-chlorophenyl}pyrrolidine-1-carboxamide; N-{3-[6-bromo-1-(methoxymethyl)-1H-imidazo[4,5-b]pyridin-2-yl]-4-chlorophenyl}pyrrolidine-1-carboxamide; N-(3-{6-bromo-1-[2-(dimethylamino)ethyl]-1H-imidazo[4,5-b]pyridin-2-yl}-4-chlorophenyl)pyrrolidine-1-carboxamide; N-(3-{6-bromo-1-[2-(morpholin-4-yl)ethyl]-1H-imidazo[4,5-b]pyridin-2-yl}-4-chlorophenyl)pyrrolidine-1-carboxamide; 3-[4-fluoro-3-(6-{4-[2-(morpholin-4-yl)ethyl]phenyl}-[1,3]oxazolo[4,5-b]pyridin-2-yl)phenyl]-1-[4-(trifluoromethyl)phenyl]urea; 3-(3-{6-[4-(dimethylamino)phenyl]-[1,3]oxazolo[4,5-b]pyridin-2-yl}-4-fluorophenyl)-1-[4-(trifluoromethyl)phenyl]urea; 3-{4-fluoro-3-[6-(6-{[2-(morpholin-4-yl)ethyl]amino}pyridin-3-yl)-[1,3]oxazolo[4,5-b]pyridin-2-yl]phenyl}-1-[4-(trifluoromethyl)phenyl]urea; 3-(4-fluoro-3-{6-[4-(morpholin-4-yl)phenyl]-[1,3]oxazolo[4,5-b]pyridin-2-yl}phenyl)-1-[4-(trifluoromethyl)phenyl]urea; 3-(4-fluoro-3-{6-[4-(methylamino)phenyl]-[1,3]oxazolo[4,5-b]pyridin-2-yl}phenyl)-1-[4-(trifluoromethyl)phenyl]urea; 3-{4-fluoro-3-[6-(3-methyl-1H-pyrazol-4-yl)-[1,3]oxazolo[4,5-b]pyridin-2-yl]phenyl}-1-[4-(trifluoromethyl)phenyl]urea; 3-(4-fluoro-3-{6-[4-(morpholin-4-ylmethyl)phenyl]-[1,3]oxazolo[4,5-b]pyridin-2-yl}phenyl)-1-[4-(trifluoromethyl)phenyl]urea; propan-2-yl N-(4-{2-[2-fluoro-5-({[4-(trifluoromethyl)phenyl]carbamoyl}amino)phenyl]-[1,3]oxazolo[4,5-b]pyridin-6-yl}phenyl)carbamate; 3-{4-fluoro-3-[6-(piperidin-1-yl)-[1,3]oxazolo[4,5-b]pyridin-2-yl]phenyl}-1-[4-(trifluoromethyl)phenyl]urea; 3-[4-fluoro-3-(6-{4-[2-(morpholin-4-yl)ethoxy]phenyl}-[1,3]oxazolo[4,5-b]pyridin-2-yl)phenyl]-1-[4-(trifluoromethyl)phenyl]urea; 3-(4-fluoro-3-{6-[4-(piperidin-1-yl)phenyl]-[1,3]oxazolo[4,5-b]pyridin-2-yl}phenyl)-1-[4-(trifluoromethyl)phenyl]urea; 3-{3-[6-(6-aminopyridin-3-yl)-[1,3]oxazolo[4,5-b]pyridin-2-yl]-4-fluorophenyl}-1-[4-(trifluoromethyl)phenyl]urea; N-(4-{2-[2-fluoro-5-({[4-(trifluoromethyl)phenyl]carbamoyl}amino)phenyl]-[1,3]oxazolo[4,5-b]pyridin-6-yl}phenyl)acetamide; methyl N-(4-{2-[2-fluoro-5-({[4-(trifluoromethyl)phenyl]carbamoyl}amino)phenyl]-[1,3]oxazolo[4,5-b]pyridin-6-yl}phenyl)carbamate; 3-(3-{6-[6-(dimethylamino)pyridin-3-yl]-[1,3]oxazolo[4,5-b]pyridin- 2-yl}-4-fluorophenyl)-1-[4-(trifluoromethyl)phenyl]urea; N-(3-{6-bromo-[1,3]oxazolo[4,5-b]pyridin-2-yl}-4-fluorophenyl)-5-ethyl-1,3,4-oxadiazole-2-carboxamide; N-(3-{6-bromo-[1,3]oxazolo[4,5-b]pyridin-2-yl}-4-fluorophenyl)-3-ethyl-1,2,4-oxadiazole-5-carboxamide; N-(3-{6-bromo-[1,3]oxazolo[4,5-b]pyridin-2-yl}-4-fluorophenyl)-5-(propan-2-yl)-1,3,4-oxadiazole-2-carboxamide; N-(3-{6-bromo-[1,3]oxazolo[4,5-b]pyridin-2-yl}-4-fluorophenyl)-5-tert-butyl-1,3,4-oxadiazole-2-carboxamide; N-(3-{6-bromo-[1,3]oxazolo[4,5-b]pyridin-2-yl}-4-fluorophenyl)-1,3-oxazole-5-carboxamide; N-(3-{6-Promo-[1,3]oxazolo[4,5-b]pyridin-2-yl}-4-fluorophenyl)-4-methyl-1,3-oxazole-5-carboxamide; N-(3-{6-bromo-[1,3]oxazolo[4,5-b]pyridin-2-yl}-4-fluorophenyl)-1,3-oxazole-4-carboxamide; N-{4-fluoro-3-[6-(4-fluorophenyl)-[1,3]oxazolo[4,5-b]pyridin-2-yl]phenyl}furan-2-carboxamide; N-{4-fluoro-3-[6-(4-phenylphenyl)-[1,3]oxazolo[4,5-b]pyridin-2-yl]phenyl}furan-2-carboxamide; N-(3-{6-chloro-3H-imidazo[4,5-b]pyridin-2-yl}-4-fluorophenyl)-furan-2-carboxamide; methyl N-(4-{2-[2-fluoro-5-(furan-2-amido)phenyl]-[1,3]oxazolo[4,5-b]pyridin-6-yl}phenyl)carbamate; N-(4-fluoro-3-{6-phenyl-[1,3]oxazolo[4,5-b]pyridin-2-yl}phenyl)pyrrolidine-1-carboxamide; N-(4-chloro-3-{6-phenyl-[1,3]oxazolo[4,5-b]pyridin-2-yl}phenyl)furan-2-carboxamide; methyl N-(4-{2-[2-chloro-5-(furan-2-amido)phenyl]-[1,3]oxazolo[4,5-b]pyridin-6-yl}phenyl)carbamate; N-(4-chloro-3-{6-methyl-[1,3]oxazolo[4,5-b]pyridin-2-yl}phenyl)furan-2-carboxamide; N-(4-chloro-3-{6-ethyl-[1,3]oxazolo[4,5-b]pyridin-2-yl}phenyl)furan-2-carboxamide; 4-fluoro-N,N-dimethyl-3-(6-{4-[2-(morpholin-4-yl)ethoxy]phenyl}-[1,3]oxazolo[4,5-b]pyridin-2-yl)aniline; and 4-fluoro-N-methyl-3-(6-{4-[2-(morpholin-4-yl)ethoxy]phenyl}-[1,3]oxazolo[4,5-b]pyridin-2-yl)aniline.

Embodiment 61. A pharmaceutical composition comprising a compound of any one of Embodiments 1 to 60 as an active ingredient and at least one excipient.

Embodiment 62. A compound, or a salt, tautomer or stereoisomer thereof, according to any one of Embodiments 1 to 60 or a pharmaceutical composition according to Embodiment 61 for use as a medicament.

Embodiment 63. A compound, or a salt, tautomer or stereoisomer thereof, according to any one of Embodiments 1 to 60 or a pharmaceutical composition according to Embodiment 61 for treating, preventing, inhibiting, ameliorating, or eradicating the pathology and/or symptomology of a parasitic disease, wherein the disease is selected from Leishmaniasis, Human African Trypanosomiasis and Chagas disease, and wherein the compound is optionally used in combination with a second agent.

Embodiment 64. A compound for treating, preventing, inhibiting, ameliorating, or eradicating the pathology and/or symptomology of a parasitic disease according to Embodiment 63, wherein the disease is Leishmaniasis.

Embodiment 65. A compound for treating, preventing, inhibiting, ameliorating, or eradicating the pathology and/or symptomology of a parasitic disease according to Embodiment 63, wherein the disease is visceral Leishmaniasis Embodiment 66. A compound for treating, preventing, inhibiting, ameliorating, or eradicating the pathology and/or symptomology of a parasitic disease according to Embodiment 63, wherein the disease is Human African Trypanosomiasis.

Embodiment 67. A compound for treating, preventing, inhibiting, ameliorating, or eradicating the pathology and/or symptomology of a parasitic disease according to Embodiment 63, wherein the disease is Chagas disease.

Embodiment 68. A compound, or a salt, tautomer or stereoisomer thereof, according to Embodiment 63 for treating, preventing, inhibiting, ameliorating, or eradicating the pathology and/or symptomology of Leishmaniasis, wherein the second agent is selected from stibogluconate, meglumine antimoniate, Amphotericin, Miltefosine and paromomycin.

Embodiment 69. A compound, or a salt, tautomer or stereoisomer thereof, according to Embodiment 63 for treating, preventing, inhibiting, ameliorating, or eradicating Human African Trypanosomiasis, wherein the second agent is selected from pentamidine, suramin, melarsoprol, eflornithine, and nifurtimox.

Embodiment 70. A compound, or a salt, tautomer or stereoisomer thereof, according to any one of Embodiment 63 for treating, preventing, inhibiting, ameliorating, or eradicating the pathology and/or symptomology of Chagas disease, wherein the second agent is selected from benznidazole, nifurtimox and Amphotericin.

Embodiment 71. A method for treating, preventing, inhibiting, ameliorating, or eradicating the pathology and/or symptomology of a disease caused by a parasite, comprising administering to a subject a therapeutically effective amount of a compound according to any one of Embodiments 1 to 60 or a composition according to Embodiment 61, wherein the disease is selected from Leishmaniasis, Human African Trypanosomiasis, and Chagas disease, and wherein the administering is optionally in combination with a second agent.

Embodiment 72. A method for treating, preventing, inhibiting, ameliorating, or eradicating the pathology and/or symptomology of a parasitic disease according to Embodiment 71, wherein the disease is Leishmaniasis.

Embodiment 73. A method for treating, preventing, inhibiting, ameliorating, or eradicating the pathology and/or symptomology of a parasitic disease according to Embodiment 71, wherein the disease is visceral Leishmaniasis Embodiment 74. A method for treating, preventing, inhibiting, ameliorating, or eradicating the pathology and/or symptomology of a parasitic disease according to Embodiment 71, wherein the disease is Human African Trypanosomiasis.

Embodiment 75. A method for treating, preventing, inhibiting, ameliorating, or eradicating the pathology and/or symptomology of a parasitic disease according to Embodiment 71, wherein the disease is Chagas disease.

Embodiment 76. A method for treating, preventing, inhibiting, ameliorating, or eradicating the pathology and/or symptomology of Leishmaniasis according to Embodiment 71, wherein the second agent selected from stibogluconate, meglumine antimoniate, Amphotericin, Miltefosine and paromomycin.

Embodiment 77. A method for treating, preventing, inhibiting, ameliorating, or eradicating the pathology and/or symptomology of Human African Trypanosomiasis according to Embodiment 71, wherein the second agent selected from pentamidine, suramin, melarsoprol, eflornithine, and nifurtimox.

Embodiment 78. A method for treating, preventing, inhibiting, ameliorating, or eradicating the pathology and/or symptomology of Chagas disease according to Embodiment 71, wherein the second agent selected from benznidazole, nifurtimox and Amphotericin.

Embodiment 79. Use of a compound according to any one of Embodiments 1 to 60, for the manufacture of a medicament for treating, preventing, inhibiting, ameliorating, or eradicating the pathology and/or symptomology of a parasitic disease, wherein the disease is selected from Leishmaniasis, Human African Trypanosomiasis and Chagas disease.

Embodiment 80. A use of a compound according to Embodiment 79 for the manufacture of a medicament for treating, preventing, inhibiting, ameliorating, or eradicating the pathology and/or symptomology of a parasitic disease, wherein the parasitic disease is Leishmaniasis.

Embodiment 81. A use of a compound according to Embodiment 79 for the manufacture of a medicament for treating, preventing, inhibiting, ameliorating, or eradicating the pathology and/or symptomology of a parasitic disease, wherein the parasitic disease is visceral Leishmaniasis.

Embodiment 82. A use of a compound according to Embodiment 79 for the manufacture of a medicament for treating, preventing, inhibiting, ameliorating, or eradicating the pathology and/or symptomology of a parasitic disease, wherein the parasitic disease is Human African Trypanosomiasis.

Embodiment 83. A use of a compound according to Embodiment 79 for the manufacture of a medicament for treating, preventing, inhibiting, ameliorating, or eradicating the pathology and/or symptomology of a parasitic disease, wherein the parasitic disease is Chagas disease.

As used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts Properties, Selection, and Use" by Stahl and Wermuth (Wiley-VCH, Weinheim, Germany, 2002).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$, $^{31}P$, $^{32}P$, $^{35}S$, $^{36}Cl$, $^{125}I$ respectively. The invention includes various isotopically labeled compounds as defined herein, for example those into which radioactive isotopes, such as $^{3}H$ and $^{14}C$, or those into which non-radioactive isotopes, such as $^{2}H$ and $^{13}C$ are present. Such isotopically labelled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease (i) mediated by Plasdmodium or (ii) associated with Plasdmodium activity, or (iii) characterized by activity (normal or abnormal) of Plasdmodium or (2) reduce or inhibit the activity of Plasdmodium; or (3) reduce or inhibit the growth of Plasdmodium. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of Plasdmodium; or at least partially reducing or inhibiting the growth of Plasdmodium.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis- (Z)- or trans- (E)- form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

General Processes for Preparing Compounds of the Invention

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "*Protective Groups in Organic Synthesis*", John Wiley and Sons, 1991.

Typically, the compounds of formula I can be prepared according to Schemes 1A to 1D, 2, 2A-2B,3, 4 and 5 provided infra, where the variables: $R_1$ to $R_8$ and others are as defined in the Summary of the Invention. The following reaction schemes are given to be illustrative, not limiting, descriptions of the synthesis of compounds of the invention. Detailed descriptions of the synthesis of compounds of the Invention are given in the Examples, infra.

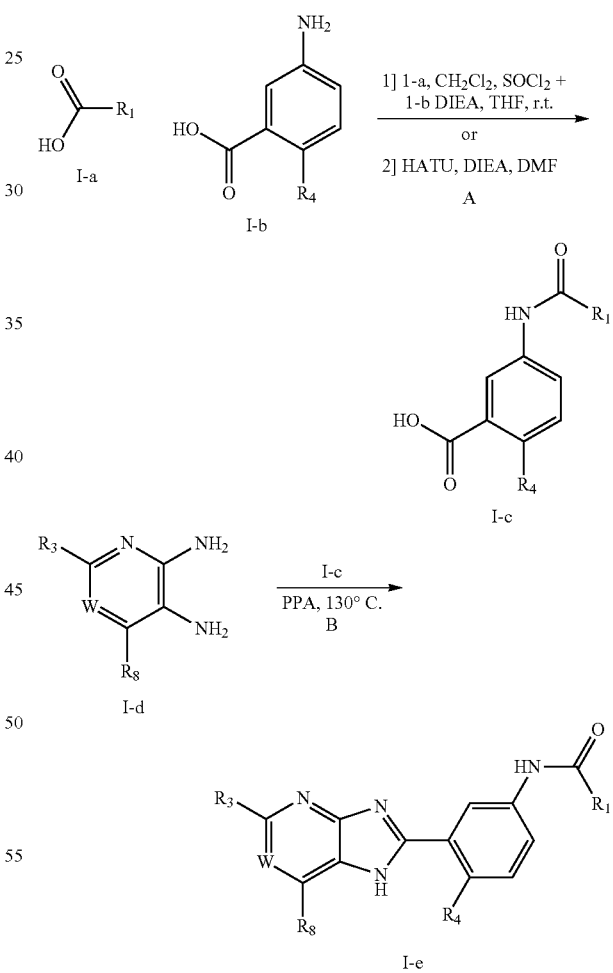

Scheme 1A. Preparation of Azabenzimidazoles compounds with a *——NH(CO)R$_1$-linker.

The Azabenzimidazole analog having a *——NH(CO)R$_1$-linker (1f) can be synthesized according to Scheme 1A.

a. Condensation of the acid (1a) with amino acid (1b) to form a amide either by acid chloride formation or direct coupling using a suitable peptide coupling agent such as HATU in presence of amine base such as Et$_3$N, DIEA (Hunig's base) at room temperature gives (1c);

b. Condensation of 1c with pyridine-2,3-diamine derivative I-d with PPA leads to formation of azabenzimidazole 1e.

Scheme 1B. Preparation of Azabenzimidazoles compounds with a *—NH(L₁L₂)R₁-linker.

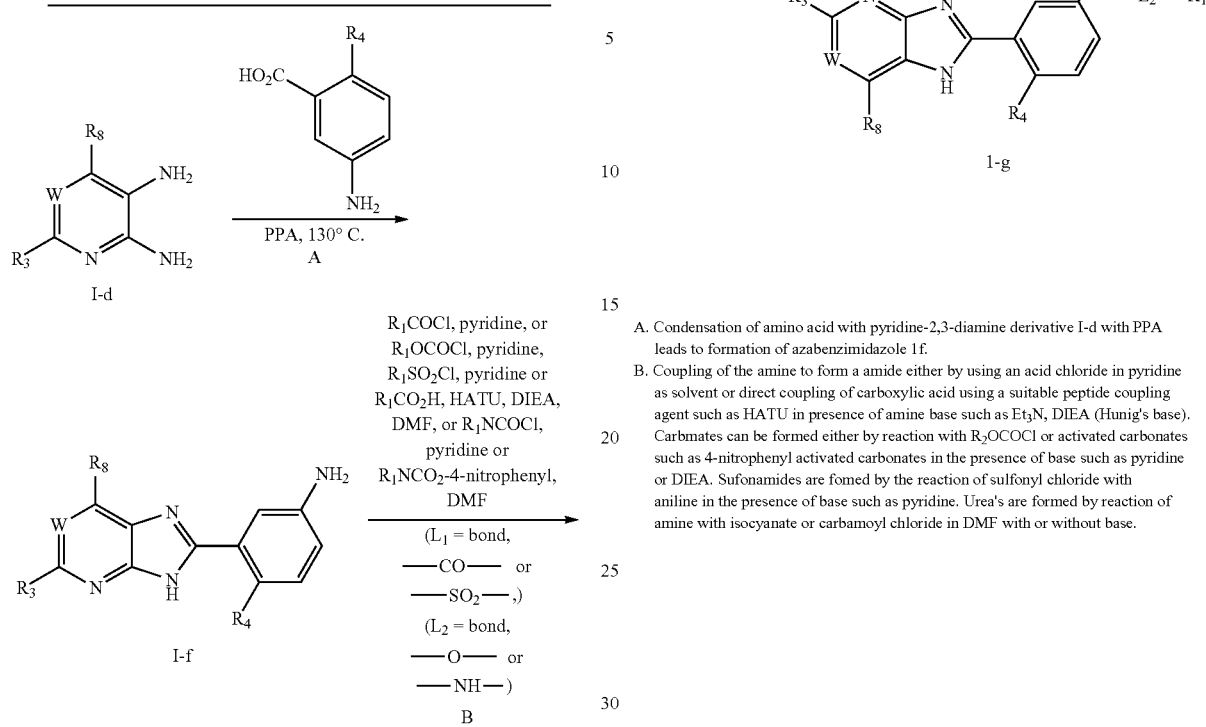

A. Condensation of amino acid with pyridine-2,3-diamine derivative I-d with PPA leads to formation of azabenzimidazole 1f.
B. Coupling of the amine to form a amide either by using an acid chloride in pyridine as solvent or direct coupling of carboxylic acid using a suitable peptide coupling agent such as HATU in presence of amine base such as Et₃N, DIEA (Hunig's base). Carbmates can be formed either by reaction with R₂OCOCl or activated carbonates such as 4-nitrophenyl activated carbonates in the presence of base such as pyridine or DIEA. Sufonamides are fomed by the reaction of sulfonyl chloride with aniline in the presence of base such as pyridine. Urea's are formed by reaction of amine with isocyanate or carbamoyl chloride in DMF with or without base.

Scheme 1C. Preparation of Azabenzimidazoles compounds where W = CR₆ and R₆ is alkylene-Ry, phenylene-Ry or heteroalkylene-Ry:

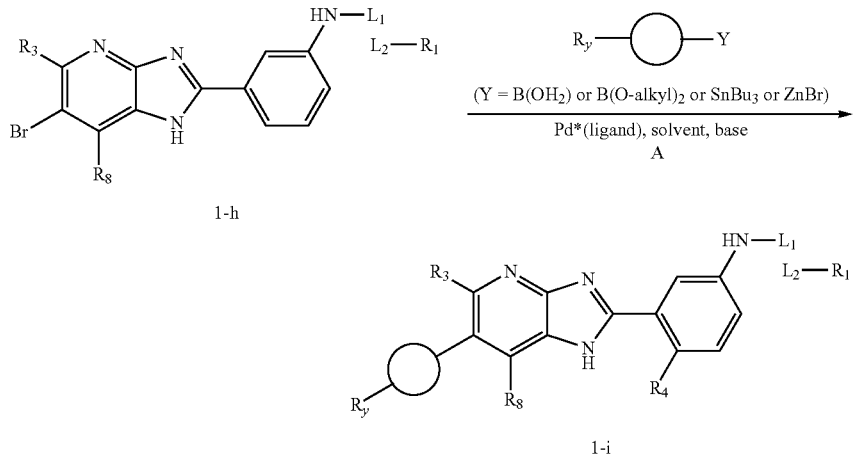

A. Introduction of R₆ group using Suzuki, Stille or Negishi couling

Scheme 1D. Preparation of Azabenzimidazoles compounds where W = CR₆ and R₆ is alkylene-Ry, phenylene-Ry or heteroalkylene-Ry:

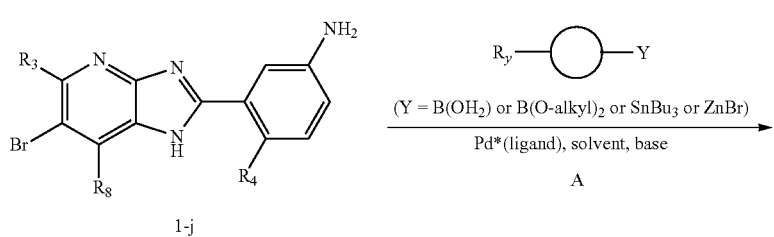

-continued

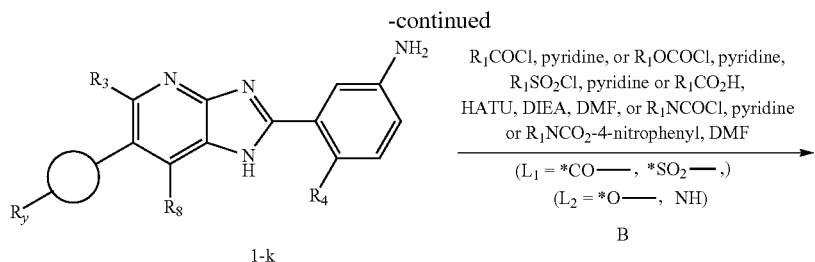

1-k

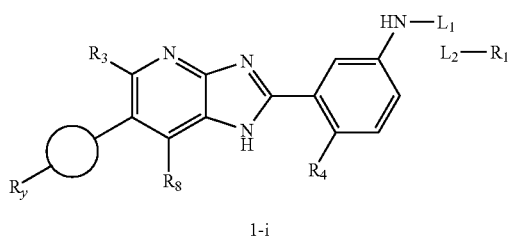

1-i

A. Introduction of R₆ group using Suzuki, Stille or Negishi couling.
B. Coupling of the amine to form a amide either by using an acid chloride in pyridine as solvent or direct coupling of carboxylic acid using a suitable peptide coupling agent such as HATU in presence of amine base such as Et₃N, DIEA (Hunig's base). Carbmates can be formed either by reaction with R₂OCOCl or activated carbonates such as 4-nitrophenyl activated carbonates in the presence of base such as pyridine or DIEA. Sufonamides are fomed by the reaction of sulfonyl chloride with aniline in the presence of base such as pyridine. Urea's are formed by reaction of amine with isocyanate or carbamoyl chloride in DMF with or without base.

Scheme 2. Preparation of Azabenzimidazoles compounds with a ―NH(L₁L₂)R₁ linker.

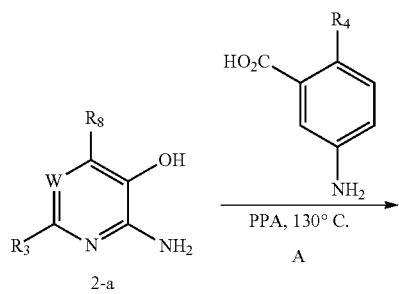

2-a

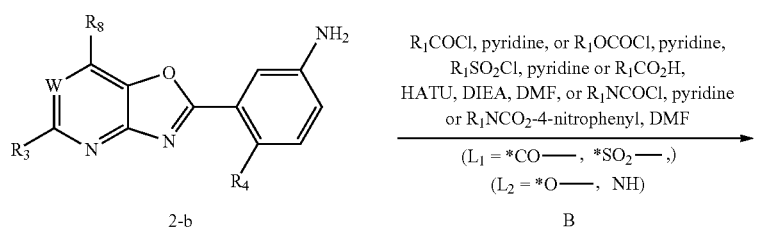

2-b

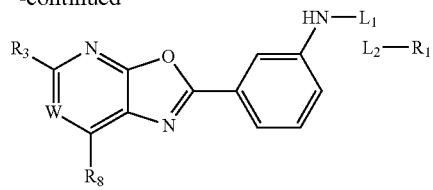

2-c

A. Condensation of amino acid with pyridine derivative 2-a with PPA leads to formation of azabenzoxazole 2-b.
B. Coupling of the amine to form a amide either by using an acid chloride in pyridine as solvent or direct coupling of carboxylic acid using a suitable peptide coupling agent such as HATU in presence of amine base such as $Et_3N$, DIEA (Hunig's base).
Carbmates can be formed either by reaction with $R_2OCOCl$ or activated carbonates such as 4-nitrophenyl activated carbonates in the presence of base such as pyridine or DIEA.
Sufonamides are fomed by the reaction of sulfonyl chloride with aniline in the presence of base such as pyridine. Urea's are formed by reaction of amine with isocyanate or carbamoyl chloride in DMF with or without base.

Scheme 2a. Preparation of Azabenzoxazole compounds with W = $CR_6$ and $R_6$ is alkylene-$R_y$, phenylene-$R_y$ or heteroalkylene-$R_y$:

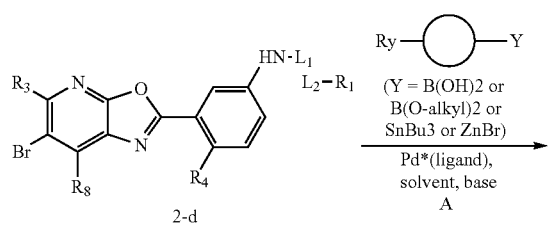 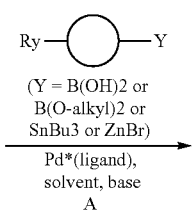 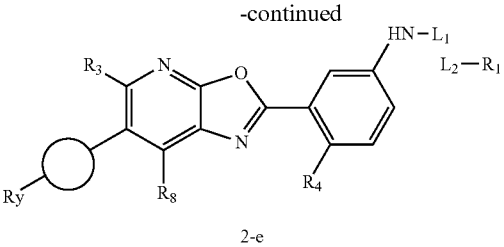

A. Introduction of R6 group using Suzuki, Stille or Negishi couling

Scheme 2b. Preparation of Azabenzimidazoles compounds W = $CR_6$ and $R_6$ is alkylene-$R_y$, phenylene-$R_y$ or heteroalkylene-$R_y$:

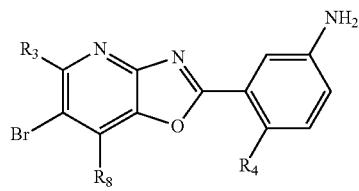 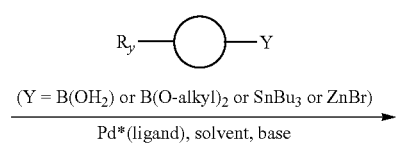

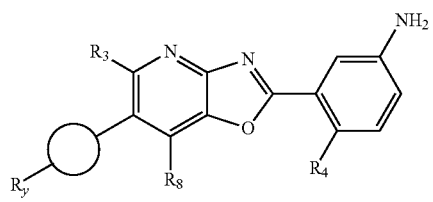 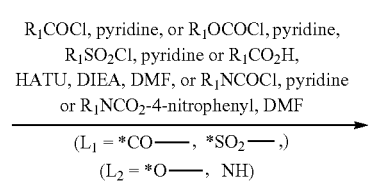

$R_1COCl$, pyridine, or $R_1OCOCl$, pyridine, $R_1SO_2Cl$, pyridine or $R_1CO_2H$, HATU, DIEA, DMF, or $R_1NCOCl$, pyridine or $R_1NCO_2$-4-nitrophenyl, DMF ($L_1$ = *CO——, *$SO_2$——,)
($L_2$ = *O——, NH)

B

-continued

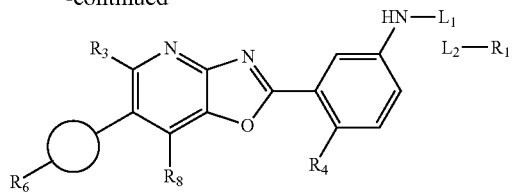

2-e

A. Introduction of $R_6$ group using Suzuki, Stille or Negishi couling.
B. Coupling of the amine to form a amide either by using an acid chloride in pyridine as solvent or direct coupling of carboxylic acid using a suitable peptide coupling agent such as HATU in presence of amine base such as $Et_3N$, DIEA (Hunig's base). Carbmates can be formed either by reaction with $R_2OCOCl$ or activated carbonates such as 4-nitrophenyl activated carbonates in the presence of base such as pyridine or DIEA. Sufonamides are fomed by the reaction of sulfonyl chloride with aniline in the presence of base such as pyridine.
Urea's are formed by reaction of amine with isocyanate or carbamoyl chloride in DMF with or without base.

Scheme 3. Preparation of Azabenzimidazole compounds with a *―NH)$R_1$-linker.

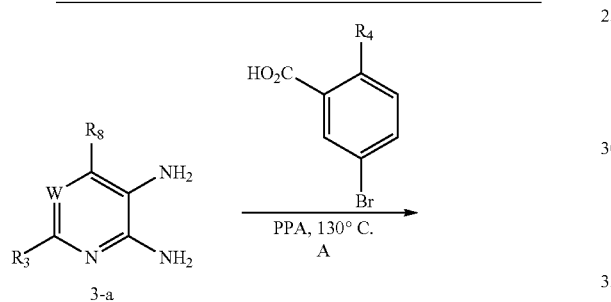

Scheme 4. Preparation of Azabenzimidazoles compounds with a *―NH(CH$_2$)$R_1$-linker.

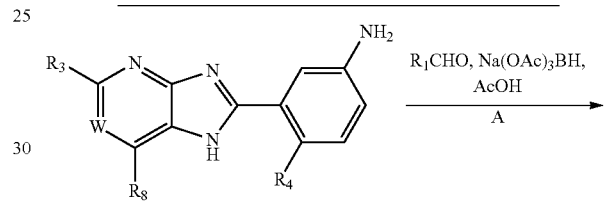

I-f

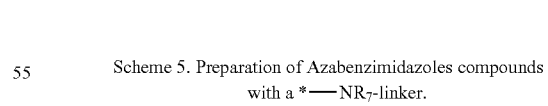

4-a

A. Reductive amination of aniline with aldehyde with sodium triacetoxy borohydride and acetic acid lead to the formation of secondary amines 4-a. Alternatively, sodium cyano borohydride can be used to achieve the same transformation.

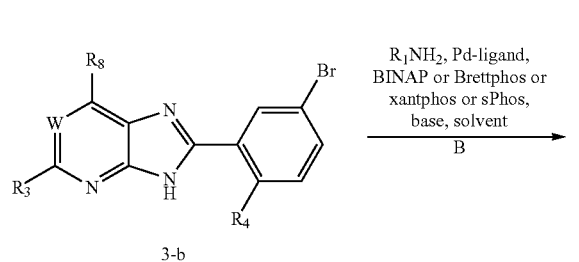

3-c

A. Condensation of benzoic acid with pyridine diamine derivative 3-a with PPA leads to formation of azabenzimidazole 3-b.
B. Buchwald amination procedure using palladium catalyst and a appropriate ligand and base to yield product 3-c Scheme 5. Preparation of Azabenzimidazoles compounds with a *―NR$_7$-linker.

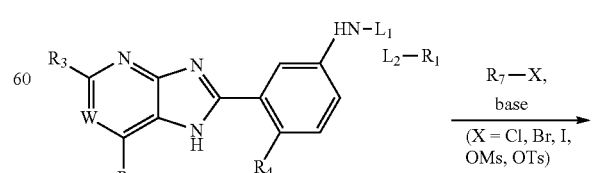

1-g

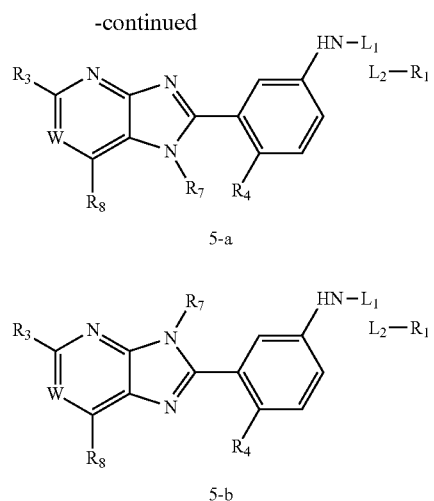

5-a 5-b

A. Introduction of alkyl group at the imidazole nitrogen by reaction an alkyl halide or mesylate in the presence of a base such as TEA or DIEA or any other appropriate base to give prodcuts such as 5-a or 5-b.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

Compounds of the invention and intermediates can also be converted into each other according to methods generally known to those skilled in the art.

Compounds of the invention are useful in the treatment and/or prevention of infections such as Leishmaniasis, Human African Trypanosomiasis, or Chagas disease.

Leishmaniasis is a disease caused by protozoan parasites that belong to the genus *Leishmania*, typically caused by *Leishmania donovani*. *Leishmania infantum*, *Leishmania braziliensis*, *Leishmania panamensis*, *Leishmania guayanensis*, *Leishmania amazonensis*, *Leishmania mexicana*, *Leishmania tropica*, or *Leishmania major*, and more typically caused by *Leishmania donovani*. These parasites are typically transmitted by the bite of an infected female sandfly from *Phlebotomus* or *Lutzomyia* genus.

Leishmaniasis is mostly a disease of the developing world, and is rarely known in the developed world outside a small number of cases, mostly in instances where troops are stationed away from their home countries. Leishmaniasis can be transmitted in many tropical and subtropical countries, and is found in parts of about 88 countries. Approximately 350 million people live in these areas. The settings in which leishmaniasis is found range from rainforests in Central and South America to deserts in West Asia and the Middle East. It affects as many as 12 million people worldwide, with 1.5-2 million new cases each year. The visceral form of leishmaniasis has an estimated incidence of 500,000 new cases and 60,000 deaths each year. More than 90 percent of the world's cases of visceral leishmaniasis are in India, Bangladesh, Nepal, Sudan, and Brazil. Kabul is estimated as the largest center of cutaneous leishmaniasis in the world, with approximately 67,500 cases as of 2004.

There are four main forms of Leishmaniasis. Cutaneous leishmaniasis is the most common form of leishmaniasis. Visceral leishmaniasis, also called kala-azar, is the most serious form in which the parasites migrate to the vital organs. Visceral leishmaniasis is caused by the parasite *Leishmania donovani*, and is potentially fatal if untreated.

Currently, no vaccines are in routine use. The two main therapies for visceral leishmaniasis are the antimony derivatives sodium stibogluconate (Pentostam®) and meglumine antimoniate (Glucantim®). Sodium stibogluconate has been used for about 70 years and resistance to this drug is a growing problem. In addition, the treatment is relatively long and painful, and can cause undesirable side effects. Amphotericin (AmBisome) is now the treatment of choice. Miltefosine (Impavido), and paromomycin are the other treatment alternatives. These drugs are known to produce a definitive cure in >90% of patients. Amphotericin (AmBisome) is expansive and has to be given intravenously; it is not affordable to most patients affected. Paromomycin, although affordable, requires intramuscular injections for 3 weeks; compliance is a major issue. Miltefosine is an oral drug and has shown to be more effective and better tolerated than other drugs. However, there are problems associated with the use of miltefosine that arise from its teratogenicity and pharmacokinetics. Miltefosine was shown to be much slower eliminated from the body and was still detectable five months after the end of treatment. The presence of subtherapeutic miltefosine concentrations in the blood beyond five months after treatment might contribute to the selection of resistant parasites and, moreover, the measures for preventing the teratogenic risks of miltefosine must be reconsidered. This led to some reluctance to taking Miltefosine by affected populations.

The Drugs for Neglected Diseases Initiative is actively facilitating the search for novel therapeutics. Our invention meets that need.

Human African trypanosomiasis (HAT), also known as African sleeping sickness, is a vector-borne parasitic disease caused by the protozoa *Trypanosoma brucei*. There are two subspecies that infect humans, *Tb. gambiense* and *Tb. rhodesiense*, with the former accounting for over 95% of reported cases and the latter accounting for the remaining reported cases. The parasites are transmitted to humans by tsetse fly (*Glossina* genus) bites which have acquired their infection from human beings or from animals harboring the human pathogenic parasites.

The disease has been recorded as occurring in 36 countries, all in subtropical and equatorial Africa. It is endemic in southeast Uganda and western Kenya. In 1995, the WHO estimated that 300,000 people were afflicted with the disease. In its 2001 report, the WHO set the figure of people at risk of infection at 60 million, of which only 4 to 5 million had access to any kind of medical monitoring. In 2006, the WHO estimated that about 70,000 people could have the disease, and many cases are believed to go unreported. About 48,000 people died of sleeping sickness in 2008. Public health efforts in prevention and the eradication of the tsetse fly population have proven to be successful in controlling the spread of the disease; under 10,000 new cases were reported in 2009 according to WHO figures, which represents a huge decrease from the estimated 300,000 new cases in 1998.

African trypanosomiasis symptoms occur in two stages. In the first stage, known as the haemolymphatic phase, the trypanosomes multiply in subcutaneous tissues, blood and lymph. The haemolymphatic phase is characterized by bouts of fever, headaches, joint pains and itching. In the second stage, the neurological phase, the parasites cross the blood-brain barrier to infect the central nervous system. It is in this stage when more obvious signs and symptoms of the disease appear: changes of behaviour, confusion, sensory disturbances and poor coordination. Disturbance of the sleep cycle, which gives the disease its name, is an important feature of the second stage of the disease. Without treatment, the disease is invariably fatal, with progressive mental deterioration leading to coma, systemic organ failure, and death.

Four drugs are registered for the treatment of sleeping sickness. The protocol depends on the stage of the disease. The current standard treatment for first-stage disease is intravenous or intramuscular pentamidine (for *T.b. gambiense*), or intravenous suramin (for *T.b. rhodesiense*). The current standard treatment for second-stage disease is: Intravenous melarsoprol, or interavenous melarsoprol in combination with oral nifurtimox, intravenous eflornithine only or eflornithine in combination with nifurtimox. All of the drugs have undesirable or sometime serious side effects. For example, 3-10% of patients those injected with Melarsoprol (Arsobal), an organoarsenical, developed reactive encephalopathy (convulsions, progressive coma, or psychotic reactions), and 10-70% of such cases result in death. There remains a need for new therapy.

Chagas disease, also called American trypanosomiasis, is a tropical parasitic disease caused by the flagellate protozoan *Trypanosoma cruzi*. *T. cruzi* is commonly transmitted to humans and other mammals by the blood-sucking "kissing bugs" of the subfamily Triatominae (family *Reduviidae*).

Chagas disease is contracted primarily in the Americas. It is endemic in twenty one Central and Latin American countries; particularly in poor, rural areas of Mexico, Central America, and South America. Large-scale population movements from rural to urban areas of Latin America and to other regions of the world have increased the geographic distribution of Chagas disease, and cases have been noted in many countries, particularly in Europe. Rarely, the disease has been found in the Southern part of the United States.

Each year, an estimated 10 to 15 million people across the world are infected with Chagas disease, most of whom do not know they are infected. Every year, 14,000 people die as a consequence of the disease. In Central and South America, Chagas kills more people than any other parasite-borne disease, including malaria. By applying published seroprevalence figures to immigrant populations, CDC estimates that more than 300,000 persons with *Trypanosoma cruzi* infection live in the United States. Most people with Chagas disease in the United States acquired their infections in endemic countries.

Chagas disease has an acute and a chronic phase. If untreated, infection is lifelong. Acute Chagas disease occurs immediately after infection, may last up to a few weeks or months, and parasites may be found in the circulating blood. Infection may be mild or asymptomatic. There may be fever or swelling around the site of inoculation (where the parasite entered into the skin or mucous membrane). Rarely, acute infection may result in severe inflammation of the heart muscle or the brain and lining around the brain. The initial acute phase is responsive to antiparasitic treatments, with 60-90% cure rates. Following the acute phase, most infected people enter into a prolonged asymptomatic form of disease (called "chronic indeterminate") during which few or no parasites are found in the blood. During this time, most people are unaware of their infection. Many people may remain asymptomatic for life and never develop Chagas-related symptoms. However, an estimated 20-30% of infected people will develop debilitating and sometimes life-threatening medical problems over the course of their lives.

The symptoms of Chagas disease vary over the course of an infection. In the early, acute stage, symptoms are mild and usually produce no more than local swelling at the site of infection. The initial acute phase is responsive to antiparasitic treatments, with 60-90% cure rates. After 4-8 weeks, individuals with active infections enter the chronic phase of Chagas disease that is asymptomatic for 60-80% of chronically infected individuals through their lifetime.

There is no vaccine against Chagas disease. Treatment for Chagas disease focuses on killing the parasite and managing signs and symptoms.

During the acute phase of Chagas disease, the drugs currently available for treatment are benznidazole and nifurtimox. Once Chagas disease reaches the chronic phase, medications aren't effective for curing the disease. Instead, treatment depends on the specific signs and symptoms. However, problems with these current therapies include their diverse side effects, the length of treatment, and the requirement for medical supervision during treatment. Resistance to the two frontline drugs has already occurred. The antifungal agent Amphotericin b has been proposed as a second-line drug, but this drug is costly and relatively toxic.

In accordance with the foregoing, the present invention further provides a method for preventing or treating Leishmaniasis, Chaga disease or Human African Trypanosomiasis in a subject in need of such treatment, which method comprises administering to said subject a therapeutically effective amount of a compound selected from Formula I or a pharmaceutically acceptable salt thereof. The required dosage will vary depending on the mode of administration, the particular condition to be treated and the effect desired.

In one embodiment of the method of the invention, the disease being treated is Leishmaniasis caused by the parasites *Leishmania donovani, Leishmania infantum, Leishmania braziliensis, Leishmania panamensis, Leishmania guayanensis, Leishmania amazonensis, Leishmania mexicana, Leishmania tropica, Leishmania major*. In one variation of the above embodiment, the disease being treated is Visceral leishmaniasis, caused by the parasite *Leishmania donovani*.

In another embodiment of the method of the invention, the disease being treated is Human African Trypanosomiasis caused by a protozoa belonging to the species *Trypanosoma brucei*. In one embodiment, the protozoa is *Trypanosoma brucei gambiense*. In another embodiment, the protozoa is *Trypanosoma brucei rhodesiense*.

In yet another embodiment of the method of the invention, the disease being treated is Chagas disease (also call American Trypanosomiasis) caused by protozoa *Trypanosoma cruzi*.

In general, compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

Compounds of the invention can be administered in therapeutically effective amounts in combination with one or more therapeutic agents (pharmaceutical combinations). In one embodiment, the compound of the invention is administered with the known treatment drugs. For example, for the treatment of Leishmaniasis, compound of the invention may be used in combination with stibogluconate, meglumine antimoniate, Amphotericin, Miltefosine and paromomycin. For the treatment of Human African Trypanosomiasis, the compound of the invention may be used in combination with pentamidine, suramin, melarsoprol, eflornithine, and nifurtimox. For the treatment of Chagas disease, the compound of the invention may be used in combination with benznidazole, nifurtimox and Amphotericin.

Where the compounds of the invention are administered in conjunction with other therapies, dosages of the co-administered compounds will of course vary depending on the type of co-drug employed, on the specific drug employed, on the condition being treated and so forth.

The invention also provides for a pharmaceutical combinations, e.g. a kit, comprising a) a first agent which is a compound of the invention as disclosed herein, in free form or in pharmaceutically acceptable salt form, and b) optionally co-agent. The kit can comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of Formula I and a co-agent, are both administered to a patient simultaneously in the form of a single entity or dosage. The term "non-fixed combination" means that the active ingredients, e.g. a compound of Formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

Biological Assays

Leishmania Donovani Axenic Amastigote Proliferation Assay

Leishmania donovani axenic amastigote parasites are grown at 37° C., 5% $CO_2$ in media made of RPMI 1640, 4 mM L-glutamine, 20% heat inactivated FBS, 100 units/ml of penicillin and 100 µg/ml of streptomycin, 23 µM Folic Acid, 100 µM Adenosine, 22 mM D-glucose, 25 mM MES. The pH of media is adjusted to 5.5 at 37° C. using HCl. 20 µL of media is first dispensed into 384 well plates and 100 nL of the compounds of invention in DMSO are added to the plate wells. At the same time control compounds and DMSO are added to plates to serve as the positive and negative controls, respectively. 40 µL of parasite culture (9600 parasites) are then added to the plate wells. The plates are then placed into incubators. After 2 day incubation, 20 µL of Cell TiterGlo (Promega) is added to the plate wells. The luminescence signal of each well is measured using the Envision reader (Perkin Elmer). The percentage inhibition of 50%, $EC_{50}$, is calculated for each of the compounds.

Compounds of the invention have an $EC_{50}$ ranging from >25 µM to 0.083 µm. Typically, the $EC_{50}$ is 20 µM or less. Significant number of the compounds has $EC_{50}$ of 1 µm or less; e.g. N-(4-chloro-3-{6-[4-(3-methylbutanamido)phenyl]-1H-imidazo[4,5-b]pyridin-2-yl}phenyl)furan-2-carboxamide (Compound 13) and N-(4-chloro-3-{6-[4-(methylamino)phenyl]-1H-imidazo[4,5-b]pyridin-2-yl}phenyl)pyrrolidine-1-carboxamide (Compound 292) and methyl N-{4-[2-(2-chloro-5-{[(propan-2-yloxy)carbonyl]amino}phenyl)-1H-imidazo[4,5-b]pyridin-6-yl]phenyl}carbamate (Compound 341) all have an $EC_{50}$ of about 0.08 µM. Selected compounds of the invention can significantly delay the proliferation of L. donovani.

The inhibitory efficacy of the compounds of the invention against L. donovani axenic amastigotes in vitro is provided in Table I.

Assay for Proliferation of Leishmania Parasites

The activity of a compound according to the present invention for inhibition of parasitemai can be assessed by the parasite proliferation assay. The assay measures the increase in the parasite number in the assayed plate well using a DNA intercalating dye, SYBR Green I® dye (INVITROGEN) to stain Leishmania cell nuclei. It is understood that the assays illustrate the invention without in any way limiting the scope of the invention.

L. donovani HU3 strain is propagated by infecting BALB/c mice through tail vein injection with $10^7$ Leishmania parasites. Infected mice are allowed to develop infection during 9-11 weeks post-infection. During this time, the parasites accumulate in the infected mouse spleens to large numbers, and the infected mice serve as the source of parasites for the in vitro measurement of compound efficacies. To assay a compound for anti-leishmanial activity, peritoneal macrophages isolated from non-infected BALB/c mice are seeded into 384-well plates at density $2 \times 10^4$ macrophages per well in 25 mL of medium (RPMI 1640, 10% fetal serum albumin, 10 mM HEPES, 1 mM sodium pyruvate, 1% Pen/Strep). Subsequently, the seeded plates are placed into an incubator set to maintain 37° C. temperature and atmosphere with 5% $CO_2$. The next day, Leishmania parasites are isolated from the spleens of mice infected for 9-11 weeks and $4 \times 10^5$ isolated parasites in 10 mL of the above media are added to each plate well. Plates are then returned into incubators and infection is allowed to proceed for 24 hours. After the infection of macrophages is completed, 5 mL of compounds of the invention in the above medium, which also contains 5% DMSO, are added to plate wells containing infected macrophages. At the same time control compounds (miltefosine and amphotericin B) and DMSO are added to plates to serve as the positive and negative controls, respectively. After the compound addition, the plates are returned into incubator and cells infected with parasites are cultured for 5 days. At the end of cultivation, 40 mL of 8% paraformaldehyde is added to plate wells and incubated for 15 min at room temperature. Following the incubation, the paraformaldehyde from plate wells is aspirated, and 40 mL of PBS containing 0.2% Triton X-100 is added to wells. After 15 min incubation, the solution is aspirated from wells again, and replaced with SybrGreen Dye solution in PBS (1:125,000 dilution). Infected cells are imaged with Evotec Opera high-content microscope, and the number of parasites in well is determined by counting parasite nuclei visualized by staining with SybrGreen dye. The percentage inhibition of 50%, $EC_{50}$, is calculated for each compound.

Compounds of the invention have $EC_{50}$ ranging from 50 µM to 76 nM (Compound 291). Typically, the $EC_{50}$ is 25 µM or less. Significant number of the compounds has $EC_{50}$ of 1 µm or less; e.g. propan-2-yl N-(4-chloro-3-{6-cyano-1H-imidazo[4,5-b]pyridin-2-yl}phenyl)carbamate (Compound 287), N-(4-chloro-3-{6-phenyl-1H-imidazo[4,5-b]pyridin-2-yl}phenyl)pyrrolidine-1-carboxamide (Compound 291) and tert-butyl N-[4-(2-{2-chloro-5-[(pyrrolidin-1-yl)carbonylamino]phenyl}-1H-imidazo[4,5-b]pyridin-6-yl)phenyl]-N-methylcarbamate (Compound 308) all have an $EC_{50}$ of about 0.08 µM. Compound of the invention can significantly delay the proliferation of L. donovani.

The inhibitory efficacy of the compounds of the invention in delaying the proliferation of L. donovani in mouse peritoneal macrophages is provided in Table I, infra.

Assay for Proliferation of Kinetoplastid Parasite Trypanosoma brucei.

The proliferation is quantified by the addition of Cell Titer Glo (Promega®) a luminescent cell viability assay that measures the number of viable cells in culture based on the quantification of cellular ATP amount, which is an indicator of metabolically active cells.

The following assay illustrates the invention without in any way limiting the scope of the invention. This parasite proliferation assay measures the increase in parasite growth using an assay that measures ATP activity, Cell Titer Glo®.

Trypanosoma brucei Lister 427 strain is grown in HMI-9 Trypanosome media for T. brucei bloodstream form. 30 µl of HMI-9 media is dispensed into 384 well assay plates. 200 nl of compounds of the invention (in DMSO), including anti-trypanosome controls (Pentamidine and suramin), are then transferred into the assay plates, as well as DMSO alone to serve as a negative control for inhibition. Then 25 µl of a suspension of T. brucei culture in HMI-9 media is dispensed into the assay plates. The final concentration of parasites in culture corresponds to 1.7% of 0.5 uM ATP activity with Cell Titer Glo® in HMI-9 media. The plates are placed in a 37° C. incubator for 48 hours in an atmospheric environment containing 5% $CO_2$. 40 µl of Cell Titer Glo® is dispensed into the plates. The plates are then read for luminescence. The percentage inhibition of 50%, $EC_{50}$, is calculated for each compound.

Compounds of the invention have $EC_{50}$ ranging from 120 µM to 6 nM (Compound 19). Typically, the $EC_{50}$ is 25 µM or less. Significant number of the compounds has $EC_{50}$ of 1 µm or less; e.g. methyl N-(4-{2-[2-chloro-5-(furan-2-amido)phenyl]-1H-imidazo[4,5-b]pyridin-6-yl}phenyl)carbamate (Compound 58) has an $EC_{50}$ of 5 nM; N-{3-[6-(4-carbamoylphenyl)-1H-imidazo[4,5-b]pyridin-2-yl]-4-chlorophenyl}furan-2-carboxamide (Compound 19) has an $EC_{50}$ of 6 nM, and N-{4-chloro-3-[6-(6-methoxypyridin-3-yl)-1H-imidazo [4,5-b]pyridin-2-yl]phenyl}furan-2-carboxamide (Compound 29) has an $EC_{50}$ of 24 nM. Compound of the invention can significantly delay the proliferation of T. brucei.

The inhibitory efficacy of the compounds of the invention in delaying the proliferation of T. brucei is provided in Table I.

Assay for Proliferation of Kinetoplastid Parasite Trypanosoma cruzi.

Compounds of the invention can be assayed to measure their capacity to inhibit proliferation of kinetoplastid parasite Trypanosoma cruzi. The screening procedure is for identifying compounds with inhibitor activity against Trypanosoma cruzi amastigotes cultured in 3T3 fibroblast cells. The assay is done using the mammalian stage (amastigotes) of T. cruzi that replicates in the intracellular space of host cells. The host cells are initially infected with the culture-derived trypomastigotes that rapidly invade and then divide as amastigotes. The protocol uses the Tulahuen strain of T. cruzi that has been engineered to express the E. coli beta-galactosidase gene (Lac-Z) (Antimicr. Agents Chemoth. 40:2592, 1996). This allows for a colorimetric readout by using the substrate CPRG and an absorbance plate reader.

3T3 fibroblast cells are re-suspended in RPMI-1640 medium without phenol red medium supplemented with 10% FBS (heat inactivated), 100 µg/ml penicillin, and 100 µg/ml streptomycin. Forty µL of suspension (1,000 cells) is dispensed into 384-well plates and incubated overnight at 37° C. temperature and in atmosphere containing 5% $CO_2$. The following day, 100 nL of compounds of the invention in DMSO are added to plate wells containing 3T3 cells. At the same time control compounds (benznidazole and nifurtimox) and DMSO are added to plates to serve as the positive and negative controls, respectively. After that, 10 µL of media containing 10,000 T. cruzi trypomastigotes are added to each plate well and plates are placed back into incubators. After 6 day incubation, 10 µL of reagent solution (0.6 mM CPRG, 0.6% NP-40 in PBS) is added to plates and incubated at room temperature for 2 hours. Absorbance is then measured on SpectraMax Gemini fluorimeter to determine relative number of T. cruzi cells present in each plate well. The percentage inhibition of 50%, $EC_{50}$, is calculated for each compound. Compounds of the invention have $EC_{50}$ ranging from >20 µM to 16 nM (Compound 291). Typically, the $EC_{50}$ is 10 µM or less. Significant number of the compounds has $EC_{50}$ of 1 µm or less; e.g. N-(4-chloro-3-{6-phenyl-1H-imidazo[4,5-b]pyridin-2-yl}phenyl)pyrrolidine -1-carboxamide (Compound 291) has an EC$_{50}$ of 16 nM; tert-butyl N-[4-(2-{2-chloro-5-[(pyrrolidin-1-yl)carbonylamino]phenyl}-1H-imidazo[4,5-b]pyridin-6-yl)phenyl]-N-methylcarbamate (Compound 332) has an EC$_{50}$ of 6 nM, and N-(4-chloro-3-{6-methyl-1H-imidazo [4,5-b]pyridin-2-yl}phenyl)-5-methanesulfonylthiophene-2-carboxamide (Compound 175) has an EC$_{50}$ of 67 nM. Compound of the invention can significantly delay the proliferation of T. brucei.

The inhibitory efficacy of the compounds of the invention in delaying the proliferation of T. Cruzi is provided in Table I.

TABLE I

Inhibitory efficacy of selected compounds of the invention against proliferation of L. donovani, T. brucei or T cruzi.

| Example No. | L. donovani amastigotes EC50 (μM) | L. donavani Macrophage EC50 (μM) | T. brucei EC50 (μM) | T cruzi EC50 (μM) |
|---|---|---|---|---|
| 1 | 2.2 | 9 | 101.8 | n.d. |
| 2 | 1.39 | 4 | 114.3 | n.d. |
| 3 | >25 | >50 | n.d. | n.d. |
| 4 | 4.2 | 25.5 | n.d. | n.d. |
| 5 | >25 | 49.4 | n.d. | n.d. |
| 6 | 1.96 | 0.65 | 108.3 | n.d. |
| 7 | 0.267 | 3.3 | 113.3 | n.d. |
| 8 | 0.75 | 1.72 | 107.5 | n.d. |
| 9 | 0.45 | 1.2 | 101.5 | n.d. |
| 10 | 0.89 | 1.12 | 107.5 | n.d. |
| 11 | 0.55 | 0.46 | 0.0064 | n.d. |
| 12 | 0.258 | 0.4 | 115.7 | n.d. |
| 13 | 0.083 | 0.115 | n.d. | n.d. |
| 14 | 3.7 | 3.14 | n.d. | n.d. |
| 15 | 6.1 | 0.72 | n.d. | n.d. |
| 16 | 2.07 | 1.63 | n.d. | n.d. |
| 17 | 0.48 | 1.57 | 111.3 | n.d. |
| 18 | 0.3 | 1.48 | n.d. | n.d. |
| 19 | 0.165 | >50 | 0.0058 | >20 |
| 20 | 0.239 | 1.78 | 0.054 | n.d. |
| 21 | 16 | 2.8 | 0.063 | n.d. |
| 22 | 19 | 4.6 | n.d. | n.d. |
| 23 | 0.32 | 0.37 | 112.9 | n.d. |
| 24 | 0.165 | 2.89 | 111 | n.d. |
| 25 | 5.6 | 9.5 | n.d. | n.d. |
| 26 | 0.68 | 2.17 | n.d. | n.d. |
| 27 | 2.66 | 24.4 | n.d. | n.d. |
| 29 | 0.234 | 2.29 | 0.0235 | 0.071 |
| 31 | 0.177 | 0.45 | n.d. | n.d. |
| 32 | >25 | 15.3 | n.d. | n.d. |
| 33 | 0.67 | 1.6 | n.d. | n.d. |
| 34 | 0.6 | 1.79 | 0.105 | n.d. |
| 35 | 0.234 | 2.11 | n.d. | n.d. |
| 36 | 1.03 | 2.27 | 0.188 | n.d. |
| 37 | 0.46 | 0.55 | n.d. | n.d. |
| 38 | >25 | >50 | n.d. | n.d. |
| 39 | 0.57 | 9.6 | n.d. | n.d. |
| 40 | 0.61 | 0.97 | 40 | n.d. |
| 41 | 5.9 | 2.2 | n.d. | n.d. |
| 42 | 1.39 | 4 | n.d. | n.d. |
| 43 | 0.73 | 6.9 | 0.0216 | n.d. |
| 44 | 0.283 | 0.82 | n.d. | n.d. |
| 45 | 1.47 | 3.4 | n.d. | n.d. |
| 46 | 0.5 | 1.33 | 0.037 | n.d. |
| 47 | 0.46 | >7.2 | 0.04 | 0.104 |
| 48 | 0.53 | 8 | 0.076 | n.d. |
| 49 | 0.44 | 1.05 | 0.0067 | n.d. |
| 50 | 0.134 | 1.64 | 0.00262 | 0.053 |
| 51 | 0.175 | 0.56 | 0.0193 | n.d. |
| 52 | 0.188 | >14.5 | 0.036 | 0.068 |
| 53 | 0.112 | 0.154 | n.d. | n.d. |
| 54 | 0.226 | 0.272 | n.d. | n.d. |
| 55 | 2.06 | 6.7 | n.d. | n.d. |
| 56 | 3.2 | 16 | n.d. | n.d. |
| 57 | 1.83 | >50 | n.d. | n.d. |
| 58 | 0.051 | 0.284 | 0.0051 | 0.0193 |
| 59 | 1.34 | 3.7 | 0.143 | n.d. |
| 60 | 0.8 | 3.5 | n.d. | n.d. |
| 61 | 1.13 | 3.2 | 0.182 | n.d. |

TABLE I-continued

Inhibitory efficacy of selected compounds of the invention against proliferation of L. donovani, T. brucei or T cruzi.

| Example No. | L. donovani amastigotes EC50 (μM) | L. donavani Macrophage EC50 (μM) | T. brucei EC50 (μM) | T cruzi EC50 (μM) |
|---|---|---|---|---|
| 62 | 19.2 | 9.4 | 0.52 | n.d. |
| 63 | 0.56 | 1.6 | 0.0217 | 0.108 |
| 64 | 0.68 | >28.9 | n.d. | n.d. |
| 65 | 0.197 | 1.58 | n.d. | n.d. |
| 66 | 4.6 | >39.1 | n.d. | n.d. |
| 67 | 2.12 | 2.5 | n.d. | n.d. |
| 68 | 2.85 | 4.9 | n.d. | n.d. |
| 69 | 18.1 | 2.74 | 0.1 | n.d. |
| 70 | 6 | 20.8 | 0.174 | 0.49 |
| 71 | 4 | 1.86 | n.d. | n.d. |
| 72 | 0.67 | 3.2 | 0.073 | n.d. |
| 73 | 0.82 | 8.2 | n.d. | n.d. |
| 74 | 0.45 | 3.09 | 112.3 | n.d. |
| 75 | 9.3 | 25.6 | n.d. | n.d. |
| 76 | >25 | >50 | n.d. | n.d. |
| 77 | 6.7 | 35 | n.d. | n.d. |
| 78 | >25 | >50 | >6.6 | n.d. |
| 79 | >25 | >50 | 12.5 | n.d. |
| 80 | 5.9 | 18.5 | 0.61 | n.d. |
| 81 | >25 | 16.9 | 10.8 | n.d. |
| 82 | >25 | >38.5 | >14.1 | n.d. |
| 83 | 7 | 23.3 | 0.93 | 1.3 |
| 84 | 6.7 | >50 | 2.13 | 2.3 |
| 85 | >25 | 21.3 | 9.3 | >11.5 |
| 86 | 0.84 | 3.09 | 0.183 | 0.069 |
| 87 | >25 | 24.4 | >6.9 | n.d. |
| 88 | >25 | >50 | n.d. | n.d. |
| 89 | 3.7 | 9.2 | 0.26 | 0.175 |
| 90 | 1.88 | 8 | n.d. | n.d. |
| 91 | 3.2 | 5.6 | n.d. | n.d. |
| 92 | >20 | >50 | n.d. | n.d. |
| 93 | >25 | >35.5 | n.d. | n.d. |
| 94 | >25 | 4.9 | n.d. | n.d. |
| 95 | >25 | >50 | >14.4 | n.d. |
| 96 | >25 | 20.7 | 8.9 | n.d. |
| 97 | >25 | >50 | >18.7 | n.d. |
| 98 | 16.7 | 23.5 | 2.91 | 1.18 |
| 99 | >25 | >50 | 6.3 | 5.5 |
| 100 | 6.3 | 6.4 | 1.42 | 2.17 |
| 101 | 13.5 | >50 | n.d. | n.d. |
| 102 | 16.1 | 11.7 | n.d. | n.d. |
| 103 | >25 | >50 | n.d. | n.d. |
| 104 | >25 | >50 | n.d. | n.d. |
| 105 | >25 | >50 | n.d. | n.d. |
| 106 | >25 | >50 | 13.3 | n.d. |
| 107 | 5.5 | 21.5 | 0.51 | n.d. |
| 108 | >25 | 16.3 | 8.3 | n.d. |
| 109 | >24.4 | >19.1 | 15.1 | n.d. |
| 110 | >25 | 23.8 | >13.6 | n.d. |
| 111 | >25 | >50 | >13.6 | n.d. |
| 112 | >25 | >50 | >24.1 | n.d. |
| 113 | 15.3 | 26.4 | 1.68 | n.d. |
| 114 | >25 | >41.5 | >11.9 | n.d. |
| 115 | 16.8 | 25.3 | 2.6 | n.d. |
| 116 | >25 | >50 | >25 | n.d. |
| 117 | >25 | >50 | >13.5 | n.d. |
| 118 | 11.1 | 21.8 | 3.2 | n.d. |
| 119 | >25 | 24.2 | >16.2 | n.d. |
| 120 | >25 | >50 | 10.5 | n.d. |
| 121 | >25 | >21.2 | >17.3 | n.d. |
| 122 | >25 | >50 | >25 | n.d. |
| 123 | 20.3 | >50 | 4.1 | n.d. |
| 124 | >25 | 13.8 | >25 | >14.3 |
| 125 | >25 | 8.6 | 10 | 9.6 |
| 126 | 1.6 | 1.63 | 0.303 | 0.148 |
| 127 | 1.2 | 4.8 | n.d. | n.d. |
| 128 | >25 | >50 | >25 | >20 |
| 129 | >25 | 27.4 | n.d. | n.d. |
| 130 | 2.01 | 15.7 | n.d. | n.d. |
| 131 | 22.1 | >50 | 5.1 | 6.8 |
| 132 | >25 | >50 | n.d. | n.d. |
| 133 | >25 | >50 | >25 | n.d. |
| 134 | 21.4 | 13.9 | 0.89 | 2.59 |

TABLE I-continued

Inhibitory efficacy of selected compounds of the invention aganist proliferation of *L. donovani*, *T. brucei* or *T cruzi*.

| Example No. | L. donovani amastigotes EC50 (μM) | L. donavani Macrophage EC50 (μM) | T. brucei EC50 (μM) | T cruzi EC50 (μM) |
|---|---|---|---|---|
| 135 | >25 | >25.9 | >1.51 | >20 |
| 136 | >25 | >50 | n.d. | n.d. |
| 137 | >25 | 15.9 | 87 | n.d. |
| 138 | >25 | >50 | >25 | >20 |
| 139 | 1.06 | 25.8 | 0.33 | n.d. |
| 140 | >25 | >50 | 6.8 | n.d. |
| 141 | 13.9 | 9.7 | 6.2 | n.d. |
| 142 | >25 | 20.7 | >14 | n.d. |
| 143 | >25 | >50 | >14.4 | n.d. |
| 144 | >25 | 26 | >11.3 | n.d. |
| 145 | >25 | >50 | 16.1 | n.d. |
| 146 | >25 | 21.7 | >14.2 | n.d. |
| 147 | >25 | 8.8 | 3.6 | 2.41 |
| 148 | >25 | >50 | >24.6 | >20 |
| 149 | >25 | 9.2 | 10.9 | 0.55 |
| 150 | >25 | 22.8 | 12.1 | 8.9 |
| 151 | 17.1 | 19.5 | 1.83 | 3.7 |
| 152 | >25 | 4.5 | 5.6 | >11.5 |
| 153 | >25 | 14.9 | n.d. | n.d. |
| 154 | >24.1 | >50 | n.d. | n.d. |
| 155 | 7.2 | >39.7 | 4.3 | n.d. |
| 156 | >25 | 27.2 | >14.2 | n.d. |
| 157 | >25 | >34.6 | 12.8 | n.d. |
| 158 | >25 | >50 | 13 | n.d. |
| 159 | >25 | >50 | >12.2 | n.d. |
| 160 | >24.6 | 20.3 | 12.4 | n.d. |
| 161 | >25 | >50 | 9.6 | n.d. |
| 162 | >25 | >50 | 1.23 | n.d. |
| 163 | >25 | >50 | >25 | n.d. |
| 164 | >25 | 23.4 | 12.6 | n.d. |
| 165 | >24.5 | 23.1 | >11.7 | n.d. |
| 166 | >25 | >27.8 | >25 | n.d. |
| 167 | >25 | 16.1 | >11.5 | n.d. |
| 168 | >25 | >50 | >16.7 | n.d. |
| 169 | >25 | >50 | >25 | n.d. |
| 170 | >25 | >50 | >25 | n.d. |
| 171 | >25 | >50 | >7.5 | 7.5 |
| 172 | >25 | 23.7 | >15.8 | n.d. |
| 173 | >25 | 18.1 | >13.8 | n.d. |
| 174 | >25 | >50 | >25 | >20 |
| 175 | >25 | >28.9 | >20.5 | 0.067 |
| 176 | >25 | >50 | n.d. | n.d. |
| 177 | 2.28 | >50 | 1.66 | n.d. |
| 178 | 23.8 | >50 | 15.2 | n.d. |
| 179 | >25 | >50 | 5 | n.d. |
| 180 | >25 | 13.2 | 8.3 | n.d. |
| 181 | >25 | >30.5 | >14.5 | n.d. |
| 182 | >25 | >50 | n.d. | n.d. |
| 183 | >25 | >50 | n.d. | n.d. |
| 184 | >25 | >50 | 8.4 | n.d. |
| 185 | 11.2 | >30.7 | 1.77 | 0.96 |
| 186 | >25 | >34.7 | 4.5 | >11.5 |
| 187 | 6.9 | >42.2 | 4.2 | >11.5 |
| 188 | 2.26 | 11.6 | 114.3 | n.d. |
| 189 | >25 | >28.9 | n.d. | n.d. |
| 190 | >24 | 20.2 | 5.8 | n.d. |
| 191 | >25 | >39.1 | >16.2 | n.d. |
| 192 | 10.2 | >37.9 | 0.49 | n.d. |
| 193 | >25 | >50 | 15.2 | n.d. |
| 194 | >25 | >50 | >11.7 | n.d. |
| 195 | 21.2 | >50 | 7.8 | 8.8 |
| 196 | >25 | 11 | 11.2 | n.d. |
| 197 | >25 | >50 | >22.3 | n.d. |
| 198 | >25 | >28.7 | 8.4 | n.d. |
| 199 | 23.7 | 21.5 | 4.4 | n.d. |
| 200 | >25 | >50 | >9.6 | n.d. |
| 201 | >25 | >50 | >10.8 | >20 |
| 202 | >25 | >50 | 1.87 | n.d. |
| 203 | >25 | >50 | >25 | n.d. |
| 204 | 23.7 | 21.5 | 4.4 | n.d. |
| 205 | 14.3 | >46.3 | 1.26 | n.d. |
| 206 | 1.56 | 13.4 | 0.174 | n.d. |
| 207 | >25 | >50 | >25 | n.d. |
| 208 | 8.7 | >32.7 | 2.48 | n.d. |
| 209 | 7.9 | 10.4 | 1.41 | n.d. |
| 210 | >22 | >37.7 | n.d. | n.d. |
| 211 | >22.8 | >27.9 | n.d. | n.d. |
| 212 | 6.6 | 22.5 | 2.65 | n.d. |
| 213 | >25 | >48 | >25 | n.d. |
| 214 | 8.4 | 27.5 | 2.25 | n.d. |
| 215 | 13.3 | 18.1 | 112.4 | n.d. |
| 216 | 2.59 | 2.83 | 0.46 | 0.7 |
| 217 | 5.9 | 10.4 | 0.8 | n.d. |
| 218 | >25 | 7.5 | 14.9 | 2.14 |
| 220 | 7.4 | 17.3 | 1.66 | n.d. |
| 221 | 5.4 | 24.1 | 5.5 | n.d. |
| 222 | >25 | >22.6 | >25 | 6.4 |
| 223 | >25 | 21.4 | 14.1 | n.d. |
| 224 | 18.7 | 11.1 | 2.61 | n.d. |
| 225 | >25 | >50 | >25 | n.d. |
| 226 | >25 | >50 | >22.2 | >20 |
| 227 | >25 | >50 | >15.2 | >20 |
| 228 | >25 | >50 | >25 | >20 |
| 229 | >25 | >50 | >23.3 | >20 |
| 230 | 5.4 | 13.3 | 1.48 | 3.6 |
| 231 | >25 | 27.9 | >23.2 | >20 |
| 232 | >25 | >50 | >25 | >20 |
| 233 | >25 | >50 | >25 | >20 |
| 234 | 2.03 | 9.7 | n.d. | n.d. |
| 235 | 3.5 | 8.8 | n.d. | n.d. |
| 236 | >25 | 28.8 | 1.11 | 17.9 |
| 237 | >25 | >50 | 8.7 | n.d. |
| 238 | >25 | 29.3 | 9.2 | >20 |
| 239 | 13.9 | >35.6 | 2.06 | n.d. |
| 240 | 2.06 | 6.1 | 0.45 | 0.7 |
| 241 | 14.2 | >47.5 | 9.7 | 10.4 |
| 242 | 4.3 | 25.5 | 0.36 | 1.38 |
| 243 | 5 | 39.6 | 0.45 | 2.58 |
| 244 | >25 | >50 | >25 | >20 |
| 245 | 1.77 | 18.8 | 0.241 | n.d. |
| 246 | >25 | >50 | >25 | n.d. |
| 247 | >25 | 26.9 | 6.4 | n.d. |
| 248 | >25 | 23.1 | n.d. | n.d. |
| 249 | >25 | >30 | 14.1 | n.d. |
| 250 | >25 | >50 | >25 | n.d. |
| 251 | >25 | >50 | >18.2 | n.d. |
| 252 | >25 | >50 | >25 | n.d. |
| 253 | >24.9 | >28.4 | >25 | n.d. |
| 254 | >25 | >50 | >25 | n.d. |
| 255 | >25 | >50 | >25 | n.d. |
| 256 | >25 | >50 | >18.1 | n.d. |
| 257 | >25 | >50 | >25 | n.d. |
| 258 | >25 | >50 | >15.4 | n.d. |
| 259 | >25 | >50 | >25 | n.d. |
| 260 | >25 | 29.3 | 17.7 | n.d. |
| 261 | >25 | >50 | 15.9 | n.d. |
| 262 | >25 | 13.5 | >22.4 | n.d. |
| 263 | >25 | >30.1 | >25 | n.d. |
| 264 | >25 | >32.3 | 11.7 | n.d. |
| 265 | >25 | 15.6 | 8.2 | n.d. |
| 266 | >25 | >40.5 | >25 | n.d. |
| 268 | >25 | >50 | n.d. | n.d. |
| 269 | >25 | >50 | n.d. | n.d. |
| 270 | 20 | >50 | 77.3 | n.d. |
| 271 | >25 | >50 | n.d. | n.d. |
| 272 | >25 | >50 | n.d. | n.d. |
| 273 | >25 | >50 | n.d. | n.d. |
| 274 | 17 | 26.7 | n.d. | n.d. |
| 275 | >25 | >50 | n.d. | n.d. |
| 276 | 1.56 | 6 | n.d. | n.d. |
| 277 | >25 | 15.2 | n.d. | n.d. |
| 278 | >25 | 3.8 | n.d. | n.d. |
| 279 | 0.57 | 2.25 | 0.311 | 0.141 |
| 280 | 21.2 | 27.4 | >13.6 | 3.4 |
| 281 | 1.98 | 6.3 | n.d. | n.d. |
| 282 | 17.5 | 3.3 | 11.2 | n.d. |

TABLE I-continued

Inhibitory efficacy of selected compounds of the invention aganist proliferation of L. donovani, T. brucei or T cruzi.

| Example No. | L. donovani amastigotes EC50 (μM) | L. donavani Macrophage EC50 (μM) | T. brucei EC50 (μM) | T cruzi EC50 (μM) |
|---|---|---|---|---|
| 283 | 4 | 11.4 | n.d. | n.d. |
| 284 | 0.7 | 4.1 | n.d. | n.d. |
| 285 | 0.73 | 5 | 115.8 | n.d. |
| 286 | 0.61 | 7.1 | 0.164 | n.d. |
| 287 | 1.44 | 0.078 | n.d. | n.d. |
| 288 | 1.59 | 0.13 | n.d. | n.d. |
| 289 | 4.2 | 8.1 | n.d. | n.d. |
| 290 | 15.6 | 17.4 | n.d. | n.d. |
| 291 | 0.076 | 0.076 | 0.0152 | 0.0161 |
| 292 | 0.08 | 0.17 | n.d. | n.d. |
| 293 | 0.38 | 2.47 | n.d. | n.d. |
| 294 | >25 | 16.9 | n.d. | n.d. |
| 295 | 2.86 | 1.27 | n.d. | n.d. |
| 296 | 0.034 | 0.126 | 112.4 | n.d. |
| 297 | 1.59 | 5.5 | 0.187 | 5.3 |
| 298 | >25 | >50 | n.d. | n.d. |
| 299 | 0.73 | 0.208 | n.d. | n.d. |
| 300 | 0.143 | 0.289 | n.d. | n.d. |
| 301 | 0.91 | 1.05 | n.d. | n.d. |
| 302 | 5.9 | 9.9 | n.d. | n.d. |
| 303 | 0.146 | 0.4 | n.d. | n.d. |
| 304 | 9.6 | 4.7 | n.d. | n.d. |
| 306 | 0.207 | 0.181 | n.d. | n.d. |
| 307 | >25 | >50 | n.d. | n.d. |
| 308 | 0.114 | 0.085 | 0.025 | 0.023 |
| 309 | 1.97 | 4.5 | 111.6 | n.d. |
| 310 | 1.95 | 4.6 | n.d. | n.d. |
| 311 | >25 | >6.9 | n.d. | n.d. |
| 312 | 1.75 | 3.7 | n.d. | n.d. |
| 332 | 0.114 | 0.085 | 0.025 | 0.023 |
| 333 | 0.66 | 0.048 | n.d. | n.d. |
| 334 | 0.26 | 0.99 | n.d. | n.d. |
| 335 | 0.6 | 1.09 | n.d. | n.d. |
| 336 | 1.89 | 2.18 | n.d. | n.d. |
| 337 | 0.119 | 0.295 | n.d. | n.d. |
| 338 | 2.4 | 0.42 | n.d. | n.d. |
| 339 | 3.7 | 1.82 | n.d. | n.d. |
| 340 | 11.7 | 9.8 | n.d. | n.d. |
| 341 | 0.08 | 0.23 | n.d. | n.d. |
| 342 | >25 | 39.1 | n.d. | n.d. |
| 343 | 0.245 | 0.51 | n.d. | n.d. |
| 344 | 7.6 | 17 | n.d. | n.d. |
| 345 | 1.97 | 1.35 | 0.277 | n.d. |
| 346 | 2.53 | 0.47 | 0.56 | n.d. |
| 347 | >25 | 7.2 | n.d. | n.d. |
| 348 | 0.249 | 0.92 | 0.0239 | 0.064 |
| 349 | 1.35 | 2.69 | 0.171 | n.d. |
| 350 | 0.68 | 1.26 | 0.8 | 0.51 |
| 351 | 1.19 | 3.7 | 0.206 | 0.243 |
| 352 | 0.253 | 49.5 | 0.45 | n.d. |
| 354 | >25 | >50 | n.d. | n.d. |
| 355 | >25 | >50 | n.d. | n.d. |
| 356 | >25 | 19.6 | 114.3 | n.d. |
| 357 | 0.6 | 2.51 | 108.3 | n.d. |
| 358 | >25 | >50 | n.d. | n.d. |
| 359 | >25 | >35.3 | n.d. | n.d. |
| 362 | >25 | 7.5 | n.d. | n.d. |
| 365 | 19.8 | >50 | n.d. | n.d. |
| 368 | 18.9 | >50 | 32.3 | n.d. |
| 369 | >25 | >50 | 90.9 | n.d. |
| 370 | 2.53 | 7.4 | 0.52 | 1.2 |
| 371 | 2.35 | 6.5 | 2.21 | 3.3 |
| 372 | >25 | 2.52 | n.d. | n.d. |
| 373 | 0.55 | 2.15 | n.d. | n.d. |
| 374 | 16.5 | 5.9 | 5.1 | 0.85 |
| 375 | 7.5 | >42.7 | 2.35 | 3.9 |
| 377 | 6.6 | 5.8 | 0.58 | 2.06 |
| 378 | 0.69 | 3.3 | 0.02 | n.d. |
| 379 | 1.49 | 8.7 | 0.69 | 13.2 |
| 380 | 5.7 | 3.3 | n.d. | n.d. |
| 381 | 2.5 | 1.6 | n.d. | n.d. |
| 385 | >23.2 | >10.9 | n.d. | n.d. |
| 386 | 4.3 | 4.3 | n.d. | n.d. |
| 387 | >25 | >50 | n.d. | n.d. |
| 388 | >25 | >50 | n.d. | n.d. |
| 389 | 11.6 | 11.4 | n.d. | n.d. |
| 390 | 12.6 | 18.2 | n.d. | n.d. |
| 391 | >25 | >12.3 | n.d. | n.d. |
| 392 | >25 | 8.4 | n.d. | n.d. |
| 393 | >12.5 | >50 | n.d. | n.d. |
| 394 | 11.7 | 4.8 | n.d. | n.d. |
| 395 | 12 | 6.8 | n.d. | n.d. |
| 396 | 16.1 | >50 | n.d. | n.d. |
| 397 | >25 | >30 | n.d. | n.d. |
| 399 | 15.8 | 5.9 | n.d. | n.d. |
| 400 | 1.62 | 4 | n.d. | n.d. |
| 401 | 4.7 | 3.12 | n.d. | n.d. |
| 402 | >24 | 10 | n.d. | n.d. |
| 403 | 17.4 | >50 | n.d. | n.d. |
| 404 | >25 | >50 | 27.7 | n.d. |
| 405 | >25 | >50 | 5 | n.d. |
| 406 | >25 | >50 | 25 | n.d. |
| 407 | >25 | >4.2 | 76.7 | n.d. |
| 408 | 3.8 | >50 | 114.3 | n.d. |
| 409 | 7.5 | >50 | 114.3 | n.d. |
| 410 | >25 | >50 | 58.4 | n.d. |
| 414 | 0.2 | 1.17 | n.d. | n.d. |
| 415 | 0.4 | 0.1 | n.d. | n.d. |
| 416 | 1.52 | 2.9 | n.d. | n.d. |
| 417 | 0.212 | 0.49 | 0.056 | n.d. |
| 418 | 1.51 | 8.4 | n.d. | n.d. |
| 419 | 0.36 | 2.46 | 113.9 | n.d. |
| 420 | >25 | >50 | n.d. | n.d. |
| 421 | >25 | >50 | n.d. | n.d. | n.d. means not determined.

EXAMPLES

The present invention is further exemplified, but not to be limited, by the following examples and intermediates that illustrate the preparation of compounds of the invention. It is understood that if there appears to be a discrepancy between the name and structure of a particular compound, the structure is to be considered correct as the compound names were generated from the structures.

Temperatures are given in degrees Celsius. If not mentioned otherwise, all evaporations are performed under reduced pressure, typically between about 15 mm Hg and 100 mm Hg (=20–133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

Synthesis of Intermediates

LCMS Analytical Methods:

Method A: Waters Acquity UPLC system: Acquity Binary Gradient Manager with Degasser; Acquity Column Compartment set at 50° C.; Acquity Diode Array Detector; Leap Technologies HTS Pal Autosampler; Antek Chemiluminescent Nitrogen Detector (CLND); Waters ZQ2000 Mass Spectrometer; HPLC Column: Thermo Syncronis C18 30×2.1 mm; Mobile Phase: (A) 95% H2O/5% MeOH/IPA (75/25, v/v)+0.05% formic acid, (B) MeOH/IPA (75/25, v/v)+0.035% formic acid; Gradient: 0.4 mL/minute, initial 2% B for 1.0 minutes, ramp to 95% B over 2.5 minutes, until 4.0 minutes, return to 2% B to at 4.25 minutes until end of run at 5.0; MS Scan: 150 to 1000 amu in 1 second; Diode Array Detector: 190 nm-400 nm.

Method B: Agilent G1379A Degasser; Agilent G1312A Binary Pump; Agilent G1315B Diode Array Detector; Leap Technologies HTS Pal Autosampler; Sedex 75 Evaporative Light Scattering Detector; Waters ZQ2000 Mass Spectrometer; HPLC Column: Thermo Accucore aQ C18 2.6 um 30×2.1 mm; Mobile Phase: (A) H2O+0.05% TFA and (B) Acetonitrile+0.05% TFA; Gradient: 1 mL/minute, initial 5% B for 0.1 minutes, ramp to 90% B over 2.5 minutes, then to 100% B at 2.61 and hold until 3.10 minutes, return to 5% B to at 3.15 minutes until end of run at 3.25. The column is re-equilibrated in the ~30 seconds between injections; MS Scan: 180 to 800 amu in 0.4 seconds; Diode Array Detector: 214 nm-400 nm

Intermediate 1

2-chloro-5-(furan-2-carboxamido)benzoic acid

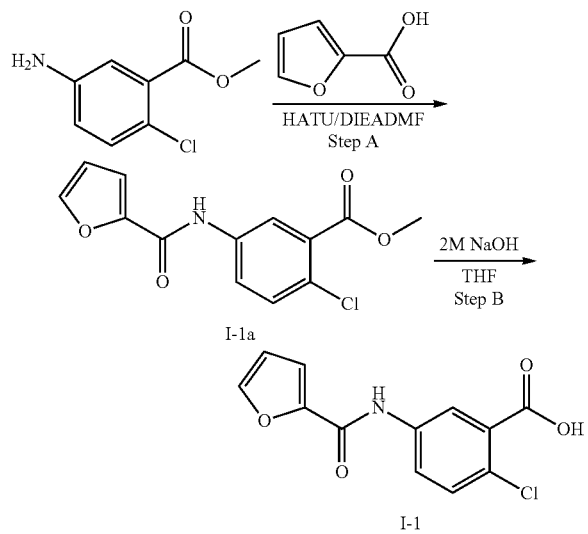

Step A: In a 500 mL round bottom flask, was transferred methyl 5-amino-2-chlorobenzoate (5 g, 27 mmol) in DCM (Volume: 150 mL) to give a yellow solution. Furan-2-carboxylic acid, (3.78 g, 33.78 mmols) was then added followed by HATU (12.83 g, 33.78 mmols) and DIEA (8.71 g, 67.55 mmols). The reaction mixture was stirred overnight. The reaction mixture was then quenched with water, followed by extraction with ethyl acetate (3×100 mL). The organics were combined, dried over MgSO4 and purified by column chromatography (0-100 EtOAC/Hex) yielding 5.68 g (20.35 mmols, 75%) of methyl 2-chloro-5-(furan-2-carboxamido)benzoate (I-1a).

Step B: In a 100 mL round bottom flask was transferred methyl 5-amino-2-chlorobenzoate (1.5 g, 5.37 mmol) in THF (Volume: 50 mL) to give a yellow solution. 2N NaOH, (10 mL) was then added. The reaction mixture was stirred overnight. The solvents were partially removed and the reaction mixture was made acidic to pH 4-5 by slow addition of 1N aqueous HCl. The white precipitate was filtered out and dried under vacuo. 1.1 g (4.15 mmols, 77%) of 2-chloro-5-(furan-2-carboxamido)benzoic acid (I-1) was isolated. $^1$H NMR (400 MHz, DMSO) δ 10.46 (s, 1H), 8.26 (d, J=2.7 Hz, 1H), 7.98 7.92 (m, 2H), 7.52 (d, J=8.8 Hz, 1H), 7.38 (dd, J=0.6, 3.5 Hz, 1H), 6.72 (dd, J=1.7, 3.5 Hz, 1H). MS M/Z=266 (M+1).

Intermediate 2

N-(3-(6-bromo-1H-imidazo[4,5-b]pyridin-2-yl)-4-chlorophenyl)furan-2-carboxamide

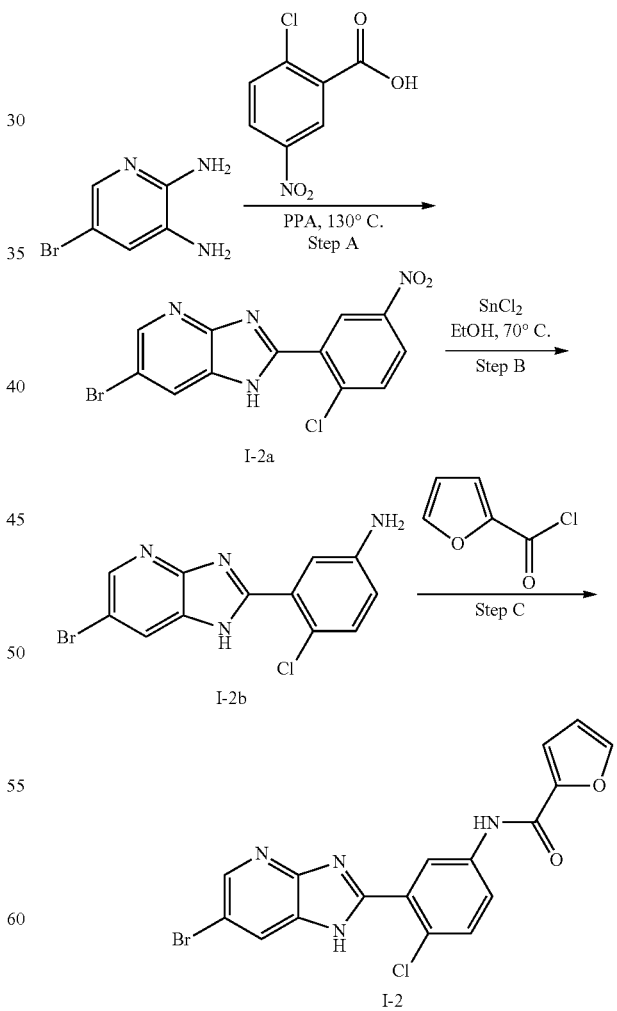

Step A: A mixture of 5-bromopyridine-2,3-diamine (15 g, 79.78 mmol, 1.00 equiv), 2-chloro-5-nitrobenzoic acid (17.7 g, 87.81 mmol, 1.10 equiv) in PPA (200 mL) was stirred overnight at 130° C. and then quenched by the addition of 300 mL of H₂O/ice. The pH value of the mixture was adjusted to 8 with sodium carbonate and the solids were collected by filtration, washed with water and dried in an oven under reduced pressure to give 36 g (crude) of 6-bromo-2-(2-chloro-5-nitrophenyl)-1H-imidazo[4,5-b]pyridine I-2a as a brown solid.

Step B: To a suspension of 6-bromo-2-(2-chloro-5-nitrophenyl)-1H-imidazo[4,5-b]pyridine I-2a (18 g, 50.91 mmol, 1.00 equiv) in ethanol (200 mL) was added SnCl₂.2H₂O (17.3 g, 76.55 mmol, 1.50 equiv) and heated to reflux overnight. The resulting mixture was concentrated under vacuum and the residue was diluted with 200 mL of H₂O. The pH value of the mixture was adjusted to 8 with sodium carbonate (sat.). A filtration was performed and the solids were applied on a silica gel column and eluted with ethyl acetate/PE (1/1) to give 12 g (73%) of 3-[6-bromo-1H-imidazo[4,5-b]pyridin-2-yl]-4-chloroaniline (I-2b) as a yellow solid. ¹H-NMR (DMSO, 400 MHz): 13.00-13.53 (m, 1H), 8.46 (s, 1H), 8.30 (brs, 1H), 7.26 (d, J=8.4 Hz, 1H), 7.05 (brs, 1H), 6.76 (dd, J=8.4, 2.8 Hz, 1H), 5.57 (brs, 2H). MS M/Z=325 (M+1).

Step C: To a suspension of 3-[6-bromo-1H-imidazo[4,5-b]pyridin-2-yl]-4-chloroaniline (15 g, 46.36 mmol, 1.00 equiv) in dichloromethane (150 mL) was added furan-2-carbonyl chloride (9.1 g, 69.72 mmol, 1.50 equiv) in a bath of ice and stirred overnight at room temperature. The reaction was then quenched by the addition of 50 mL of methanol and concentrated under vacuum. The residue was applied onto a silica gel column with ethyl acetate/petroleum ether (1/2) to give 8.9 g (46%) of N-(3-[6-bromo-1H-imidazo[4,5-b]pyridin-2-yl]-4-chlorophenyl)furan-2-carboxamide (I-2) as a light yellow solid. ¹H-NMR: (DMSO, 300 MHz): 13.09-13.79 (m, 1H), 10.53 (s, 1H), 8.51 (s, 1H), 8.36 (brs, 2H), 7.98-8.02 (m, 2H), 7.68 (d, J=9.0 Hz, 1H), 7.40 (d, J=3.3 Hz, 1H), 6.74 (dd, J=3.3, 1.8 Hz, 1H). MS M/Z=419 (M+1).

Intermediate 3

4-chloro-3-[6-methyl-1H-imidazo[4,5-b]pyridin-2-yl]aniline

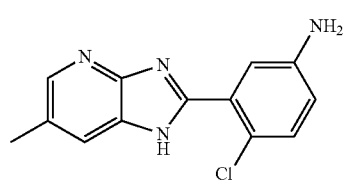

I-3

Intermediate I-3 was synthesized in a similar fashion as described in the synthesis of I-2b using 5-methylpyridine-2,3-diamine. ¹H-NMR: (DMSO, 400 MHz): 12.59-13.04 (m, 1H), 8.23 (s, 1H), 7.81 (brs, 1H), 7.25 (d, J=8.4 Hz, 1H), 7.05 (brs, 1H), 6.74 (dd, J=8.4, 2.8 Hz, 1H), 5.53 (brs, 2H), 2.44 (s, 3H). MS M/Z=259 (M+1).

Intermediate 4

2-(5-bromo-2-chlorophenyl)-6-methyl-1H-imidazo[4,5-b]pyridine

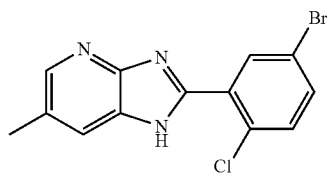

I-4

Intermediate I-4 was synthesized in a similar fashion as described in the synthesis of I-2a using 5-methylpyridine-2,3-diamine and 5-bromo-2-chlorobenzoic acid. ¹H NMR (400 MHz, DMSO) δ 8.18 (d, J=2.4 Hz, 1H), 8.07 (s, 1H), 7.68 (s, 1H), 7.60 (dd, J=2.2, 8.4 Hz, 1H), 7.51 (d, J=8.5 Hz, 1H), 2.39 (s, 3H). MS M/Z=322/324 (M+1).

Intermediate 5

3-[6-bromo-1H-imidazo[4,5-b]pyridin-2-yl]-4-fluoroaniline

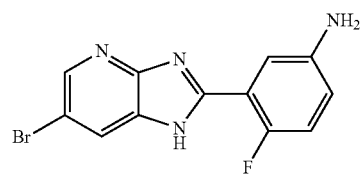

I-5

Compound I-5 was synthesized in a similar fashion as described in the synthesis of I-2b using 2-fluoro-5-nitrobenzoic acid. ¹H-NMR: (DMSO, 400 MHz): 13.38-13.59 (m, 1H), 8.39 (s, 1H), 8.23 (brs, 1H), 7.25 (dd, J=8.8, 2.0 Hz, 1H), 7.36-7.39 (m, 1H), 6.74 (dd, J=11.2, 8.8 Hz, 1H), 5.48 (brs, 2H). MS M/Z=307/309 (M+1).

Intermediate 6

N-(3-(6-bromo-1H-imidazo[4,5-b]pyridin-2-yl)-4-fluorophenyl)furan-2-carboxamide

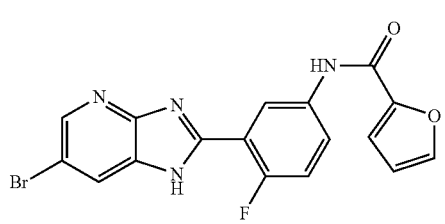

I-6

Intermediate I-6 was synthesized in a similar fashion as described in the synthesis of I-2 using 3-[6-bromo-1H-imidazo[4,5-b]pyridin-2-yl]-4-fluoroaniline (I-3). ¹H NMR (300 MHz, MeOH): δ 8.81-8.42 (2H, m), 8.25-8.0 (3H, m), 7.66-7.40 (2H, m), 6.70 (1H, s); MS M/Z=400.4 (M+1).

Intermediate 7

4-chloro-3-[6-(trifluoromethyl)-1H-imidazo[4,5-b]pyridin-2-yl]aniline

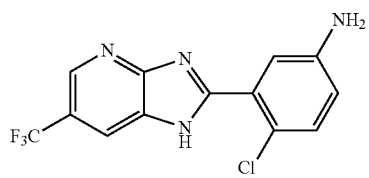

I-7

Intermediate I-7 was synthesized in a similar fashion as described in the synthesis of I-2b using 5-trifluoromethylpyridine-2,3-diamine. $^1$H NMR (300 MHz, DMSO): δ13.18-13.90 (m, 1H), 8.75 (s, 1H), 8.24-8.52 (m, 1H), 7.27 (d, J=8.7 Hz, 1H), 7.00-7.16 (m, 1H), 6.77 (dd, J=8.7, 2.7 Hz, 1H), 5.37 (brs, 2H). MS M/Z=313 (M+1).

Intermediate 8

2-(5-amino-2-chlorophenyl)-1H-imidazo[4,5-b]pyridine-6-carbonitrile

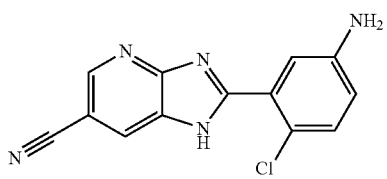

I-8

Intermediate I-8 was synthesized in a similar fashion as described in the synthesis of I-2b using 5,6-diaminonicotinonitrile. $^1$H NMR (400 MHz, DMSO) δ 8.74 (d, J=1.8 Hz, 1H), 8.55 (s, 1H), 7.25 (d, J=8.7 Hz, 1H), 7.07 (d, J=2.6 Hz, 1H), 6.74 (dd, J=2.7, 8.6 Hz, 1H), 5.54 (s, 2H).

LCMS M/Z=270.1 (M+1). RT=1.11: Method B.

Intermediate 9

N-(3-(6-bromo-1H-imidazo[4,5-b]pyridin-2-yl)-4-chlorophenyl)pyrrolidine-1-carboxamide

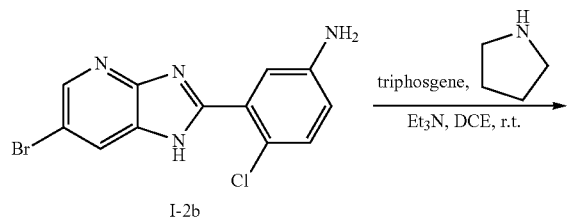

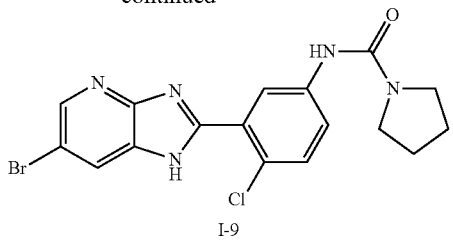

I-9

To a suspension of 3-[6-bromo-1H-imidazo[4,5-b]pyridin-2-yl]-4-chloroaniline (I-2b) (6.7 g, 20.71 mmol, 1.00 equiv) in DCE (200 mL) was added trisphosgene (4.2 mg, 14.10 mmol, 0.70 equiv), followed added triethylamine (12.5 g, 123.53 mmol, 5.97 equiv) and pyrrolidine (1.5 g, 21.09 mmol, 1.02 equiv) in a bath of ice. The reaction mixture was stirred overnight at room temperature and then quenched by the addition of water. The resulting mixture was extracted with dichloromethane and the combined organic layer was washed with brine, dried over anhydrous sodium sulfate and concentrated under vacuum. The residue was applied onto a silica gel column with ethyl acetate/petroleum ether (1/1) to give 3.1 g (36%) of N-(3-[6-bromo-1H-imidazo[4,5-b]pyridin-2-yl]-4-chlorophenyl)pyrrolidine-1-carboxamide (I-9) as a white solid. $^1$H-NMR: (d$_6$-DMSO, 400 MHz): 13.09-13.59 (m, 1H), 8.07-8.52 (m, 4H), 7.81 (m, 1H), 7.53 (d, J=8.8 Hz, 1H), 3.36 (s, 4H), 1.86 (s, 4H). MS M/Z=422 (M+1).

Intermediate 10

N-(3-(6-bromo-1H-imidazo[4,5-b]pyridin-2-yl)-4-fluorophenyl)pyrrolidine-1-carboxamide

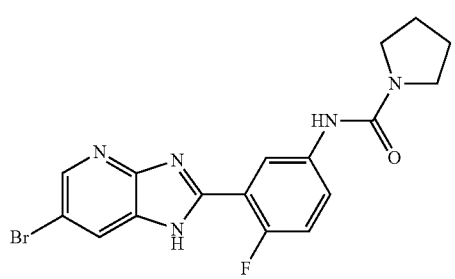

I-10

Intermediate I-10 was synthesized in a similar fashion as described in the synthesis of I-9 using 3-[6-bromo-1H-imidazo[4,5-b]pyridin-2-yl]-4-fluoroaniline I-5. $^1$H NMR (300 MHz, MeOH): δ 8.81-8.42 (2H, m), 8.25-8.0 (3H, m), 7.66-7.40 (2H, m), 6.70 (1H, s); MS M/Z=401.0 (M+1). RT=1.59: Method B.

Intermediate 11

Isopropyl (3-(6-bromo-1H-imidazo[4,5-b]pyridin-2-yl)-4-chlorophenyl)carbamate

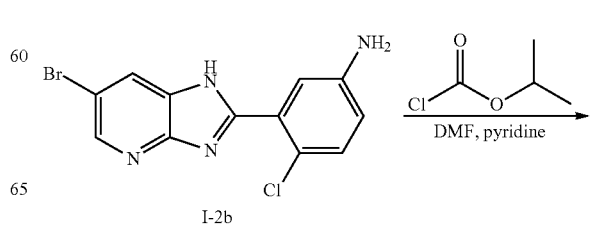

-continued

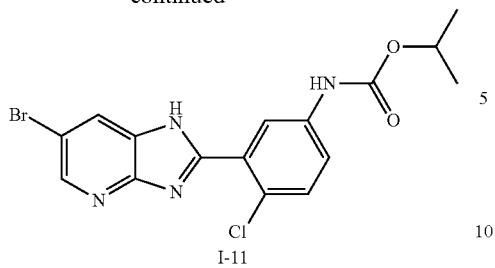

I-11

To a suspension of 3-[6-bromo-1H-imidazo[4,5-b]pyridin-2-yl]-4-chloroaniline (I-2b) (1 g, 3.08 mmol, 1.00 equiv) in DMF (10 mL) at 0° C. was added 0.5 ml of pyridine followed by isopropyl chloroformate (solution 1M in toluene) (3.85 ml, 3.85 mmol, 1.25 equiv). The reaction mixture was stirred overnight at room temperature and then quenched by the addition of water. The resulting mixture was extracted with ethyl acetate and the combined organic layer was washed with brine, dried over anhydrous sodium sulfate and concentrated under vacuum. The residue was purified by flash chromatography (0 to 100% Ethyl acetate/Hexanes) to afford the title compound I-11. $^1$H NMR (400 MHz, DMSO) δ 9.95 (s, 1H), 8.49 (s, 1H), 8.34 (s, 1H), 8.02 (s, 1H), 7.63 (s, 1H), 7.57 (d, J=8.8, 1H), 4.97 4.80 (m, 1H), 1.26 (d, J=6.2, 6H); MS M/Z=409.0 (M+1). RT=1.77: Method B.

Intermediate 12

Methyl (4-(2-(5-amino-2-chlorophenyl)-1H-imidazo[4,5-b]pyridin-6-yl)phenyl)carbamate

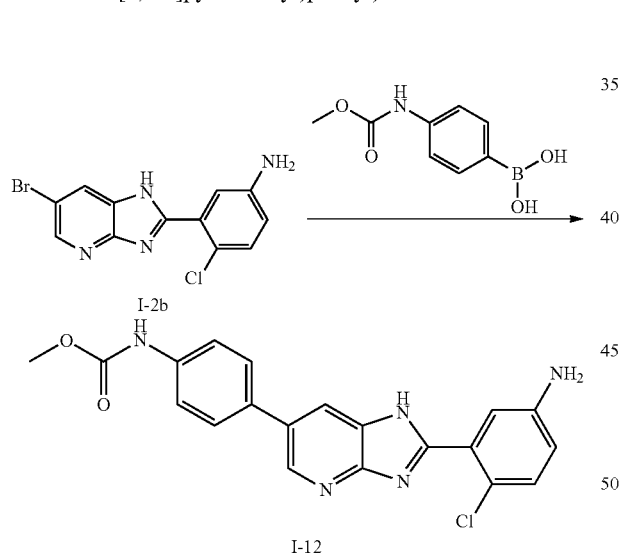

I-12

To a solution of bromide I-2b (30 mg, 0.093 mmol, 1 eq.) in THF:H$_2$O (4:1) solvent (0.3 mM) was added (4-((methoxycarbonyl)amino)phenyl)boronic acid (27 mg, 0.139 mmol, 1.5 eq.), K$_2$HPO$_4$(s) (40 mg, 0.232 mmol, 2.5 eq.) and Pd-DPP (Palladium diphenylphosphine supported on silica, silicycle) (0.26 mmol/g loading, 0.1 eq.). The vial was sealed and evacuated of air with vacuum and purged with nitrogen gas. The reaction vial was heated for 1 hour at 150° C. in the microwave. The vial was left to cool, and filtered. The filter was washed twice with THF:H$_2$O (4:1) solvent. The filtrate was collected, concentrated in vacuo, and the remaining residue was purified by HPLC. $^1$H NMR (400 MHz, DMSO) δ 9.79 (s, 1H), 8.65 (d, 1H), 8.16 (d, 1H), 7.79 7.67 (m, 2H), 7.66 7.50 (m, 2H), 7.25 (t, J=8.0 Hz, 1H), 7.07 (d, 1H), 6.74 (s, 1H), 5.54 (d, J=12.9 Hz, 2H), 3.69 (s, 3H). LCMS M/Z=394.1 (M+1). RT=1.33: Method B.

Intermediate 13 tert-butyl (4-(2-(5-amino-2-chlorophenyl)-1H-imidazo[4,5-b]pyridin-6-yl)phenyl)(methyl)carbamate

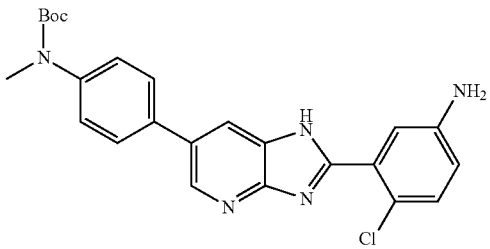

I-13

Compound I-13 was synthesized by Suzuki coupling of I-2b with (4-((tert-butoxycarbonyl)-(methyl)amino)phenyl)boronic acid using a protocol similar to one described in the synthesis of I-12.

Intermediate 14

3-(6-Chloro-1H-imidazo[4,5-b]pyridin-2-yl)-4-fluoroaniline

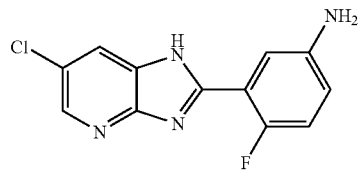

I-14

Intermediate I-14 was synthesized in a similar fashion as described in the synthesis of I-2b using 5-chloropyridine-2,3-diamine.

Intermediate 15

4-Fluoro-3-(6-phenyl-1H-imidazo[4,5-b]pyridin-2-yl)aniline

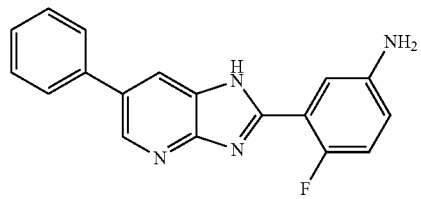

I-15

Compound I-15 was synthesized by Suzuki coupling of I-4 with phenyl boronic acid using a protocol similar to one described in the synthesis of I-12. $^1$H NMR (400 MHz, DMSO) δ 8.54 (d, 1H), 8.10 (d, 1H), 7.99-7.88 (m, 1H), 7.73-7.57 (m, 3H), 7.42 (t, J=7.4 Hz, 2H), 7.35-7.26 (m, 2H), 7.17-7.02 (m, 1H), 5.45-5.29 (m, 2H)). MS M/Z=305.1 (M+1).

Intermediate 16

4-Fluoro-3-(6-(thiophen-3-yl)-1H-imidazo[4,5-b]pyridin-2-yl)aniline

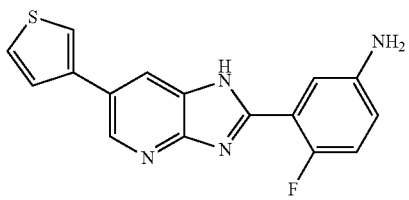

I-16

Compound I-16 was synthesized by Suzuki coupling of I-4 with thiophene-3-boronic acid using a protocol similar as in the synthesis of I-12. $^1$H NMR (600 MHz, DMSO) δ 8.74 (d, J=2.1 Hz, 1H), 8.21 (d, J=2.0 Hz, 1H), 8.01-7.96 (m, 1H), 7.73-7.66 (m, 3H), 7.37 (tdd, J=2.3, 4.3, 9.4 Hz, 1H), 7.19 (ddd, J=8.4 Hz, 11.2, 16.4, 1H), 5.45 (d, J=20.8 Hz, 2H). MS M/Z=311.1 (M+1).

Intermediate 17

2-Fluoro-5-(furan-2-carboxamido)benzoic acid

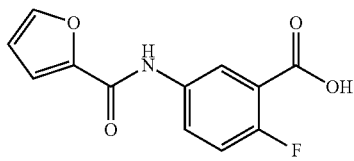

I-17

Intermediate I-17 was synthesized in a similar fashion as described in the synthesis of I-1 using 2-Fluoro-5-nitrobenzoic acid. $^1$H NMR (400 MHz, DMSO) δ 13.29 (s, 1H), 10.39 (s, 1H), 8.30 (dd, J=2.8 Hz, 6.7, 1H), 8.00 (ddd, J=2.9, 4.2, 9.0 Hz, 1H), 7.96 (dd, J=0.8, 1.7 Hz, 1H), 7.36 (dd, J=0.8, 3.5 Hz, 1H), 7.31 (dd, J=9.0, 10.5 Hz, 1H), 6.72 (dd, J=1.7, 3.5 Hz, 1H). MS M/Z=250.0 (M+1).

Intermediate 18

1-(3-(6-bromooxazolo[4,5-b]pyridin-2-yl)-4-fluorophenyl)-3-(4-(trifluoromethyl)phenyl)urea

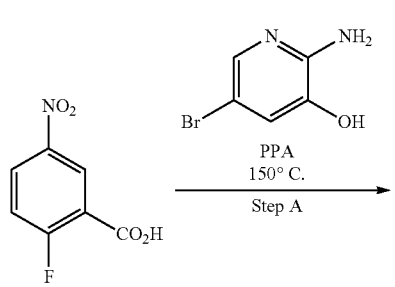

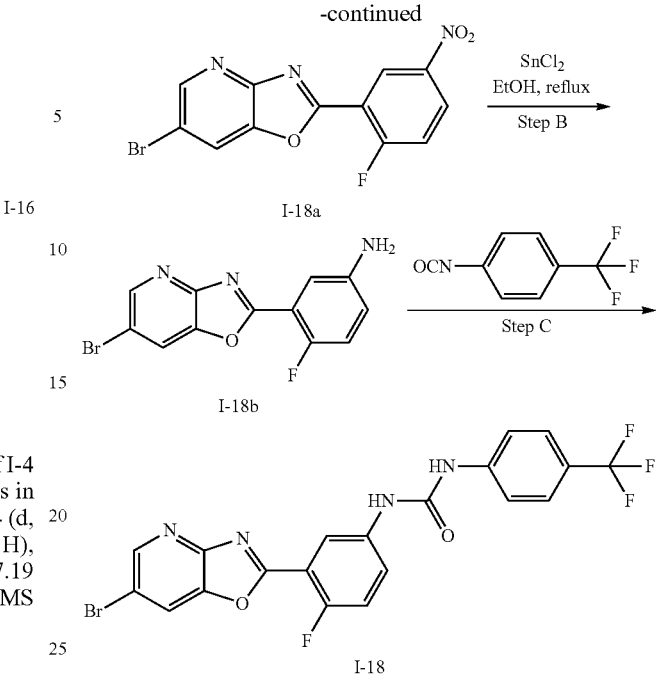

Step A and B: Compound I-18b was synthesized in a similar fashion as described in the synthesis of I-21 using 2-fluoro-5-nitrobenzoic acid.

Step C: In a 40 ml vial was placed 3-[6-bromo-[1,3]oxazolo[4,5-b]pyridin-2-yl]-4-fluoroaniline (I-18b) (25 mg, 0.081 mmol, 1.00 equiv) in dichloromethane (5 mL). To the resulting solution, 4-CF$_3$ phenyl isocyanate (23 mg, 0.121 mmol, 1.5 eq.) was added and the reaction was stirred overnight at room temperature. The reaction mixture was quenched with water and extracted with ethyl acetate (3×5 mL). All organics were combined and dried over sodium sulfate and concentrated under reduce pressure. The crude reaction was purified by reverse phase HPLC to yield 1-(3-(6-bromooxazolo[4,5-b]pyridin-2-yl)-4-fluorophenyl)-3-(4-(trifluoromethyl)phenyl)urea (I-18). The TFA salt was neutralized by passing a methanolic solution of the compound through bicarbonate resin. LCMS M/Z=495.0 (M+1). RT=2.24: Method B.

Intermediate 19

N-(3-(6-bromooxazolo[4,5-b]pyridin-2-yl)-4-fluorophenyl)furan-2-carboxamide

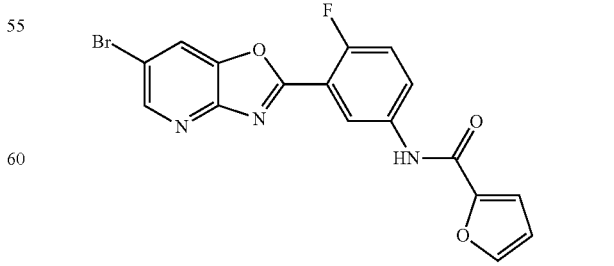

I-19

Intermediate I-19 was synthesized in a similar fashion as described in the synthesis of I-2 using [6-bromo-[1,3]oxazolo

[4,5-b]pyridin-2-yl]-4-fluoroaniline (I-18b). $^1$H NMR (400 MHz, CDCl3): δ 9.39-9.42 (m, 1H), 8.65 (s, 1H), 8.43 (s, 1H), 8.12-8.18 (m, 1H), 8.03 (s, 1H), 7.59 (m, 1H), 7.30-7.37 (m, 2H), 6.62-6.63 (m, 1H). MS M/Z=403 (M+1).

Intermediate 20

N-(3-(6-bromooxazolo[4,5-b]pyridin-2-yl)-4-fluorophenyl)pyrrolidine-1-carboxamide

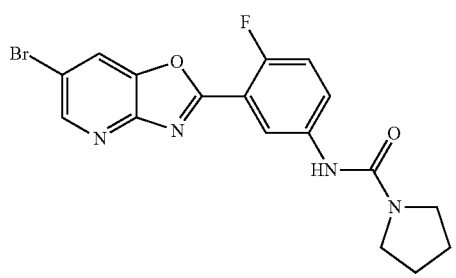

I-20

Intermediate I-20 was synthesized in a similar fashion as described in the synthesis of I-8 using [6-bromo-[1,3]oxazolo[4,5-b]pyridin-2-yl]-4-fluoroaniline (I-18b).

Intermediate 21

N-(3-(6-bromooxazolo[4,5-b]pyridin-2-yl)-4-chlorophenyl)furan-2-carboxamide

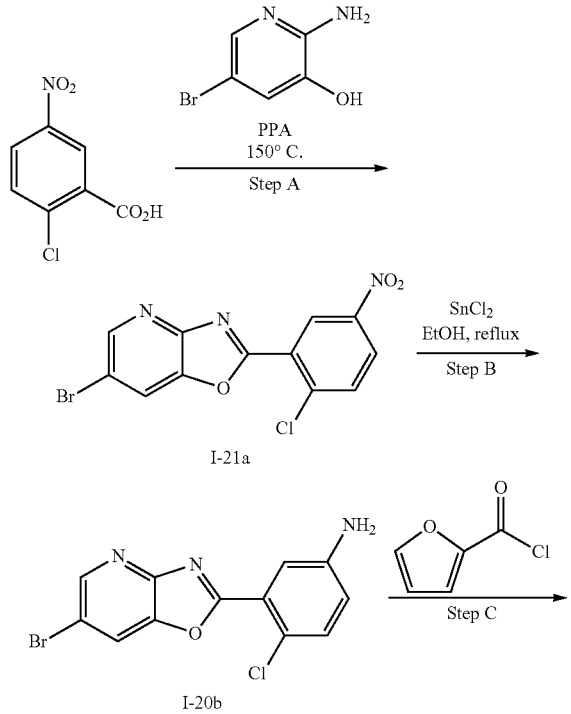

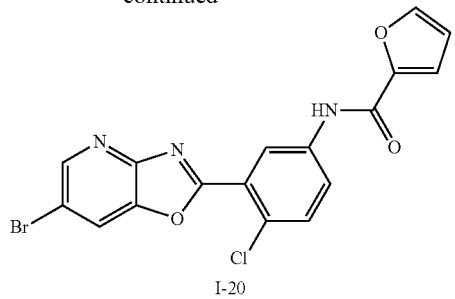

I-20

Step A: Into a 1000-mL round-bottom flask, was placed 2-amino-5-bromopyridin-3-ol (20 g, 105.81 mmol, 1.00 equiv), 2-chloro-5-nitrobenzoic acid (21.4 g, 106.17 mmol, 1.00 equiv), PPA (300 mL). The resulting solution was stirred for 3 h at 150° C. in an oil bath. The reaction was then quenched by the addition of 1 L of water/ice. The reaction mixture was cooled with a water/ice bath. The solids were collected by filtration. The solid was dried in an oven under reduced pressure. This resulted in 28 g (75%) of 6-bromo-2-(2-chloro-5-nitrophenyl)-[1,3]oxazolo[4,5-b]pyridine I-21a as a gray solid.

Step B: Into a 1000-mL round-bottom flask purged and maintained with an inert atmosphere of nitrogen, was placed 6-bromo-2-(2-chloro-5-nitrophenyl)-[1,3]oxazolo[4,5-b]pyridine (15 g, 42.31 mmol, 1.00 equiv), SnCl$_2$.2H$_2$O (51 g, 226.01 mmol, 5.34 equiv), ethanol (400 mL). The resulting solution was stirred for 3 h at 80° C. in an oil bath. The resulting mixture was concentrated under vacuum, then diluted with 1000 mL of water and dissolved in 1000 mL of ethyl acetate. The resulting solution was extracted with 2×1000 mL of ethyl acetate and the organic layers combined and dried over anhydrous sodium sulfate and concentrated under vacuum. This resulted in 5.6 g (39%) of 3-[6-bromo-[1,3]oxazolo[4,5-b]pyridin-2-yl]-4-chloroaniline I-21b as a yellow solid. $^1$H NMR (300 MHz, DMSO): δ 8.70 (s, 2H), 7.32-7.50 (m, 2H), 6.83-6.84 (m, 1H). MS M/Z=324 (M+1).

Step C: Intermediate I-21 was synthesized in a similar fashion as described in the synthesis of I-2 using [3-[6-bromo-[1,3]oxazolo[4,5-b]pyridin-2-yl]-4-chloroaniline (I-21b). $^1$H NMR (400 MHz, CDCl$_3$): δ 8.74 (s, 1H), 8.49 (s, 1H), 8.24 (s, 1H), 8.15 (s, 1H), 8.00-8.1 (m, 1H), 7.52-7.58 (m, 2H), 7.29 (m, 1H), 6.59-6.66 (m, 1H). MS M/Z=418 (M+1).

Intermediate 22

N-(4-chloro-3-(6-vinyloxazolo[4,5-b]pyridin-2-yl)phenyl)furan-2-carboxamide

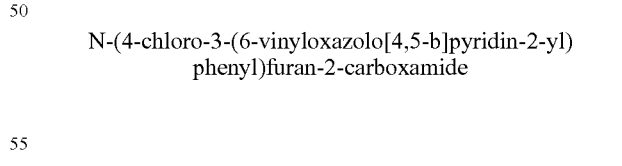

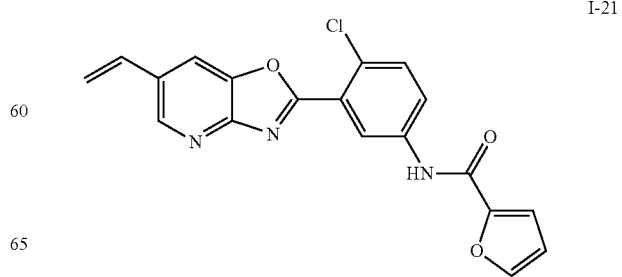

I-21

To a solution of bromide I-21 (1 gm, 2.39 mmol, 1 eq.) in THF solvent (0.3 mM) was added tributyl vinyl tin (947 mg, 2.99 mmol, 1.25 eq) and Pd-DPP (Palladium diphenylphosphine supported on silica, silicycle) (0.26 mmol/g loading, catalytic). The vial was sealed and evacuated of air with vacuum and purged with nitrogen gas. The reaction vial was heated for 6 hour at 110° C. The vial was left to cool, and concentrated. The residue was purified by flash chromatography (0 to 100% Ethyl acetate/Hexanes) to afford the title compound I-22.

Intermediate 23

4-fluoro-3-(6-(4-(2-morpholinoethoxy)phenyl)oxazolo[4,5-b]pyridin-2-yl)aniline

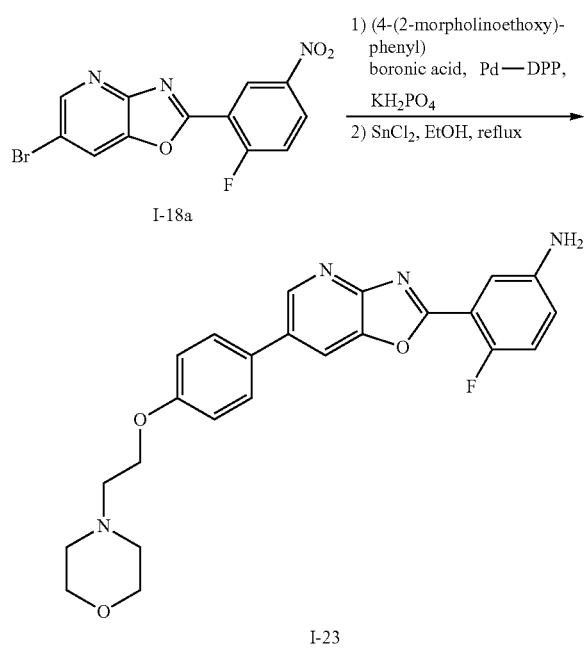

The Intermediate 4-fluoro-3-(6-(4-(2-morpholinoethoxy) phenyl)oxazolo[4,5-b]pyridin-2-yl)aniline I-23 was synthesized in two steps:

Step 1: Suzuki coupling of I-18a with (4-(2-morpholinoethoxy)phenyl) boronic acid using a protocol similar to one described in the synthesis of I-12.

Step 2: Reduction of nitro group using tin chloride using a protocol similar to one described in the synthesis of I-21b.

Synthesis of Final Compounds

Example 1

N-(4-chloro-3-{6-methyl-1H-imidazo[4,5-b]pyridin-2-yl}phenyl)furan-2-carboxamide

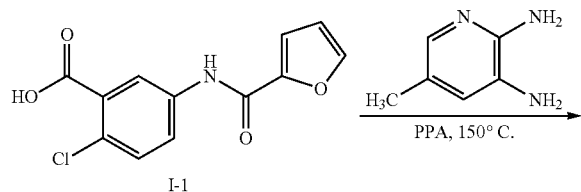

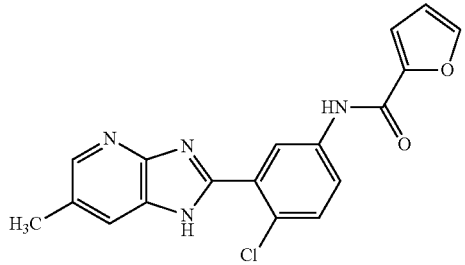

Example 1

In a 40 mL vial was transferred 2-chloro-5-(furan-2-carboxamido)benzoic acid (I-1) (1 g, 3.75 mmol) in polyphosphoric acid (10 mL), and the 2,3-diamino-5-methyl-pyridine (578 mg, 4.69 mmols, 1.25 eq) was added. The dark brown reaction mixture was heated at 150° C. for 4 hrs. The reaction mixture was then quenched with solid sodium carbonate and extracted with ethyl acetate (3×50 mL). The organic phases were combined, dried over sodium sulfate and concentrated under reduced pressure. Purification by column chromatography (0-100 EtOAC/Hex), afforded 80 mg (0.22 mmols, 6%) of the title compound (Example 1). $^1$H NMR (400 MHz, MeOD) δ 8.36-8.25 (m, 1H), 8.20 (s, 1H), 8.04-7.94 (m, 1H), 7.93-7.83 (m, 1H), 7.77 (s, 1H), 7.61 (d, J=8.8 Hz, 1H), 7.31 (d, J=3.5 Hz, 1H), 6.67 (dd, J=1.7, 3.5 Hz, 1H), 2.53 (s, 3H). LCMS M/Z=353.0 (M+1). RT=1.39: Method B.

Syntheses of Examples 2 to 5

Examples 2 to 5 were synthesized using a protocol analogous to the protocol used in the synthesis of 1 using 5-chloropyridine-2,3-diamine, 4-methylpyridine-2,3-diamine, pyrimidine-4,5-diamine and 5,6-dimethyl-2,3-diamine respectively.

Example 6

N-[4-chloro-3-(6-{4-[2-(morpholin-4-yl)ethyl]phenyl}-1H-imidazo[4,5-b]pyridin-2-yl)phenyl]furan-2-carboxamide

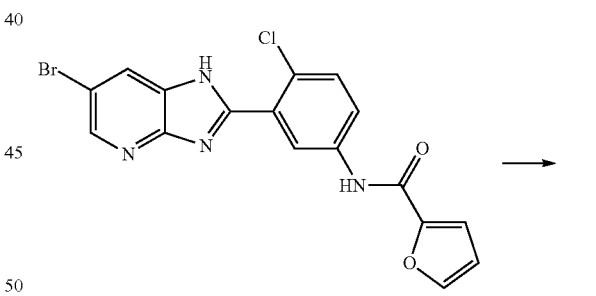

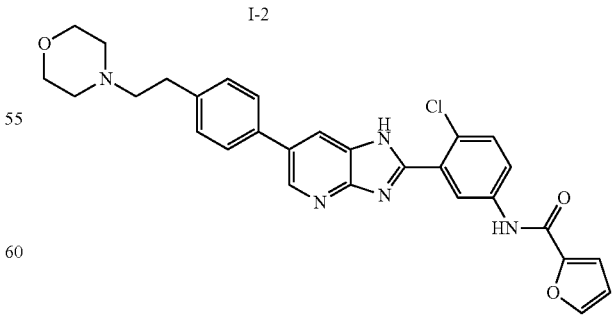

Example 6

To a solution of bromide I-2 (60 mg, 0.143 mmol, 1 eq.) in THF:H$_2$O (4:1) solvent (0.3 mM) was added (4-(2-morpholinoethyl)phenyl)boronic acid (50 mg, 0.215 mmol, 1.5 eq.), K₃PO₄(s) (102 mg, 0.588 mmol, 4 eq.) and Pd-DPP (Palladium diphenylphosphine supported on silica, silicycle) (0.26 mmol/g loading) (0.1 eq.). The vial was sealed and evacuated of air with vacuum and purged with nitrogen gas. The reaction vial was heated for 1 hour at 120° C. in the microwave. The vial was left to cool, and filtered. The filter was washed twice with THF:H₂O (4:1). The filtrate was collected, concentrated in vacuo, and the remaining residue was purified by HPLC to afford Example 6. The TFA salt was neutralized by passing a methanolic solution of the compound through a bicarbonate resin. ¹H NMR (400 MHz, MeOD) δ 8.88 (s, 1H), 8.62 (s, 1H), 8.56 (d, J=2.6 Hz, 1H), 7.85 (dd, J=2.6, 8.8 Hz, 1H), 7.75 (d, J=8.3 Hz, 2H), 7.70 (dd, J=0.7, 1.7 Hz, 1H), 7.63 (d, J=8.8 Hz, 1H), 7.47 (d, J=8.3 Hz, 2H), 7.24 (dd, J=0.7, 3.5 Hz, 1H), 6.59 (dd, J=1.8, 3.5 Hz, 1H), 4.03 (dd, J=3.3, 13.0 Hz, 2H), 3.74 (t, J=11.7 Hz, 2H), 3.53 (d, J=12.6 Hz, 2H), 3.45-3.35 (m, 2H), 3.19-3.06 (m, 4H). LCMS M/Z=528.1 (M+1). RT=1.29: Method B.

Syntheses of Examples 7 to 73

Examples 7 to 73 were synthesized from the intermediate I-2 in a protocol analogous to procedure described above using the corresponding boronic acid or boronic ester.

Example 74

N-(4-chloro-3-{6-ethenyl-1H-imidazo[4,5-b]pyridin-2-yl}phenyl)furan-2-carboxamide

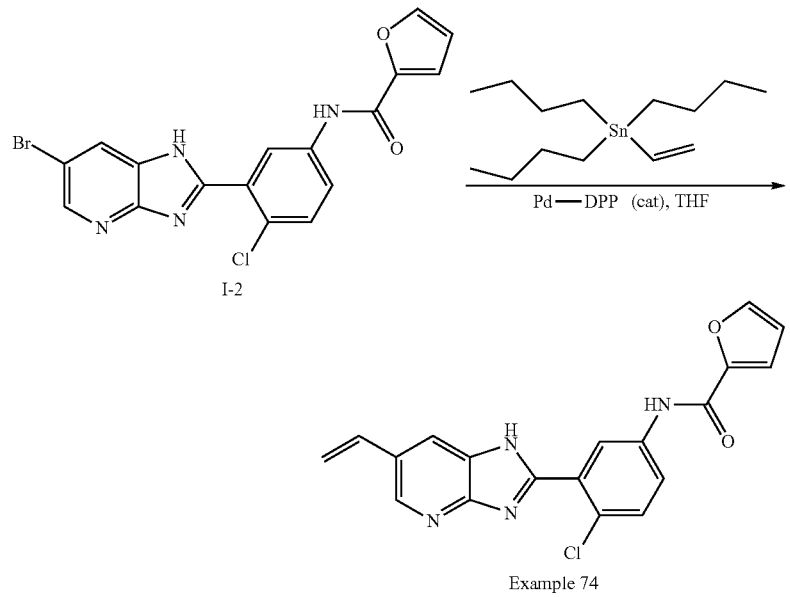

Example 74

To a solution of bromide I-2 (25 mg, 0.059 mmol, 1 eq.) in THF (0.3 mM) was added tributyl(vinyl)tin (46 mg, 0.147 mmol, 2.5 eq.) and Pd-DPP (Palladium diphenylphosphine supported on silica, silicycle) (0.26 mmol/g loading) (0.1 eq.). The vial was sealed and evacuated of air with vacuum and purged with nitrogen gas. The reaction vial was heated for 3 hours at 100° C. in the microwave. The reaction mixture was left to cool, quenched with ice cold sodium carbonate solution and extracted with ethyl acetate. The organics were combined, dried over MgSO4 and concentrated under reduced pressure. The remaining residue was purified by reverse phase HPLC to give Example 74. The TFA salt was neutralized by passing a methanolic solution of the compound through a bicarbonate resin. ¹H NMR (400 MHz, DMSO) δ 10.52 (s, 1H), 8.54 (s, 1H), 8.34 (s, 2H), 8.00 (d, J=2.4 Hz, 1H), 7.97 (s, 1H), 7.65 (d, J=8.8 Hz, 1H), 7.39 (d, J=3.5 Hz, 1H), 6.92 (dd, J=11.1, 17.7 Hz, 1H), 6.73 (dd, J=1.7, 3.4 Hz, 1H), 5.98 (d, J=17.7 Hz, 1H), 5.34 (d, J=11.0 Hz, 1H). LCMS M/Z=365.1 (M+1). RT=0.82: Method B.

Example 75

N-(4-chloro-3-{6-propyl-1H-imidazo[4,5-b]pyridin-2-yl}phenyl)furan-2-carboxamide

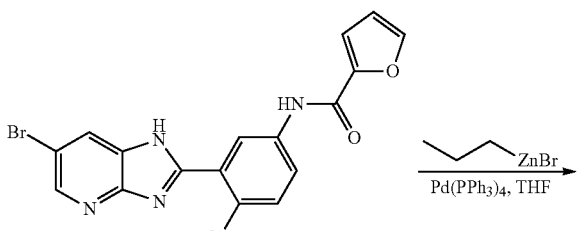

-continued

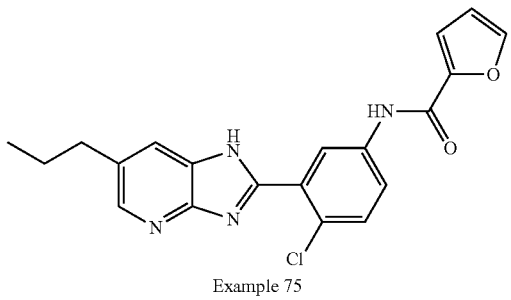

Example 75

To a solution of bromide I-2 (20 mg, 0.047 mmol, 1 eq.) in THF (0.3 mM) was added propylzinc(II) bromide (0.5M in THF) (0.238 ml, 0.119 mmol, 2.5 eq.) and Tetrakis(triphenylphosphine)palladium(0) (0.1 eq.). The vial was sealed and evacuated of air with vacuum and purged with nitrogen gas. The reaction vial was heated for 45 nm at 150° C. in the microwave. The reaction mixture was left to cool, quenched with water and extracted with ethyl acetate. The organics were combined, dried over MgSO$_4$ and concentrated under reduced pressure. The remaining residue was purified by reverse phase HPLC to give Example 75. The TFA salt was neutralized by passing a methanolic solution of the compound through a bicarbonate resin.

Syntheses of Examples 76 and 77

Examples 76 and 77 were synthesized in a protocol analogous to procedure described above using isobutyl and isopropyl zinc bromides, respectively.

Example 78

N-(4-chloro-3-{6-methyl-1H-imidazo[4,5-b]pyridin-2-yl}phenyl)-2-(2,3-difluorophenyl)acetamide

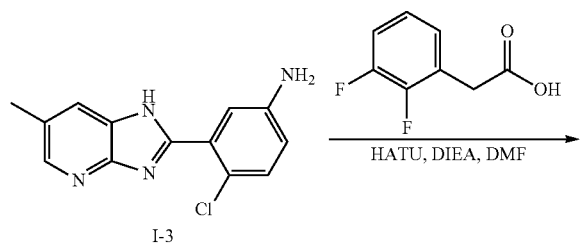

Example 78

To a solution of intermediate I-3 (30 mg, 0.115 mmol, 1 eq.) and 2-(2,3-difluorophenyl)acetic acid (20 mg, 0.115 mmol 1.1 eq.) in DMF solvent (0.3 mM) was added HATU (65 mg, 0.172 mmol, 1.5 eq.) and DIEA (0.050 ml, 0.287 mmol, 2.5 eq.). The resultant mixture was stirred at room temperature overnight. The mixture was then quenched with water and extracted twice with ethyl acetate. The organic extracts were combined, washed with saturated NaCl (aq), dried over MgSO$_4$(s), concentrated under reduced pressure and purified by reverse phase HPLC to afford the title compound 78. The TFA salt was neutralized by passing a methanolic solution of the compound through a bicarbonate resin. $^1$H NMR (400 MHz, DMSO) δ 10.61 (s, 1H), 8.18 (m, 2H), 8.05 7.68 (m, 2H), 7.61 (d, J=8.8 Hz, 1H), 7.41-7.29 (m, 1H), 7.28 7.08 (m, 2H), 3.85 (s, 2H), 2.44 (s, 3H). LCMS M/Z=413.1 (M+1). RT=1.51: Method B.

Syntheses of Examples 79 to 203

Examples 79 to 203 were synthesized from the intermediate I-3A in a protocol analogous to procedure described above using the corresponding carboxylic acid.

Example 204

N-(4-Chloro-3-{6-methyl-1H-imidazo[4,5-b]pyridin-2-yl}phenyl)cyclopentanecarboxamide Example 204

To a solution of intermediate I-3 (30 mg, 0.115 mmol, 1 eq.) in DMF was added DIEA (0.050 ml, 0.287 mmol, 2.5 eq.) followed by cyclopentanecarbonyl chloride (17 mg, 0.13 mmol, 1.1 eq.) The resultant mixture was stirred at room temperature overnight. The crude reaction mixture was purified by reverse phase HPLC to afford Example 204. The TFA salt was neutralized by passing a methanolic solution of the compound through a bicarbonate resin. $^1$H NMR (400 MHz, DMSO) δ 10.69 (s, 1H), 9.07 (d, J=1.7 Hz, 1H), 8.72 (dd, J=1.6, 4.8 Hz, 1H), 8.26 (m, 3H), 7.93 (dd, J=2.6, 8.8 Hz, 1H), 7.79 (s, 1H), 7.60 (d, J=8.8 Hz, 1H), 7.57 7.46 (m, 1H), 2.38 (s, 3H). LCMS M/Z=364.1 (M+1). RT=1.08: Method B.

Syntheses of Examples 205 to 213

Examples 205 to 213 were synthesized from the intermediate I-3 in a protocol analogous to procedure described above using the corresponding carbonyl chloride.

Example 214

2-Fluoroethyl N-(4-chloro-3-{6-methyl-1H-imidazo[4,5-b]pyridin-2-yl}phenyl)carbamate

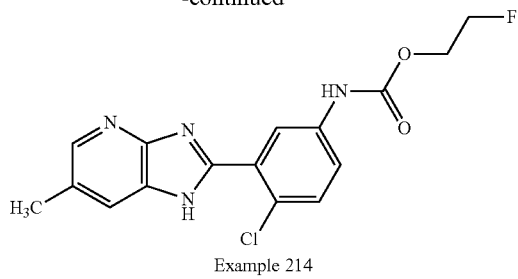

Example 214

To a solution of intermediate I-3 (30 mg, 0.12 mmol, 1 eq.) and DIEA (50.5 uL, 0.29 mmol, 2.5 eq.) in DMF solvent was added 2-Fluoroethyl choloroformate (1.1 eq.) and the resultant mixture was stirred at room temperature overnight. At completion of reaction, the mixture was quenched with methanol and the crude reaction mixture was purified by reverse phase HPLC. The TFA salt was neutralized by passing a methanolic solution of the compound through a bicarbonate resin. $^1$H NMR (400 MHz, DMSO) δ 10.14 (s, 1H), 8.19 (s, 1H), 7.93 (s, 1H), 7.78 (s, 1H), 7.58 (dd, J=2.6, 8.8 Hz, 1H), 7.51 (d, J=8.8 Hz, 1H), 4.74 4.45 (m, 2H), 4.45 4.17 (m, 2H), 2.37 (s, 3H). LCMS M/Z=349.0 (M+1). RT=1.27: Method B.

Syntheses of Examples 215 to 225

Examples 215 to 225 were synthesized from the intermediate I-3 in a protocol analogous to procedure described above using the corresponding chloroformate.

Example 226

1-(4-Chloro-3-{6-methyl-1H-imidazo[4,5-b]pyridin-2-yl}phenyl)-3-[2-(dimethylamino)ethyl]urea Step A: To a solution of 4-nitrophenylchloroformate (116 mg, 0.579 mmol, 1.5 eq.) in acetonitrile was added the intermediate I-3 (100 mg, 0.386 mmol, 1.0 eq.) and the resultant mixture was stirred at room temperature overnight. The solvent was removed under reduced pressure and the crude product was used for the next step.

Step B: To the activated carbamate (15 mg, 0.035 mmol, 1.0 eq.) dissolved in acetonitrile was added N1,N1-dimethylethane-1,2-diamine (8 mg, 0.088 mmol, 2.5 eq.). At completion of reaction, the mixture was quenched with methanol and the crude reaction mixture was purified by reverse phase HPLC. The TFA salt was neutralized by passing a methanolic solution of the compound through a bicarbonate resin. $^1$H NMR (400 MHz, MeOD) δ 8.20 (s, 1H), 8.08 (d, J=2.3 Hz, 1H), 7.89 (d, J=8.3 Hz, 1H), 7.80 (s, 1H), 7.51 (d, J=8.8 Hz, 1H), 7.20 (t, J=7.9 Hz, 1H), 7.06 (d, J=8.1 Hz, 1H), 7.00 (d, J=2.1 Hz, 1H), 6.68 (dd, J=2.2, 8.0 Hz, 1H), 3.30-3.23 (m, 6H), 2.43 (s, 3H), 2.02-1.88 (m, 4H). LCMS M/Z=373.1 (M+1). RT=1.02: Method B Syntheses of Examples 227 to 236

Examples 227 to 236 were synthesized in a similar fashion using appropriate amine.

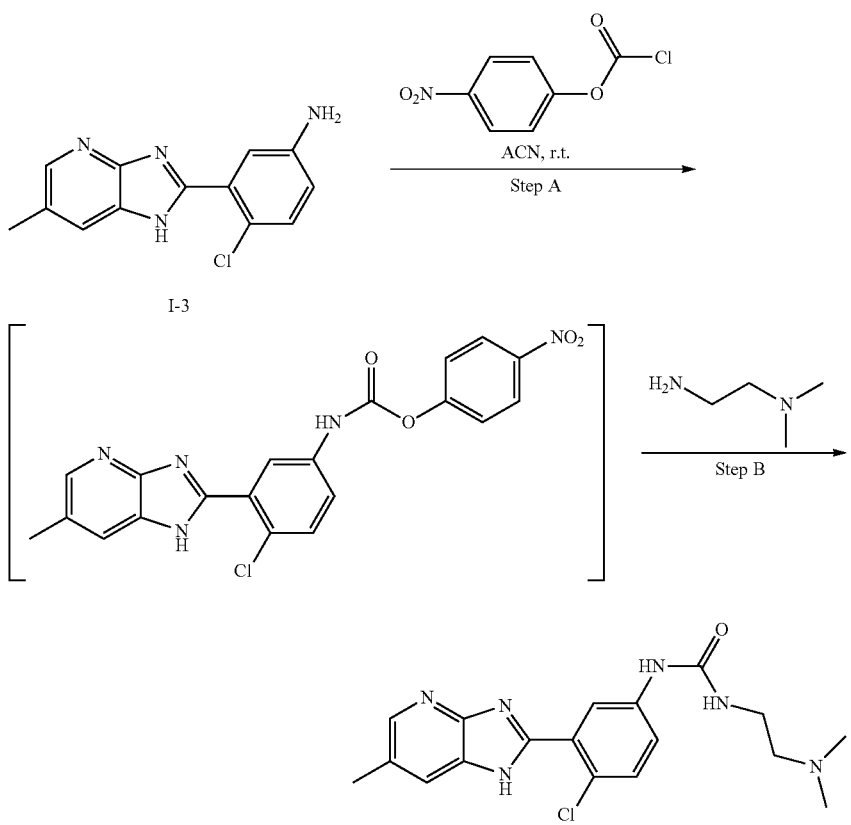

Example 226

Example 237

N-(4-chloro-3-{6-methyl-1H-imidazo[4,5-b]pyridin-2-yl}phenyl)morpholine-4-carboxamide

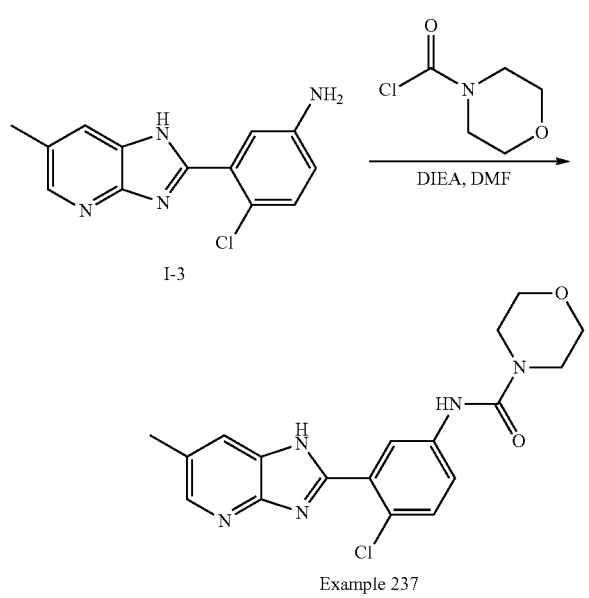

Example 237

To a solution of intermediate I-3 (30 mg, 0.115 mmol, 1 eq.) in DMF was added DIEA (0.050 ml, 0.287 mmol, 2.5 eq.) followed by morpholine-4-carbonyl chloride (17 mg, 0.13 mmol, 1.1 eq.) The resultant mixture was stirred at room temperature overnight. The crude reaction mixture was purified by reverse phase HPLC to afford Example 237. The TFA salt was neutralized by passing a methanolic solution of the compound through a bicarbonate resin. $^1$H NMR (400 MHz, DMSO) δ 8.81 (s, 1H), 8.14 (s, 1H), 7.99 (d, J=2.6 Hz, 1H), 7.73 (s, 1H), 7.63 (dd, J=2.6, 8.8 Hz, 1H), 7.42 (d, J=8.8 Hz, 1H), 3.59-3.48 (m, 4H), 3.43-3.34 (m, 4H), 2.36 (s, 3H). LCMS M/Z=372.1 (M+1). RT=1.17: Method B.

Syntheses of Examples 38 to 246

Examples 238 to 246 were synthesized in a similar fashion as 237 using the appropriate carbonyl chloride.

Example 247

1-(4-Chloro-3-{6-methyl-1H-imidazo[4,5-b]pyridin-2-yl}phenyl)-3-cyclobutylurea

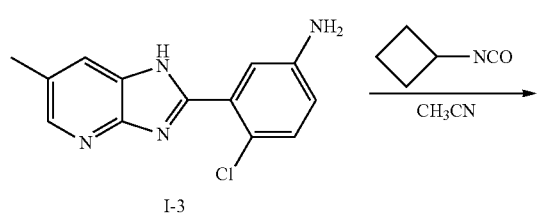

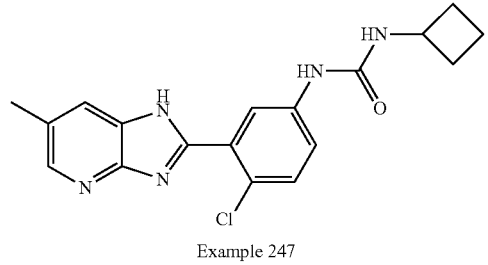

Example 247

To a solution of amine I-3 (30 mg, 0.12 mmol, 1 eq.) in dry acetonitrile was added isocyanatocyclobutane (1.5 eq.) and the resultant mixture was stirred at room temperature overnight. At completion of reaction, the mixture was quenched with methanol and the crude reaction mixture was purified by reverse phase HPLC. The TFA salt was neutralized by passing a methanolic solution of the compound through a bicarbonate resin. $^1$H NMR (400 MHz, MeOD) δ 8.29 (s, 1H), 7.89 (s, 1H), 7.83 (d, J=2.6 Hz, 1H), 7.62 (dd, J=2.5, 8.8 Hz, 1H), 7.48 (d, J=8.8 Hz, 1H), 2.53 (s, 3H), 2.37 2.27 (m, 2H), 2.00-1.86 (m, 2H), 1.77-1.64 (m, 2H). LCMS M/Z=356.1 (M+1). RT=1.31: Method B.

Syntheses of Examples 248 to 249

Examples 248 and 249 were synthesized in a similar fashion as 247 using the appropriate amine.

Example 250

N-(4-chloro-3-{6-methyl-1H-imidazo[4,5-b]pyridin-2-yl}phenyl)-1-phenylmethanesulfonamide

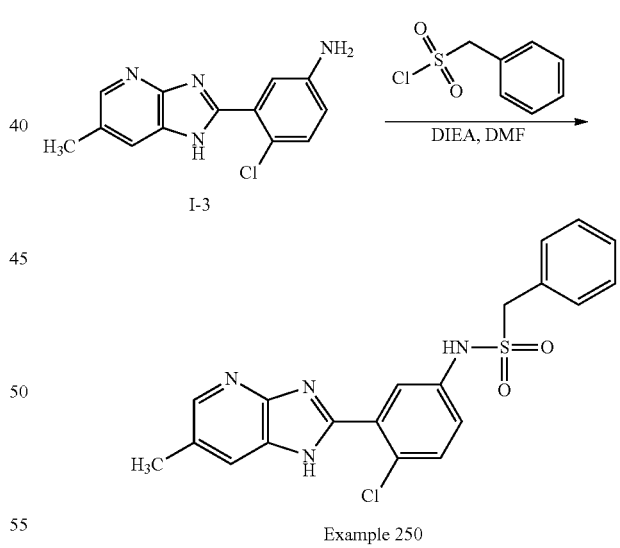

Example 250

To a solution of amine I-3 (30 mg, 0.12 mmol, 1 eq.) and DIEA (50.5 uL, 0.29 mmol, 2.5 eq.) in DMF solvent was added phenylmethanesulfonyl chloride (1.1 eq.) and the resultant mixture was stirred at room temperature overnight. At completion of reaction, the mixture was quenched with methanol and the crude reaction mixture was purified by reverse phase HPLC. The TFA salt was neutralized by passing a methanolic solution of the compound through a bicarbonate resin. $^1$H NMR (400 MHz, DMSO) δ 8.17 (s, 1H), 7.80 (s, 1H), 7.41 (s, 1H), 7.33 (d, J=8.7 Hz, 1H), 7.28-7.14 (m, 5H), 7.08 (d, J=6.4 Hz, 1H), 4.24 (s, 2H), 2.37 (s, 3H). LCMS M/Z=413.1 (M+1). RT=1.50: Method B.

Syntheses of Examples 251 to 255

Examples 251 to 255 were synthesized using the protocol described above using the appropriate sulfonyl chloride.

Example 256

4-chloro-N-(4-chlorophenyl)-3-{6-methyl-1H-imidazo[4,5-b]pyridin-2-yl}aniline

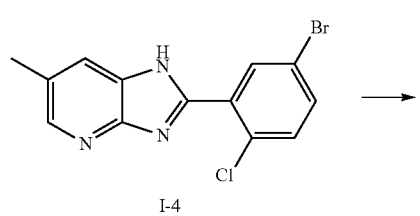

I-4

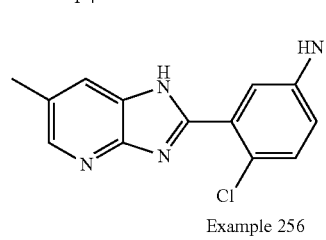

Example 256

To a solution of bromide I-4 (15 mg, 0.046 mmol, 1 eq.) and 4-chloroaniline DIEA (, 0.116 mmol, 2.5 eq.) in degassed tert-butanol was added potassium tert-butoxide (solution 1M in THF) (184 ul, 0.184 mmol, 4 eq.), BINAP (2.8 mg, 0.004 mmol, 0.1 eq) and Pd$_2$(dba)$_3$ (2.1 mg, 0.002 mmol, 0.05 eq). The resultant mixture was heated at 100° C. for 72 hrs. The reaction was filtered and the residue purified by reverse phase HPLC to afford Example 256. The TFA salt was neutralized by passing a methanolic solution of the compound through a bicarbonate resin. $^1$H NMR (400 MHz, DMSO) δ 8.65 (s, 1H), 8.23 (s, 1H), 7.82 (s, 1H), 7.51 (s, 1H), 7.47 (d, J=8.7 Hz, 1H), 7.31 (d, J=8.7 Hz, 2H), 7.20 (dd, J=2.8, 8.8 Hz, 1H), 7.14 (d, J=8.8 Hz, 2H), 2.43 (s, 3H). LCMS M/Z=369.1 (M+1). RT=1.67: Method B.

Synthesis of Example 257

Example 257 was synthesized using the protocol described above using morpholine as the amine.

Syntheses of Examples 258 to 261

Examples 258 to 261 were synthesized using a protocol analogous to the one described above using Chloro(2-dicyclohexylphosphino-2',4',6'-tri-1-propyl-1,1'-biphenyl)[2-(2-aminoethyl)phenyl]palladium(II) as catalyst.

Syntheses of Examples 262 to 263

Examples 262 and 263 were synthesized using 2-(Dicyclohexylphosphino)3,6-dimethoxy -2',4',6'-triisopropyl-1,1'-biphenyl ligand (Brettphos), Pd$_2$(dba)$_3$ as catalyst and Cs$_2$CO$_3$ as base.

Synthesis of Example 264

Example 264 was synthesized using Chloro(2-dicyclohexylphosphino-2',6'-dimethoxy-1,1'-biphenyl)[2-(2-aminoethylphenyl)]palladium (II) (Sphos Palladacycle)

Synthesis of Example 265

Example 265 was synthesized using 2 4,5-Bis(diphenylphosphino)-9,9-dimethylxanthene ligand (Xantphos), Pd$_2$(dba)$_3$ as catalyst and K$_3$PO$_4$ as base.

Example 266

4-chloro-N-(furan-2-ylmethyl)-3-{6-methyl-1H-imidazo[4,5-b]pyridin-2-yl}aniline

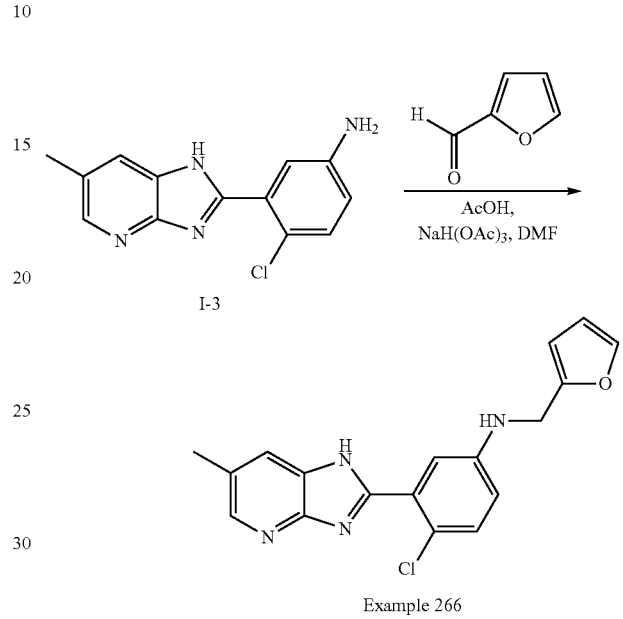

Example 266

To a solution of intermediate I-3 (30 mg, 0.12 mmol, 1 eq.) in DMF were added furan-2-carbaldehyde (12 mg, 0.13 mmol, 1.1 eq), acetic acid glacial (10 ul) and NaH(OAc)3 (35 mg, 0.16 mmol, 1.4 eq). The resultant mixture stirred overnight at room temperature. The reaction was quenched with water, extracted with ethyl acetate and the combined organics were dried over MgSO$_4$, concentrated under reduce pressure and purified by reverse phase HPLC to afford Example 266. The TFA salt was neutralized by passing a methanolic solution of the compound through a bicarbonate resin. MS M/Z=339.1 (M+1). RT=1.49: Method B.

Example 267

N-(4-Fluoro-3-(6-methyl-3H-imidazo[4,5-b]pyridin-2-yl)phenyl)furan-2-carboxamide

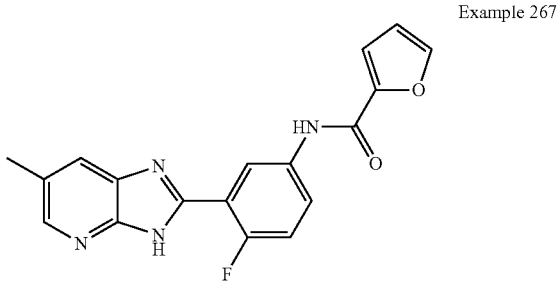 [SMILES: Cc1cnc2[nH]c(-c3cc(NC(=O)c4ccco4)ccc3F)nc2c1]

Example 267

Examples 267 to 275 were prepared using the same synthesis as Example 78, using 2-fluoro-5-nitrobenzoic acid instead of 2-chloro-5-nitrobenzoic acid, and the appropriate carboxylic acid in the last step.

Example 276

N-{4-Chloro-3-[6-(trifluoromethyl)-1H-imidazo[4,5-b]pyridin-2-yl]phenyl}furan-2-carboxamide

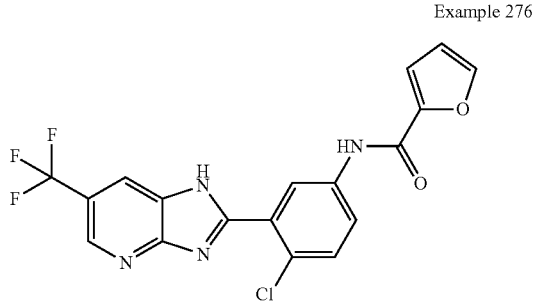 [SMILES: O=C(Nc1ccc(Cl)c(-c2nc3ncc(C(F)(F)F)cc3[nH]2)c1)c1ccco1]

Example 276

Example 276 was prepared from intermediate I-7 and furan-2-carboxylic acid using the same protocol described in Example 78. ¹H NMR (400 MHz, MeOD) δ 8.76 (d, J=1.5 Hz, 1H), 8.38 (d, J=1.8 Hz, 1H), 8.28 (d, J=2.6 Hz, 1H), 8.00 (dd, J=2.6, 8.8 Hz, 1H), 7.81-7.75 (m, 1H), 7.64 (d, J=8.8 Hz, 1H), 7.32 (d, J=3.5 Hz, 1H), 6.67 (dd, J=1.8, 3.5 Hz, 1H). LCMS M/Z=407.1 (M+1). RT=1.67: Method B Syntheses of Examples 277 to 285

Examples 277 to 285 were synthesized in a protocol analogous to procedure described above using the corresponding carboxylic acid.

Example 286

N-(4-chloro-3-{6-cyano-1H-imidazo[4,5-b]pyridin-2-yl}phenyl)furan-2-carboxamide

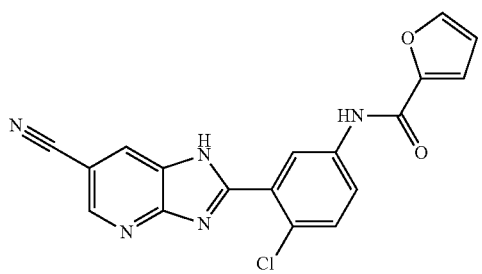

Example 286

Synthesis of Example 286

Example 286 was prepared from intermediate I-8 and furan-2-carboxylic acid using the same protocol described in Example 78. ¹H NMR (400 MHz, DMSO) δ 10.51 (s, 1H), 8.72 (s, 1H), 8.55 (s, 1H), 8.38 (d, J=2.6 Hz, 1H), 7.99 (d, J=2.5 Hz, 1H), 7.96 (s, 1H), 7.63 (d, J=8.8 Hz, 1H), 7.39 (d, J=3.4 Hz, 1H), 6.72 (dd, J=1.7, 3.4 Hz, 1H). LCMS M/Z=364.1 (M+1). RT=0.79: Method B.

Example 287

Propan-2-yl N-(4-chloro-3-{6-cyano-1H-imidazo[4,5-b]pyridin-2-yl}phenyl)carbamate

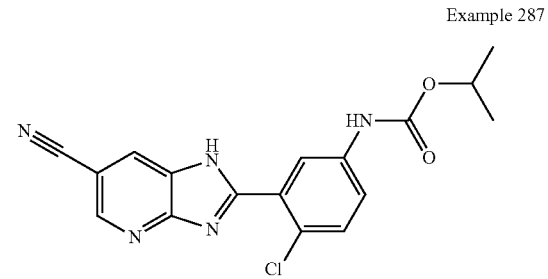 [SMILES: CC(C)OC(=O)Nc1ccc(Cl)c(-c2nc3ncc(C#N)cc3[nH]2)c1]

Example 287

Example 287 was prepared from intermediate I-8 and isopropryl chloroformate using the same protocol as in Example 214. ¹H NMR (400 MHz, DMSO) δ 9.89 (s, 1H), 8.66 (s, 1H), 8.47 (s, 1H), 8.06 (s, 1H), 7.61 (d, J=8.7, 1H), 7.52 (d, J=8.8, 1H), 4.96 4.83 (m, 1H), 1.26 (d, J=6.2, 6H). LCMS M/Z=356.1 (M+1). RT=2.93: Method A.

Syntheses of Examples 288 to 290

Examples 288 to 290 were synthesized in a protocol analogous to procedure described above using the corresponding alkyl chloroformate.

Example 291

N-(4-chloro-3-{6-phenyl-1H-imidazo[4,5-b]pyridin-2-yl}phenyl)pyrrolidine-1-carboxamide

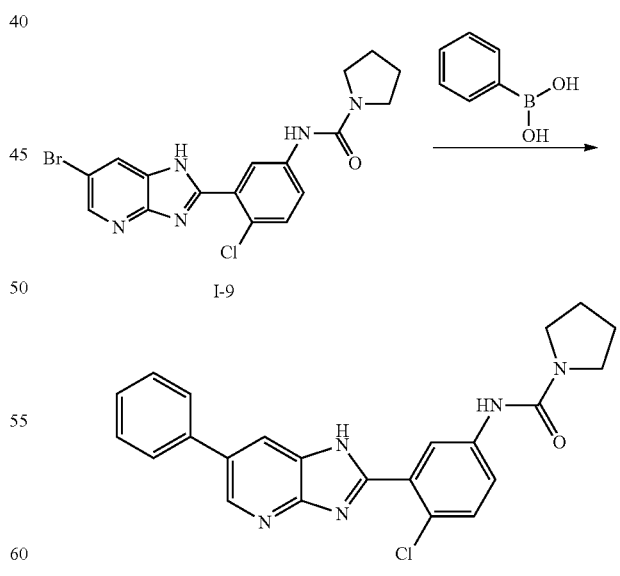

Example 291

Example 291 was prepared from intermediate I-9 and phenylboronic acid using the same protocol as in Example 6. NMR (400 MHz, DMSO) δ 8.72 (dd, J=2.0 Hz, 1H), 8.51 (d, 1H), 8.29 (dd, J=2.3 Hz, 1H), 8.12 (dd, J=2.4 Hz, 1H), 7.79

(m, 2H), 7.56-7.50 (m, 2H), 7.42 (m, 1H), 3.37 (s, 4H), 1.87 (s, 4H). LCMS M/Z=418.1 (M+1). RT=1.56: Method B.

Syntheses of Examples 292 to 308

Examples 292 to 308 were synthesized in a protocol analogous to procedure described above using the corresponding boronic acid or ester.

Example 309

N-(4-fluoro-3-{6-phenyl-1H-imidazo[4,5-b]pyridin-2-yl}phenyl)pyrrolidine-1-carboxamide

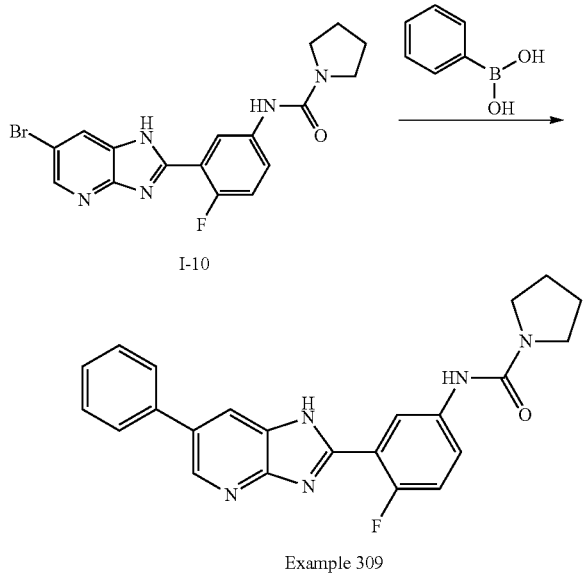

Example 309

Example 309 was prepared from intermediate I-10 and phenylboronic acid using the same protocol as in Example 6. ¹H NMR (300 MHz, CDCl₃): δ 8.69 (1H, s), 8.19 (1H, s), 8.09 (1H, dd, J=3.5, 8.3 Hz), 8.07 (1H, m), 7.66 (2H, d, J=6.9 Hz), 7.52 (2H, t, J=7.2 Hz), 7.43 (1H, m), 7.16 (1H, dd, J=9.0, 10.8 Hz), 6.60 (1H, s), 3.48 (4H, t, J=6.6 Hz), 1.99 (4H, t, J=6.3 Hz); LCMS M/Z=402.1 (M+1). RT=3.25: Method A.

Syntheses of Examples 310 to 332

Examples 310 to 332 were synthesized in a protocol analogous to procedure described above using the corresponding boronic acid or ester.

Example 333

Propan-2-yl N-(4-chloro-3-{6-phenyl-1H-imidazo[4,5-b]pyridin-2-yl}phenyl)carbamate

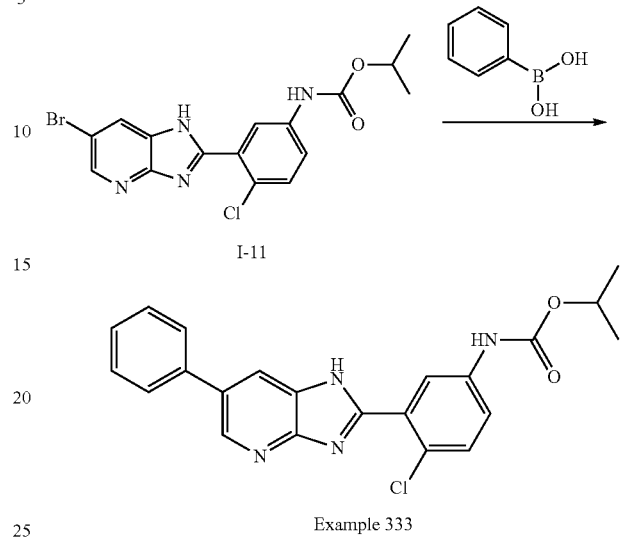

Example 333

Example 333 was prepared from intermediate I-11 and phenylboronic acid using the same protocol as in Example 6. ¹H NMR (400 MHz, DMSO) δ 9.96 (s, 1H), 8.70 (s, 1H), 8.26 (s, 1H), 8.05 (s, 1H), 7.81-7.76 (m, 2H), 7.65 (dd, J=2.6, 8.8 Hz, 1H), 7.58 (d, J=8.8 Hz, 1H), 7.53 (dd, J=4.8, 10.5 Hz, 2H), 7.41 (t, J=7.4 Hz, 1H), 5.00 4.82 (m, 1H), 1.28 (d, J=6.3 Hz, 6H). LCMS M/Z=407.1 (M+1). RT=3.49: Method A.

Syntheses of Examples 334 to 342

Examples 334 to 342 were synthesized in a protocol analogous to procedure described above using the corresponding boronic acid or ester.

Example 343

Methyl N-[4-(2-{2-chloro-5-[(3,3-difluoropyrrolidin-1-yl)carbonylamino]phenyl}-1H-imidazo[4,5-b]pyridin-6-yl)phenyl]carbamate

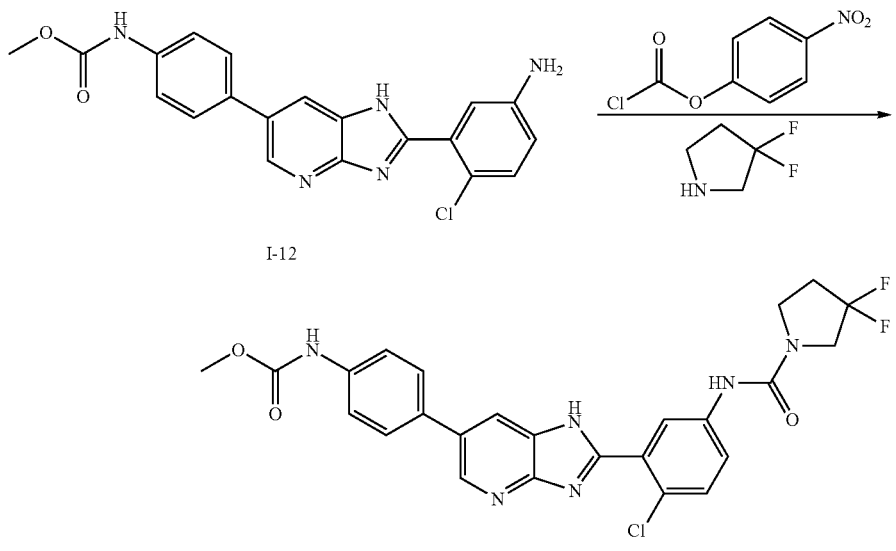

Example 343

Example 343 was prepared from intermediate I-12 and 3,3-difluoropyrrolidine using the same protocol as in Example 226.

Synthesis of Examples 344

Example 344 was synthesized in a protocol analogous to the procedure described above using azetidine.

Example 345

N-(4-chloro-3-{6-[4-(methylamino)phenyl]-1H-imidazo[4,5-b]pyridin-2-yl}phenyl)-4-methylthiophene-2-carboxamide

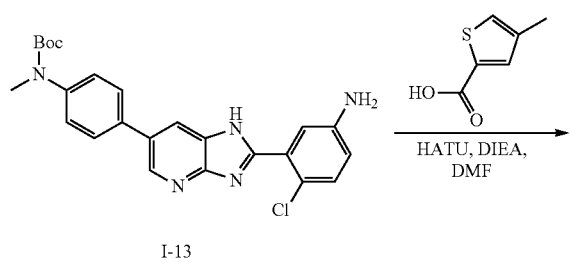

I-13

-continued

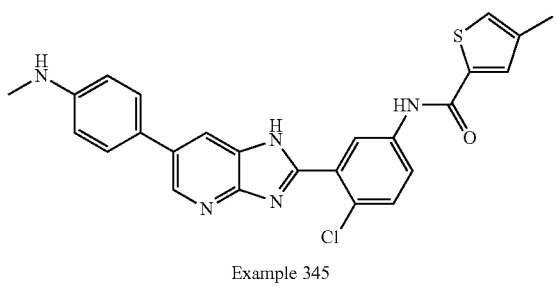

Example 345

Example 345 was prepared from intermediate I-13 and 4-methylthiophene-2-carboxylic acid using the same protocol as in Example 78. An additional treatment with a solution of TFA in DCM (2:8) for 1 hour, followed by evaporation of solvent, was necessary to afford Example 345. The TFA salt was neutralized by passing a methanolic solution of the compound through a bicarbonate resin. $^1$H NMR (400 MHz, DMSO) δ 10.43 (s, 1H), 8.57 (s, 1H), 8.29 (s, 1H), 7.93 (d, J=7.9 Hz, 2H), 7.84 (s, 1H), 7.59 (d, J=8.8 Hz, 1H), 7.53-7.29 (m, 3H), 6.60 (d, J=8.4 Hz, 2H), 5.80 (s, 1H), 2.66 (d, J=4.9 Hz, 3H), 2.21 (s, 3H). LCMS M/Z=474.1 (M+1). RT=1.33: Method B.

Syntheses of Examples 346 to 349

Examples 346 to 349 were synthesized in a protocol analogous to procedure described above using the corresponding carboxylic acid.

Example 350

2-Methoxyethyl N-(4-chloro-3-{6-[4-(methylamino)phenyl]-1H-imidazo[4,5-b]pyridin-2-yl}phenyl)carbamate

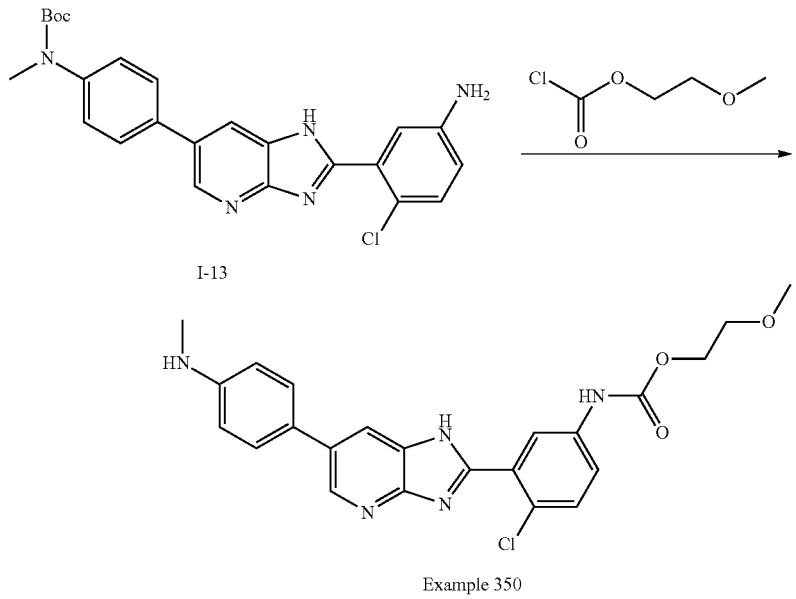

Example 350

Example 350 was prepared from intermediate I-13 and methoxyethyl chloroformate using the same protocol as in Example 214. An additional treatment with a solution of TFA in DCM (2:8) for 1 hour, followed by evaporation of solvent, was necessary to afford Example 350. The TFA salt was neutralized by passing a methanolic solution of the compound through a bicarbonate resin. $^1$H NMR (400 MHz, DMSO) δ 10.11 (s, 1H), 8.60 (s, 1H), 8.09 (s, 1H), 8.01 (s, 1H), 7.69 7.59 (m, 1H), 7.57 (d, J=8.8 Hz, 1H), 7.51 (d, J=8.6 Hz, 2H), 6.67 (d, J=8.6 Hz, 2H), 5.82 (d, J=5.2 Hz, 1H), 4.27 4.17 (m, 2H), 3.62-3.51 (m, 2H), 3.41 (s, 3H), 2.72 (d, J=4.9 Hz, 3H). LCMS M/Z=452.1 (M+1). RT=1.28: Method B.

Synthesis of Example 351

Example 351 was synthesized in a protocol analogous to the procedure described above using ethyl chloroformate.

Example 352

N-{3-[6-(aminomethyl)-1H-imidazo[4,5-b]pyridin-2-yl]-4-chlorophenyl}furan-2-carboxamide

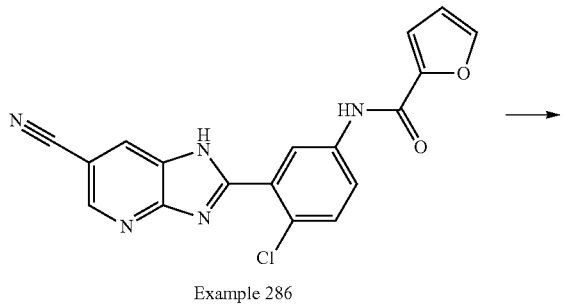

Example 286

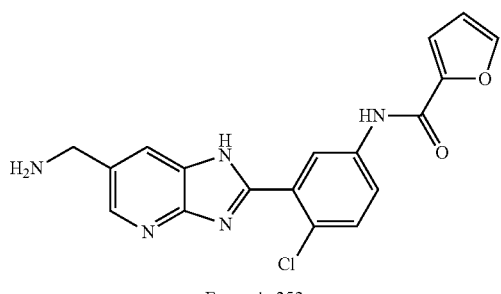

Example 352

To a solution of Example 286 (70 mg, 0.192 mmol, 1 eq.) in ethyl acetate was added 5% Pd/C (0.1 eq.) and the resultant mixture was hydrogenated (using a hydrogen balloon) at room temperature overnight. The reaction was filtered through Celite®, concentrated and purified by reverse phase HPLC to give Example 352. The TFA salt was neutralized by passing a methanolic solution of the compound through a bicarbonate resin. MS M/Z=370.1 (M+1).

Example 353

N-(3-(6-chloro-1H-imidazo[4,5-b]pyridin-2-yl)-4-fluorophenyl)pyrrolidine-1-carboxamide

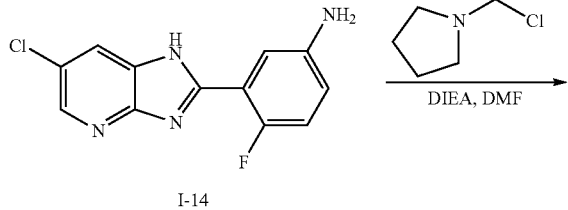

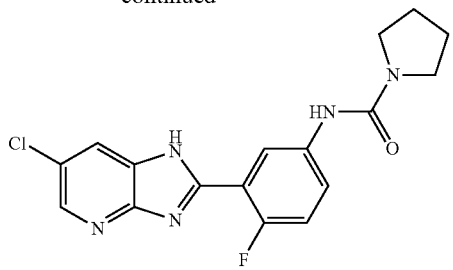

Example 353

Example 353 was prepared from intermediate I-14 and pyrrolidine-1-carbonyl chloride using the same protocol as Example 237. $^1$H NMR (300 MHz, MeOD): δ 8.46 (1H, d, J=7.8 Hz), 8.05-7.87 (3H, m), 7.41 (1H, dd, J=9.3, 10.5 Hz), 3.52 (4H, t, J=6.8 Hz), 2.01 (4H, t, J=6.0 Hz); MS M/Z=360.4 (M+1).

Syntheses of Examples 354 to 355

Examples 354 and 355 were synthesized in a protocol analogous to the procedure described above with dimethyl and diethyl carbamic chloride respectively.

Synthesis of Example 356

Example 356 was synthesized from intermediate I-14 in a protocol analogous to the procedure described for Example 248.

Example 357

N-(3-{6-chloro-1H-imidazo[4,5-b]pyridin-2-yl}-4-fluorophenyl)furan-2-carboxamide

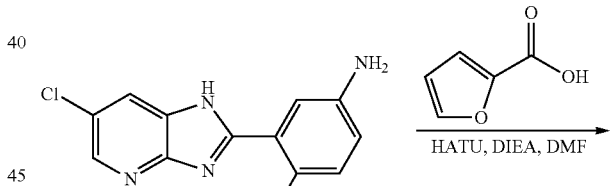

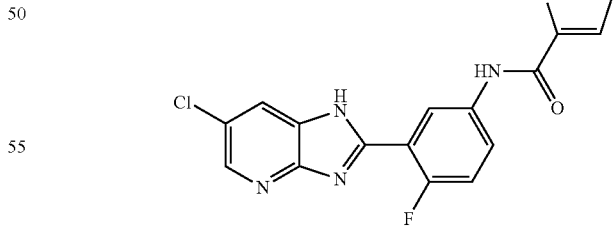

Example 357

Example 357 was prepared from intermediate I-14 and furan-2-carboxylic acid using the same protocol as in Example 78. $^1$H NMR (400 MHz, DMSO) δ 10.48 (s, 1H), 8.66 (s, 1H), 8.42 (s, 1H), 8.14 (s, 1H), 7.97 (s, 2H), 7.52 7.40 (m, 1H), 7.39 (d, J=3.3 Hz, 1H), 6.73 (dd, J=1.6, 3.2 Hz, 1H). MS M/Z=357.1 (M+1). RT=1.57: Method B.

Syntheses of Examples 358 to 359

Examples 358 and 359 were synthesized in a protocol analogous to the procedure described above with the appropriate carboxylic acid.

Example 360

N-(3-{6-bromo-3H-imidazo[4,5-b]pyridin-2-yl}-4-fluorophenyl)-2-oxoimidazolidine-1-carboxamide

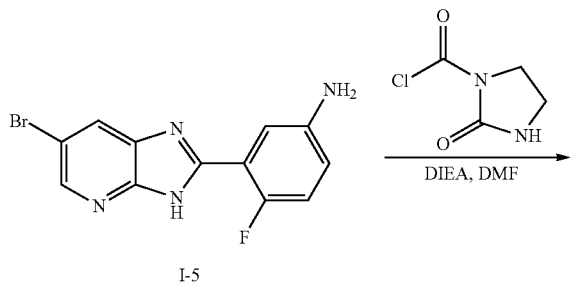

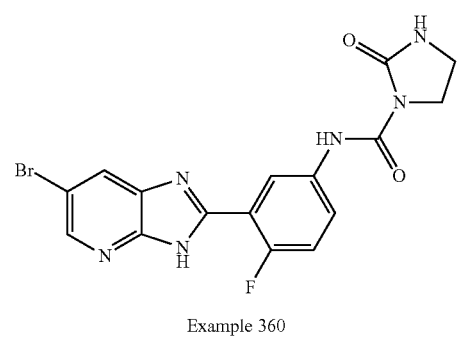

Example 360

Example 360 was prepared from intermediate I-5 and 2-oxoimidazolidine-1-carbonyl chloride using the same protocol as Example 237.

Syntheses of Examples 361 to 365

Examples 361 to 365 were synthesized in a protocol analogous to the procedure described above with the appropriate carbonyl chloride.

Example 366

N-(3-{6-bromo-3H-imidazo[4,5-b]pyridin-2-yl}-4-fluorophenyl)cyclopropanecarboxamide

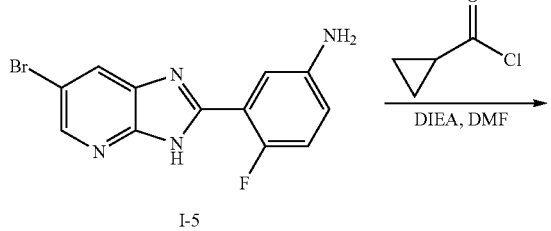

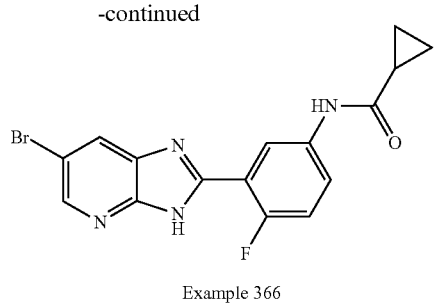

Example 366

Example 366 was prepared from intermediate I-5 and cyclopropanecarbonyl chloride using the same protocol as Example 204. $^1$H NMR (300 MHz, MeOD): δ 10.49 (1H, s), 8.50-8.4 (3H, m), 7.80 (1H, dd, J=1.8, 9.0 Hz), 7.42 (1H, dd, J=9.3, 10.8 Hz), 1.82 (1H, m), 0.86-0.74 (4H, m); MS M/Z=376.4 (M+1).

Synthesis of Example 367

Example 367 was synthesized in a protocol analogous to the procedure described above with cyclopentanecarbonyl chloride.

Syntheses of Examples 368 to 369

Examples 368 and 369 were prepared from intermediate I-5 and cyclopropanecarbonyl chloride using the same protocol as Example 78 with the appropriate carboxylic acid.

Example 370

Ethyl N-(3-{6-bromo-1H-imidazo[4,5-b]pyridin-2-yl}-4-chlorophenyl)carbamate

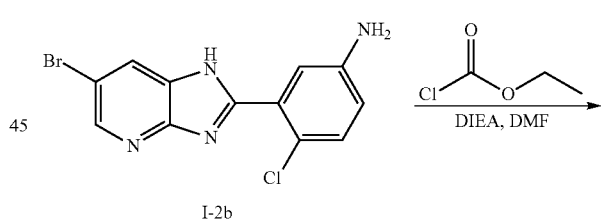

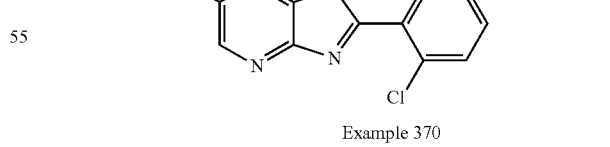

Example 370

Example 370 was prepared following a procedure analogous to Example 214 using I-2b and ethyl chloroformate. $^1$H NMR (400 MHz, DMSO) δ 10.00 (s, 1H), 8.48 (d, J=1.9 Hz, 1H), 8.33 (s, 1H), 8.00 (s, 1H), 7.65 (dd, J=2.5, 8.8 Hz, 1H), 7.57 (d, J=8.8 Hz, 1H), 4.15 (q, J=7.1 Hz, 2H), 1.25 (t, J=7.1 Hz, 3H). LCMS M/Z=394.9 (M+1). RT=1.64: Method B.

Synthesis of Example 371

Example 371 was synthesized using the protocol described above using 2-methoxyethyl chloroformate.

Example 372

N-(3-{6-bromo-1H-imidazo[4,5-b]pyridin-2-yl}-4-chlorophenyl)-5-[(dimethylamino)methyl]furan-2-carboxamide

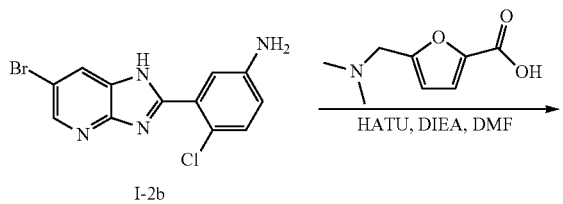

I-2b

-continued

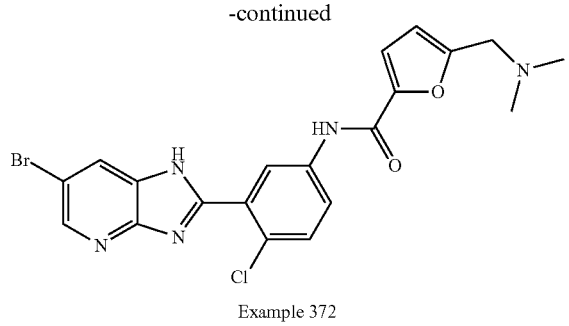

Example 372

Example 372 was prepared following a procedure analogous to Example 78 using I-2b and 5-((dimethylamino)methyl)furan-2-carboxylic acid. $^1$H NMR (400 MHz, DMSO) δ 10.42 (s, 1H), 8.49 (d, J=1.9 Hz, 1H), 8.33 (s, 2H), 8.01 (dd, J=2.6, 8.8 Hz, 1H), 7.65 (d, J=8.8 Hz, 1H), 7.36 (d, J=3.4 Hz, 1H), 6.53 (d, J=3.4 Hz, 1H), 3.52 (s, 2H), 2.19 (s, 6H). M/Z=474.0 (M+1). RT=1.33: Method B.

Synthesis of Example 373

Examples 373 was synthesized using the protocol described above using 5-fluorofuran-2-carboxylic acid.

Syntheses of Examples 374 to 375

Example 374 and 375 were prepared from intermediate I-2b and cyclopentylcarbonyl chloride and pyrazine-2-carbonyl chloride respectively, using the same protocol as Example 3-127.

Example 376

N-{4-chloro-3-[6-(2-oxo-2,3-dihydro-1H-indol-5-yl)-1H-imidazo[4,5-b]pyridin-2-yl]phenyl}pyrazine-2-carboxamide

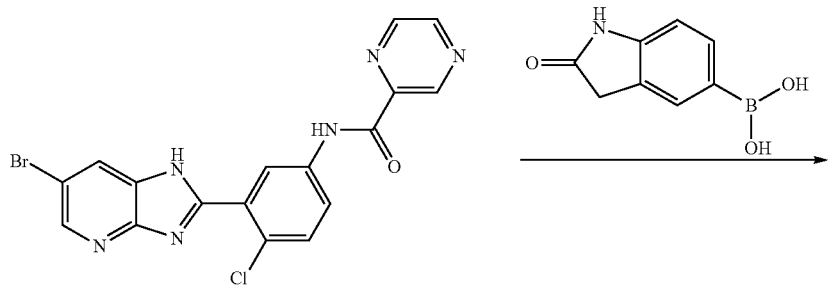

Example 375

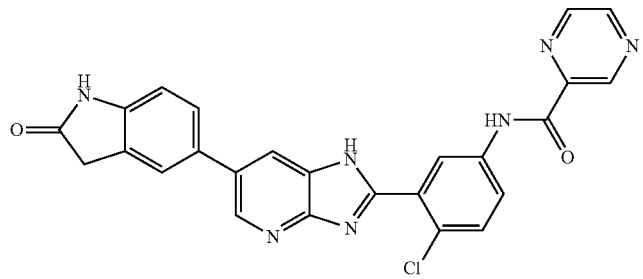

Example 376

Example 376 was prepared from Example 375 and (2-oxoindolin-5-yl)boronic acid using the same protocol as in Example 6. $^1$H NMR (400 MHz, DMSO) δ 11.02 (s, 1H), 10.41 (s, 1H), 9.25 (d, J=1.4 Hz, 1H), 8.89 (d, J=2.5 Hz, 1H), 8.84-8.71 (m, 1H), 8.50 (s, 2H), 8.00 (d, 2H), 7.66-7.53 (m, 2H), 7.49 (d, J=7.9 Hz, 1H), 6.87 (d, J=8.0 Hz, 1H), 3.50 (s, 2H). LCMS M/Z=482.1 (M+1). RT=1.38: Method B.

Syntheses of Examples 377, 378 and 379

Examples 377, 378 and 379 were synthesized in a protocol analogous to procedure described above starting from Examples 374, 370 and 371 respectively.

Example 380

N-(4-fluoro-3-{6-phenyl-1H-imidazo[4,5-b]pyridin-2-yl}phenyl)-5-methylfuran-2-carboxamide

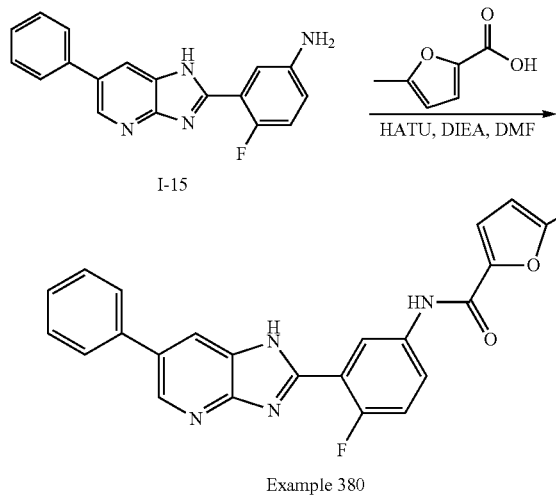

Example 380

Example 380 was prepared following a procedure analogous to Example 78 using I-15 and 5-methylfuran-2-carboxylic acid. $^1$H NMR (400 MHz, DMSO) δ 10.08 (s, 1H), 8.69 (s, 1H), 8.58-8.47 (m, 1H), 8.27 (s, 1H), 8.20-8.07 (m, 1H), 7.79 (d, J=7.9 Hz, 2H), 7.53 (s, 3H), 7.42 (s, 1H), 7.31 (s, 1H), 6.37 (s, 1H), 2.42 (s, 3H). LCMS M/Z=413.2 (M+1). RT=1.68: Method B.

Example 381

N-{4-fluoro-3-[6-(thiophen-3-yl)-1H-imidazo[4,5-b]pyridin-2-yl]phenyl}-5-methylfuran-2-carboxamide

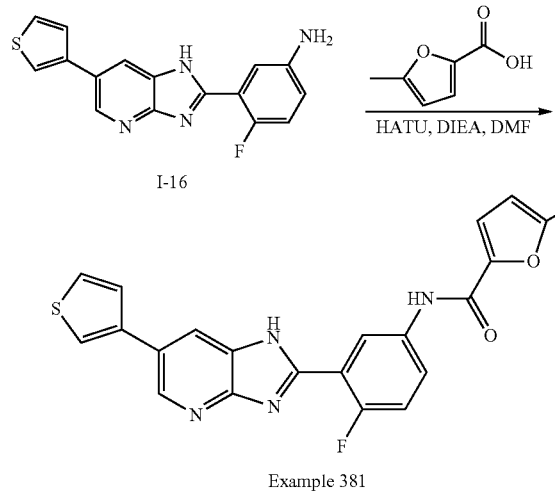

Example 381

Example 381 was prepared following a procedure analogous to Example 78 using I-16 and 5-methylfuran-2-carboxylic acid. $^1$H NMR (400 MHz, DMSO) δ 10.03-9.92 (m, 1H), 8.66-8.57 (m, 1H), 8.53-8.43 (m, 1H), 8.21-8.07 (m, 2H), 7.94-7.85 (m, 1H), 7.67 (s, 2H), 7.51-7.37 (m, 1H), 7.29 (s, 1H), 6.36 (s, 1H), 2.41 (s, 3H). LCMS M/Z=419.1 (M+1). RT=1.65: Method B.

Example 382

N-(3-{5-chloro-3H-imidazo[4,5-b]pyridin-2-yl}-4-fluorophenyl)furan-2-carboxamide

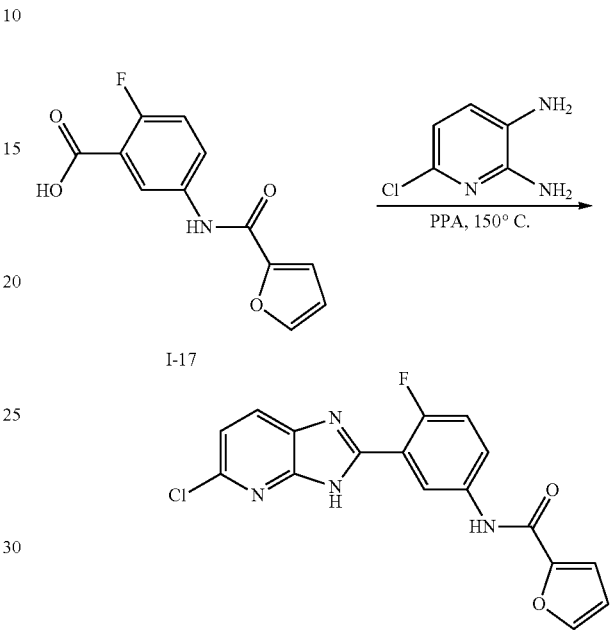

Example 382

Example 382 was prepared following a procedure analogous to Example 1 using I-17 and 6-chloropyridine-2,3-diamine. $^1$H NMR (300 MHz, MeOD): 8.75 (1H, m), 8.60 (1H, dd, J=3.0, 6.3 Hz), 8.47 (1H, d, J=8.4 Hz), 8.13 (1H, d, J=1.5 Hz) 7.88-7.76 (3H, m), 7.09 (1H, dd, J=1.8, 3.4 Hz); LCMS M/Z=357.6 (M+1).

Syntheses of Examples 383 to 384

Examples 383 and 384 were synthesized using the protocol described above using 5-fluoropyridine-2,3-diamine and 4,5-dichloropyridine-2,3-diamine respectively.

Example 385

N-{3-[6-bromo-3-(methoxymethyl)-3H-imidazo[4,5-b]pyridin-2-yl]-4-chlorophenyl}pyrrolidine-1-carboxamide

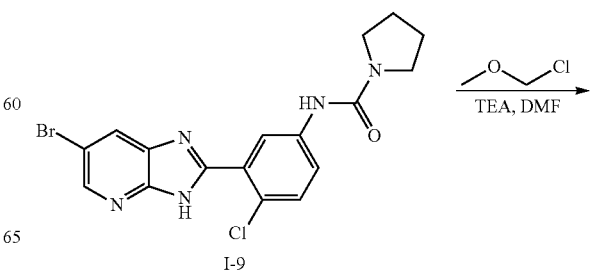

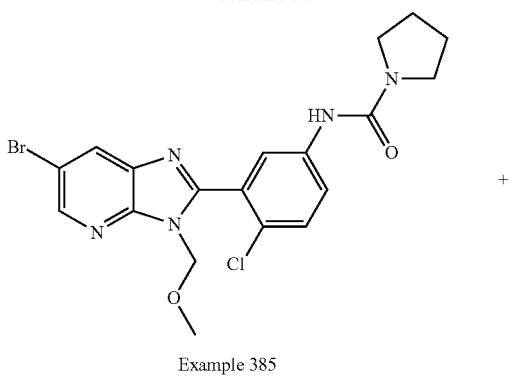

Example 385

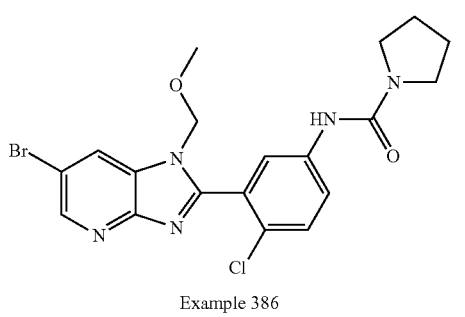

Example 386

To a solution of amine I-9 (20 mg, 0.047 mmol, 1 eq.) and TEA (20 uL, 0.14 mmol, 3 eq.) in DMF was added chloro-(methoxy)methane (1 eq.) and the resultant mixture was stirred at room temperature overnight. At completion of reaction, the mixture was quenched with methanol and the crude reaction mixture was purified by reverse phase HPLC leading to 385 (less polar) and 386 (more polar).

The structure of example 385 was confirmed by proton NMR, carbon NMR, COSY, ROESY, HMQC and HMBC studies. Example 385: $^1$H NMR (400 MHz, DMSO) δ 8.58 (d, J=2.1 Hz, 1H), 8.51 (d, J=2.1 Hz, 1H), 8.48 (s, 1H), 7.87 (d, J=2.7 Hz, 1H), 7.78 (dd, J=2.6, 8.9 Hz, 1H), 7.54 (d, J=8.8 Hz, 1H), 5.48 (s, 2H), 3.40 3.31 (m, 4H), 3.10 (s, 3H), 1.89-1.77 (m, 4H). M/Z=464.0 (M+1). RT=3.13: Method A. Example 386: $^1$H NMR (400 MHz, DMSO) δ 8.60 (d, J=2.2 Hz, 1H), 8.55 (d, J=2.2 Hz, 1H), 8.48 (s, 1H), 7.87 (d, J=2.7 Hz, 1H), 7.78 (dd, J=2.7, 8.8 Hz, 1H), 7.54 (d, J=8.9 Hz, 1H), 5.48 (s, 2H), 3.39-3.30 (m, 4H), 3.06 (s, 3H), 1.92-1.81 (m, 4H). LCMS M/Z=464.0 (M+1). RT=2.94: Method A.

Examples 387 and 388 were synthesized using the protocol described above with the appropriate alkyl chloride.

Example 389

3-[4-Fluoro-3-(6-{4-[2-(morpholin-4-yl)ethyl]phenyl}-[3]oxazolo[4,5-b]pyridin-2-yl)phenyl]-1-[4-(trifluoromethyl)phenyl]urea

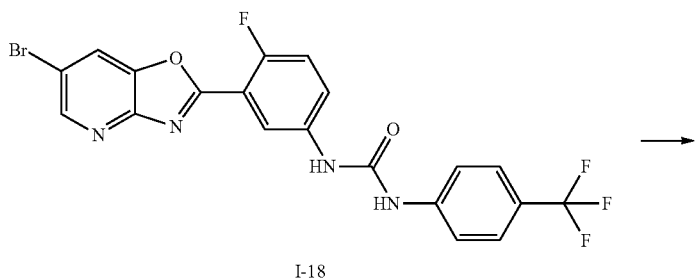

I-18

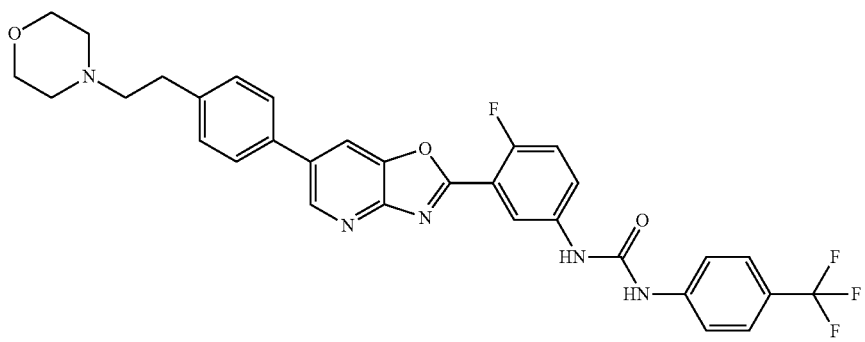

Example 389

Example 389 was synthesized by Suzuki coupling of I-18 with (4-(2-morpholinoethyl)phenyl) boronic acid using a protocol similar to one described in the synthesis of Example 6. $^1$H NMR (400 MHz, MeOD) δ 8.73 (d, J=2.0 Hz, 1H), 8.37 (dd, J=2.8, 6.2 Hz, 1H), 8.31 (d, J=2.0 Hz, 1H), 7.71-7.65 (m, 1H), 7.63-7.56 (m, 4H), 7.50 (d, J=8.6 Hz, 2H), 7.32 (d, J=8.2 Hz, 2H), 7.26 (dd, J=9.1, 10.4 Hz, 1H), 3.66-3.61 (m, 4H), 2.81 (dd, J=6.6, 9.6 Hz, 2H), 2.57 (dd, J=6.7, 9.6 Hz, 2H), 2.49 (s, 4H). LCMS M/Z=606.2 (M+1). RT=1.82: Method B.

Syntheses of Examples 390 to 403

Examples 390 to 403 were synthesized in a protocol analogous to procedure described above using the corresponding boronic acids or esters.

Example 404

N-(3-{6-bromo-[1,3]oxazolo[4,5-b]pyridin-2-yl}-4-fluorophenyl)-5-ethyl-1,3,4-oxadiazole-2-carboxamide

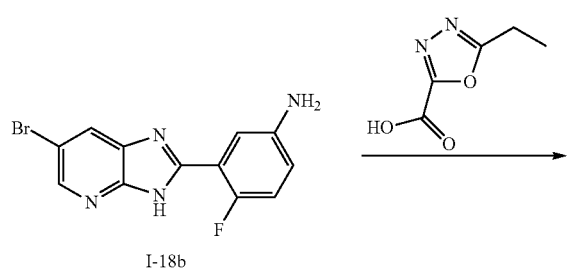

I-18b

Example 404

Example 404 was synthesized by amide coupling of I-18b with 5-ethyl-1,3,4-oxadiazole-2-carboxylic acid using a protocol similar to one described in the synthesis of Example 78. $^1$H NMR (400 MHz, MeOD) δ 8.76 (dd, J=2.7, 6.3 Hz, 1H), 8.69 (d, J=2.0 Hz, 1H), 8.49 (d, J=2.0 Hz, 1H), 8.11-8.04 (m, 1H), 7.45 (dd, J=9.2, 10.3 Hz, 1H), 3.05 (q, J=7.6 Hz, 2H), 1.45 (t, J=7.6 Hz, 3H). M/Z=432.0 (M+1). RT=1.79: Method B.

Syntheses of Examples 405 to 410

Examples 405 to 410 were synthesized in a protocol analogous to procedure described above using the corresponding carboxylic acid.

Example 411

N-{4-fluoro-3-[6-(4-fluorophenyl)-[1,3]oxazolo[4,5-b]pyridin-2-yl]phenyl}furan-2-carboxamide

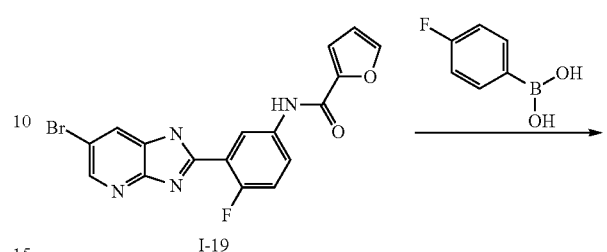

I-19

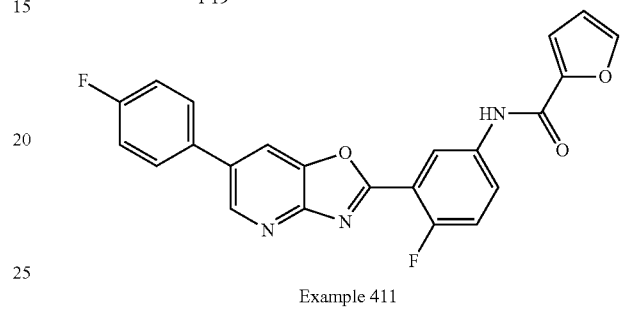

Example 411

Example 411 was synthesized by Suzuki coupling of I-19 with ((4-fluorophenyl)boronic acid using a protocol similar to one described in the synthesis of Example 6. $^1$H NMR (300 MHz, CDCl$_3$): δ 8.86 (1H, s), 8.48 (1H, dd, J=2.7, 4.8 Hz), 8.36 (1H, s), 8.12-8.10 (1H, m), 8.09 (1H, d, J=1.3 Hz) 7.64-7.60 (3H, m), 7.50-7.45 (4H, m), 6.0 (1H, dd, J=1.2, 2.8 Hz); MS M/Z=418.5 (M+1).

Syntheses of Examples 412 to 414

Examples 412 to 414 were synthesized in a protocol analogous to procedure described above using the corresponding boronic acid or ester.

Example 415

N-(4-fluoro-3-{6-phenyl-[1,3]oxazolo[4,5-b]pyridin-2-yl}phenyl)pyrrolidine-1-carboxamide

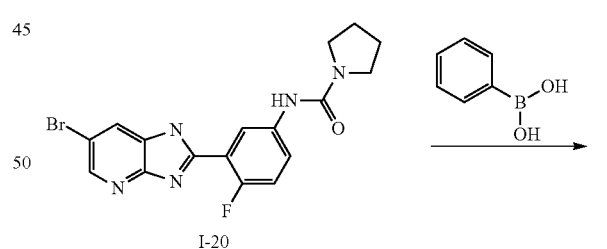

I-20

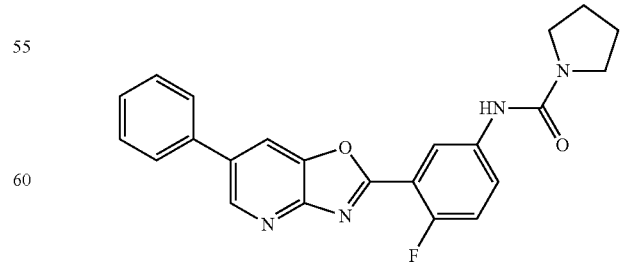

Example 415

Examples 415 was synthesized by Suzuki coupling of I-20 with phenylboronic acid using a protocol similar to one described in the synthesis of Example 6. ¹H NMR (400 MHz, DMSO) δ 8.85 (d, J=1.9 Hz, 1H), 8.54 (d, J=1.9 Hz, 1H), 8.52 8.42 (m, 2H), 7.87-7.73 (m, 3H), 7.48 (t, J=7.5 Hz, 2H), 7.43 7.27 (m, 2H), 3.34 (t, J=6.4 Hz, 4H), 1.81 (s, 4H). LCMS M/Z=403.14 (M+1). RT=1.89: Method B.

Example 416

N-(4-chloro-3-{6-phenyl-[1,3]oxazolo[4,5-b]pyridin-2-yl}phenyl)-furan-2-carboxamide

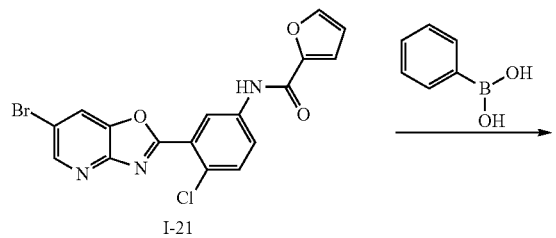

I-21

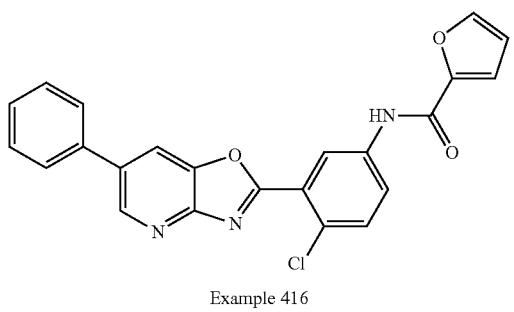

Example 416

Synthesis of Example 416

Example 416 was synthesized by Suzuki coupling of I-21 with phenylboronic acid using a protocol similar to one described in the synthesis of Example 6.

Synthesis of Example 417

Example 417 were synthesized in a protocol analogous to procedure described above using (4-((methoxycarbonyl)amino)phenyl)boronic acid.

Example 418

N-(4-chloro-3-{6-methyl-[1,3]oxazolo[4,5-b]pyridin-2-yl}phenyl)-furan-2-carboxamide

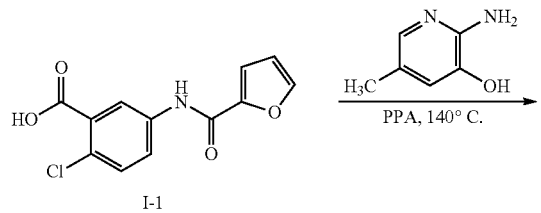

I-1

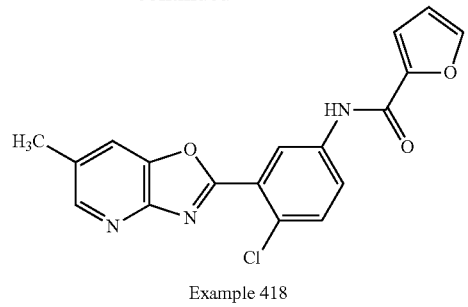

Example 418

Example 418 was synthesized using I-1 and 2-amino-3-hydroxy-5-methylpyridine using a protocol used in the synthesis of Example 1. ¹H NMR (400 MHz, MeOD) δ 8.63 (d, J=2.6 Hz, 1H), 8.45 (d, J=1.1 Hz, 1H), 8.05 (t, J=4.0 Hz, 1H), 8.00 (dt, J=3.4, 10.1 Hz, 1H), 7.81-7.76 (m, 1H), 7.64 (d, J=8.8 Hz, 1H), 7.33 (d, J=3.5 Hz, 1H), 6.68 (dd, J=1.8, 3.5 Hz, 1H), 2.57 (s, 3H). LCMS M/Z=354.0 (M+1). RT=1.76: Method B.

Example 419

N-(4-chloro-3-{6-ethyl-[1,3]oxazolo[4,5-b]pyridin-2-yl}phenyl)-furan-2-carboxamide

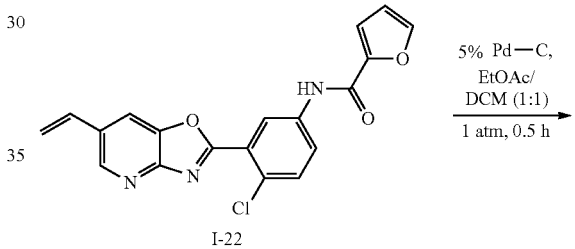

I-22

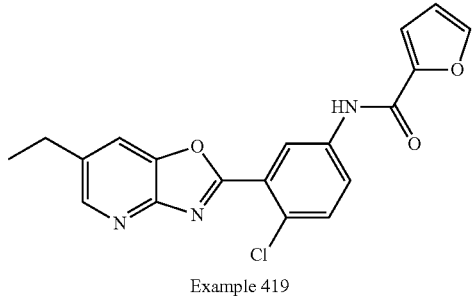

Example 419

N-(4-chloro-3-(6-vinyloxazolo[4,5-b]pyridin-2-yl)phenyl)-furan-2-carboxamide (I-22) was dissolved in EtOAc/dichloromethane (1:1; 12 ml). To the solution, catalytic amount of 5 wt % Pd—C was added. The reaction was stirred under hydrogen atmosphere for 30 minutes. LCMS indicated that the reaction was complete with a formation of new peak of desired mass 368.1 (M+1). The reaction was filtered to remove palladium on carbon and the filterate wasn concentrated under reduced pressure. The crude product was purified by column chromatography to yield the desired product N-(4-chloro-3-(6-ethyloxazolo[4,5-b]pyridin-2-yl)phenyl)furan-2-carboxamide (Example 419). ¹H NMR (400 MHz, DMSO) δ 10.63 (s, 1H), 8.73 (d, J=2.6 Hz, 1H), 8.51 (d, J=1.8 Hz, 1H), 8.21 (d, J=1.5 Hz, 1H), 8.12-8.03 (m, 1H), 8.00 (dd, J=6.3, 7.0 Hz, 1H), 7.74 (t, J=10.6 Hz, 1H), 7.46-7.38 (m, 1H), 6.75 (dd, J=1.7, 3.5 Hz, 1H), 2.83 (q, J=7.6, 2H), 1.34-1.22 (m, 3H). LCMS M/Z=368.1 (M+1). RT=3.20: Method A.

Example 420

4-Fluoro-N,N-dimethyl-3-(6-{4-[2-(morpholin-4-yl)ethoxy]phenyl}-[1,3]oxazolo[4,5-b]pyridin-2-yl)aniline

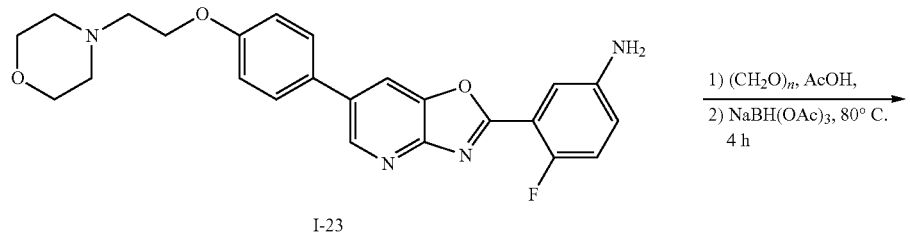

I-23

1) (CH$_2$O)$_n$, AcOH,
2) NaBH(OAc)$_3$, 80° C.
4 h

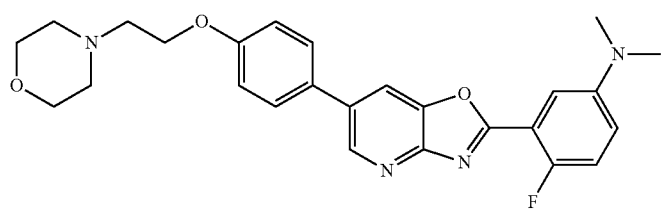

Example 420

In a 40 ml vial, 4-fluoro-3-(6-(4-(2-morpholinoethoxy)phenyl)oxazolo[4,5-b]pyridin-2-yl)aniline I-23 (15 mg, 0.032 mmol, 1.0 eq.) was dissolved in AcOH. Paraformadelhyde (30 mg) was added and reaction was heated for one hour. Sodium triacetoxy borohydride (16 mg, 0.08 mmol, 2.5 eq) was added and the reaction was heated to 80° C. for 4 hours. LCMS indicated that the reaction was complete with a formation of new peak of desired mass 463.2 (M+1). The reaction was concentrated under reduced pressure. The crude reaction was dissolved in DMF and filtered through a frit funnel to remove the insoluble matter. The clear filtrate by purified by HPLC to get the desired 4-fluoro-N,N-dimethyl-3-(6-(4-(2-morpholinoethoxy)phenyl)oxazolo[4,5-b]pyridin-2-yl)aniline (Example 420). The TFA salt was neutralized by passing a methanolic solution of the compound through a bicarbonate resin. M/Z=463.2 (M+1). RT=1.35: Method B.

Example 421

4-Fluoro-N-methyl-3-(6-{4-[2-(morpholin-4-yl)ethoxy]phenyl}-[1,3]oxazolo[4,5-b]pyridin-2-yl)aniline

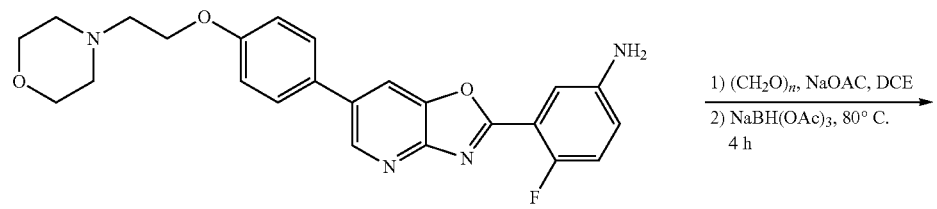

I-23

1) (CH$_2$O)$_n$, NaOAC, DCE
2) NaBH(OAc)$_3$, 80° C.
4 h

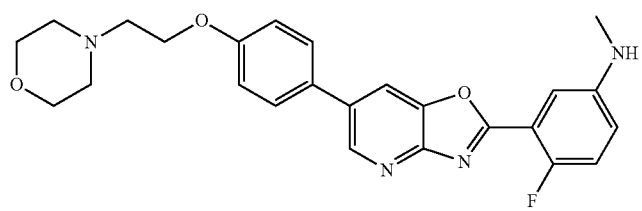

Example 421

In a 40 ml vial 4-fluoro-3-(6-(4-(2-morpholinoethoxy) phenyl)oxazolo[4,5-b]pyridin-2-yl)aniline I-23 (15 mg, 0.032 mmol, 1.0 eq.) was dissolved in DCE. Paraformaldehyde (30 mg) followed by sodium acetate (2.62 mg, 0.032 mmol, 1.0 eq) was added and reaction was heated for one hour. Sodium triacetoxy borohydride (16 mg, 0.08 mmol, 2.5 eq) was added and the reaction was heated to 80° C. for 4 hours. LCMS indicated that the reaction was complete with a formation of new peak of desired mass 449.2 (M+1). The reaction was concentrated under reduced pressure. The crude reaction was dissolved in DMF and filtered through a frit funnel to remove the insoluble matter. The clear filtrate by purified by HPLC to get the desired product 4-fluoro-N-methyl-3-(6-(4-(2-morpholinoethoxy)phenyl)oxazolo[4,5-b]pyridin-2-yl)aniline (Example 421). The TFA salt was neutralized by passing a methanolic solution of the compound through a bicarbonate resin. MS M/Z=449.2 (M+1). RT=1.33: Method B.

TABLE II

Listing of the Exemplified Compounds of the Invention

| Ex. No. | Structure | $^1$H NMR and/or mass and/or (retention time (mins)) |
|---|---|---|
| 1 | 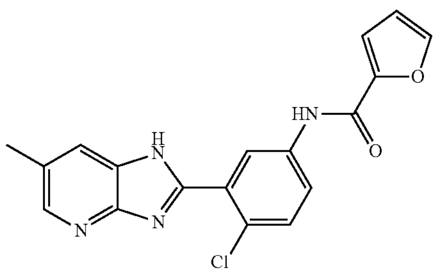 [SMILES: Cc1cnc2nc(-c3cc(NC(=O)c4ccco4)ccc3Cl)[nH]c2c1] | $^1$H NMR (400 MHz, MeOD) δ 8.36-8.25 (m, 1H), 8.20 (s, 1H), 8.04-7.94 (m, 1H), 7.93-7.83 (m, 1H), 7.77 (s, 1H), 7.61 (d, J = 8.8, 1H), 7.31 (d, J = 3.5, 1H), 6.67 (dd, J = 1.7, 3.5, 1H), 2.53 (s, 3H). M/Z = 353.0 (M + 1). RT = 1.39: Method B. |
| 2 | 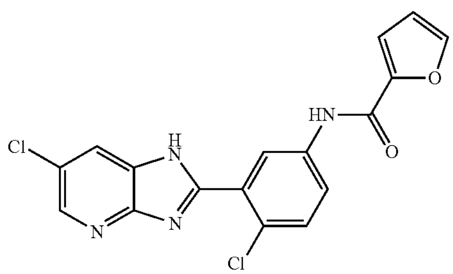 [SMILES: O=C(Nc1ccc(Cl)c(-c2nc3ncc(Cl)cc3[nH]2)c1)c1ccco1] | $^1$H NMR (400 MHz, MeOD) δ 8.43 (d, J = 2.2, 1H), 8.24 (d, J = 2.6, 1H), 8.11 (d, J = 2.2, 1H), 7.97 (dd, J = 2.6, 8.8, 1H), 7.77 (d, J = 1.2, 1H), 7.61 (d, J = 8.8, 1H), 7.33-7.29 (m, 1H), 6.66 (dd, J = 1.8, 3.5, 1H). M/Z = 373.0 (M + 1). RT = 1.61: Method B. |
| 3 | 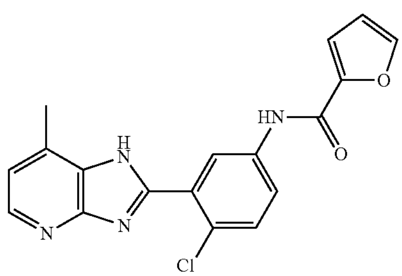 [SMILES: Cc1ccnc2nc(-c3cc(NC(=O)c4ccco4)ccc3Cl)[nH]c12] | M/Z = 353.1 (M + 1). RT = 1.24: Method B. |
| 4 | 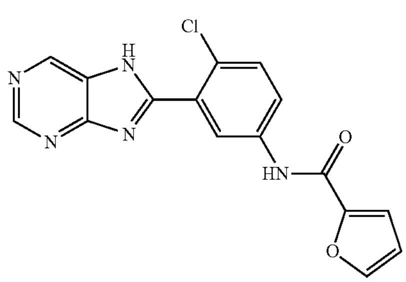 [SMILES: O=C(Nc1ccc(Cl)c(-c2nc3ncncc3[nH]2)c1)c1ccco1] | M/Z = 340.0 (M + 1). RT = 1.26: Method B. |

TABLE II-continued

Listing of the Exemplified Compounds of the Invention

| Ex. No. | Structure | ¹H NMR and/or mass and/or (retention time (mins)) |
|---|---|---|
| 5 | 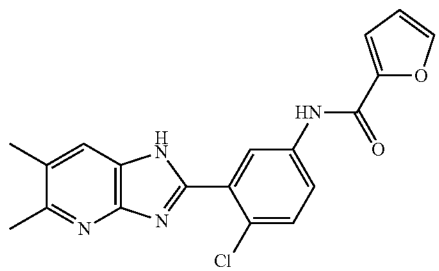 [SMILES: Cc1cc2[nH]c(-c3cc(NC(=O)c4ccco4)ccc3Cl)nc2nc1C] | M/Z = 367.0 (M + 1). RT = 0.66: Method B. |
| 6 | 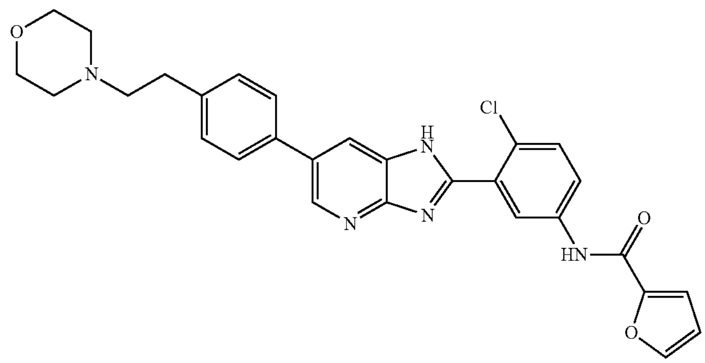 [SMILES: O=C(Nc1ccc(Cl)c(-c2nc3ncc(-c4ccc(CCN5CCOCC5)cc4)cc3[nH]2)c1)c1ccco1] | ¹H NMR (400 MHz, MeOD) δ 8.88 (s, 1H), 8.62 (s, 1H), 8.56 (d, J = 2.6 Hz, 1H), 7.85 (dd, J = 2.6, 8.8 Hz, 1H), 7.75 (d, J = 8.3 Hz, 2H), 7.70 (dd, J = 0.7, 1.7 Hz, 1H), 7.63 (d, J = 8.8 Hz, 1H), 7.47 (d, J = 8.3 Hz, 2H), 7.24 (dd, J = 0.7, 3.5 Hz, 1H), 6.59 (dd, J = 1.8, 3.5 Hz, 1H), 4.03 (dd, J = 3.3, 13.0 Hz, 2H), 3.74 (t, J = 11.7 Hz, 2H), 3.53 (d, J = 12.6 Hz, 2H), 3.45-3.35 (m, 2H), 3.19-3.06 (m, 4H). M/Z = 528.1 (M + 1). RT = 1.29: Method B. |
| 7 | 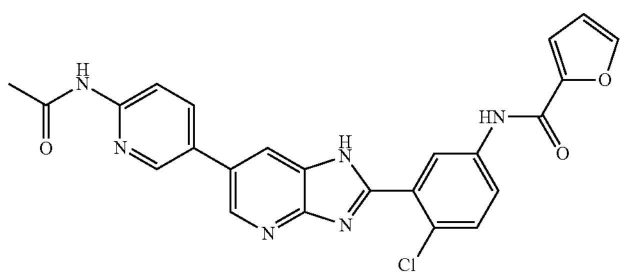 | M/Z = 479.1 (M + 1). RT = 1.33: Method B. |
| 8 | 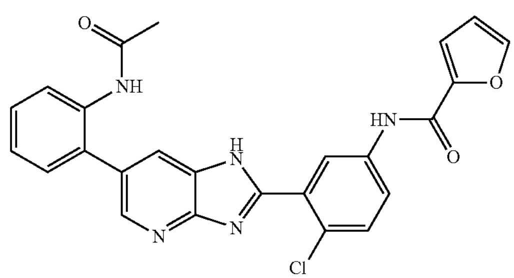 [SMILES: CC(=O)Nc1ccccc1-c1cnc2nc(-c3cc(NC(=O)c4ccco4)ccc3Cl)[nH]c2c1] | M/Z = 472.0 (M + 1). RT = 1.43: Method B. |
| 9 | 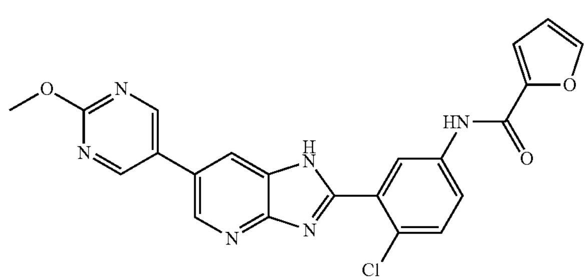 [SMILES: COc1ncc(-c2cnc3nc(-c4cc(NC(=O)c5ccco5)ccc4Cl)[nH]c3c2)cn1] | M/Z = 447.1 (M + 1). RT = 1.44: Method B. |

TABLE II-continued

Listing of the Exemplified Compounds of the Invention

| Ex. No. | Structure | ¹H NMR and/or mass and/or (retention time (mins)) |
|---|---|---|
| 10 | 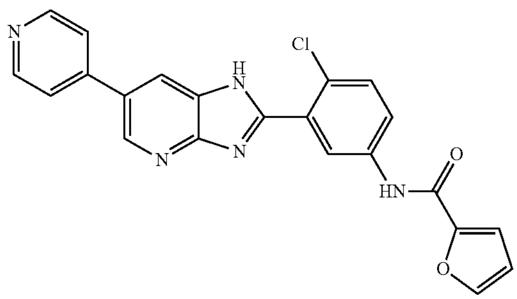 [SMILES: O=C(Nc1ccc(Cl)c(-c2nc3ncc(-c4ccncc4)cc3[nH]2)c1)c1ccco1] | M/Z = 416.1 (M + 1). RT = 1.23: Method B. |
| 11 | 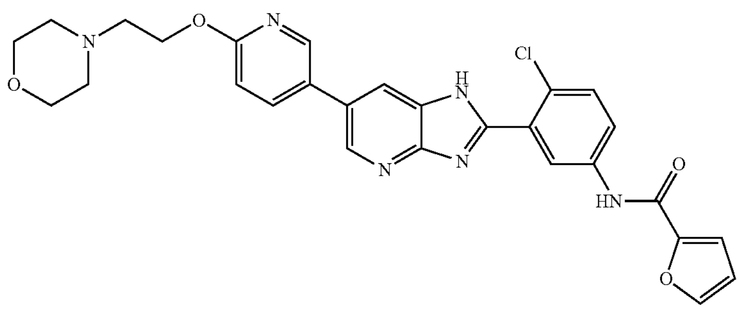 [SMILES: O=C(Nc1ccc(Cl)c(-c2nc3ncc(-c4ccc(OCCN5CCOCC5)nc4)cc3[nH]2)c1)c1ccco1] | ¹H NMR (400 MHz, DMSO) δ 10.39 (s, 1H), 8.45 (d, J = 2.4 Hz, 2H), 8.35 (d, J = 2.7 Hz, 1H), 8.05 (s, 1H), 8.02 (dd, J = 2.6, 8.6 Hz, 1H), 7.90 (dd, J = 0.7, 1.7 Hz, 1H), 7.86 (dd, J = 2.6, 8.8 Hz, 1H), 7.48 (d, J = 8.7 Hz, 1H), 7.35 (dd, J = 0.7, 3.5 Hz, 1H), 6.86 (d, J = 8.4 Hz, 1H), 6.65 (dd, J = 1.7, 3.5 Hz, 1H), 4.41-4.30 (m, 2H), 3.51 (dd, J = 5.1, 9.6 Hz, 4H), 2.64 (dd, J = 3.8, 9.7 Hz, 2H), 2.41 (s, 4H). M/Z = 545.3 (M + 1). RT = 1.32: Method B. |
| 12 | 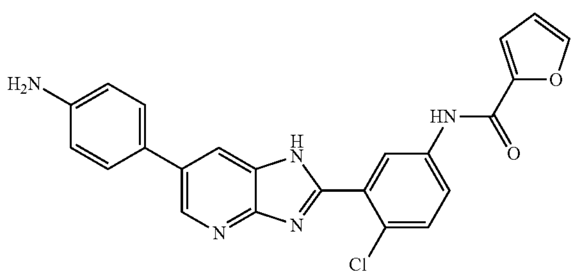 [SMILES: Nc1ccc(-c2cnc3nc(-c4cc(NC(=O)c5ccco5)ccc4Cl)[nH]c3c2)cc1] | M/Z = 430.1 (M + 1). RT = 1.24: Method B. |
| 13 | 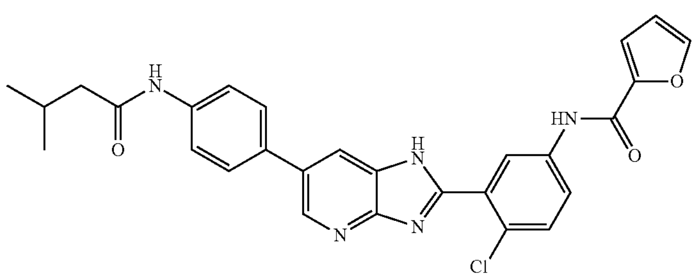 [SMILES: CC(C)CC(=O)Nc1ccc(-c2cnc3nc(-c4cc(NC(=O)c5ccco5)ccc4Cl)[nH]c3c2)cc1] | M/Z = 514.1 (M + 1). RT = 0.95: Method B. |
| 14 | 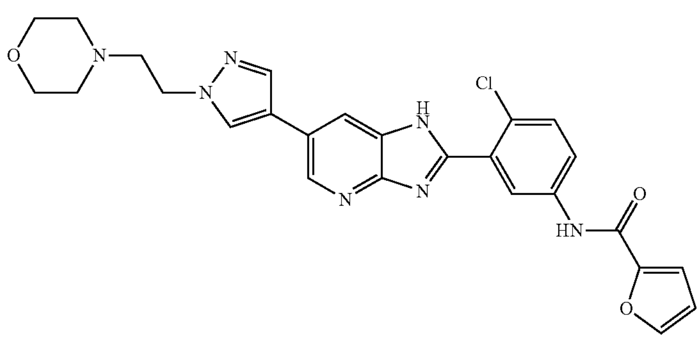 [SMILES: O=C(Nc1ccc(Cl)c(-c2nc3ncc(-c4cnn(CCN5CCOCC5)c4)cc3[nH]2)c1)c1ccco1] | ¹H NMR (400 MHz, DMSO) δ 10.51 (s, 1H), 8.64 (d, J = 1.8 Hz, 1H), 8.37 (d, J = 2.5 Hz, 1H), 8.31 (s, 1H), 8.13 (s, 1H), 8.03-7.91 (m, 3H), 7.62 (d, J = 8.8 Hz, 1H), 7.41 (d, J = 3.5 Hz, 1H), 6.73 (dd, J = 1.7, 3.5 Hz, 1H), 4.32-4.23 (m, 2H), 3.64-3.51 (m, 5H), 2.76 (q, J = 6.6 Hz, 2H), 2.45 (s, 4H). M/Z = 518.2 (M + 1). RT = 2.20: Method A. |

TABLE II-continued

Listing of the Exemplified Compounds of the Invention

| Ex. No. | Structure | $^1$H NMR and/or mass and/or (retention time (mins)) |
|---|---|---|
| 15 | 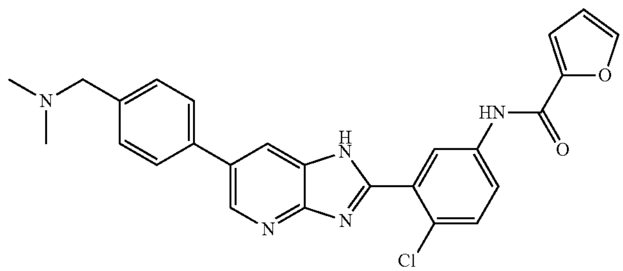 [SMILES: CN(C)Cc1ccc(-c2cnc3nc(-c4cc(NC(=O)c5ccco5)ccc4Cl)[nH]c3c2)cc1] | $^1$H NMR (600 MHz, DMSO) δ 10.54 (s, 1H), 9.69 (s, 1H), 8.78 (s, 1H), 8.40 (s, 1H), 8.36 (s, 1H), 7.99-7.95 (m, 2H), 7.93 (d, J = 8.3 Hz, 2H), 7.67 (d, J = 8.8 Hz, 1H), 7.63 (d, J = 8.3 Hz, 2H), 7.40 (d, J = 2.8 Hz, 1H), 6.73 (dd, J = 1.7, 3.5 Hz, 1H), 4.36 (d, J = 5.3 Hz, 2H), 2.79 (d, J = 4.8 Hz, 6H). M/Z = 472.14 (M + 1). RT = 1.31: Method B. |
| 16 | 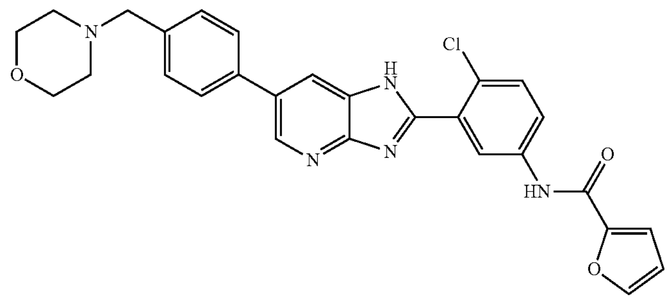 [SMILES: O=C(Nc1ccc(Cl)c(-c2nc3ncc(-c4ccc(CN5CCOCC5)cc4)cc3[nH]2)c1)c1ccco1] | M/Z = 514.2 (M + 1). RT = 1.59: Method B. |
| 17 | 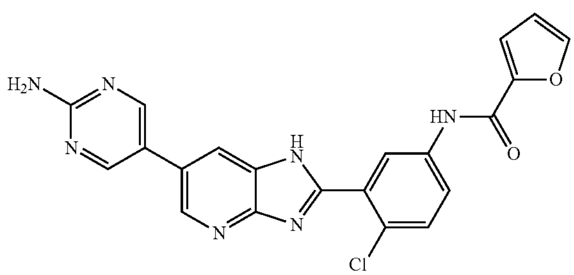 [SMILES: Nc1ncc(-c2cnc3nc(-c4cc(NC(=O)c5ccco5)ccc4Cl)[nH]c3c2)cn1] | M/Z = 432.1 (M + 1). RT = 0.68: Method B. |
| 18 | 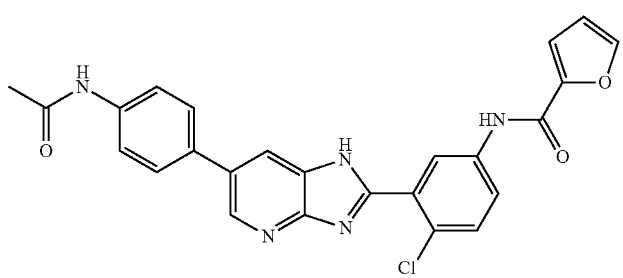 [SMILES: CC(=O)Nc1ccc(-c2cnc3nc(-c4cc(NC(=O)c5ccco5)ccc4Cl)[nH]c3c2)cc1] | $^1$H NMR (400 MHz, MeOD) δ 8.77-8.62 (m, 1H), 8.26 (s, 2H), 8.06-7.93 (m, 1H), 7.79 (s, 1H), 7.76-7.67 (m, 4H), 7.64 (d, J = 8.8 Hz, 1H), 7.32 (d, J = 3.4 Hz, 1H), 6.68 (d, J = 1.7 Hz, 1H), 2.17 (s, 3H). M/Z = 472.1 (M + 1). RT = 1.48: Method B. |
| 19 | 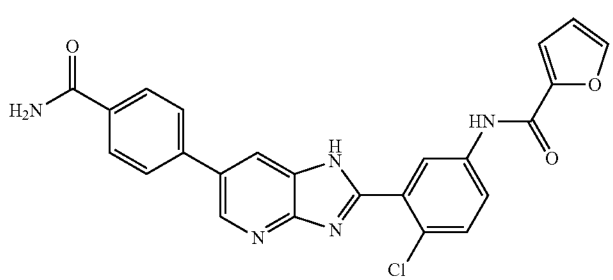 [SMILES: NC(=O)c1ccc(-c2cnc3nc(-c4cc(NC(=O)c5ccco5)ccc4Cl)[nH]c3c2)cc1] | M/Z = 458.1 (M + 1). RT = 1.40: Method B. |

TABLE II-continued

Listing of the Exemplified Compounds of the Invention

| Ex. No. | Structure | $^1$H NMR and/or mass and/or (retention time (mins)) |
|---|---|---|
| 20 | 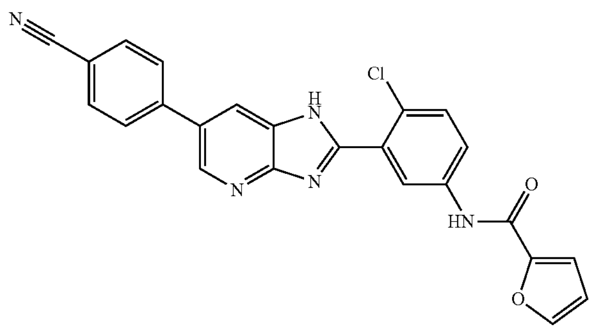 [SMILES: N#Cc1ccc(-c2cnc3nc(-c4cc(NC(=O)c5ccco5)ccc4Cl)[nH]c3c2)cc1] | M/Z = 440.1 (M + 1). RT = 1.61: Method B. |
| 21 | 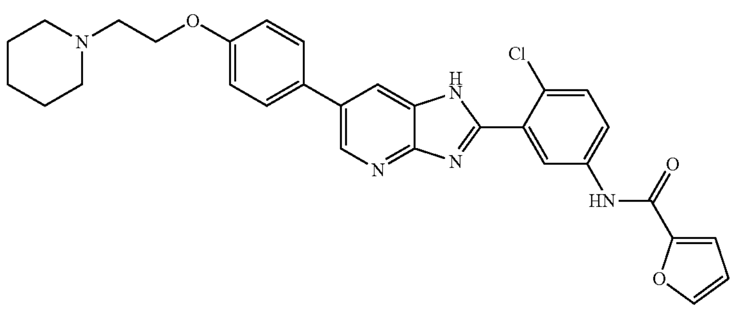 [SMILES: O=C(Nc1ccc(Cl)c(-c2nc3ncc(-c4ccc(OCCN5CCCCC5)cc4)cc3[nH]2)c1)c1ccco1] | M/Z = 542.18 (M + 1). RT = 1.24: method B. |
| 22 | 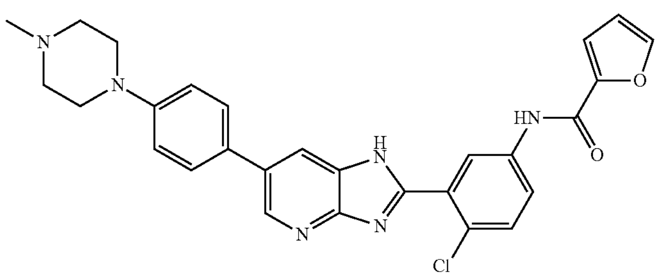 [SMILES: CN1CCN(c2ccc(-c3cnc4nc(-c5cc(NC(=O)c6ccco6)ccc5Cl)[nH]c4c3)cc2)CC1] | $^1$H NMR (400 MHz, DMSO) δ 10.40 (s, 1H), 8.42 (s, 1H), 8.34 (d, J = 2.7 Hz, 1H), 7.94 (s, 1H), 7.90 (dd, J = 0.7, 1.7 Hz, 1H), 7.86 (dd, J = 2.7, 8.8 Hz, 1H), 7.50 (dd, J = 8.8, 15.5 Hz, 3H), 7.36 (dd, J = 0.8, 3.5 Hz, 1H), 6.98 (d, J = 8.9 Hz, 2H), 6.65 (dd, J = 1.7, 3.5 Hz, 1H), 3.16-3.08 (m, 4H), 2.40 (d, J = 5.1 Hz, 4H), 2.17 (s, 3H). M/Z = 513.17 (M + 1). RT = 1.2: Method B. |
| 23 | 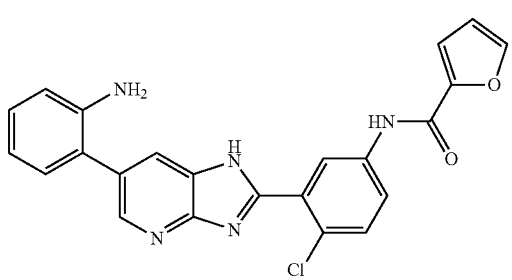 [SMILES: Nc1ccccc1-c1cnc2nc(-c3cc(NC(=O)c4ccco4)ccc3Cl)[nH]c2c1] | $^1$H NMR (400 MHz, MeOD) δ 8.50 (s, 1H), 8.26 (s, 1H), 8.13 (s, 1H), 8.00 (d, J = 7.3 Hz, 1H), 7.78 (dd, J = 0.8, 1.7 Hz, 1H), 7.63 (d, J = 8.8 Hz, 1H), 7.32 (dd, J = 0.7, 3.5 Hz, 1H), 7.23-7.11 (m, 2H), 6.89 (d, J = 7.1 Hz, 1H), 6.83 (td, J = 1.1 Hz, 7.4, 1H), 6.67 (dd, J = 1.7, 3.5 Hz, 1H). M/Z = 430.1 (M + 1). RT = 1.43: Method B. |
| 24 | 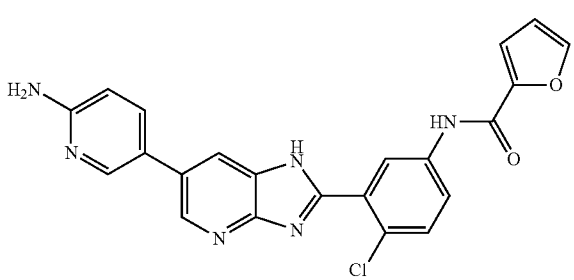 | M/Z = 431.1 (M + 1). RT = 1.23: Method B. |

TABLE II-continued

Listing of the Exemplified Compounds of the Invention

| Ex. No. | Structure | ¹H NMR and/or mass and/or (retention time (mins)) |
|---|---|---|
| 25 | 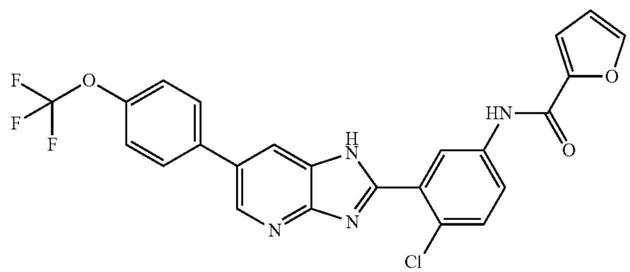 [SMILES: O=C(Nc1ccc(Cl)c(-c2nc3ncc(-c4ccc(OC(F)(F)F)cc4)cc3[nH]2)c1)c1ccco1] | M/Z = 499.1 (M + 1). RT = 1.91: Method B. |
| 26 | 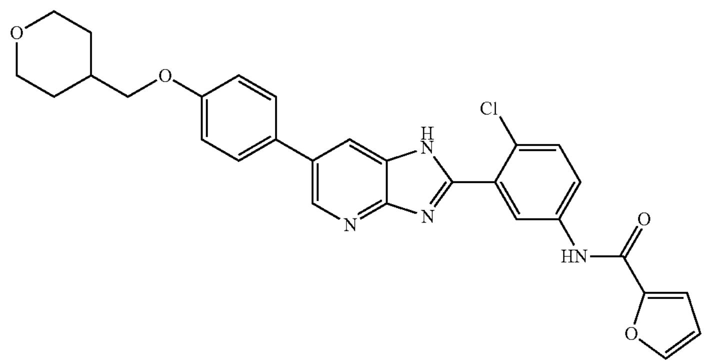 [SMILES: O=C(Nc1ccc(Cl)c(-c2nc3ncc(-c4ccc(OCC5CCOCC5)cc4)cc3[nH]2)c1)c1ccco1] | M/Z = 529.1 (M + 1). RT = 1.73: Method B. |
| 27 | 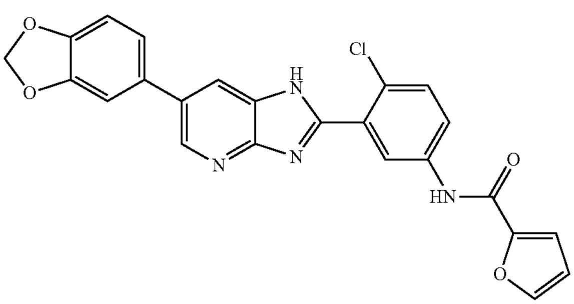 [SMILES: O=C(Nc1ccc(Cl)c(-c2nc3ncc(-c4ccc5c(c4)OCO5)cc3[nH]2)c1)c1ccco1] | M/Z = 459.1 (M + 1). RT = 1.61: Method B. |
| 28 | 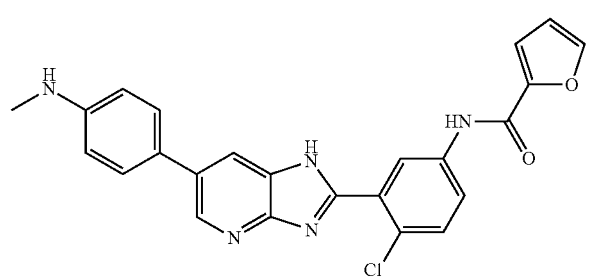 [SMILES: CNc1ccc(-c2cnc3nc(-c4cc(NC(=O)c5ccco5)ccc4Cl)[nH]c3c2)cc1] | ¹H NMR (400 MHz, MeOD) δ 8.64 (s, 1H), 8.24 (d, J = 2.2 Hz, 1H), 8.14 (s, 1H), 8.00 (d, J = 6.5 Hz, 1H), 7.78 (dd, J = 0.8 Hz, 1.7, 1H), 7.62 (d, J = 8.8 Hz, 1H), 7.57-7.47 (m, 2H), 7.32 (dd, J = 0.8, 3.5 Hz, 1H), 6.83-6.72 (m, 2H), 6.67 (dd, J = 1.7, 3.5 Hz, 1H), 2.84 (s, 3H). M/Z = 443.9 (M + 1). RT = 1.24: Method B. |
| 29 | 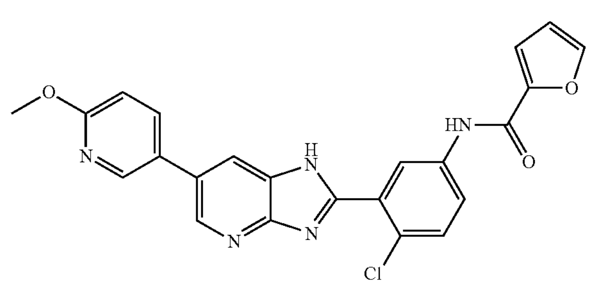 [SMILES: COc1ccc(-c2cnc3nc(-c4cc(NC(=O)c5ccco5)ccc4Cl)[nH]c3c2)cn1] | M/Z = 446.1 (M + 1). RT = 1.55: Method B. |

TABLE II-continued

Listing of the Exemplified Compounds of the Invention

| Ex. No. | Structure | ¹H NMR and/or mass and/or (retention time (mins)) |
|---|---|---|
| 30 | 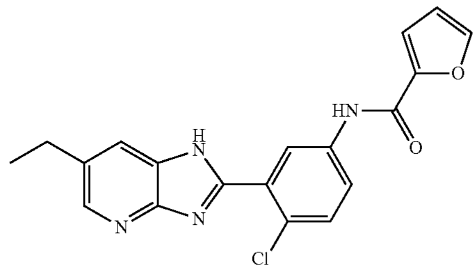 [SMILES: CCc1cnc2nc(-c3cc(NC(=O)c4ccco4)ccc3Cl)[nH]c2c1] | ¹H NMR (400 MHz, DMSO) δ 10.51 (s, 1H), 8.27 (brs, 2H), 8.07-7.89 (m, 2H), 7.80 (s, 1H), 7.63 (d, J = 8.8 Hz, 1H), 7.39 (d, J = 3.3 Hz, 1H), 6.72 (dd, J = 1.7, 3.4 Hz, 1H), 2.77 (q, J = 7.4 Hz, 2H), 1.27 (t, J = 7.6 Hz, 3H). M/Z = 367.0 (M + 1). RT = 0.78: Method B. |
| 31 | 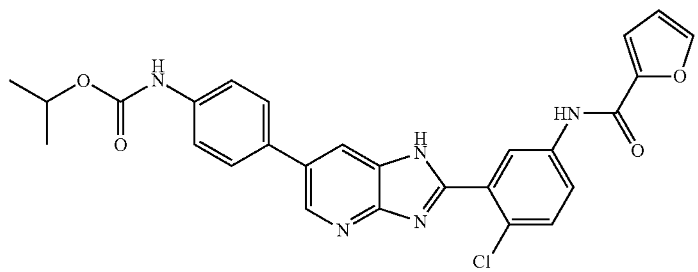 [SMILES: CC(C)OC(=O)Nc1ccc(-c2cnc3nc(-c4cc(NC(=O)c5ccco5)ccc4Cl)[nH]c3c2)cc1] | M/Z = 516.1 (M + 1). RT = 3.11: Method A. |
| 32 | 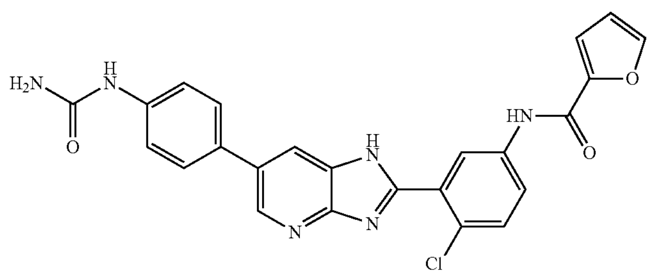 [SMILES: NC(=O)Nc1ccc(-c2cnc3nc(-c4cc(NC(=O)c5ccco5)ccc4Cl)[nH]c3c2)cc1] | ¹H NMR (400 MHz, MeOD) δ 8.69 (d, J = 1.9 Hz, 1H), 8.25 (d, J = 2.6 Hz, 1H), 8.23 (d, J = 1.8 Hz, 1H), 8.01 (dd, J = 2.6, 8.8 Hz, 1H), 7.78 (d, J = 0.9 Hz, 1H), 7.70-7.60 (m, 3H), 7.60-7.52 (m, 2H), 7.32 (d, J = 3.5 Hz, 1H), 6.67 (dd, J = 1.7, 3.5 Hz, 1H). M/Z = 473.1 (M + 1). RT = 1.36: Method B. |
| 33 | 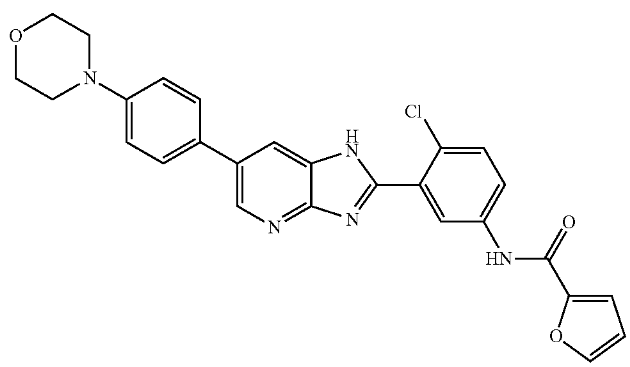 [SMILES: O=C(Nc1ccc(Cl)c(-c2nc3ncc(-c4ccc(N5CCOCC5)cc4)cc3[nH]2)c1)c1ccco1] | M/Z = 461.1 (M + 1). RT = 1.33: Method B. |
| 34 | 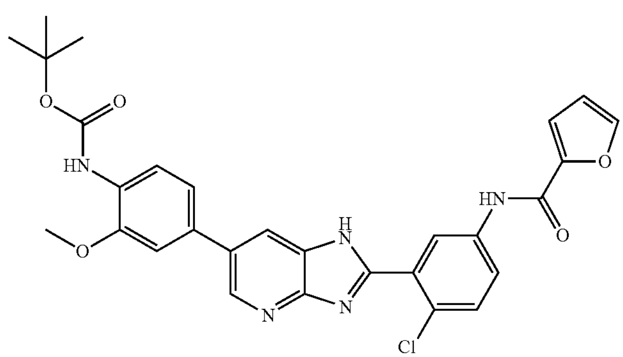 [SMILES: COc1cc(-c2cnc3nc(-c4cc(NC(=O)c5ccco5)ccc4Cl)[nH]c3c2)ccc1NC(=O)OC(C)(C)C] | M/Z = 560.2 (M + 1). RT = 1.90: Method B. |

TABLE II-continued

Listing of the Exemplified Compounds of the Invention

| Ex. No. | Structure | ¹H NMR and/or mass and/or (retention time (mins)) |
|---|---|---|
| 35 | 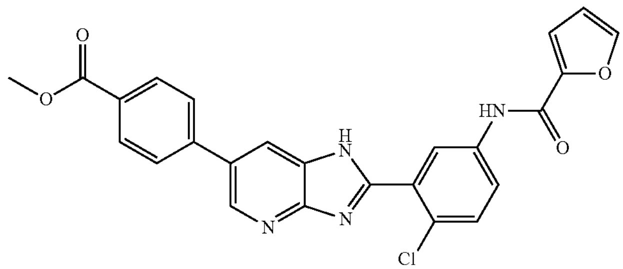 [SMILES: COC(=O)c1ccc(-c2cnc3nc(-c4cc(NC(=O)c5ccco5)ccc4Cl)[nH]c3c2)cc1] | M/Z = 473.1 (M + 1). RT = 2.53: Method A. |
| 36 | 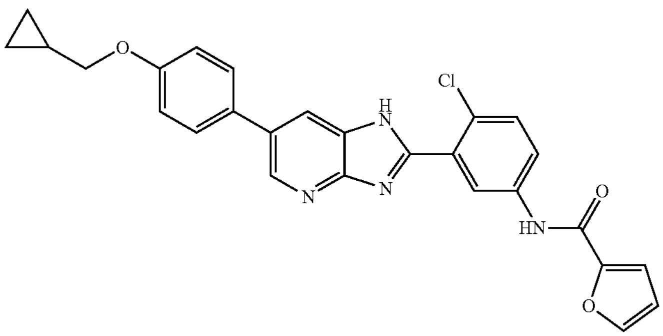 [SMILES: O=C(Nc1ccc(Cl)c(-c2nc3ncc(-c4ccc(OCC5CC5)cc4)cc3[nH]2)c1)c1ccco1] | M/Z = 485.1 (M + 1). RT = 1.76: Method B. |
| 37 | 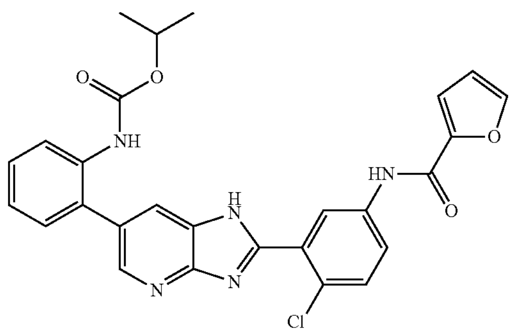 [SMILES: CC(C)OC(=O)Nc1ccccc1-c1cnc2nc(-c3cc(NC(=O)c4ccco4)ccc3Cl)[nH]c2c1] | M/Z = 516.1 (M + 1). RT = 1.65: Method B. |
| 38 | 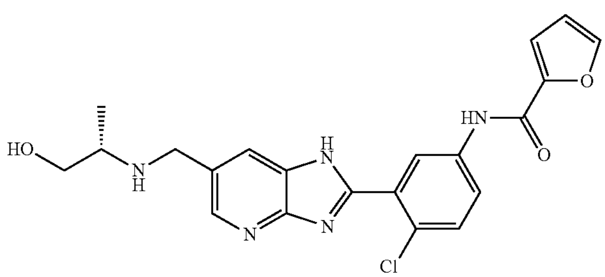 [SMILES: C[C@@H](CO)NCc1cnc2nc(-c3cc(NC(=O)c4ccco4)ccc3Cl)[nH]c2c1] | M/Z = 426.1 (M + 1). RT = 1.19: Method B. |
| 39 | 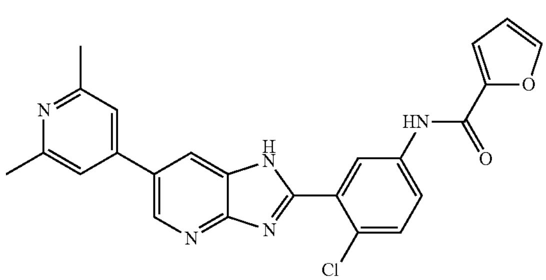 [SMILES: Cc1cc(-c2cnc3nc(-c4cc(NC(=O)c5ccco5)ccc4Cl)[nH]c3c2)cc(C)n1] | M/Z = 444.1 (M + 1). RT = 1.28: Method B. |

TABLE II-continued

Listing of the Exemplified Compounds of the Invention

| Ex. No. | Structure | ¹H NMR and/or mass and/or (retention time (mins)) |
|---|---|---|
| 40 | 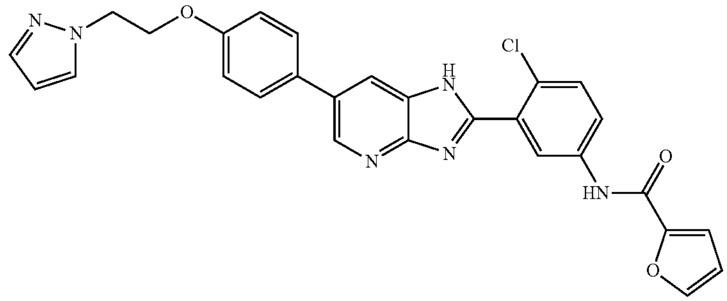 [SMILES: O=C(Nc1ccc(Cl)c(-c2nc3ncc(-c4ccc(OCCn5cccn5)cc4)cc3[nH]2)c1)c1ccco1] | M/Z = 525.1 (M + 1). RT = 1.61: Method B. |
| 41 | 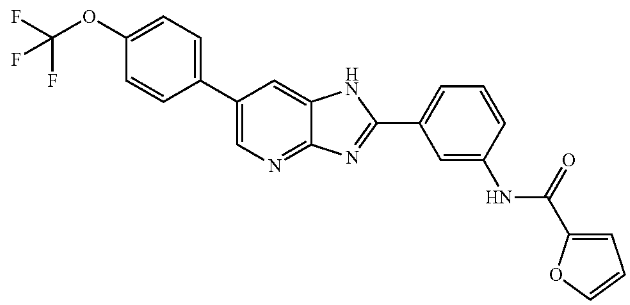 [SMILES: O=C(Nc1cccc(-c2nc3ncc(-c4ccc(OC(F)(F)F)cc4)cc3[nH]2)c1)c1ccco1] | M/Z = 465.1 (M + 1). RT = 1.75: Method B. |
| 42 | 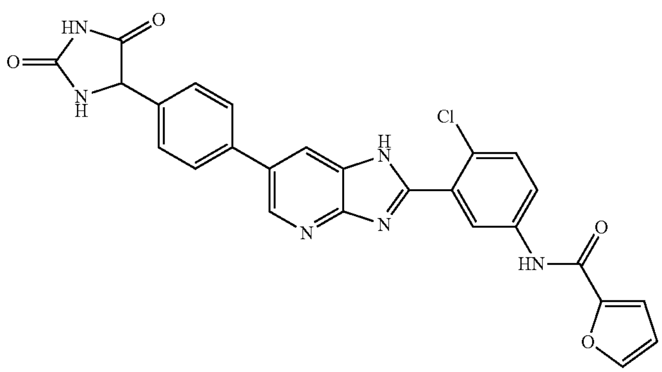 [SMILES: O=C1NC(=O)C(c2ccc(-c3cnc4nc(-c5cc(NC(=O)c6ccco6)ccc5Cl)[nH]c4c3)cc2)N1] | M/Z = 513.1 (M + 1). RT = 1.53: Method B. |
| 43 | 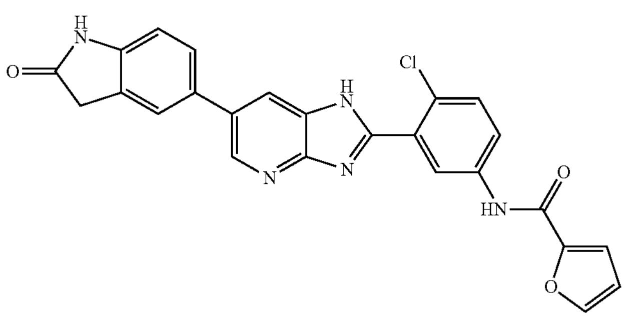 [SMILES: O=C1Cc2cc(-c3cnc4nc(-c5cc(NC(=O)c6ccco6)ccc5Cl)[nH]c4c3)ccc2N1] | M/Z = 470.1 (M + 1). RT = 1.26: Method B. |

TABLE II-continued

Listing of the Exemplified Compounds of the Invention

| Ex. No. | Structure | ¹H NMR and/or mass and/or (retention time (mins)) |
|---|---|---|
| 44 | 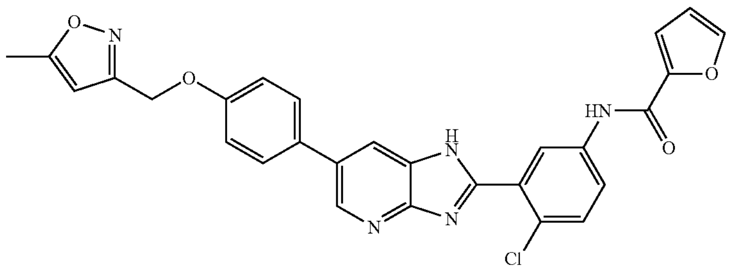 [SMILES: Cc1cc(COc2ccc(-c3cnc4nc(-c5cc(NC(=O)c6ccco6)ccc5Cl)[nH]c4c3)cc2)no1] | M/Z = 526.1 (M + 1). RT = 2.58: Method A. |
| 45 | 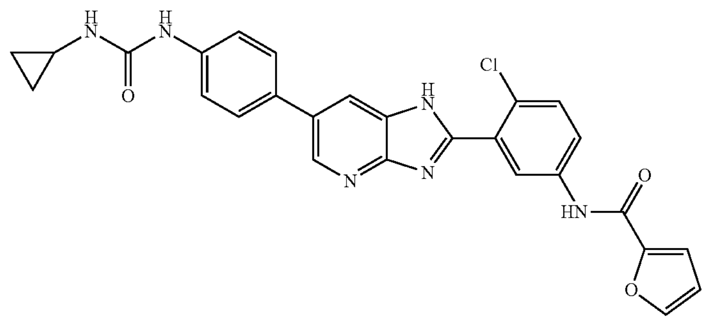 [SMILES: O=C(Nc1ccc(-c2cnc3nc(-c4cc(NC(=O)c5ccco5)ccc4Cl)[nH]c3c2)cc1)NC1CC1] | M/Z = 513.1 (M + 1). RT = 2.3: Method A. |
| 46 | 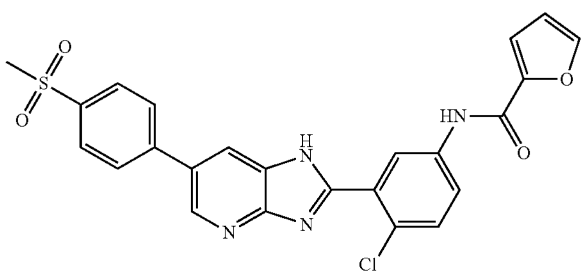 [SMILES: CS(=O)(=O)c1ccc(-c2cnc3nc(-c4cc(NC(=O)c5ccco5)ccc4Cl)[nH]c3c2)cc1] | ¹H NMR (400 MHz, DMSO) δ 10.44 (s, 1H), 8.64 (d, J = 2.1 Hz, 1H), 8.34 (d, J = 2.6 Hz, 1H), 8.25 (s, 1H), 8.03-7.92 (m, 4H), 7.92-7.86 (m, 2H), 7.53 (d, J = 8.8 Hz, 1H), 7.35 (dd, J = 0.8, 3.5 Hz, 1H), 6.66 (dt, J = 1.7, 3.5 Hz, 1H), 3.21 (s, 3H). M/Z = 493.1 (M + 1). RT = 1.48: Method B. |
| 47 | 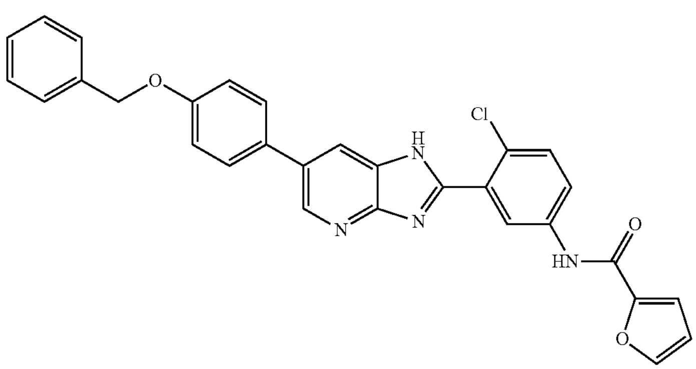 [SMILES: O=C(Nc1ccc(Cl)c(-c2nc3ncc(-c4ccc(OCc5ccccc5)cc4)cc3[nH]2)c1)c1ccco1] | M/Z = 521.1 (M + 1). RT = 1.87: Method B. |
| 48 | 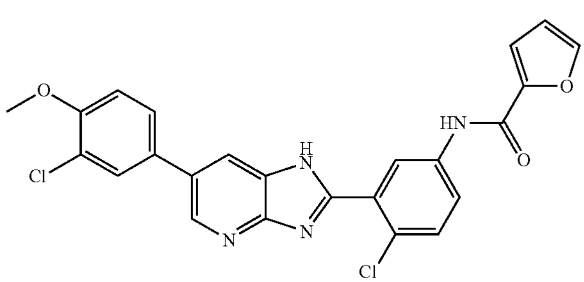 [SMILES: COc1ccc(-c2cnc3nc(-c4cc(NC(=O)c5ccco5)ccc4Cl)[nH]c3c2)cc1Cl] | ¹H NMR (400 MHz, DMSO) δ 10.38 (s, 1H), 8.40 (s, 1H), 8.35 (d, J = 2.6 Hz, 1H), 7.98 (s, 1H), 7.87 (dd, J = 4.8 Hz, 2H), 7.71 (s, 1H), 7.61 (d, J = 8.6 Hz, 1H), 7.45 (d, J = 8.8 Hz, 1H), 7.36 (d, J = 3.5 Hz, 1H), 7.26-7.09 (m, 2H), 6.65 (dd, J = 1.7, 3.5 Hz, 1H), 3.84 (s, 3H). M/Z = 479.1 (M + 1). RT = 1.69: Method B. |

TABLE II-continued

Listing of the Exemplified Compounds of the Invention

| Ex. No. | Structure | ¹H NMR and/or mass and/or (retention time (mins)) |
|---|---|---|
| 49 | 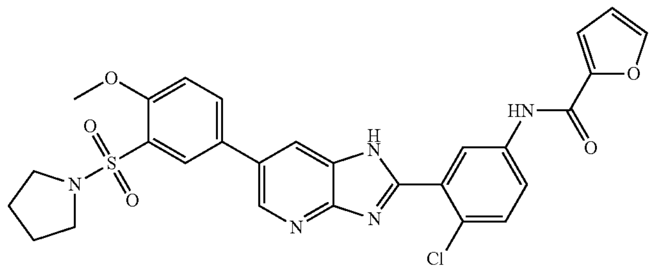 [SMILES: COc1ccc(-c2cnc3nc(-c4cc(NC(=O)c5ccco5)ccc4Cl)[nH]c3c2)cc1S(=O)(=O)N1CCCC1] | ¹H NMR (400 MHz, DMSO) δ 10.48 (s, 1H), 8.59 (d, J = 1.9 Hz, 1H), 8.33 (s, 1H), 8.17 (s, 1H), 7.97 (dd, J = 2.2, 7.1 Hz, 2H), 7.92 (dd, J = 3.9, 4.7 Hz, 2H), 7.58 (d, J = 8.8, 1H), 7.39-7.29 (m, 2H), 6.67 (dd, J = 1.7, 3.5 Hz, 1H), 3.91 (s, 3H), 3.23 (d, J = 6.6 Hz, 4H), 1.71 (td, J = 3.7, 7.0 Hz, 4H). M/Z = 578.1 (M +1 ). RT = 1.41: Method B. |
| 50 | 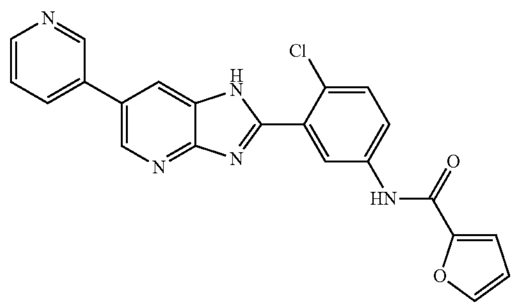 [SMILES: O=C(Nc1ccc(Cl)c(-c2nc3ncc(-c4cccnc4)cc3[nH]2)c1)c1ccco1] | M/Z = 416.1 (M + 1). RT = 1.16: Method B. |
| 51 | 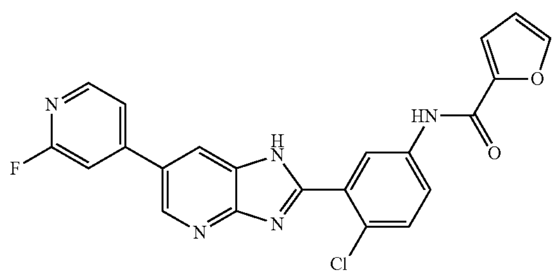 [SMILES: O=C(Nc1ccc(Cl)c(-c2nc3ncc(-c4ccnc(F)c4)cc3[nH]2)c1)c1ccco1] | M/Z = 434.1 (M + 1). RT = 0.85: Method B. |
| 52 | 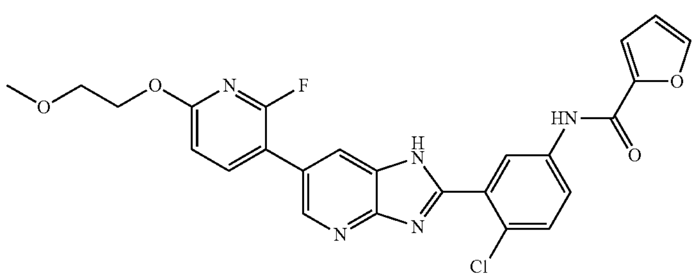 [SMILES: COCCOc1ccc(-c2cnc3nc(-c4cc(NC(=O)c5ccco5)ccc4Cl)[nH]c3c2)c(F)n1] | ¹H NMR (400 MHz, DMSO) δ 10.40 (s, 1H), 8.35 (d, J = 2.7 Hz, 1H), 8.32 (s, 1H), 8.06 (dd, J = 8.2, 10.4 Hz, 1H), 7.96 (s, 1H), 7.90 (dd, J = 0.7, 1.7 Hz, 1H), 7.87 (dd, J = 2.5, 8.8 Hz, 1H), 7.48 (d, J = 8.8 Hz, 1H), 7.36 (dd, J = 0.7, 3.5 Hz, 1H), 6.85 (d, J = 8.2 Hz, 1H), 6.65 (dd, J = 1.7, 3.5 Hz, 1H), 4.39-4.27 (m, 2H), 3.67-3.56 (m, 2H), 3.27-3.22 (m, 3H). M/Z = 508.1 (M + 1). RT = 1.68: Method B. |
| 53 | 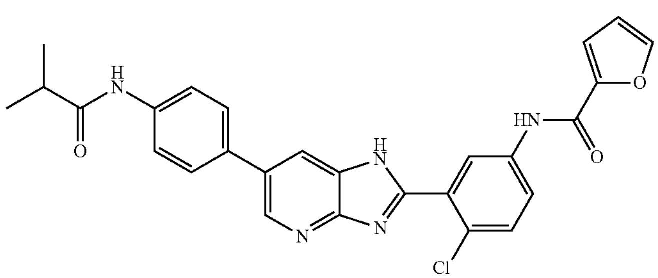 [SMILES: CC(C)C(=O)Nc1ccc(-c2cnc3nc(-c4cc(NC(=O)c5ccco5)ccc4Cl)[nH]c3c2)cc1] | M/Z = 500.1 (M + 1). RT = 3.12: Method A. |

TABLE II-continued

Listing of the Exemplified Compounds of the Invention

| Ex. No. | Structure | $^1$H NMR and/or mass and/or (retention time (mins)) |
|---|---|---|
| 54 | 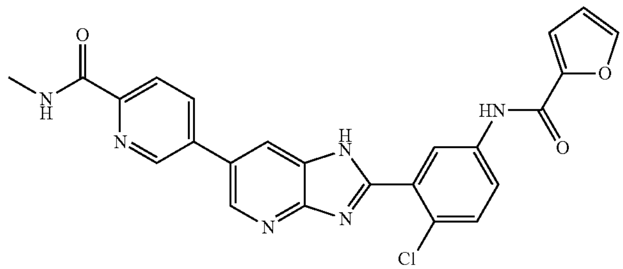 [SMILES: CNC(=O)c1ccc(-c2cnc3nc(-c4cc(NC(=O)c5ccco5)ccc4Cl)[nH]c3c2)cn1] | $^1$H NMR (400 MHz, DMSO) δ 10.55 (s, 1H), 9.08 (s, 1H), 8.87 (s, 2H), 8.51 (s, 1H), 8.46-8.31 (m, 2H), 8.14 (d, J = 7.9 Hz, 1H), 8.00 (m, 2H), 7.68 (d, J = 8.8 Hz, 1H), 7.41 (s, 1H), 6.74 (s, 1H), 3.16 (s, 1H), 2.86 (s, 3H). M/Z = 473.1 (M + 1). RT = 1.44: Method B. |
| 55 | 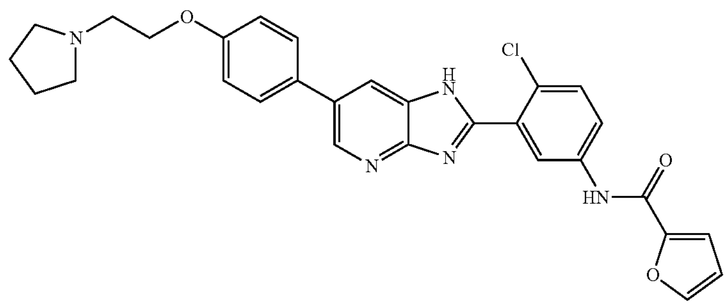 [SMILES: O=C(Nc1ccc(Cl)c(-c2nc3ncc(-c4ccc(OCCN5CCCC5)cc4)cc3[nH]2)c1)c1ccco1] | M/Z = 528.1 (M + 1). RT = 1.38: Method B. |
| 56 | 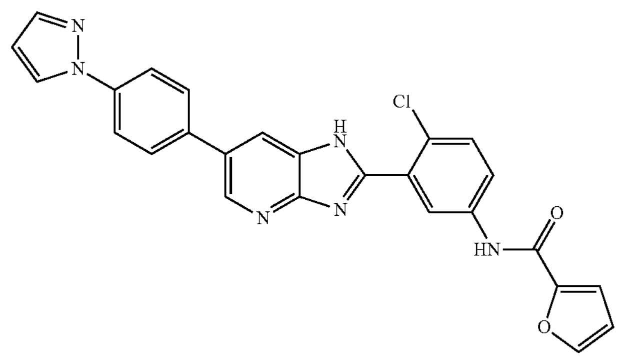 [SMILES: O=C(Nc1ccc(Cl)c(-c2nc3ncc(-c4ccc(-n5cccn5)cc4)cc3[nH]2)c1)c1ccco1] | M/Z = 481.1 (M + 1). RT = 1.65: Method B. |
| 57 | 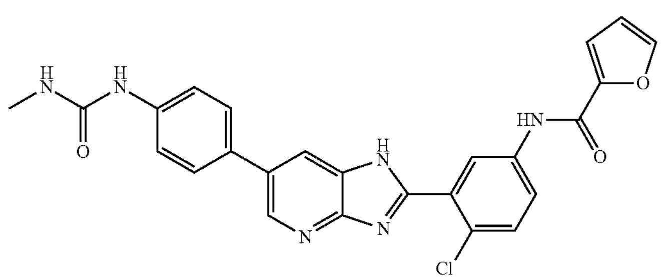 [SMILES: CNC(=O)Nc1ccc(-c2cnc3nc(-c4cc(NC(=O)c5ccco5)ccc4Cl)[nH]c3c2)cc1] | M/Z = 487.1 (M + 1). RT = 1.27: Method B. |
| 58 | 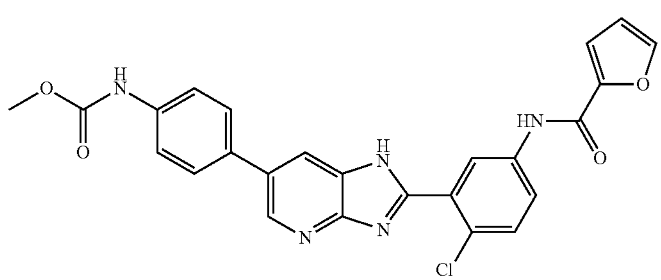 [SMILES: COC(=O)Nc1ccc(-c2cnc3nc(-c4cc(NC(=O)c5ccco5)ccc4Cl)[nH]c3c2)cc1] | M/Z = 488.1 (M + 1). RT = 2.40: Method A. |

TABLE II-continued

Listing of the Exemplified Compounds of the Invention

| Ex. No. | Structure | ¹H NMR and/or mass and/or (retention time (mins)) |
|---|---|---|
| 59 | 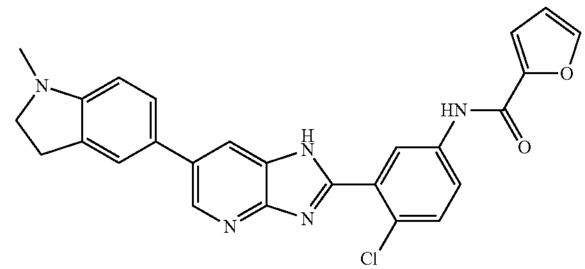 [SMILES: CN1CCc2cc(-c3cnc4nc(-c5cc(NC(=O)c6ccco6)ccc5Cl)[nH]c4c3)ccc21] | M/Z = 470.1 (M + 1). RT = 2.68: Method A. |
| 60 | 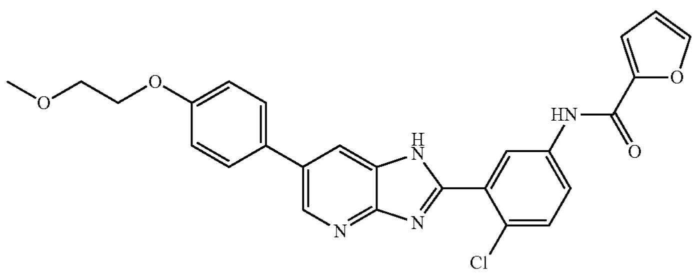 [SMILES: COCCOc1ccc(-c2cnc3nc(-c4cc(NC(=O)c5ccco5)ccc4Cl)[nH]c3c2)cc1] | M/Z = 489.1 (M + 1). RT = 2.42: Method A. |
| 61 | 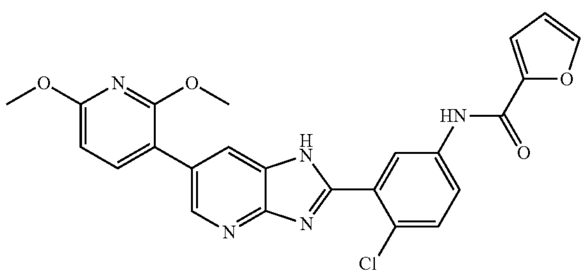 [SMILES: COc1ccc(-c2cnc3nc(-c4cc(NC(=O)c5ccco5)ccc4Cl)[nH]c3c2)c(OC)n1] | ¹H NMR (400 MHz, DMSO) δ 10.48 (s, 1H), 8.47 (d, J = 2.0 Hz, 1H), 8.32 (d, J = 2.5 Hz, 1H), 8.11 (d, J = 2.0 Hz, 1H), 7.98-7.91 (m, 2H), 7.79 (d, J = 8.1 Hz, 1H), 7.58 (t, J = 9.7 Hz, 1H), 7.34 (dd, J = 0.8, 3.5 Hz, 1H), 6.67 (dd, J = 1.7, 3.5 Hz, 1H), 6.48 (d, J = 8.1 Hz, 1H), 3.87 (d, J = 4.6 Hz, 6H). M/Z = 476.1 (M + 1). RT = 1.64: Method B. |
| 62 | 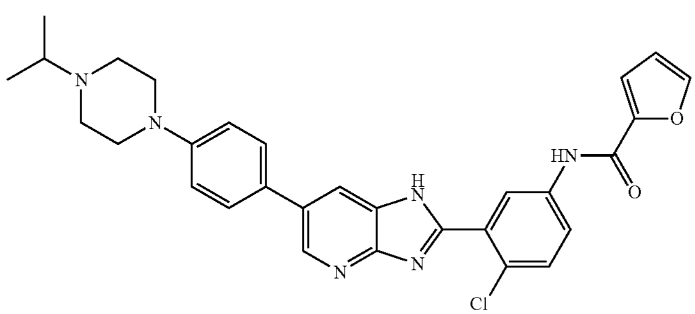 [SMILES: CC(C)N1CCN(c2ccc(-c3cnc4nc(-c5cc(NC(=O)c6ccco6)ccc5Cl)[nH]c4c3)cc2)CC1] | M/Z = 541.2 (M + 1). RT = 1.31: Method B. |
| 63 | 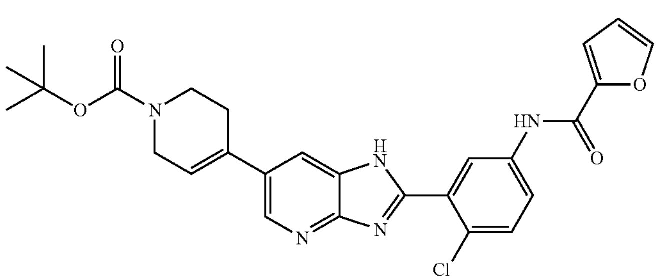 [SMILES: CC(C)(C)OC(=O)N1CC=C(c2cnc3nc(-c4cc(NC(=O)c5ccco5)ccc4Cl)[nH]c3c2)CC1] | M/Z = 520.2 (M + 1). RT = 1.76: Method B. |

TABLE II-continued

Listing of the Exemplified Compounds of the Invention

| Ex. No. | Structure | ¹H NMR and/or mass and/or (retention time (mins)) |
|---|---|---|
| 64 | 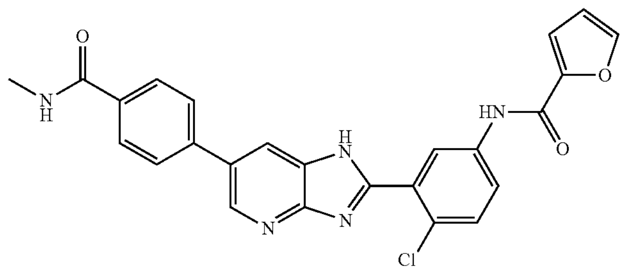 | ¹H NMR (600 MHz, DMSO) δ 10.53 (s, 1H), 8.79 (d, 1H), 8.52 (d, J = 4.6 Hz, 1H), 8.45 (d, 1H), 8.28 (d, 1H), 7.97 (m, J = 5.5 Hz, 3H), 7.90 (d, J = 7.2 Hz, 2H), 7.66 (d, J = 8.8 Hz, 1H), 7.40 (d, J = 3.1 Hz, 1H), 6.73 (dd, J = 1.7, 3.5 Hz, 1H), 2.82 (d, J = 4.5 Hz, 3H). M/Z = 472.1 (M + 1). RT = 1.50: Method B. |
| 65 | 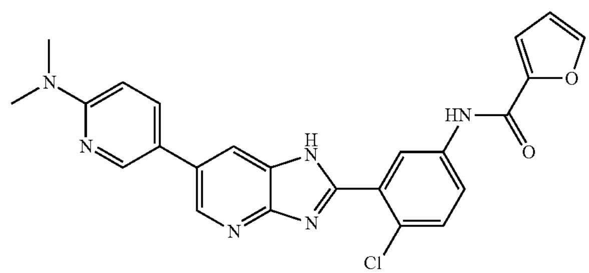 [SMILES: CN(C)c1ccc(-c2cnc3nc(-c4cc(NC(=O)c5ccco5)ccc4Cl)[nH]c3c2)cn1] | M/Z = 459.1 (M + 1). RT = 1.41: Method B. |
| 66 | 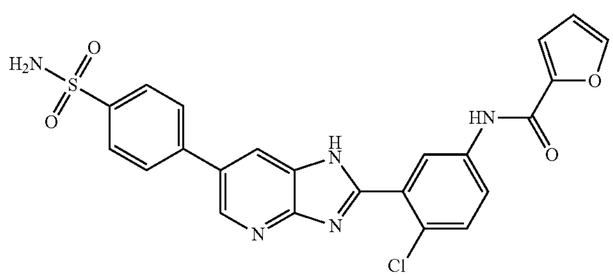 [SMILES: NS(=O)(=O)c1ccc(-c2cnc3nc(-c4cc(NC(=O)c5ccco5)ccc4Cl)[nH]c3c2)cc1] | M/Z = 494.1 (M + 1). RT = 1.42: Method B. |
| 67 | 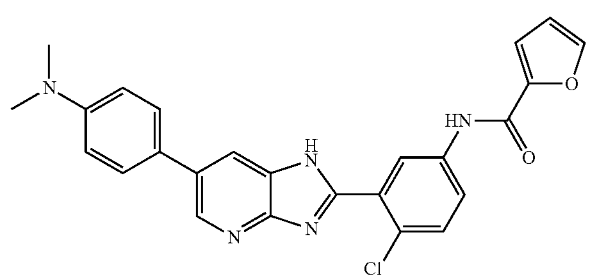 [SMILES: CN(C)c1ccc(-c2cnc3nc(-c4cc(NC(=O)c5ccco5)ccc4Cl)[nH]c3c2)cc1] | M/Z = 458.1 (M + 1). RT = 1.34: Method B. |
| 68 | 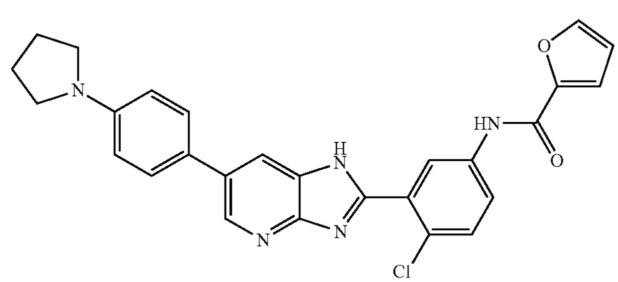 [SMILES: O=C(Nc1ccc(Cl)c(-c2nc3ncc(-c4ccc(N5CCCC5)cc4)cc3[nH]2)c1)c1ccco1] | M/Z = 484.1 (M + 1). RT = 1.07: Method B. |

TABLE II-continued

Listing of the Exemplified Compounds of the Invention

| Ex. No. | Structure | ¹H NMR and/or mass and/or (retention time (mins)) |
|---|---|---|
| 69 | 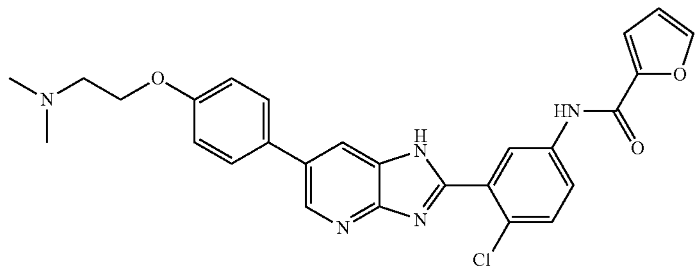 [SMILES: CN(C)CCOc1ccc(-c2cnc3nc(-c4cc(NC(=O)c5ccco5)ccc4Cl)[nH]c3c2)cc1] | M/Z = 502.1 (M + 1). RT = 1.74: Method B. |
| 70 | 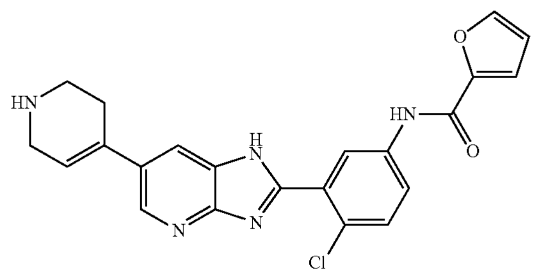 [SMILES: O=C(Nc1ccc(Cl)c(-c2nc3ncc(C4=CCNCC4)cc3[nH]2)c1)c1ccco1] | M/Z = 420.1 (M + 1). RT = 1.18: Method B. |
| 71 | 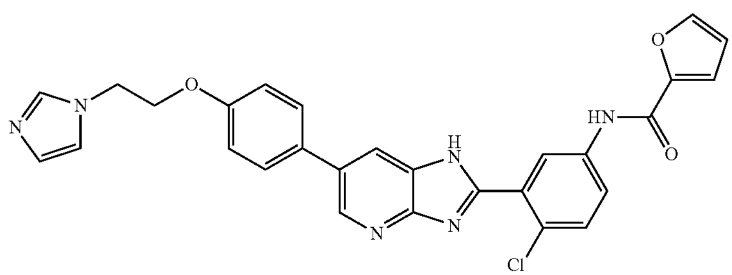 [SMILES: O=C(Nc1ccc(Cl)c(-c2nc3ncc(-c4ccc(OCCn5ccnc5)cc4)cc3[nH]2)c1)c1ccco1] | ¹H NMR (400 MHz, MeOD) δ 8.66 (s, 1H), 8.26 (d, J = 2.8, 1H), 8.20 (s, 1H), 8.00 (dd, J = 2.6, 8.7 Hz, 1H), 7.78 (s, 2H), 7.65 (dd, J = 8.8, 11.4 Hz, 3H), 7.32 (d, J = 3.9 Hz, 1H), 7.28 (s, 1H), 7.09 (d, J = 8.8 Hz, 2H), 7.00 (s, 1H), 6.67 (dd, J = 1.7, 3.6 Hz, 1H), 4.48 (t, J = 4.8 Hz, 2H), 4.35 (t, J = 5.0 Hz, 2H). M/Z = 525.1 (M + 1). RT = 1.30: Method B. |
| 72 | 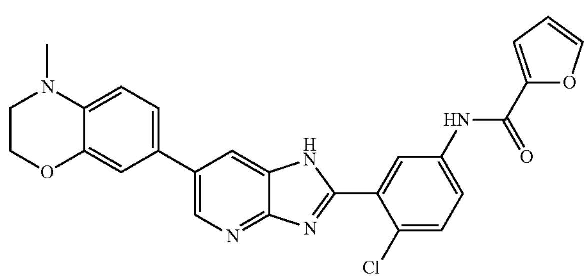 [SMILES: CN1CCOc2cc(-c3cnc4nc(-c5cc(NC(=O)c6ccco6)ccc5Cl)[nH]c4c3)ccc21] | M/Z = 486.1 (M + 1). RT = 1.66: Method B. |
| 73 | 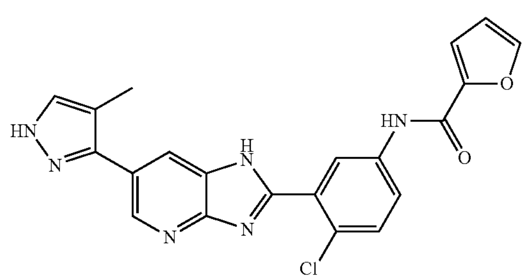 [SMILES: Cc1c[nH]nc1-c1cnc2nc(-c3cc(NC(=O)c4ccco4)ccc3Cl)[nH]c2c1] | M/Z = 419.1 (M + 1). RT = 1.76: Method B. |

TABLE II-continued

Listing of the Exemplified Compounds of the Invention

| Ex. No. | Structure | ¹H NMR and/or mass and/or (retention time (mins)) |
|---|---|---|
| 74 | 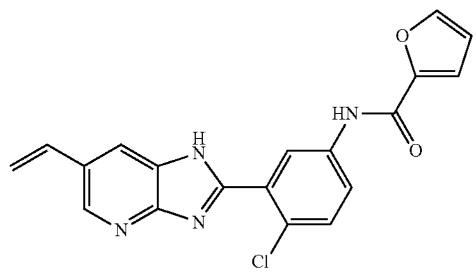 [SMILES: C=Cc1cnc2nc(-c3cc(NC(=O)c4ccco4)ccc3Cl)[nH]c2c1] | ¹H NMR (400 MHz, DMSO) δ 10.52 (s, 1H), 8.54 (s, 1H), 8.34 (s, 2H), 8.00 (d, J = 2.4 Hz, 1H), 7.97 (s, 1H), 7.65 (d, J = 8.8 Hz, 1H), 7.39 (d, J = 3.5 Hz, 1H), 6.92 (dd, J = 11.1, 17.7 Hz, 1H), 6.73 (dd, J = 1.7, 3.4 Hz, 1H), 5.98 (d, J = 17.7 Hz, 1H), 5.34 (d, J = 11.0 Hz, 1H). M/Z = 365.1 (M + 1). RT = 0.82: Method B. |
| 75 | 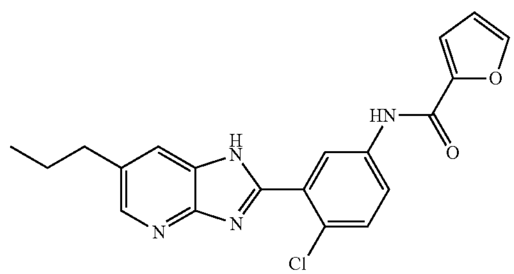 [SMILES: CCCc1cnc2nc(-c3cc(NC(=O)c4ccco4)ccc3Cl)[nH]c2c1] | M/Z = 381.1 (M + 1). RT = 2.96: Method A. |
| 76 | 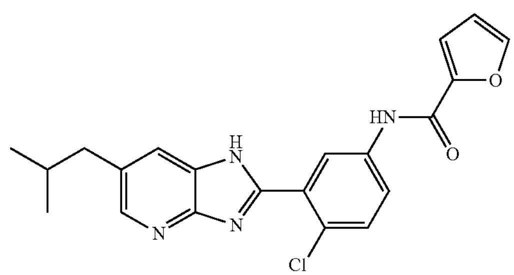 [SMILES: CC(C)Cc1cnc2nc(-c3cc(NC(=O)c4ccco4)ccc3Cl)[nH]c2c1] | M/Z = 395.1 (M + 1). RT = 1.62: Method B. |
| 77 | 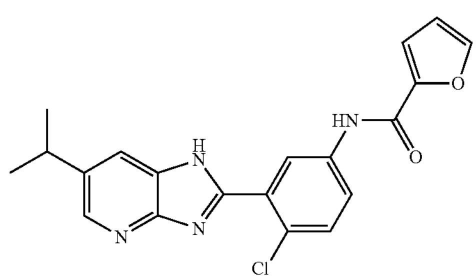 [SMILES: CC(C)c1cnc2nc(-c3cc(NC(=O)c4ccco4)ccc3Cl)[nH]c2c1] | M/Z = 381.1 (M + 1). RT = 1.55: Method B. |
| 78 | 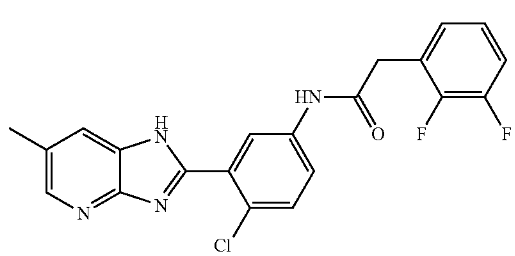 [SMILES: Cc1cnc2nc(-c3cc(NC(=O)Cc4cccc(F)c4F)ccc3Cl)[nH]c2c1] | ¹H NMR (400 MHz, DMSO) δ 10.61 (s, 1H), 8.18 (m, 2H), 8.05-7.68 (m, 2H), 7.61 (d, J = 8.8 Hz, 1H), 7.41-7.29 (m, 1H), 7.28-7.08 (m, 2H), 3.85 (s, 2H), 2.44 (s, 3H). M/Z = 413.1 (M + 1). RT = 1.51: Method B. |

TABLE II-continued

Listing of the Exemplified Compounds of the Invention

| Ex. No. | Structure | $^1$H NMR and/or mass and/or (retention time (mins)) |
|---|---|---|
| 79 | 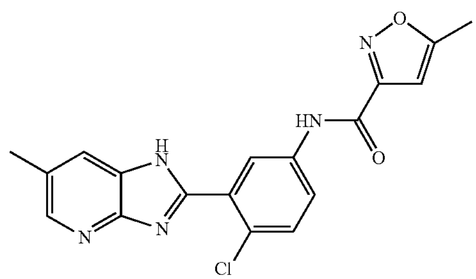 | M/Z = 368.1 (M + 1). RT = 1.34: Method B. |
| 80 | 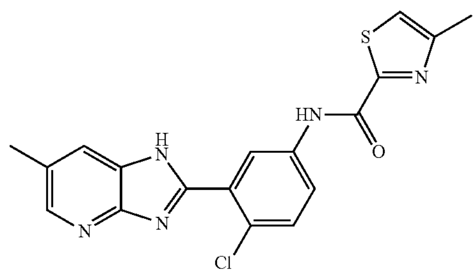 | M/Z = 384.0 (M + 1). RT = 1.44: Method B. |
| 81 | 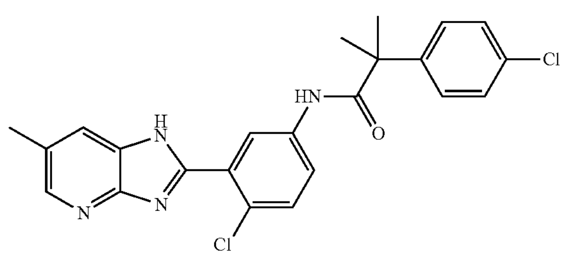 | $^1$H NMR (400 MHz, DMSO) δ 9.48 (s, 1H), 8.40-8.03 (m, 2H), 7.88 (dd, J = 2.6, 8.8 Hz, 2H), 7.56 (d, J = 8.8 Hz, 1H), 7.51-7.30 (m, 4H), 2.44 (s, 3H), 1.57 (s, 6H). M/Z = 349.1 (M + 1). RT = 1.27: Method B. |
| 82 | 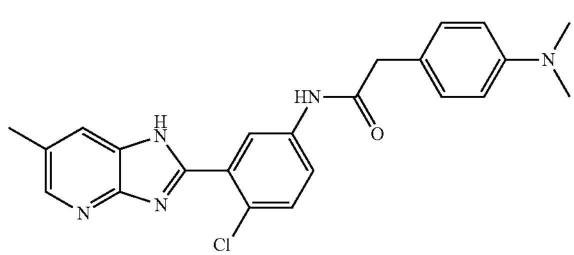 | $^1$H NMR (400 MHz, DMSO) δ 10.41 (s, 1H), 8.27 (s, 1H), 8.17 (s, 1H), 7.87 (s, 1H), 7.78 (dd, J = 2.6, 8.8 Hz, 1H), 7.58 (d, J = 8.8 Hz, 1H), 7.17 (d, J = 8.7 Hz, 2H), 6.72 (d, J = 8.6 Hz, 2H), 3.52 (s, 2H), 2.87 (s, 6H), 2.45 (s, 3H). M/Z = 420.1 (M + 1). RT = 1.13: Method B. |
| 83 | 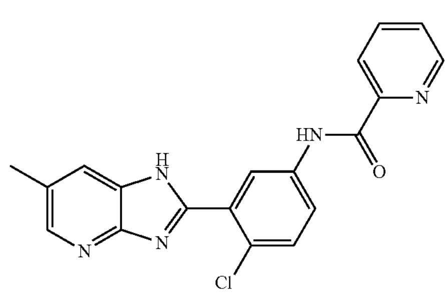 [SMILES: Cc1cnc2nc(-c3cc(NC(=O)c4ccccn4)ccc3Cl)[nH]c2c1] | $^1$H NMR (400 MHz, DMSO) δ 11.02 (s, 1H), 8.85-8.72 (m, 1H), 8.55 (s, 1H), 8.27 (s, 1H), 8.18 (dd, J = 3.9, 4.9 Hz, 1H), 8.13-8.06 (m, 2H), 7.87 (s, 1H), 7.71 (ddd, J = 1.3, 4.8, 7.5 Hz, 1H), 7.66 (d, J = 8.8 Hz, 1H), 2.46 (s, 3H). M/Z = 364.1 (M + 1). RT = 1.36: Method B. |

TABLE II-continued

Listing of the Exemplified Compounds of the Invention

| Ex. No. | Structure | ¹H NMR and/or mass and/or (retention time (mins)) |
|---|---|---|
| 84 | 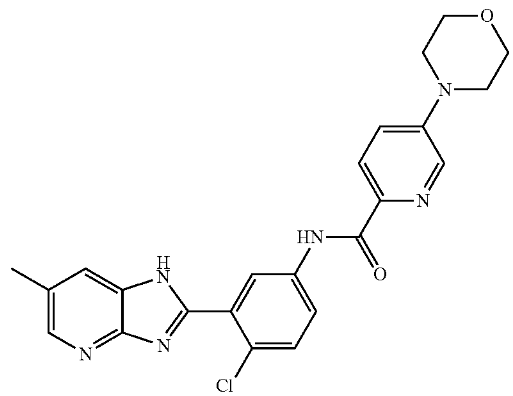 | M/Z = 449.2 (M + 1). RT = 0.80: Method B. |
| 85 | 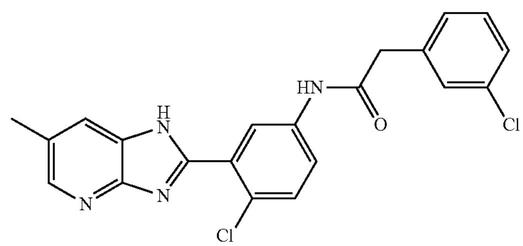 [SMILES: Cc1cnc2nc(-c3cc(NC(=O)Cc4cccc(Cl)c4)ccc3Cl)[nH]c2c1] | M/Z = 411.1 (M + 1). RT = 1.44: Method B. |
| 86 | 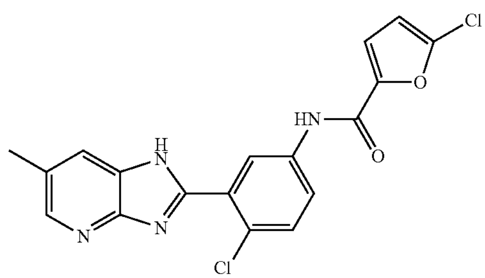 | ¹H NMR (400 MHz, MeOD) δ 8.47 (d, J = 1.1 Hz, 1H), 8.45 (d, J = 2.6 Hz, 1H), 8.28 (s, 1H), 7.92 (dd, J = 2.6, 8.8 Hz, 1H), 7.64 (d, J = 8.8 Hz, 1H), 7.34 (d, J = 3.6 Hz, 1H), 6.57 (d, J = 3.6, 1H), 2.62 (s, 3H). M/Z = 387.1 (M + 1). RT = 1.44: Method B. |
| 87 | 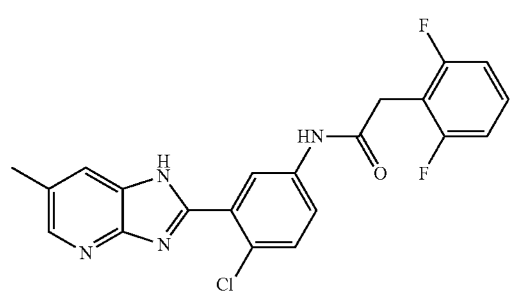 [SMILES: Cc1cnc2nc(-c3cc(NC(=O)Cc4c(F)cccc4F)ccc3Cl)[nH]c2c1] | ¹H NMR (400 MHz, MeOD) δ 8.30 (s, 1H), 8.07 (d, J = 2.6 Hz, 1H), 7.89 (s, 1H), 7.83 (dd, J = 2.6, 8.8 Hz, 1H), 7.57 (d, J = 8.8 Hz, 1H), 7.40-7.29 (m, 1H), 7.05-6.95 (m, 2H), 3.86 (s, 2H), 2.53 (s, 3H). M/Z = 413.1 (M + 1). RT = 1.47: Method B. |
| 88 | 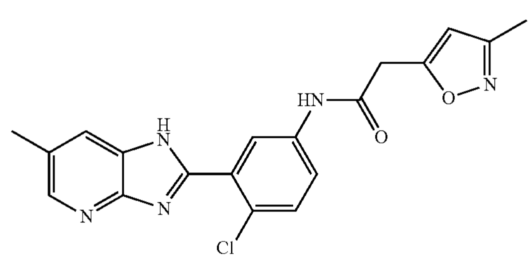 | ¹H NMR (400 MHz, DMSO) δ 10.58 (s, 1H), 8.19 (s, 2H), 7.69 (d, J = 8.8 Hz, 2H),7.55 (d, J = 8.8 Hz, 1H). 6.23 (s, 1H), 3.87 (s, 2H), 2.38 (s, 3H), 2.14 (s, 3H). M/Z = 382.0 (M + 1). RT = 1.26: Method B. |

TABLE II-continued
Listing of the Exemplified Compounds of the Invention
| Ex. No. | Structure | ¹H NMR and/or mass and/or (retention time (mins)) |
|---|---|---|
| 89 | 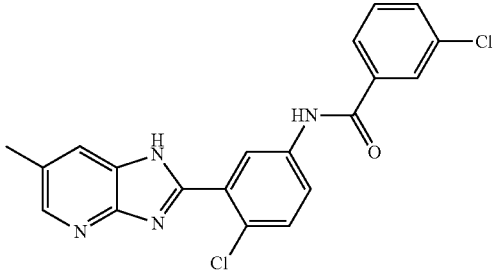 [SMILES: Cc1cnc2nc(-c3cc(NC(=O)c4cccc(Cl)c4)ccc3Cl)[nH]c2c1] | M/Z = 397.0 (M + 1). RT = 1.6: Method B. |
| 90 | 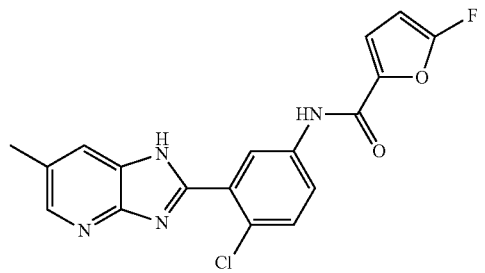 [SMILES: Cc1cnc2nc(-c3cc(NC(=O)c4ccc(F)o4)ccc3Cl)[nH]c2c1] | M/Z = 371.0 (M + 1). RT = 1.32: Method B. |
| 91 | 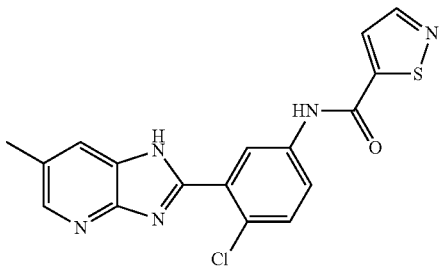 | ¹H NMR (400 MHz, DMSO) δ 8.76 (d, J = 1.8 Hz, 1H), 8.32 (s, 1H), 8.26 (s, 1H), 8.16 (d, J = 1.7 Hz, 1H), 7.99 (dd, J = 2.6, 8.8 Hz, 1H), 7.86 (s, 1H), 7.69 (d, J = 8.8 Hz, 1H), 2.45 (s, 3H). M/Z = 370.1 (M + 1). RT = 1.30: Method B. |
| 92 | 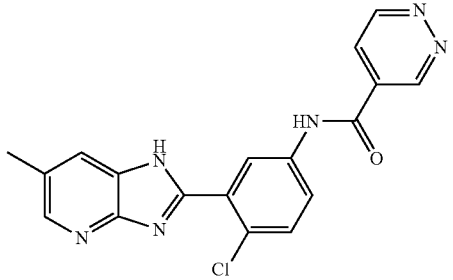 [SMILES: Cc1cnc2nc(-c3cc(NC(=O)c4ccnnc4)ccc3Cl)[nH]c2c1] | M/Z = 365.1 (M + 1). RT = 1.14: Method B. |
| 93 | 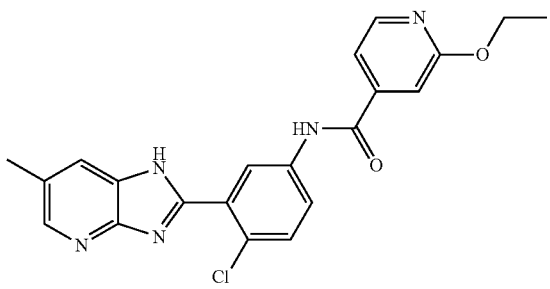 [SMILES: CCOc1cc(C(=O)Nc2ccc(Cl)c(-c3nc4ncc(C)cc4[nH]3)c2)ccn1] | M/Z = 408.2 (M + 1). RT = 1.55: Method B. |

TABLE II-continued

Listing of the Exemplified Compounds of the Invention

| Ex. No. | Structure | ¹H NMR and/or mass and/or (retention time (mins)) |
|---|---|---|
| 94 | 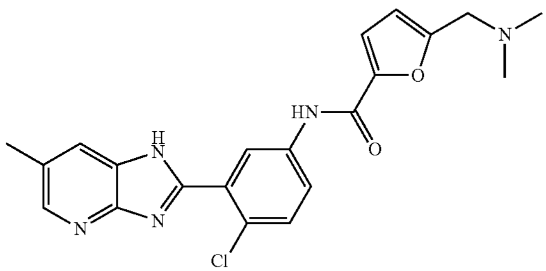 | M/Z = 410.2 (M + 1). RT = 1.08: Method B. |
| 95 | 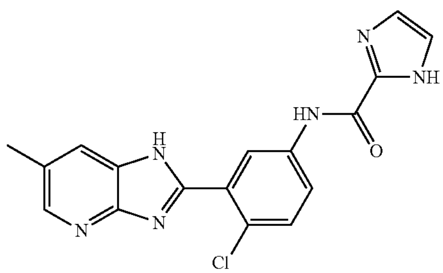 [SMILES: Cc1cnc2nc(-c3cc(NC(=O)c4ncc[nH]4)ccc3Cl)[nH]c2c1] | M/Z = 353.1 (M + 1). RT = 1.12: Method B. |
| 96 | 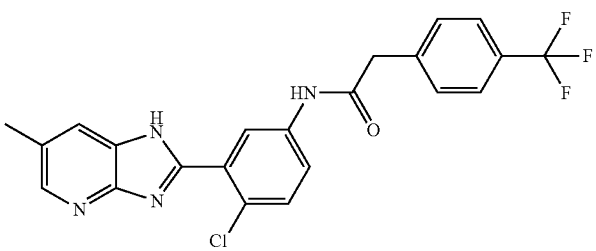 [SMILES: Cc1cnc2nc(-c3cc(NC(=O)Cc4ccc(C(F)(F)F)cc4)ccc3Cl)[nH]c2c1] | ¹H NMR (400 MHz, DMSO) δ 10.60 (s, 1H), 8.26 (s, 2H), 7.78 (d, J = 6.8 Hz, 2H), 7.71 (d, J = 8.2 Hz, 2H), 7.62-7.55 (m, 3H), 3.82 (s, 2H), 2.45 (s, 3H). M/Z = 445.1 (M + 1). RT = 1.67: Method B. |
| 97 | 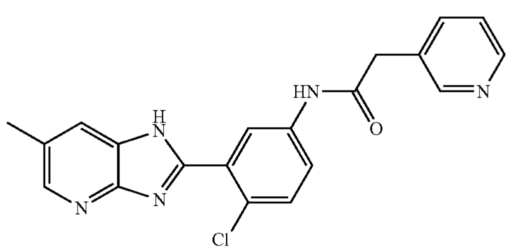 | ¹H NMR (400 MHz, DMSO) δ 10.52 (s, 1H), 8.45 (d, 2H), 8.15 (d, 2H), 7.71 (m, 3H), 7.53 (d, J = 8.8 Hz, 1H), 7.32 (s, 1H), 3.69 (s, 2H), 2.37 (s, 3H). M/Z = 368.1 (M + 1). RT = 1.91: Method B. |
| 98 | 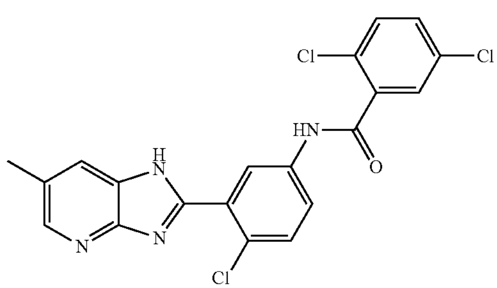 [SMILES: Cc1cnc2nc(-c3cc(NC(=O)c4cc(Cl)ccc4Cl)ccc3Cl)[nH]c2c1] | M/Z = 431.1 (M + 1). RT = 1.60: Method B |

TABLE II-continued
Listing of the Exemplified Compounds of the Invention
| Ex. No. | Structure | ¹H NMR and/or mass and/or (retention time (mins)) |
|---|---|---|
| 99 | 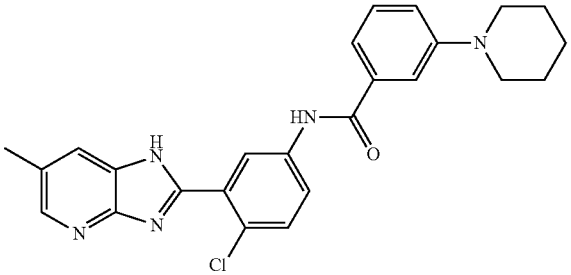 [SMILES: Cc1cnc2nc(-c3cc(NC(=O)c4cccc(N5CCCCC5)c4)ccc3Cl)[nH]c2c1] | ¹H NMR (400 MHz, DMSO) δ 10.45 (s, 1H), 8.47-8.17 (m, 2H), 8.07-7.73 (m, 2H), 7.65 (d, J = 8.8 Hz, 1H), 7.47 (s, 1H), 7.35 (d, J = 5.7 Hz, 2H), 7.22-7.08 (m, 1H), 3.27-3.18 (m, 4H), 2.46 (s, 3H), 1.70-1.60 (m, 4H), 1.60-1.50 (m, 2H). M/Z = 446.2 (M + 1). RT = 1.21: Method B. |
| 100 | 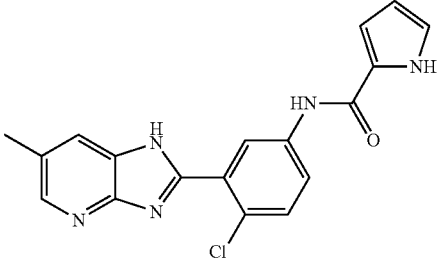 [SMILES: Cc1cnc2nc(-c3cc(NC(=O)c4ccc[nH]4)ccc3Cl)[nH]c2c1] | ¹H NMR (400 MHz, DMSO) δ 11.66 (s, 1H), 10.01 (s, 1H), 8.35-8.20 (m, 2H), 8.00-7.90 (m, 2H), 7.57 (d, J = 8.8 Hz, 1H), 7.05 (d, J = 3.8 Hz, 1H), 6.93 (dd, J = 2.7, 4.0 Hz, 1H), 6.18-6.06 (m, 1H), 2.41 (s, 3H). M/Z = 352.1 (M + 1). RT = 1.31: Method B. |
| 101 | 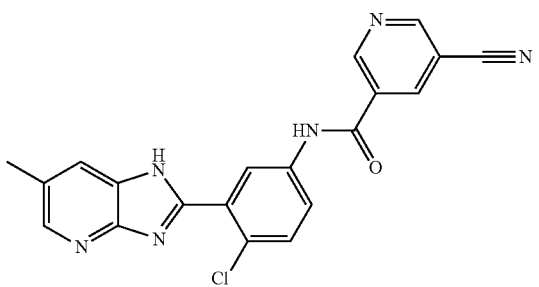 [SMILES: Cc1cnc2nc(-c3cc(NC(=O)c4cncc(C#N)c4)ccc3Cl)[nH]c2c1] | M/Z = 389.1 (M + 1). RT = 2.64: Method A. |
| 102 | 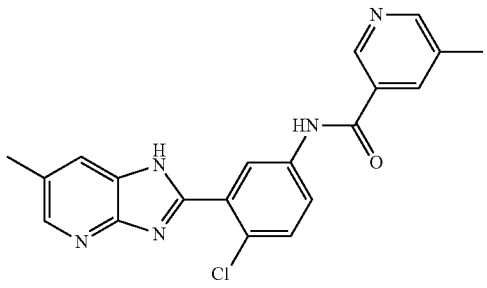 | M/Z = 378.1 (M + 1). RT = 2.70: Method A. |
| 103 | 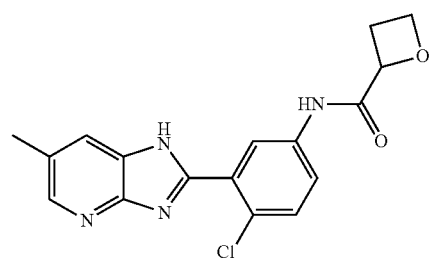 [SMILES: Cc1cnc2nc(-c3cc(NC(=O)C4CCO4)ccc3Cl)[nH]c2c1] | M/Z = 343.1 (M + 1). RT = 2.34: Method A. |

TABLE II-continued

Listing of the Exemplified Compounds of the Invention

| Ex. No. | Structure | $^1$H NMR and/or mass and/or (retention time (mins)) |
|---|---|---|
| 104 | 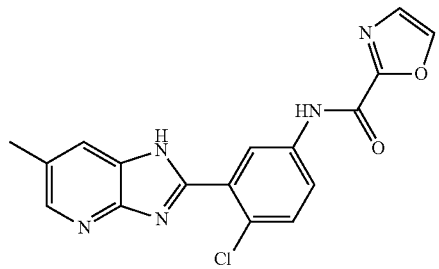 [SMILES: Cc1cnc2nc(-c3cc(NC(=O)c4ncco4)ccc3Cl)[nH]c2c1] | M/Z = 354.1 (M + 1). RT = 1.18: Method B. |
| 105 | 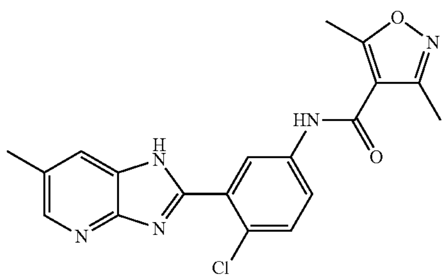 | M/Z = 382.1 (M + 1). RT = 1.29: Method B. |
| 106 | 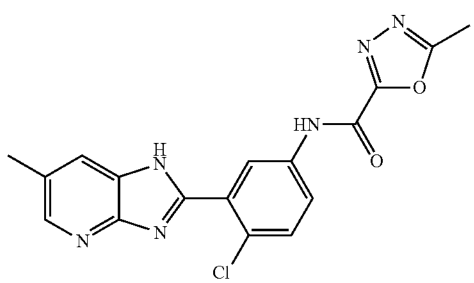 | $^1$H NMR (400 MHz, DMSO) δ 8.26 (s, 1H), 8.15 (s, 1H), 7.81 (d, J = 8.8 Hz, 1H), 7.75 (s, 1H), 7.52 (d, J = 8.7 Hz, 1H), 2.54 (s, 3H), 2.37 (s, 3H). M/Z = 369.1 (M + 1). RT = 0.65: Method B. |
| 107 | 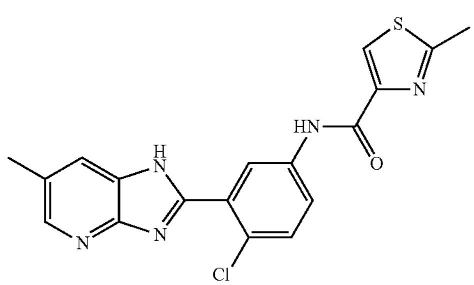 | $^1$H NMR (400 MHz, DMSO) δ 10.55 (s, 1H), 8.46 (d, J = 2.6 Hz, 1H), 8.37-8.29 (m, 1H), 8.23 (d, J = 1.7 Hz, 1H), 8.01 (dd, J = 2.7, 8.8 Hz, 1H), 7.82 (s, 1H), 7.61 (d, J = 8.8 Hz, 1H), 2.78 (s, 3H), 2.44 (s, 3H). M/Z = 384.0 (M + 1). RT = 1.23: Method B. |
| 108 | 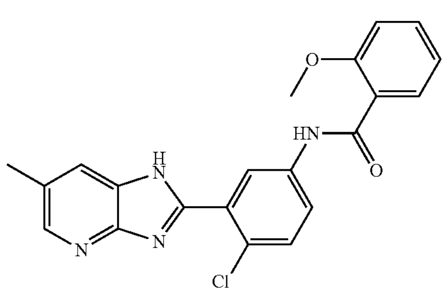 [SMILES: COc1ccccc1C(=O)Nc1ccc(Cl)c(-c2nc3ncc(C)cc3[nH]2)c1] | $^1$H NMR (400 MHz, DMSO) δ 10.46 (s, 1H), 8.37 (d, J = 5.1 Hz, 2H), 8.01 (s, 1H), 7.97-7.85 (m, 1H), 7.70-7.57 (m, 2H), 7.59-7.44 (m, 1H), 7.20 (d, J = 8.1 Hz, 1H), 7.13-6.97 (m, 1H), 2.49 (s, 3H). M/Z = 393.1 (M + 1). RT = 0.54: Method B. |

TABLE II-continued
Listing of the Exemplified Compounds of the Invention
| Ex. No. | Structure | ¹H NMR and/or mass and/or (retention time (mins)) |
|---|---|---|
| 109 | 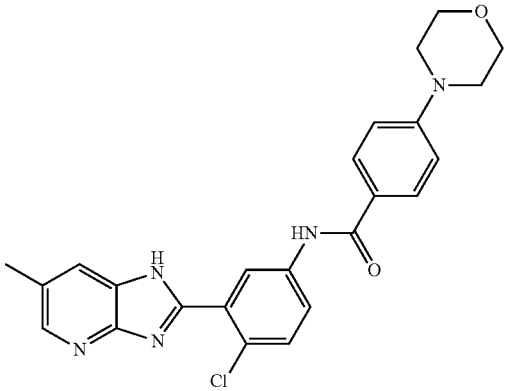 [SMILES: Cc1cnc2nc(-c3cc(NC(=O)c4ccc(N5CCOCC5)cc4)ccc3Cl)[nH]c2c1] | M/Z = 448.14 (M + 1). RT = 1.43: Method B. |
| 110 | 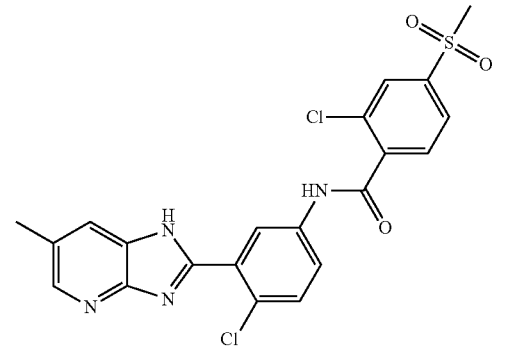 [SMILES: Cc1cnc2nc(-c3cc(NC(=O)c4ccc(S(C)(=O)=O)cc4Cl)ccc3Cl)[nH]c2c1] | M/Z = 475.0 (M + 1). RT = 1.24: Method B. |
| 111 | 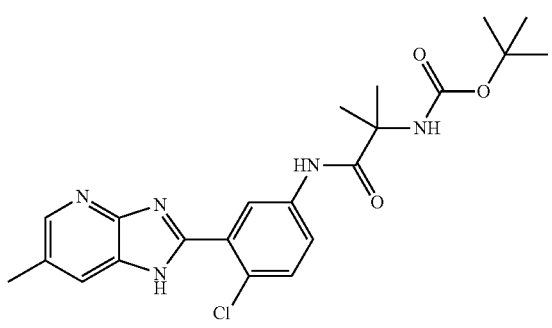 [SMILES: Cc1cnc2nc(-c3cc(NC(=O)C(C)(C)NC(=O)OC(C)(C)C)ccc3Cl)[nH]c2c1] | M/Z = 444.1 (M + 1). RT = 1.42: Method B. |
| 112 | 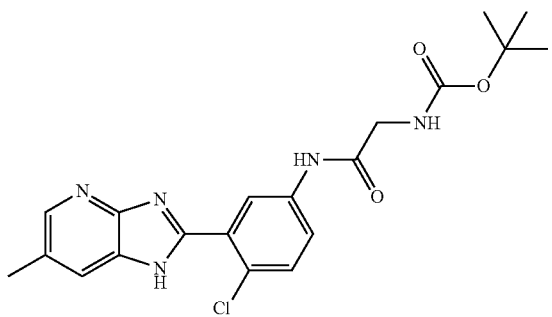 [SMILES: Cc1cnc2nc(-c3cc(NC(=O)CNC(=O)OC(C)(C)C)ccc3Cl)[nH]c2c1] | M/Z = 416.1 (M + 1). RT = 1.36: Method B. |

TABLE II-continued

Listing of the Exemplified Compounds of the Invention

| Ex. No. | Structure | ¹H NMR and/or mass and/or (retention time (mins)) |
|---|---|---|
| 113 | 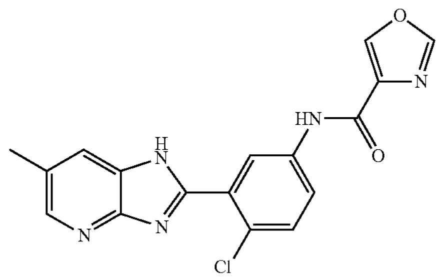 [SMILES: Cc1cnc2nc(-c3cc(NC(=O)c4cocn4)ccc3Cl)[nH]c2c1] | ¹H NMR (400 MHz, DMSO) δ 10.55 (s, 1H), 8.87 (d, J = 0.9 Hz, 1H), 8.66 (d, J = 0.9 Hz, 1H), 8.41 (d, J = 2.4 Hz, 1H), 8.26 (d, J = 1.6 Hz, 1H), 8.00 (dd, J = 2.6, 8.8 Hz, 1H), 7.85 (s, 1H), 7.64 (d, J = 8.8 Hz, 1H), 2.45 (s, 3H). M/Z = 354.1 (M + 1). RT = 0.65: Method B. |
| 114 | 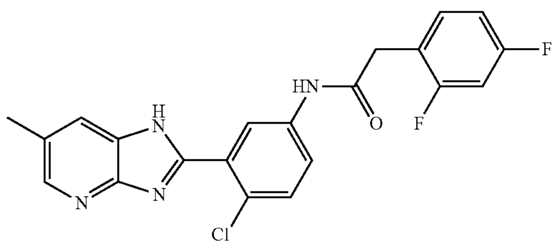 [SMILES: Cc1cnc2nc(-c3cc(NC(=O)Cc4ccc(F)cc4F)ccc3Cl)[nH]c2c1] | ¹H NMR (400 MHz, DMSO) δ 10.57 (s, 1H), 8.26 (s, 2H), 7.80 (s, 1H), 7.81-7.74 (m, 1H), 7.60 (d, J = 8.8, 1H), 7.46 (td, J = 6.8, 8.6 Hz, 1H), 7.29-7.19 (m, 1H), 7.07 (ddd, J = 2.5, 5.5, 8.5 Hz, 1H), 3.77 (s, 2H), 2.44 (s, 3H). M/Z = 413.1 (M + 1). RT = 0.86: Method B. |
| 115 | 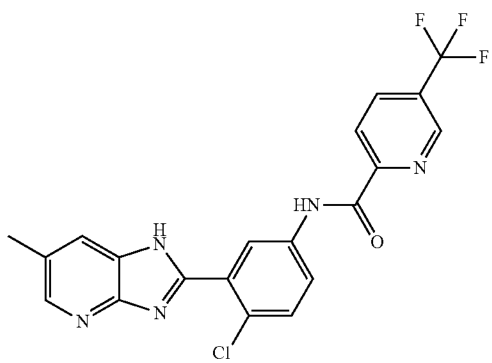 [SMILES: Cc1cnc2nc(-c3cc(NC(=O)c4ccc(C(F)(F)F)cn4)ccc3Cl)[nH]c2c1] | ¹H NMR (400 MHz, DMSO) δ 11.20 (d, J = 6.7 Hz, 1H), 9.14 (s, 1H), 8.64-8.47 (m, 2H), 8.36 (d, J = 8.2 Hz, 1H), 8.28 (dd, J = 1.5 Hz,1H), 8.10 (dd, J = 2.4, 8.8 Hz, 1H), 7.87 (d, 1H), 7.69 (dd, J = 5.7, 8.8 Hz, 1H), 2.46 (d, J = 4.3 Hz, 3H). M/Z = 432.1 (M + 1). RT = 0.94: Method B. |
| 116 | 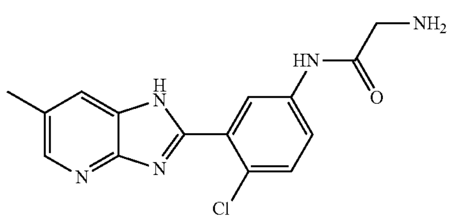 [SMILES: Cc1cnc2nc(-c3cc(NC(=O)CN)ccc3Cl)[nH]c2c1] | M/Z = 316.1 (M + 1). RT = 0.99: Method B. |
| 117 | 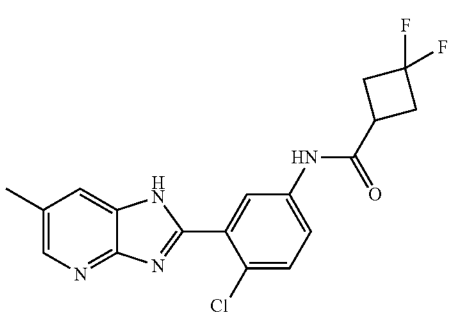 [SMILES: Cc1cnc2nc(-c3cc(NC(=O)C4CC(F)(F)C4)ccc3Cl)[nH]c2c1] | M/Z = 377.1 (M + 1). RT = 1.40: Method B. |

TABLE II-continued

Listing of the Exemplified Compounds of the Invention

| Ex. No. | Structure | ¹H NMR and/or mass and/or (retention time (mins)) |
|---|---|---|
| 118 | 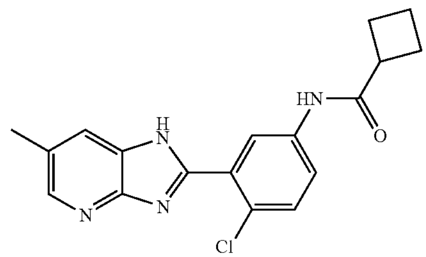 [SMILES: Cc1cnc2nc(-c3cc(NC(=O)C4CCC4)ccc3Cl)[nH]c2c1] | M/Z = 341.1 (M + 1). RT = 1.32: Method B. |
| 119 | 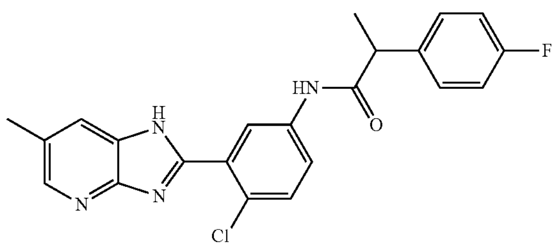 [SMILES: Cc1cnc2nc(-c3cc(NC(=O)C(C)c4ccc(F)cc4)ccc3Cl)[nH]c2c1] | ¹H NMR (400 MHz, DMSO) δ 10.43 (s, 1H), 8.23 (d, J = 1.5 Hz, 1H), 8.18 (d, J = 2.2 Hz, 1H), 7.86-7.80 (m, 1H), 7.77 (dd, J = 2.6, 8.8 Hz, 1H), 7.56 (d, J = 8.8 Hz, 1H), 7.46-7.39 (m, 2H), 7.21-7.11 (m, 2H), 3.86 (q, J = 6.9 Hz, 1H), 2.44 (s, 3H), 1.42 (d, J = 7.0 Hz, 3H). M/Z = 409.1 (M + 1). RT = 1.58: Method B. |
| 120 | 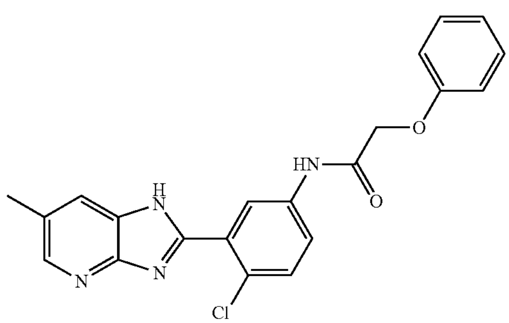 [SMILES: Cc1cnc2nc(-c3cc(NC(=O)COc4ccccc4)ccc3Cl)[nH]c2c1] | ¹H NMR (400 MHz, DMSO) δ 10.36 (s, 1H), 8.19 (s, 2H), 7.79 (dd, J = 2.6, 8.8 Hz, 2H), 7.55 (d, J = 8.8, 1H), 7.26 (dd, J = 7.4, 8.7 Hz, 2H), 6.93 (dd, J = 7.6, 17.8, Hz 3H), 4.67 (s, 2H), 2.38 (s, 3H). M/Z = 393.1 (M + 1). RT = 0.85: Method B. |
| 121 | 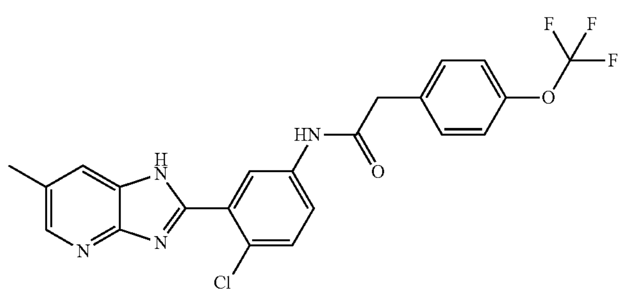 [SMILES: Cc1cnc2nc(-c3cc(NC(=O)Cc4ccc(OC(F)(F)F)cc4)ccc3Cl)[nH]c2c1] | ¹H NMR (400 MHz, DMSO) δ 10.49 (s, 1H), 8.19 (s, 1H), 8.11 (s, 1H), 7.78 (s, 1H), 7.71 (dd, J = 2.6, 8.8 Hz, 1H), 7.53 (d, J = 8.8 Hz, 1H), 7.40 (d, J = 8.7 Hz, 2H), 7.27 (d, J = 8.0 Hz, 2H), 3.67 (s, 2H), 2.38 (s, 3H). M/Z = 461.1 (M + 1). RT = 1.71: Method B. |
| 122 | 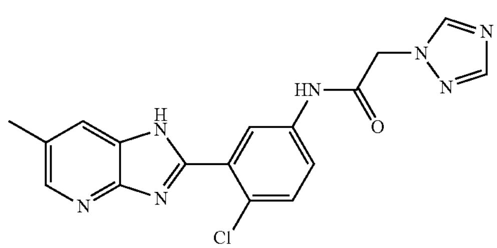 | ¹H NMR (400 MHz, DMSO) δ 10.69 (s, 1H), 8.50 (s, 1H), 8.09 (d, 2H), 7.94 (s, 1H), 7.77 (d, 2H), 7.56 (d, J = 8.7 Hz, 1H), 5.12 (s, 2H), 2.37 (s, 3H). M/Z = 368.1 (M + 1). RT = 1.08: Method B. |

TABLE II-continued

Listing of the Exemplified Compounds of the Invention

| Ex. No. | Structure | ¹H NMR and/or mass and/or (retention time (mins)) |
|---|---|---|
| 123 | 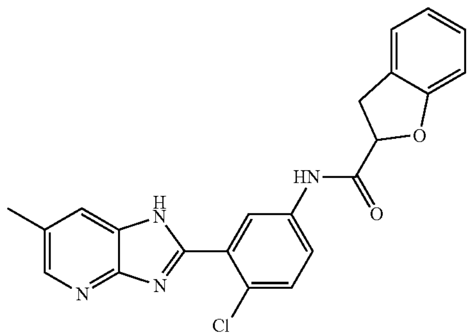 [SMILES: Cc1cnc2nc(-c3cc(NC(=O)C4Cc5ccccc5O4)ccc3Cl)[nH]c2c1] | M/Z = 405.1 (M + 1). RT = 1.53: Method B. |
| 124 | 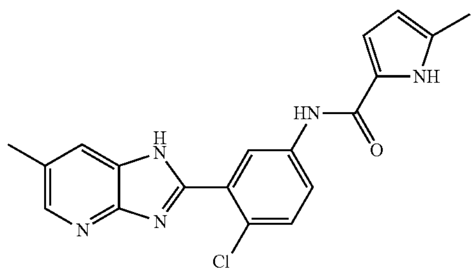 | M/Z = 366.1 (M + 1). RT = 1.40: Method B. |
| 125 | 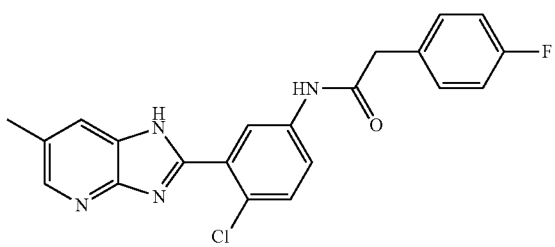 [SMILES: Cc1cnc2nc(-c3cc(NC(=O)Cc4ccc(F)cc4)ccc3Cl)[nH]c2c1] | M/Z = 395.1 (M + 1). RT = 1.49: Method B. |
| 126 | 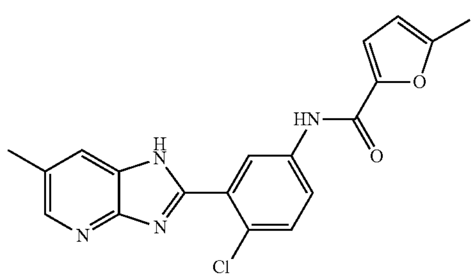 | M/Z = 367.1 (M + 1). RT = 1.33: Method B. |
| 127 | 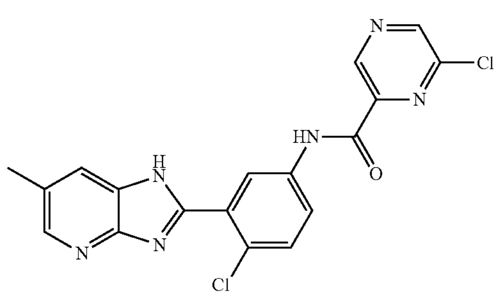 [SMILES: Cc1cnc2nc(-c3cc(NC(=O)c4cncc(Cl)n4)ccc3Cl)[nH]c2c1] | ¹H NMR (400 MHz, DMSO) δ 11.04 (s, 1H), 9.26 (s, 1H), 9.10 (s, 1H), 8.49 (s, 1H), 8.29 (s, 1H), 8.10 (dd, J = 2.7, 8.8 Hz, 1H), 7.90 (s, 1H), 7.70 (d, J = 8.8 Hz, 1H), 2.46 (s, 3H). M/Z = 399.1 (M + 1). RT = 1.40: Method B. |

TABLE II-continued
Listing of the Exemplified Compounds of the Invention
| Ex. No. | Structure | ¹H NMR and/or mass and/or (retention time (mins)) |
|---|---|---|
| 128 | 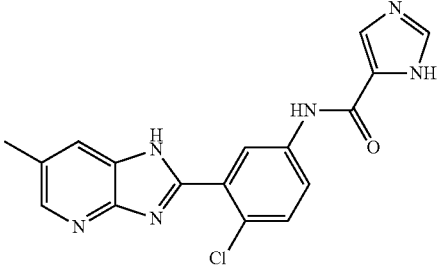 [SMILES: Cc1cnc2nc(-c3cc(NC(=O)c4cnc[nH]4)ccc3Cl)[nH]c2c1] | M/Z = 353.1 (M + 1). RT = 1.06: Method B. |
| 129 | 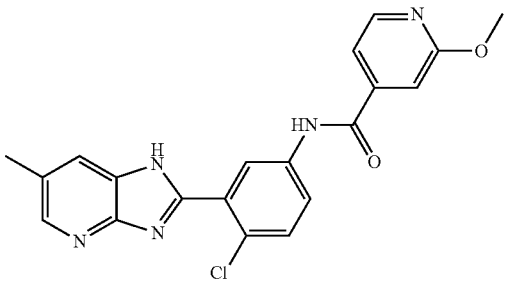 | M/Z = 394.1 (M + 1). RT = 1.48: Method B. |
| 130 | 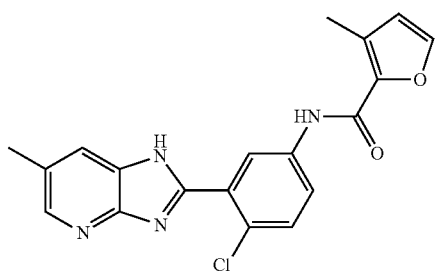 [SMILES: Cc1cnc2nc(-c3cc(NC(=O)c4occc4C)ccc3Cl)[nH]c2c1] | M/Z = 367.1 (M + 1). RT = 1.41: Method B. |
| 131 | 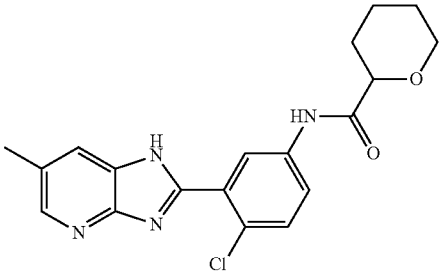 [SMILES: Cc1cnc2nc(-c3cc(NC(=O)C4CCCCO4)ccc3Cl)[nH]c2c1] | M/Z = 371.1 (M + 1). RT = 0.77: Method B. |
| 132 | 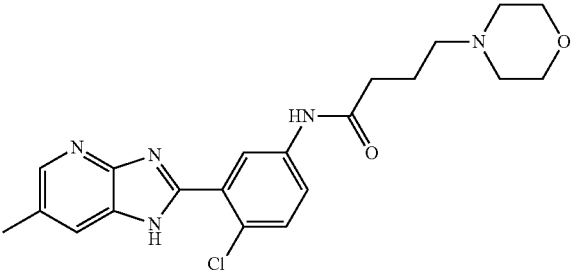 [SMILES: Cc1cnc2nc(-c3cc(NC(=O)CCCN4CCOCC4)ccc3Cl)[nH]c2c1] | M/Z = 414.1 (M + 1). RT = 1.31: Method B. |

TABLE II-continued

Listing of the Exemplified Compounds of the Invention

| Ex. No. | Structure | ¹H NMR and/or mass and/or (retention time (mins)) |
|---|---|---|
| 133 | 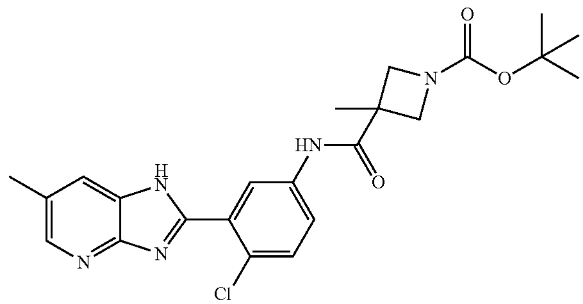 [SMILES: Cc1cnc2nc(-c3cc(NC(=O)C4(C)CN(C(=O)OC(C)(C)C)C4)ccc3Cl)[nH]c2c1] | M/Z = 456.1 (M + 1). RT = 1.52: Method B. |
| 134 | 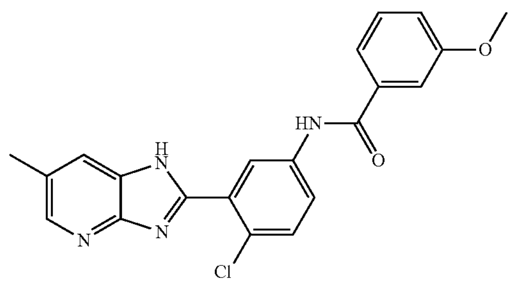 | ¹H NMR (400 MHz, DMSO) δ 10.54 (s, 1H), 8.50-8.17 (m, 2H), 8.02 (dd, J = 2.5, 8.8 Hz, 1H), 7.98-7.69 (m, 1H), 7.66 (d, J = 8.8 Hz, 1H), 7.58 (d, J = 7.8 Hz, 1H), 7.54-7.50 (m, 1H), 7.47 (t, J = 7.9 Hz, 1H), 7.19 (ddd, J = 0.8, 2.6, 8.2 Hz, 1H), 3.85 (s, 3H), 2.46 (s, 3H). M/Z = 393.1 (M + 1). RT = 1.47: Method B. |
| 135 | 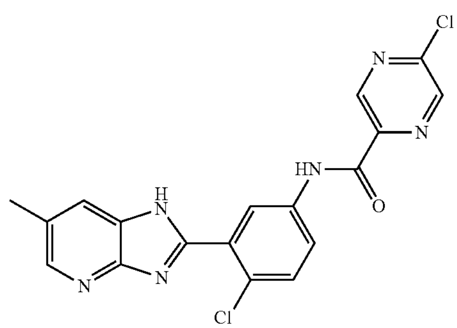 [SMILES: Cc1cnc2nc(-c3cc(NC(=O)c4cnc(Cl)cn4)ccc3Cl)[nH]c2c1] | M/Z = 399.1 (M + 1). RT = 1.51: Method B. |
| 136 | 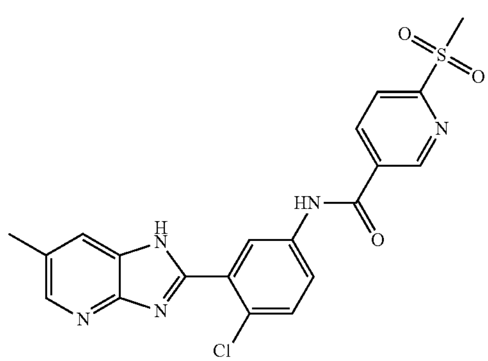 | M/Z = 442.1 (M + 1). RT = 1.25: Method B. |

TABLE II-continued

Listing of the Exemplified Compounds of the Invention

| Ex. No. | Structure | ¹H NMR and/or mass and/or (retention time (mins)) |
|---|---|---|
| 137 | 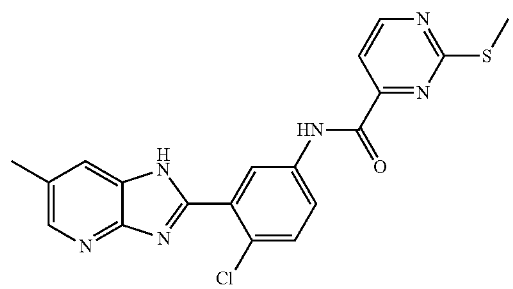 | M/Z = 411.1 (M + 1). RT = 2.94: Method A. |
| 138 | 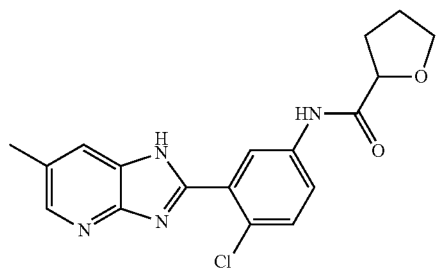 [SMILES: Cc1cnc2nc(-c3cc(NC(=O)C4CCCO4)ccc3Cl)[nH]c2c1] | M/Z = 357.1 (M + 1). RT = 1.19: Method B. |
| 139 | 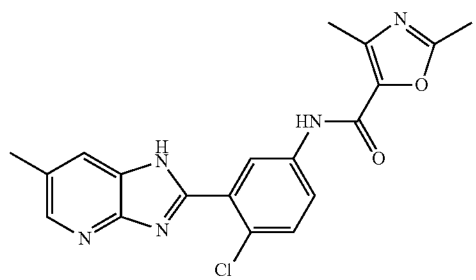 | M/Z = 382.1 (M + 1). RT = 2.20: Method A. |
| 140 | 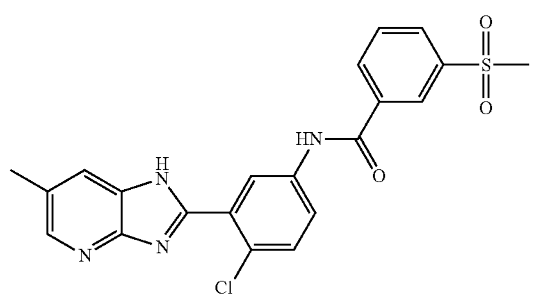 | ¹H NMR (400 MHz, DMSO) δ 10.84 (s, 1H), 8.52 (s, 1H), 8.47-8.21 (m, 3H), 8.17 (d, J = 8.3 Hz, 1H), 8.04 (d, J = 6.5 Hz, 1H), 7.98-7.74 (m, 2H), 7.69 (d, J = 8.8 Hz, 1H), 3.31 (d, J = 4.0 Hz, 3H), 2.46 (s, 3H). M/Z = 441.0 (M + 1). RT = 1.34: Method B. |
| 141 | 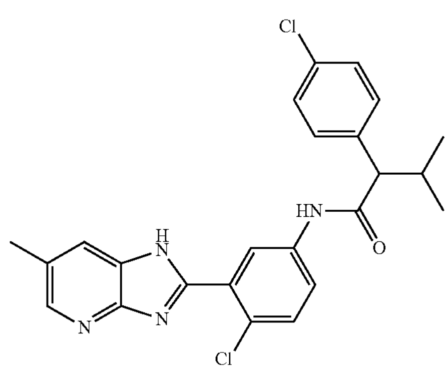 [SMILES: Cc1cnc2nc(-c3cc(NC(=O)C(c4ccc(Cl)cc4)C(C)C)ccc3Cl)[nH]c2c1] | ¹H NMR (400 MHz, DMSO) δ 10.48 (d, J = 7.8 Hz, 1H), 8.33-8.08 (m, 2H), 7.95-7.66 (m, 2H), 7.57 (dd, J = 4.5, 8.7 Hz, 1H), 7.41 (s, 4H), 3.32-3.23 (m, 1H), 2.45 (s, 3H), 2.38-2.26 (m, 1H), 1.02 (d, J = 6.4 Hz, 3H), 0.68 (d, J = 6.7 Hz, 3H). M/Z = 453.1 (M + 1). RT = 1.47: Method B. |

TABLE II-continued

Listing of the Exemplified Compounds of the Invention

| Ex. No. | Structure | ¹H NMR and/or mass and/or (retention time (mins)) |
|---|---|---|
| 142 | 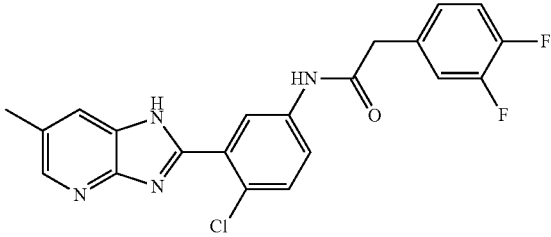 [SMILES: Cc1cnc2nc(-c3cc(NC(=O)Cc4ccc(F)c(F)c4)ccc3Cl)[nH]c2c1] | M/Z = 413.1 (M + 1). RT = 0.88: Method B. |
| 143 | 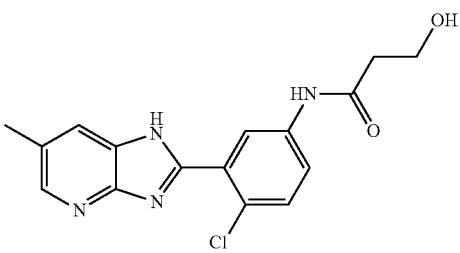 [SMILES: Cc1cnc2nc(-c3cc(NC(=O)CCO)ccc3Cl)[nH]c2c1] | M/Z = 331.1 (M + 1). RT = 1.07: Method B. |
| 144 | 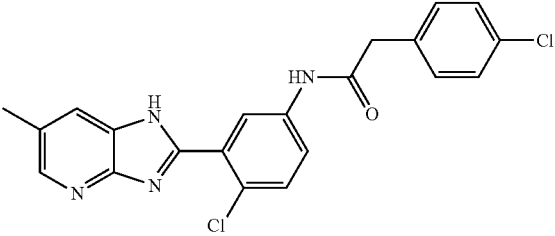 [SMILES: Cc1cnc2nc(-c3cc(NC(=O)Cc4ccc(Cl)cc4)ccc3Cl)[nH]c2c1] | ¹H NMR (400 MHz, MeOD) δ 8.19 (s, 1H), 7.97 (s, 1H), 7.82-7.65 (m, 2H), 7.45 (d, J = 8.8 Hz, 1H), 7.28-7.20 (m, 4H), 3.60 (s, 2H), 2.42 (s, 3H). M/Z = 411.1 (M + 1). RT = 1.59: Method B. |
| 145 | 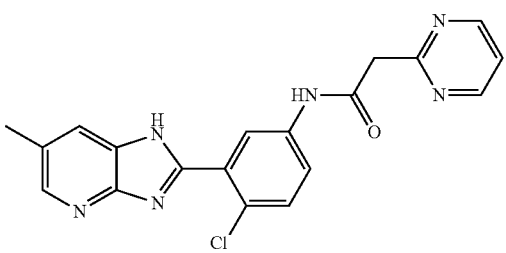 [SMILES: Cc1cnc2nc(-c3cc(NC(=O)Cc4ncccn4)ccc3Cl)[nH]c2c1] | ¹H NMR (400 MHz, DMSO) δ 10.56 (s, 1H), 8.72 (d, J = 4.9 Hz, 2H), 8.18 (s, 2H), 7.96-7.61 (m, 2H), 7.53 (d, J = 8.8 Hz, 1H), 7.35 (t, J = 4.9 Hz, 1H), 3.96 (s, 2H), 2.37 (s, 3H). M/Z = 379.1 (M + 1). RT = 1.12: Method B. |
| 146 | 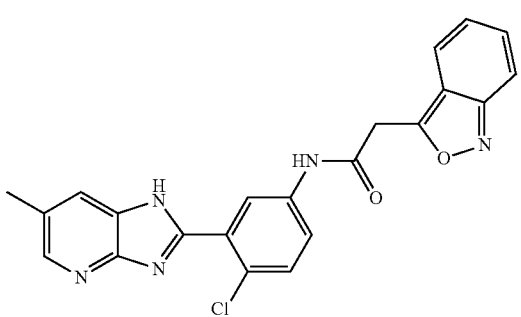 [SMILES: Cc1cnc2nc(-c3cc(NC(=O)Cc4onc5ccccc45)ccc3Cl)[nH]c2c1] | ¹H NMR (400 MHz, DMSO) δ 10.78 (s, 1H), 8.18 (s, 1H), 8.13 (s, 1H), 7.85 (d, J = 7.9 Hz, 1H), 7.77 (s, 1H), 7.73-7.65 (m, 2H), 7.63-7.51 (m, 2H), 7.34 (t, J = 7.5 Hz, 1H), 4.16 (s, 2H), 2.37 (s, 3H). M/Z = 418.1 (M + 1). RT = 1.52: Method B. |

TABLE II-continued

Listing of the Exemplified Compounds of the Invention

| Ex. No. | Structure | $^1$H NMR and/or mass and/or (retention time (mins)) |
|---|---|---|
| 147 | 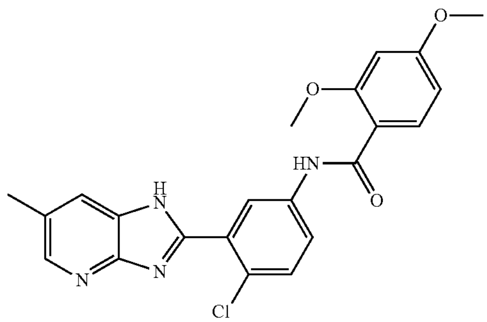 | $^1$H NMR (400 MHz, DMSO) δ 10.20 (s, 1H), 8.27 (s, 2H), 7.95 (dd, J = 2.6, 8.8 Hz, 1H), 7.87 (s, 1H), 7.74 (d, J = 8.6 Hz, 1H), 7.62 (d, J = 8.8 Hz, 1H), 6.72 (d, J = 2.3 Hz, 1H), 6.68 (dd, J = 2.3, 8.6 Hz, 1H), 3.95 (s, 3H), 3.85 (s, 3H), 2.46 (s, 3H). M/Z = 423.1 (M + 1). RT = 1.55: Method B. |
| 148 | 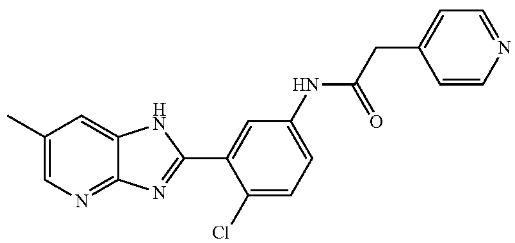 [SMILES: Cc1cnc2nc(-c3cc(NC(=O)Cc4ccncc4)ccc3Cl)[nH]c2c1] | M/Z = 378.1 (M + 1). RT = 1.04: Method B. |
| 149 | 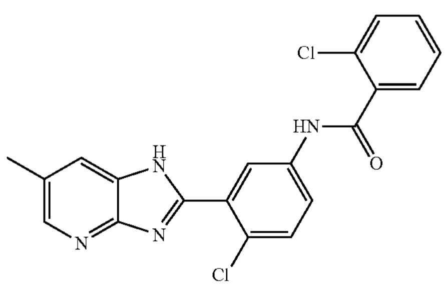 [SMILES: Cc1cnc2nc(-c3cc(NC(=O)c4ccccc4Cl)ccc3Cl)[nH]c2c1] | M/Z = 397.1 (M + 1). RT = 1.45: Method B. |
| 150 | 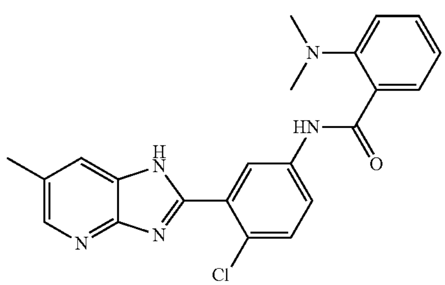 [SMILES: Cc1cnc2nc(-c3cc(NC(=O)c4ccccc4N(C)C)ccc3Cl)[nH]c2c1] | M/Z = 406.1 (M + 1). RT = 1.21: Method B. |
| 151 | 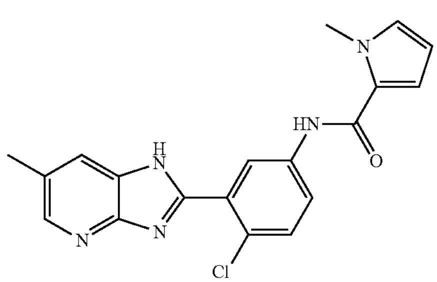 [SMILES: Cc1cnc2nc(-c3cc(NC(=O)c4cccn4C)ccc3Cl)[nH]c2c1] | $^1$H NMR (400 MHz, DMSO) δ 9.99 (s, 1H), 8.28 (s, 1H), 8.23 (s, 1H), 7.91-7.82 (m, 2H), 7.54 (t, J = 6.3 Hz, 1H), 7.03 (dd, J = 1.7, 4.0 Hz, 1H), 7.00-6.94 (m, 1H), 6.05 (dd, J = 2.5 Hz, 4.0, 1H), 3.82 (s, 3H), 2.40 (s, 3H). M/Z = 366.1 (M + 1). RT = 1.43: Method B. |

TABLE II-continued

Listing of the Exemplified Compounds of the Invention

| Ex. No. | Structure | ¹H NMR and/or mass and/or (retention time (mins)) |
|---|---|---|
| 152 | 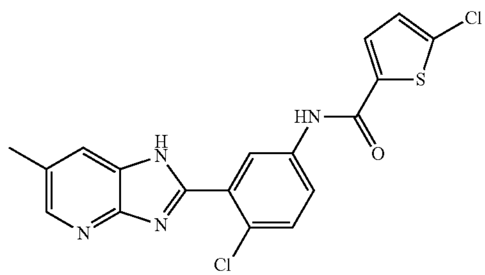 [SMILES: Cc1cnc2nc(-c3cc(NC(=O)c4ccc(Cl)s4)ccc3Cl)[nH]c2c1] | ¹H NMR (400 MHz, DMSO) δ 10.66 (s, 1H), 8.36 (s, 1H), 8.33 (d, J = 2.6 Hz, 1H), 8.01 (s, 1H), 7.98-7.93 (m, 2H), 7.68 (d, J = 8.8 Hz, 1H), 7.30 (d, J = 4.1 Hz, 1H), 2.48 (s, 3H). M/Z = 403.0 (M + 1). RT = 1.61: Method B. |
| 153 | 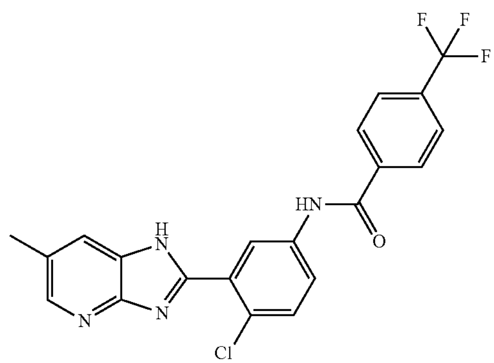 | M/Z = 431.1 (M + 1). RT = 1.62: Method B. |
| 154 | 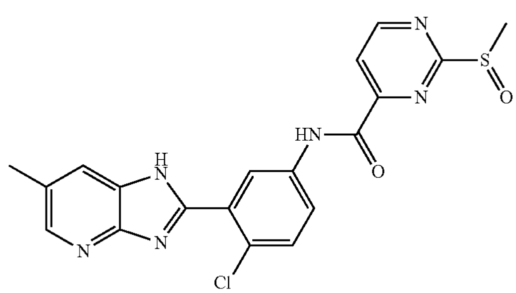 | M/Z = 427.1 (M + 1). RT = 1.20: Method B. |
| 155 | 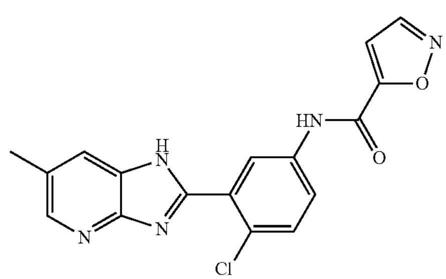 [SMILES: Cc1cnc2nc(-c3cc(NC(=O)c4ccno4)ccc3Cl)[nH]c2c1] | M/Z = 354.1 (M + 1). RT = 1.23: Method B. |
| 156 | 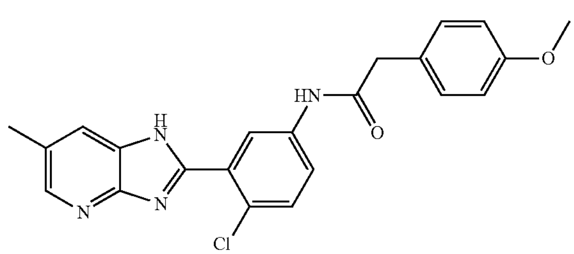 | M/Z = 407.1 (M + 1). RT = 0.82: Method B. |

TABLE II-continued

Listing of the Exemplified Compounds of the Invention

| Ex. No. | Structure | ¹H NMR and/or mass and/or (retention time (mins)) |
|---|---|---|
| 157 | 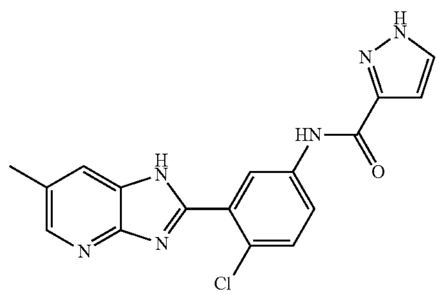 [SMILES: Cc1cnc2nc(-c3cc(NC(=O)c4cc[nH]n4)ccc3Cl)[nH]c2c1] | M/Z = 353.1 (M + 1). RT = 0.64: Method B. |
| 158 | 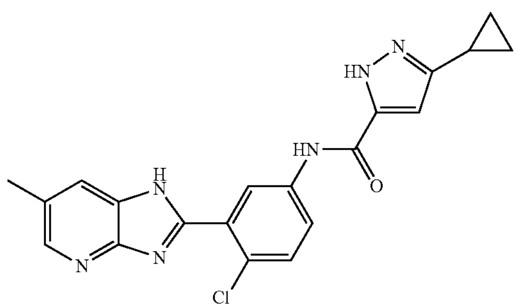 [SMILES: Cc1cnc2nc(-c3cc(NC(=O)c4cc(C5CC5)n[nH]4)ccc3Cl)[nH]c2c1] | ¹H NMR (400 MHz, DMSO) δ 10.34 (s, 1H), 8.62-8.31 (m, 1H), 8.26 (s, 1H), 8.00 (dd, J = 2.6, 8.8 Hz, 1H), 7.97-7.67 (m, 1H), 7.61 (d, J = 8.8 Hz, 1H), 6.44 (s, 1H), 2.45 (s, 3H), 1.97 (s, 1H), 0.98 (s, 2H), 0.75 (s, 2H). M/Z = 393.1 (M + 1). RT = 1.39: Method B. |
| 159 | 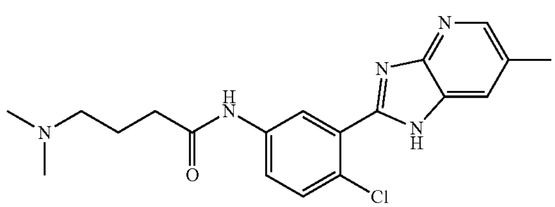 | M/Z = 372.1 (M + 1). RT = 1.06: Method B. |
| 160 | 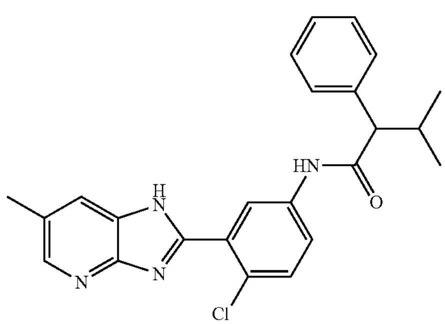 [SMILES: Cc1cnc2nc(-c3cc(NC(=O)C(c4ccccc4)C(C)C)ccc3Cl)[nH]c2c1] | M/Z = 419.1 (M + 1). RT = 1.42: Method B. |
| 161 | 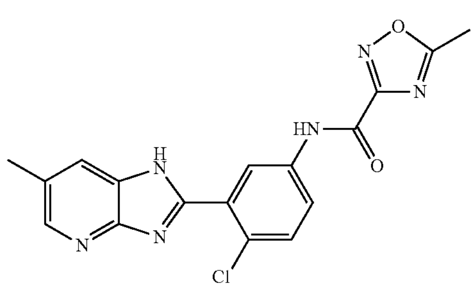 | ¹H NMR (400 MHz, DMSO) δ 8.33 (s, 1H), 8.19 (s, 1H), 7.89 (dd, J = 2.4, 8.8 Hz, 1H), 7.79 (s, 1H), 7.61 (d, J = 8.8 Hz, 1H), 2.66 (s, 3H), 2.38 (s, 3H). M/Z = 369.1 (M + 1). RT = 1.22: Method B. |

US 9,233,961 B2

199                                                                                                                 200

TABLE II-continued

Listing of the Exemplified Compounds of the Invention

| Ex. No. | Structure | ¹H NMR and/or mass and/or (retention time (mins)) |
|---|---|---|
| 162 | 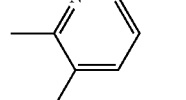 | ¹H NMR (400 MHz, DMSO) δ 10.88 (s, 1H), 8.25 (s, 1H), 8.19 (d, J = 9.8 Hz, 1H), 8.18 (s, 1H), 7.85 (d, J = 7.9 Hz, 1H), 7.80 (dd, J = 2.6, 8.7 Hz, 2H), 7.62 (t, J = 7.9 Hz, 1H), 2.59 (s, 3H), 2.38 (s, 3H). M/Z = 446.1 (M + 1). RT = 1.52: Method B. |
| 163 | 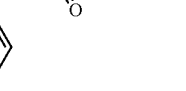 | ¹H NMR (400 MHz, DMSO) δ 10.07 (s, 1H), 8.31 (s, 1H), 8.20 (d, J = 2.6 Hz, 1H), 7.97 (s, 1H), 7.78 (dd, J = 2.6, 8.8 Hz, 1H), 7.55 (dd, J = 8.8, 14.0 Hz, 1H), 4.78 (d, J = 6.1 Hz, 2H), 4.29 (d, J = 6.1 Hz, 2H), 2.42 (s, 3H), 1.55 (s, 3H). M/Z = 357.1 (M + 1). RT = 0.64: Method B. |
| 164 | 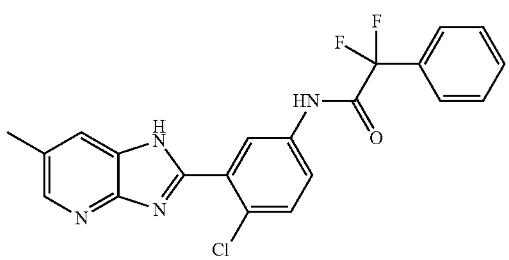 [SMILES: Cc1cnc2nc(-c3cc(NC(=O)C(F)(F)c4ccccc4)ccc3Cl)[nH]c2c1] | ¹H NMR (400 MHz, DMSO) δ 8.28 (s, 1H), 8.26 (s, 1H), 7.89 (dd, J = 2.7, 8.8 Hz, 1H), 7.85 (s, 1H), 7.70 (dd, J = 1.7, 7.7 Hz, 2H), 7.66 (d, J = 8.8 Hz, 1H), 7.62-7.54 (m, 3H), 2.45 (s, 3H). M/Z = 413.1 (M + 1). RT = 1.60: Method B. |
| 165 | 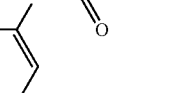 | M/Z = 421.1 (M + 1). RT = 1.59: Method B. |
| 166 | 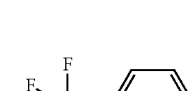 | M/Z = 442.1 (M + 1). RT = 1.43: Method B. |

TABLE II-continued

Listing of the Exemplified Compounds of the Invention

| Ex. No. | Structure | ¹H NMR and/or mass and/or (retention time (mins)) |
|---|---|---|
| 167 | 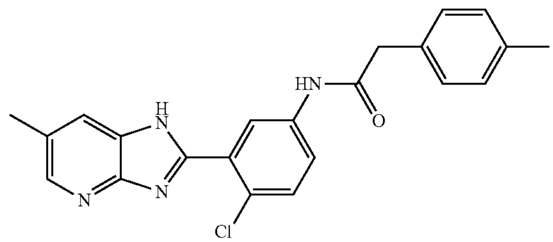 | ¹H NMR (400 MHz, DMSO) δ 10.40 (s, 1H), 8.18 (s, 1H), 8.10 (s, 1H), 7.77 (s, 1H), 7.71 (dd, J = 2.6, 8.8 Hz, 1H), 7.51 (d, J = 8.8 Hz, 1H), 7.16 (d, J = 8.0 Hz, 2H), 7.06 (d, J = 8.0 Hz, 2H), 3.55 (s, 2H), 2.37 (s, 3H), 2.20 (s, 3H). M/Z = 391.1 (M + 1). RT = 0.89: Method B. |
| 168 | 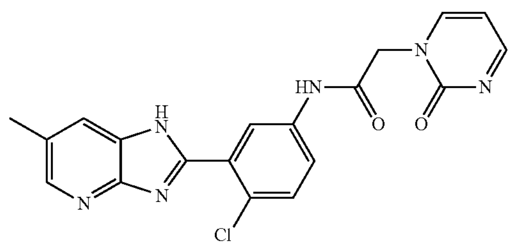 [SMILES: Cc1cnc2nc(-c3cc(NC(=O)Cn4cccnc4=O)ccc3Cl)[nH]c2c1] | ¹H NMR (400 MHz, DMSO) δ 10.70 (d, J = 8.9 Hz, 1H), 8.64-8.46 (m, 1H), 8.22 (s, 1H), 8.15 (d, J = 1.9 Hz, 1H), 8.12 (dd, J = 2.2, 4.0 Hz, 1H), 8.05 (d, J = 2.4 Hz, 1H), 7.85 (s, 0H), 7.74-7.67 (m, 1H), 7.56 (dd, J = 5.9, 8.7 Hz, 1H), 6.43 (dd, J = 4.3, 6.2 Hz, 1H), 4.69 (d, J = 2.4 Hz, 2H), 2.37 (d, J = 5.1 Hz, 3H). M/Z = 395.1 (M + 1). RT = 1.04: Method B. |
| 169 | 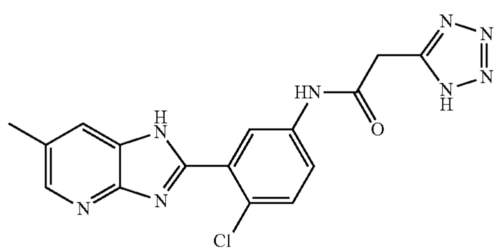 [SMILES: Cc1cnc2nc(-c3cc(NC(=O)Cc4nnn[nH]4)ccc3Cl)[nH]c2c1] | ¹H NMR (400 MHz, DMSO) δ 10.75 (s, 1H), 8.28 (s, 1H), 8.15 (s, 1H), 7.92 (s, 1H), 7.70 (dd, J = 2.6, 8.8 Hz, 1H), 7.58 (d, J = 8.8 Hz, 1H), 4.13 (s, 2H), 2.41 (s, 3H). M/Z = 369.1 (M + 1). RT = 1.12: Method B. |
| 170 | 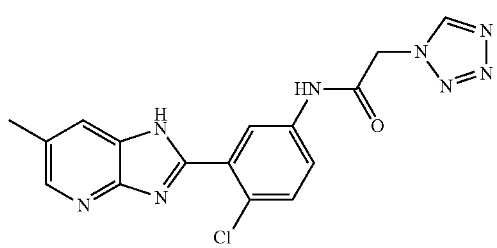 [SMILES: Cc1cnc2nc(-c3cc(NC(=O)Cn4cnnn4)ccc3Cl)[nH]c2c1] | ¹H NMR (400 MHz, DMSO) δ 10.84 (s, 1H), 9.37 (s, 1H), 8.25-8.00 (m, 2H), 7.92-7.63 (m, 2H), 7.57 (d, J = 8.5 Hz, 1H), 5.48 (s, 2H), 2.37 (s, 3H). M/Z = 369.1 (M + 1). RT = 1.17: Method B. |
| 171 | 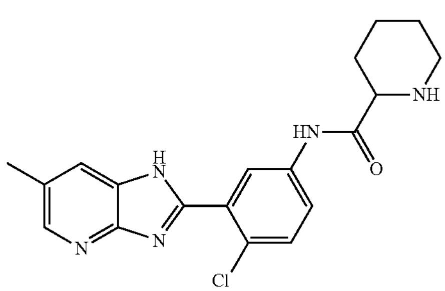 [SMILES: Cc1cnc2nc(-c3cc(NC(=O)C4CCCCN4)ccc3Cl)[nH]c2c1] | M/Z = 370.1 (M + 1). RT = 1.04: Method B. |
| 172 | 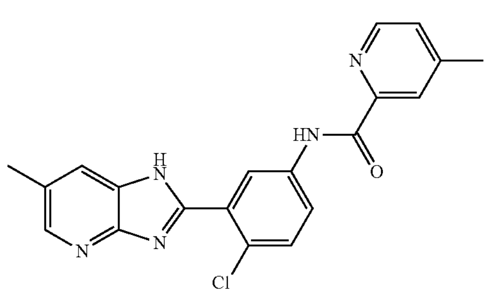 | ¹H NMR (400 MHz, MeOD) δ 8.57 (d, J = 5.1 Hz, 1H), 8.33 (d, J = 10.4 Hz, 2H), 8.06 (t, J = 5.0 Hz, 2H), 7.91 (s, 1H), 7.64 (d, J = 8.8 Hz, 1H), 7.46 (dd, J = 0.8, 5.0 Hz, 1H), 2.54 (s, 3H), 2.49 (s, 3H). M/Z = 378.1 (M + 1). RT = 1.46: Method B. |

TABLE II-continued

Listing of the Exemplified Compounds of the Invention

| Ex. No. | Structure | ¹H NMR and/or mass and/or (retention time (mins)) |
|---|---|---|
| 173 | 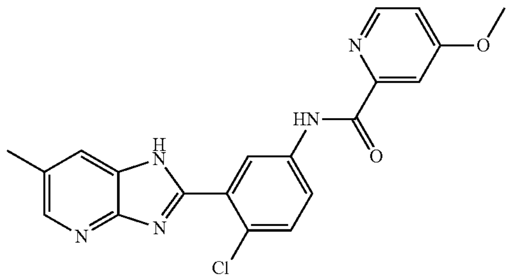 | ¹H NMR (400 MHz, DMSO) δ 10.91 (s, 1H), 8.52 (d, J = 5.7Hz, 1H), 8.47 (d, J = 2.4 Hz, 1H), 8.18 (d, J = 1.5 Hz, 1H), 8.01 (dd, J = 2.6, 8.8 Hz, 1H), 7.78 (s, 1H), 7.62 (d, J = 2.6 Hz, 1H), 7.58 (d, J = 8.8 Hz, 1H), 7.21 (dd, J = 2.6, 5.7 Hz, 1H), 3.89 (s, 3H), 2.39 (s, 3H). M/Z = 394.1 (M + 1). RT = 1.36: Method B. |
| 174 | 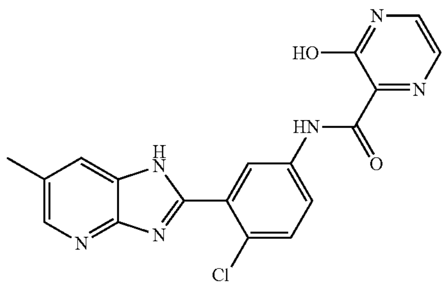 [SMILES: Cc1cnc2nc(-c3cc(NC(=O)c4nccnc4O)ccc3Cl)[nH]c2c1] | M/Z = 381.1 (M + 1). RT = 1.14: Method B. |
| 175 | 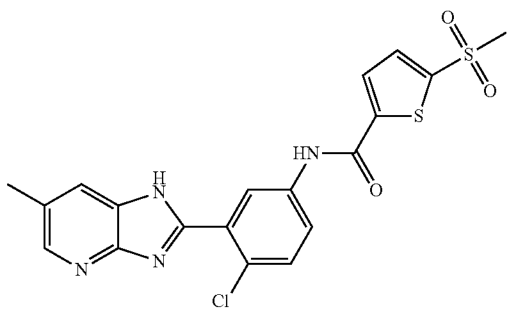 | ¹H NMR (400 MHz, MeOD) δ 8.43 (d, J = 2.6 Hz, 1H), 8.41 (d, J = 1.2 Hz, 1H), 8.23 (s, 1H), 7.96 (d, J = 4.1 Hz, 1H), 7.91 (dd, J = 2.6, 8.8 Hz, 1H), 7.77 (d, J = 4.1 Hz, 1H), 7.68 (s, 1H), 7.62 (d, J = 8.8 Hz, 1H), 3.28 (d, J = 5.4 Hz, 3H), 2.62 (s, 3H). M/Z = 447.0 (M + 1). RT = 1.36: Method B. |
| 176 | 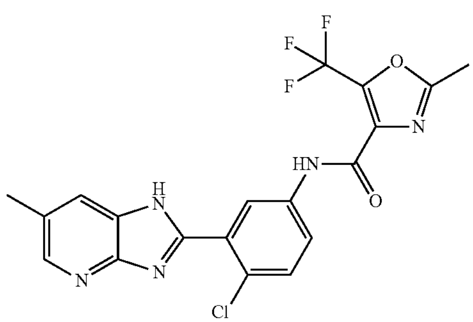 | M/Z = 436.1 (M + 1). RT = 0.89: Method B. |
| 177 | 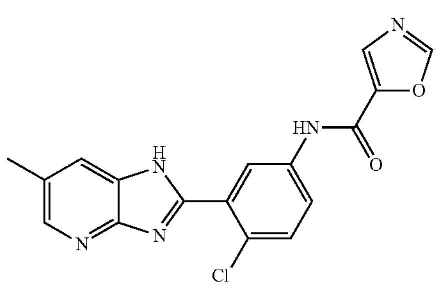 [SMILES: Cc1cnc2nc(-c3cc(NC(=O)c4cnco4)ccc3Cl)[nH]c2c1] | ¹H NMR (400 MHz, DMSO) δ 8.63 (d, J = 4.0 Hz, 1H), 8.26 (d, J = 2.6 Hz, 1H), 8.17 (d, J = 1.7 Hz, 1H). 7.98 (s, 1H), 7.89 (dd, J = 2.7, 8.8 Hz, 1H), 7.78 (d, J = 14.5 Hz, 1H), 7.58 (d, J = 8.8 Hz, 1H), 2.37 (s, 3H). M/Z = 354.1 (M + 1). RT = 1.17: Method B. |

TABLE II-continued

Listing of the Exemplified Compounds of the Invention

| Ex. No. | Structure | ¹H NMR and/or mass and/or (retention time (mins)) |
|---|---|---|
| 178 | 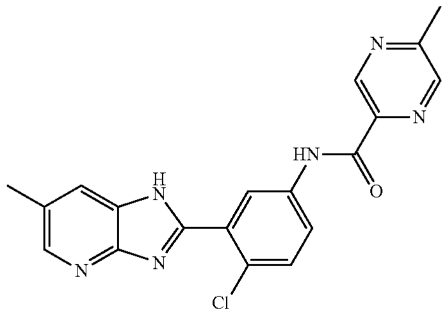 | ¹H NMR (400 MHz, DMSO) δ 11.05 (s, 1H), 9.18 (d, J = 1.3 Hz, 1H), 8.73 (s, 1H), 8.52 (d, J = 2.5 Hz, 1H), 8.27 (d, J = 1.7 Hz, 1H), 8.09 (dd, J = 2.6, 8.8 Hz, 1H), 7.86 (s, 1H), 7.67 (d, J = 8.8 Hz, 1H), 2.65 (s, 3H), 2.46 (s, 2H); M/Z = 379.1 (M + 1). RT = 1.30: Method B. |
| 179 | 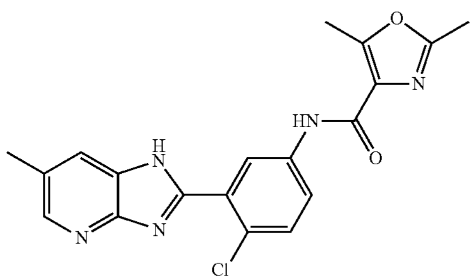 | ¹H NMR (400 MHz, DMSO) δ 10.34 (s, 1H), 8.47 (d, J = 2.5 Hz, 1H), 8.24 (d, J = 1.7 Hz, 1H), 7.94 (dd, J = 2.6, 8.8 Hz, 1H), 7.83 (s, 1H), 7.59 (d, J = 8.8 Hz, 1H), 2.59 (s, 3H), 2.47 (s, 3H), 2.45 (s, 3H). M/Z = 382.1 (M +1 ). RT = 1.39: Method B. |
| 180 | 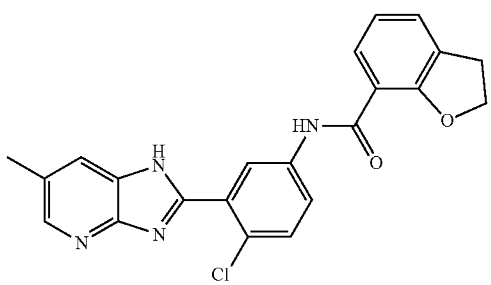 [SMILES: Cc1cnc2nc(-c3cc(NC(=O)c4cccc5c4OCC5)ccc3Cl)[nH]c2c1] | ¹H NMR (400 MHz, DMSO) δ 10.09 (s, 1H), 8.38 (s, 1H), 8.34 (d, J = 2.5 Hz, 1H), 8.05 (s, 1H), 8.02-7.91 (m, 1H), 7.66 (t, J = 10.5 Hz, 1H), 7.63 (s, 1H), 7.53-7.41 (m, 1H), 7.00 (t, J = 7.6 Hz, 1H), 4.76 (t, J = 8.8 Hz, 2H), 3.28 (t, J = 8.7 Hz, 2H), 2.49 (s, 3H). M/Z = 405.1 (M + 1). RT = 2.47: Method A. |
| 181 | 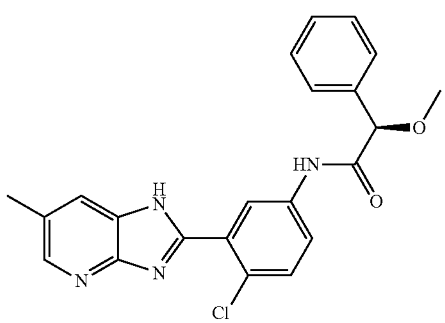 | ¹H NMR (400 MHz, DMSO) δ 10.40 (s, 1H), 8.31 (d, J = 14.1, 1H), 8.22 (s, 1H), 7.95-7.71 (m, 2H), 7.59 (d, J = 8.6, 1H), 7.50 (d, J = 7.1, 2H), 7.45-7.29 (m, 3H), 4.88 (s, 1H), 3.39 (s, 3H), 2.45 (s, 3H). M/Z = 407.1 (M + 1). RT = 1.48: Method B. |
| 182 | 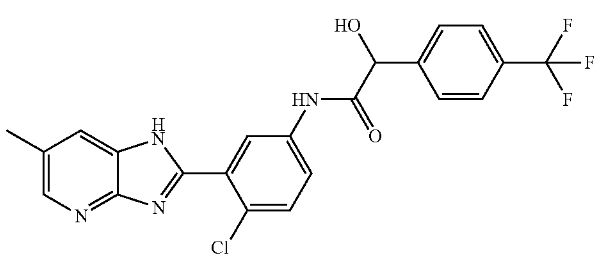 [SMILES: Cc1cnc2nc(-c3cc(NC(=O)C(O)c4ccc(C(F)(F)F)cc4)ccc3Cl)[nH]c2c1] | M/Z = 461.1 (M + 1). RT = 1.60: Method B. |

TABLE II-continued

Listing of the Exemplified Compounds of the Invention

| Ex. No. | Structure | ¹H NMR and/or mass and/or (retention time (mins)) |
|---|---|---|
| 183 | 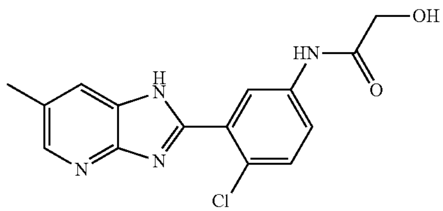 [SMILES: Cc1cnc2nc(-c3cc(NC(=O)CO)ccc3Cl)[nH]c2c1] | M/Z = 317.1 (M + 1). RT = 1.05: Method B. |
| 184 | 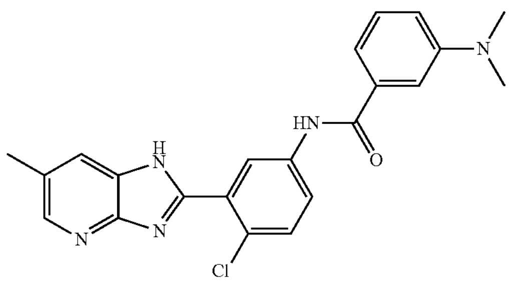 | ¹H NMR (400 MHz, MeOD) δ 8.31 (s, 1H), 8.19 (d, J = 2.6 Hz, 1H), 8.00 (dd, J = 2.5, 8.8 Hz, 1H), 7.90 (s, 1H), 7.62 (d, J = 8.8 Hz, 1H), 7.37-7.31 (m, 1H), 7.32-7.28 (m, 1H), 7.25 (s, 1H), 7.27-7.21 (m, 1H), 6.99 (dd, J = 2.3, 8.0 Hz, 1H), 3.02 (s, 6H), 2.54 (s, 3H). M/Z = 406.1 (M + 1). RT = 1.22: Method B. |
| 185 | 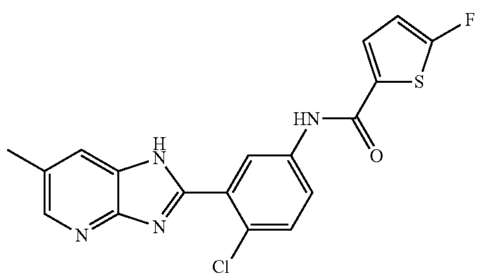 [SMILES: Cc1cnc2nc(-c3cc(NC(=O)c4ccc(F)s4)ccc3Cl)[nH]c2c1] | M/Z = 387.0 (M + 1). RT = 1.18: Method B. |
| 186 | 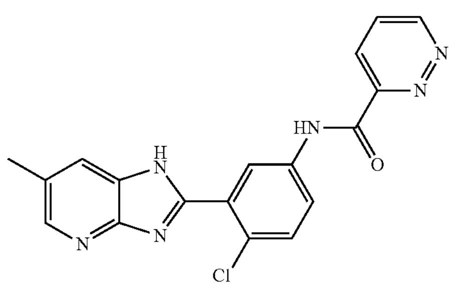 [SMILES: Cc1cnc2nc(-c3cc(NC(=O)c4cccnn4)ccc3Cl)[nH]c2c1] | ¹H NMR (400 MHz, MeOD) δ 9.40 (dd, J = 1.6, 5.1 Hz, 1H), 8.58 (d, J = 2.6 Hz, 1H), 8.48 (s, 1H), 8.44 (dd, J = 1.6, 8.5 Hz, 1H), 8.27 (s, 1H), 8.12 (dd, J = 2.6, 8.8 Hz, 1H), 7.97 (dd, J = 5.1, 8.5 Hz, 1H), 7.70 (d, J = 8.8 Hz, 1H), 2.62 (s, 3H). M/Z = 365.1 (M + 1). RT = 1.22: Method B. |
| 187 | 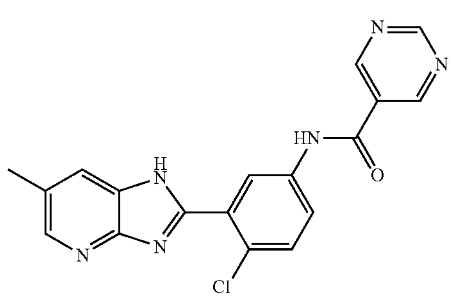 | M/Z = 365.1 (M + 1). RT = 1.13: Method B. |

TABLE II-continued
Listing of the Exemplified Compounds of the Invention
| Ex. No. | Structure | ¹H NMR and/or mass and/or (retention time (mins)) |
|---|---|---|
| 188 | 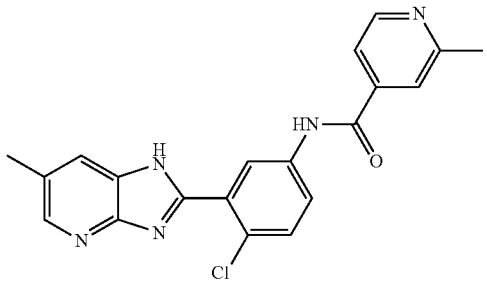 | M/Z = 378.1 (M + 1). RT = 1.10: Method B. |
| 189 | 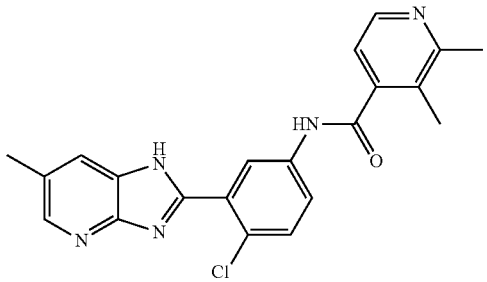 | M/Z = 392.1 (M + 1). RT = 1.11: Method B. |
| 190 | 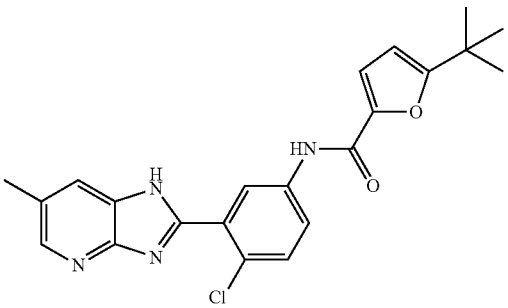 [SMILES: Cc1cnc2nc(-c3cc(NC(=O)c4ccc(C(C)(C)C)o4)ccc3Cl)[nH]c2c1] | M/Z = 409.1 (M + 1). RT = 1.40: Method B. |
| 191 | 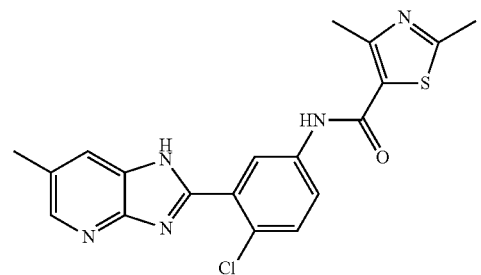 | M/Z = 398.1 (M + 1). RT = 0.74: Method B. |
| 192 | 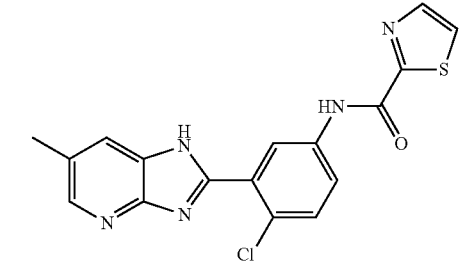 [SMILES: Cc1cnc2nc(-c3cc(NC(=O)c4nccs4)ccc3Cl)[nH]c2c1] | M/Z = 370.1 (M + 1). RT = 0.75: Method B. |

TABLE II-continued

Listing of the Exemplified Compounds of the Invention

| Ex. No. | Structure | ¹H NMR and/or mass and/or (retention time (mins)) |
|---|---|---|
| 193 | 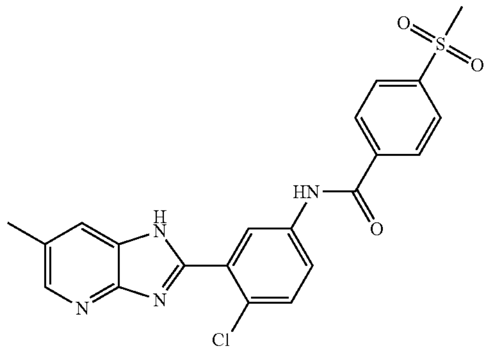 [SMILES: Cc1cnc2nc(-c3cc(NC(=O)c4ccc(S(C)(=O)=O)cc4)ccc3Cl)[nH]c2c1] | 1H NMR (400 MHz, DMSO) δ 10.75 (s, 1H), 8.32 (s, 1H), 8.20 (s, 1H), 8.17-8.01 (m, 4H), 7.94 (dd, J = 2.6, 8.8 Hz, 1H), 7.79 (s, 1H), 7.61 (d, J = 8.8 Hz, 1H), 3.24 (s, 3H), 2.38 (s, 3H). M/Z = 441.1 (M + 1). RT = 1.37: Method B. |
| 194 | 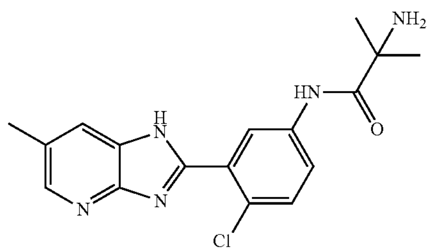 [SMILES: Cc1cnc2nc(-c3cc(NC(=O)C(C)(C)N)ccc3Cl)[nH]c2c1] | M/Z = 344.1 (M + 1). RT = 1.01: Method B. |
| 195 | 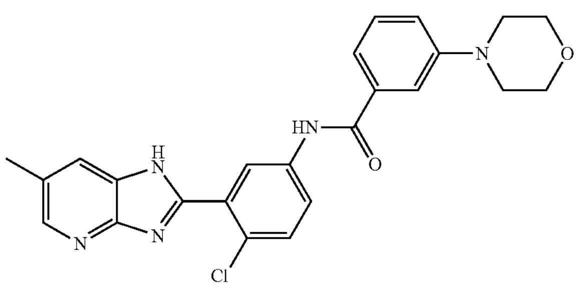 [SMILES: Cc1cnc2nc(-c3cc(NC(=O)c4cccc(N5CCOCC5)c4)ccc3Cl)[nH]c2c1] | M/Z = 448.1 (M + 1). RT = 1.40: Method B. |
| 196 | 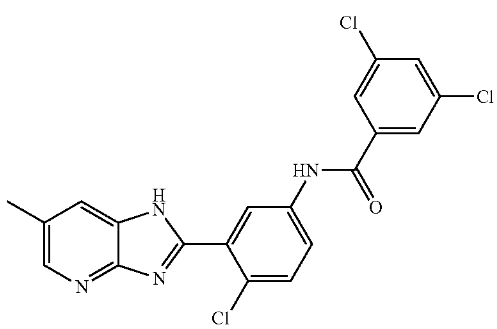 [SMILES: Cc1cnc2nc(-c3cc(NC(=O)c4cc(Cl)cc(Cl)c4)ccc3Cl)[nH]c2c1] | M/Z = 431.0 (M + 1). RT = 1.74 |
| 197 | 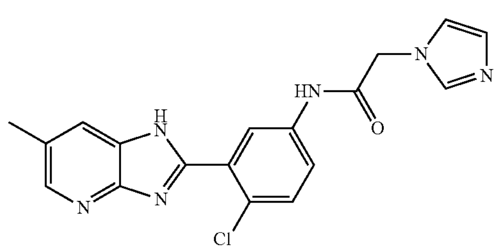 [SMILES: Cc1cnc2nc(-c3cc(NC(=O)Cn4ccnc4)ccc3Cl)[nH]c2c1] | ¹H NMR (400 MHz, DMSO) δ 10.82 (s, 1H), 9.03 (s, 1H), 8.21 (s, 1H), 8.13 (s, 1H), 7.80 (s, 1H), 7.68 (dd, J = 4.1, 7.3 Hz, 2H), 7.64 (s, 1H), 7.58 (d, J = 8.8 Hz, 1H), 5.20 (s, 2H), 2.38 (s, 3H). M/Z = 367.1 (M + 1). RT = 0.51: Method B. |

TABLE II-continued

Listing of the Exemplified Compounds of the Invention

| Ex. No. | Structure | ¹H NMR and/or mass and/or (retention time (mins)) |
|---|---|---|
| 198 | 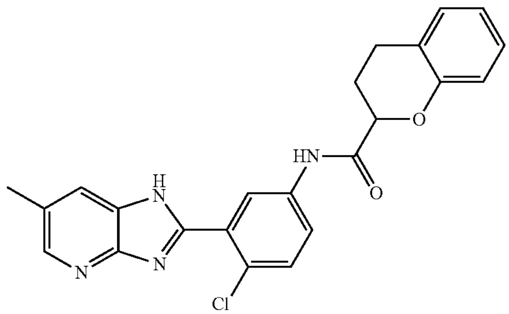 [SMILES: Cc1cnc2nc(-c3cc(NC(=O)C4CCc5ccccc5O4)ccc3Cl)[nH]c2c1] | ¹H NMR (400 MHz, DMSO) δ 10.24 (d, J = 10.6 Hz, 1H), 8.25 (dd, J = 2.1, 14.0 Hz, 1H), 8.15 (d, J = 2.4 Hz, 1H), 7.91-7.67 (m, 2H), 7.56 (dd, J = 5.9, 8.8 Hz, 1H), 7.05 (dd, J = 7.5, 15.4 Hz, 2H), 6.87 (d, J = 8.3 Hz, 1H), 6.81 (dd, J = 4.7, 11.1 Hz, 1H), 4.69 (dd, J = 1.8, 9.1 Hz, 1H). 2.90-2.76 (m, 1H), 2.74-2.62 (m, 1H), 2.38 (d, J = 5.0 Hz, 3H), 2.19 (d, J = 13.7 Hz, 1H), 1.98 (d, J = 8.6 Hz, 1H). M/Z = 419.1 (M + 1). RT = 0.93: Method B. |
| 199 | 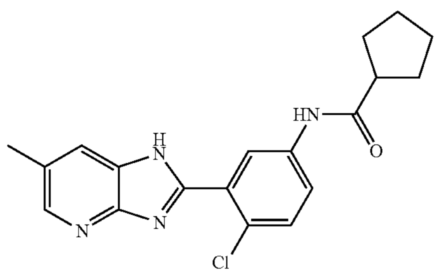 [SMILES: Cc1cnc2nc(-c3cc(NC(=O)C4CCCC4)ccc3Cl)[nH]c2c1] | ¹H NMR (400 MHz, DMSO) δ 10.21 (s, 1H), 8.25 (s, 1H), 8.20 (s, 1H), 7.84 (s, 1H), 7.78 (dd, J = 2.6, 8.8 Hz, 1H), 7.57 (d, J = 8.8 Hz, 1H), 3.34 (s, 2H), 2.80 (p, J = 7.9 Hz, 1H), 2.45 (s, 3H), 1.96-1.79 (m, 2H), 1.81-1.63 (m, 4H), 1.57 (dt, J = 6.0, 7.5 Hz, 2H). M/Z = 355.1 (M + 1). RT = 0.81: Method B. |
| 200 | 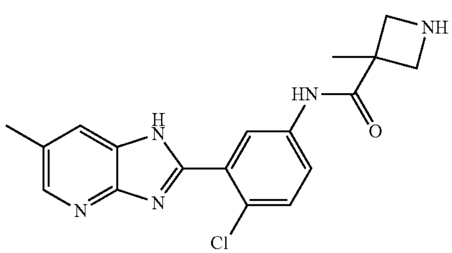 [SMILES: Cc1cnc2nc(-c3cc(NC(=O)C4(C)CNC4)ccc3Cl)[nH]c2c1] | M/Z = 356.1 (M + 1). RT = 1.04: Method B. |
| 201 | 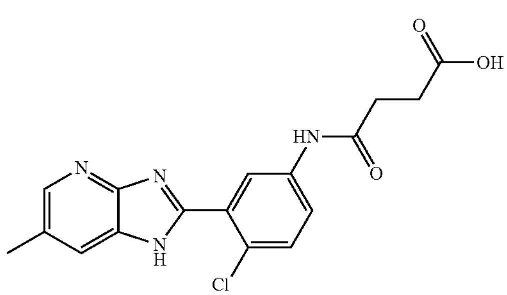 [SMILES: Cc1cnc2nc(-c3cc(NC(=O)CCC(=O)O)ccc3Cl)[nH]c2c1] | M/Z = 359.1 (M + 1). RT = 1.13: Method B. |
| 202 | 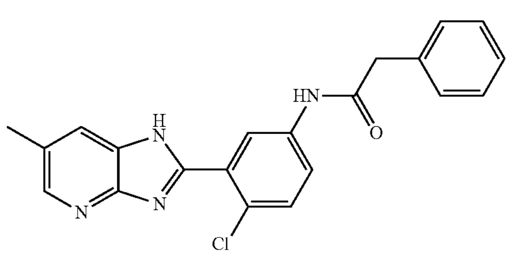 | M/Z = 377.2 (M + 1). RT = 1.48: Method B. |

TABLE II-continued

Listing of the Exemplified Compounds of the Invention

| Ex. No. | Structure | ¹H NMR and/or mass and/or (retention time (mins)) |
|---|---|---|
| 203 | 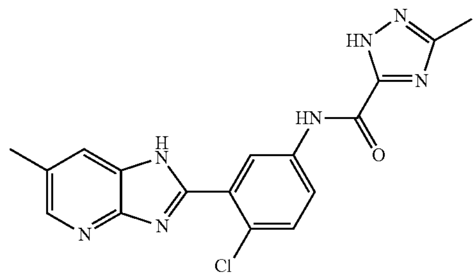 | ¹H NMR (400 MHz, DMSO) δ 10.37 (s, 1H), 8.37 (d, J = 2.5 Hz, 1H), 8.18 (s, 1H), 7.91 (dd, J = 2.6, 8.8 Hz, 1H), 7.78 (s, 1H), 7.51 (d, J = 8.8 Hz, 1H), 2.38 (s, 3H), 2.26 (s, 3H). M/Z = 368.1 (M + 1). RT = 1.12: Method B. |
| 204 | 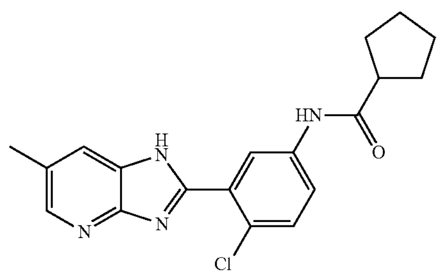 | ¹H NMR (400 MHz, DMSO) δ 10.21 (s, 1H), 8.25 (s, 1H), 8.20 (s, 1H), 7.84 (s, 1H), 7.78 (dd, J = 2.6, 8.8 Hz, 1H), 7.57 (d, J = 8.8Hz, 1H), 3.34 (s, 2H), 2.80 (p, J = 7.9 Hz, 1H), 2.45 (s, 3H), 1.96-1.79 (m, 2H), 1.81-1.63 (m, 4H), 1.57 (dt, J = 6.0, 7.5 Hz, 2H). M/Z = 355.1 (M + 1). RT = 0.81: Method B. |
| 205 | 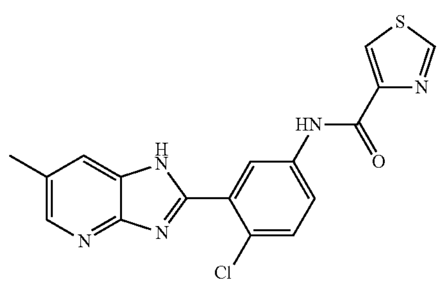 | M/Z = 370.0 (M + 1). RT = 1.26: Method B. |
| 206 | 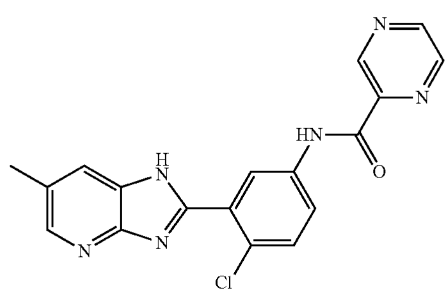 [SMILES: Cc1cnc2nc(-c3cc(NC(=O)c4cnccn4)ccc3Cl)[nH]c2c1] | ¹H NMR (400 MHz, DMSO) δ 11.04 (s, 1H), 9.25 (d, J = 1.4 Hz, 1H), 8.95-8.69 (m, 2H), 8.46 (d, J = 2.6 Hz, 1H), 8.17 (d, J = 1.7 Hz, 1H), 8.00 (dd, J = 2.7, 8.8 Hz, 1H), 7.77 (s, 1H), 7.59 (d, J = 8.8 Hz, 1H), 2.38 (s, 3H). M/Z = 365.1 (M + 1). RT = 1.24: Method B. |
| 207 | 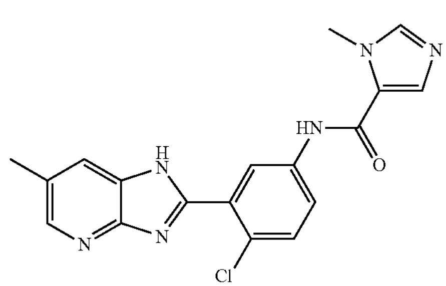 [SMILES: Cc1cnc2nc(-c3cc(NC(=O)c4cncn4C)ccc3Cl)[nH]c2c1] | M/Z = 367.1 (M + 1). RT = 0.56: Method B. |

TABLE II-continued

Listing of the Exemplified Compounds of the Invention

| Ex. No. | Structure | ¹H NMR and/or mass and/or (retention time (mins)) |
|---|---|---|
| 208 | 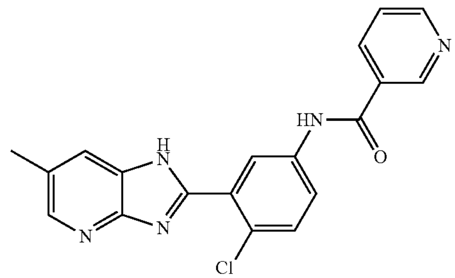 | ¹H NMR (400 MHz, DMSO) δ 10.69 (s, 1H), 9.07 (d, J = 1.7 Hz, 1H), 8.72 (dd, J = 1.6, 4.8 Hz, 1H), 8.26 (m, 3H), 7.93 (dd, J = 2.6, 8.8 Hz, 1H), 7.79 (s, 1H), 7.60 (d, J = 8.8 Hz, 1H), 7.57-7.46 (m, 1H), 2.38 (s, 3H). M/Z = 364.1 (M + 1). RT = 1.08: Method B. |
| 209 | 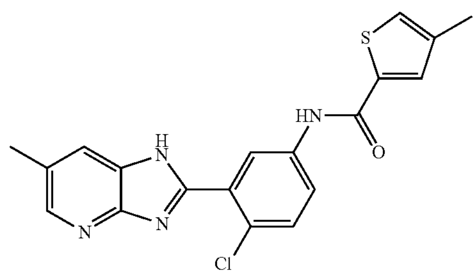 | ¹H NMR (400 MHz, DMSO) δ 10.41 (s, 1H), 8.23 (d, J = 13.1 Hz, 1H), 8.20 (s, 1H), 7.91 (dd, J = 2.6, 8.8 Hz, 1H), 7.82 (t, J = 8.8 Hz, 2H). 7.57 (d, J = 8.8 Hz, 1H), 7.43 (s, 1H), 2.38 (s, 3H), 2.21 (s, 3H). M/Z = 383.1 (M + 1). RT = 1.50: Method B. |
| 210 | 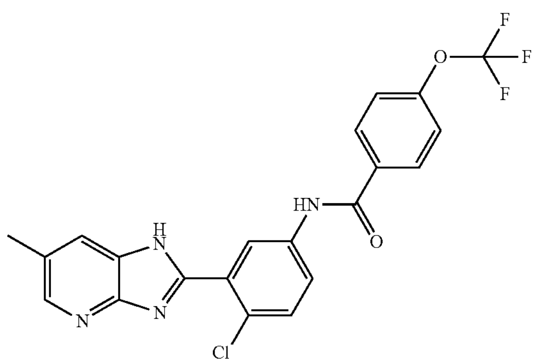 [SMILES: Cc1cnc2nc(-c3cc(NC(=O)c4ccc(OC(F)(F)F)cc4)ccc3Cl)[nH]c2c1] | M/Z = 447.1 (M + 1). RT = 0.98: Method B. |
| 211 | 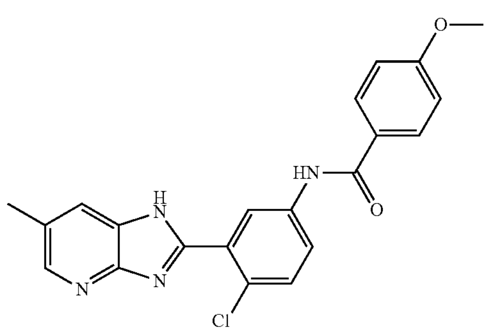 | M/Z = 393.1 (M + 1). RT = 0.82: Method B. |
| 212 | 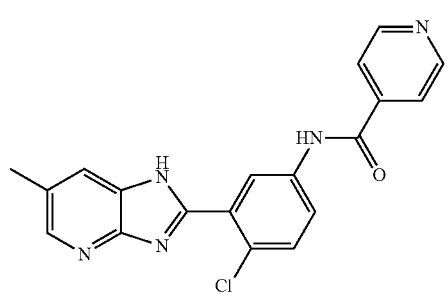 [SMILES: Cc1cnc2nc(-c3cc(NC(=O)c4ccncc4)ccc3Cl)[nH]c2c1] | ¹H NMR (400 MHz, DMSO) δ 10.79 (s, 1H), 8.78 (s, 2H), 8.35 (d, J = 2.5 Hz, 1H), 8.27 (s, 1H), 7.96-7.91 (m, 1H), 7.90 (s, 1H), 7.86 (d, J = 4.8 Hz, 2H), 7.63 (d, J = 8.8 Hz, 1H), 2.41 (s, 3H). M/Z = 364.1 (M + 1). RT = 1.11: Method B. |

TABLE II-continued

Listing of the Exemplified Compounds of the Invention

| Ex. No. | Structure | ¹H NMR and/or mass and/or (retention time (mins)) |
|---|---|---|
| 213 | 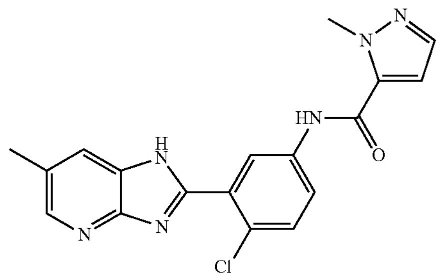 [SMILES: Cc1cnc2nc(-c3cc(NC(=O)c4ccnn4C)ccc3Cl)[nH]c2c1] | M/Z = 367.1 (M + 1). RT = 0.71: Method B. |
| 214 | 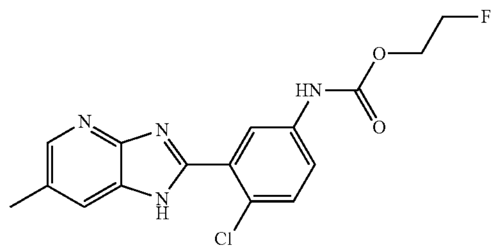 [SMILES: Cc1cnc2nc(-c3cc(NC(=O)OCCF)ccc3Cl)[nH]c2c1] | ¹H NMR (400 MHz, DMSO) δ 10.14 (s, 1H), 8.19 (s, 1H), 7.93 (s, 1H), 7.78 (s, 1H), 7.58 (dd, J = 2.6, 8.8 Hz, 1H), 7.51 (d, J = 8.8 Hz, 1H), 4.74-4.45 (m, 2H), 4.45-4.17 (m, 2H), 2.37 (s, 3H). M/Z = 349.0 (M + 1). RT = 1.27: Method B. |
| 215 | 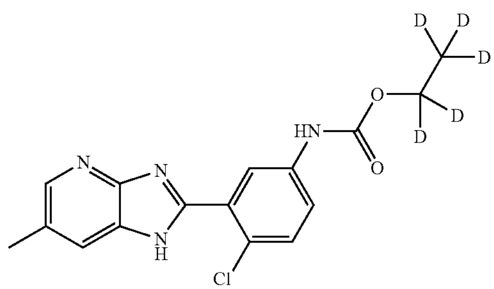 [SMILES: [2H]C([2H])([2H])C([2H])([2H])OC(=O)Nc1ccc(Cl)c(-c2nc3ncc(C)cc3[nH]2)c1] | ¹H NMR (400 MHz, DMSO) δ 9.88 (s, 1H), 8.12 (s, 1H), 7.92 (s, 1H), 7.80-7.63 (m, 1H), 7.59-7.50 (m, 1H), 7.46 (d, J = 8.7 Hz, 1H), 2.36 (s, 3H). M/Z = 336.1 (M + 1). RT = 1.28: Method B. |
| 216 | 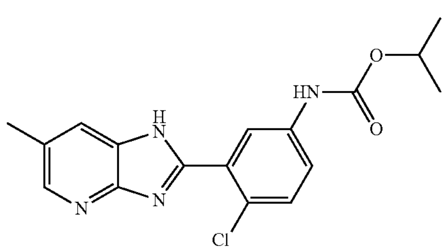 [SMILES: Cc1cnc2nc(-c3cc(NC(=O)OC(C)C)ccc3Cl)[nH]c2c1] | M/Z = 345.1 (M + 1). RT = 2.86: Method A. |
| 217 | 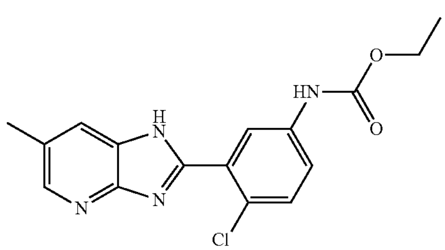 [SMILES: CCOC(=O)Nc1ccc(Cl)c(-c2nc3ncc(C)cc3[nH]2)c1] | M/Z = 331.1 (M + 1). RT = 1.34: Method B. |

TABLE II-continued

Listing of the Exemplified Compounds of the Invention

| Ex. No. | Structure | ¹H NMR and/or mass and/or (retention time (mins)) |
|---|---|---|
| 218 | 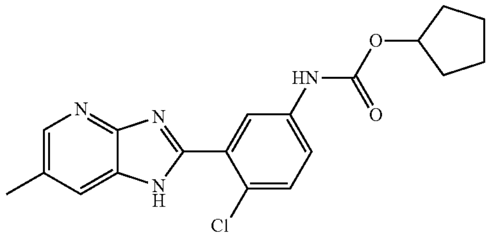 [SMILES: Cc1cnc2nc(-c3cc(NC(=O)OC4CCCC4)ccc3Cl)[nH]c2c1] | M/Z = 371.1 (M + 1). RT = 1.53: Method B. |
| 219 | 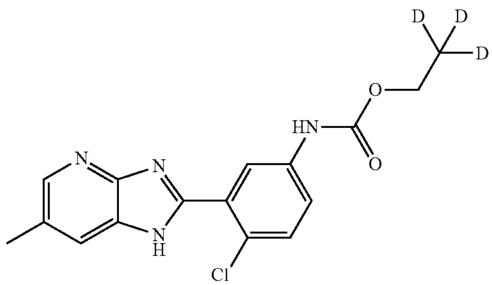 [SMILES: [2H]C([2H])([2H])COC(=O)Nc1ccc(Cl)c(-c2nc3ncc(C)cc3[nH]2)c1] | ¹H NMR (400 MHz, DMSO) δ 10.02 (s, 1H), 8.31 (s, 1H), 8.02 (s, 1H), 7.93 (s, 1H), 7.68-7.62 (m, 1H), 7.58 (d, J = 8.8 Hz, 1H), 4.14 (s, 2H), 2.47 (s, 3H). M/Z = 334.2 (M + 1). RT = 1.32: Method B. |
| 220 | 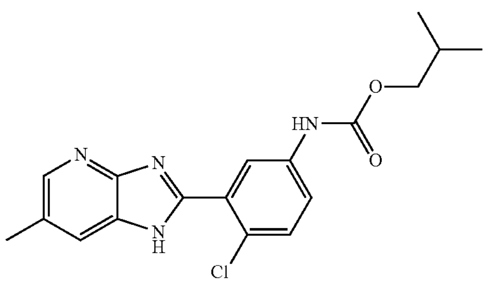 [SMILES: Cc1cnc2nc(-c3cc(NC(=O)OCC(C)C)ccc3Cl)[nH]c2c1] | ¹H NMR (400 MHz, DMSO) δ 9.92 (s, 1H), 8.16 (s, 1H), 7.94 (s, 1H), 7.75 (s, 1H), 7.56 (dd, J = 2.5, 8.8 Hz, 1H), 7.48 (d, J = 8.8 Hz, 1H), 3.83 (d, J = 6.7 Hz, 2H), 2.31 (s, 3H), 1.92-1.80 (m, 1H), 0.87 (d, J = 6.7 Hz, 6H). M/Z = 359.1 (M + 1). RT = 1.32: Method B. |
| 222 | 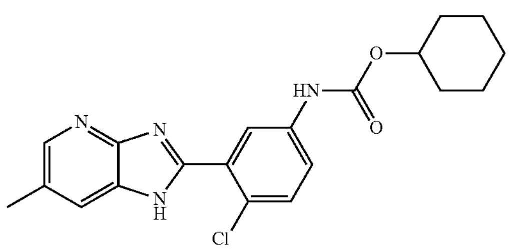 [SMILES: Cc1cnc2nc(-c3cc(NC(=O)OC4CCCCC4)ccc3Cl)[nH]c2c1] | ¹H NMR (400 MHz, DMSO) δ 9.90 (s, 1H), 8.22 (s, 1H), 7.94 (s, 1H), 7.83 (s, 1H), 7.61-7.52 (m, 1H), 7.50 (d, J = 8.8 Hz, 1H), 4.58 (s, 1H), 2.39 (s, 3H), 1.82 (s, 2H), 1.64 (s, 2H), 1.44 (s, 1H), 1.41-1.22 (m, 4H), 1.17 (s, 1H). M/Z = 385.1 (M + 1). RT = 1.63: Method B. |
| 223 | 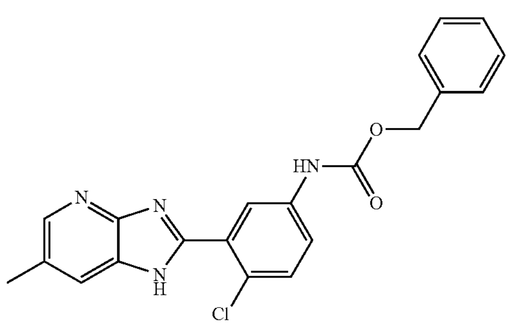 [SMILES: Cc1cnc2nc(-c3cc(NC(=O)OCc4ccccc4)ccc3Cl)[nH]c2c1] | ¹H NMR (400 MHz, DMSO) δ 10.08 (s, 1H), 8.18 (s, 1H), 7.94 (s, 1H), 7.77 (s, 1H), 7.57 (dd, J = 2.5, 8.8 Hz, 1H), 7.50 (d, J = 8.8 Hz, 1H), 7.41-7.20 (m, 5H), 5.11 (s, 2H), 2.37 (s, 3H). M/Z = 393.1 (M + 1). RT = 1.59: Method B. |

TABLE II-continued

Listing of the Exemplified Compounds of the Invention

| Ex. No. | Structure | $^1$H NMR and/or mass and/or (retention time (mins)) |
|---|---|---|
| 224 | 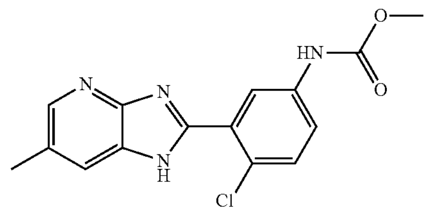 | M/Z = 317.1 (M + 1). RT = 1.20: Method B. |
| 225 | 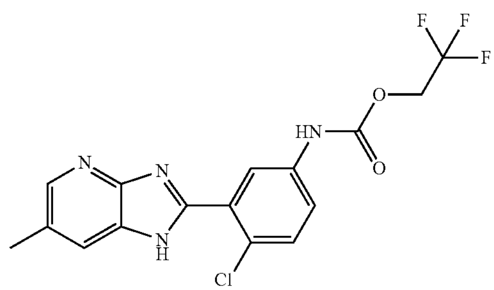 [SMILES: Cc1cnc2nc(-c3cc(NC(=O)OCC(F)(F)F)ccc3Cl)[nH]c2c1] | M/Z = 385.1 (M + 1). RT = 1.52: Method B. |
| 226 | 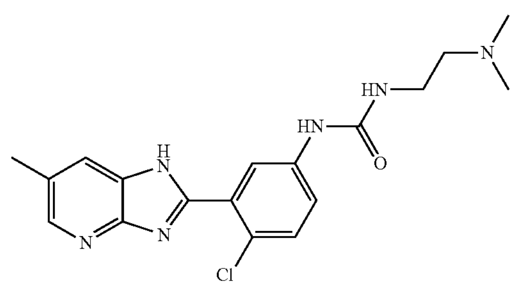 | $^1$H NMR (400 MHz, MeOD) δ 8.20 (s, 1H), 8.08 (d, J = 2.3 Hz, 1H), 7.89 (d, J = 8.3 Hz, 1H), 7.80 (s, 1H), 7.51 (d, J = 8.8 Hz, 1H), 7.20 (t, J = 7.9 Hz, 1H), 7.06 (d, J = 8.1 Hz, 1H), 7.00 (d, J = 2.1 Hz, 1H), 6.68 (dd, J = 2.2, 8.0 Hz, 1H), 3.30-3.23 (m, 6H), 2.43 (s, 3H), 2.02-1.88 (m, 4H). M/Z = 373.1 (M + 1). RT = 1.02: Method B. |
| 227 | 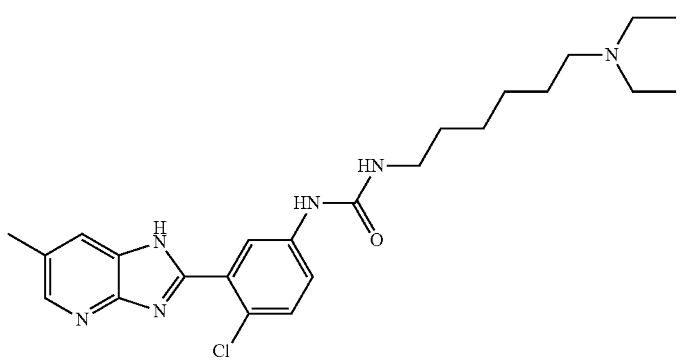 [SMILES: CCN(CC)CCCCCCNC(=O)Nc1ccc(Cl)c(-c2nc3ncc(C)cc3[nH]2)c1] | M/Z = 457.3 (M + 1). RT = 1.19: Method B. |
| 228 | 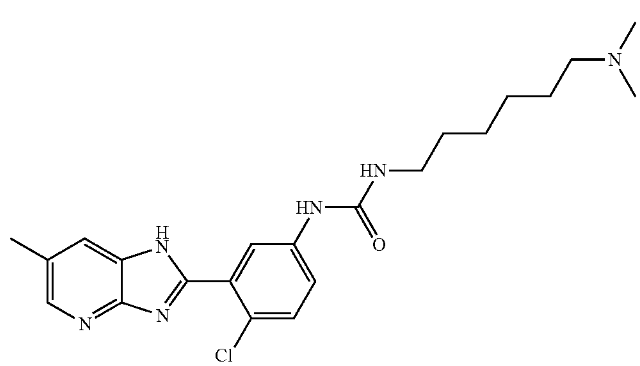 | M/Z = 429.2 (M + 1). RT = 1.11: Method B. |

TABLE II-continued

Listing of the Exemplified Compounds of the Invention

| Ex. No. | Structure | ¹H NMR and/or mass and/or (retention time (mins)) |
|---|---|---|
| 229 | 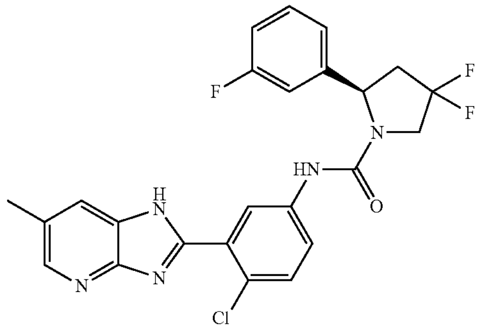 [SMILES: Cc1cnc2nc(-c3cc(NC(=O)N4CC(F)(F)C[C@@H]4c4cccc(F)c4)ccc3Cl)[nH]c2c1] | M/Z = 486.1 (M + 1). RT = 1.68: Method B. |
| 230 | 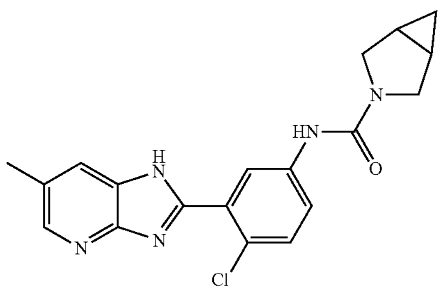 [SMILES: Cc1cnc2nc(-c3cc(NC(=O)N4CC5CC5C4)ccc3Cl)[nH]c2c1] | M/Z = 368.1 (M + 1). RT = 1.29: Method B. |
| 231 | 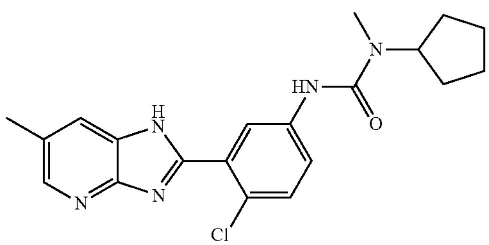 [SMILES: Cc1cnc2nc(-c3cc(NC(=O)N(C)C4CCCC4)ccc3Cl)[nH]c2c1] | M/Z = 384.1 (M + 1). RT = 1.45: Method B. |
| 232 | 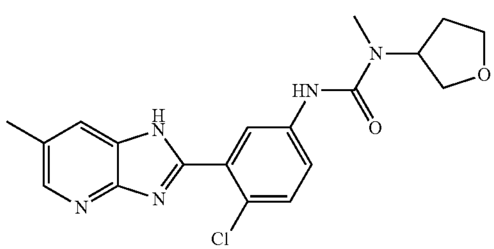 [SMILES: Cc1cnc2nc(-c3cc(NC(=O)N(C)C4CCOC4)ccc3Cl)[nH]c2c1] | M/Z = 386.1 (M + 1). RT = 1.19: Method B. |
| 233 | 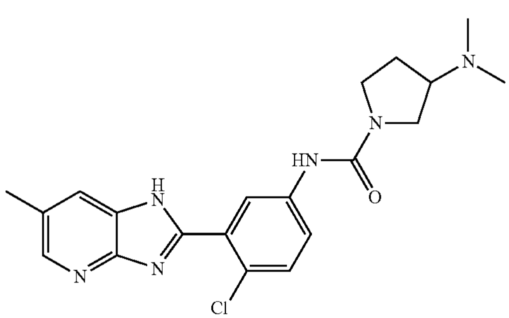 | M/Z = 399.1 (M + 1). RT = 1.03: Method B. |

TABLE II-continued
Listing of the Exemplified Compounds of the Invention
| Ex. No. | Structure | ¹H NMR and/or mass and/or (retention time (mins)) |
|---|---|---|
| 234 | 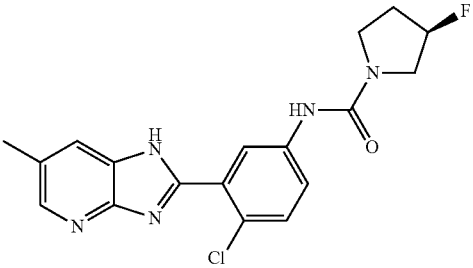 [SMILES: Cc1cnc2nc(-c3cc(NC(=O)N4CC[C@@H](F)C4)ccc3Cl)[nH]c2c1] | M/Z = 374.1 (M + 1). RT= 1.23: Method B. |
| 235 | 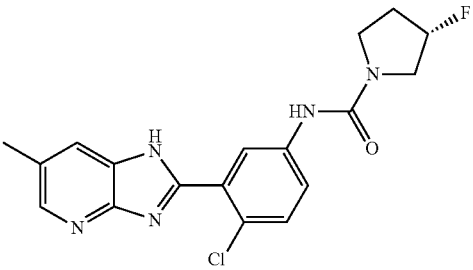 [SMILES: Cc1cnc2nc(-c3cc(NC(=O)N4CC[C@H](F)C4)ccc3Cl)[nH]c2c1] | M/Z = 374.1 (M + 1). RT = 1.23: Method B. |
| 236 | 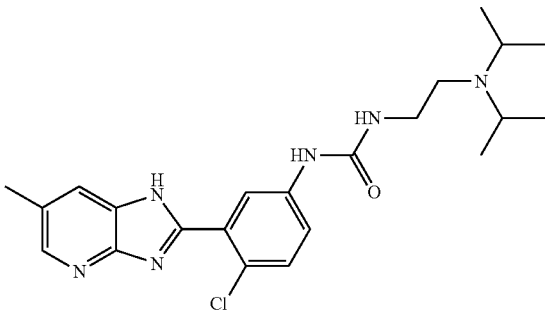 [SMILES: Cc1cnc2nc(-c3cc(NC(=O)NCCN(C(C)C)C(C)C)ccc3Cl)[nH]c2c1] | ¹H NMR (400 MHz, DMSO) δ 9.35 (d, 1H), 8.52 (s, 1H), 8.26 (d, 1H), 8.13-7.72 (m, 2H), 7.60 (d, J = 10.5 Hz, 1H), 7.52 (d, J = 7.7 Hz, 1H), 6.57 (d, J = 5.5 Hz, 1H), 3.66 (d, J = 4.8 Hz, 2H), 3.39 (s, 2H), 3.14 (s, 2H), 2.45 (s, 3H), 1.29 (d, J = 4.1 Hz, 12H). M/Z = 429.2 (M + 1). RT = 1.17: Method B. |
| 237 | 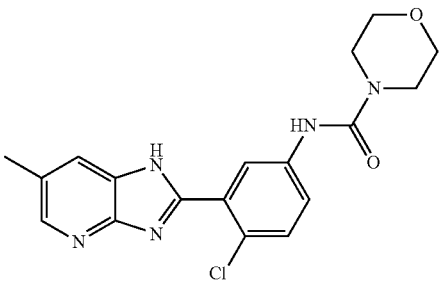 [SMILES: Cc1cnc2nc(-c3cc(NC(=O)N4CCOCC4)ccc3Cl)[nH]c2c1] | ¹H NMR (400 MHz, DMSO) δ 8.81 (s, 1H), 8.14 (s, 1H), 7.99 (d, J = 2.6 Hz, 1H), 7.73 (s, 1H), 7.63 (dd, J = 2.6, 8.8 Hz, 1H), 7.42 (d, J = 8.8 Hz, 1H), 3.59-3.48 (m, 4H), 3.43-3.34 (m, 4H), 2.36 (s, 3H). M/Z = 372.1 (M + 1). RT = 1.17: Method B. |
| 238 | 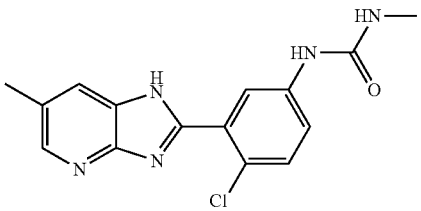 | M/Z = 316.1 (M + 1). RT = 1.06: Method B. |

TABLE II-continued
Listing of the Exemplified Compounds of the Invention
| Ex. No. | Structure | ¹H NMR and/or mass and/or (retention time (mins)) |
|---|---|---|
| 239 | 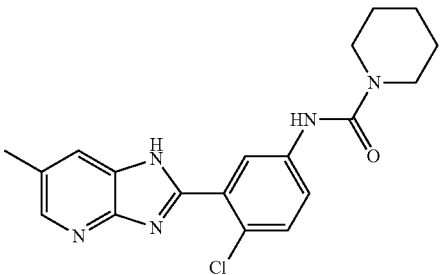 [SMILES: Cc1cnc2nc(-c3cc(NC(=O)N4CCCCC4)ccc3Cl)[nH]c2c1] | M/Z = 370.1 (M + 1). RT = 1.37: Method B. |
| 240 | 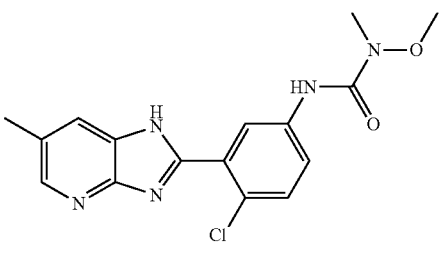 | M/Z = 346.1 (M + 1). RT = 1.61: Method B. |
| 241 | 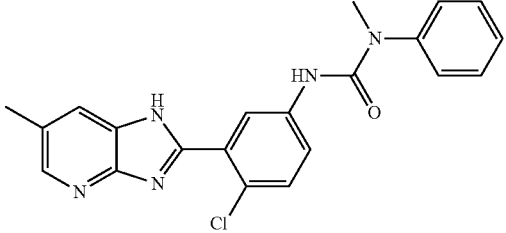 [SMILES: Cc1cnc2nc(-c3cc(NC(=O)N(C)c4ccccc4)ccc3Cl)[nH]c2c1] | M/Z = 392.1 (M + 1). RT = 1.43: Method B. |
| 242 | 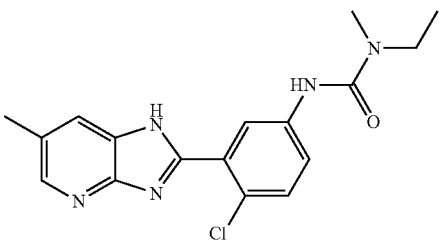 [SMILES: CCN(C)C(=O)Nc1ccc(Cl)c(-c2nc3ncc(C)cc3[nH]2)c1] | M/Z = 344.1 (M + 1). RT = 1.21: Method B. |
| 243 | 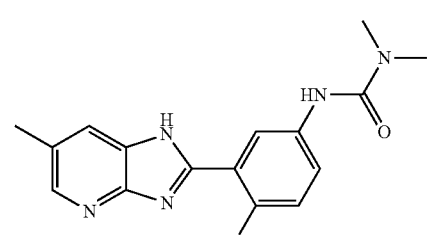 | M/Z = 330.1 (M + 1). RT = 1.10: Method B. |

TABLE II-continued

Listing of the Exemplified Compounds of the Invention

| Ex. No. | Structure | ¹H NMR and/or mass and/or (retention time (mins)) |
|---|---|---|
| 244 | 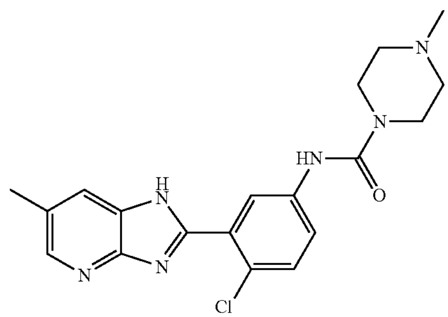 | M/Z = 385.1 (M + 1). RT = 1.01: Method B. |
| 245 | 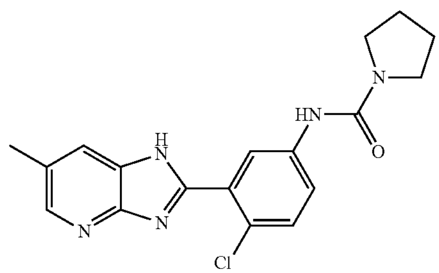 | M/Z = 356.1 (M + 1). RT = 1.24: Method B. |
| 246 | 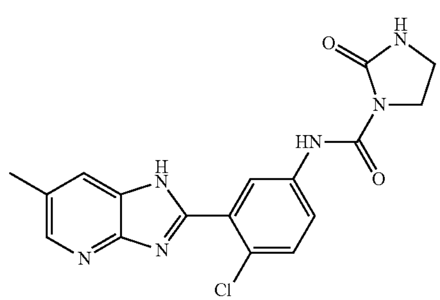 [SMILES: Cc1cnc2nc(-c3cc(NC(=O)N4CCNC4=O)ccc3Cl)[nH]c2c1] | M/Z = 371.1 (M + 1). RT = 1.29: Method B. |
| 247 | 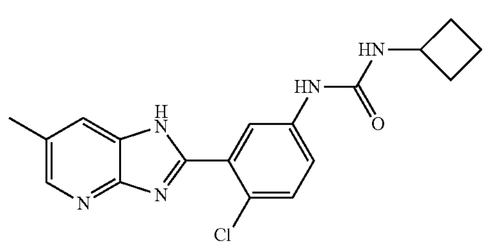 [SMILES: Cc1cnc2nc(-c3cc(NC(=O)NC4CCC4)ccc3Cl)[nH]c2c1] | ¹H NMR (400 MHz, MeOD) δ 8.29 (s, 1H), 7.89 (s, 1H), 7.83 (d, J = 2.6 Hz, 1H), 7.62 (dd, J = 2.5, 8.8 Hz, 1H), 7.48 (d, J = 8.8 Hz, 1H), 2.53 (s, 3H), 2.37-2.27 (m, 2H), 2.00-1.86 (m, 2H), 1.77-1.64 (m, 2H). M/Z = 356.1 (M + 1). RT = 1.31: Method B. |
| 248 | 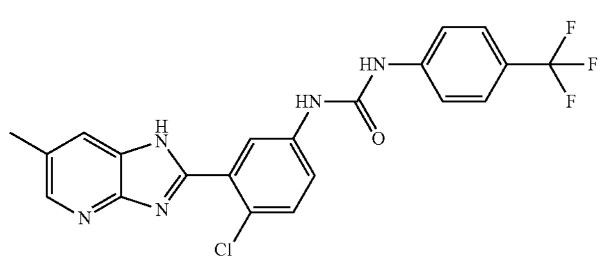 [SMILES: Cc1cnc2nc(-c3cc(NC(=O)Nc4ccc(C(F)(F)F)cc4)ccc3Cl)[nH]c2c1] | M/Z = 446.1 (M + 1). RT = 1.66: Method B. |

TABLE II-continued

Listing of the Exemplified Compounds of the Invention

| Ex. No. | Structure | ¹H NMR and/or mass and/or (retention time (mins)) |
|---|---|---|
| 249 | 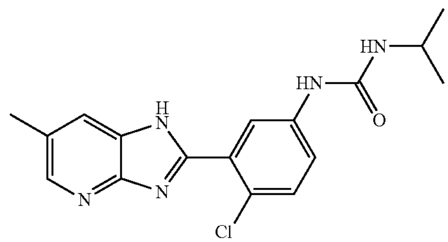 [SMILES: Cc1cnc2nc(-c3cc(NC(=O)NC(C)C)ccc3Cl)[nH]c2c1] | M/Z = 344.1 (M + 1). RT = 1.27: Method B. |
| 250 | 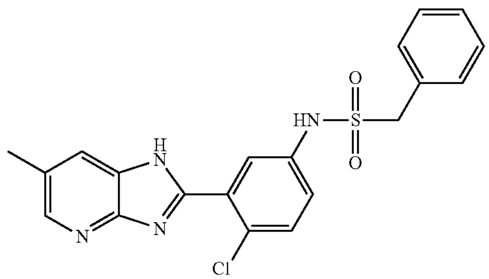 [SMILES: Cc1cnc2nc(-c3cc(NS(=O)(=O)Cc4ccccc4)ccc3Cl)[nH]c2c1] | ¹H NMR (400 MHz, DMSO) δ 8.17 (s, 1H), 7.80 (s, 1H), 7.41 (s, 1H), 7.33 (d, J = 8.7 Hz, 1H), 7.28-7.14 (m, 5H), 7.08 (d, J = 6.4 Hz, 1H), 4.24 (s, 2H), 2.37 (s, 3H). M/Z = 413.1 (M + 1). RT = 1.50: Method B. |
| 251 | 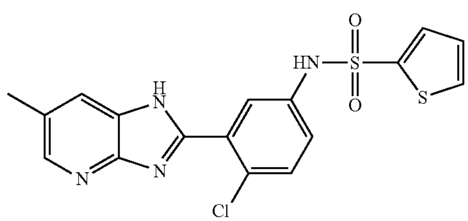 [SMILES: Cc1cnc2nc(-c3cc(NS(=O)(=O)c4cccs4)ccc3Cl)[nH]c2c1] | M/Z = 405.0 (M + 1). RT = 1.42: Method B. |
| 252 | 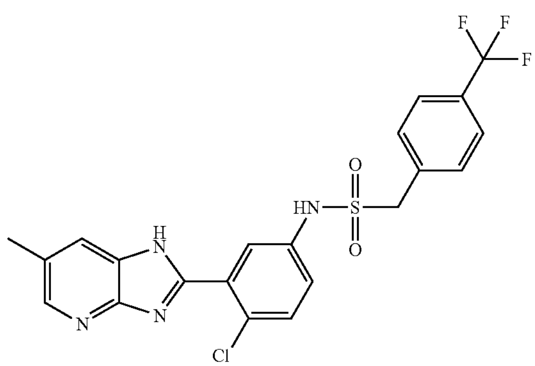 [SMILES: Cc1cnc2nc(-c3cc(NS(=O)(=O)Cc4ccc(C(F)(F)F)cc4)ccc3Cl)[nH]c2c1] | M/Z = 481.1 (M + 1). RT = 1.64: Method B. |
| 253 | 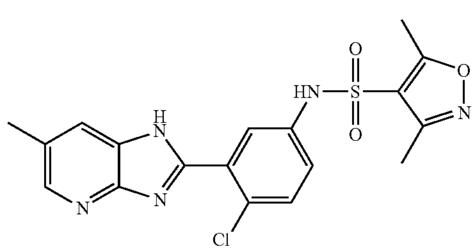 [SMILES: Cc1cnc2nc(-c3cc(NS(=O)(=O)c4c(C)noc4C)ccc3Cl)[nH]c2c1] | M/Z = 418.0 (M + 1). RT = 1.45: Method B. |

TABLE II-continued

Listing of the Exemplified Compounds of the Invention

| Ex. No. | Structure | ¹H NMR and/or mass and/or (retention time (mins)) |
|---|---|---|
| 254 | 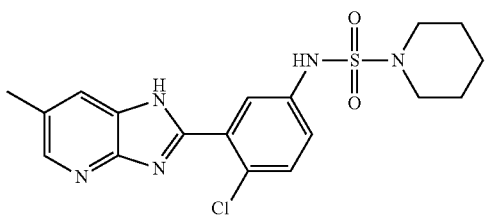 [SMILES: Cc1cnc2nc(-c3cc(NS(=O)(=O)N4CCCCC4)ccc3Cl)[nH]c2c1] | M/Z = 406.1 (M + 1). RT = 1.47: Method B. |
| 255 | 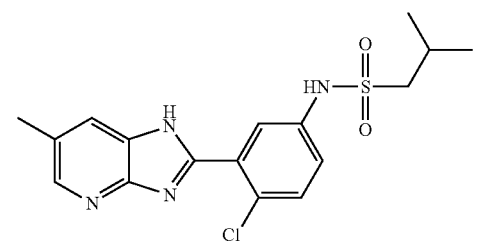 [SMILES: Cc1cnc2nc(-c3cc(NS(=O)(=O)CC(C)C)ccc3Cl)[nH]c2c1] | M/Z = 379.1 (M + 1). RT = 1.41: Method B. |
| 256 | 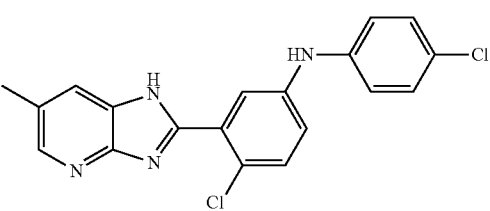 [SMILES: Cc1cnc2nc(-c3cc(Nc4ccc(Cl)cc4)ccc3Cl)[nH]c2c1] | ¹H NMR (400 MHz, DMSO) δ 8.65 (s, 1H), 8.23 (s, 1H), 7.82 (s, 1H), 7.51 (s, 1H), 7.47 (d, J = 8.7 Hz, 1H), 7.31 (d, J = 8.7 Hz, 2H), 7.20 (dd, J = 2.8, 8.8 Hz, 1H), 7.14 (d, J = 8.8 Hz, 2H), 2.43 (s, 3H). M/Z = 369.1 (M + 1). RT = 1.67: Method B. |
| 257 | 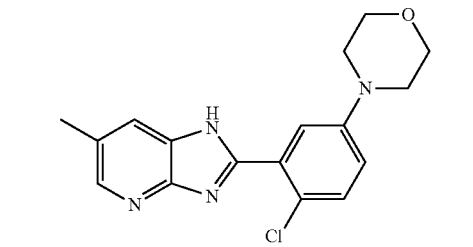 [SMILES: Cc1cnc2nc(-c3cc(N4CCOCC4)ccc3Cl)[nH]c2c1] | M/Z = 329.1 (M + 1). RT = 1.24: Method B. |
| 258 | 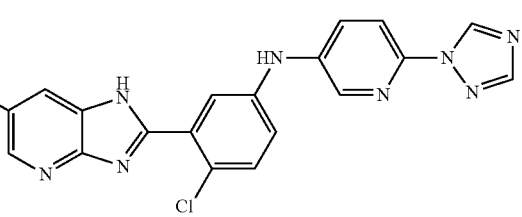 | ¹H NMR (400 MHz, DMSO) δ 9.24 (d, J = 2.8 Hz, 1H), 8.97 (d, J = 9.7 Hz, 1H), 8.43-8.13 (m, 3H), 7.96-7.60 (m, 4H), 7.54 (t, J = 6.8 Hz, 1H), 7.33-7.24 (m, 1H), 2.44 (d, J = 5.4 Hz, 3H). M/Z = 403.1 (M + 1). RT = 1.36: Method B. |
| 259 | 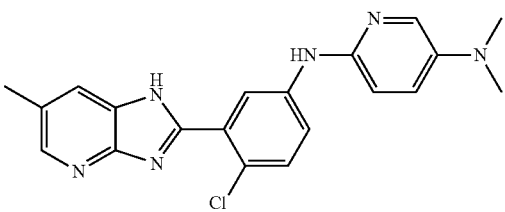 | M/Z = 379.1 (M + 1). RT = 1.15: Method B. |

TABLE II-continued

Listing of the Exemplified Compounds of the Invention

| Ex. No. | Structure | ¹H NMR and/or mass and/or (retention time (mins)) |
|---|---|---|
| 260 | 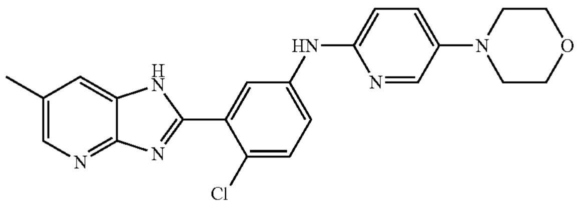 [SMILES: Cc1cnc2nc(-c3cc(Nc4ccc(N5CCOCC5)cn4)ccc3Cl)[nH]c2c1] | M/Z = 421.1 (M + 1). RT = 1.14: Method B. |
| 261 | 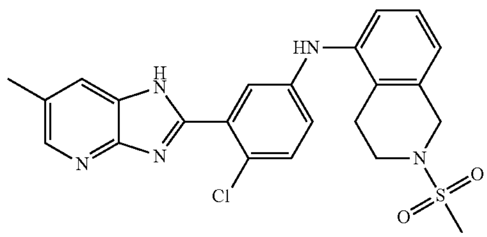 [SMILES: Cc1cnc2nc(-c3cc(Nc4cccc5c4CCN(S(C)(=O)=O)C5)ccc3Cl)[nH]c2c1] | M/Z = 468.1 (M + 1). RT = 1.50: Method B. |
| 262 | 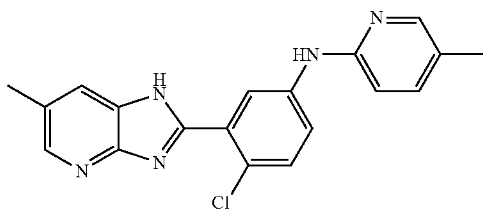 | ¹H NMR (400 MHz, DMSO) δ 9.28 (d, J = 9.4 Hz, 1H), 8.31-8.11 (m, 2H), 8.06-7.73 (m, 3H), 7.50-7.43 (m, 2H), 6.80 (d, J = 8.4, 1H), 2.45 (s, 3H), 2.18 (s, 3H). M/Z = 350.1 (M + 1). RT = 1.08: Method B. |
| 263 | 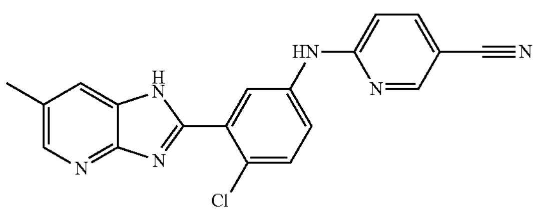 [SMILES: Cc1cnc2nc(-c3cc(Nc4ccc(C#N)cn4)ccc3Cl)[nH]c2c1] | M/Z = 361.1 (M + 1). RT = 1.30: Method B. |
| 264 | 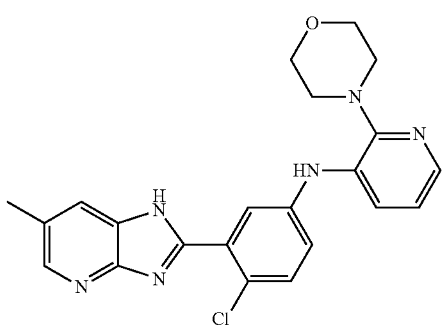 [SMILES: Cc1cnc2nc(-c3cc(Nc4cccnc4N4CCOCC4)ccc3Cl)[nH]c2c1] | M/Z = 421.1 (M + 1). RT = 1.14: Method B. |
| 265 | 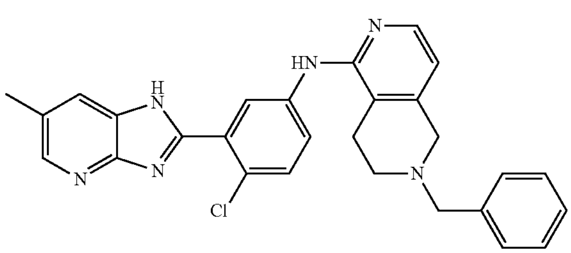 [SMILES: Cc1cnc2nc(-c3cc(Nc4nccc5c4CCN(Cc4ccccc4)C5)ccc3Cl)[nH]c2c1] | M/Z = 481.2 (M + 1). RT = 1.12: Method B. |

TABLE II-continued

Listing of the Exemplified Compounds of the Invention

| Ex. No. | Structure | ¹H NMR and/or mass and/or (retention time (mins)) |
|---|---|---|
| 266 | 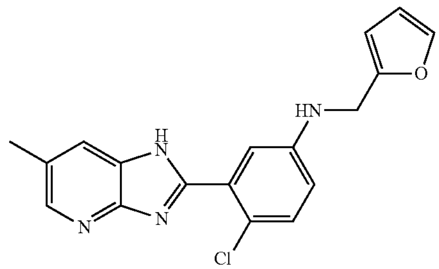 [SMILES: Cc1cnc2nc(-c3cc(NCc4ccco4)ccc3Cl)[nH]c2c1] | M/Z = 339.1 (M + 1). RT = 1.49: Method B. |
| 267 | 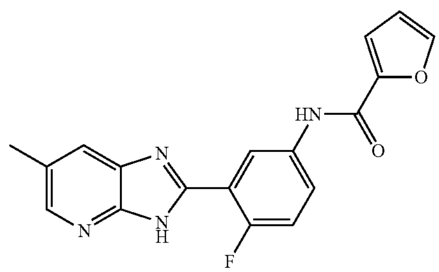 [SMILES: Cc1cnc2[nH]c(-c3cc(NC(=O)c4ccco4)ccc3F)nc2c1] | ¹H NMR (300 MHz, MeOD): δ 8.45 (1H, dd, J = 9.0, 10.8 Hz), 8.28 (1H, brs), 8.02-7.98 (1H, m), 7.86 (1H, s), 7.78-7.75 (1H, m), 7.42-7.35 (2H, m), 6.68 (1H, dd, J = 1.8, 3.6 Hz); M/Z = 337.6 (M + 1). |
| 268 | 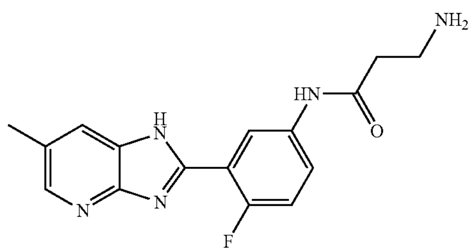 [SMILES: Cc1cnc2nc(-c3cc(NC(=O)CCN)ccc3F)[nH]c2c1] | M/Z = 314.1 (M + 1). RT = 0.94: Method B. |
| 269 | 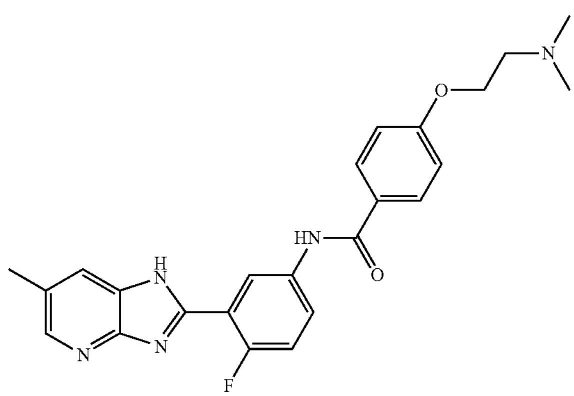 | M/Z = 434.2 (M + 1). RT= 1.13: Method B. |
| 270 | 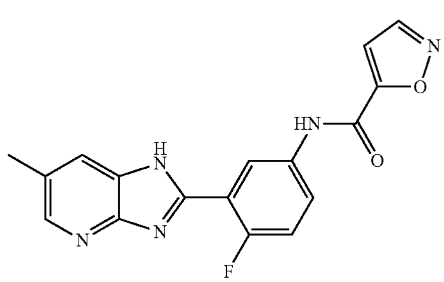 [SMILES: Cc1cnc2nc(-c3cc(NC(=O)c4ccno4)ccc3F)[nH]c2c1] | M/Z = 338.1 (M + 1). RT = 1.20: Method B. |

TABLE II-continued

Listing of the Exemplified Compounds of the Invention

| Ex. No. | Structure | $^1$H NMR and/or mass and/or (retention time (mins)) |
|---|---|---|
| 271 | 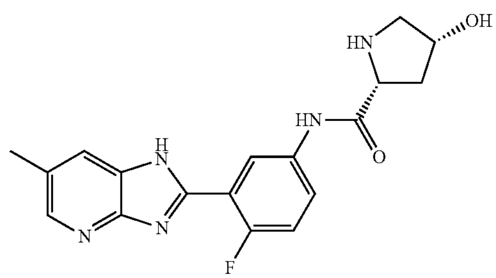 [SMILES: Cc1cnc2nc(-c3cc(NC(=O)[C@H]4C[C@@H](O)CN4)ccc3F)[nH]c2c1] | M/Z = 356.1 (M + 1). RT = 1.12: Method B. |
| 272 | 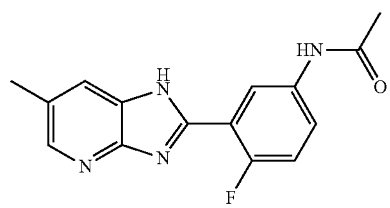 [SMILES: CC(=O)Nc1ccc(F)c(-c2nc3ncc(C)cc3[nH]2)c1] | M/Z = 285.1 (M + 1). RT = 1.03: Method B. |
| 273 | 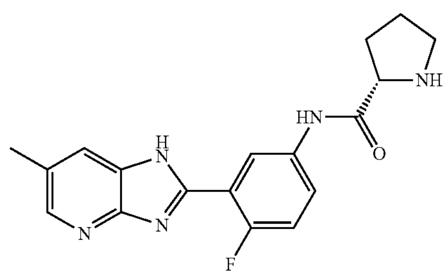 [SMILES: Cc1cnc2nc(-c3cc(NC(=O)[C@@H]4CCCN4)ccc3F)[nH]c2c1] | M/Z = 340.2 (M + 1). RT = 1.07: Method B. |
| 274 | 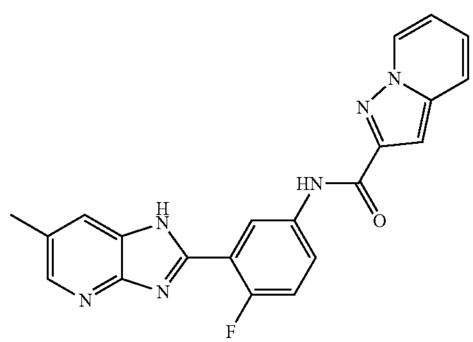 [SMILES: Cc1cnc2nc(-c3cc(NC(=O)c4cc5ccccn5n4)ccc3F)[nH]c2c1] | M/Z = 387.1 (M + 1). RT = 1.37: Method B. |
| 275 | 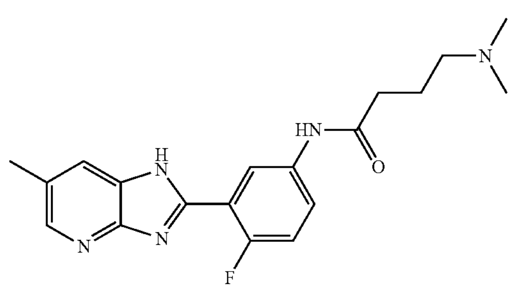 | M/Z = 356.2 (M + 1). RT = 1.13: Method B. |

TABLE II-continued

Listing of the Exemplified Compounds of the Invention

| Ex. No. | Structure | $^1$H NMR and/or mass and/or (retention time (mins)) |
|---|---|---|
| 276 | 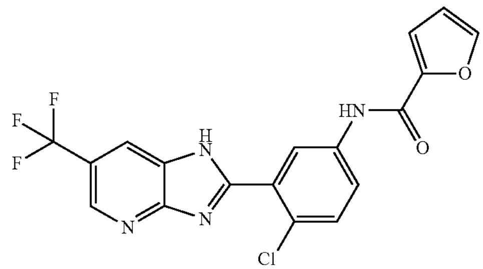 [SMILES: O=C(Nc1ccc(Cl)c(-c2nc3ncc(C(F)(F)F)cc3[nH]2)c1)c1ccco1] | $^1$H NMR (400 MHz, MeOD) δ 8.76 (d, J = 1.5 Hz, 1H), 8.38 (d, J = 1.8 Hz, 1H), 8.28 (d, J = 2.6 Hz, 1H), 8.00 (dd, J = 2.6, 8.8 Hz, 1H), 7.81-7.75 (m, 1H), 7.64 (d, J = 8.8 Hz, 1H), 7.32 (d, J = 3.5 Hz, 1H), 6.67 (dd, J = 1.8, 3.5 Hz, 1H). M/Z = 407.1 (M + 1). RT = 1.67: Method B. |
| 277 | 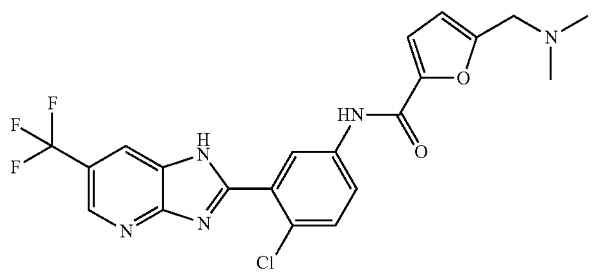 [SMILES: CN(C)Cc1ccc(C(=O)Nc2ccc(Cl)c(-c3nc4ncc(C(F)(F)F)cc4[nH]3)c2)o1] | $^1$H NMR (400 MHz, DMSO) δ 10.44 (s, 1H), 8.77 (s, 1H), 8.47 (s, 1H), 8.36 (s, 1H), 8.02 (dd, J = 2.6, 8.8 Hz, 1H), 7.67 (d, J = 8.8 Hz, 1H), 7.37 (d, J = 3.4 Hz, 1H), 6.54 (t, J = 5.8 Hz, 1H), 3.52 (s, 2H), 2.19 (s, 6H). M/Z = 464.1 (M + 1). RT = 1.42: Method B. |
| 278 | 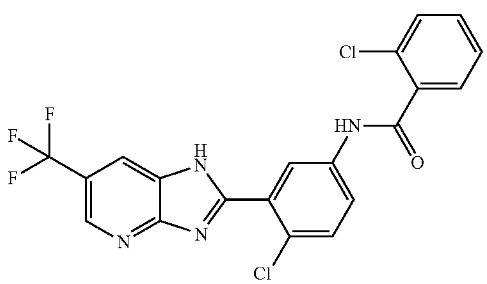 [SMILES: O=C(Nc1ccc(Cl)c(-c2nc3ncc(C(F)(F)F)cc3[nH]2)c1)c1ccccc1Cl] | M/Z = 451.0 (M + 1). RT = 1.90: Method B. |
| 279 | 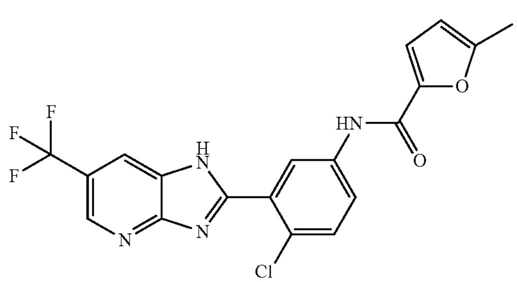 [SMILES: Cc1ccc(C(=O)Nc2ccc(Cl)c(-c3nc4ncc(C(F)(F)F)cc4[nH]3)c2)o1] | M/Z = 421.1 (M + 1). RT = 1.48: Method B. |
| 280 | 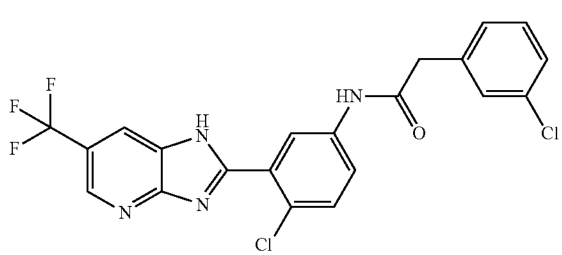 [SMILES: O=C(Cc1cccc(Cl)c1)Nc1ccc(Cl)c(-c2nc3ncc(C(F)(F)F)cc3[nH]2)c1] | $^1$H NMR (400 MHz, DMSO) δ 10.57 (s, 1H), 8.73 (s, 1H), 8.43 (s, 1H), 8.22 (d, J = 2.3 Hz, 1H), 7.80 (dd, J = 2.6, 8.8 Hz, 1H), 7.62 (d, J = 8.8 Hz, 1H), 7.43 (d, J = 1.8 Hz, 1H), 7.41-7.26 (m, 3H), 3.72 (s, 2H). M/Z = 465.1 (M + 1). RT = 2.01: Method B. |

TABLE II-continued

Listing of the Exemplified Compounds of the Invention

| Ex. No. | Structure | ¹H NMR and/or mass and/or (retention time (mins)) |
|---|---|---|
| 281 | 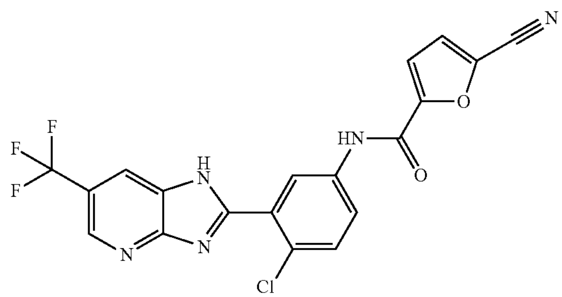 [SMILES: N#Cc1ccc(C(=O)Nc2ccc(Cl)c(-c3nc4ncc(C(F)(F)F)cc4[nH]3)c2)o1] | M/Z = 432.0 (M + 1). RT = 3.12: Method A. |
| 282 | 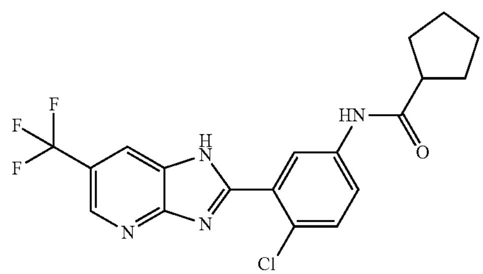 [SMILES: O=C(Nc1ccc(Cl)c(-c2nc3ncc(C(F)(F)F)cc3[nH]2)c1)C1CCCC1] | M/Z = 409.1 (M + 1). RT = 1.91: Method B. |
| 283 | 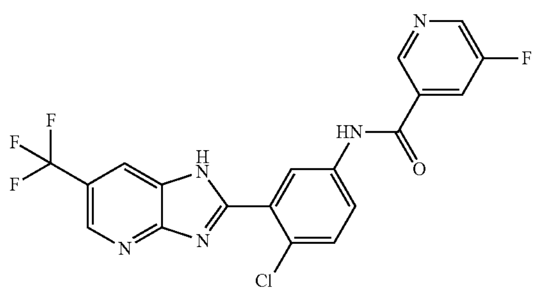 [SMILES: O=C(Nc1ccc(Cl)c(-c2nc3ncc(C(F)(F)F)cc3[nH]2)c1)c1cncc(F)c1] | M/Z = 436.1 (M + 1). RT = 1.73: Method B. |
| 284 | 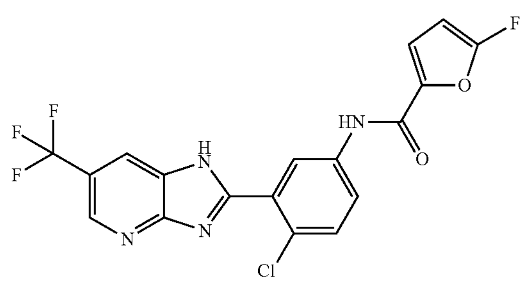 [SMILES: O=C(Nc1ccc(Cl)c(-c2nc3ncc(C(F)(F)F)cc3[nH]2)c1)c1ccc(F)o1] | M/Z = 425.1 (M + 1). RT = 1.77: Method B. |
| 285 | 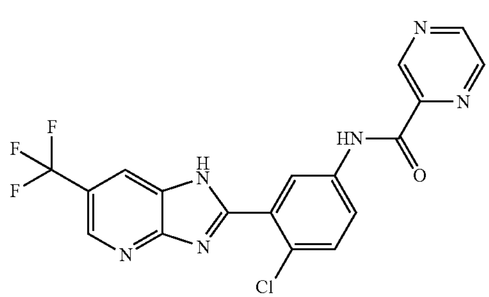 [SMILES: O=C(Nc1ccc(Cl)c(-c2nc3ncc(C(F)(F)F)cc3[nH]2)c1)c1cnccn1] | ¹H NMR (400 MHz, MeOD) δ 9.37 (d, J = 1.4 Hz, 1H), 8.85 (d, J = 2.5 Hz, 1H), 8.78-8.75 (m, 2H), 8.43 (d, J = 2.6 Hz, 1H), 8.39 (d, J = 1.7 Hz, 1H), 8.10 (dd, J = 2.6, 8.8 Hz, 1H), 7.67 (d, J = 8.8, 1H). M/Z = 419.1 (M + 1). RT = 1.64: Method B. |

TABLE II-continued

Listing of the Exemplified Compounds of the Invention

| Ex. No. | Structure | ¹H NMR and/or mass and/or (retention time (mins)) |
|---|---|---|
| 286 | 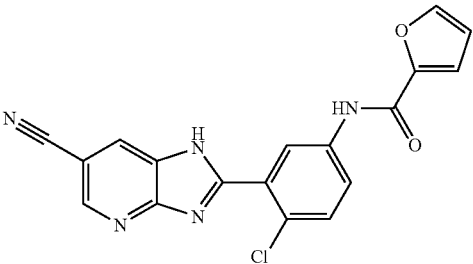 [SMILES: N#Cc1cnc2nc(-c3cc(NC(=O)c4ccco4)ccc3Cl)[nH]c2c1] | ¹H NMR (400 MHz, DMSO) δ 10.51 (s, 1H), 8.72 (s, 1H), 8.55 (s, 1H), 8.38 (d, J = 2.6 Hz, 1H), 7.99 (d, J = 2.5 Hz, 1H), 7.96 (s, 1H), 7.63 (d, J = 8.8 Hz, 1H), 7.39 (d, J = 3.4 Hz, 1H), 6.72 (dd, J = 1.7, 3.4 Hz, 1H). M/Z = 364.1 (M + 1). RT = 0.79: Method B |
| 287 | 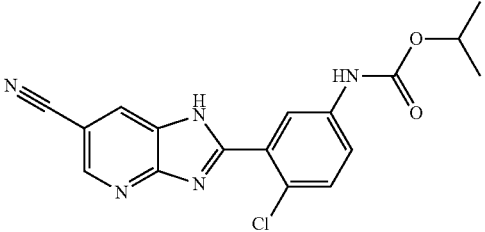 [SMILES: CC(C)OC(=O)Nc1ccc(Cl)c(-c2nc3ncc(C#N)cc3[nH]2)c1] | ¹H NMR (400 MHz, DMSO) δ 9.89 (s, 1H), 8.66 (s, 1H), 8.47 (s, 1H), 8.06 (s, 1H), 7.61 (d, J = 8.7, 1H), 7.52 (d, J = 8.8, 1H), 4.96-4.83 (m, 1H), 1.26 (d, J = 6.2, 6H). M/Z = 356.1 (M + 1). RT = 2.93: Method A. |
| 288 | 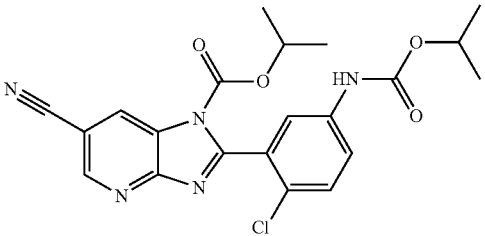 [SMILES: CC(C)OC(=O)Nc1ccc(Cl)c(-c2nc3ncc(C#N)cc3n2C(=O)OC(C)C)c1] | M/Z = 442.1 (M + 1). RT = 2.01: Method B. |
| 289 | 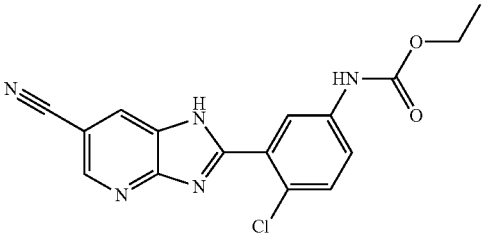 [SMILES: CCOC(=O)Nc1ccc(Cl)c(-c2nc3ncc(C#N)cc3[nH]2)c1] | M/Z = 342.1 (M + 1). RT = 2.78: Method A. |
| 290 | 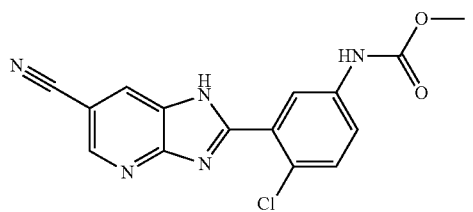 [SMILES: COC(=O)Nc1ccc(Cl)c(-c2nc3ncc(C#N)cc3[nH]2)c1] | M/Z = 328.1 (M + 1). RT = 2.62: Method A. |
| 291 | 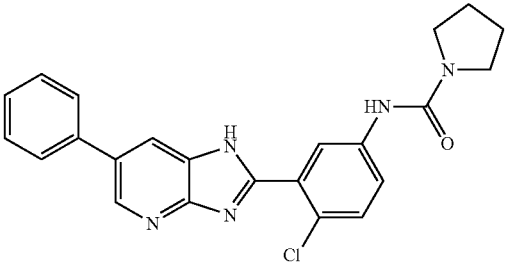 [SMILES: O=C(Nc1ccc(Cl)c(-c2nc3ncc(-c4ccccc4)cc3[nH]2)c1)N1CCCC1] | ¹H NMR (400 MHz, DMSO) δ 8.72 (dd, J = 2.0 Hz, 1H), 8.51 (d, 1H), 8.29 (dd, J = 2.3 Hz, 1H), 8.12 (dd, J = 2.4 Hz, 1H), 7.79 (m, 2H), 7.56-7.50 (m, 2H), 7.42 (m, 1H), 3.37 (s, 4H), 1.87 (s, 4H). M/Z = 418.1 (M + 1). RT = 1.56: Method B. |

TABLE II-continued

Listing of the Exemplified Compounds of the Invention

| Ex. No. | Structure | $^1$H NMR and/or mass and/or (retention time (mins)) |
|---|---|---|
| 292 | 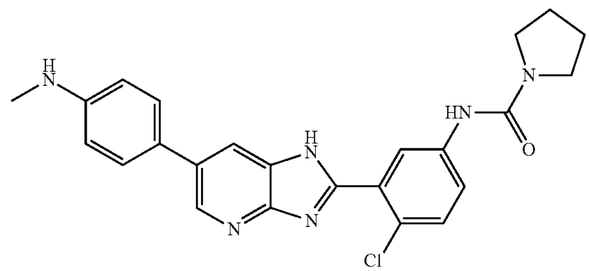 [SMILES: CNc1ccc(-c2cnc3nc(-c4cc(NC(=O)N5CCCC5)ccc4Cl)[nH]c3c2)cc1] | $^1$H NMR (400 MHz, MeOD) δ 8.82 (d, J = 1.8 Hz, 1H), 8.49 (d, J = 1.9 Hz, 1H), 8.20 (d, J = 2.6 Hz, 1H), 7.77 (d, J = 8.7 Hz, 2H), 7.68 (dd, J = 2.7, 8.8 Hz, 1H), 7.57 (d, J = 8.8 Hz, 1H), 7.19 (d, J = 8.6 Hz, 2H), 3.55-3.44 (m, 4H), 3.02-2.96 (m, 3H), 2.04-1.94 (m, 4H). M/Z = 447.2 (M + 1). RT = 1.27: Method B. |
| 293 | 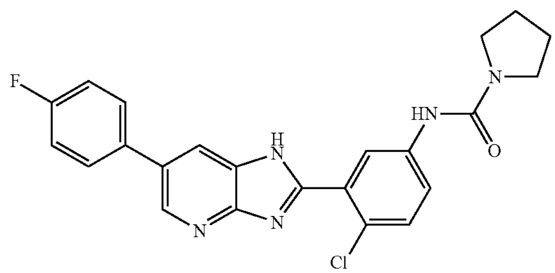 [SMILES: O=C(Nc1ccc(Cl)c(-c2nc3ncc(-c4ccc(F)cc4)cc3[nH]2)c1)N1CCCC1] | M/Z = 436.12 (M + 1). RT = 3.12: Method A. |
| 294 | 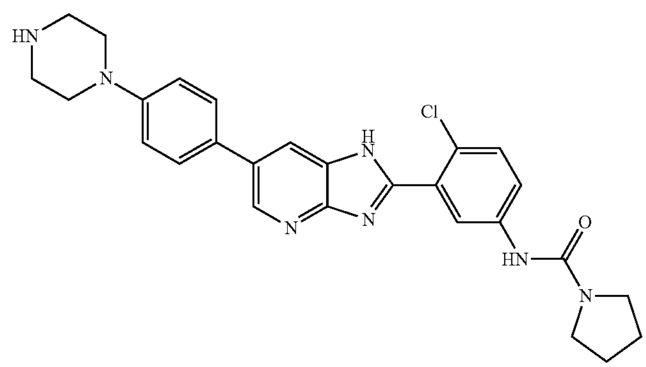 [SMILES: O=C(Nc1ccc(Cl)c(-c2nc3ncc(-c4ccc(N5CCNCC5)cc4)cc3[nH]2)c1)N1CCCC1] | M/Z = 502.2 (M + 1). RT = 2.20: Method A. |
| 295 | 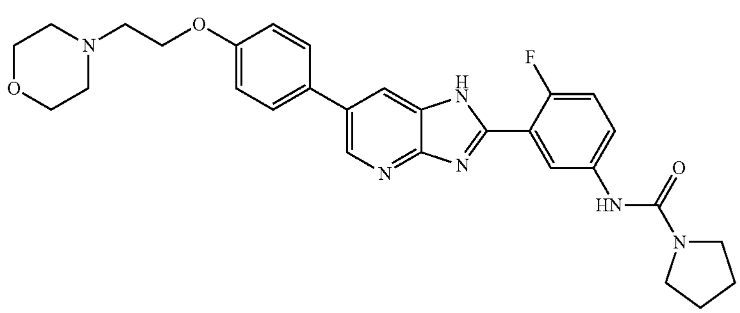 [SMILES: O=C(Nc1ccc(F)c(-c2nc3ncc(-c4ccc(OCCN5CCOCC5)cc4)cc3[nH]2)c1)N1CCCC1] | $^1$H NMR (400 MHz, MeOD) δ 8.71 (s, 1H), 8.51 (dd, J = 2.3, 7.4 Hz, 1H), 8.38 (d, J = 1.9 Hz, 1H), 8.01-7.94 (m, 1H), 7.73 (d, J = 8.8 Hz, 2H), 7.41 (dd, J = 8.7, 10.2, 1H), 7.20 (d, J = 8.8 Hz, 2H), 4.52-4.43 (m, 2H), 3.75-3.67 (m, 2H), 3.54 (t, J = 6.7 Hz, 4H), 2.10-1.96 (m, 4H). M/Z = 531.3 (M + 1). RT = 1.24: Method B. |
| 296 | 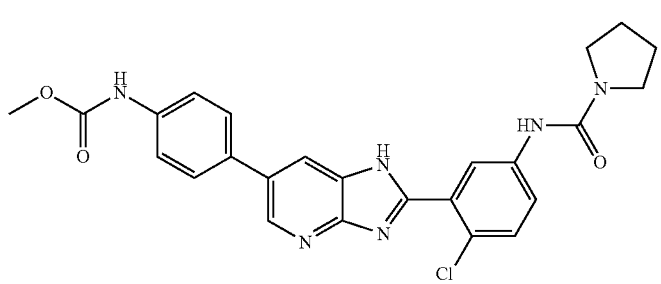 [SMILES: COC(=O)Nc1ccc(-c2cnc3nc(-c4cc(NC(=O)N5CCCC5)ccc4Cl)[nH]c3c2)cc1] | M/Z = 491.1 (M + 1). RT = 1.32: Method B. |

TABLE II-continued

Listing of the Exemplified Compounds of the Invention

| Ex. No. | Structure | ¹H NMR and/or mass and/or (retention time (mins)) |
|---|---|---|
| 297 | 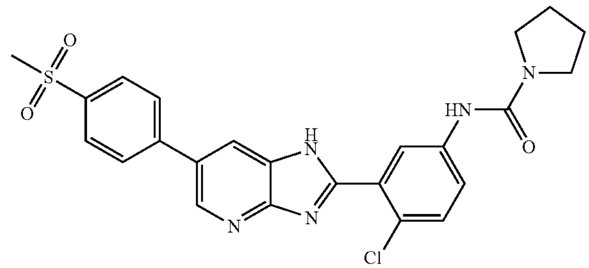 [SMILES: CS(=O)(=O)c1ccc(-c2cnc3nc(-c4cc(NC(=O)N5CCCC5)ccc4Cl)[nH]c3c2)cc1] | M/Z = 496.1 (M + 1). RT = 1.31: Method B. |
| 298 | 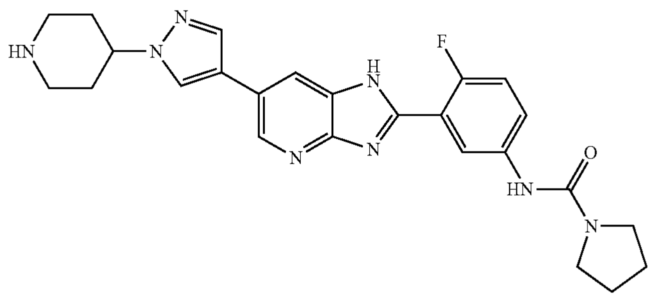 [SMILES: O=C(Nc1ccc(F)c(-c2nc3ncc(-c4cnn(C5CCNCC5)c4)cc3[nH]2)c1)N1CCCC1] | M/Z = 475.2 (M + 1). RT = 1.2: Method B. |
| 299 | 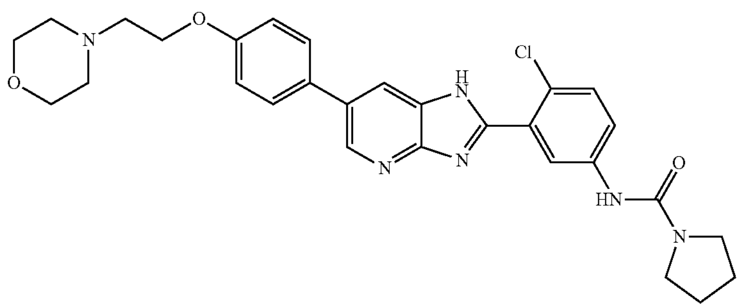 [SMILES: O=C(Nc1ccc(Cl)c(-c2nc3ncc(-c4ccc(OCCN5CCOCC5)cc4)cc3[nH]2)c1)N1CCCC1] | M/Z = 547.2 (M + 1). RT = 1.27: Method B. |
| 300 | 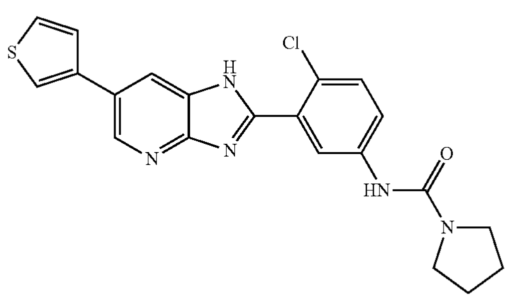 [SMILES: O=C(Nc1ccc(Cl)c(-c2nc3ncc(-c4ccsc4)cc3[nH]2)c1)N1CCCC1] | M/Z = 424.1 (M + 1). RT = 1.53: Method B. |
| 301 | 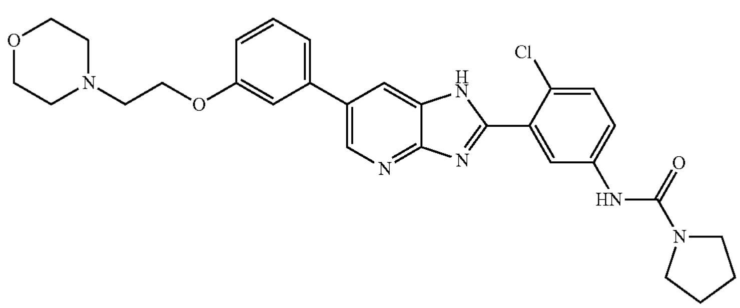 [SMILES: O=C(Nc1ccc(Cl)c(-c2nc3ncc(-c4cccc(OCCN5CCOCC5)c4)cc3[nH]2)c1)N1CCCC1] | M/Z = 547.2 (M + 1). RT = 2.22: Method A. |

TABLE II-continued

Listing of the Exemplified Compounds of the Invention

| Ex. No. | Structure | ¹H NMR and/or mass and/or (retention time (mins)) |
|---|---|---|
| 302 | 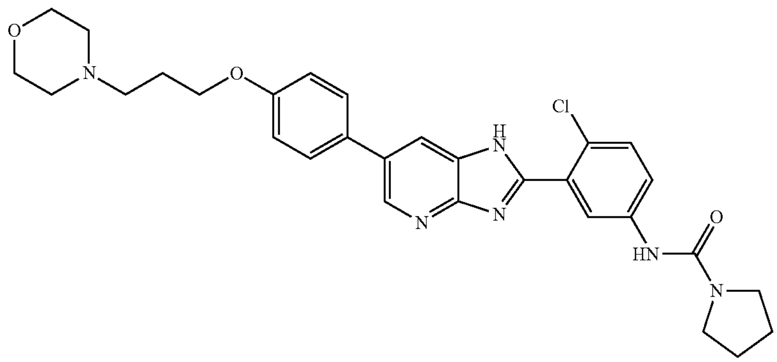 [SMILES: O=C(Nc1ccc(Cl)c(-c2nc3ncc(-c4ccc(OCCCN5CCOCC5)cc4)cc3[nH]2)c1)N1CCCC1] | M/Z = 561.2 (M + 1). RT = 1.32: Method A. |
| 303 | 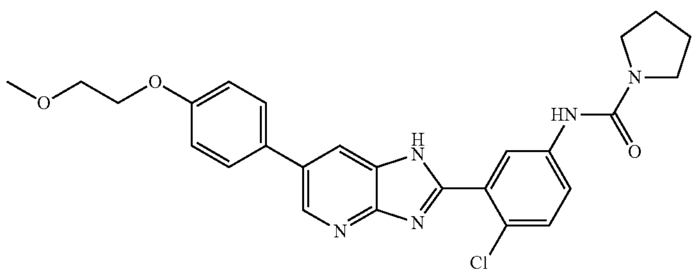 [SMILES: COCCOc1ccc(-c2cnc3nc(-c4cc(NC(=O)N5CCCC5)ccc4Cl)[nH]c3c2)cc1] | ¹H NMR (400 MHz, MeOD) δ 8.78 (d, J = 1.6 Hz, 1H), 8.42 (d, J = 1.9 Hz, 1H), 8.15(d, J = 2.6 Hz, 1H), 7.69 (dd, J = 1.7, 8.7 Hz, 3H), 7.56 (d, J = 8.8 Hz, 1H), 7.16-7.09 (m, 2H), 4.20 (dd, J = 3.7, 5.4, 2H), 3.82-3.76 (m, 2H), 3.54-3.46 (m, 4H), 3.47-3.44 (m, 3H). M/Z = 492.2 (M + 1). RT = 2.98: Method A. |
| 304 | 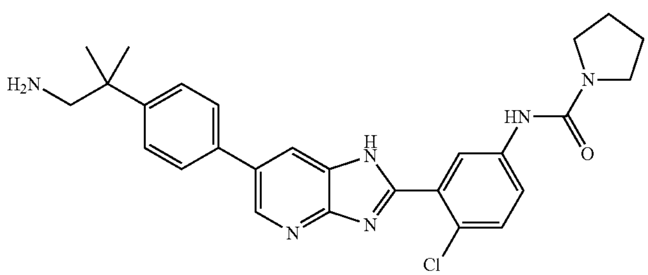 [SMILES: CC(C)(CN)c1ccc(-c2cnc3nc(-c4cc(NC(=O)N5CCCC5)ccc4Cl)[nH]c3c2)cc1] | M/Z = 489.2 (M + 1). RT = 1.33: Method B. |
| 305 | 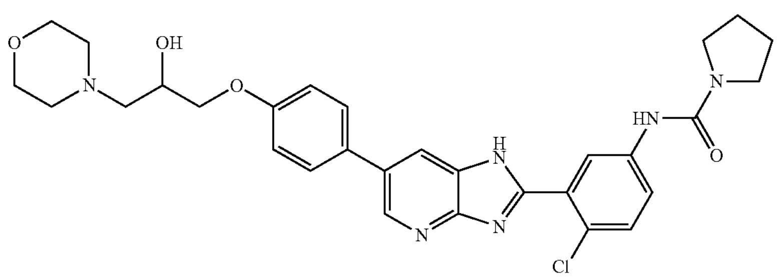 [SMILES: O=C(Nc1ccc(Cl)c(-c2nc3ncc(-c4ccc(OCC(O)CN5CCOCC5)cc4)cc3[nH]2)c1)N1CCCC1] | M/Z = 577.4 (M + 1). RT = 1.27: Method B. |
| 306 | 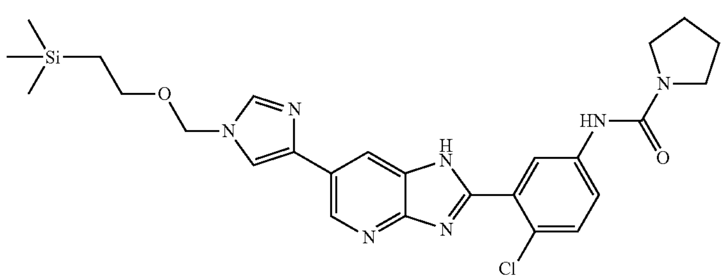 [SMILES: C[Si](C)(C)CCOCn1cnc(-c2cnc3nc(-c4cc(NC(=O)N5CCCC5)ccc4Cl)[nH]c3c2)c1] | M/Z = 538.2 (M + 1). RT = 3.16: Method A. |

TABLE II-continued

Listing of the Exemplified Compounds of the Invention

| Ex. No. | Structure | $^1$H NMR and/or mass and/or (retention time (mins)) |
|---|---|---|
| 307 | 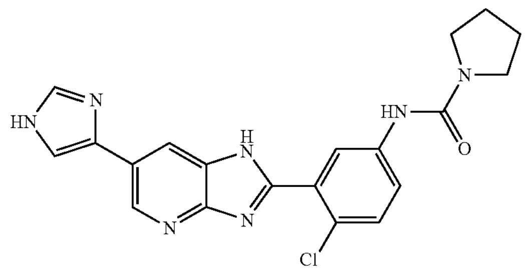 [SMILES: O=C(Nc1ccc(Cl)c(-c2nc3ncc(-c4c[nH]cn4)cc3[nH]2)c1)N1CCCC1] | $^1$H NMR (400 MHz, MeOD) δ 9.07 (s, 1H), 8.82 (d, J = 2.0 Hz, 1H), 8.41 (d, J = 2.1 Hz, 1H), 8.06 (d, J = 1.0 Hz, 1H), 8.03 (d, J = 2.6 Hz, 1H), 7.71-7.59 (m, 2H), 7.53 (t, J = 9.9 Hz, 2H), 3.47 (t, J = 6.7 Hz, 6H), 1.97 (s, 6H). M/Z = 408.1 (M + 1). RT = 1.16: Method B. |
| 308 | 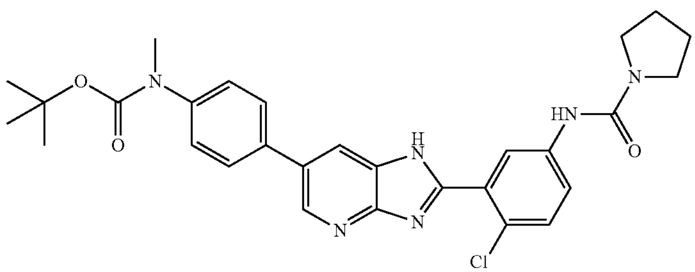 [SMILES: CN(C(=O)OC(C)(C)C)c1ccc(-c2cnc3nc(-c4cc(NC(=O)N5CCCC5)ccc4Cl)[nH]c3c2)cc1] | M/Z = 547.2 (M + 1). RT = 1.82: Method B. |
| 309 | 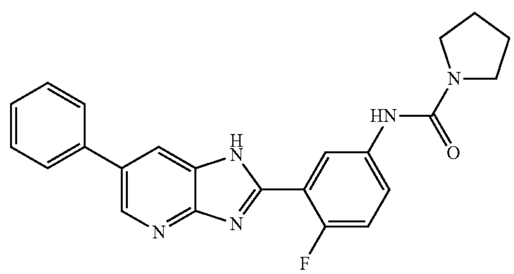 [SMILES: O=C(Nc1ccc(F)c(-c2nc3ncc(-c4ccccc4)cc3[nH]2)c1)N1CCCC1] | $^1$H NMR (300 MHz, CDCl$_3$): δ 8.69 (1H, s), 8.19 (1H, s), 8.09 (1H, dd, J = 3.5, 8.3 Hz), 8.07 (1H, m), 7.66 (2H, d, J = 6.9 Hz), 7.52 (2H, t, J = 7.2 Hz), 7.43 (1H, m), 7.16 (1H, dd, J = 9.0, 10.8 Hz), 6.60 (1H, s), 3.48 (4H, t, J = 6.6 Hz), 1.99 (4H, t, J = 6.3 Hz); M/Z = 402.1 (M + 1). RT = 3.25: Method A. |
| 310 | 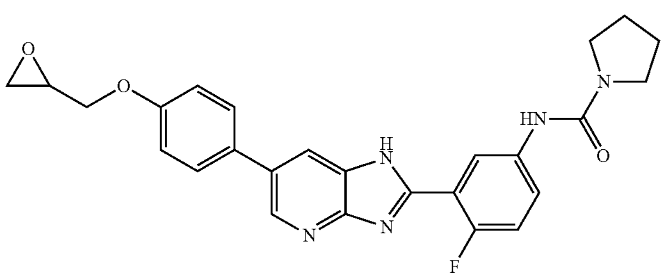 [SMILES: O=C(Nc1ccc(F)c(-c2nc3ncc(-c4ccc(OCC5CO5)cc4)cc3[nH]2)c1)N1CCCC1] | M/Z = 474.2 (M + 1). RT = 2.33: Method A. |
| 311 | 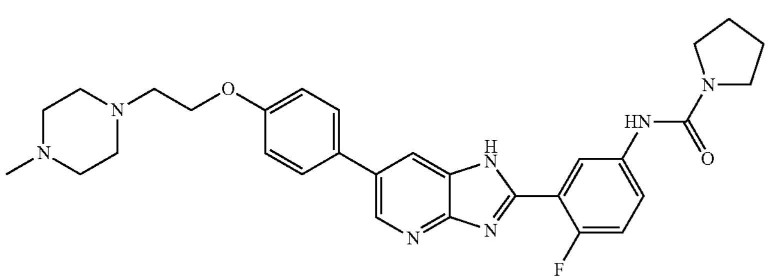 [SMILES: CN1CCN(CCOc2ccc(-c3cnc4nc(-c5cc(NC(=O)N6CCCC6)ccc5F)[nH]c4c3)cc2)CC1] | M/Z = 544.2 (M + 1). RT = 1.23: Method B. |

TABLE II-continued

Listing of the Exemplified Compounds of the Invention

| Ex. No. | Structure | ¹H NMR and/or mass and/or (retention time (mins)) |
|---|---|---|
| 312 | 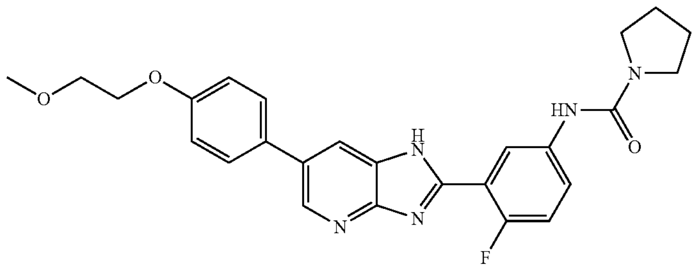 [SMILES: COCCOc1ccc(-c2cnc3nc(-c4cc(NC(=O)N5CCCC5)ccc4F)[nH]c3c2)cc1] | ¹H NMR (400 MHz, MeOD) δ 8.71 (s, 1H), 8.50 (dd, J = 2.3, 7.4 Hz, 1H), 8.37 (d, J = 1.8 Hz, 1H), 8.02-7.94 (m, 1H), 7.68 (dd, J = 2.4, 9.2 Hz, 2H), 7.41 (dd, J = 8.7, 10.2 Hz, 1H), 7.13 (d, J = 6.9 Hz, 2H), 4.26-4.14 (m, 2H), 3.85-3.74 (m, 2H), 3.60-3.51 (m, 4H), 3.48-3.43 (m, 3H), 2.03 (s, 4H). M/Z = 476.2 (M + 1). RT = 1.59: Method B. |
| 313 | 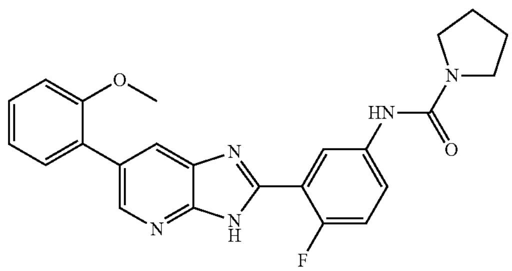 [SMILES: COc1ccccc1-c1cnc2[nH]c(-c3cc(NC(=O)N4CCCC4)ccc3F)nc2c1] | ¹H NMR (300 MHz, MeOD): δ 8.63(1H, s), 8.28 (2H, brs), 8.14-8.06 (2H, m), 7.42-7.39 (2H, m), 7.24-7.06 (3H, m), 6.48 (1H, s), 3.87 (3H, s), 3.47 (4H, t, J = 6.3 Hz), 1.99 (4H, t, J = 6.0 Hz); M/Z = 432.4 (M + 1). |
| 314 | 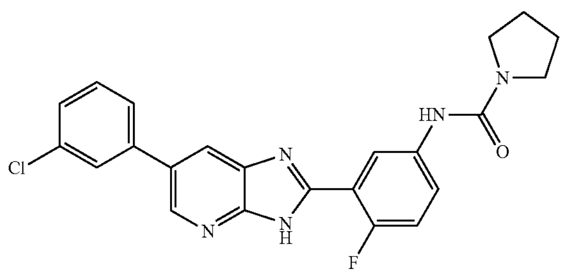 | ¹H NMR (300 MHz, MeOD): δ 8.60 (1H, s), 8.12 (2H, brs), 7.99-7.96 (1H, m), 7.93-7.90 (1H, m), 7.61 (1H, t, J = 1.2 Hz), 7.49-7.38 (3H, m), 7.15 (1H, t, J = 4.2 Hz), 3.49 (4H, t, J = 6.3 Hz), 1.97 (4H, t, J = 6.0 Hz); M/Z = 436.5 (M + 1). |
| 315 | 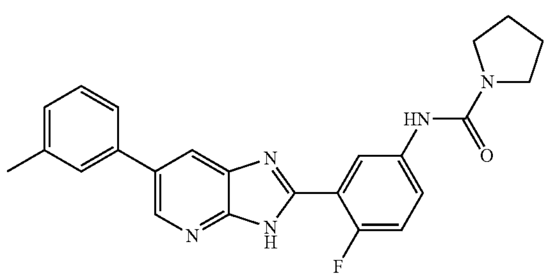 [SMILES: Cc1cccc(-c2cnc3[nH]c(-c4cc(NC(=O)N5CCCC5)ccc4F)nc3c2)c1] | ¹H NMR (300 MHz, MeOD): δ 8.68 (1H, s), 8.21 (2H, brs), 8.09-8.05 (2H, m), 7.46-7.23 (5H, m), 6.55 (1H, s), 3.48 (4H, t, J = 6.3 Hz), 1.99 (4H, t, J =6.8 Hz); M/Z = 416.5 (M + 1). |
| 316 | 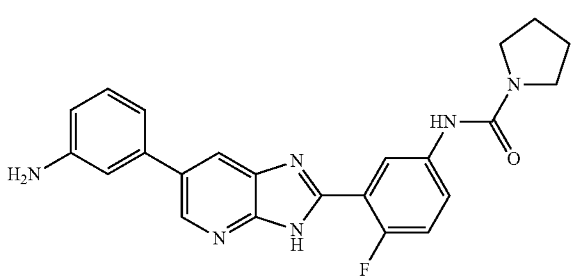 [SMILES: Nc1cccc(-c2cnc3[nH]c(-c4cc(NC(=O)N5CCCC5)ccc4F)nc3c2)c1] | ¹H NMR (300 MHz, MeOD): δ 8.61 (1H, d, J = 2.1 Hz), 8.12 (1H, J = 2.1 Hz), 7.89-7.86 (2H, m), 7.28-7.15 (2H, m), 7.00-6.96 (2H, m), 6.78 (1H, dd, J = 2.3, 4.8 Hz), 3.48 (4H, t, J = 6.3 Hz), 1.98 (4H, t, J = 6.8 Hz); M/Z = 417.4(M + 1). |

TABLE II-continued

Listing of the Exemplified Compounds of the Invention

| Ex. No. | Structure | ¹H NMR and/or mass and/or (retention time (mins)) |
|---|---|---|
| 317 | 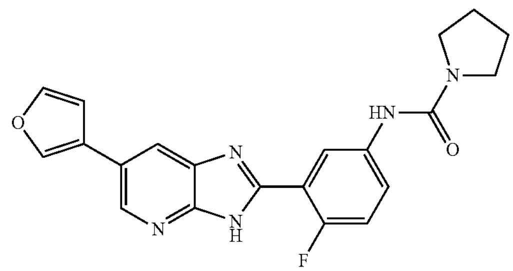 [SMILES: O=C(Nc1ccc(F)c(-c2nc3cc(-c4ccoc4)cnc3[nH]2)c1)N1CCCC1] | ¹H NMR (300 MHz, MeOD): δ 8.52 (1H, s), 8.06 (1H, s), 8.06-7.98 (3H, m), 7.55 (1H, s), 7.19 (1H, t, J = 2.3, 3.7 Hz), 6.80 (1H, s), 3.48 (4H, t, J = 6.3 Hz), 1.98 (4H, t, J = 6.8 Hz); M/Z = 393.1 (M + 1). |
| 318 | 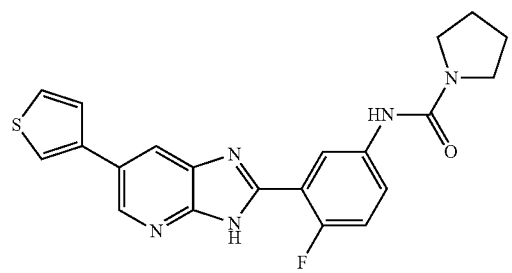 [SMILES: O=C(Nc1ccc(F)c(-c2nc3cc(-c4ccsc4)cnc3[nH]2)c1)N1CCCC1] | ¹H NMR (300 MHz, MeOD): δ 8.69 (1H, s), 8.15 (1H, s), 7.89-7.75 (2H, m), 7.58 (1H, s), 7.47-7.40 (2H, m), 7.22 (1H, t, J = 4.4 Hz), 3.51 (4H, t, J = 6.8 Hz), 2.00 (4H, t, J = 6.9 Hz); M/Z = 408.6 (M + 1). |
| 319 | 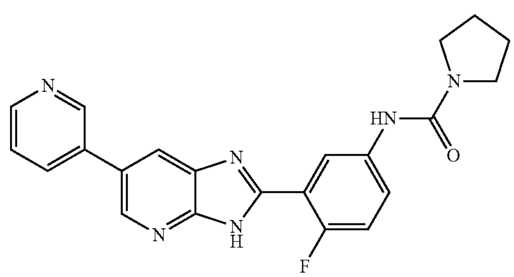 [SMILES: O=C(Nc1ccc(F)c(-c2nc3cc(-c4cccnc4)cnc3[nH]2)c1)N1CCCC1] | ¹H NMR (300 MHz, MeOD): δ 8.68 (1H, s), 8.61 (1H, brs), 8.20 (1H, s), 7.98-7.9 (3H, m), 7.47 (1H, d, J = 1.9 Hz), 7.29-7.14 (2H, m), 3.48 (4H, t, J = 6.3 Hz), 1.99 (4H, t, J = 6.8 Hz); M/Z = 403.4 (M + 1). |
| 320 | 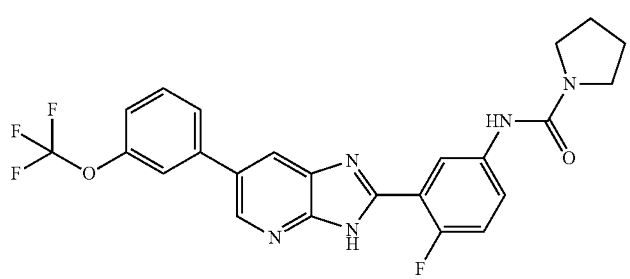 [SMILES: O=C(Nc1ccc(F)c(-c2nc3cc(-c4cccc(OC(F)(F)F)c4)cnc3[nH]2)c1)N1CCCC1] | ¹H NMR (300 MHz, MeOD): δ 8.69 (1H, d, J = 2.1 Hz), 8.23 (1H, d, J = 4.5 Hz), 8.01 (1H, brs), 7.86-7.8 (2H, m), 7.63-7.53 (2H, m), 7.31-7.21 (2H, m), 3.52 (4H, t, J = 6.3 Hz), 2.01 (4H, t, J = 6.8 Hz); M/Z = 408.1 (M + 1). |
| 321 | 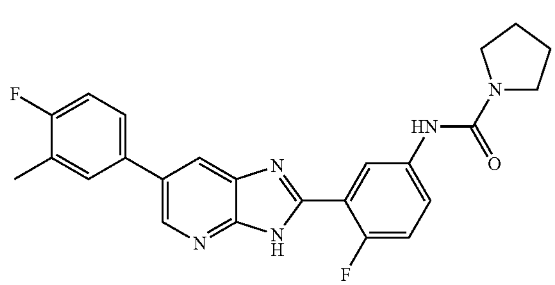 [SMILES: Cc1cc(-c2cnc3[nH]c(-c4cc(NC(=O)N5CCCC5)ccc4F)nc3c2)ccc1F] | ¹H NMR (300 MHz, MeOD): δ 8.59 (1H, s), 8.09 (1H, s), 7.93-7.80 (2H, m), 7.47-7.40 (2H, m), 7.20-7.11 (2H, m), 3.48 (4H, t, J = 6.3 Hz), 1.99 (4H, t, J = 6.8 Hz); M/Z = 434.4 (M + 1). |

TABLE II-continued

Listing of the Exemplified Compounds of the Invention

| Ex. No. | Structure | ¹H NMR and/or mass and/or (retention time (mins)) |
|---|---|---|
| 322 | 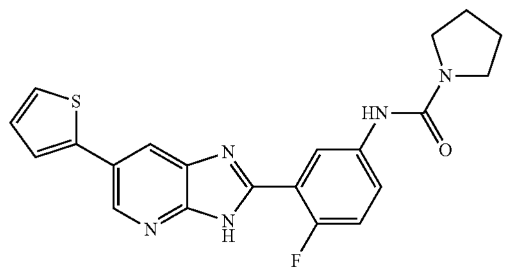 [SMILES: O=C(Nc1ccc(F)c(-c2nc3cc(-c4cccs4)cnc3[nH]2)c1)N1CCCC1] | ¹H NMR (300 MHz, MeOD): δ 8.70 (1H, d, J = 14 Hz), 8.24 (1H, d, J = 19.5 Hz), 7.98-7.90 (2H, m), 7.43-7.39 (2H, m), 7.17-7.10 (2H, m), 3.48 (4H, t, J = 6.3 Hz), 1.98 (4H, t, J = 6.8 Hz); M/Z = 408.1 (M + 1). |
| 323 | 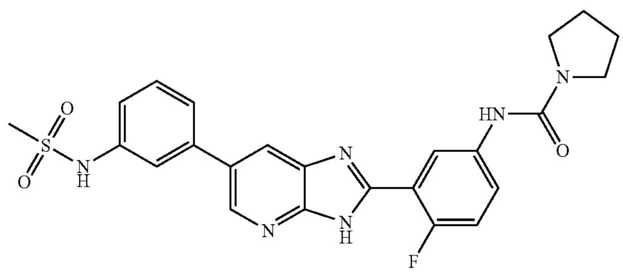 [SMILES: CS(=O)(=O)Nc1cccc(-c2cnc3[nH]c(-c4cc(NC(=O)N5CCCC5)ccc4F)nc3c2)c1] | ¹H NMR (300 MHz, MeOD): δ 8.68 (1H, d, J = 21.0 Hz), 8.20 (1H, d, J = 18 Hz) 7.90-7.88 (2H, m), 7.50-7.20 (5H, m), 3.48 (4H, t, J = 6.7 Hz), 3.02 (3H, s), 1.98 (4H, t, J = 6.0 Hz); M/Z = 495.5 (M + 1). |
| 324 | 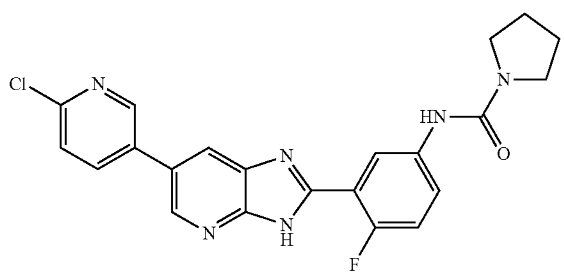 [SMILES: O=C(Nc1ccc(F)c(-c2nc3cc(-c4ccc(Cl)nc4)cnc3[nH]2)c1)N1CCCC1] | ¹H NMR (300 MHz, MeOD): δ 8.64 (1H, d, J = 1.2 Hz), 8.19 (1H, brs), 8.03 (1H, dd, J = 2.4, 12.2 Hz), 7.93-7.82 (2H, m), 7.53-7.47 (2H, m), 7.20 (1H, dd, J = 9.3, 10.8 Hz), 3.48 (4H, t, J = 6.7 Hz), 1.99 (4H, t, J = 6.0 Hz); M/Z = 437.8 (M + 1). |
| 325 | 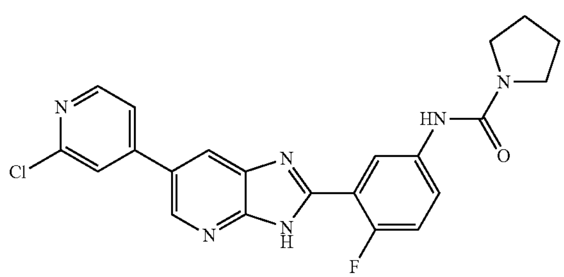 [SMILES: O=C(Nc1ccc(F)c(-c2nc3cc(-c4ccnc(Cl)c4)cnc3[nH]2)c1)N1CCCC1] | ¹H NMR (300 MHz, MeOD): δ 8.70 (1H, s), 8.45 (1H, d, J = 5.1 Hz). 8.23 (1H, s), 7.94-7.79 (2H, m), 7.69 (1H, d, J = 1.2 Hz), 7.60 (1H, dd, J = 1.5, 5.2 Hz), 7.20 (1H, dd, J = 9.0, 10.8 Hz), 3.49 (4H, t, J = 6.7 Hz), 1.98 (4H, t, J = 6.0 Hz); M/Z = 437.8 (M + 1). |
| 326 | 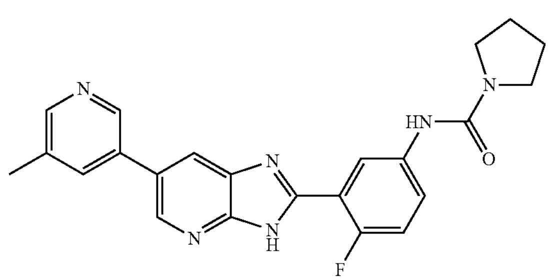 [SMILES: Cc1cncc(-c2cnc3[nH]c(-c4cc(NC(=O)N5CCCC5)ccc4F)nc3c2)c1] | ¹H NMR (300 MHz, MeOD): δ 8.67-8.55 (2H, m), 8.39 (1H, d, J = 5.1 Hz), 8.20 (1H, d, J = 14 Hz), 7.90-7.81 (3H, m), 7.19 (1H, dd, J = 3.5, 7.8 Hz), 3.48 (4H, t, J = 6.8 Hz), 1.98 (4H, t, J = 6.0 Hz); M/Z = 418.3 (M + 1). |

TABLE II-continued

Listing of the Exemplified Compounds of the Invention

| Ex. No. | Structure | ¹H NMR and/or mass and/or (retention time (mins)) |
|---|---|---|
| 327 | 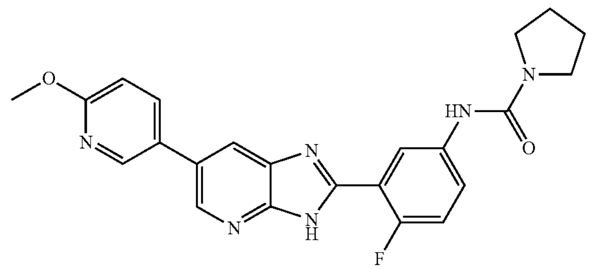 [SMILES: COc1ccc(-c2cnc3[nH]c(-c4cc(NC(=O)N5CCCC5)ccc4F)nc3c2)cn1] | ¹H NMR (300 MHz, MeOD): δ 8.64 (1H, d, J = 14 Hz), 8.39 (1H, d, J = 9 Hz), 8.13-7.89 (4H, m), 7.19 (1H, m), 6.91 (1H, d, J = 8.2 Hz), 4.17 (3H, s), 3.49 (4H, t, J = 6.7 Hz), 1.98 (4H, t, J = 6.0 Hz); M/Z = 433.5 (M + 1). |
| 328 | 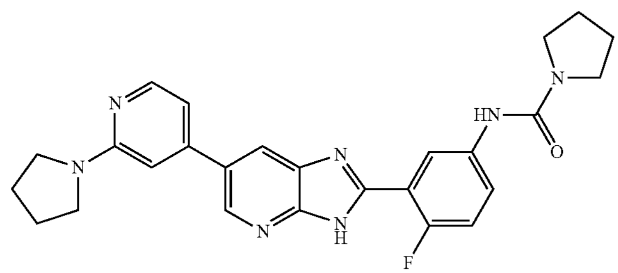 [SMILES: O=C(Nc1ccc(F)c(-c2nc3cc(-c4ccnc(N5CCCC5)c4)cnc3[nH]2)c1)N1CCCC1] | ¹H NMR (300 MHz, MeOD): δ 8.64 (1H, brs), 8.49 (1H, s), 8.13-8.05 (2H, m), 7.77 (1H, dd, J = 6.6, 9.0 Hz), 7.29 (1H, m ), 6.51 (2H, m), 3.56-3.51 (8H, m), 2.09-1.98 (8H, m); M/Z = 472.4 (M + 1) |
| 329 | 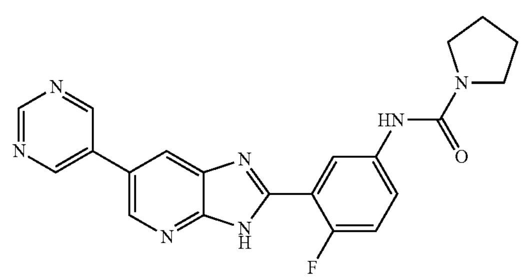 [SMILES: O=C(Nc1ccc(F)c(-c2nc3cc(-c4cncnc4)cnc3[nH]2)c1)N1CCCC1] | ¹H NMR (300 MHz, MeOD): δ 9.21-9.07 (3H, m), 8.72-8.68 (1H, m), 8.27-8.18 (1H, m), 7.81-7.75 (2H, m), 7.24 (1H, t, J = 9.2 Hz), 3.49 (4H, t, J = 6.7 Hz), 1.98 (4H, t, J = 6.0 Hz); M/Z = 404.5 (M + 1). |
| 330 | 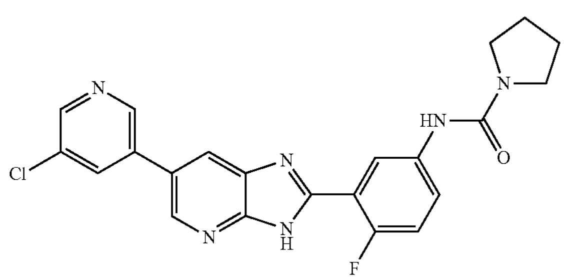 [SMILES: O=C(Nc1ccc(F)c(-c2nc3cc(-c4cncc(Cl)c4)cnc3[nH]2)c1)N1CCCC1] | ¹H NMR (300 MHz, MeOD): δ 8.69 (1H, s), 8.56 (1H, s), 8.23-8.15 (3H, m), 7.92-7.79 (2H, m), 7.24 (1H, dd, J =1.5, 5.2 Hz), 3.49 (4H, t, J = 6.7 Hz), 1.98 (4H, t, J = 6.0 Hz); M/Z = 437.7 (M + 1). |
| 331 | 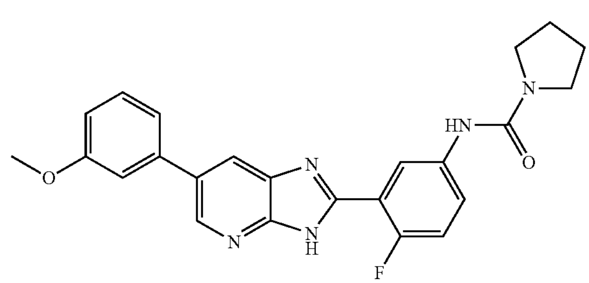 [SMILES: COc1cccc(-c2cnc3[nH]c(-c4cc(NC(=O)N5CCCC5)ccc4F)nc3c2)c1] | ¹H NMR (300 MHz, MeOD): δ 8.66 (1H, s), 8.17 (2H, brs), 7.72 (1H, brs), 7.41 (1H, t, 7.8 Hz), 7.24 (3H, m), 6.99 (1H, dd, J = 3.8, 6.9 Hz), 3.88 (3H, s), 3.50 (4H, t, J = 6.6 Hz), 2.00 (4H, t, J = 6.3 Hz); M/Z = 432.4 (M + 1). |

TABLE II-continued

Listing of the Exemplified Compounds of the Invention

| Ex. No. | Structure | ¹H NMR and/or mass and/or (retention time (mins)) |
|---|---|---|
| 332 | 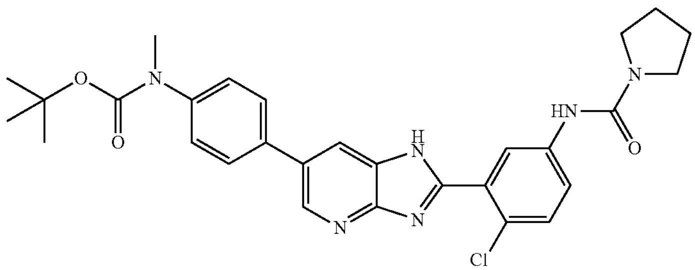 [SMILES: CN(C(=O)OC(C)(C)C)c1ccc(-c2cnc3nc(-c4cc(NC(=O)N5CCCC5)ccc4Cl)[nH]c3c2)cc1] | M/Z = 547.2 (M + 1). RT = 1.82: Method B. |
| 333 | 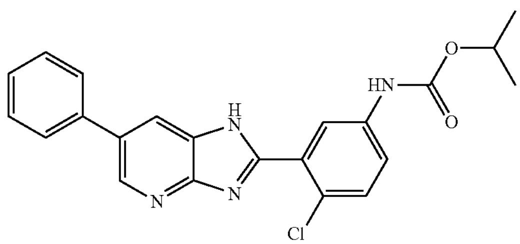 [SMILES: CC(C)OC(=O)Nc1ccc(Cl)c(-c2nc3ncc(-c4ccccc4)cc3[nH]2)c1] | ¹H NMR (400 MHz, DMSO) δ 9.96 (s, 1H), 8.70 (s, 1H), 8.26 (s, 1H), 8.05 (s, 1H), 7.81-7.76 (m, 2H), 7.65 (dd, J = 2.6, 8.8 Hz, 1H), 7.58 (d, J = 8.8 Hz, 1H), 7.53 (dd, J = 4.8, 10.5 Hz, 2H), 7.41 (t, J = 7.4 Hz, 1H), 5.00-4.82 (m, 1H), 1.28 (d, J = 6.3 Hz, 6H). M/Z = 407.1 (M + 1). RT = 3.49: Method A. |
| 334 | 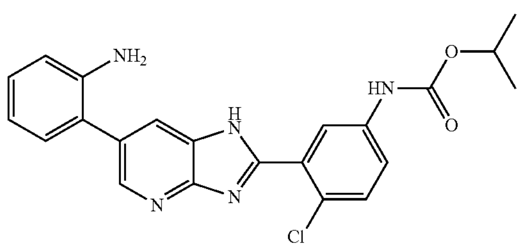 [SMILES: CC(C)OC(=O)Nc1ccc(Cl)c(-c2nc3ncc(-c4ccccc4N)cc3[nH]2)c1] | M/Z = 422.1 (M + 1). RT = 1.50: Method B. |
| 335 | 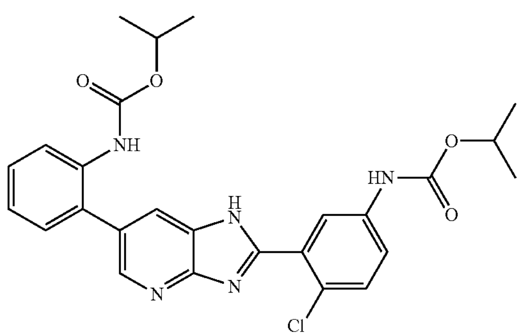 [SMILES: CC(C)OC(=O)Nc1ccc(Cl)c(-c2nc3ncc(-c4ccccc4NC(=O)OC(C)C)cc3[nH]2)c1] | ¹H NMR (400 MHz, DMSO) δ 9.96 (s, 1H), 8.79 (s, 1H), 8.35 (d, 1H), 8.07 (d, 1H), 7.92 (d, 1H), 7.73-7.52 (m, 2H), 7.48-7.38 (m, 4H), 7.33 (dd, J = 7.4, 8.7 Hz, 1H), 5.00-4.84 (m, 1H), 4.77-4.60 (m, 1H), 1.28 (d, J = 6.3 Hz, 6H), 1.05 (d, J = 6.2 Hz, 6H). M/Z = 508.1 (M + 1). RT = 1.75: Method B. |
| 336 | 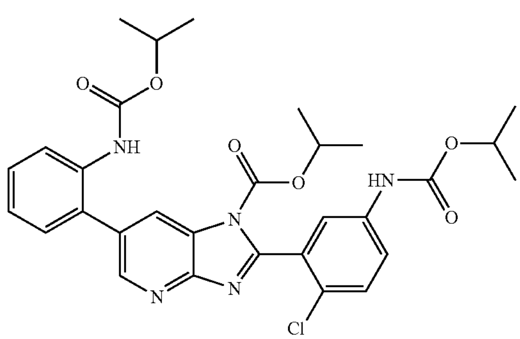 [SMILES: CC(C)OC(=O)Nc1ccc(Cl)c(-c2nc3ncc(-c4ccccc4NC(=O)OC(C)C)cc3n2C(=O)OC(C)C)c1] | M/Z = 594.2 (M + 1). RT = 3.58: Method A. |

TABLE II-continued

Listing of the Exemplified Compounds of the Invention

| Ex. No. | Structure | ¹H NMR and/or mass and/or (retention time (mins)) |
| --- | --- | --- |
| 337 | 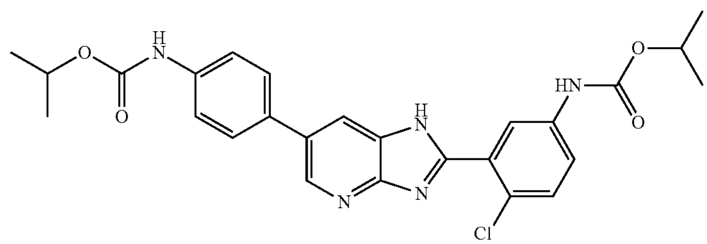 [SMILES: CC(C)OC(=O)Nc1ccc(-c2cnc3nc(-c4cc(NC(=O)OC(C)C)ccc4Cl)[nH]c3c2)cc1] | M/Z = 508.1 (M + 1). RT = 3.26: Method A. |
| 338 | 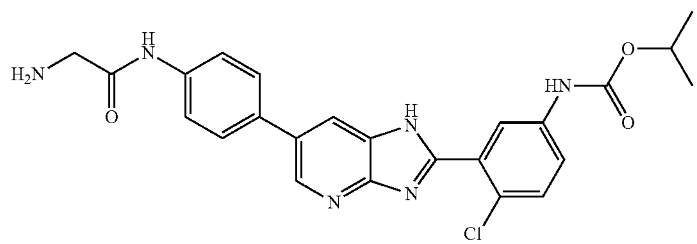 [SMILES: CC(C)OC(=O)Nc1ccc(Cl)c(-c2nc3ncc(-c4ccc(NC(=O)CN)cc4)cc3[nH]2)c1] | M/Z = 479.2 (M + 1). RT = 1.44: Method B. |
| 339 | 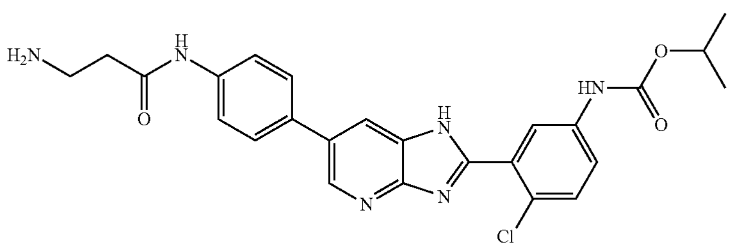 [SMILES: CC(C)OC(=O)Nc1ccc(Cl)c(-c2nc3ncc(-c4ccc(NC(=O)CCN)cc4)cc3[nH]2)c1] | M/Z = 493.1 (M + 1). RT = 2.39: Method A. |
| 340 | 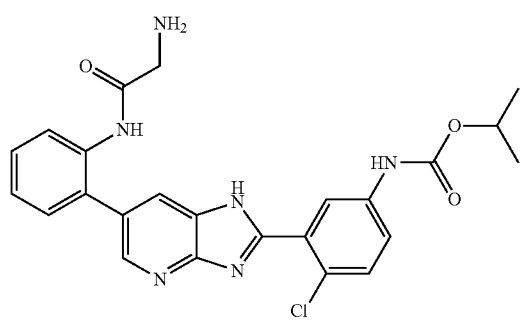 [SMILES: CC(C)OC(=O)Nc1ccc(Cl)c(-c2nc3ncc(-c4ccccc4NC(=O)CN)cc3[nH]2)c1] | M/Z = 479.1 (M + 1). RT = 1.49: Method B. |
| 341 | 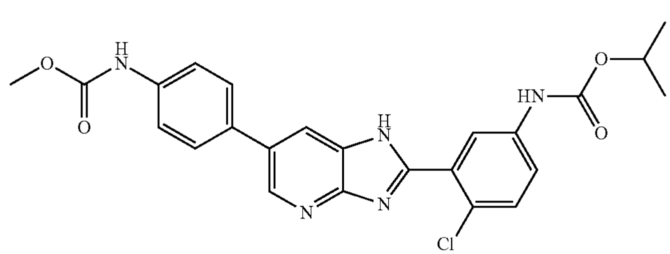 [SMILES: COC(=O)Nc1ccc(-c2cnc3nc(-c4cc(NC(=O)OC(C)C)ccc4Cl)[nH]c3c2)cc1] | M/Z = 480.1 (M + 1). RT = 1.65: Method B. |

TABLE II-continued

Listing of the Exemplified Compounds of the Invention

| Ex. No. | Structure | ¹H NMR and/or mass and/or (retention time (mins)) |
|---|---|---|
| 342 | 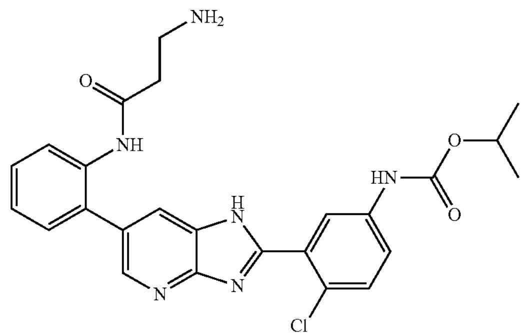 [SMILES: CC(C)OC(=O)Nc1ccc(Cl)c(-c2nc3ncc(-c4ccccc4NC(=O)CCN)cc3[nH]2)c1] | M/Z = 493.2 (M + 1). RT = 2.46: Method A. |
| 343 | 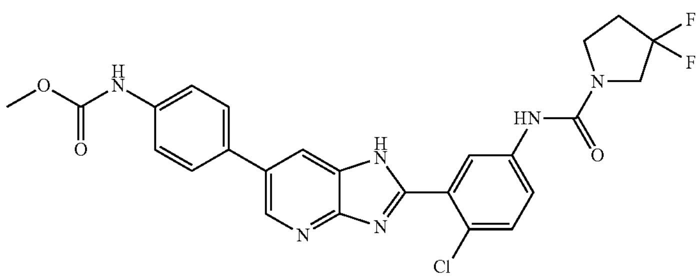 [SMILES: COC(=O)Nc1ccc(-c2cnc3nc(-c4cc(NC(=O)N5CCC(F)(F)C5)ccc4Cl)[nH]c3c2)cc1] | ¹H NMR (400 MHz, DMSO) δ 9.78 (s, 1H), 8.72 (s, 1H), 8.65 (s, 1H), 8.17 (s, 1H), 8.13 (s, 1H), 7.76 (dd, J = 2.6, 8.9 Hz, 2H), 7.70 (d, J = 8.7 Hz, 2H), 7.59 (d, J = 8.5 Hz, 1H), 7.56-7.46 (m, 1H), 4.05 (t, J = 7.9 Hz, 1H), 3.84 (t, J = 13.3 Hz, 3H), 3.69 (s, 3H), 3.65 (t, J = 7.4 Hz, 2H). M/Z = 527.1 (M + 1). RT = 2.95: Method A. |
| 344 | 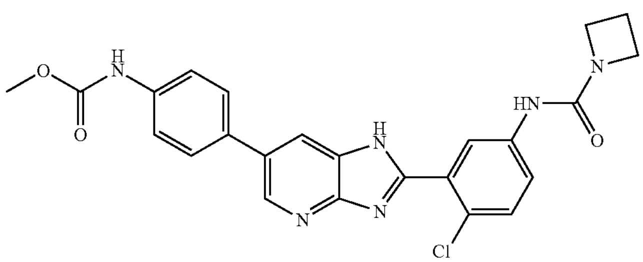 [SMILES: COC(=O)Nc1ccc(-c2cnc3nc(-c4cc(NC(=O)N5CCC5)ccc4Cl)[nH]c3c2)cc1] | M/Z = 477.1 (M + 1). RT= 1.44: Method B. |
| 345 | 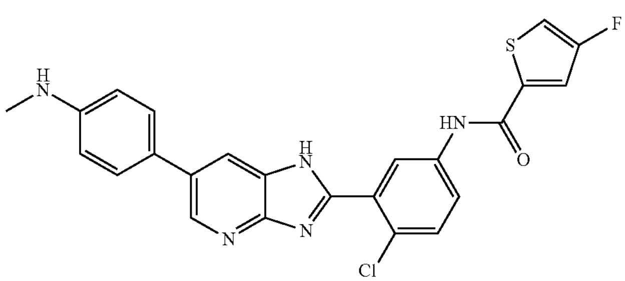 | ¹H NMR (400 MHz, DMSO) δ 10.43 (s, 1H), 8.57 (s, 1H), 8.29 (s, 1H), 7.93 (d, J = 7.9 Hz, 2H), 7.84 (s, 1H), 7.59 (d, J = 8.8 Hz, 1H), 7.53-7.29 (m, 3H), 6.60 (d, J = 8.4 Hz, 2H), 5.80 (s, 1H), 2.66 (d, J = 4.9 Hz, 3H), 2.21 (s, 3H), M/Z = 474.1 (M + 1). RT = 1.33: Method B. |
| 346 | 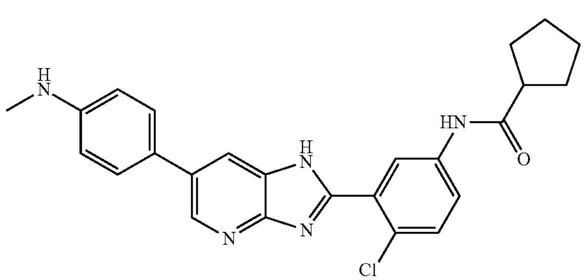 | ¹H NMR (400 MHz, DMSO) δ 10.15 (s, 1H), 8.54 (s, 1H), 8.12 (s, 2H), 7.72 (d, J = 8.0, 1H), 7.52 (d, J = 8.8 Hz, 1H), 7.45 (d, J = 8.6 Hz, 2H), 6.60 (d, J = 8.7 Hz, 2H), 5.80 (s, 1H), 2.72 (dd, J = 7.7, 15.7 Hz, 1H), 2.66 (s, 3H), 1.80 (d, J = 8.1 Hz, 2H), 1.73-1.55 (m, 4H), 1.55-1.42 (m, 2H). M/Z = 446.2 (M + 1). RT = 2.45: Method A. |

TABLE II-continued

Listing of the Exemplified Compounds of the Invention

| Ex. No. | Structure | ¹H NMR and/or mass and/or (retention time (mins)) |
|---|---|---|
| 347 | 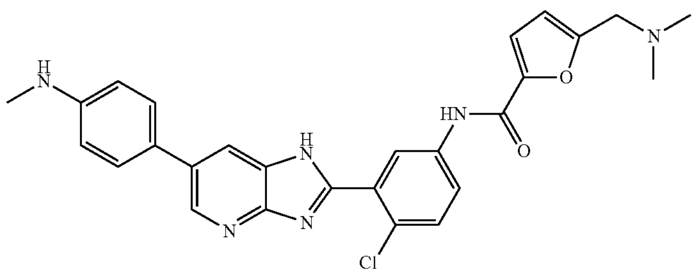 | M/Z = 501.2 (M + 1). RT = 1.16: Method B. |
| 348 | 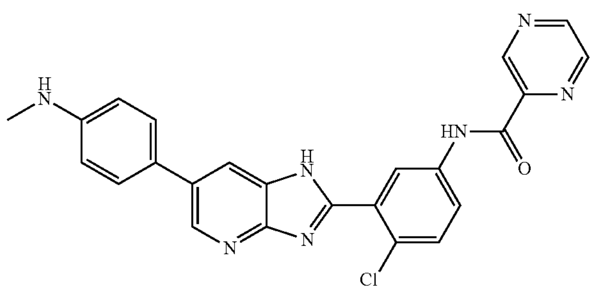 [SMILES: CNc1ccc(-c2cnc3nc(-c4cc(NC(=O)c5cnccn5)ccc4Cl)[nH]c3c2)cc1] | M/Z = 456.1 (M + 1). RT = 1.31: Method B. |
| 349 | 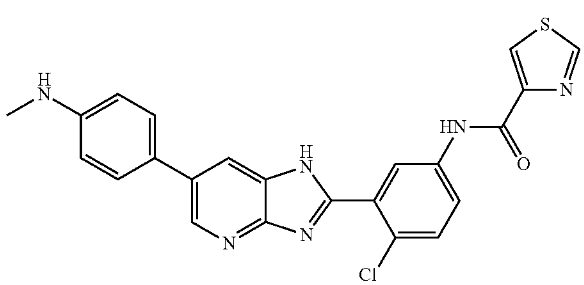 [SMILES: CNc1ccc(-c2cnc3nc(-c4cc(NC(=O)c5cscn5)ccc4Cl)[nH]c3c2)cc1] | ¹H NMR (400 MHz, DMSO) δ 10.68 (s, 1H), 9.23 (d, J = 1.9, 1H), 8.57 (s, 1H), 8.50 (d, J = 1.9, 1H), 8.44 (s, 1H), 8.06 (s, 1H), 7.99 (dd, J = 2.6, 8.8, 1H), 7.59 (d, J = 8.8, 1H), 7.47 (d, J = 8.6, 2H), 6.61 (d, J = 8.6, 2H), 2.67 (s, 3H), M/Z = 461.1 (M + 1). RT = 2.22: Method A. |
| 350 | 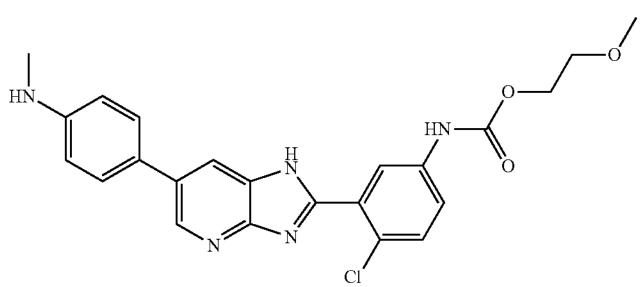 | ¹H NMR (400 MHz, DMSO) δ 10.11 (s, 1H), 8.60 (s, 1H), 8.09 (s, 1H), 8.01 (s, 1H), 7.69-7.59 (m, 1H), 7.57 (d, J = 8.8 Hz, 1H), 7.51 (d, J = 8.6 Hz, 2H), 6.67 (d, J = 8.6 Hz, 2H), 5.82 (d, J = 5.2 Hz, 1H), 4.27-4.17 (m, 2H), 3.62-3.51 (m, 2H), 3.41 (s, 3H), 2.72 (d, J = 4.9 Hz, 3H). M/Z = 452.1 (M + 1). RT = 1.28: Method B. |
| 351 | 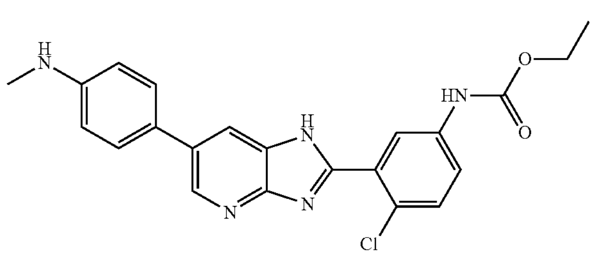 [SMILES: CCOC(=O)Nc1ccc(Cl)c(-c2nc3ncc(-c4ccc(NC)cc4)cc3[nH]2)c1] | ¹H NMR (400 MHz, DMSO) δ 9.99 (s, 1H), 8.62 (s, 1H), 8.10 (s, 1H), 8.01 (s, 1H), 7.94 (d, J = 7.0 Hz, 1H), 7.65 (dd, J = 5.4 Hz, 11.7, 1H), 7.58 (t, J = 8.4 Hz, 1H), 7.55-7.46 (m, 2H), 6.67 (d, J = 8.4 Hz, 1H), 4.15 (q, J = 7.1 Hz, 2H), 2.72 (s, 3H), 1.25 (t, J = 7.1 Hz, 3H). M/Z = 422.1 (M + 1). RT = 1.35: Method B. |

TABLE II-continued

Listing of the Exemplified Compounds of the Invention

| Ex. No. | Structure | ¹H NMR and/or mass and/or (retention time (mins)) |
|---|---|---|
| 352 | 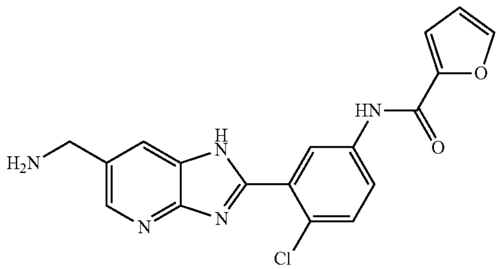 [SMILES: NCc1cnc2nc(-c3cc(NC(=O)c4ccco4)ccc3Cl)[nH]c2c1] | M/Z = 368.1 (M + 1). RT = 1.10: Method B. |
| 353 | 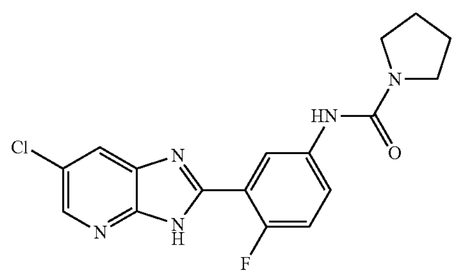 [SMILES: O=C(Nc1ccc(F)c(-c2nc3cc(Cl)cnc3[nH]2)c1)N1CCCC1] | ¹H NMR (300 MHz, MeOD): δ 8.46 (1H, d, J = 7.8 Hz), 8.05-7.87 (3H, m), 7.41 (1H, dd, J = 9.3, 10.5 Hz), 3.52 (4H, t, J = 6.8 Hz), 2.01 (4H, t, J = 6.0 Hz); M/Z = 360.4 (M + 1). |
| 354 | 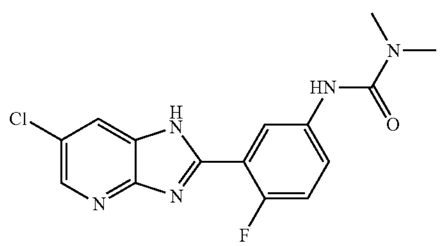 [SMILES: CN(C)C(=O)Nc1ccc(F)c(-c2nc3ncc(Cl)cc3[nH]2)c1] | M/Z = 334.1 (M + 1). RT = 1.23: Method B. |
| 355 | 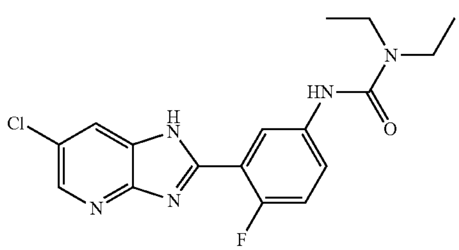 [SMILES: CCN(CC)C(=O)Nc1ccc(F)c(-c2nc3ncc(Cl)cc3[nH]2)c1] | M/Z = 362.1 (M + 1). RT = 1.49: Method B. |
| 356 | 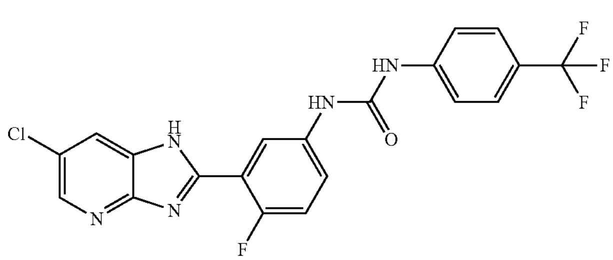 | M/Z = 450.1 (M + 1). RT = 1.98: Method B. |

TABLE II-continued

Listing of the Exemplified Compounds of the Invention

| Ex. No. | Structure | ¹H NMR and/or mass and/or (retention time (mins)) |
|---|---|---|
| 357 | 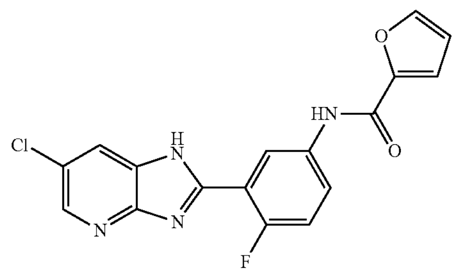 [SMILES: O=C(Nc1ccc(F)c(-c2nc3ncc(Cl)cc3[nH]2)c1)c1ccco1] | ¹H NMR (400 MHz, DMSO) δ 10.48 (s, 1H), 8.66 (s, 1H), 8.42 (s, 1H), 8.14 (s, 1H), 7.97 (s, 2H), 7.52-7.40 (m, 1H), 7.39 (d, J = 3.3 Hz, 1H), 6.73 (dd, J = 1.6, 3.2 Hz, 1H). M/Z = 357.1 (M + 1). RT = 1.57: Method B. |
| 358 | 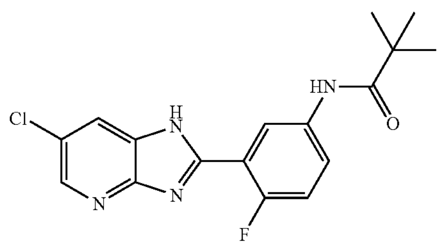 [SMILES: CC(C)(C)C(=O)Nc1ccc(F)c(-c2nc3ncc(Cl)cc3[nH]2)c1] | M/Z = 347.1 (M + 1). RT = 1.65: Method B. |
| 359 | 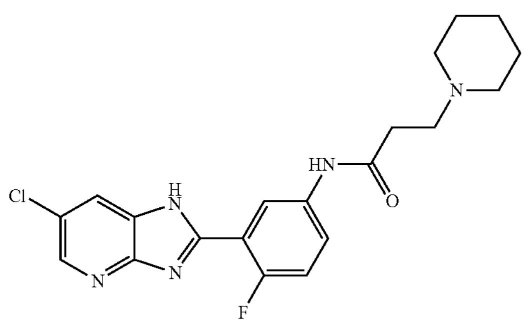 [SMILES: O=C(CCN1CCCCC1)Nc1ccc(F)c(-c2nc3ncc(Cl)cc3[nH]2)c1] | M/Z = 402.1 (M + 1). RT = 1.27: Method B. |
| 360 | 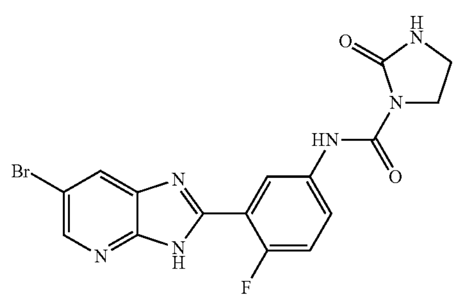 [SMILES: O=C1NCCN1C(=O)Nc1ccc(F)c(-c2nc3cc(Br)cnc3[nH]2)c1] | ¹H NMR (300 MHz, MeOD): δ 10.63 (1H, s), 8.50 (1H, s), 8.29-8.22 (2H, m), 7.94 (1H, s), 7.78 (1H, m), 7.52 (1H, dd, J = 8.5, 10.5 Hz), 3.86 (2H, t, J = 7.8 Hz), 3.41 (2H, m); M/Z = 421.0 (M + 1). |
| 361 | 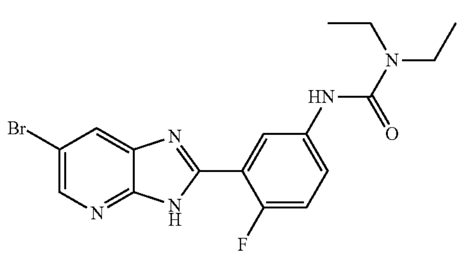 [SMILES: CCN(CC)C(=O)Nc1ccc(F)c(-c2nc3cc(Br)cnc3[nH]2)c1] | ¹H NMR (300 MHz, MeOD): δ 8.58 (1H, brs), 8.22 (1H, brs), 7.89-7.80 (2H, m), 7.22 (1H, dd, J = 9.3, 10.8 Hz), 3.46 (4H, q, J = 6.9, 14.1 Hz), 1.28 (6H, t, J = 7.2 Hz); M/Z = 408.3 (M + 1). |

TABLE II-continued

Listing of the Exemplified Compounds of the Invention

| Ex. No. | Structure | $^1$H NMR and/or mass and/or (retention time (mins)) |
|---|---|---|
| 362 | 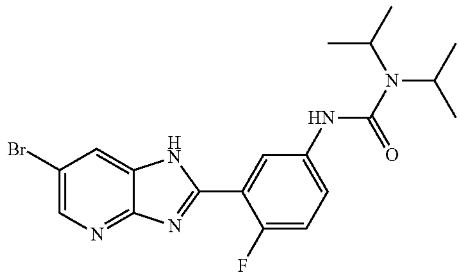 [SMILES: CC(C)N(C(=O)Nc1ccc(F)c(-c2nc3ncc(Br)cc3[nH]2)c1)C(C)C] | M/Z = 434.1 (M + 1). RT = 1.74: Method B. |
| 363 | 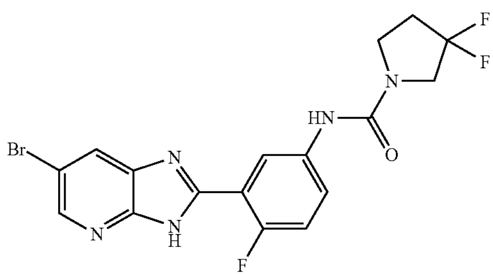 [SMILES: O=C(Nc1ccc(F)c(-c2nc3cc(Br)cnc3[nH]2)c1)N1CCC(F)(F)C1] | $^1$H NMR (300 MHz, MeOD): δ 8.48 (1H, brs), 8.16 (1H, brs), 8.07 (1H, dd, J = 3.0, 9.2 Hz), 7.84-7.8 (1H, m), 7.24 (1H, dd, J = 9.3, 10.5 Hz), 3.88-3.77 (4H, m), 2.49 (2H, m); M/Z = 441.9 (M + 1). |
| 364 | 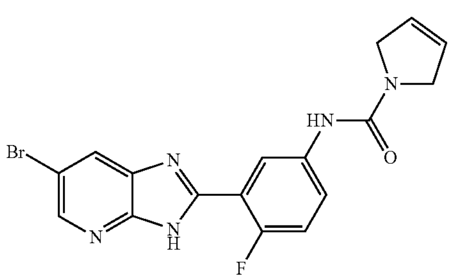 [SMILES: O=C(Nc1ccc(F)c(-c2nc3cc(Br)cnc3[nH]2)c1)N1CC=CC1] | $^1$H NMR (300 MHz, MeOD): δ 8.51 (1H, d, J = 14.5 Hz), 8.20-8.08 (2H, m), 7.8-7.75 (2H, m), 7.24 (1H, dd, J = 3.1, 10.5 Hz), 5.91 (2H, d, J = 3.5 Hz), 3.33 (4H, m); M/Z = 403.5 (M + 1). |
| 365 | 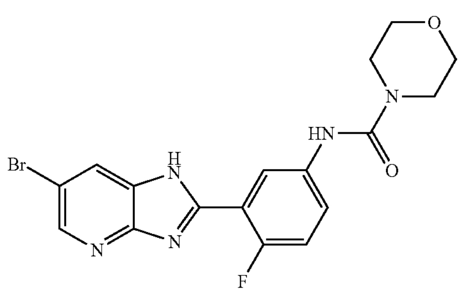 [SMILES: O=C(Nc1ccc(F)c(-c2nc3ncc(Br)cc3[nH]2)c1)N1CCOCC1] | M/Z = 420.0 (M + 1). RT = 1.42: Method B. |
| 366 | 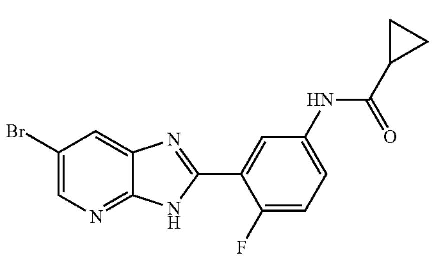 [SMILES: O=C(Nc1ccc(F)c(-c2nc3cc(Br)cnc3[nH]2)c1)C1CC1] | $^1$H NMR (300 MHz, MeOD): δ 10.49 (1H, s), 8.50-8.4 (3H, m), 7.80 (1H, dd, J = 1.8, 9.0 Hz), 7.42 (1H, dd, J = 9.3, 10.8 Hz), 1.82 (1H, m), 0.86-0.74 (4H, m); M/Z = 376.4 (M + 1). |

TABLE II-continued

Listing of the Exemplified Compounds of the Invention

| Ex. No. | Structure | ¹H NMR and/or mass and/or (retention time (mins)) |
|---|---|---|
| 367 | 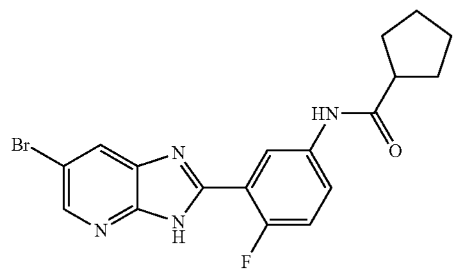 [SMILES: O=C(Nc1ccc(F)c(-c2nc3cc(Br)cnc3[nH]2)c1)C1CCCC1] | ¹H NMR (300 MHz, MeOD): δ 8.46 (1H, brs), 8.13 (1H, brs), 8.07 (1H, dd, J = 1.5, 6.3 Hz), 7.22 (1H, dd, J = 9.3, 10.8 Hz), 2.89 (1H, m) 2.03-1.76 (8H, m): M/Z = 404.6 (M + 1). |
| 368 | 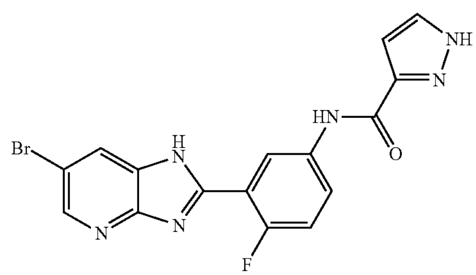 [SMILES: O=C(Nc1ccc(F)c(-c2nc3ncc(Br)cc3[nH]2)c1)c1cc[nH]n1] | M/Z = 401.0 (M + 1). RT = 1.39: Method B. |
| 369 | 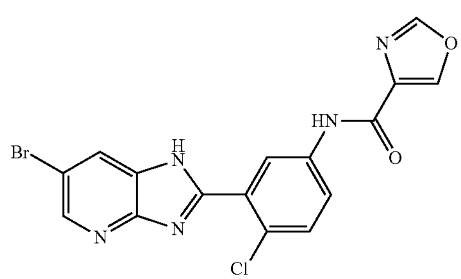 [SMILES: O=C(Nc1ccc(Cl)c(-c2nc3ncc(Br)cc3[nH]2)c1)c1cocn1] | M/Z = 417.9 (M + 1). RT = 1.55: Method B. |
| 370 | 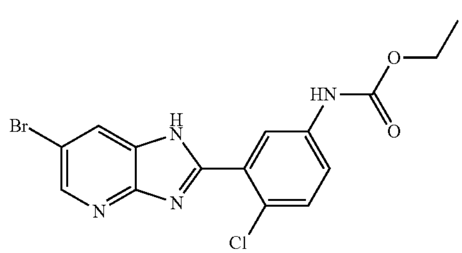 [SMILES: CCOC(=O)Nc1ccc(Cl)c(-c2nc3ncc(Br)cc3[nH]2)c1] | ¹H NMR (400 MHz, DMSO) δ 10.00 (s, 1H), 8.48 (d, J = 1.9 Hz, 1H), 8.33 (s, 1H), 8.00 (s, 1H), 7.65 (dd, J = 2.5, 8.8 Hz, 1H), 7.57 (d, J = 8.8 Hz, 1H), 4.15 (q, J = 7.1 Hz, 2H), 1.25 (t, J = 7.1 Hz, 3H). M/Z = 394.9 (M + 1). RT = 1.64: Method B. |
| 371 | 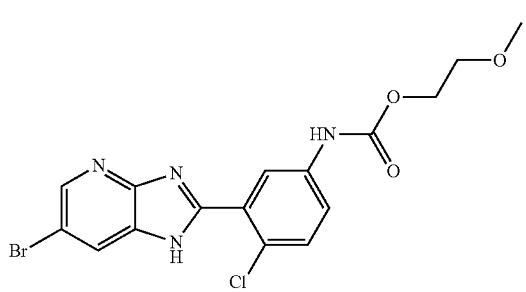 [SMILES: COCCOC(=O)Nc1ccc(Cl)c(-c2nc3ncc(Br)cc3[nH]2)c1] | M/Z = 424.9 (M + 1). RT = 1.61: Method B. |

TABLE II-continued

Listing of the Exemplified Compounds of the Invention

| Ex. No. | Structure | ¹H NMR and/or mass and/or (retention time (mins)) |
|---|---|---|
| 372 | 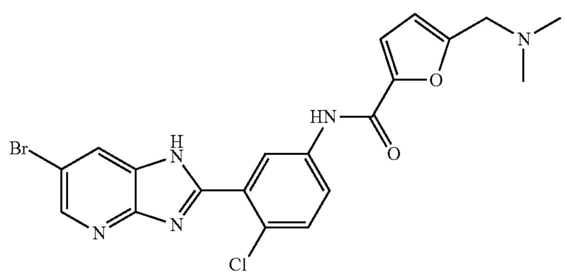 [SMILES: CN(C)Cc1ccc(C(=O)Nc2ccc(Cl)c(-c3nc4ncc(Br)cc4[nH]3)c2)o1] | ¹H NMR (400 MHz, DMSO) δ 10.42 (s, 1H), 8.49 (d, J = 1.9 Hz, 1H), 8.33 (s, 2H), 8.01 (dd, J = 2.6, 8.8 Hz, 1H), 7.65 (d, J = 8.8 Hz, 1H), 7.36 (d, J = 3.4 Hz, 1H), 6.53 (d, J = 3.4 Hz, 1H), 3.52 (s, 2H), 2.19 (s, 6H). M/Z = 474.0 (M + 1). RT = 1.33: Method B. |
| 373 | 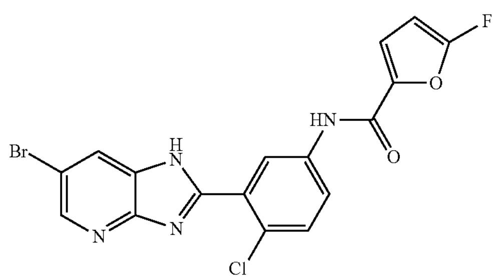 [SMILES: O=C(Nc1ccc(Cl)c(-c2nc3ncc(Br)cc3[nH]2)c1)c1ccc(F)o1] | M/Z = 434.9 (M + 1). RT = 3.09: Method A. |
| 374 | 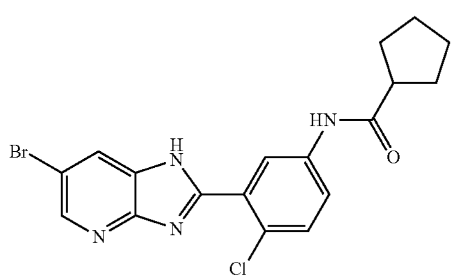 [SMILES: O=C(Nc1ccc(Cl)c(-c2nc3ncc(Br)cc3[nH]2)c1)C1CCCC1] | M/Z = 419.0 (M + 1). RT = 1.81: Method B. |
| 375 | 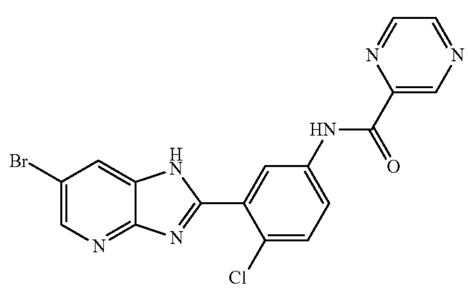 [SMILES: O=C(Nc1ccc(Cl)c(-c2nc3ncc(Br)cc3[nH]2)c1)c1cnccn1] | M/Z = 428.9 (M + 1). RT = 1.54: Method B. |
| 376 | 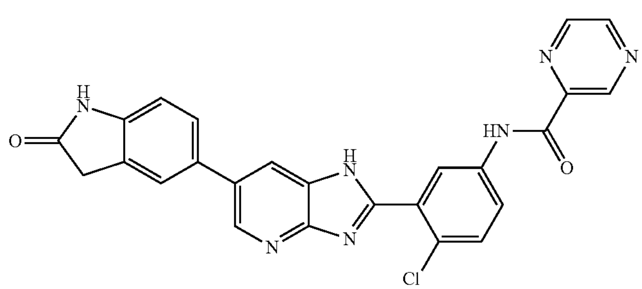 [SMILES: O=C1Cc2cc(-c3cnc4nc(-c5cc(NC(=O)c6cnccn6)ccc5Cl)[nH]c4c3)ccc2N1] | ¹H NMR (400 MHz, DMSO) δ 11.02 (s, 1H), 10.41 (s, 1H), 9.25 (d, J = 1.4 Hz, 1H), 8.89 (d, J = 2.5 Hz, 1H), 8.84-8.71 (m, 1H), 8.50 (s, 2H), 8.00 (d, 2H), 7.66-7.53 (m, 2H), 7.49 (d, J = 7.9 Hz, 1H), 6.87 (d, J = 8.0 Hz, 1H), 3.50 (s, 2H). M/Z = 482.1 (M + 1). RT = 1.38: Method B. |

TABLE II-continued

Listing of the Exemplified Compounds of the Invention

| Ex. No. | Structure | $^1$H NMR and/or mass and/or (retention time (mins)) |
|---|---|---|
| 377 | 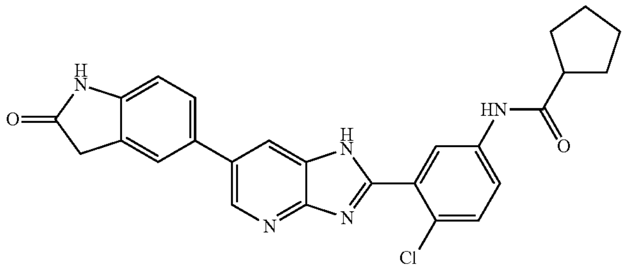 [SMILES: O=C1Cc2cc(-c3cnc4nc(-c5cc(NC(=O)C6CCCC6)ccc5Cl)[nH]c4c3)ccc2N1] | M/Z = 472.1 (M + 1). RT = 1.52: Method B.. |
| 378 | 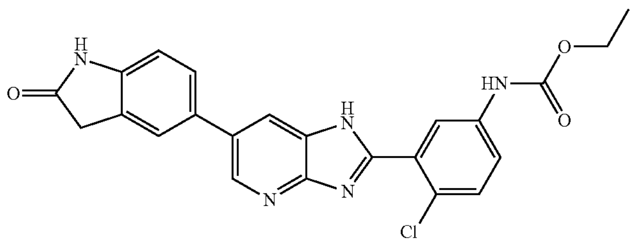 [SMILES: CCOC(=O)Nc1ccc(Cl)c(-c2nc3ncc(-c4ccc5c(c4)CC(=O)N5)cc3[nH]2)c1] | $^1$H NMR (400 MHz, DMSO) δ 10.44 (s, 1H), 9.96 (s, 1H), 8.58 (s, 1H), 8.12 (s, 1H), 7.95 (s, 1H), 7.64-7.47 (m, 4H), 6.88 (d, J = 8.0 Hz, 1H), 4.09 (q, J = 7.1 Hz, 2H), 1.19 (t, J = 7.1 Hz, 3H). M/Z = 448.2 (M + 1). RT = 1.43: Method B. |
| 379 | 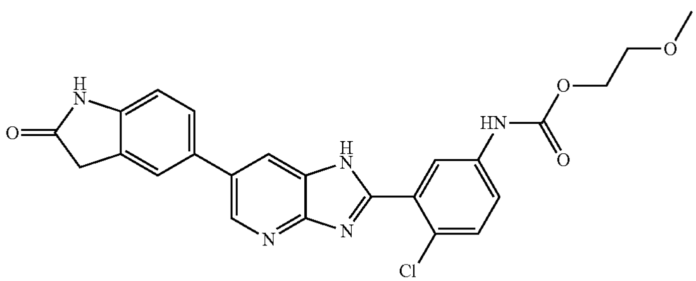 [SMILES: COCCOC(=O)Nc1ccc(Cl)c(-c2nc3ncc(-c4ccc5c(c4)CC(=O)N5)cc3[nH]2)c1] | M/Z = 478.1 (M + 1). RT = 1.39: Method B. |
| 380 | 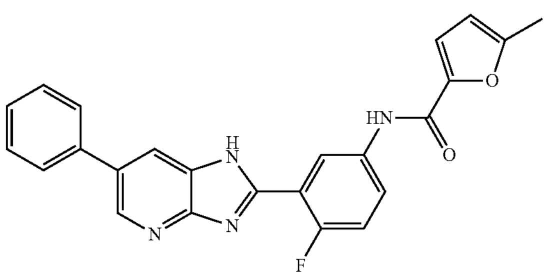 [SMILES: Cc1ccc(C(=O)Nc2ccc(F)c(-c3nc4ncc(-c5ccccc5)cc4[nH]3)c2)o1] | $^1$H NMR (400 MHz, DMSO) δ 10.08 (s, 1H), 8.69 (s,1H), 8.58-8.47 (m, 1H), 8.27 (s, 1H), 8.20-8.07 (m, 1H), 7.79 (d, J = 7.9 Hz, 2H), 7.53 (s, 3H), 7.42 (s, 1H), 7.31 (s, 1H), 6.37 (s, 1H), 2.42 (s, 3H), M/Z = 413.2 (M + 1). RT = 1.68: Method B. |
| 381 | 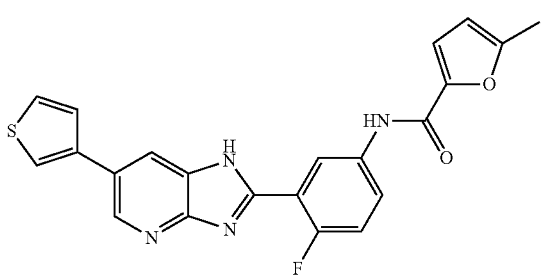 [SMILES: Cc1ccc(C(=O)Nc2ccc(F)c(-c3nc4ncc(-c5ccsc5)cc4[nH]3)c2)o1] | $^1$H NMR (400 MHz, DMSO) δ 10.03-9.92 (m, 1H), 8.66-8.57 (m, 1H), 8.53-8.43 (m, 1H), 8.21-8.07 (m, 2H), 7.94-7.85 (m, 1H), 7.67 (s, 2H), 7.51-7.37 (m, 1H), 7.29 (s, 1H), 6.36 (s, 1H), 2.41 (s, 3H). M/Z = 419.1 (M + 1). RT = 1.65: Method B. |

TABLE II-continued

Listing of the Exemplified Compounds of the Invention

| Ex. No. | Structure | ¹H NMR and/or mass and/or (retention time (mins)) |
|---|---|---|
| 382 | 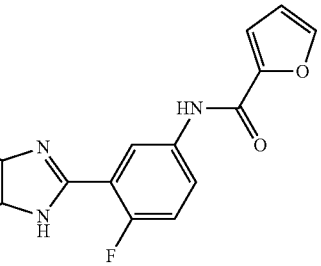 | ¹H NMR (300 MHz, MeOD): 8.75 (1H, m), 8.60 (1H, dd, J = 3.0, 6.3 Hz), 8.47 (1H, d, J = 8.4 Hz), 8.13 (1H, d, J = 1.5 Hz) 7.88-7.76 (3H, m), 7.09 (1H, dd, J = 1.8, 3.4 Hz); M/Z = 357.6 (M + 1). |
| 383 | 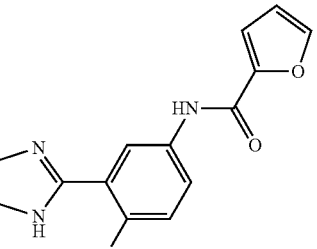 | ¹H NMR (300 MHz, MeOD): δ 8.35-8.19 (3H, m), 7.81-7.77 (2H, m), 7.33-7.32 (2H, m), 6.64 (1H, s); M/Z = 341.2 (M + 1). |
| 384 | 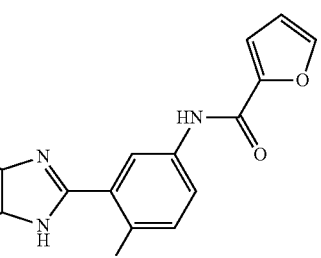 | ¹H NMR (300 MHz, MeOD): δ 8.45 (1H, dd, J = 9.0, 10.8 Hz), 8.28 (1H, brs), 8.02-7.98 (1H, m), 7.86 (1H, s), 7.78-7.75 (1H, m), 7.42-7.35 (2H, m), 6.68 (1H, dd, J = 1.8, 3.6 Hz); M/Z = 337.6 (M + 1). |
| 385 | 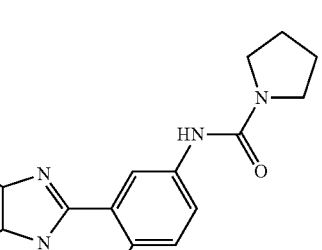 | ¹H NMR (400 MHz, DMSO) δ 8.58 (d, J = 2.1 Hz, 1H), 8.51 (d, J = 2.1 Hz, 1H), 8.48 (s, 1H), 7.87 (d, J = 2.7 Hz, 1H), 7.78 (dd, J = 2.6, 8.9 Hz, 1H), 7.54 (d, J = 8.8 Hz, 1H), 5.48 (s, 2H), 3.40-3.31 (m, 4H), 3.10 (s, 3H), 1.89-1.77 (m, 4H). M/Z = 464.0 (M + 1). RT = 3.13: Method A. |
| 386 | 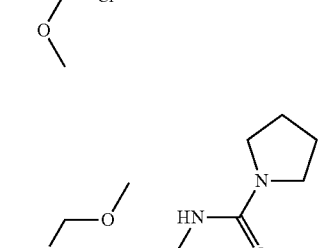 | ¹H NMR (400 MHz, DMSO) δ 8.60 (d, J = 2.2 Hz, 1H), 8.55 (d, J = 2.2 Hz, 1H), 8.48 (s, 1H), 7.87 (d, J = 2.7 Hz, 1H), 7.78 (dd, J = 2.7, 8.8 Hz, 1H), 7.54 (d, J = 8.9 Hz, 1H), 5.48 (s, 2H), 3.39-3.30 (m, 4H), 3.06 (s, 3H), 1.92-1.81 (m, 4H). M/Z = 464.0 (M + 1). RT = 2.94: Method A. |

TABLE II-continued

Listing of the Exemplified Compounds of the Invention

| Ex. No. | Structure | ¹H NMR and/or mass and/or (retention time (mins)) |
|---|---|---|
| 387 | 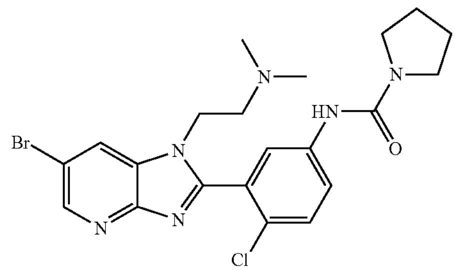 [SMILES: CN(C)CCn1c(-c2cc(NC(=O)N3CCCC3)ccc2Cl)nc2ncc(Br)cc21] | M/Z = 491.1 (M + 1). RT = 2.18: Method A. |
| 388 | 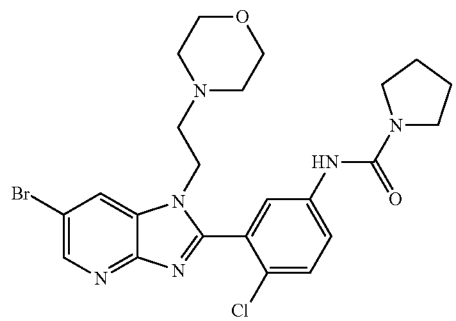 [SMILES: O=C(Nc1ccc(Cl)c(-c2nc3ncc(Br)cc3n2CCN2CCOCC2)c1)N1CCCC1] | M/Z = 533.1 (M + 1). RT = 2.57: Method A. |
| 389 | 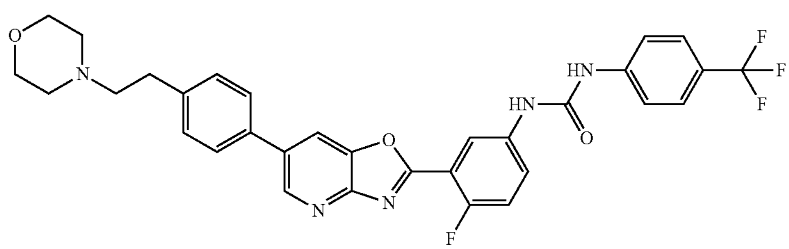 [SMILES: O=C(Nc1ccc(C(F)(F)F)cc1)Nc1ccc(F)c(-c2nc3ncc(-c4ccc(CCN5CCOCC5)cc4)cc3o2)c1] | ¹H NMR (400 MHz, MeOD) δ 8.73 (d, J = 2.0 Hz, 1H), 8.37 (dd, J = 2.8, 6.2 Hz, 1H), 8.31 (d, J = 2.0 Hz, 1H), 7.71-7.65 (m, 1H), 7.63-7.56 (m, 4H), 7.50 (d, J = 8.6 Hz, 2H), 7.32 (d, J = 8.2 Hz, 2H), 7.26 (dd, J = 9.1, 10.4 Hz, 1H), 3.66-3.61 (m, 4H), 2.81 (dd, J = 6.6, 9.6 Hz, 2H), 2.57 (dd, J = 6.7, 9.6 Hz, 2H), 2.49 (s, 4H). M/Z = 606.2 (M + 1). RT = 1.82: Method B. |
| 390 | 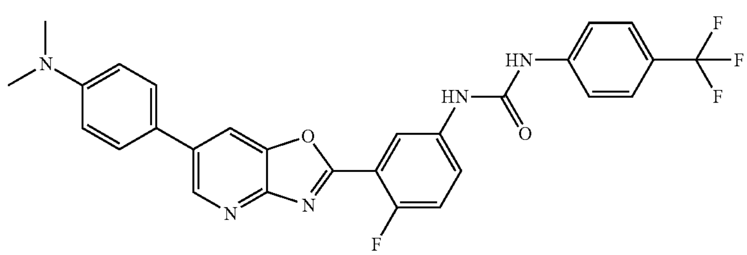 [SMILES: CN(C)c1ccc(-c2cnc3nc(-c4cc(NC(=O)Nc5ccc(C(F)(F)F)cc5)ccc4F)oc3c2)cc1] | M/Z = 536.1 (M + 1). RT 2.02: Method B. |
| 391 | 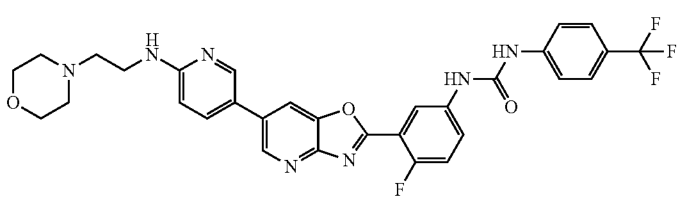 [SMILES: O=C(Nc1ccc(C(F)(F)F)cc1)Nc1ccc(F)c(-c2nc3ncc(-c4ccc(NCCN5CCOCC5)nc4)cc3o2)c1] | M/Z = 622.2 (M + 1). RT = 1.59: Method B. |

TABLE II-continued

Listing of the Exemplified Compounds of the Invention

| Ex. No. | Structure | ¹H NMR and/or mass and/or (retention time (mins)) |
|---|---|---|
| 392 | 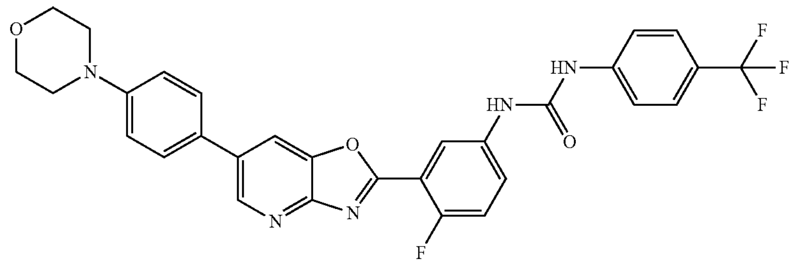 [SMILES: O=C(Nc1ccc(C(F)(F)F)cc1)Nc1ccc(F)c(-c2nc3ncc(-c4ccc(N5CCOCC5)cc4)cc3o2)c1] | M/Z = 578.2 (M + 1). RT = 2.17: Method B. |
| 393 | 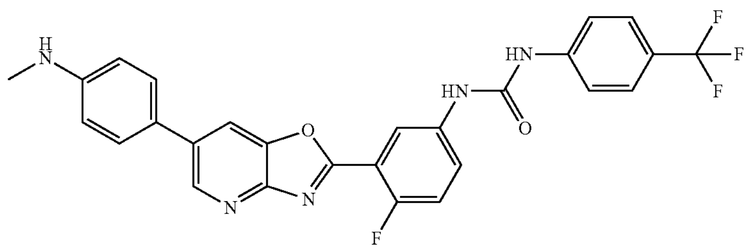 | M/Z = 522.1 (M + 1). RT = 1.92: Method B. |
| 394 | 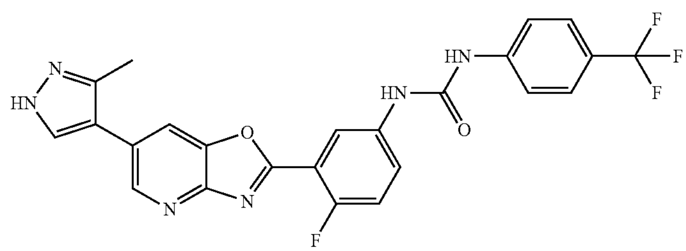 [SMILES: Cc1n[nH]cc1-c1cnc2nc(-c3cc(NC(=O)Nc4ccc(C(F)(F)F)cc4)ccc3F)oc2c1] | M/Z = 497.1 (M + 1). RT = 1.89: Method B. |
| 395 | 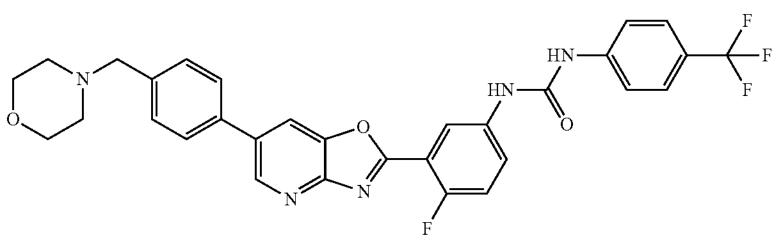 [SMILES: O=C(Nc1ccc(C(F)(F)F)cc1)Nc1ccc(F)c(-c2nc3ncc(-c4ccc(CN5CCOCC5)cc4)cc3o2)c1] | M/Z = 592.2 (M + 1). RT = 1.75: Method B. |
| 396 | 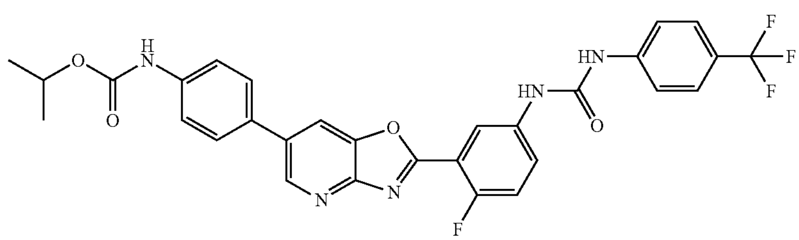 [SMILES: CC(C)OC(=O)Nc1ccc(-c2cnc3nc(-c4cc(NC(=O)Nc5ccc(C(F)(F)F)cc5)ccc4F)oc3c2)cc1] | M/Z = 594.1 (M + 1). RT = 2.29: Method B. |
| 397 | 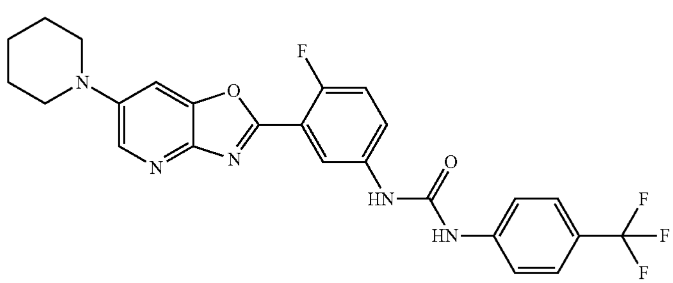 [SMILES: O=C(Nc1ccc(C(F)(F)F)cc1)Nc1ccc(F)c(-c2nc3ncc(N4CCCCC4)cc3o2)c1] | M/Z = 500.1 (M + 1). RT = 2.13: Method B. |

TABLE II-continued

Listing of the Exemplified Compounds of the Invention

| Ex. No. | Structure | ¹H NMR and/or mass and/or (retention time (mins)) |
|---|---|---|
| 398 | 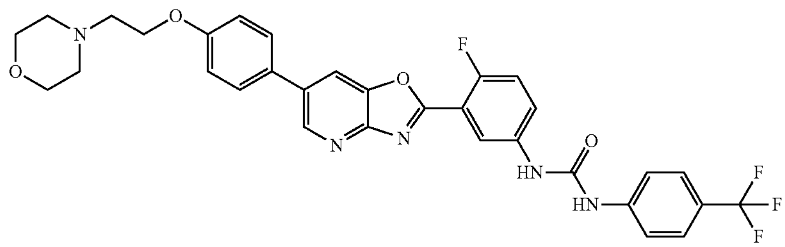 [SMILES: O=C(Nc1ccc(C(F)(F)F)cc1)Nc1ccc(F)c(-c2nc3ncc(-c4ccc(OCCN5CCOCC5)cc4)cc3o2)c1] | M/Z = 622.2 (M + 1). RT = 1.75: Method B. |
| 399 | 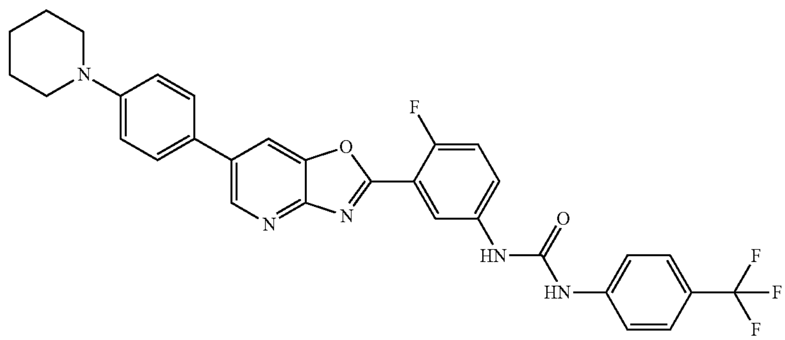 [SMILES: O=C(Nc1ccc(C(F)(F)F)cc1)Nc1ccc(F)c(-c2nc3ncc(-c4ccc(N5CCCCC5)cc4)cc3o2)c1] | M/Z = 576.2 (M + 1). RT = 1.83: Method B. |
| 400 | 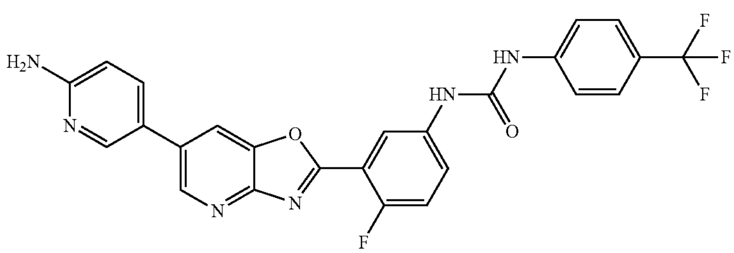 [SMILES: Nc1ccc(-c2cnc3nc(-c4cc(NC(=O)Nc5ccc(C(F)(F)F)cc5)ccc4F)oc3c2)cn1] | M/Z = 509.1 (M + 1). RT = 1.65: Method B. |
| 401 | 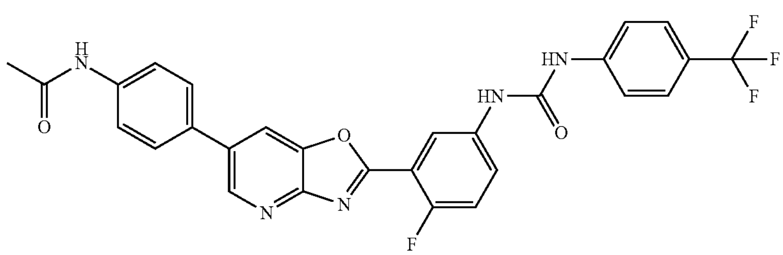 [SMILES: CC(=O)Nc1ccc(-c2cnc3nc(-c4cc(NC(=O)Nc5ccc(C(F)(F)F)cc5)ccc4F)oc3c2)cc1] | M/Z = 550.1 (M + 1). RT = 2.05: Method B. |
| 402 | 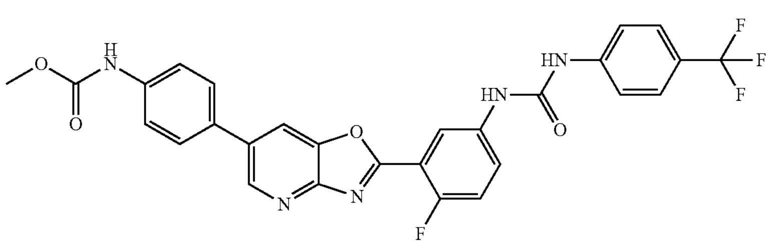 [SMILES: COC(=O)Nc1ccc(-c2cnc3nc(-c4cc(NC(=O)Nc5ccc(C(F)(F)F)cc5)ccc4F)oc3c2)cc1] | M/Z = 566.1 (M + 1). RT = 2.13: Method B. |

TABLE II-continued

Listing of the Exemplified Compounds of the Invention

| Ex. No. | Structure | ¹H NMR and/or mass and/or (retention time (mins)) |
|---|---|---|
| 403 | 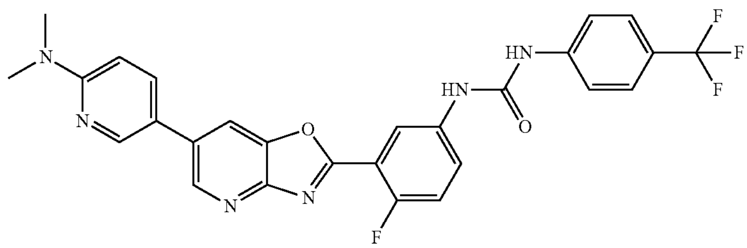 | M/Z = 537.1 (M + 1). RT = 1.76: Method B. |
| 404 | 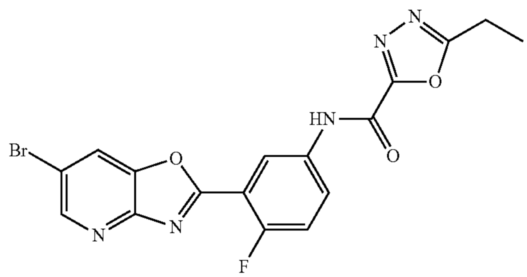 [SMILES: CCc1nnc(C(=O)Nc2ccc(F)c(-c3nc4ncc(Br)cc4o3)c2)o1] | ¹H NMR (400 MHz, MeOD) δ 8.76 (dd, J = 2.7, 6.3 Hz, 1H), 8.69 (d, J = 2.0 Hz, 1H), 8.49 (d, J = 2.0 Hz, 1H), 8.11-8.04 (m, 1H), 7.45 (dd, J = 9.2, 10.3 Hz, 1H), 3.05 (q, J = 7.6 Hz, 2H), 1.45 (t, J = 7.6 Hz, 3H). M/Z = 432.0 (M + 1). RT = 1.79: Method B. |
| 405 | 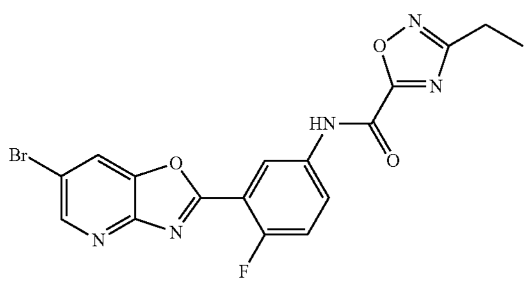 [SMILES: CCc1noc(C(=O)Nc2ccc(F)c(-c3nc4ncc(Br)cc4o3)c2)n1] | M/Z = 432.0 (M + 1). RT = 1.94: Method B. |
| 406 | 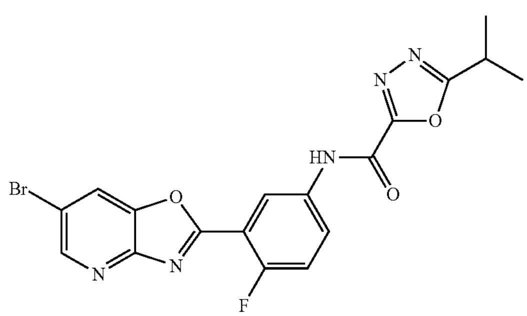 [SMILES: CC(C)c1nnc(C(=O)Nc2ccc(F)c(-c3nc4ncc(Br)cc4o3)c2)o1] | M/Z = 446.0 (M + 1). RT = 1.90: Method B. |
| 407 | 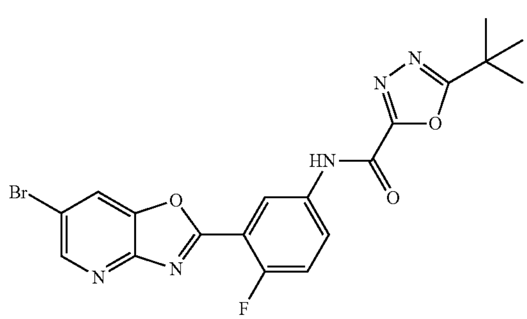 [SMILES: CC(C)(C)c1nnc(C(=O)Nc2ccc(F)c(-c3nc4ncc(Br)cc4o3)c2)o1] | M/Z = 460.0 (M + 1). RT = 1.97: Method B. |

TABLE II-continued

Listing of the Exemplified Compounds of the Invention

| Ex. No. | Structure | ¹H NMR and/or mass and/or (retention time (mins)) |
|---|---|---|
| 408 | 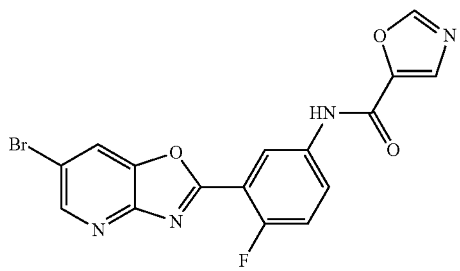 [SMILES: O=C(Nc1ccc(F)c(-c2nc3ncc(Br)cc3o2)c1)c1cnco1] | M/Z = 402.9 (M + 1). RT = 1.63: Method B. |
| 409 | 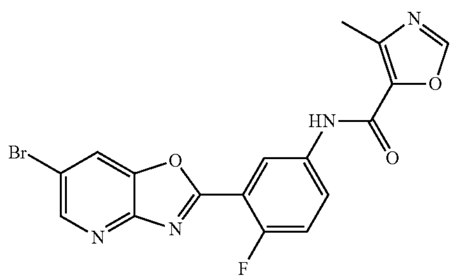 [SMILES: Cc1ncoc1C(=O)Nc1ccc(F)c(-c2nc3ncc(Br)cc3o2)c1] | M/Z = 416.9 (M + 1). RT = 1.76: Method B. |
| 410 | 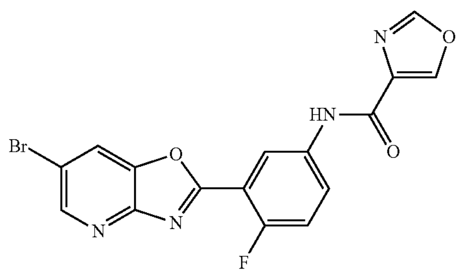 [SMILES: O=C(Nc1ccc(F)c(-c2nc3ncc(Br)cc3o2)c1)c1cocn1] | M/Z = 402.9 (M + 1). RT = 1.72: Method B. |
| 411 | 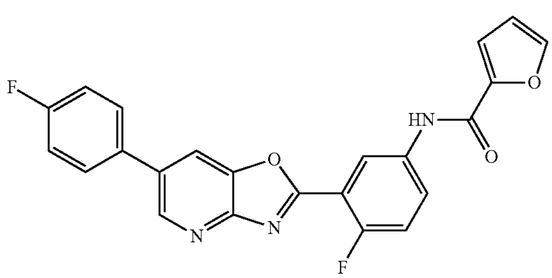 [SMILES: O=C(Nc1ccc(F)c(-c2nc3ncc(-c4ccc(F)cc4)cc3o2)c1)c1ccco1] | ¹H NMR (300 MHz, CDCl₃): δ 8.86 (1H, s), 8.48 (1H, dd, J = 2.7, 4.8 Hz), 8.36 (1H, s), 8.12-8.10 (1H, m), 8.09 (1H, d, J = 1.3 Hz) 7.64-7.60 (3H, m), 7.50-7.45 (4H, m), 6.0 (1H, dd, J = 1.2, 2.8 Hz); M/Z = 418.5 (M + 1). |
| 412 | 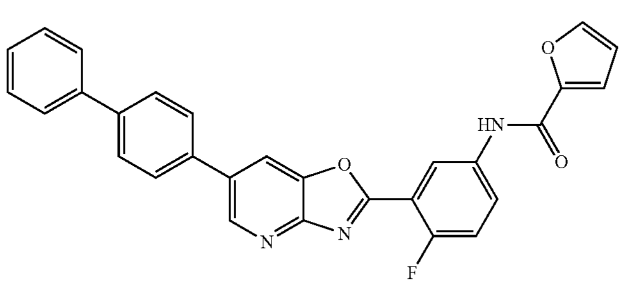 [SMILES: O=C(Nc1ccc(F)c(-c2nc3ncc(-c4ccc(-c5ccccc5)cc4)cc3o2)c1)c1ccco1] | ¹H NMR (300 MHz, CDCl₃): δ 10.57 (1H, s), 8.99 (1H, s), 8.88 (1H, dd, J = 0.9, 2.2 Hz), 8.67 (1H, s), 8.09-8.06 (1H, m), 8.0-7.95 (3H, m), 7.90-7.75 (4H, m), 7.51-7.40 (5H, m), 6.75 (1H, s); M/Z = 476.3 (M + 1). |

TABLE II-continued

Listing of the Exemplified Compounds of the Invention

| Ex. No. | Structure | ¹H NMR and/or mass and/or (retention time (mins)) |
|---|---|---|
| 413 | 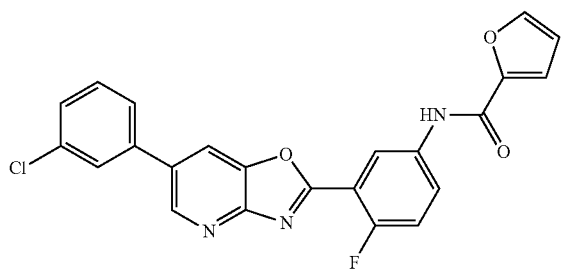 [SMILES: O=C(Nc1ccc(F)c(-c2nc3ncc(-c4cccc(Cl)c4)cc3o2)c1)c1ccco1] | ¹H NMR (300 MHz, DMSO): δ 10.54 (1H, s), 8.94-8.70 (3H, m), 8.10-7.95 (4H, m), 8.80-7.45 (4H, m), 6.73 (1H, s); M/Z = 436.1 (M + 1). |
| 414 | 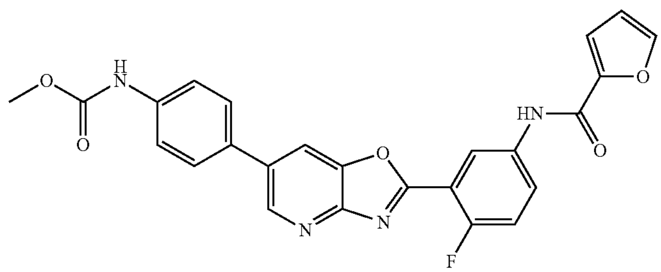 [SMILES: COC(=O)Nc1ccc(-c2cnc3nc(-c4cc(NC(=O)c5ccco5)ccc4F)oc3c2)cc1] | M/Z = 473.1 (M + 1). RT = 3.09: Method A. |
| 415 | 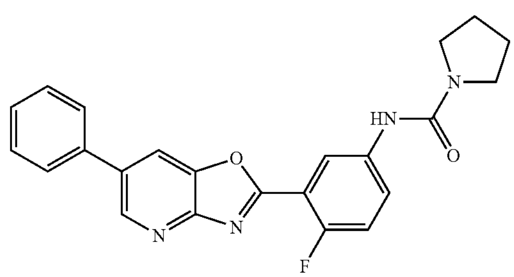 [SMILES: O=C(Nc1ccc(F)c(-c2nc3ncc(-c4ccccc4)cc3o2)c1)N1CCCC1] | ¹H NMR (400 MHz, DMSO) δ 8.85 (d, J = 1.9 Hz, 1H), 8.54 (d, J = 1.9 Hz, 1H), 8.52-8.42 (m, 2H), 7.87-7.73 (m, 3H), 7.48 (t, J = 7.5 Hz, 2H), 7.43-7.27 (m, 2H), 3.34 (t, J = 6.4 Hz, 4H), 1.81 (s, 4H). M/Z = 403.14 (M + 1). RT = 1.89: Method B. |
| 416 | 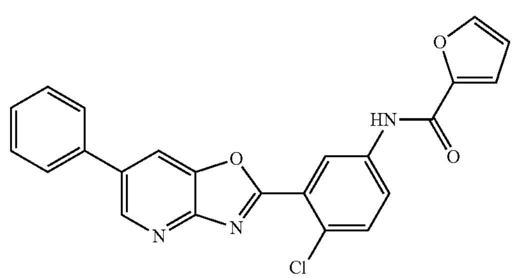 [SMILES: O=C(Nc1ccc(Cl)c(-c2nc3ncc(-c4ccccc4)cc3o2)c1)c1ccco1] | M/Z = 416.1 (M + 1). RT = 2.14: Method B. |
| 417 | 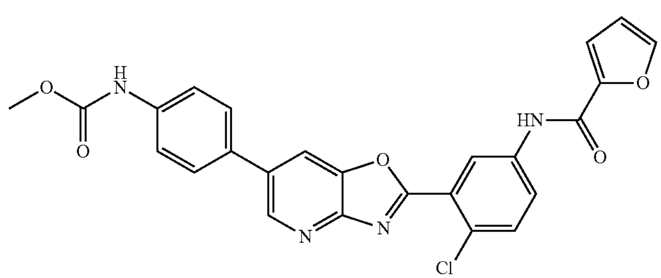 [SMILES: COC(=O)Nc1ccc(-c2cnc3nc(-c4cc(NC(=O)c5ccco5)ccc4Cl)oc3c2)cc1] | M/Z = 489.1 (M + 1). RT = 1.91: Method B. |

TABLE II-continued

Listing of the Exemplified Compounds of the Invention

| Ex. No. | Structure | $^1$H NMR and/or mass and/or (retention time (mins)) |
|---|---|---|
| 418 | 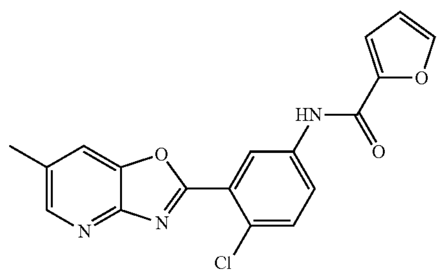 [SMILES: Cc1cnc2nc(-c3cc(NC(=O)c4ccco4)ccc3Cl)oc2c1] | $^1$H NMR (400 MHz, MeOD) δ 8.63 (d, J = 2.6 Hz, 1H), 8.45 (d, J = 1.1 Hz, 1H), 8.05 (t, J = 4.0 Hz, 1H), 8.00 (dt, J = 3.4, 10.1 Hz, 1H), 7.81-7.76 (m, 1H), 7.64 (d, J = 8.8 Hz, 1H), 7.33 (d, J = 3.5 Hz, 1H), 6.68 (dd, J = 1.8, 3.5 Hz, 1H), 2.57 (s, 3H). M/Z = 354.0 (M + 1). RT = 1.76: Method B. |
| 419 | 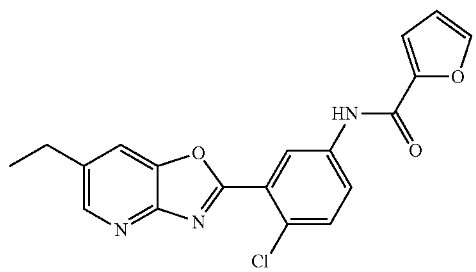 [SMILES: CCc1cnc2nc(-c3cc(NC(=O)c4ccco4)ccc3Cl)oc2c1] | $^1$H NMR (400 MHz, DMSO) δ 10.63 (s, 1H), 8.73 (d, J = 2.6 Hz, 1H), 8.51 (d, J = 1.8 Hz, 1H), 8.21 (d, J = 1.5 Hz, 1H), 8.12-8.03 (m, 1H), 8.00 (dd, J = 6.3, 7.0 Hz, 1H), 7.74 (t, J = 10.6 Hz, 1H), 7.46-7.38 (m, 1H), 6.75 (dd, J = 1.7, 3.5 Hz, 1H). 2.83 (q, J = 7.6, 2H), 1.34-1.22 (m, 3H). M/Z = 368.1 (M + 1). RT = 3.20: Method A. |
| 420 | 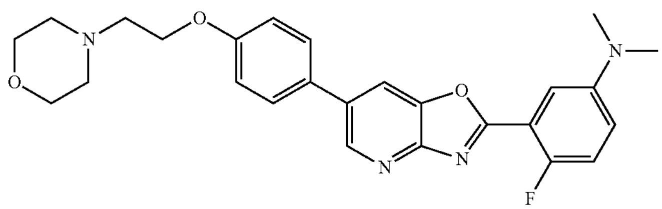 [SMILES: CN(C)c1ccc(F)c(-c2nc3ncc(-c4ccc(OCCN5CCOCC5)cc4)cc3o2)c1] | M/Z = 463.2 (M + 1). RT = 1.35: Method B. |
| 421 | 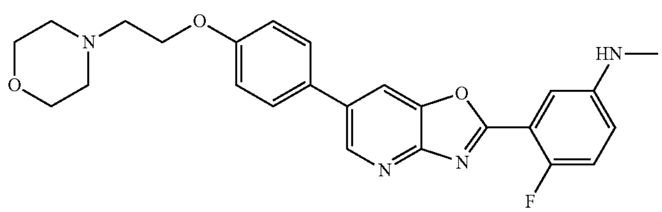 [SMILES: CNc1ccc(F)c(-c2nc3ncc(-c4ccc(OCCN5CCOCC5)cc4)cc3o2)c1] | M/Z = 449.2 (M + 1). RT = 1.33: Method B. |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:

1. A compound of Formula I:

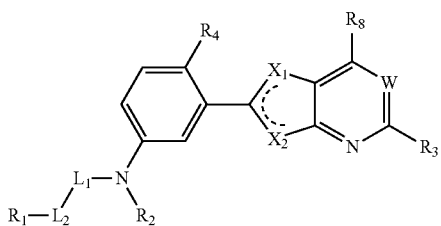

I or a pharmaceutically acceptable salt, tautomer, or stereoisomer thereof; wherein
$X_1$ is N or O, or $NR_5$;
$X_2$ is N or $NR_7$, provided that one of $X_1$ and $X_2$ is N;
W is $CR_6$ or N;
$L_1$ is a bond, —C(O)— or —S(O)$_2$—,
$L_2$ is selected from a bond, —$CR_{9a},R_{9b}$—, —$NR_{10}$—, and —O—, wherein $R_{9a}$ is hydrogen, halo or $C_{1-4}$alkyl, $R_{9b}$ is selected from hydrogen, halo, hydroxyl, $C_{1-4}$alkyl, and $C_{1-4}$alkoxy; and $R_{10}$ is hydrogen or $C_{1-4}$alkyl;
$R_1$ is selected from hydrogen, $C_{1-6}$alkyl, $C_{1-4}$alkoxy, $C_{6-10}$aryl, $C_{5-10}$heteroaryl, $C_{3-7}$cycloalkyl, $C_{5-6}$heterocycloalkyl, and $C_{9-10}$heterocyclyl, wherein
the $C_{1-6}$alkyl or $C_{1-4}$alkoxy is unsubstituted or substituted with 1 to 2 substituents independently selected from halo, hydroxy, $C_{1-4}$alkoxy, $C_{5-6}$aryloxy, hydroxycarbonyl, $C_{1-4}$alkoxycarbonyl, amino, $C_{1-4}$alkyamino, $C_{1-4}$alkoxycarbonylamino, $C_{5-6}$aryl, and $C_{5-6}$heterocycloalkyl; and
the $C_{6-10}$aryl and $C_{5-10}$heteroaryl, $C_{3-7}$cycloalkyl, $C_{5-6}$heterocycloalkyl or $C_{9-10}$heterocyclyl is unsubstituted or substituted with 1 to 3 substituents independently selected from halo, cyano, hydroxyl, oxo, $C_{1-4}$alkyl, benzyl, halo$C_{1-4}$alkyl, $C_{1-4}$alkoxy$C_{1-4}$alkyl, $C_{1-4}$alkylamino$C_{1-4}$alkyl, $C_{1-4}$alkoxy, halo $C_{1-4}$alkoxy, amino, $C_{1-4}$alkylamino, $C_{1-4}$alkoxycarbonyl, $C_{1-4}$alkylthio, $C_{1-4}$alkylsulfonyl, $C_{5-6}$heteroaryl, halo$C_{5-6}$heteroaryl, $C_{3-6}$cycloalkyl, and $C_{5-6}$heterocycloalkyl; or —N($R_2$)-$L_1$-$L_2$-$R_1$ together forms a nitro group;

$R_2$ is hydrogen, $C_{1-4}$alkyl or —C(O)$C_{5-6}$heteroaryl;

$R_3$ is hydrogen, halo or $C_{1-4}$alkyl;

$R_4$ is selected from hydrogen, halo, $C_{1-4}$alkyl, halo $C_{1-4}$alkyl, $C_{1-4}$alkylsulfonyl, $C_{5-6}$heteroaryl, and $C_{5-6}$heterocycloalkyl;

$R_5$ is selected from hydrogen, $C_{1-4}$alkyl, —C(O) OC$_{1-4}$alkyl, wherein the $C_{1-4}$alkyl portion of $C_{1-4}$alkyl or —C(O)OC$_{1-4}$alkyl is unsubstituted or substituted by amino, $C_{1-4}$alkylamino, or $C_{5-6}$heterocycloalkyl;

$R_6$ is selected from halo, cyano, $C_{1-4}$alkyl, $C_{1-4}$alkenyl, $C_{1-4}$alkoxy, $C_{1-4}$alkylsulfonyl, $C_{3-6}$cycloalkylsulfonyl, $C_{1-4}$alkylphosphinyl oxide, $C_{1-4}$alkylcarbonylamino, phenyl, $C_{5-6}$heteroaryl, $C_{5-6}$heteraryl, $C_{4-6}$heterocycloalkyl, and $C_{6-10}$heterocyclyl, wherein the $C_{1-6}$alkyl, $C_{1-4}$alkenyl or $C_{1-4}$alkoxy of $R_6$ is unsubstituted or substituted by 1 to 2 substituents independently selected from halo, amino, $C_{1-4}$alkylamino, and hydroxyl-substituted $C_{1-4}$alkylamino;

the pheny or $C_{5-6}$heteroaryl of $R_6$ is unsubstituted or substituted by 1 to 2 substituents independently selected from halo, cyano, $C_{1-4}$alkyl, halo$C_{1-4}$alkyl, $C_{1-4}$alkylamino$C_{1-4}$alkyl, amino$C_{1-4}$alkyl, $C_{4-6}$heterocycloalky$C_{1-4}$alkyl, $C_{1-4}$alkylsilanyl$C_{1-4}$alkoxy$C_{1-4}$alkyl, $C_{1-4}$alkoxy, halo$C_{1-4}$alkoxy, $C_{1-4}$alkoxy$C_{1-4}$alkoxy, amino$C_{1-4}$alkoxy, phenyl $C_{1-4}$alkoxy, $C_{5-6}$heteroaryl$C_{1-4}$alkoxy, $C_{3-6}$cycloalky$C_{1-4}$alkoxy, $C_{3-6}$heterocycloalky$C_{1-4}$alkoxy, $C_{1-4}$alkylcarbonyl, aminocarbonyl, $C_{1-4}$alkylaminocarbonyl, $C_{1-4}$alkoxycarbonyl, amino, $C_{1-4}$alkylamino, $C_{4-6}$heterocycloalky$C_{1-4}$alkylamino, $C_{4-6}$heterocycloalky$C_{1-4}$alkylamino, —NHC(O)$R_{14}$ S(O)$_2$$R_{15}$, phenyl, $C_{5-6}$heteraryl, $C_{5-6}$heterocycloalkyl, and $C_{9-10}$heterocyclyl, the $C_{3-6}$heterocycloalkyl or $C_{6-10}$heterocyclyl of $R_6$ is unsubstituted or substituted by 1 to 2 substituents independently selected from $C_{1-4}$alkyl, oxo, and $C_{1-4}$alkoxycarbonyl, wherein $R_{14}$ is selected from $C_{1-4}$alkyl, amino$C_{1-4}$alkyl, amino, $C_{1-4}$alkylamino, cyclopropylamino, $C_{1-4}$alkoxy, $C_{1-4}$alkylsulfonyl, and $C_{1-4}$alkylaminosulfonyl $R_{15}$ is selected from $C_{1-4}$alkyl, amino, $C_{3-6}$cycloalkyl, and $C_{5-6}$heterocycloalkyl; and the phenyl, $C_{5-6}$heteraryl, $C_{5-6}$heterocycloalkyl or $C_{9-10}$heterocyclyl substituent of the phenyl or $C_{5-6}$heteroaryl of $R_6$ is unsubstituted or substituted by 1 to 3 substituents independently selected from $C_{1-4}$alkyl and oxo;

$R_7$ is selected from hydrogen, $C_{1-4}$alkyl and —C(O) $C_{5-6}$heteroaryl; and $R_8$ is hydrogen or halo.

2. The compound of claim 1, wherein the compound is of Formula 1a:

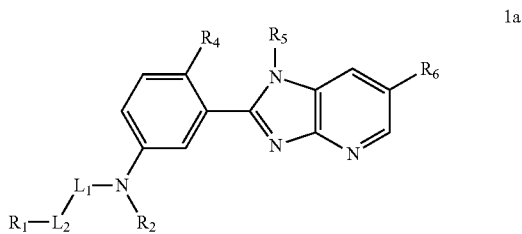

3. The compound according to claim 2, wherein $L_1$ is —C(O)—.

4. The compound according to claim 3, wherein $L_2$ is selected from a bond, —CR$_{9a}$R$_{9b}$—, —NR$_{10}$—, and —O—, wherein R$_{9a}$ is selected from hydrogen, fluoro, hydroxyl, methyl, isopropyl and methoxy, R$_{9b}$ is selected from hydrogen, fluoro and methyl, and R$_{10}$ is selected from hydrogen, methyl, ethyl, and isopropyl.

5. The compound according to claim 4, wherein $R_1$ is selected from hydrogen, $C_{1-6}$alkyl, $C_{1-6}$alkoxy, $C_{6-10}$aryl, $C_{5-10}$heteroaryl, $C_{3-7}$cycloalkyl, $C_{5-6}$heterocycloalkyl, and $C_{9-10}$heterocyclyl, wherein the $C_{1-6}$alkyl or $C_{1-6}$alkoxy is unsubstituted or substituted with 1 to 2 substituents independently selected from —OH, fluoro, —CF$_3$, OCH$_3$, phenoxy. —C(O)OH, —NH$_2$, —N(CH$_3$)$_2$, —N(CH$_2$CH$_3$)$_2$, —N(CH (CH$_3$)$_2$)$_2$, —NHC(O)OC(CH$_3$)$_3$, phenyl, and morpholinyl;

the $C_{6-10}$aryl, $C_{5-10}$heteroaryl, $C_{3-7}$cycloalkyl, $C_{5-6}$heterocycloalkyl, or $C_{9-10}$heterocyclyl is unsubstituted or substituted by 1 to 3 substituents independently selected from fluoro, chloro, cyano, oxo, hydroxy, methyl, ethyl, isopropy, t-butyl, trifluoromethyl, methoxymethyl, dimethylaminomethyl, benzyl, methoxy, ethoxy, trifluoromethoxy, t-butoxycarbony dimethylamino, methylthio, methylsulfonyl, fluorophenyl, triazolyl, pyrimidinyl, cyclopropyl, piperidinyl, and morpholinyl.

6. The compound according to claim 5, wherein $R_2$ is hydrogen, methyl, or —C(O)-furan-2-yl.

7. The compound according to claim 6, wherein $R_4$ is selected from hydrogen, fluoro, chloro, methyl, trifluoromethyl, methylsulfonyl, pyridin3-yl, and morpholinyl.

8. The compound according to claim 7, wherein $R_5$ is selected from hydrogen, —CH$_2$O(CH$_3$), —(CH$_2$)$_2$-morpholinyl, —(CH$_2$)$_2$N(CH$_3$)$_2$, —C(O)OCH(CH$_3$)$_2$, and —C(O)O(CH$_3$).

9. The compound according to claim 8, wherein $R_6$ is selected from halo, cyano, $C_{1-4}$alkyl, $C_{1-4}$alkenyl, $C_{1-4}$alkoxy, $C_{1-4}$alkylsulfonyl, $C_{3-6}$cycloalkylsulfonyl, $C_{1-4}$alkylphosphinyl oxide, $C_{1-4}$alkylcarbonylamino, phenyl, $C_{5-6}$heteroaryl, $C_{5-6}$heteraryl, $C_{4-6}$heterocycloalkyl, $C_{6-10}$heterocyclyl, wherein the $C_{1-6}$alkyl, $C_{1-4}$alkenyl or $C_{1-4}$alkoxy of $R_6$ is unsubstituted or substituted by 1 to 2 substituents independently selected from halo, —NH$_2$, —NH(CH$_3$), —N(CH$_3$)$_2$, —NH(CH$_2$CH$_3$), N(CH$_2$CH$_3$)$_2$, —NHCH$_2$CH(OH) (CH$_3$), —NHCH(CH$_3$)CH$_2$(OH);

the phenyl or $C_{5-6}$heteroaryl of $R_6$ is unsubstituted or substituted by 1 to 2 substituents independently selected from fluoro, chloro, cyano, methyl, trifluoromethyl, —(CH$_2$)—N(CH$_3$)$_2$, —(CH$_2$)$_2$—N(CH$_3$)$_2$, —CH (CH$_3$)$_2$CH$_2$NH$_2$, —CH$_2$O(CH$_2$)$_2$Si(CH$_3$)$_3$, —(CH₂)₁₋₂-morpholinyl, methoxy, ethoxy, trifluoromethoxy, —O(CH₂)₂OCH₃, —O(CH₂)₂N(CH₃)₂, —OCH₂-phenyl, —OCH₂-5-methylisoxazol-3-yl, —O(CH₂)₂-1H-imidazol-1-yl, —O(CH₂)₂-1H-pyrazol-1-yl, —OCH₂-cyclopropyl, —OCH₂-oxiran-2-yl, —O(CH₂)₂-pyrrolidin-1-yl, —OCH₂-tetrahydro-2H-pyran-4-yl, —O(CH₂)₂-piperidin-1-yl, —O(CH₂)₂-4-methylpiperazin-1-yl, —O(CH₂)₂₋₃-morpholinyl, —OCH₂CH(OH)CH₂-morpholinyl, —C(O)CH₃, —C(O)NH₂, —C(O)NHCH₃, —C(O)OCH₃, —NH₂, —NHCH₃, —N(CH₃)₂, —NH(CH₂)₂-morpholinyl, —NHC(O)CH₃, —NHC(O)CH(CH₃)₂, —NHC(O)CH₂CH(CH₃)₂, —NHC(O)CH₂NH₂, —NHC(O)(CH₂)₂NH₂, —NHC(O)NH₂, —NHC(O)NHCH₃, —NHC(O)NH-cyclopropyl, —NHC(O)OCH₃, —NHC(O)OCH(CH₃)₂, —NHC(O)OC(CH₃)₃, —N(CH₃)C(O)OC(CH₃)₃, —NHS(O)₂CH₃, —NHS(O)₂CH(CH₃)₂, —NHS(O)₂NH(CH₃), —S(O)₂CH₃, —S(O)₂NH₂, —S(O)₂-pyrrolidinyl, phenyl, pyrazolyl, pyrrolidinyl, piperidinyl, piperazinyl, C₁₋₄alkylpiperazinyl, pyrrolidinyl, piperidinyl, morpholinyl, C₁₋₄alkyldihydro-2H-benzo[b][1,4]oxazinyl, and dioxoimidazolidinyl; and the C₃₋₆heterocycloalkyl or C₆₋₉heterocyclyl of R₆ is unsubstituted or substituted by 1 to 2 substituents independently selected from methyl and —C(O)OC(CH₃)₃.

10. The compound according to claim 8, wherein R₆ is selected from chloro, bromo, cyano, methyl, ethyl, ethenyl, trifluoromethyl, —(CH₂)₂-morpholinyl, ethoxy, amino, —N(H)C(O)CH₃, —N(H)C(O)OCH₃, —NHC(O)OC(CH₃)₃, phenyl, pyridinyl, pyrimidinyl, 1-t-butylcarbonyl-5,6-dihydropyridin-4-yl, 4-methyl-3,4-dihydro-2H-benzo[b][1,4]oxazin-7-yl, 1-methyl-indolin-5-yl, and 2-oxo-indolin-5-yl, wherein the phenyl is unsubstituted or substituted with 1 to 2 substituents independently selected from fluoro-, chloro, cyano, —CF₃, —NH₂, —(CH₂)₂—N(CH₃)₂, —C(CH₃)₂CH₂NH₂, 4-methyl-piperazinyl, —(CH₂)₁₋₂-morpholinyl, —OCH₃, —OCF₃, 4-O(CH₂)₂OCH₃, 4-O(CH₂)N(CH₃)₂, —O(CH₂)-cyclopropyl, —OCH₂-oxiranyl, —O(CH₂)-pyrrolidinyl, —O(CH₂)-tetrahyropyanyl, —O(CH₂)-(5-methylisooxazolyl, —O(CH₂)-methylpiperizinyl, —O(CH₂)₂₋₃-morpholinyl, —OCH₂-imidazolyl, —O(CH₂)₂-pyrazolyl, —C(O)OCH₃, —NHCH₃, —N(CH₃)₂, —NHC(O)CH₃, —NHC(O)CH₃, —NHC(O)CH(CH₃)₂—, —N(H)C(O)CH₂CH(CH₃)₂, —N(H)C(O)OCH₃, —NHC(O)OCH(CH₃)₂, —NHC(O)OC(CH₃)₃, —N(CH₃)C(O)OC(CH₃)₃, —N(H)C(O)CH₂NH₂—, —NHC(O)NH-cyclopropyl, —S(O)₂CH₃, —N(H)S(O)₃CH(CH₃)₂, —S(O)₂-pyrrolidin-1-yl, -pyrrolidinyl, -piperidinyl, -4-CH(CH₃)₂-piperazinyl, -2,4-dioxoimidazolidinyl, and 2-oxo-indolinyl; and the pyridinyl or pyrimidinyl is unsubstituted or substituted with 1 to 2 substituents independently selected from fluoro, methyl, —(CH₂)₂-morpholinyl, methoxy, —C(O)NHCH₃, amino, —N(CH₃)₂, —NHC(O)CH₃, pyrazol-4-yl, thiophen-3-y, thiophen-2-y, —CH₂O(CH₂)₂Si(CH₃)₃-1-imidazol4-yl, and -methylpyrazol-3-y.

11. The compound according to claim 1, wherein the compound is of Formula 1c:

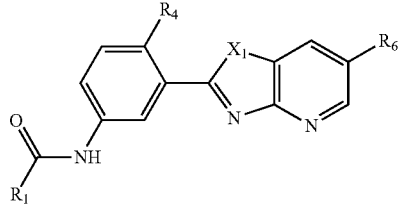

1c wherein

X₁ is O or NR₅;

R₁ is selected from —CH₂-4-fluorophenyl, —OCH₂CH₃, —O(CH₂)₂OCH₃, —OCH(CH₃)₂, —O-cyclopentyl, —N(CH₃)(OCH₃), —N(CH(CH₃)₂)₂, cyclopentoxy, 3-chlorophenyl, 2-chlorophenyl, 2,4dimethoxyphenyl, 4-trifluoromethyphenyl, pyrrol-2-yl, furan-2-yl, 5-fluorofuran-2-yl, 5-chlorofuran-2-yl, 5-cyanofuran-2-yl, 5-methylfuranyl, 5-dimethylaminomethyl-furan-2-yl, 4-methylthiophen-2-yl, isothiazol-5-yl, thiazol-4-yl, 5-t-butyloxadiazol-2-yl, pyrazinyl, cyclopentyl, pyrrolidinyl, 3,3-difluoropyrrolidinyl, and 2-oxoindolin-6-yl;

R₄ is selected from hydrogen, halo, C₁₋₄alkyl, and halo C₁₋₄alkyl;

R₅ is selected from hydrogen, —CH₂O(CH₃), —(CH₂)₂-morpholinyl, —(CH₂)₂N(CH₃)₂, —C(O)OCH(CH₃)₂, and —C(O)O(CH₃);

R₆ is selected from chloro, bromo, cyano, methyl, ethyl, ethenyl, trifluoromethyl, —(CH₂)₂-morpholinyl, ethoxy, amino, —N(H)C(O)CH₃, —N(H)C(O)OCH₃, —NHC(O)OC(CH₃)₃, phenyl, pyridinyl, pyrimidinyl, 1-t-butylcarbonyl-5,6-dihydropyridin-4-yl, 4-methyl-3,4-dihydro-2H-benzo[b][1,4]oxazin-7-yl, 1-methyl-indolin-5-yl, and 2-oxo-indolin-5-yl, wherein the phenyl is unsubstituted or substituted by 1 to 2 substituents independently selected from fluoro-, chloro, cyano, —CF₃, —NH₂, —(CH₂)₂—N(CH₃)₂, —C(CH₃)₂CH₂NH₂, 4-methyl-piperazinyl, —(CH₂)₁₋₂-morpholinyl, —OCH₃, —OCF₃, 4-O(CH₂)₂OCH₃, 4-O(CH₂)N(CH₃)₂, —O(CH₂)-cyclopropyl, —OCH₂-oxiranyl, —O(CH₂)-pyrrolidinyl, —O(CH₂)-tetrahyropyanyl, —O(CH₂)-(5-methylisooxazolyl, —O(CH₂)-methylpiperizinyl, —O(CH₂)₂₋₃-morpholinyl, —OCH₂-imidazolyl, —O(CH₂)₂-pyrazolyl, —C(O)OCH₃, —NHCH₃, —N(CH₃)₂, —NHC(O)CH₃, —NHC(O)CH₃, —NHC(O)CH(CH₃)₂—, —N(H)C(O)CH₂CH(CH₃)₂, —N(H)C(O)OCH₃, —NHC(O)OCH(CH₃)₂, —NHC(O)OC(CH₃)₃, —N(CH₃)C(O)OC(CH₃)₃, —N(H)C(O)CH₂NH₂—, —NHC(O)NH-cyclopropyl, —S(O)₂CH₃, —N(H)S(O)₃CH(CH₃)₂, —S(O)₂-pyrrolidin-1-yl, pyrrolidinyl, piperidinyl, 4-CH(CH₃)₂-piperazinyl, -2,4-dioxoimidazolidinyl, and 2-oxo-indolinyl; and the pyridinyl or pyrimidinyl is unsubstituted or substituted with 1 to 2 substituents independently selected from fluoro, methyl, —(CH₂)₂-morpholinyl, methoxy, —C(O)NHCH₃, amino, —N(CH₃)₂, —NHC(O)CH₃, pyrazol-4-yl, thiophen-3-y, thiophen-2-y, —CH₂O(CH₂)₂Si(CH₃)₃-1-imidazol4-yl, and -methylpyrazol-3-y.

12. The compound according to claim 11, wherein $X_1$ is $NR_5$.

13. The compound according to claim 12, wherein $R_1$ is selected from isopropoxy, furan-2-yl, pyrazin-2-yl, cyclopentyl, pyrrolidinyl, and 3,3-difluoro pyrrolidinyl.

14. The compound according to claim 13, wherein $R_4$ is halo.

15. The compound according to claim 14, wherein $R_5$ is hydrogen.

16. The compound according to claim 15, wherein $R_6$ is selected from bromo, cyano, —(CH$_2$)$_2$-morpholinyl, amino, —N(H)C(O)OCH$_3$, phenyl, 2-fluoro-pyridin-4-yl, 2-C(O)NHCH$_3$pyridin5-yl, -2-(morpholinylethyl)pyridin-5-yl, thiophen3-yl, and —CH$_2$O(CH$_2$)$_2$Si(CH$_3$)$_3$-1-imidazol4-yl, wherein
the phenyl is unsubstituted or substituted at the para-position by a substituent independently selected from —(CH$_2$)$_2$N(CH$_3$)$_2$, —O(CH$_2$)$_2$OCH$_3$, —O(CH$_2$)$_2$-pyrazolyl, —O(CH$_2$)-5-methylisooxazolyl, —O(CH$_2$)$_{2-3}$-morpholinyl, —NHCH$_3$, —N(H)C(O)CH(CH$_3$)$_2$, —N(H)C(O)CH$_2$CH(CH$_3$)$_2$, —NHC(O)C(CH$_3$)$_3$, —N(H)C(O)CH$_2$NH$_2$, —N(H)C(O)OCH$_3$, and —N(CH$_3$)C(O)OC(CH$_3$)$_3$, or at the ortho-position by a substituent selected from amino and —NHC(O)OCH(CH$_3$)$_2$.

17. The compound according to claim 1, wherein the compound is selected from the group consisting of:
N-(4-chloro-3-{6-methyl-1H-imidazo[4,5-b]pyridin-2-yl}phenyl)-furan-2-carboxamide;
N-(4-chloro-3-{6-chloro-1H-imidazo[4,5-b]pyridin-2-yl}phenyl)furan-2-carboxamide;
N-(4-chloro-3-{7-methyl-1H-imidazo[4,5-b]pyridin-2-yl}phenyl)-furan-2-carboxamide;
N-[4-chloro-3-(7H-purin-8-yl)phenyl]furan-2-carboxamide;
N-(4-chloro-3-{5,6-dimethyl-1H-imidazo[4,5-b]pyridin-2-yl}phenyl)furan-2-carboxamide;
N-[4-chloro-3-(6-{4-[2-(morpholin-4-yl)ethyl]phenyl}-1H-imidazo[4,5-b]pyridin-2-yl)phenyl]furan-2-carboxamide;
N-{4-chloro-3-[6-(6-acetamidopyridin-3-yl)-1H-imidazo[4,5-b]pyridin-2-yl]phenyl}furan-2-carboxamide;
N-{4-chloro-3-[6-(2-acetamidophenyl)-1H-imidazo[4,5-b]pyridin-2-yl]phenyl}furan-2-carboxamide;
N-{4-chloro-3-[6-(2-methoxypyrimidin-5-yl)-1H-imidazo[4,5-b]pyridin-2-yl]phenyl}furan-2-carboxamide;
N-{4-chloro-3-[6-(pyridin-4-yl)-1H-imidazo[4,5-b]pyridin-2-yl]phenyl}furan-2-carboxamide;
N-[4-chloro-3-(6-{6-[2-(morpholin-4-yl)ethoxy]pyridin-3-yl}-1H-imidazo[4,5-b]pyridin-2-yl)phenyl]furan-2-carboxamide;
N-{3-[6-(4-aminophenyl)-1H-imidazo[4,5-b]pyridin-2-yl]-4-chlorophenyl}furan-2-carboxamide;
N-(4-chloro-3-{6-[4-(3-methylbutanamido)phenyl]-1H-imidazo[4,5-b]pyridin-2-yl}phenyl)furan-2-carboxamide;
N-(4-chloro-3-(6-{1-[2-(morpholin-4-yl)ethyl]-1H-pyrazol-4-yl}-1H-imidazo[4,5-b]pyridin-2-yl)phenyl]furan-2-carboxamide;
N-[4-chloro-3-(6-{4-[(dimethylamino)methyl]phenyl}-1H-imidazo[4,5-b]pyridin-2-yl)phenyl]furan-2-carboxamide;
N-(4-chloro-3-{6-[4-(morpholin-4-ylmethyl)phenyl]-1H-imidazo[4,5-b]pyridin-2-yl}phenyl)furan-2-carboxamide;
N-{3-[6-(2-aminopyrimidin-5-yl)-1H-imidazo[4,5-b]pyridin-2-yl]-4-chlorophenyl}furan-2-carboxamide;
N-{4-chloro-3-[6-(4-acetamidophenyl)-1H-imidazo[4,5-b]pyridin-2-yl]phenyl}furan-2-carboxamide;
N-{3-[6-(4-carbamoylphenyl)-1H-imidazo[4,5-b]pyridin-2-yl]-4-chlorophenyl}furan-2-carboxamide;
N-{4-chloro-3-[6-(4-cyanophenyl)-1H-imidazo[4,5-b]pyridin-2-yl]phenyl}furan-2-carboxamide;
N-[4-chloro-3-(6-{4-[2-(piperidin-1-yl)ethoxy]phenyl}-1H-imidazo[4,5-b]pyridin-2-yl)phenyl]furan-2-carboxamide;
N-(4-chloro-3-{6-[4-(4-methylpiperazin-1-yl)phenyl]-1H-imidazo[4,5-b]pyridin-2-yl}phenyl)furan-2-carboxamide;
N-{3-[6-(2-aminophenyl)-1H-imidazo[4,5-b]pyridin-2-yl]-4-chlorophenyl}furan-2-carboxamide;
N-{3-[6-(6-aminopyridin-3-yl)-1H-imidazo[4,5-b]pyridin-2-yl]-4-chlorophenyl}furan-2-carboxamide;
N-(4-chloro-3-{6-[4-(trifluoromethoxy)phenyl]-1H-imidazo[4,5-b]pyridin-2-yl}phenyl)furan-2-carboxamide;
N-(4-chloro-3-{6-[4-(oxan-4-ylmethoxy)phenyl]-1H-imidazo[4,5-b]pyridin-2-yl}phenyl)furan-2-carboxamide;
N-{3-[6-(2H-1,3-benzodioxol-5-yl)-1H-imidazo[4,5-b]pyridin-2-yl]-4-chlorophenyl}furan-2-carboxamide;
N-(4-chloro-3-{6-[4-(methylamino)phenyl]-1H-imidazo[4,5-b]pyridin-2-yl}phenyl)furan-2-carboxamide;
N-{4-chloro-3-[6-(6-methoxypyridin-3-yl)-1H-imidazo[4,5-b]pyridin-2-yl]phenyl}furan-2-carboxamide;
N-(4-chloro-3-{6-ethyl-1H-imidazo[4,5-b]pyridin-2-yl}phenyl)furan-2-carboxamide;
propan-2-yl N-(4-{2-[2-chloro-5-(furan-2-amido)phenyl]-1H-imidazo[4,5-b]pyridin-6-yl}phenyl)carbamate;
N-(3-{6-[4-(carbamoylamino)phenyl]-1H-imidazo[4,5-b]pyridin-2-yl}-4-chlorophenyl)furan-2-carboxamide;
N-(4-chloro-3-{6-[4-(morpholin-4-yl)phenyl]-1H-imidazo[4,5-b]pyridin-2-yl}phenyl)furan-2-carboxamide;
tert-butyl N-(4-{2-[2-chloro-5-(furan-2-amido)phenyl]-1H-imidazo[4,5-b]pyridin-6-yl}-2-methoxyphenyl)carbamate;
methyl 4-{2-[2-chloro-5-(furan-2-amido)phenyl]-1H-imidazo[4,5-b]pyridin-6-yl}benzoate;
N-(4-chloro-3-{6-[4-(cyclopropylmethoxy)phenyl]-1H-imidazo[4,5-b]pyridin-2-yl}phenyl)furan-2-carboxamide;
propan-2-yl N-(2-{2-[2-chloro-5-(furan-2-amido)phenyl]-1H-imidazo[4,5-b]pyridin-6-yl}phenyl)carbamate;
N-{4-chloro-3-[6-({[(2S)-1-hydroxypropan-2-yl]amino}methyl)-1H-imidazo[4,5-b]pyridin-2-yl]phenyl}furan-2-carboxamide;
N-{4-chloro-3-[6-(2,6-dimethylpyridin-4-yl)-1H-imidazo[4,5-b]pyridin-2-yl]phenyl}furan-2-carboxamide;
N-[4-chloro-3-(6-{4-[2-(1H-pyrazol-1-yl)ethoxy]phenyl}-1H-imidazo[4,5-b]pyridin-2-yl)phenyl]furan-2-carboxamide;
N-(3-{6-[4-(trifluoromethoxy)phenyl]-1H-imidazo[4,5-b]pyridin-2-yl}phenyl)furan-2-carboxamide;
N-(4-chloro-3-{6-[4-(2,5-dioxoimidazolidin-4-yl)phenyl]-1H-imidazo[4,5-b]pyridin-2-yl}phenyl)furan-2-carboxamide;
N-{4-chloro-3-[6-(2-oxo-2,3-dihydro-1H-indol-5-yl)-1H-imidazo[4,5-b]pyridin-2-yl]phenyl}furan-2-carboxamide;
N-[4-chloro-3-(6-{4-[(5-methyl-1,2-oxazol-3-yl)methoxy]phenyl}-1H-imidazo[4,5-b]pyridin-2-yl)phenyl]furan-2-carboxamide;

N-[4-chloro-3-(6-{4-[(cyclopropylcarbamoyl)amino]phenyl}-1H-imidazo[4,5-b]pyridin-2-yl)phenyl]furan-2-carboxamide;
N-{4-chloro-3-[6-(4-methanesulfonylphenyl)-1H-imidazo[4,5-b]pyridin-2-yl]phenyl}furan-2-carboxamide;
N-(3-{6-[4-(benzyloxy)phenyl]-1H-imidazo[4,5-b]pyridin-2-yl}-4-chlorophenyl)furan-2-carboxamide;
N-{4-chloro-3-[6-(3-chloro-4-methoxyphenyl)-1H-imidazo[4,5-b]pyridin-2-yl]phenyl}furan-2-carboxamide;
N-(4-chloro-3-{6-[4-methoxy-3-(pyrrolidine-1-sulfonyl)phenyl]-1H-imidazo[4,5-b]pyridin-2-yl}phenyl)furan-2-carboxamide;
N-{4-chloro-3-[6-(pyridin-3-yl)-1H-imidazo[4,5-b]pyridin-2-yl]phenyl}furan-2-carboxamide;
N-{4-chloro-3-[6-(2-fluoropyridin-4-yl)-1H-imidazo[4,5-b]pyridin-2-yl]phenyl}furan-2-carboxamide;
N-(4-chloro-3-{6-[2-fluoro-6-(2-methoxyethoxy)pyridin-3-yl]-1H-imidazo[4,5-b]pyridin-2-yl}phenyl)furan-2-carboxamide;
N-(4-chloro-3-{6-[4-(2-methylpropanamido)phenyl]-1H-imidazo[4,5-b]pyridin-2-yl}phenyl)furan-2-carboxamide;
5-{2-[2-chloro-5-(furan-2-amido)phenyl]-1H-imidazo[4,5-b]pyridin-6-yl}-N-methylpyridine-2-carboxamide;
N-[4-chloro-3-(6-{4-[2-(pyrrolidin-1-yl)ethoxy]phenyl}-1H-imidazo[4,5-b]pyridin-2-yl)phenyl]furan-2-carboxamide;
N-(4-chloro-3-{6-[4-(1H-pyrazol-1-yl)phenyl]-1H-imidazo[4,5-b]pyridin-2-yl}phenyl)furan-2-carboxamide;
N-[4-chloro-3-(6-{4-[(methylcarbamoyl)amino]phenyl}-1H-imidazo[4,5-b]pyridin-2-yl)phenyl]furan-2-carboxamide;
methyl N-(4-{2-[2-chloro-5-(furan-2-amido)phenyl]-1H-imidazo[4,5-b]pyridin-6-yl}phenyl)carbamate;
N-{4-chloro-3-[6-(1-methyl-2,3-dihydro-1H-indol-5-yl)-1H-imidazo[4,5-b]pyridin-2-yl]phenyl}furan-2-carboxamide;
N-(4-chloro-3-{6-[4-(2-methoxyethoxy)phenyl]-1H-imidazo[4,5-b]pyridin-2-yl}phenyl)furan-2-carboxamide;
N-{4-chloro-3-[6-(2,6-dimethoxypyridin-3-yl)-1H-imidazo[4,5-b]pyridin-2-yl]phenyl}furan-2-carboxamide;
N-[4-chloro-3-(6-{4-[4-(propan-2-yl)piperazin-1-yl]phenyl}-1H-imidazo[4,5-b]pyridin-2-yl)phenyl]furan-2-carboxamide;
tert-butyl 4-{2-[2-chloro-5-(furan-2-amido)phenyl]-1H-imidazo[4,5-b]pyridin-6-yl}-1,2,3,6-tetrahydropyridine-1-carboxylate;
N-(4-chloro-3-{6-[4-(methylcarbamoyl)phenyl]-1H-imidazo[4,5-b]pyridin-2-yl}phenyl)furan-2-carboxamide;
N-{4-chloro-3-[6-[6-(dimethylamino)pyridin-3-yl]-1H-imidazo[4,5-b]pyridin-2-yl]phenyl}furan-2-carboxamide;
N-{4-chloro-3-[6-(4-sulfamoylphenyl)-1H-imidazo[4,5-b]pyridin-2-yl]phenyl}furan-2-carboxamide;
N-(4-chloro-3-{6-[4-(dimethylamino)phenyl]-1H-imidazo[4,5-b]pyridin-2-yl}phenyl)furan-2-carboxamide;
N-(4-chloro-3-{6-[4-(pyrrolidin-1-yl)phenyl]-1H-imidazo[4,5-b]pyridin-2-yl}phenyl)furan-2-carboxamide;
N-[4-chloro-3-(6-{4-[2-(dimethylamino)ethoxy]phenyl}-1H-imidazo[4,5-b]pyridin-2-yl)phenyl]furan-2-carboxamide;
N-{4-chloro-3-[6-(1,2,3,6-tetrahydropyridin-4-yl)-1H-imidazo[4,5-b]pyridin-2-yl]phenyl}furan-2-carboxamide;
N-[4-chloro-3-(6-{4-[2-(1H-imidazol-1-yl)ethoxy]phenyl}-1H-imidazo[4,5-b]pyridin-2-yl)phenyl]furan-2-carboxamide;
N-{4-chloro-3-[6-(4-methyl-3,4-dihydro-2H-1,4-benzoxazin-7-yl)-1H-imidazo[4,5-b]pyridin-2-yl]phenyl}furan-2-carboxamide;
N-{4-chloro-3-[6-(4-methyl-1H-pyrazol-3-yl)-1H-imidazo[4,5-b]pyridin-2-yl]phenyl}furan-2-carboxamide;
N-(4-chloro-3-{6-ethenyl-1H-imidazo[4,5-b]pyridin-2-yl}phenyl)furan-2-carboxamide;
N-(4-chloro-3-{6-propyl-1H-imidazo[4,5-b]pyridin-2-yl}phenyl)furan-2-carboxamide;
N-{4-chloro-3-[6-(2-methylpropyl)-1H-imidazo[4,5-b]pyridin-2-yl]phenyl}furan-2-carboxamide;
N-{4-chloro-3-[6-(propan-2-yl)-1H-imidazo[4,5-b]pyridin-2-yl]phenyl}furan-2-carboxamide;
N-(4-chloro-3-{6-methyl-1H-imidazo[4,5-b]pyridin-2-yl}phenyl)-2-(2,3-difluorophenyl)acetamide;
N-(4-chloro-3-{6-methyl-1H-imidazo[4,5-b]pyridin-2-yl}phenyl)-5-methyl-1,2-oxazole-3-carboxamide;
N-(4-chloro-3-{6-methyl-1H-imidazo[4,5-b]pyridin-2-yl}phenyl)-4-methyl-1,3-thiazole-2-carboxamide;
N-(4-chloro-3-{6-methyl-1H-imidazo[4,5-b]pyridin-2-yl}phenyl)-2-(4-chlorophenyl)-2-methylpropanamide;
N-(4-chloro-3-{6-methyl-1H-imidazo[4,5-b]pyridin-2-yl}phenyl)-2-[4-(dimethylamino)phenyl]acetamide;
N-(4-chloro-3-{6-methyl-1H-imidazo[4,5-b]pyridin-2-yl}phenyl)pyridine-2-carboxamide;
N-(4-chloro-3-{6-methyl-1H-imidazo[4,5-b]pyridin-2-yl}phenyl)-5-(morpholin-4-yl)pyridine-2-carboxamide;
N-(4-chloro-3-{6-methyl-1H-imidazo[4,5-b]pyridin-2-yl}phenyl)-2-(3-chlorophenyl)acetamide;
5-chloro-N-(4-chloro-3-{6-methyl-1H-imidazo[4,5-b]pyridin-2-yl}phenyl)furan-2-carboxamide;
N-(4-chloro-3-{6-methyl-1H-imidazo[4,5-b]pyridin-2-yl}phenyl)-2-(2,6-difluorophenyl)acetamide;
N-(4-chloro-3-{6-methyl-1H-imidazo[4,5-b]pyridin-2-yl}phenyl)-2-(3-methyl-1,2-oxazol-5-yl)acetamide;
3-chloro-N-(4-chloro-3-{6-methyl-1H-imidazo[4,5-b]pyridin-2-yl}phenyl)benzamide;
N-(4-chloro-3-{6-methyl-1H-imidazo[4,5-b]pyridin-2-yl}phenyl)-5-fluorofuran-2-carboxamide;
N-(4-chloro-3-{6-methyl-1H-imidazo[4,5-b]pyridin-2-yl}phenyl)-1,2-thiazole-5-carboxamide;
N-(4-chloro-3-{6-methyl-1H-imidazo[4,5-b]pyridin-2-yl}phenyl)pyridazine-4-carboxamide;
N-(4-chloro-3-{6-methyl-1H-imidazo[4,5-b]pyridin-2-yl}phenyl)-2-ethoxypyridine-4-carboxamide;
N-(4-chloro-3-{6-methyl-1H-imidazo[4,5-b]pyridin-2-yl}phenyl)-5-[(dimethylamino)methyl]furan-2-carboxamide;
N-(4-chloro-3-{6-methyl-1H-imidazo[4,5-b]pyridin-2-yl}phenyl)-1H-imidazole-2-carboxamide;
N-(4-chloro-3-{6-methyl-1H-imidazo[4,5-b]pyridin-2-yl}phenyl)-2-[4-(trifluoromethyl)phenyl]acetamide;
N-(4-chloro-3-{6-methyl-1H-imidazo[4,5-b]pyridin-2-yl}phenyl)-2-(pyridin-3-yl)acetamide;
2,5-dichloro-N-(4-chloro-3-{6-methyl-1H-imidazo[4,5-b]pyridin-2-yl}phenyl)benzamide;
N-(4-chloro-3-{6-methyl-1H-imidazo[4,5-b]pyridin-2-yl}phenyl)-3-(piperidin-1-yl)benzamide;
N-(4-chloro-3-{6-methyl-1H-imidazo[4,5-b]pyridin-2-yl}phenyl)-1H-pyrrole-2-carboxamide;
N-(4-chloro-3-{6-methyl-1H-imidazo[4,5-b]pyridin-2-yl}phenyl)-5-cyanopyridine-3-carboxamide;
N-(4-chloro-3-{6-methyl-1H-imidazo[4,5-b]pyridin-2-yl}phenyl)-5-methylpyridine-3-carboxamide;
N-(4-chloro-3-{6-methyl-1H-imidazo[4,5-b]pyridin-2-yl}phenyl)oxetane-2-carboxamide;

N-(4-chloro-3-{6-methyl-1H-imidazo[4,5-b]pyridin-2-yl}phenyl)-1,3-oxazole-2-carboxamide;
N-(4-chloro-3-{6-methyl-1H-imidazo[4,5-b]pyridin-2-yl}phenyl)-3,5-dimethyl-1,2-oxazole-4-carboxamide;
N-(4-chloro-3-{6-methyl-1H-imidazo[4,5-b]pyridin-2-yl}phenyl)-5-methyl-1,3,4-oxadiazole-2-carboxamide;
N-(4-chloro-3-{6-methyl-1H-imidazo[4,5-b]pyridin-2-yl}phenyl)-2-methyl-1,3-thiazole-4-carboxamide;
N-(4-chloro-3-{6-methyl-1H-imidazo[4,5-b]pyridin-2-yl}phenyl)-2-methoxybenzamide;
N-(4-chloro-3-{6-methyl-1H-imidazo[4,5-b]pyridin-2-yl}phenyl)-4-(morpholin-4-yl)benzamide;
2-chloro-N-(4-chloro-3-{6-methyl-1H-imidazo[4,5-b]pyridin-2-yl}phenyl)-4-methanesulfonylbenzamide;
tert-butyl N-{1-[(4-chloro-3-{6-methyl-1H-imidazo[4,5-b]pyridin-2-yl}phenyl)carbamoyl]-1-methylethyl}carbamate;
tert-butyl N-{[(4-chloro-3-{6-methyl-1H-imidazo[4,5-b]pyridin-2-yl}phenyl)carbamoyl]methyl}carbamate;
N-(4-chloro-3-{6-methyl-1H-imidazo[4,5-b]pyridin-2-yl}phenyl)-1,3-oxazole-4-carboxamide;
N-(4-chloro-3-{6-methyl-1H-imidazo[4,5-b]pyridin-2-yl}phenyl)-2-(2,4-difluorophenyl)acetamide;
N-(4-chloro-3-{6-methyl-1H-imidazo[4,5-b]pyridin-2-yl}phenyl)-5-(trifluoromethyl)pyridine-2-carboxamide;
2-amino-N-(4-chloro-3-{6-methyl-1H-imidazo[4,5-b]pyridin-2-yl}phenyl)acetamide;
N-(4-chloro-3-{6-methyl-1H-imidazo[4,5-b]pyridin-2-yl}phenyl)-3,3-difluorocyclobutane-1-carboxamide;
N-(4-chloro-3-{6-methyl-1H-imidazo[4,5-b]pyridin-2-yl}phenyl)cyclobutanecarboxamide;
N-(4-chloro-3-{6-methyl-1H-imidazo[4,5-b]pyridin-2-yl}phenyl)-2-(4-fluorophenyl)propanamide;
N-(4-chloro-3-{6-methyl-1H-imidazo[4,5-b]pyridin-2-yl}phenyl)-2-phenoxyacetamide;
N-(4-chloro-3-{6-methyl-1H-imidazo[4,5-b]pyridin-2-yl}phenyl)-2-[4-(trifluoromethoxy)phenyl]acetamide;
N-(4-chloro-3-{6-methyl-1H-imidazo[4,5-b]pyridin-2-yl}phenyl)-2-(1H-1,2,4-triazol-1-yl)acetamide;
N-(4-chloro-3-{6-methyl-1H-imidazo[4,5-b]pyridin-2-yl}phenyl)-2,3-dihydro-1-benzofuran-2-carboxamide;
N-(4-chloro-3-{6-methyl-1H-imidazo[4,5-b]pyridin-2-yl}phenyl)-5-methyl-1H-pyrrole-2-carboxamide;
N-(4-chloro-3-{6-methyl-1H-imidazo[4,5-b]pyridin-2-yl}phenyl)-2-(4-fluorophenyl)acetamide;
N-(4-chloro-3-{6-methyl-1H-imidazo[4,5-b]pyridin-2-yl}phenyl)-5-methylfuran-2-carboxamide;
6-chloro-N-(4-chloro-3-{6-methyl-1H-imidazo[4,5-b]pyridin-2-yl}phenyl)pyrazine-2-carboxamide;
N-(4-chloro-3-{6-methyl-1H-imidazo[4,5-b]pyridin-2-yl}phenyl)-1H-imidazole-5-carboxamide;
N-(4-chloro-3-{6-methyl-1H-imidazo[4,5-b]pyridin-2-yl}phenyl)-2-methoxypyridine-4-carboxamide;
N-(4-chloro-3-{6-methyl-1H-imidazo[4,5-b]pyridin-2-yl}phenyl)-3-methylfuran-2-carboxamide;
N-(4-chloro-3-{6-methyl-1H-imidazo[4,5-b]pyridin-2-yl}phenyl)oxane-2-carboxamide;
N-(4-chloro-3-{6-methyl-1H-imidazo[4,5-b]pyridin-2-yl}phenyl)-4-(morpholin-4-yl)butanamide;
tert-butyl 3-[(4-chloro-3-{6-methyl-1H-imidazo[4,5-b]pyridin-2-yl}phenyl)carbamoyl]-3-methylazetidine-1-carboxylate;
N-(4-chloro-3-{6-methyl-1H-imidazo[4,5-b]pyridin-2-yl}phenyl)-3-methoxybenzamide;
5-chloro-N-(4-chloro-3-{6-methyl-1H-imidazo[4,5-b]pyridin-2-yl}phenyl)pyrazine-2-carboxamide;
N-(4-chloro-3-{6-methyl-1H-imidazo[4,5-b]pyridin-2-yl}phenyl)-6-methanesulfonylpyridine-3-carboxamide;
N-(4-chloro-3-{6-methyl-1H-imidazo[4,5-b]pyridin-2-yl}phenyl)-2-(methylsulfanyl)pyrimidine-4-carboxamide;
N-(4-chloro-3-{6-methyl-1H-imidazo[4,5-b]pyridin-2-yl}phenyl)oxolane-2-carboxamide;
N-(4-chloro-3-{6-methyl-1H-imidazo[4,5-b]pyridin-2-yl}phenyl)-2,4-dimethyl-1,3-oxazole-5-carboxamide;
N-(4-chloro-3-{6-methyl-1H-imidazo[4,5-b]pyridin-2-yl}phenyl)-3-methanesulfonylbenzamide;
N-(4-chloro-3-{6-methyl-1H-imidazo[4,5-b]pyridin-2-yl}phenyl)-2-(4-chlorophenyl)-3-methylbutanamide;
N-(4-chloro-3-{6-methyl-1H-imidazo[4,5-b]pyridin-2-yl}phenyl)-2-(3,4-difluorophenyl)acetamide;
N-(4-chloro-3-{6-methyl-1H-imidazo[4,5-b]pyridin-2-yl}phenyl)-3-hydroxypropanamide;
N-(4-chloro-3-{6-methyl-1H-imidazo[4,5-b]pyridin-2-yl}phenyl)-2-(4-chlorophenyl)acetamide;
N-(4-chloro-3-{6-methyl-1H-imidazo[4,5-b]pyridin-2-yl}phenyl)-2-(pyrimidin-2-yl)acetamide;
2-(2,1-benzoxazol-3-yl)-N-(4-chloro-3-{6-methyl-1H-imidazo[4,5-b]pyridin-2-yl}phenyl)acetamide;
N-(4-chloro-3-{6-methyl-1H-imidazo[4,5-b]pyridin-2-yl}phenyl)-2,4-dimethoxybenzamide;
N-(4-chloro-3-{6-methyl-1H-imidazo[4,5-b]pyridin-2-yl}phenyl)-2-(pyridin-4-yl)acetamide;
2-chloro-N-(4-chloro-3-{6-methyl-1H-imidazo[4,5-b]pyridin-2-yl}phenyl)benzamide;
N-(4-chloro-3-{6-methyl-1H-imidazo[4,5-b]pyridin-2-yl}phenyl)-2-(dimethylamino)benzamide;
N-(4-chloro-3-{6-methyl-1H-imidazo[4,5-b]pyridin-2-yl}phenyl)-1-methyl-1H-pyrrole-2-carboxamide;
5-chloro-N-(4-chloro-3-{6-methyl-1H-imidazo[4,5-b]pyridin-2-yl}phenyl)thiophene-2-carboxamide;
N-(4-chloro-3-{6-methyl-1H-imidazo[4,5-b]pyridin-2-yl}phenyl)-4-(trifluoromethyl)benzamide;
N-(4-chloro-3-{6-methyl-1H-imidazo[4,5-b]pyridin-2-yl}phenyl)-2-methanesulfinylpyrimidine-4-carboxamide;
N-(4-chloro-3-{6-methyl-1H-imidazo[4,5-b]pyridin-2-yl}phenyl)-1,2-oxazole-5-carboxamide;
N-(4-chloro-3-{6-methyl-1H-imidazo[4,5-b]pyridin-2-yl}phenyl)-2-(4-methoxyphenyl)acetamide;
N-(4-chloro-3-{6-methyl-1H-imidazo[4,5-b]pyridin-2-yl}phenyl)-1H-pyrazole-3-carboxamide;
N-(4-chloro-3-{6-methyl-1H-imidazo[4,5-b]pyridin-2-yl}phenyl)-3-cyclopropyl-1H-pyrazole-5-carboxamide;
N-(4-chloro-3-{6-methyl-1H-imidazo[4,5-b]pyridin-2-yl}phenyl)-4-(dimethylamino)butanamide;
N-(4-chloro-3-{6-methyl-1H-imidazo[4,5-b]pyridin-2-yl}phenyl)-3-methyl-2-phenylbutanamide;
N-(4-chloro-3-{6-methyl-1H-imidazo[4,5-b]pyridin-2-yl}phenyl)-5-methyl-1,2,4-oxadiazole-3-carboxamide;
N-(4-chloro-3-{6-methyl-1H-imidazo[4,5-b]pyridin-2-yl}phenyl)-2-methyl-6-(trifluoromethyl)pyridine-3-carboxamide;
N-(4-chloro-3-{6-methyl-1H-imidazo[4,5-b]pyridin-2-yl}phenyl)-3-methyloxetane-3-carboxamide;
N-(4-chloro-3-{6-methyl-1H-imidazo[4,5-b]pyridin-2-yl}phenyl)-2,2-difluoro-2-phenylacetamide;
N-(4-chloro-3-{6-methyl-1H-imidazo[4,5-b]pyridin-2-yl}phenyl)-2-(4-methoxyphenyl)propanamide;
N-(4-chloro-3-{6-methyl-1H-imidazo[4,5-b]pyridin-2-yl}phenyl)-5-(pyrazin-2-yl)pyridine-2-carboxamide;

N-(4-chloro-3-{6-methyl-1H-imidazo[4,5-b]pyridin-2-yl}phenyl)-2-(4-methylphenyl)acetamide;
N-(4-chloro-3-{6-methyl-1H-imidazo[4,5-b]pyridin-2-yl}phenyl)-2-(2-oxo-1,2-dihydropyrimidin-1-yl)acetamide;
N-(4-chloro-3-{6-methyl-1H-imidazo[4,5-b]pyridin-2-yl}phenyl)-2-(1H-1,2,3,4-tetrazol-5-yl)acetamide;
N-(4-chloro-3-{6-methyl-1H-imidazo[4,5-b]pyridin-2-yl}phenyl)-2-(1H-1,2,3,4-tetrazol-1-yl)acetamide;
N-(4-chloro-3-{6-methyl-1H-imidazo[4,5-b]pyridin-2-yl}phenyl)piperidine-2-carboxamide;
N-(4-chloro-3-{6-methyl-1H-imidazo[4,5-b]pyridin-2-yl}phenyl)-4-methylpyridine-2-carboxamide;
N-(4-chloro-3-{6-methyl-1H-imidazo[4,5-b]pyridin-2-yl}phenyl)-4-methoxypyridine-2-carboxamide;
N-(4-chloro-3-{6-methyl-1H-imidazo[4,5-b]pyridin-2-yl}phenyl)-3-hydroxypyrazine-2-carboxamide;
N-(4-chloro-3-{6-methyl-1H-imidazo[4,5-b]pyridin-2-yl}phenyl)-5-methanesulfonylthiophene-2-carboxamide;
N-(4-chloro-3-{6-methyl-1H-imidazo[4,5-b]pyridin-2-yl}phenyl)-2-methyl-5-(trifluoromethyl)-1,3-oxazole-4-carboxamide;
N-(4-chloro-3-{6-methyl-1H-imidazo[4,5-b]pyridin-2-yl}phenyl)-1,3-oxazole-5-carboxamide;
N-(4-chloro-3-{6-methyl-1H-imidazo[4,5-b]pyridin-2-yl}phenyl)-5-methylpyrazine-2-carboxamide;
N-(4-chloro-3-{6-methyl-1H-imidazo[4,5-b]pyridin-2-yl}phenyl)-2,5-dimethyl-1,3-oxazole-4-carboxamide;
N-(4-chloro-3-{6-methyl-1H-imidazo[4,5-b]pyridin-2-yl}phenyl)-2,3-dihydro-1-benzofuran-7-carboxamide;
(2R)-N-(4-chloro-3-{6-methyl-1H-imidazo[4,5-b]pyridin-2-yl}phenyl)-2-methoxy-2-phenylacetamide;
N-(4-chloro-3-{6-methyl-1H-imidazo[4,5-b]pyridin-2-yl}phenyl)-2-hydroxy-2-[4-(trifluoromethyl)phenyl]acetamide;
N-(4-chloro-3-{6-methyl-1H-imidazo[4,5-b]pyridin-2-yl}phenyl)-2-hydroxyacetamide;
N-(4-chloro-3-{6-methyl-1H-imidazo[4,5-b]pyridin-2-yl}phenyl)-3-(dimethylamino)benzamide;
N-(4-chloro-3-{6-methyl-1H-imidazo[4,5-b]pyridin-2-yl}phenyl)-5-fluorothiophene-2-carboxamide;
N-(4-chloro-3-{6-methyl-1H-imidazo[4,5-b]pyridin-2-yl}phenyl)pyridazine-3-carboxamide;
N-(4-chloro-3-{6-methyl-1H-imidazo[4,5-b]pyridin-2-yl}phenyl)pyrimidine-5-carboxamide;
N-(4-chloro-3-{6-methyl-1H-imidazo[4,5-b]pyridin-2-yl}phenyl)-2-methylpyridine-4-carboxamide;
N-(4-chloro-3-{6-methyl-1H-imidazo[4,5-b]pyridin-2-yl}phenyl)-2,3-dimethylpyridine-4-carboxamide;
5-tert-butyl-N-(4-chloro-3-{6-methyl-1H-imidazo[4,5-b]pyridin-2-yl}phenyl)furan-2-carboxamide;
N-(4-chloro-3-{6-methyl-1H-imidazo[4,5-b]pyridin-2-yl}phenyl)-2,4-dimethyl-1,3-thiazole-5-carboxamide;
N-(4-chloro-3-{6-methyl-1H-imidazo[4,5-b]pyridin-2-yl}phenyl)-1,3-thiazole-2-carboxamide;
N-(4-chloro-3-{6-methyl-1H-imidazo[4,5-b]pyridin-2-yl}phenyl)-4-methanesulfonylbenzamide;
2-amino-N-(4-chloro-3-{6-methyl-1H-imidazo[4,5-b]pyridin-2-yl}phenyl)-2-methylpropanamide;
N-(4-chloro-3-{6-methyl-1H-imidazo[4,5-b]pyridin-2-yl}phenyl)-3-(morpholin-4-yl)benzamide;
3,5-dichloro-N-(4-chloro-3-{6-methyl-1H-imidazo[4,5-b]pyridin-2-yl}phenyl)benzamide;
N-(4-chloro-3-{6-methyl-1H-imidazo[4,5-b]pyridin-2-yl}phenyl)-2-(1H-imidazol-1-yl)acetamide;
N-(4-chloro-3-{6-methyl-1H-imidazo[4,5-b]pyridin-2-yl}phenyl)-3,4-dihydro-2H-1-benzopyran-2-carboxamide;
N-(4-chloro-3-{6-methyl-1H-imidazo[4,5-b]pyridin-2-yl}phenyl)cyclopentanecarboxamide;
N-(4-chloro-3-{6-methyl-1H-imidazo[4,5-b]pyridin-2-yl}phenyl)-3-methylazetidine-3-carboxamide;
3-[(4-chloro-3-{6-methyl-1H-imidazo[4,5-b]pyridin-2-yl}phenyl)carbamoyl]propanoic acid;
N-(4-chloro-3-{6-methyl-1H-imidazo[4,5-b]pyridin-2-yl}phenyl)-2-phenylacetamide;
N-(4-chloro-3-{6-methyl-1H-imidazo[4,5-b]pyridin-2-yl}phenyl)-3-methyl-1H-1,2,4-triazole-5-carboxamide;
N-(4-chloro-3-{6-methyl-1H-imidazo[4,5-b]pyridin-2-yl}phenyl)cyclopentanecarboxamide;
N-(4-chloro-3-{6-methyl-1H-imidazo[4,5-b]pyridin-2-yl}phenyl)-1,3-thiazole-4-carboxamide;
N-(4-chloro-3-{6-methyl-1H-imidazo[4,5-b]pyridin-2-yl}phenyl)pyrazine-2-carboxamide;
N-(4-chloro-3-{6-methyl-1H-imidazo[4,5-b]pyridin-2-yl}phenyl)-1-methyl-1H-imidazole-5-carboxamide;
N-(4-chloro-3-{6-methyl-1H-imidazo[4,5-b]pyridin-2-yl}phenyl)pyridine-3-carboxamide;
N-(4-chloro-3-{6-methyl-1H-imidazo[4,5-b]pyridin-2-yl}phenyl)-4-methylthiophene-2-carboxamide;
N-(4-chloro-3-{6-methyl-1H-imidazo[4,5-b]pyridin-2-yl}phenyl)-4-(trifluoromethoxy)benzamide;
N-(4-chloro-3-{6-methyl-1H-imidazo[4,5-b]pyridin-2-yl}phenyl)-4-methoxybenzamide;
N-(4-chloro-3-{6-methyl-1H-imidazo[4,5-b]pyridin-2-yl}phenyl)pyridine-4-carboxamide;
N-(4-chloro-3-{6-methyl-1H-imidazo[4,5-b]pyridin-2-yl}phenyl)-1-methyl-1H-pyrazole-5-carboxamide;
2-fluoroethyl N-(4-chloro-3-{6-methyl-1H-imidazo[4,5-b]pyridin-2-yl}phenyl)carbamate;
ethyl N-(4-chloro-3-{6-methyl-1H-imidazo[4,5-b]pyridin-2-yl}phenyl)carbamate;
propan-2-yl N-(4-chloro-3-{6-methyl-1H-imidazo[4,5-b]pyridin-2-yl}phenyl)carbamate;
ethyl N-(4-chloro-3-{6-methyl-1H-imidazo[4,5-b]pyridin-2-yl}phenyl)carbamate;
cyclopentyl N-(4-chloro-3-{6-methyl-1H-imidazo[4,5-b]pyridin-2-yl}phenyl)carbamate;
ethyl N-(4-chloro-3-{6-methyl-1H-imidazo[4,5-b]pyridin-2-yl}phenyl)carbamate;
2-methylpropyl N-(4-chloro-3-{6-methyl-1H-imidazo[4,5-b]pyridin-2-yl}phenyl)carbamate;
2-methoxyethyl N-(4-chloro-3-{6-methyl-1H-imidazo[4,5-b]pyridin-2-yl}phenyl)carbamate;
cyclohexyl N-(4-chloro-3-{6-methyl-1H-imidazo[4,5-b]pyridin-2-yl}phenyl)carbamate;
benzyl N-(4-chloro-3-{6-methyl-1H-imidazo[4,5-b]pyridin-2-yl}phenyl)carbamate;
methyl N-(4-chloro-3-{6-methyl-1H-imidazo[4,5-b]pyridin-2-yl}phenyl)carbamate;
2,2,2-trifluoroethyl N-(4-chloro-3-{6-methyl-1H-imidazo[4,5-b]pyridin-2-yl}phenyl)carbamate;
1-(4-chloro-3-{6-methyl-1H-imidazo[4,5-b]pyridin-2-yl}phenyl)-3-[2-(dimethylamino)ethyl]urea;
1-(4-chloro-3-{6-methyl-1H-imidazo[4,5-b]pyridin-2-yl}phenyl)-3-[6-(diethylamino)hexyl]urea;
1-(4-chloro-3-{6-methyl-1H-imidazo[4,5-b]pyridin-2-yl}phenyl)-3-[6-(dimethylamino)hexyl]urea;
N-(4-chloro-3-{6-methyl-1H-imidazo[4,5-b]pyridin-2-yl}phenyl)-4,4-difluoro-2-(3-fluorophenyl)pyrrolidine-1-carboxamide;

N-(4-chloro-3-{6-methyl-1H-imidazo[4,5-b]pyridin-2-yl}phenyl)-3-azabicyclo[3.1.0]hexane-3-carboxamide;
1-(4-chloro-3-{6-methyl-1H-imidazo[4,5-b]pyridin-2-yl}phenyl)-3-cyclopentyl-3-methylurea;
1-(4-chloro-3-{6-methyl-1H-imidazo[4,5-b]pyridin-2-yl}phenyl)-3-methyl-3-(oxolan-3-yl)urea;
N-(4-chloro-3-{6-methyl-1H-imidazo[4,5-b]pyridin-2-yl}phenyl)-3-(dimethylamino)pyrrolidine-1-carboxamide;
(3R)-N-(4-chloro-3-{6-methyl-1H-imidazo[4,5-b]pyridin-2-yl}phenyl)-3-fluoropyrrolidine-1-carboxamide;
(3S)-N-(4-chloro-3-{6-methyl-1H-imidazo[4,5-b]pyridin-2-yl}phenyl)-3-fluoropyrrolidine-1-carboxamide;
3-{2-[bis(propan-2-yl)amino]ethyl}-1-(4-chloro-3-{6-methyl-1H-imidazo[4,5-b]pyridin-2-yl}phenyl)urea;
N-(4-chloro-3-{6-methyl-1H-imidazo[4,5-b]pyridin-2-yl}phenyl)morpholine-4-carboxamide;
1-(4-chloro-3-{6-methyl-1H-imidazo[4,5-b]pyridin-2-yl}phenyl)-3-methylurea;
N-(4-chloro-3-{6-methyl-1H-imidazo[4,5-b]pyridin-2-yl}phenyl)piperidine-1-carboxamide;
1-(4-chloro-3-{6-methyl-1H-imidazo[4,5-b]pyridin-2-yl}phenyl)-3-methoxy-3-methylurea;
3-(4-chloro-3-{6-methyl-1H-imidazo[4,5-b]pyridin-2-yl}phenyl)-1-methyl-1-phenylurea;
1-(4-chloro-3-{6-methyl-1H-imidazo[4,5-b]pyridin-2-yl}phenyl)-3-ethyl-3-methylurea;
1-(4-chloro-3-{6-methyl-1H-imidazo[4,5-b]pyridin-2-yl}phenyl)-3,3-dimethylurea;
N-(4-chloro-3-{6-methyl-1H-imidazo[4,5-b]pyridin-2-yl}phenyl)-4-methylpiperazine-1-carboxamide;
N-(4-chloro-3-{6-methyl-1H-imidazo[4,5-b]pyridin-2-yl}phenyl)pyrrolidine-1-carboxamide;
N-(4-chloro-3-{6-methyl-1H-imidazo[4,5-b]pyridin-2-yl}phenyl)-2-oxoimidazolidine-1-carboxamide;
1-(4-chloro-3-{6-methyl-1H-imidazo[4,5-b]pyridin-2-yl}phenyl)-3-cyclobutylurea;
3-(4-chloro-3-{6-methyl-1H-imidazo[4,5-b]pyridin-2-yl}phenyl)-1-[4-(trifluoromethyl)phenyl]urea;
1-(4-chloro-3-{6-methyl-1H-imidazo[4,5-b]pyridin-2-yl}phenyl)-3-(propan-2-yl)urea;
N-(4-chloro-3-{6-methyl-1H-imidazo[4,5-b]pyridin-2-yl}phenyl)-1-phenylmethanesulfonamide;
N-(4-chloro-3-{6-methyl-1H-imidazo[4,5-b]pyridin-2-yl}phenyl)thiophene-2-sulfonamide;
N-(4-chloro-3-{6-methyl-1H-imidazo[4,5-b]pyridin-2-yl}phenyl)-1-[4-(trifluoromethyl)phenyl]methanesulfonamide;
N-(4-chloro-3-{6-methyl-1H-imidazo[4,5-b]pyridin-2-yl}phenyl)-3,5-dimethyl-1,2-oxazole-4-sulfonamide;
N-(4-chloro-3-{6-methyl-1H-imidazo[4,5-b]pyridin-2-yl}phenyl)piperidine-1-sulfonamide;
N-(4-chloro-3-{6-methyl-1H-imidazo[4,5-b]pyridin-2-yl}phenyl)-2-methylpropane-1-sulfonamide;
4-chloro-N-(4-chlorophenyl)-3-{6-methyl-1H-imidazo[4,5-b]pyridin-2-yl}aniline;
4-(4-chloro-3-{6-methyl-1H-imidazo[4,5-b]pyridin-2-yl}phenyl)morpholine;
N-(4-chloro-3-{6-methyl-1H-imidazo[4,5-b]pyridin-2-yl}phenyl)-6-(1H-1,2,4-triazol-1-yl)pyridin-3-amine;
2-N-(4-chloro-3-{6-methyl-1H-imidazo[4,5-b]pyridin-2-yl}phenyl)-5-N,5-N-dimethylpyridine-2,5-diamine;
N-(4-chloro-3-{6-methyl-1H-imidazo[4,5-b]pyridin-2-yl}phenyl)-5-(morpholin-4-yl)pyridin-2-amine;
N-(4-chloro-3-{6-methyl-1H-imidazo[4,5-b]pyridin-2-yl}phenyl)-2-methanesulfonyl-1,2,3,4-tetrahydroisoquinolin-5-amine;
N-(4-chloro-3-{6-methyl-1H-imidazo[4,5-b]pyridin-2-yl}phenyl)-5-methylpyridin-2-amine;
6-[(4-chloro-3-{6-methyl-1H-imidazo[4,5-b]pyridin-2-yl}phenyl)amino]pyridine-3-carbonitrile;
N-(4-chloro-3-{6-methyl-1H-imidazo[4,5-b]pyridin-2-yl}phenyl)-2-(morpholin-4-yl)pyridin-3-amine;
6-benzyl-N-(4-chloro-3-{6-methyl-1H-imidazo[4,5-b]pyridin-2-yl}phenyl)-5,6,7,8-tetrahydro-2,6-naphthyridin-1-amine;
4-chloro-N-(furan-2-ylmethyl)-3-{6-methyl-1H-imidazo[4,5-b]pyridin-2-yl}aniline;
N-(4-Fluoro-3-(6-methyl-3H-imidazo[4,5-b]pyridin-2-yl)phenyl)furan-2-carboxamide;
3-amino-N-(4-fluoro-3-{6-methyl-1H-imidazo[4,5-b]pyridin-2-yl}phenyl)propanamide;
4-[2-(dimethylamino)ethoxy]-N-(4-fluoro-3-{6-methyl-1H-imidazo[4,5-b]pyridin-2-yl}phenyl)benzamide;
N-(4-fluoro-3-{6-methyl-1H-imidazo[4,5-b]pyridin-2-yl}phenyl)-1,2-oxazole-5-carboxamide;
(2R,4R)-N-(4-fluoro-3-{6-methyl-1H-imidazo[4,5-b]pyridin-2-yl}phenyl)-4-hydroxypyrrolidine-2-carboxamide;
N-(4-fluoro-3-{6-methyl-1H-imidazo[4,5-b]pyridin-2-yl}phenyl)acetamide;
(2S)-N-(4-fluoro-3-{6-methyl-1H-imidazo[4,5-b]pyridin-2-yl}phenyl)pyrrolidine-2-carboxamide;
N-(4-fluoro-3-{6-methyl-1H-imidazo[4,5-b]pyridin-2-yl}phenyl)pyrazolo[1,5-a]pyridine-2-carboxamide;
4-(dimethylamino)-N-(4-fluoro-3-{6-methyl-1H-imidazo[4,5-b]pyridin-2-yl}phenyl)butanamide;
N-{4-chloro-3-[6-(trifluoromethyl)-1H-imidazo[4,5-b]pyridin-2-yl]phenyl}furan-2-carboxamide;
N-{4-chloro-3-[6-(trifluoromethyl)-1H-imidazo[4,5-b]pyridin-2-yl]phenyl}-5-[(dimethylamino)methyl]furan-2-carboxamide;
2-chloro-N-{4-chloro-3-[6-(trifluoromethyl)-1H-imidazo[4,5-b]pyridin-2-yl]phenyl}benzamide;
N-{4-chloro-3-[6-(trifluoromethyl)-1H-imidazo[4,5-b]pyridin-2-yl]phenyl}-5-methylfuran-2-carboxamide;
N-{4-chloro-3-[6-(trifluoromethyl)-1H-imidazo[4,5-b]pyridin-2-yl]phenyl}-2-(3-chlorophenyl)acetamide;
N-{4-chloro-3-[6-(trifluoromethyl)-1H-imidazo[4,5-b]pyridin-2-yl]phenyl}-5-cyanofuran-2-carboxamide;
N-{4-chloro-3-[6-(trifluoromethyl)-1H-imidazo[4,5-b]pyridin-2-yl]phenyl}cyclopentanecarboxamide;
N-{4-chloro-3-[6-(trifluoromethyl)-1H-imidazo[4,5-b]pyridin-2-yl]phenyl}-5-fluoropyridine-3-carboxamide;
N-{4-chloro-3-[6-(trifluoromethyl)-1H-imidazo[4,5-b]pyridin-2-yl]phenyl}-5-fluorofuran-2-carboxamide;
N-{4-chloro-3-[6-(trifluoromethyl)-1H-imidazo[4,5-b]pyridin-2-yl]phenyl}pyrazine-2-carboxamide;
N-(4-chloro-3-{6-cyano-1H-imidazo[4,5-b]pyridin-2-yl}phenyl)furan-2-carboxamide;
propan-2-yl N-(4-chloro-3-{6-cyano-1H-imidazo[4,5-b]pyridin-2-yl}phenyl)carbamate;
propan-2-yl 2-(2-chloro-5-{[(propan-2-yloxy)carbonyl]amino}phenyl)-6-cyano-1H-imidazo[4,5-b]pyridine-1-carboxylate;
ethyl N-(4-chloro-3-{6-cyano-1H-imidazo[4,5-b]pyridin-2-yl}phenyl)carbamate;
methyl N-(4-chloro-3-{6-cyano-1H-imidazo[4,5-b]pyridin-2-yl}phenyl)carbamate;
N-(4-chloro-3-{6-phenyl-1H-imidazo[4,5-b]pyridin-2-yl}phenyl)pyrrolidine-1-carboxamide;
N-(4-chloro-3-{6-[4-(methylamino)phenyl]-1H-imidazo[4,5-b]pyridin-2-yl}phenyl)pyrrolidine-1-carboxamide;

N-{4-chloro-3-[6-(4-fluorophenyl)-1H-imidazo[4,5-b]pyridin-2-yl]phenyl}pyrrolidine-1-carboxamide;
N-(4-chloro-3-{6-[4-(piperazin-1-yl)phenyl]-1H-imidazo[4,5-b]pyridin-2-yl}phenyl)pyrrolidine-1-carboxamide;
N-[4-fluoro-3-(6-{4-[2-(morpholin-4-yl)ethoxy]phenyl}-1H-imidazo[4,5-b]pyridin-2-yl)phenyl]pyrrolidine-1-carboxamide;
methyl N-[4-(2-{2-chloro-5-[(pyrrolidin-1-yl)carbonylamino]phenyl}-1H-imidazo[4,5-b]pyridin-6-yl)phenyl]carbamate;
N-{4-chloro-3-[6-(4-methanesulfonylphenyl)-1H-imidazo[4,5-b]pyridin-2-yl]phenyl}pyrrolidine-1-carboxamide;
N-(4-fluoro-3-{6-[1-(piperidin-4-yl)-1H-pyrazol-4-yl]-1H-imidazo[4,5-b]pyridin-2-yl}phenyl)pyrrolidine-1-carboxamide;
N-[4-chloro-3-(6-{4-[2-(morpholin-4-yl)ethoxy]phenyl}-1H-imidazo[4,5-b]pyridin-2-yl)phenyl]pyrrolidine-1-carboxamide;
N-{4-chloro-3-[6-(thiophen-3-yl)-1H-imidazo[4,5-b]pyridin-2-yl]phenyl}pyrrolidine-1-carboxamide;
N-[4-chloro-3-(6-{3-[2-(morpholin-4-yl)ethoxy]phenyl}-1H-imidazo[4,5-b]pyridin-2-yl)phenyl]pyrrolidine-1-carboxamide;
N-[4-chloro-3-(6-{4-[3-(morpholin-4-yl)propoxy]phenyl}-1H-imidazo[4,5-b]pyridin-2-yl)phenyl]pyrrolidine-1-carboxamide;
N-(4-chloro-3-{6-[4-(2-methoxyethoxy)phenyl]-1H-imidazo[4,5-b]pyridin-2-yl}phenyl)pyrrolidine-1-carboxamide;
N-(3-{6-[4-(1-amino-2-methylpropan-2-yl)phenyl]-1H-imidazo[4,5-b]pyridin-2-yl}-4-chlorophenyl)pyrrolidine-1-carboxamide;
N-[4-chloro-3-(6-{4-[2-hydroxy-3-(morpholin-4-yl)propoxy]phenyl}-1H-imidazo[4,5-b]pyridin-2-yl)phenyl]pyrrolidine-1-carboxamide;
N-{4-chloro-3-[6-(1-{[2-(trimethylsilyl)ethoxy]methyl}-1H-imidazol-4-yl)-1H-imidazo[4,5-b]pyridin-2-yl]phenyl}pyrrolidine-1-carboxamide;
N-{4-chloro-3-[6-(1H-imidazol-4-yl)-1H-imidazo[4,5-b]pyridin-2-yl]phenyl}pyrrolidine-1-carboxamide;
tert-butyl N-[4-(2-{2-chloro-5-[(pyrrolidin-1-yl)carbonylamino]phenyl}-1H-imidazo[4,5-b]pyridin-6-yl)phenyl]-N-methylcarbamate;
N-(4-fluoro-3-{6-phenyl-1H-imidazo[4,5-b]pyridin-2-yl}phenyl)pyrrolidine-1-carboxamide;
N-(4-fluoro-3-{6-[4-(oxiran-2-ylmethoxy)phenyl]-1H-imidazo[4,5-b]pyridin-2-yl}phenyl)pyrrolidine-1-carboxamide;
N-[4-fluoro-3-(6-{4-[2-(4-methylpiperazin-1-yl)ethoxy]phenyl}-1H-imidazo[4,5-b]pyridin-2-yl)phenyl]pyrrolidine-1-carboxamide;
N-(4-fluoro-3-{6-[4-(2-methoxyethoxy)phenyl]-1H-imidazo[4,5-b]pyridin-2-yl}phenyl)pyrrolidine-1-carboxamide;
N-{4-fluoro-3-[6-(2-methoxyphenyl)-3H-imidazo[4,5-b]pyridin-2-yl]phenyl}pyrrolidine-1-carboxamide;
N-{3-[6-(3-chlorophenyl)-3H-imidazo[4,5-b]pyridin-2-yl]-4-fluorophenyl}pyrrolidine-1-carboxamide;
N-{4-fluoro-3-[6-(3-methylphenyl)-3H-imidazo[4,5-b]pyridin-2-yl]phenyl}pyrrolidine-1-carboxamide;
N-{3-[6-(3-aminophenyl)-3H-imidazo[4,5-b]pyridin-2-yl]-4-fluorophenyl}pyrrolidine-1-carboxamide;
N-{4-fluoro-3-[6-(furan-3-yl)-3H-imidazo[4,5-b]pyridin-2-yl]phenyl}pyrrolidine-1-carboxamide;
N-{4-fluoro-3-[6-(thiophen-3-yl)-3H-imidazo[4,5-b]pyridin-2-yl]phenyl}pyrrolidine-1-carboxamide;
N-{4-fluoro-3-[6-(pyridin-3-yl)-3H-imidazo[4,5-b]pyridin-2-yl]phenyl}pyrrolidine-1-carboxamide;
N-(3-{6-bromo-3H-imidazo[4,5-b]pyridin-2-yl}-4-fluorophenyl)-2,5-dihydro-1H-pyrrole-1-carboxamide;
N-{4-fluoro-3-[6-(4-fluoro-3-methylphenyl)-3H-imidazo[4,5-b]pyridin-2-yl]phenyl}pyrrolidine-1-carboxamide;
N-{4-fluoro-3-[6-(thiophen-2-yl)-3H-imidazo[4,5-b]pyridin-2-yl]phenyl}pyrrolidine-1-carboxamide;
N-{4-fluoro-3-[6-(3-methanesulfonamidophenyl)-3H-imidazo[4,5-b]pyridin-2-yl]phenyl}pyrrolidine-1-carboxamide;
N-{3-[6-(6-chloropyridin-3-yl)-3H-imidazo[4,5-b]pyridin-2-yl]-4-fluorophenyl}pyrrolidine-1-carboxamide;
N-{3-[6-(2-chloropyridin-4-yl)-3H-imidazo[4,5-b]pyridin-2-yl]-4-fluorophenyl}pyrrolidine-1-carboxamide;
N-{4-fluoro-3-[6-(5-methylpyridin-3-yl)-3H-imidazo[4,5-b]pyridin-2-yl]phenyl}pyrrolidine-1-carboxamide;
N-{4-fluoro-3-[6-(6-methoxypyridin-3-yl)-3H-imidazo[4,5-b]pyridin-2-yl]phenyl}pyrrolidine-1-carboxamide;
N-(4-fluoro-3-{6-[2-(pyrrolidin-1-yl)pyridin-4-yl]-3H-imidazo[4,5-b]pyridin-2-yl}phenyl)pyrrolidine-1-carboxamide;
N-{4-fluoro-3-[6-(pyrimidin-5-yl)-3H-imidazo[4,5-b]pyridin-2-yl]phenyl}pyrrolidine-1-carboxamide;
N-{3-[6-(5-chloropyridin-3-yl)-3H-imidazo[4,5-b]pyridin-2-yl]-4-fluorophenyl}pyrrolidine-1-carboxamide;
N-{4-fluoro-3-[6-(2-methoxypyrimidin-5-yl)-3H-imidazo[4,5-b]pyridin-2-yl]phenyl}pyrrolidine-1-carboxamide;
tert-butyl N-[4-(2-{2-chloro-5-[(pyrrolidin-1-yl)carbonylamino]phenyl}-1H-imidazo[4,5-b]pyridin-6-yl)phenyl]-N-methylcarbamate;
propan-2-yl N-(4-chloro-3-{6-phenyl-1H-imidazo[4,5-b]pyridin-2-yl}phenyl)carbamate;
propan-2-yl N-{3-[6-(2-aminophenyl)-1H-imidazo[4,5-b]pyridin-2-yl]-4-chlorophenyl}carbamate;
propan-2-yl N-{4-chloro-3-[6-(2-{[(propan-2-yloxy)carbonyl]amino}phenyl)-1H-imidazo[4,5-b]pyridin-2-yl]phenyl}carbamate;
propan-2-yl 2-(2-chloro-5-{[(propan-2-yloxy)carbonyl]amino}phenyl)-6-(2-{[(propan-2-yloxy)carbonyl]amino}phenyl)-1H-imidazo[4,5-b]pyridine-1-carboxylate;
propan-2-yl N-{4-[2-(2-chloro-5-{[(propan-2-yloxy)carbonyl]amino}phenyl)-1H-imidazo[4,5-b]pyridin-6-yl]phenyl}carbamate;
propan-2-yl N-(3-{6-[4-(2-aminoacetamido)phenyl]-1H-imidazo[4,5-b]pyridin-2-yl}-4-chlorophenyl)carbamate;
propan-2-yl N-(3-{6-[4-(3-aminopropanamido)phenyl]-1H-imidazo[4,5-b]pyridin-2-yl}-4-chlorophenyl)carbamate;
propan-2-yl N-(3-{6-[2-(2-aminoacetamido)phenyl]-1H-imidazo[4,5-b]pyridin-2-yl}-4-chlorophenyl)carbamate;
methyl N-{4-[2-(2-chloro-5-{[(propan-2-yloxy)carbonyl]amino}phenyl)-1H-imidazo[4,5-b]pyridin-6-yl]phenyl}carbamate;
propan-2-yl N-(3-{6-[2-(3-aminopropanamido)phenyl]-1H-imidazo[4,5-b]pyridin-2-yl}-4-chlorophenyl)carbamate;

methyl N-[4-(2-{2-chloro-5-[(3,3-difluoropyrrolidin-1-yl)carbonylamino]phenyl}-1H-imidazo[4,5-b]pyridin-6-yl)phenyl]carbamate;
methyl N-[4-(2-{5-[(azetidin-1-yl)carbonylamino]-2-chlorophenyl}-1H-imidazo[4,5-b]pyridin-6-yl)phenyl]carbamate;
N-(4-chloro-3-{6-[4-(methylamino)phenyl]-1H-imidazo[4,5-b]pyridin-2-yl}phenyl)-4-methylthiophene-2-carboxamide;
N-(4-chloro-3-{6-[4-(methylamino)phenyl]-1H-imidazo[4,5-b]pyridin-2-yl}phenyl)cyclopentanecarboxamide;
N-(4-chloro-3-{6-[4-(methylamino)phenyl]-1H-imidazo[4,5-b]pyridin-2-yl}phenyl)-5-[(dimethylamino)methyl]furan-2-carboxamide;
N-(4-chloro-3-{6-[4-(methylamino)phenyl]-1H-imidazo[4,5-b]pyridin-2-yl}phenyl)pyrazine-2-carboxamide;
N-(4-chloro-3-{6-[4-(methylamino)phenyl]-1H-imidazo[4,5-b]pyridin-2-yl}phenyl)-1,3-thiazole-4-carboxamide;
2-methoxyethyl N-(4-chloro-3-{6-[4-(methylamino)phenyl]-1H-imidazo[4,5-b]pyridin-2-yl}phenyl)carbamate;
ethyl N-(4-chloro-3-{6-[4-(methylamino)phenyl]-1H-imidazo[4,5-b]pyridin-2-yl}phenyl)carbamate;
N-{3-[6-(aminomethyl)-1H-imidazo[4,5-b]pyridin-2-yl]-4-chlorophenyl}furan-2-carboxamide;
N-(3-(6-chloro-1H-imidazo[4,5-b]pyridin-2-yl)-4-fluorophenyl)pyrrolidine-1-carboxamide;
1-(3-{6-chloro-1H-imidazo[4,5-b]pyridin-2-yl}-4-fluorophenyl)-3,3-dimethylurea;
1-(3-{6-chloro-1H-imidazo[4,5-b]pyridin-2-yl}-4-fluorophenyl)-3,3-diethylurea;
3-(3-{6-chloro-1H-imidazo[4,5-b]pyridin-2-yl}-4-fluorophenyl)-1-[4-(trifluoromethyl)phenyl]urea;
N-(3-{6-chloro-1H-imidazo[4,5-b]pyridin-2-yl}-4-fluorophenyl)-furan-2-carboxamide;
N-(3-{6-chloro-1H-imidazo[4,5-b]pyridin-2-yl}-4-fluorophenyl)-2,2-dimethylpropanamide;
N-(3-{6-chloro-1H-imidazo[4,5-b]pyridin-2-yl}-4-fluorophenyl)-3-(piperidin-1-yl)propanamide;
N-(3-{6-bromo-3H-imidazo[4,5-b]pyridin-2-yl}-4-fluorophenyl)-2-oxoimidazolidine-1-carboxamide;
1-(3-{6-bromo-3H-imidazo[4,5-b]pyridin-2-yl}-4-fluorophenyl)-3,3-diethylurea;
1-(3-{6-bromo-1H-imidazo[4,5-b]pyridin-2-yl}-4-fluorophenyl)-3,3-bis(propan-2-yl)urea;
N-(3-{6-bromo-3H-imidazo[4,5-b]pyridin-2-yl}-4-fluorophenyl)-3,3-difluoropyrrolidine-1-carboxamide;
N-(3-{6-bromo-3H-imidazo[4,5-b]pyridin-2-yl}-4-fluorophenyl)-2,5-dihydro-1H-pyrrole-1-carboxamide;
N-(3-{6-bromo-1H-imidazo[4,5-b]pyridin-2-yl}-4-fluorophenyl)morpholine-4-carboxamide;
N-(3-{6-bromo-3H-imidazo[4,5-b]pyridin-2-yl}-4-fluorophenyl)cyclopropanecarboxamide;
N-(3-{6-bromo-3H-imidazo[4,5-b]pyridin-2-yl}-4-fluorophenyl)cyclopentanecarboxamide;
N-(3-{6-bromo-1H-imidazo[4,5-b]pyridin-2-yl}-4-fluorophenyl)-1H-pyrazole-3-carboxamide;
N-(3-{6-bromo-1H-imidazo[4,5-b]pyridin-2-yl}-4-chlorophenyl)-1,3-oxazole-4-carboxamide;
ethyl N-(3-{6-bromo-1H-imidazo[4,5-b]pyridin-2-yl}-4-chlorophenyl)carbamate;
2-methoxyethyl N-(3-{6-bromo-1H-imidazo[4,5-b]pyridin-2-yl}-4-chlorophenyl)carbamate;
N-(3-{6-bromo-1H-imidazo[4,5-b]pyridin-2-yl}-4-chlorophenyl)-5-[(dimethylamino)methyl]furan-2-carboxamide;
N-(3-{6-bromo-1H-imidazo[4,5-b]pyridin-2-yl}-4-chlorophenyl)-5-fluorofuran-2-carboxamide;
N-(3-{6-bromo-1H-imidazo[4,5-b]pyridin-2-yl}-4-chlorophenyl)cyclopentanecarboxamide;
N-(3-{6-bromo-1H-imidazo[4,5-b]pyridin-2-yl}-4-chlorophenyl)pyrazine-2-carboxamide;
N-{4-chloro-3-[6-(2-oxo-2,3-dihydro-1H-indol-5-yl)-1H-imidazo[4,5-b]pyridin-2-yl]phenyl}pyrazine-2-carboxamide;
N-{4-chloro-3-[6-(2-oxo-2,3-dihydro-1H-indol-5-yl)-1H-imidazo[4,5-b]pyridin-2-yl]phenyl}cyclopentanecarboxamide;
ethyl N-{4-chloro-3-[6-(2-oxo-2,3-dihydro-1H-indol-5-yl)-1H-imidazo[4,5-b]pyridin-2-yl]phenyl}carbamate;
2-methoxyethyl N-{4-chloro-3-[6-(2-oxo-2,3-dihydro-1H-indol-5-yl)-1H-imidazo[4,5-b]pyridin-2-yl]phenyl}carbamate;
N-(4-fluoro-3-{6-phenyl-1H-imidazo[4,5-b]pyridin-2-yl}phenyl)-5-methylfuran-2-carboxamide;
N-{4-fluoro-3-[6-(thiophen-3-yl)-1H-imidazo[4,5-b]pyridin-2-yl]phenyl}-5-methylfuran-2-carboxamide;
N-(3-{5-chloro-3H-imidazo[4,5-b]pyridin-2-yl}-4-fluorophenyl)-furan-2-carboxamide;
N-(4-fluoro-3-{6-fluoro-3H-imidazo[4,5-b]pyridin-2-yl}phenyl)-furan-2-carboxamide;
N-(3-{6,7-dichloro-3H-imidazo[4,5-b]pyridin-2-yl}-4-fluorophenyl)-furan-2-carboxamide;
N-{3-[6-bromo-3-(methoxymethyl)-3H-imidazo[4,5-b]pyridin-2-yl]-4-chlorophenyl}pyrrolidine-1-carboxamide;
N-{3-[6-bromo-1-(methoxymethyl)-1H-imidazo[4,5-b]pyridin-2-yl]-4-chlorophenyl}pyrrolidine-1-carboxamide;
N-(3-{6-bromo-1-[2-(dimethylamino)ethyl]-1H-imidazo[4,5-b]pyridin-2-yl}-4-chlorophenyl)pyrrolidine-1-carboxamide;
N-(3-{6-bromo-1-[2-(morpholin-4-yl)ethyl]-1H-imidazo[4,5-b]pyridin-2-yl}-4-chlorophenyl)pyrrolidine-1-carboxamide;
3-[4-fluoro-3-(6-{4-[2-(morpholin-4-yl)ethyl]phenyl}-[1,3]oxazolo[4,5-b]pyridin-2-yl)phenyl]-1-[4-(trifluoromethyl)phenyl]urea;
3-(3-{6-[4-(dimethylamino)phenyl]-[1,3]oxazolo[4,5-b]pyridin-2-yl}-4-fluorophenyl)-1-[4-(trifluoromethyl)phenyl]urea;
3-{4-fluoro-3-[6-(6-{[2-(morpholin-4-yl)ethyl]amino}pyridin-3-yl)-[1,3]oxazolo[4,5-b]pyridin-2-yl]phenyl}-1-[4-(trifluoromethyl)phenyl]urea;
3-(4-fluoro-3-{6-[4-(morpholin-4-yl)phenyl]-[1,3]oxazolo[4,5-b]pyridin-2-yl}phenyl)-1-[4-(trifluoromethyl)phenyl]urea;
3-(4-fluoro-3-{6-[4-(methylamino)phenyl]-[1,3]oxazolo[4,5-b]pyridin-2-yl}phenyl)-1-[4-(trifluoromethyl)phenyl]urea;
3-{4-fluoro-3-[6-(3-methyl-1H-pyrazol-4-yl)-[1,3]oxazolo[4,5-b]pyridin-2-yl]phenyl}-1-[4-(trifluoromethyl)phenyl]urea;
3-(4-fluoro-3-{6-[4-(morpholin-4-ylmethyl)phenyl]-[1,3]oxazolo[4,5-b]pyridin-2-yl}phenyl)-1-[4-(trifluoromethyl)phenyl]urea;
propan-2-yl N-(4-{2-[2-fluoro-5-({[4-(trifluoromethyl)phenyl]carbamoyl}amino)phenyl]-[1,3]oxazolo[4,5-b]pyridin-6-yl}phenyl)carbamate;
3-{4-fluoro-3-[6-(piperidin-1-yl)-[1,3]oxazolo[4,5-b]pyridin-2-yl]phenyl}-1-[4-(trifluoromethyl)phenyl]urea;

3-[4-fluoro-3-(6-{4-[2-(morpholin-4-yl)ethoxy]phenyl}[1,3]oxazolo[4,5-b]pyridin-2-yl)phenyl]-1-[4-(trifluoromethyl)phenyl]urea;

3-(4-fluoro-3-{6-[4-(piperidin-1-yl)phenyl]-[1,3]oxazolo[4,5-b]pyridin-2-yl}phenyl)-1-[4-(trifluoromethyl)phenyl]urea;

3-{3-[6-(6-aminopyridin-3-yl)-[1,3]oxazolo[4,5-b]pyridin-2-yl]-4-fluorophenyl}-1-[4-(trifluoromethyl)phenyl]urea;

N-(4-{2-[2-fluoro-5-({[4-(trifluoromethyl)phenyl]carbamoyl}amino)phenyl]-[1,3]oxazolo[4,5-b]pyridin-6-yl}phenyl)acetamide;

methyl N-(4-{2-[2-fluoro-5-({[4-(trifluoromethyl)phenyl]carbamoyl}amino)phenyl]-[1,3]oxazolo[4,5-b]pyridin-6-yl}phenyl)carbamate;

3-(3-{6-[6-(dimethylamino)pyridin-3-yl]-[1,3]oxazolo[4,5-b]pyridin-2-yl}-4-fluorophenyl)-1-[4-(trifluoromethyl)phenyl]urea;

N-(3-{6-bromo-[1,3]oxazolo[4,5-b]pyridin-2-yl}-4-fluorophenyl)-5-ethyl-1,3,4-oxadiazole-2-carboxamide;

N-(3-{6-bromo-[1,3]oxazolo[4,5-b]pyridin-2-yl}-4-fluorophenyl)-3-ethyl-1,2,4-oxadiazole-5-carboxamide;

N-(3-{6-bromo-[1,3]oxazolo[4,5-b]pyridin-2-yl}-4-fluorophenyl)-5-(propan-2-yl)-1,3,4-oxadiazole-2-carboxamide;

N-(3-{6-bromo-[1,3]oxazolo[4,5-b]pyridin-2-yl}-4-fluorophenyl)-5-tert-butyl-1,3,4-oxadiazole-2-carboxamide;

N-(3-{6-bromo-[1,3]oxazolo[4,5-b]pyridin-2-yl}-4-fluorophenyl)-1,3-oxazole-5-carboxamide;

N-(3-{6-bromo-[1,3]oxazolo[4,5-b]pyridin-2-yl}-4-fluorophenyl)-4-methyl-1,3-oxazole-5-carboxamide;

N-(3-{6-bromo-[1,3]oxazolo[4,5-b]pyridin-2-yl}-4-fluorophenyl)-1,3-oxazole-4-carboxamide;

N-{4-fluoro-3-[6-(4-fluorophenyl)-[1,3]oxazolo[4,5-b]pyridin-2-yl]phenyl}furan-2-carboxamide;

N-{4-fluoro-3-[6-(4-phenylphenyl)-[1,3]oxazolo[4,5-b]pyridin-2-yl]phenyl}furan-2-carboxamide;

N-(3-{6-chloro-3H-imidazo[4,5-b]pyridin-2-yl}-4-fluorophenyl)furan-2-carboxamide;

methyl N-(4-{2-[2-fluoro-5-(furan-2-amido)phenyl]-[1,3]oxazolo[4,5-b]pyridin-6-yl}phenyl)carbamate;

N-(4-fluoro-3-{6-phenyl-[1,3]oxazolo[4,5-b]pyridin-2-yl}phenyl)pyrrolidine-1-carboxamide;

N-(4-chloro-3-{6-phenyl-[1,3]oxazolo[4,5-b]pyridin-2-yl}phenyl)furan-2-carboxamide;

methyl N-(4-{2-[2-chloro-5-(furan-2-amido)phenyl]-[1,3]oxazolo[4,5-b]pyridin-6-yl}phenyl)carbamate;

N-(4-chloro-3-{6-methyl-[1,3]oxazolo[4,5-b]pyridin-2-yl}phenyl)furan-2-carboxamide;

N-(4-chloro-3-{6-ethyl-[1,3]oxazolo[4,5-b]pyridin-2-yl}phenyl)furan-2-carboxamide;

4-fluoro-N,N-dimethyl-3-(6-{4-[2-(morpholin-4-yl)ethoxy]phenyl}-[1,3]oxazolo[4,5-b]pyridin-2-yl)aniline; and 4-fluoro-N-methyl-3-(6-{4-[2-(morpholin-4-yl)ethoxy]phenyl}-[1,3]oxazolo[4,5-b]pyridin-2-yl)aniline.

18. A pharmaceutical composition comprising a compound of any one of claims 1 to 17 as an active ingredient and at least one excipient.

19. A method for treating, a disease caused by a parasite, comprising administering to a subject a therapeutically effective amount of a compound according to any one of claims 1-17, wherein the disease is selected from Leishmaniasis, Human African Trypanosomiasis and Chagas disease, and wherein the administering is optionally in combination with a second agent.

20. A method for treating, a disease caused by a parasite, comprising administering to a subject a therapeutically effective amount of a composition according to claim 18, wherein the disease is selected from Leishmaniasis, Human African Trypanosomiasis and Chagas disease, and wherein the administering is optionally in combination with a second agent.

* * * * *